US010590090B2

(12) United States Patent
Koltun et al.

(10) Patent No.: US 10,590,090 B2
(45) Date of Patent: Mar. 17, 2020

(54) 2,5-DISUBSTITUTED 3-METHYL PYRAZINES AND 2,5,6-TRISUBSTITUTED 3-METHYL PYRAZINES AS ALLOSTERIC SHP2 INHIBITORS

(71) Applicant: Revolution Medicines, Inc., Redwood City, CA (US)

(72) Inventors: Elena S. Koltun, Redwood City, CA (US); Kevin Mellem, Redwood City, CA (US); Adrian Gill, Redwood City, CA (US); Gert Kiss, Redwood City, CA (US); Christopher Semko, Redwood City, CA (US); Naing Aay, Redwood City, CA (US); Andreas Buckl, Redwood City, CA (US); Ashutosh Jogalekar, Redwood City, CA (US); Walter Won, Redwood City, CA (US)

(73) Assignee: REVOLUTION MEDICINES, INC., Redwood City, CA (US)

( * ) Notice: Subject to any disclaimer, the term of this patent is extended or adjusted under 35 U.S.C. 154(b) by 0 days.

(21) Appl. No.: 16/228,324

(22) Filed: Dec. 20, 2018

(65) Prior Publication Data
US 2019/0210977 A1    Jul. 11, 2019

Related U.S. Application Data

(63) Continuation of application No. PCT/US2017/041577, filed on Jul. 11, 2017.

(60) Provisional application No. 62/361,249, filed on Jul. 12, 2016, provisional application No. 62/449,523, filed on Jan. 23, 2017.

(51) Int. Cl.
| | | |
|---|---|---|
| A61K 31/497 | (2006.01) | |
| C07D 241/20 | (2006.01) | |
| C07D 403/12 | (2006.01) | |
| C07D 403/04 | (2006.01) | |
| C07D 241/18 | (2006.01) | |
| A61P 35/02 | (2006.01) | |
| A61P 35/04 | (2006.01) | |
| C07D 401/04 | (2006.01) | |
| C07D 477/26 | (2006.01) | |
| C07D 487/04 | (2006.01) | |

(52) U.S. Cl.
CPC ............ *C07D 241/20* (2013.01); *A61P 35/02* (2018.01); *A61P 35/04* (2018.01); *C07D 241/18* (2013.01); *C07D 401/04* (2013.01); *C07D 403/04* (2013.01); *C07D 403/12* (2013.01); *C07D 477/26* (2013.01); *C07D 487/04* (2013.01)

(58) Field of Classification Search
CPC ... A61K 31/497; C07D 401/04; C07D 401/14

USPC ...................................... 514/255.05; 544/405
See application file for complete search history.

(56) References Cited

U.S. PATENT DOCUMENTS

| | | |
|---|---|---|
| 5,262,564 A | 11/1993 | Kun et al. |
| 9,394,368 B2 | 7/2016 | Brogdon et al. |
| 2006/0189664 A1 | 8/2006 | Barth et al. |
| 2012/0266264 A1 | 10/2012 | Lee |
| 2013/0005949 A1 | 1/2013 | Fertig et al. |
| 2016/0031976 A1 | 2/2016 | Seubert et al. |

FOREIGN PATENT DOCUMENTS

| | | |
|---|---|---|
| EP | 0 579 835 A1 | 1/1994 |
| WO | WO 93/09664 | 5/1993 |
| WO | WO 98/56376 | 12/1998 |
| WO | WO 01/16097 A1 | 3/2001 |
| WO | WO 2004/024719 A1 | 3/2004 |
| WO | WO 2010/011666 A2 | 1/2010 |
| WO | WO 2011/022440 A2 | 2/2011 |
| WO | WO 2015/107493 A1 | 7/2015 |
| WO | WO 2015/107494 A1 | 7/2015 |
| WO | WO 2015/107495 A1 | 7/2015 |
| WO | WO 2016/161282 A1 | 10/2016 |
| WO | WO 2016/203404 A1 | 12/2016 |
| WO | WO 2016/203405 A1 | 12/2016 |
| WO | WO 2016/203406 A1 | 12/2016 |
| WO | WO 2017/156397 A1 | 9/2017 |
| WO | WO 2017/211303 A1 | 12/2017 |
| WO | WO 2017/216706 A1 | 12/2017 |
| WO | WO 2018/013597 A1 | 1/2018 |
| WO | WO 2018/057884 A1 | 3/2018 |
| WO | WO 2018/081091 A1 | 5/2018 |
| WO | WO 2018/130928 A1 | 7/2018 |
| WO | WO 2018/136264 A1 | 7/2018 |
| WO | WO 2018/136265 A1 | 7/2018 |
| WO | WO 2018/172984 A1 | 9/2018 |
| WO | WO 2018/218133 A1 | 11/2018 |
| WO | WO 2019/051084 A1 | 3/2019 |
| WO | WO 2019/075265 A1 | 4/2019 |
| WO | WO 2019/118909 A1 | 6/2019 |

OTHER PUBLICATIONS

International Search Report and Written Opinion dated Dec. 20, 2017, for PCT/US2017/041577, 18 pages.
Chen et al., "Allosteric inhibition of SHP2 phosphatase inhibits cancers driven by receptor tyrosine kinases," Nature 2016, 535, 148-152.
Fortanet et al., "Allosteric Inhibition of SHP2: Identification of a Potent, Selective, and Orally Efficacious Phosphatase Inhibitor," J. Med. Chem. 2016, 59, 7773-7782.

(Continued)

*Primary Examiner* — Jeffrey H Murray
(74) *Attorney, Agent, or Firm* — Cooley LLP

(57) ABSTRACT

The present disclosure is directed to inhibitors of SHP2, such as pyrazine compounds, and their use in the treatment of disease associated with SHP2 modulation, such as Noonan Syndrome, Leopard Syndrome, juvenile myelomonocytic leukemias, neuroblastoma, melanoma, acute myeloid leukemia and cancers of the breast, lung and colon. Also disclosed are pharmaceutical compositions comprising the same.

50 Claims, No Drawings

(56) References Cited

OTHER PUBLICATIONS

Lachelle et al., "Identification of an allosteric benzothiazolopyrimidone inhibitor of the oncogenic protein tyrosine phosphatase SHP2," Bioorg. Med. Chem. 2017, 17, 31394-31399.
Xie et al., "Allosteric Inhibitors of SHP2 with Therapeutic Potential for Cancer Treatment," J. Med. Chem. 2017, 60, 10205-10219.
U.S. Appl. No. 16/518,796, filed Jan. 9, 2018, Gill et al.
U.S. Appl. No. 16/518,798, filed Jan. 9, 2018, Blank et al.
International Search Report and Written Opinion dated Sep. 21, 2018, for PCT/US2018/013018, 10 pages.
International Search Report and Written Opinion dated Apr. 5, 2018, for PCT/US2018/013023, 13 pages.
International Search Report and Written Opinion dated Jan. 24, 2019, for PCT/US2018/055502, 16 pages.
International Search Report and Written Opinion dated Dec. 12, 2018, for PCT/US2018/049744, 13 pages.
International Search Report and Written Opinion dated Feb. 20, 2019, for PCT/US2018/065817, 11 pages.
Chen et al., "Identification of demethylincisterol A3 as a selective inhibitor of protein tyrosine phosphatase Shp2," Eur J Pharmacol. Jan. 15, 2017;795:124-133.
Meurer et al., "Synthesis and SAR of 5, 6-diarylpyridines as human CB1 inverse agonists," Bioorg Med Chem Lett. Feb. 1, 2005;15(3):645-51.
Mohi et al., "The role of Shp2 (PTPN11) in cancer," Curr Opin Genet Dev. Feb. 2007;17(1):23-30.
Nichols et al., "RAS nucleotide cycling underlies the SHP2 phosphatase dependence of mutant BRAF-, NF1- and RAS-driven cancers," Nat Cell Biol. Sep. 2018;20(9):1064-1073.
Ruess et al., "Mutant KRAS-driven cancers depend on PTPN11/SHP2 phosphatase," Nat Med. Jul. 2018;24(7):954-960.
Database Registry [Online] Chemical Abstracts Service, Columbus, Ohio, US; Apr. 27, 2011 (Apr. 27, 2011), XP002787392, retrieved from STN Database accession No. 1286273-60-6 compound with CAS registry No. 1286273-60-6.
Database Registry [Online] Chemical Abstracts Service, Columbus, Ohio, US; Nov. 9, 2007 (Nov. 9, 2007), XP002787393, retrieved from stn Database accession No. 952723-55-6 compound with CAS registry No. 952723-55-6.
Database Registry [Online] Chemical Abstracts Service, Columbus, Ohio, US; Jan. 22, 2015 (Jan. 22, 2015), XP002787394, retrieved from stn Database accession No. 1643677-14-8 compound with CAS registry No. 1643677-14-8.
Database Registry [Online] Chemical Abstracts Service, Columbus, Ohio, US; Nov. 16, 1984 (Nov. 16, 1984), XP002787395, retrieved from stn Database accession No. 86663-20-9 compound with CAS registry No. 86663-20-9.
Database Registry [Online] Chemical Abstracts Service, Columbus, Ohio, US; Dec. 18, 1984 (Dec. 18, 1984), XP002787396, retrieved from stn Database accession No. 93034-72-1 compound with CAS registry No. 93034-72-1.
Database Registry [Online] Chemical Abstracts Service, Columbus, Ohio, US; Nov. 16, 1984 (Nov. 16, 1984), XP002787397, retrieved from stn Database accession No. 68559-45-5 compound with CAS registry No. 68559-45-5.
Database Registry [Online] Chemical Abstracts Service, Columbus, Ohio, US; Nov. 23, 2004 (Nov. 23, 2004), XP002787398, retrieved from stn Database accession No. 786652-86-6 compound with CAS registry No. 786652-86-6.
Database Registry [Online] Chemical Abstracts Service, Columbus, Ohio, US; Nov. 23, 2004 (Nov. 23, 2004), XP002787399, retrieved from stn Database accession No. 786652-83-3 compound with CAS registry No. 786652-83-3.
Database Registry [Online] Chemical Abstracts Service, Columbus, Ohio, US; Apr. 6, 1990 (Apr. 6, 1990), XP002787400, Database accession No. 126317-60-0 compound with CAS registry No. 126317-60-0.
Database Registry [Online] Chemical Abstracts Service, Columbus, Ohio, US; May 31, 2006 (May 31, 2006), XP002787401, retrieved from stn Database accession No. 886208-65-7 compound with CAS registry No. 886208-65-7.
Database Registry [Online] Chemical Abstracts Service, Columbus, Ohio, US; Aug. 27, 2010 (Aug. 27, 2010), XP002787406, retrieved from stn Database accession No. 1239320-06-9 compound with CAS registry No. 1239320-06-9.

2,5-DISUBSTITUTED 3-METHYL PYRAZINES AND 2,5,6-TRISUBSTITUTED 3-METHYL PYRAZINES AS ALLOSTERIC SHP2 INHIBITORS

CROSS REFERENCE TO RELATED APPLICATIONS

This application is a by-pass continuation which claims priority to PCT Application No. PCT/US17/41577 filed Jul. 11, 2017, which claims the benefit of U.S. Provisional Application No. 62/361,249, filed Jul. 12, 2016, and U.S. Provisional Application No. 62/449,523, filed Jan. 23, 2017, the contents of which are incorporated herein by reference in their entireties.

FIELD OF THE DISCLOSURE

The present disclosure relates to inhibitors of protein tyrosine phosphatase SHP2 useful in the treatment of diseases or disorders. Specifically, this disclosure is concerned with compounds and compositions inhibiting SHP2, methods of treating diseases associated with SHP2, and methods of synthesizing these compounds.

BACKGROUND OF THE DISCLOSURE

SH2 domain-containing protein tyrosine phosphatase-2 (SHP2) is a non-receptor protein tyrosine phosphatase encoded by the PTPN1 1 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N—SH2 and C—SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N—SH2 and PTP domains. Stimulation by, for example, cytokines or growth factors leads to exposure of the catalytic site resulting in enzymatic activation of SHP2.

Mutations in the PTPN1 1 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present disclosure fulfill the need for small molecules to that inhibit the activity of SHP2.

SUMMARY OF THE DISCLOSURE

The present disclosure relates to compounds capable of inhibiting the activity of SHP2. The disclosure further provides a process for the preparation of compounds disclosed herein, pharmaceutical preparations comprising such compounds and methods of using such compounds and compositions in the management of diseases or disorders associated with the aberrant activity of SHP2.

One aspect of the disclosure relates to compounds of Formula I:

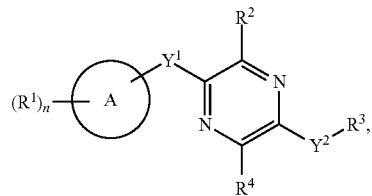

and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to compounds of Formula II:

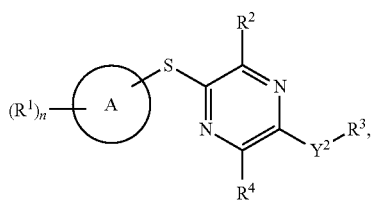

II and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to compounds of Formula III:

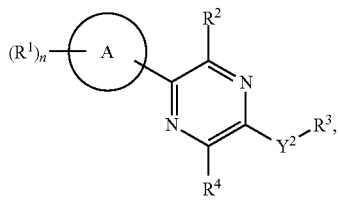

and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N(R^a)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure related to compounds of Formula I-V1:

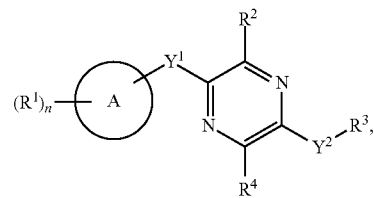

and pharmaceutically acceptable salts, prodrugs, solvates, hydrates, tautomers, or isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —$S(O)_2$—, —$S(O)_2$—NH—, —C(=$CH_2$)—, —CH—, or —S(O)—;

$Y^2$ is —$NR^a$—, wherein the bond on the left side of $Y^2$, as drawn, is bound to the pyrazine ring and the bond on the right side of the $Y^2$ moiety, as drawn, is bound to $R^3$;

$R^a$ and $R^4$, together with the atom or atoms to which they are attached, are combined to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^b$ is independently, at each occurrence, —H, -D, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$, —$NR^5C(O)R^6$, heterocycle, aryl, heteroaryl, —$(CH_2)_nOH$, —$C_1$-$C_6$alkyl, —$CF_3$, —$CHF_2$, or —$CH_2F$;

$R^3$ is independently —H, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, spiroheterocycle, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN; and n is independently, at each occurrence, 0, 1, 2, 3, 4, 5, 6, 7, 8, 9, or 10.

One aspect of the disclosure related to compounds of Formula I-V2:

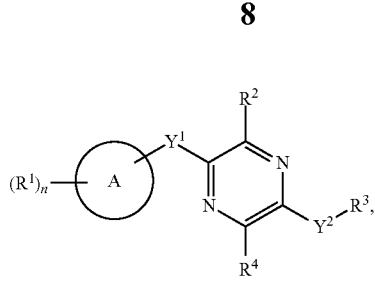

I-V2 and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —$S(O)_2$—, —$S(O)_2$—NH—, —C(=$CH_2$)—, —CH—, or —S(O)—;

$Y^2$ is —$NR^a$—, wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^b$ is independently, at each occurrence, —H, -D, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^4$ is independently —H, -D, —C$_1$-C$_6$alkyl, —C$_1$-C$_6$haloalkyl, —C$_1$-C$_6$hydroxyalkyl, —CF$_2$OH, —CHFOH, —NH—NHR$^5$, —NH—OR$^5$, —O—NR$^5$R$^6$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN; and n is independently, at each occurrence, 0, 1, 2, 3, 4, 5, 6, 7, 8, 9, or 10.

One aspect of the disclosure relates to compounds of Formula I-W:

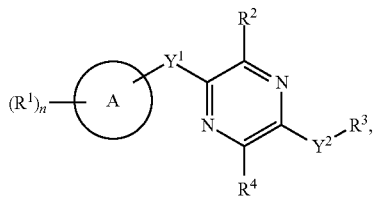

I-W and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

Y$^1$ is —S—, a direct bond, —NH—, —S(O)$_2$—, —S(O)$_2$—NH—, —C(=CH$_2$)—, —CH—, or —S(O)—;

Y$^2$ is —NR$^a$—, —(CR$^a_2$)$_m$—, —C(O)—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the pyrazine ring and the bond on the right side of the Y$^2$ moiety, as drawn, is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is independently —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, —C$_1$-C$_6$alkyl, 3- to 12-membered heterocyclyl, or —(CH$_2$)$_n$-aryl, wherein each alkyl or cycloalkyl is optionally substituted with one or more —NH$_2$, or wherein 2 R$^a$, together with the carbon atom to which they are both attached, can combine to form a 3- to 8-membered cycloalkyl;

R$^b$ is independently, at each occurrence, —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is independently —H, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$—R$^b$, wherein each alkyl, spiroheterocycle, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

R$^4$ is independently —H, -D, —C$_1$-C$_6$alkyl, —C$_1$-C$_6$haloalkyl, —C$_1$-C$_6$hydroxyalkyl —CF$_2$OH, —CHFOH—NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-X:

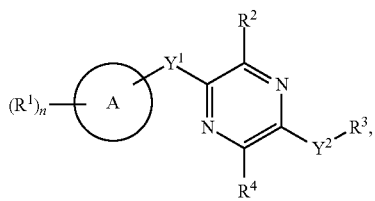

I-X and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

Y$^1$ is —S— or a direct bond;

Y$^2$ is —NR$^a$—, —(CR$^a{}_2$)$_m$—, —C(O)—, —C(R$^a$)$_2$NH—, —(CR$^a{}_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the pyrazine ring and the bond on the right side of the Y$^2$ moiety, as drawn, is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is independently —OR$^b$, —CN, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is independently —H, —C$_1$-C$_6$alkyl, or a 3- to 12-membered monocyclic or polycyclic heterocycle, wherein each alkyl or heterocycle is optionally substituted with one or more —C$_1$-C$_6$alkyl, —OH, or —NH$_2$; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, or —NH$_2$;

R$^4$ is independently —H, -D, —C$_1$-C$_6$alkyl, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl or heteroaryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-Y:

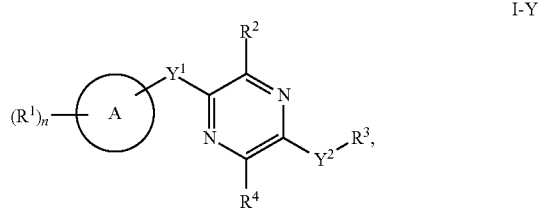

I-Y and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_nOH$, —$C_1$-$C_6$alkyl, —$CF_3$, —$CHF_2$, or —$CH_2F$;

$R^3$ is independently —H, —$C_1$-$C_6$alkyl, a 3- to 12-membered monocyclic or polycyclic heterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$;

$R^4$ is independently —H, -D, —$C_1$-$C_6$alkyl, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —$NHS(O)_2NHR^5$, —$S(O)_2OH$, —$C(O)OR^5$, —$NH(CH_2)_nOH$, —$C(O)NH(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, halogen, or oxo; wherein each aryl or heteroaryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

One aspect of the disclosure relates to compounds of Formula I-Z:

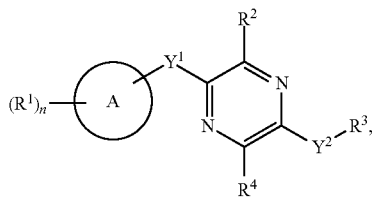

I-Z and pharmaceutically acceptable salts, prodrugs, solvates, hydrates, tautomers, or isomers thereof, wherein:

A is a 5- to 12-membered monocyclic or polycyclic cycloalkyl, heterocycloalkyl, aryl, or heteroaryl;

$Y^1$ is —S—, a direct bond, —NH—, —S(O)$_2$—, —S(O)$_2$—NH—, —C(=CH$_2$)—, —CH—, or —S(O)—;

$Y^2$ is —NR$^a$—, —(CR$^a{}_2$)$_m$—, —C(R$^a$)$_2$NH—, —(CR$^a{}_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —OC(O)N(R$^a$)—, —N(R$^a$)C(O)O—, —C(O)N(R$^a$)O—, —N(R$^a$)C(S)—, or —C(S)N(R$^a$)—; where in the bond on the left side of $Y^2$, as drawn, is bound to the pyrazine ring and the bond on the right side of the $Y^2$ moiety, as drawn, is bound to $R^3$;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ is independently —OR$^b$, —NH$_2$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

$R^a$ is independently, at each occurrence —OH, —C$_3$-C$_8$cycloalkyl, or —C$_1$-C$_6$alkyl, wherein each alkyl or cycloalkyl is optionally substituted with one or more —NH$_2$, wherein 2R$^a$, together with the carbon atom to which they are both attached, can combine to form a 3- to 8-membered cycloalkyl;

$R^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

$R^3$ is independently —H, —C$_1$-C$_6$alkyl, a 3- to 12-membered monocyclic or polycyclic heterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

$R^4$ is independently —C$_1$-C$_6$alkyl, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl or heteroaryl is optionally substituted with one or more —OH, —NH$_2$, or halogen;

$R^a$ and $R^4$, together with the atom or atoms to which they are attached, are combined to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

$R^5$ and $R^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Another aspect of the disclosure relates to methods of treating a disease associated with SHP2 modulation in a subject in need thereof, comprising administering to the subject an effective amount of one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof).

Another aspect of the disclosure relates to methods of inhibiting SHP2. The method comprises administering to a patient in need thereof, an effective amount of one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof).

Another aspect of the disclosure is directed to pharmaceutical compositions comprising one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), and a pharmaceutically acceptable carrier. The pharmaceutically acceptable carrier can further comprise an excipient, diluent, or surfactant. The pharmaceutical composition can be effective for treating a disease associated with SHP2 modulation in a subject in need thereof.

Another aspect of the disclosure relates to methods of treating a disease associated with SHP2 modulation in a subject in need thereof, comprising administering to the subject an effective amount of a pharmaceutical composition comprising one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof).

Another aspect of the disclosure relates to methods of inhibiting SHP2 comprising administering to a patient in need thereof, an effective amount of a pharmaceutical composition comprising one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof).

Another aspect of the disclosure relates to one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), for use in treating or preventing a disease associated with SHP2 modulation. One aspect of the disclosure relates to pharmaceutical compositions comprising one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), and a pharmaceutically acceptable carrier, for use in treating of preventing a disease associated with SHP2 modulation.

Another aspect of the disclosure relates to the use of one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), in the manufacture of a medicament for treating or preventing a disease associated with SHP2 modulation. Another aspect of the disclosure relates to the use of pharmaceutical compositions comprising one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), and a pharmaceutically acceptable carrier, in the manufacture of a medicament for treating or preventing a disease associated with SHP2 modulation.

Another aspect of the disclosure relates to one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), for use as a medicament. Another aspect of the disclosure relates to pharmaceutical compositions comprising one or more compounds disclosed herein (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), for use as a medicament. In some embodiments, the medicament is used for treating or preventing a disease associated with SHP2 modulation.

The present disclosure also provides compounds and pharmaceutical compositions that are useful in inhibiting SHP2.

DETAILED DESCRIPTION OF THE DISCLOSURE

In a first aspect, compounds of Formula I are described:

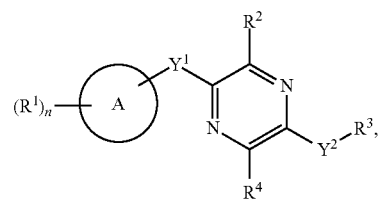

I wherein A, $R^1$, $R^2$, $R^3$, $R^4$, $Y^1$, $Y^2$, and n are described as above.

In another aspect, compounds of the Formula II are described:

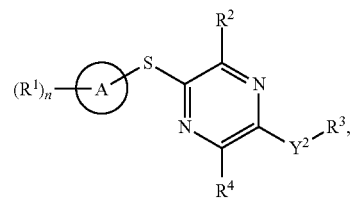

II wherein A, $R^1$, $R^2$, $R^3$, $R^4$, $Y^2$, and n are described as above.

In another aspect, compounds of the Formula III are described:

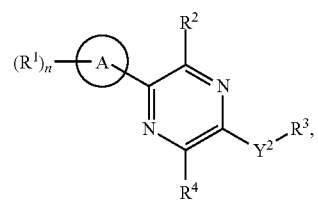

III wherein A, $R^1$, $R^2$, $R^3$, $R^4$, $Y^2$, and n are described as above.

One aspect of the disclosure relates to compounds of Formula I-V1:

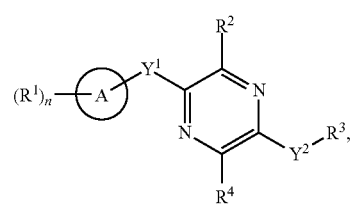

I-V1 wherein A, $R^1$, $R^3$, $R^4$, $Y^1$, $Y^2$, and n are described as above.

One aspect of the disclosure relates to compounds of Formula I-V2:

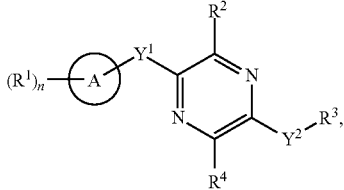

I-V2 wherein A, $R^1$, $R^3$, $R^4$, $Y^1$, $Y^2$, and n are described as above.

One aspect of the disclosure relates to compounds of Formula I-W:

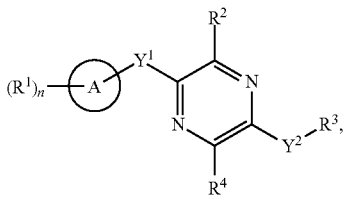

I-W wherein A, $R^1$, $R^2$, $R^3$, $R^4$, $Y^1$, $Y^2$, and n are described as above.

One aspect of the disclosure relates to compounds of Formula I-X:

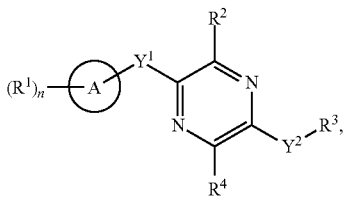

I-X wherein A, $R^1$, $R^2$, $R^3$, $R^4$, $Y^1$, $Y^2$, and n are described as above.

One aspect of the disclosure relates to compounds of Formula I-Y:

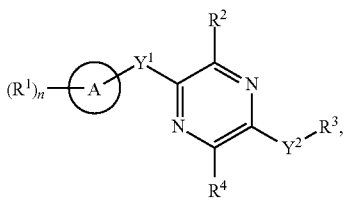

I-Y wherein A, $R^1$, $R^2$, $R^3$, $R^4$, $Y^1$, $Y^2$, and n are described as above.

One aspect of the disclosure relates to compounds of Formula I-Z:

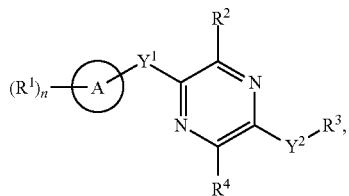

I-Z wherein A, $R^1$, $R^2$, $R^3$, $R^4$, $Y^1$, $Y^2$, and n are described as above.

The details of the disclosure are set forth in the accompanying description below. Although methods and materials similar or equivalent to those described herein can be used in the practice or testing of the present disclosure, illustrative methods and materials are now described. Other features, objects, and advantages of the disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this disclosure belongs. All patents and publications cited in this specification are incorporated herein by reference in their entireties.

Each embodiment described herein may be taken alone or in combination with any one or more other embodiments.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bonded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted.

Unless otherwise specifically defined, "heteroaryl" means a monovalent or multivalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also means a bicyclic heteroaromatic group wherein the heteroatom is selected from N, S, P, and O. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, benzo[d]imidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, 1-methyl-1H-indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, isoindolin-1-one, indolin-2-one, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, 2-methylbenzo[d]oxazolyl, 1,2,3,4-tetrahydropyrrolo[1,2-a]pyrimidyl, 2,3-dihydrobenzofuranyl, benzooxazolyl, benzoisoxazolyl, benzo[d]isoxazolyl, benzo[d]oxazolyl, furo[2,3-b]pyridinyl, benzothiophenyl, 1,5-naphthyridinyl, furo[3,2-b]pyridinyl, [1,2,4]triazolo[1,5-a]pyridinyl, benzo[1,2,3]triazolyl, 1-methyl-1H-benzo[d][1,2,3]triazolyl, imidazo[1,2-a]pyrimidinyl, [1,2,4]triazolo[4,3-b]pyridazinyl, quinoxalinyl, benzo[c][1,2,5]thiadiazolyl, benzo[c][1,2,5]oxadiazolyl, 1,3-dihydro-2H-benzo[d]imidazol-2-one, 3,4-dihydro-2H-pyrazolo[1,5-b][1,2]oxazinyl, 3,4-dihydro-2H-benzo[b][1,4]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, benzo[d][1,3]dioxolyl, pyrazolo[1,5-a]pyridinyl, and derivatives thereof.

"Alkyl" refers to a straight or branched chain saturated hydrocarbon. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon-carbon double bond and which may be straight or branched having about 2 to about 6 carbon atoms in the chain. Certain alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon-carbon triple bond and which may be straight or branched having about 2 to about 6 carbon atoms in the chain. Certain alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

In some embodiments, the terms "heterocyclyl" or "heterocycloalkyl" or "heterocycle" refer to monocyclic or polycyclic 3 to 24-membered rings containing carbon and heteroatoms selected from oxygen, phosphorus, nitrogen, and sulfur and wherein there are no delocalized π electrons (aromaticity) shared among the ring carbon or heteroatoms. Heterocyclyl rings include, but are not limited to, oxetanyl, azetidinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocycloalkyl ring can also be fused or bridged, e.g., can be a bicyclic ring.

In some embodiments "heterocyclyl" or "heterocycloalkyl" or "heterocycle" is a saturated, partially saturated or unsaturated, mono or bicyclic ring containing 3-24 atoms of which at least one atom is chosen from nitrogen, sulfur or oxygen, which may, unless otherwise specified, be carbon or nitrogen linked, wherein a —CH$_2$— group can optionally be replaced by a —C(O)— or a ring sulfur atom may be optionally oxidised to form the S-oxides. "Heterocyclyl" can be a saturated, partially saturated or unsaturated, mono or bicyclic ring containing 5 or 6 atoms of which at least one atom is chosen from nitrogen, sulfur or oxygen, which may, unless otherwise specified, be carbon or nitrogen linked, wherein a —CH$_2$— group can optionally be replaced by a —C(O)— or a ring sulfur atom may be optionally oxidised to form S-oxide(s). Non-limiting examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydro thienyl, 2,4-dioxoimidazolidinyl, 2-oxo-1,3,4-(4-triazolinyl), 2-oxazolidinonyl, 5,6-dihydro uracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

As used herein, the term "halo" or "halogen" means a fluoro, chloro, bromo, or iodo group.

The term "carbonyl" refers to a functional group comprising a carbon atom double-bonded to an oxygen atom. It can be abbreviated herein as "oxo," as C(O), or as C=O.

"Spirocycle" or "spirocyclic" means carbogenic bicyclic ring systems with both rings connected through a single atom. The ring can be different in size and nature, or identical in size and nature. Examples include spiropentane, spirohexane, spiroheptane, spirooctane, spirononane, or spirodecane. One or both of the rings in a spirocycle can be fused to another carbocyclic, heterocyclic, aromatic, or heteroaromatic ring. One or more of the carbon atoms in the spirocycle can be substituted with a heteroatom (e.g., O, N, S, or P). A $C_5$-$C_{12}$ spirocycle is a spirocycle containing between 5 and 12 carbon atoms. One or more of the carbon atoms can be substituted with a heteroatom.

The term "spirocyclic heterocycle," "spiroheterocyclyl," or "spiroheterocycle" is understood to mean a spirocycle wherein at least one of the rings is a heterocycle (e.g., at least one of the rings is furanyl, morpholinyl, or piperadinyl). A spirocyclic heterocycle can contain between 5 and 12 atoms, at least one of which is a heteroatom selected from N, O, S and P.

The disclosure also includes pharmaceutical compositions comprising an effective amount of one or more disclosed compounds and a pharmaceutically acceptable carrier. As used herein "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, surfactant, or emulsifier that has been approved by the United States Food and Drug Administration as being acceptable for use in humans or domestic animals.

The disclosure includes pharmaceutically acceptable salts of the compounds described herein. Representative "pharmaceutically acceptable salts" include, but are not limited to, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

"Pharmaceutically acceptable salt" also includes both acid and base addition salts. "Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. For example, inorganic salts include, but are not limited to, ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the disclosure.

For example, compounds of the present disclosure can exist in tautomeric form. In some embodiments of the compounds disclosed herein (e.g., compounds of Formula I, II, III, I-V1, I-V2, I-W, I-X, I-Y, or I-Z), $R^2$ can be oxygen and tautomers of the compounds can exist in equilibrium:

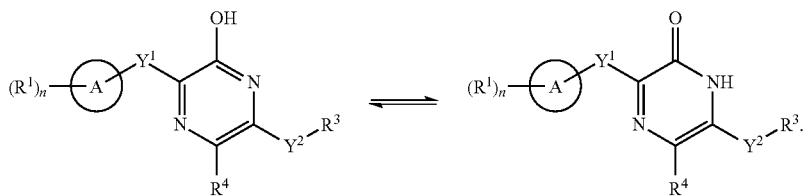

The disclosure includes prodrugs of the compounds described herein. The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The disclosure includes solvates of the compounds described herein. The term "solvate" refers to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The disclosure includes isomers of the compounds described herein. The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of the present disclosure may have one or more asymmetric carbon atom and may occur as racemates, racemic mixtures and as individual enantiomers or diastereomers.

The term "stereoisomers" refers to the set of compounds which have the same number and type of atoms and share the same bond connectivity between those atoms, but differ in three dimensional structure. The term "stereoisomer" refers to any member of this set of compounds. For instance, a stereoisomer may be an enantiomer or a diastereomer. The disclosure includes stereoisomers of the compounds described herein.

In addition, the present disclosure embraces all geometric and positional isomers. For example, if a compound of the present disclosure incorporates a double bond or a fused ring, both the cis- and trans-forms, as well as mixtures, are embraced within the scope of the disclosure. If the compound contains a double bond, the substituent may be in the E or Z configuration. If the compound contains a disubstituted cycloalkyl, the cycloalkyl substituent may have a cis or trans configuration.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers. The disclosure includes enantiomers of the compounds described herein. Each compound herein disclosed includes all the enantiomers that conform to the general structure of the compound. The compounds may be in a racemic or enantiomerically pure form, or any other form in terms of stereochemistry. In some embodiments the compounds are the (S)-enantiomer. In other embodiments the compounds are the (R)-enantiomer. In yet other embodiments, the compounds are the (+) or (−) enantiomers In some embodiments, compounds and compositions of the disclosure may be enriched to provide predominantly one enantiomer of a compound described herein. An enantiomerically enriched mixture may comprise, for example, at least 60 mol percent of one enantiomer, or more preferably at least 75, 80, 85, 90, 95, 96, 97, 98, 99, 99.5 or even 100 mol percent. In some embodiments, the compound described herein enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2 mol percent of the second enantiomer.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers. The disclosure includes diastereomers of the compounds described herein.

In some embodiments, the compounds and compositions of the disclosure may be enriched to provide predominantly one diastereomer of a compound disclosed herein. A diastereomerically enriched mixture may comprise, for example, at least 60 mol percent of one diastereomer, or more preferably at least 75, 99, 95, 96, 97, 98, 99, or even 100 mol percent.

The compounds described herein further include all pharmaceutically acceptable isotopically labeled compounds. An "isotopically" or "radio-labeled" compound is a compound where one or more atoms are replaced or substituted by an atom having an atomic mass or mass number different from the atomic mass or mass number typically found in nature (i.e., naturally occurring). For example, in some embodiments, in the compounds described herein hydrogen atoms are replaced or substituted by one or more deuterium or tritium. Certain isotopically labeled compounds of this disclosure, for example, those incorporating a radioactive isotope, are useful in drug and/or substrate tissue distribution studies. The radioactive isotopes tritium, i.e., $^3H$, and carbon 14, i.e., $^{14}C$, are particularly useful for this purpose in view of their ease of incorporation and ready means of detection. Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances. Suitable isotopes that may be incorporated in compounds described herein include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I, and $^{131}$I. Substitution with positron emitting isotopes, such as $^{11}$C, $^{18}$F, $^{15}$O, and $^{13}$N, can be useful in Positron Emission Topography (PET) studies.

An "effective amount" when used in connection with a compound is an amount effective for treating or preventing a disease in a subject as described herein.

The term "carrier," as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "prevent" or "preventing" with regard to a subject refers to keeping a disease or disorder from afflicting the subject. Preventing includes prophylactic treatment. For instance, preventing can include administering to the subject one or more compounds disclosed herein before a subject is afflicted with a disease and the administration will keep the subject from being afflicted with the disease.

The term "disorder" is used in this disclosure to mean, and is used interchangeably with, the terms disease, condition, or illness, unless otherwise indicated.

The term "administer," "administering," or "administration" as used in this disclosure refers to either directly administering one or more disclosed compounds or a pharmaceutically acceptable salt of one or more disclosed compounds or a composition comprising one or more disclosed compounds to a subject, or administering a prodrug derivative or analog of the compound or a pharmaceutically acceptable salt of the compound or composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

Compounds of the Disclosure

In one or more embodiments of the compounds of Formula I, the compound is of the Formula I-A:

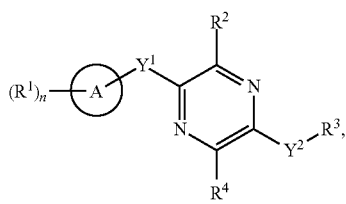

I-A and pharmaceutically acceptable salts, prodrugs, solvates, hydrates, tautomers, and isomers thereof, wherein:

A is aryl;

$Y^1$ is —S— or a direct bond;

$Y^2$ is —NR$^a$—, —(CR$^a_2$)$_m$—, —C(O)—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ is independently —OR$^b$, —CN, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

$R^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

$R^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^3$ is independently —C$_1$-C$_6$alkyl or a 3- to 12-membered monocyclic or polycyclic heterocycle, wherein each alkyl or heterocycle is optionally substituted with one or more —C$_1$-C$_6$alkyl, —OH, or —NH$_2$; or $R^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, or —NH$_2$;

$R^4$ is independently —H, -D, or —C$_1$-C$_6$alkyl, wherein each alkyl is optionally substituted with one or more —OH, —NH$_2$, halogen, or oxo; or $R^a$ and $R^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of the compounds of Formula I, the compound is of the Formula I-B:

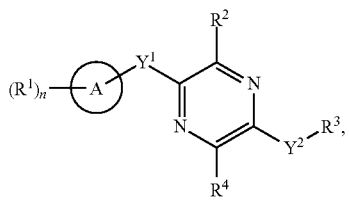

I-B and pharmaceutically acceptable salts, prodrugs, solvates, hydrates, tautomers, and isomers thereof, wherein:

A is heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of the compounds of the Formula I-W, the compound is of the Formula I-W1:

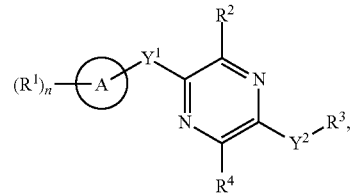

I-W1 and pharmaceutically acceptable salts, prodrugs, solvates, hydrates, tautomers, or isomers thereof, wherein:

A is heterocycloalkyl, aryl, or heteroaryl, wherein heterocycloalkyl, aryl, and heteroaryl are 5- to 12-membered monocyclic or 5- to 12-membered polycyclic;

$Y^1$ is —S— or a direct bond;

$Y^2$ is —$NR^a$—, —$(CR^a{}_2)_m$—, —C(O)—, —$C(R^a)_2$NH—, or —$(CR^a{}_2)_mO$—; where in the bond on the left side of $Y^2$, as drawn, is bound to the pyrazine ring and the bond on the right side of the $Y^2$ moiety, as drawn, is bound to $R^3$;

$R^1$ is independently, at each occurrence, —H, —$C_1$-$C_6$alkyl, —OH, —$OR^6$, halogen, —CN, —$NR^5R^6$, —$S(O)_2R^5$, —$NR^5C(O)R^6$, monocyclic or polycyclic heterocyclyl, spiroheterocyclyl, heteroaryl, or oxo, wherein each alkyl, heterocyclyl, spiroheterocyclyl, or heteroaryl is optionally substituted with one or more —OH, halogen, oxo, =O, —CN, —$R^5$, —$OR^5$, —$NR^5R^6$, or —$S(O)_2R^5$;

$R^2$ is independently —$OR^b$, —CN, —$C_1$-$C_6$alkyl, —$C_2$-$C_6$alkenyl, halogen, —$C(O)OR^b$, —$C_3$-$C_8$cycloalkyl, or aryl; wherein each alkyl, cycloalkyl, or aryl is optionally substituted with one or more —OH, halogen, —$OR^5$, or —$NR^5R^6$;

$R^a$ is independently, at each occurrence, —H or —$C_1$-$C_6$alkyl, wherein each alkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —$C_1$-$C_6$alkyl, —$C_3$-$C_8$cycloalkyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, —$(CH_2)_n$-aryl, heterocyclyl, or heteroaryl is optionally substituted with one or more —OH, halogen, —$R^5$, —$OR^5$, —$NR^5R^6$, —$NR^5C(O)R^6$, heterocycle, aryl, heteroaryl, —$(CH_2)_nOH$, —$CF_3$, —$CHF_2$, or —$CH_2F$;

$R^3$ is independently —H, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$-$R^b$, wherein each alkyl, spiroheterocycle, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^4$ is independently —H, —$C_1$-$C_6$alkyl, —$C_1$-$C_6$haloalkyl, —$C_1$-$C_6$hydroxyalkyl —$CF_2OH$, —CHFOH—$NHR^5$, —$OR^5$, —$NHC(O)R^5$, —NHC(O)$NHR^5$, —$C(O)OR^5$, —$NH(CH_2)_nOH$, —$C(O)NH(CH_2)_nOH$, —$C(O)NH(CH_2)_nR^b$, —$C(O)R^b$, $NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^5$ and $R^6$ are independently, at each occurrence, —H, —$C_1$-$C_6$alkyl, —$C_3$-$C_8$cycloalkyl, a monocyclic or polycyclic 3- to 12-membered heterocycle, —$OR^7$, halogen, —$NR^7R^8$, or —CN;

$R^7$ and $R^8$ are independently, at each occurrence, —H, —$C_1$-$C_6$alkyl, —$C_3$-$C_8$cycloalkyl, —$OR^b$, or a monocyclic or polycyclic 3- to 12-membered heterocycle, wherein each alkyl, cycloalkyl, or heterocycle is optionally substituted with one or more —OH, —$NH_2$, or —CN;

m is independently, at each occurrence, 1, 2, 3, 4, 5 or 6; and n is independently, at each occurrence, 0, 1, 2, 3, 4, 5, 6, 7, 8, 9, or 10.

In one or more embodiments of the compounds of Formula I-W1, $Y^2$ is —$(CR^a{}_2)_m$—. In one or more embodiments of the compounds of Formula I-W1, $Y^2$ is —$NR^a$—.

In one or more embodiments of the compounds of Formula I-W or I-W1, the compound is of the Formula I-W2:

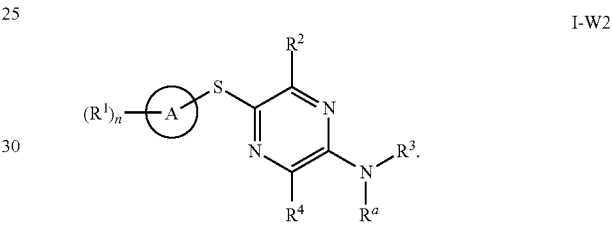

I-W2

In one or more embodiments of Formula I-W2, A is heterocycloalkyl. In one or more embodiments of Formula I-W2, A is aryl. In one or more embodiments of Formula I-W2, A is heteroaryl. In one or more embodiments of Formula I-W2, A is pyridinyl.

In one or more embodiments of Formula I-W2, n is independently, at each occurrence, 0, 1, 2, or 3.

In one or more embodiments of Formula I-W2, $R^1$ is independently, at each occurrence, optionally substituted —$C_1$-$C_6$alkyl, halogen, or —$NR^5R^6$. In certain such embodiments, $R^5$ and $R^6$ are both —H. In one or more embodiments of Formula I-W2, $R^1$ is independently, at each occurrence, methyl, fluoro, chloro, or —$NH_2$.

In one or more embodiments of Formula I-W2, $R^2$ is $OR^b$. In certain such embodiments, $R^b$ is H or optionally substituted —$C_1$-$C_6$alkyl. In one or more embodiments of Formula I-W2, $R^2$ is —CN. In one or more embodiments of Formula I-W2, $R^2$ is optionally substituted —$C_1$-$C_6$alkyl. In certain such embodiments, $R^2$ is methyl.

In one or more embodiments of Formula I-W2, $R^4$ is —$C_1$-$C_6$alkyl, which is optionally substituted with one or more —OH, —$NH_2$, halogen, or oxo. In one or more embodiments of Formula I-W2, $R^4$ is —$C_1$-$C_6$alkyl, which is substituted with one or more —OH. In certain such embodiments, $R^4$ is —$CH_2$—OH. In one or more embodiments of Formula I-W2, $R^4$ is —H. In one or more embodiments of Formula I-W2, $R^4$ is —CN. In one or more embodiments of Formula I-W2, $R^4$ is —$C_1$-$C_6$haloalkyl or —$C_1$-$C_6$hydroxyalkyl. In one or more embodiments of Formula I-W2, $R^4$ is —$CF_2OH$ or —CHFOH.

In one or more embodiments of Formula I-W2, $R^3$ is —$C_1$-$C_6$alkyl, which is optionally substituted with one or more —$C_1$-$C_6$alkyl, —OH, —$NH_2$, —$OR^b$, —$NHR^b$, —(CH$_2$)$_n$OH, heterocyclyl, or spiroheterocyclyl. In one or more embodiments of Formula I-W2, R$^3$ is —C$_1$-C$_6$alkyl, which is optionally substituted with one or more —C$_1$-C$_6$alkyl, —OH, —NH$_2$, —OR$^b$, —NHR$^b$, or —(CH$_2$)$_n$OH.

In one or more embodiments of Formula I-W2, R$^3$ is an optionally substituted 3- to 12-membered monocyclic or polycyclic heterocycle. In certain such embodiments, R$^a$ is —H. In one or more embodiments of Formula I-W2, R$^3$ is an optionally substituted 3- to 12-membered monocyclic heterocycle. In certain such embodiments, R$^a$ is —H. In one or more embodiments of Formula I-W2, R$^3$ is an optionally substituted 3- to 12-membered polycyclic heterocycle. In certain such embodiments, R$^a$ is —H. In one or more embodiments of Formula I-W2, R$^3$ is an optionally substituted 5- to 12-membered polycyclic spiroheterocycle. In certain such embodiments, R$^a$ is —H.

In one or more embodiments of Formula I-W2, R$^3$ and R$^a$ together with the atom to which they are attached combine to form a 3- to 12-membered monocyclic heterocycle, which is optionally substituted with one or more —C$_1$-C$_6$alkyl, —OH, —NH$_2$, halogen, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

In one or more embodiments of Formula I-W2, R$^3$ and R$^a$ together with the atoms to which they are attached combine to form a 3- to 12-membered polycyclic heterocycle, which is optionally substituted with one or more —C$_1$-C$_6$alkyl, —OH, —NH$_2$, halogen, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

In one or more embodiments of Formula I-W2, R$^3$ and R$^a$ together with the atoms to which they are attached combine to form a 5- to 12-membered spiroheterocycle, which is optionally substituted with one or more —C$_1$-C$_6$alkyl, —OH, —NH$_2$, halogen, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

In one or more embodiments of Formula I-W2, R$^3$ and R$^a$ together with the atoms to which they are attached combine to form a 10- to 12-membered spiroheterocycle, which is optionally substituted with one or more —C$_1$-C$_6$alkyl, —OH, —NH$_2$, halogen, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

In one or more embodiments of Formula I-W2, R$^a$ and R$^4$ together with the atom to which they are attached combine to form an optionally substituted monocyclic or polycyclic 3- to 12-membered cycloalkyl. In certain such embodiments, the cycloalkyl is substituted with oxo.

In one or more embodiments of Formula I-W2, R$^a$ and R$^4$ together with the atom to which they are attached combine to form an optionally substituted monocyclic or polycyclic 3- to 12-membered heterocycle. In certain such embodiments, the heterocycle is substituted with oxo.

In one or more embodiments of the compounds of the Formula I-W or I-W1, the compound is of the Formula I-W3:

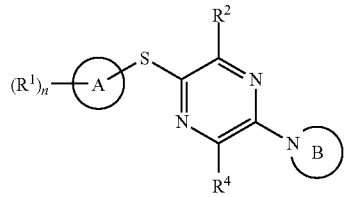

I-W3 wherein:

B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —C$_1$-C$_6$alkyl, halogen, —OH, —OR$^b$, —(CH$_2$)$_n$OH, —CONHR$^b$, —(CH$_2$)$_n$NH$_2$, —NHR$^b$, heteroaryl, heterocyclyl, —CF$_3$, —CHF$_2$, —CH$_2$F, =O, or —NH$_2$. In certain such embodiments, the heterocycle or spiroheterocycle is optionally substituted with one or more —C$_1$-C$_6$alkyl, halogen, —OH, —OR$^b$, —CONHR$^b$, heteroaryl, —CF$_3$, —CHF$_2$, —CH$_2$F, or —NH$_2$.

In one or more embodiments of Formula I-W3, A is heterocycloalkyl. In one or more embodiments of Formula I-W3, A is aryl. In one or more embodiments of Formula I-W3, A is heteroaryl. In one or more embodiments of Formula I-W3, A is pyridinyl.

In one or more embodiments of Formula I-W3, n is independently, at each occurrence, 0, 1, 2, or 3.

In one or more embodiments of Formula I-W3, R$^1$ is independently, at each occurrence, —C$_1$-C$_6$alkyl, halogen, or —NR$^5$R$^6$. In certain such embodiments, R$^5$ and R$^6$ are both —H. In one or more embodiments of Formula I-W3, R$^1$ is independently, at each occurrence, methyl, fluoro, chloro, or —NH$_2$.

In one or more embodiments of Formula I-W3, R$^2$ is OR$^b$. In certain such embodiments, R$^b$ is H or optionally substituted —C$_1$-C$_6$alkyl. In one or more embodiments of Formula I-W3, R$^2$ is —CN. In one or more embodiments of Formula I-W3, R$^2$ is optionally substituted —C$_1$-C$_6$alkyl. In certain such embodiments, R$^2$ is methyl.

In one or more embodiments of Formula I-W3, R$^4$ is —C$_1$-C$_6$alkyl, which is optionally substituted with one or more —OH, —NH$_2$, halogen, or oxo. In one or more embodiments of Formula I-W3, R$^4$ is optionally substituted —C$_1$-C$_6$alkyl, which is substituted with one or more —OH. In certain such embodiments, R$^4$ is —CH$_2$—OH. In one or more embodiments of Formula I-W3, R$^4$ is —H. In one or more embodiments of Formula I-W3, R$^4$ is —CN. In one or more embodiments of Formula I-W3, R$^4$ is —C$_1$-C$_6$haloalkyl or —C$_1$-C$_6$hydroxyalkyl. In one or more embodiments of Formula I-W3, R$^4$ is —CF$_2$OH or —CHFOH.

In one or more embodiments of the compounds of Formula I-W or I-W1, the compound is of the Formula I-W4:

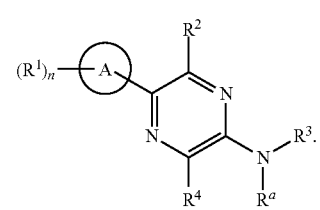

I-W4

In one or more embodiments of Formula I-W4, A is heterocycloalkyl. In one or more embodiments of Formula I-W4, A is aryl. In one or more embodiments of Formula I-W4, A is heteroaryl. In one or more embodiments of Formula I-W4, A is pyridinyl.

In one or more embodiments of Formula I-W4, n is independently, at each occurrence, 0, 1, 2, or 3.

In one or more embodiments of Formula I-W4, R$^1$ is independently, at each occurrence, —C$_1$-C$_6$alkyl, halogen, or —NR$^5$R$^6$. In certain such embodiments, R$^5$ and R$^6$ are both —H. In one or more embodiments of Formula I-W4, $R^1$ is independently, at each occurrence, methyl, fluoro, chloro, or —$NH_2$.

In one or more embodiments of Formula I-W4, $R^2$ is $OR^b$. In certain such embodiments, $R^b$ is H or optionally substituted —$C_1$-$C_6$alkyl. In one or more embodiments of Formula I-W4, $R^2$ is —CN. In one or more embodiments of Formula I-W4, $R^2$ is optionally substituted —$C_1$-$C_6$alkyl. In certain such embodiments, $R^2$ is methyl.

In one or more embodiments of Formula I-W4, $R^4$ is —$C_1$-$C_6$alkyl, which is optionally substituted with one or more —OH, —$NH_2$, halogen, or oxo. In one or more embodiments of Formula I-W4, $R^4$ is —$C_1$-$C_6$alkyl, which is substituted with one or more —OH. In certain such embodiments, $R^4$ is —$CH_2$—OH. In one or more embodiments of Formula I-W4, $R^4$ is —H. In one or more embodiments of Formula I-W4, $R^4$ is —CN. In one or more embodiments of Formula I-W4, $R^4$ is —$C_1$-$C_6$haloalkyl or —$C_1$-$C_6$hydroxyalkyl. In one or more embodiments of Formula I-W4, $R^4$ is —$CF_2$OH or —CHFOH.

In one or more embodiments of Formula I-W4, $R^3$ is —$C_1$-$C_6$alkyl, which is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl. In one or more embodiments of Formula I-W4, $R^3$ is —$C_1$-$C_6$alkyl, which is optionally substituted with one or more —$C_1$-$C_6$alkyl, —OH, —$NH_2$, —$OR^b$, —$NHR^b$, or —$(CH_2)_n$OH.

In one or more embodiments of Formula I-W4, $R^3$ is an optionally substituted 3- to 12-membered monocyclic or polycyclic heterocycle. In certain such embodiments, $R^a$ is —H. In one or more embodiments of Formula I-W4, $R^3$ is an optionally substituted 3- to 12-membered monocyclic heterocycle. In certain such embodiments, $R^a$ is —H. In one or more embodiments of Formula I-W4, $R^3$ is an optionally substituted 3- to 12-membered polycyclic heterocycle. In certain such embodiments, $R^a$ is —H. In one or more embodiments of Formula I-W4, $R^3$ is an optionally substituted 5- to 12-membered polycyclic spiroheterocycle. In certain such embodiments, $R^a$ is —H.

In one or more embodiments of Formula I-W4, $R^3$ and $R^a$ together with the atom to which they are attached combine to form a 3- to 12-membered monocyclic heterocycle, which is optionally substituted with one or more —$C_1$-$C_6$alkyl, —OH, —$NH_2$, halogen, heteroaryl, heterocyclyl, —$(CH_2)_n$$NH_2$, —$COOR^b$, —$CONHR^b$, —$CONH(CH_2)_n$$COOR^b$, —$NHCOOR^b$, —$CF_3$, —$CHF_2$, or —$CH_2$F.

In one or more embodiments of Formula I-W4, $R^3$ and $R^a$ together with the atoms to which they are attached combine to form a 3- to 12-membered polycyclic heterocycle, which is optionally substituted with one or more —$C_1$-$C_6$alkyl, —OH, —$NH_2$, halogen, heteroaryl, heterocyclyl, —$(CH_2)_n$$NH_2$, —$COOR^b$, —$CONHR^b$, —$CONH(CH_2)_n$$COOR^b$, —$NHCOOR^b$, —$CF_3$, —$CHF_2$, or —$CH_2$F.

In one or more embodiments of Formula I-W4, $R^3$ and $R^a$ together with the atoms to which they are attached combine to form a 5- to 12-membered spiroheterocycle, which is optionally substituted with one or more —$C_1$-$C_6$alkyl, —OH, —$NH_2$, halogen, heteroaryl, heterocyclyl, —$(CH_2)_n$$NH_2$, —$COOR^b$, —$CONHR^b$, —$CONH(CH_2)_n$$COOR^b$, —$NHCOOR^b$, —$CF_3$, —$CHF_2$, or —$CH_2$F.

In one or more embodiments of Formula I-W4, $R^3$ and $R^a$ together with the atoms to which they are attached combine to form a 10- to 12-membered spiroheterocycle, which is optionally substituted with one or more —$C_1$-$C_6$alkyl, —OH, —$NH_2$, halogen, heteroaryl, heterocyclyl, —$(CH_2)_n$$NH_2$, —$COOR^b$, —$CONHR^b$, —$CONH(CH_2)_n$$COOR^b$, —$NHCOOR^b$, —$CF_3$, —$CHF_2$, or —$CH_2$F.

In one or more embodiments of Formula I-W4, $R^a$ and $R^4$ together with the atom to which they are attached combine to form an optionally substituted monocyclic or polycyclic 3- to 12-membered cycloalkyl. In certain such embodiments, the cycloalkyl is substituted with oxo.

In one or more embodiments of Formula I-W4, $R^a$ and $R^4$ together with the atom to which they are attached combine to form an optionally substituted monocyclic or polycyclic 3- to 12-membered heterocycle. In certain such embodiments, the heterocycle is substituted with oxo.

In one or more embodiments of the compounds of the Formula I-W or I-W1, the compound is of the Formula I-W5:

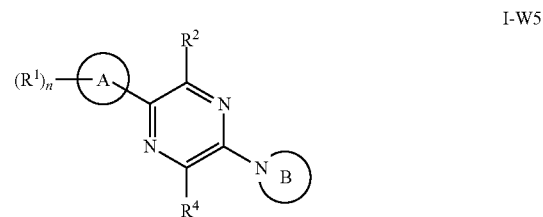

I-W5 wherein:

B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —$C_1$-$C_6$alkyl, halogen, —OH, —$OR^b$, —$(CH_2)_n$$NH_2$, —$(CH_2)_n$OH, —$CONHR^b$, —$NHR^b$, heteroaryl, heterocyclyl, —$CF_3$, —$CHF_2$, —$CH_2$F, =O, or —$NH_2$. In certain such embodiments, the heterocycle or spiroheterocycle is optionally substituted with one or more —$C_1$-$C_6$alkyl, halogen, —OH, —$OR^b$, —$CONHR^b$, heteroaryl, —$CF_3$, —$CHF_2$, —$CH_2$F, or —$NH_2$.

In one or more embodiments of Formula I-W5, A is heterocycloalkyl. In one or more embodiments of Formula I-W5, A is aryl. In one or more embodiments of Formula I-W5, A is heteroaryl. In one or more embodiments of Formula I-W5, A is pyridinyl.

In one or more embodiments of Formula I-W5, n is independently, at each occurrence, 0, 1, 2, or 3.

In one or more embodiments of Formula I-W5, $R^1$ is independently, at each occurrence, optionally substituted —$C_1$-$C_6$alkyl, halogen, or —$NR^5R^6$. In certain such embodiments, $R^5$ and $R^6$ are both —H. In one or more embodiments of Formula I-W5, $R^1$ is independently, at each occurrence, methyl, fluoro, chloro, or —$NH_2$.

In one or more embodiments of Formula I-W5, $R^2$ is $OR^b$. In certain such embodiments, $R^b$ is H or optionally substituted —$C_1$-$C_6$alkyl. In one or more embodiments of Formula I-W5, $R^2$ is —CN. In one or more embodiments of Formula I-W5, $R^2$ is optionally substituted —$C_1$-$C_6$alkyl. In certain such embodiments, $R^2$ is methyl.

In one or more embodiments of Formula I-W5, $R^4$ is —$C_1$-$C_6$alkyl, which is optionally substituted with one or more —OH, —$NH_2$, halogen, or oxo. In one or more embodiments of Formula I-W5, $R^4$ is —$C_1$-$C_6$alkyl, which is substituted with one or more —OH. In certain such embodiments, $R^4$ is —$CH_2$—OH. In one or more embodiments of Formula I-W5, $R^4$ is —H. In one or more embodiments of Formula I-W5, $R^4$ is —CN. In one or more embodiments of Formula I-W5, $R^4$ is —$C_1$-$C_6$haloalkyl or —$C_1$-$C_6$hydroxyalkyl. In one or more embodiments of Formula I-W5, $R^4$ is —$CF_2$OH or —CHFOH.

The present disclosure provides a compound of Formula I-W2 or I-W4 having one, two, three, four, or more of the following features:
a) A is heterocycloalkyl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) $R^3$ and $R^a$ together with the atom to which they are attached combine to form a 3- to 12-membered monocyclic or polycyclic heterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W2 or I-W4 having one, two, three, four, or more of the following features:
a) A is aryl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) $R^3$ and $R^a$ together with the atom to which they are attached combine to form a 3- to 12-membered monocyclic or polycyclic heterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W2 or I-W4 having one, two, three, four, or more of the following features:
a) A is heteroaryl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) $R^3$ and $R^a$ together with the atom to which they are attached combine to form a 3- to 12-membered monocyclic or polycyclic heterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W2 or I-W4 having one, two, three, four, or more of the following features:
a) A is pyridinyl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) $R^3$ and $R^a$ together with the atom to which they are attached combine to form a 3- to 12-membered monocyclic or polycyclic heterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W2 or I-W4 having one, two, three, four, or more of the following features:
a) A is heterocycloalkyl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) $R^3$ and $R^a$ together with the atom to which they are attached combine to form a 5- to 12-membered spiroheterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W2 or I-W4 having one, two, three, four, or more of the following features:
a) A is aryl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) $R^3$ and $R^a$ together with the atom to which they are attached combine to form a 5- to 12-membered spiroheterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W2 or I-W4 having one, two, three, four, or more of the following features:
a) A is heteroaryl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) $R^3$ and $R^a$ together with the atom to which they are attached combine to form a 5- to 12-membered spiroheterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W2 or I-W4 having one, two, three, four, or more of the following features:
a) A is pyridinyl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) $R^3$ and $R^a$ together with the atom to which they are attached combine to form a 5- to 12-membered spiroheterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W3 or I-W5 having one, two, three, four, or more of the following features:
a) A is heterocycloalkyl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) B is a 3- to 12-membered monocyclic or polycyclic heterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W3 or I-W5 having one, two, three, four, or more of the following features:
a) A is aryl;
b) n is independently, at each occurrence, 1 or 2;

c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) B is a 3- to 12-membered monocyclic or polycyclic heterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W3 or I-W5 having one, two, three, four, or more of the following features:
a) A is heteroaryl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) B is a 3- to 12-membered monocyclic or polycyclic heterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W3 or I-W5 having one, two, three, four, or more of the following features:
a) A is pyridinyl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) B is a 3- to 12-membered monocyclic or polycyclic heterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W3 or I-W5 having one, two, three, four, or more of the following features:
a) A is heterocycloalkyl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) B is a 5- to 12-membered spiroheterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W3 or I-W5 having one, two, three, four, or more of the following features:
a) A is aryl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) B is a 5- to 12-membered spiroheterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W3 or I-W5 having one, two, three, four, or more of the following features:
a) A is heteroaryl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) B is a 5- to 12-membered spiroheterocycle, which is optionally substituted with one or more —$C_1$-$C_6$alkyl, —OH, —$NH_2$, or halogen; and
f) $R^4$ is —$CH_2$—OH.

The present disclosure provides a compound of Formula I-W3 or I-W5 having one, two, three, four, or more of the following features:
a) A is pyridinyl;
b) n is independently, at each occurrence, 1 or 2;
c) $R^1$ is independently, at each occurrence, optionally substituted —$C_1$-$C_6$alkyl, halogen, —$OCH_3$ or —$NH_2$;
d) $R^2$ is optionally substituted —$C_1$-$C_6$alkyl, such as methyl;
e) B is a 5- to 12-membered spiroheterocycle, which is optionally substituted with one or more —$C_1$-$C_6$alkyl, —OH, —$NH_2$, or halogen; and
f) $R^4$ is —$CH_2$—OH.

In one or more embodiments of the compounds of Formula I-W, the compound is of Formula I-W6:

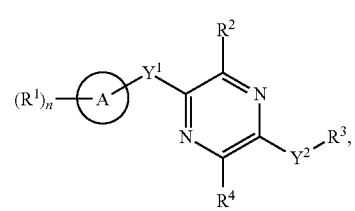

I-W6 and pharmaceutically acceptable salts, prodrugs, solvates, hydrates, tautomers, or isomers thereof, wherein:

A is a 5- to 12-membered monocyclic or polycyclic heteroaryl;

$Y^1$ is —S—;

$Y^2$ is —$NR^a$—; wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —$(CH_2)_n$$NH_2$, —$COOR^b$, —$CONHR^b$, —$CONH(CH_2)_n COOR^b$, —$NHCOOR^b$, —$CF_3$, —$CHF_2$, or —$CH_2F$;

$R^1$ is independently, at each occurrence, —H, —$C_1$-$C_6$alkyl, —OH, halogen, —$NO_2$, —CN, —$NR^5R^6$, —$SR^5$, —$C(O)R^5$, or —$CO_2R^5$;

$R^2$ is —$C_1$-$C_6$alkyl;

$R^b$ is independently, at each occurrence, —H or —$C_1$-$C_6$alkyl;

$R^4$ is —H, —$C_1$-$C_6$alkyl, —$C_1$-$C_6$haloalkyl, —$C_1$-$C_6$hydroxyalkyl, —$CF_2OH$, —CHFOH, —$C(O)NH(CH_2)_n$OH, —$C(O)NH(CH_2)_n R^b$, —$C(O)R^b$, —$C(O)NR^5R^6$, —OH, or —CN, wherein alkyl is optionally substituted with one or more —OH, —$NH_2$, halogen, or oxo; or $R^5$ and $R^6$ are each independently, at each occurrence, —H or —$C_1$-$C_6$alkyl; and n is independently, at each occurrence, 1, 2, 3, 4, 5, 6, 7, 8, 9, or 10.

In one or more embodiments of the compounds of Formula I-W, the compound is of Formula I-W7:

I-W7

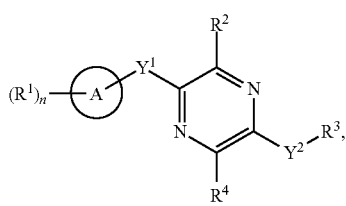

and pharmaceutically acceptable salts, prodrugs, solvates, hydrates, tautomers, or isomers thereof, wherein:

A is a 5- to 12-membered monocyclic or polycyclic heteroaryl;

$Y^1$ is a direct bond;

$Y^2$ is —$NR^a$—; wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —$(CH_2)_n$$NH_2$, —$COOR^b$, —$CONHR^b$, —$CONH(CH_2)_nCOOR^b$, —$NHCOOR^b$, —$CF_3$, —$CHF_2$, or —$CH_2F$;

$R^1$ is independently, at each occurrence, —H, —$C_1$-$C_6$alkyl, —OH, halogen, —$NO_2$, —CN, —$NR^5R^6$, —$SR^5$, —$C(O)R^5$, or —$CO_2R^5$;

$R^2$ is —$C_1$-$C_6$alkyl;

$R^b$ is independently, at each occurrence, —H or —$C_1$-$C_6$alkyl;

$R^4$ is —H, —$C_1$-$C_6$alkyl, —$C_1$-$C_6$haloalkyl, —$C_1$-$C_6$hydroxyalkyl, —$CF_2OH$, —CHFOH, —$C(O)NH(CH_2)_nOH$, —$C(O)NH(CH_2)_nR^b$, —$C(O)R^b$, —$C(O)NR^5R^6$, —OH, or —CN, wherein alkyl is optionally substituted with one or more —OH, —$NH_2$, halogen, or oxo; or $R^5$ and $R^6$ are each independently, at each occurrence, —H or —$C_1$-$C_6$alkyl; and n is independently, at each occurrence, 1, 2, 3, 4, 5, 6, 7, 8, 9, or 10.

In one or more embodiments of the compounds of Formula II, the compound is of the Formula II-A:

II-A

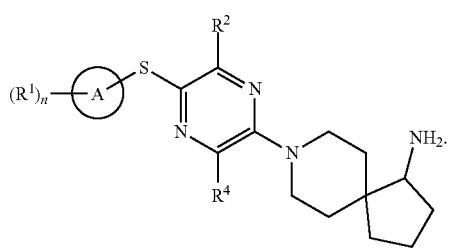

In one or more embodiments of the compounds of the Formula II-A, the compound is of the Formula II-A1:

II-A1

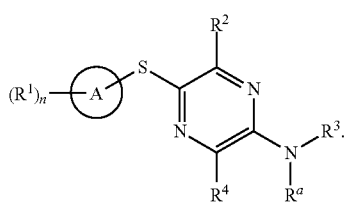

wherein:

B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —$C_1$-$C_6$alkyl, —OH, or —$NH_2$.

In one or more embodiments of the compounds of Formula II-A, the compound is of the Formula II-A2:

II-A2

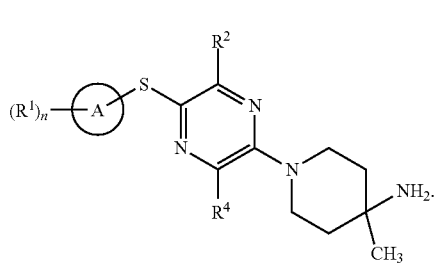

In one or more embodiments of the compounds of Formula II-A, the compound is of the Formula II-A3:

II-A3

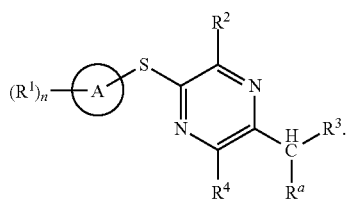

In one or more embodiments of the compounds of Formula II, the compound is of the Formula II-B:

II-B

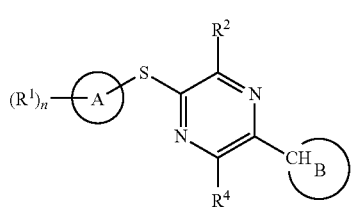

In one or more embodiments of the compounds of Formula II-B, the compound is of the Formula II-B1:

II-B1

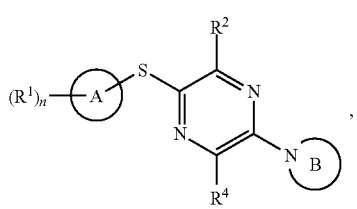

wherein:

B forms a 3- to 12-membered monocyclic or polycyclic heterocycle or a 5- to 12-membered spiroheterocycle along with the carbon atom to which it is attached, wherein the heterocycle or spiroheterocycle is optionally substituted with one or more —$C_1$-$C_6$alkyl, —OH, or —$NH_2$.

In one or more embodiments of the compounds of Formula II-B, the compound is of the Formula II-B2:

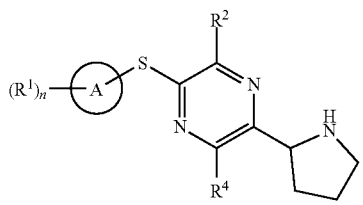

In one or more embodiments of the compounds of Formula II-B, the compound is of the Formula II-B3:

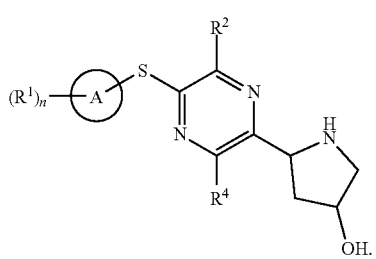

In one or more embodiments of the compounds of Formula II-B, the compound is of the Formula II-B4:

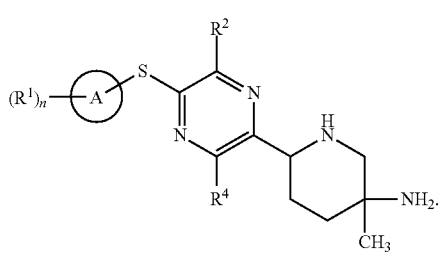

In one or more embodiments of the compounds of Formula II-B, the compound is of the Formula II-B5:

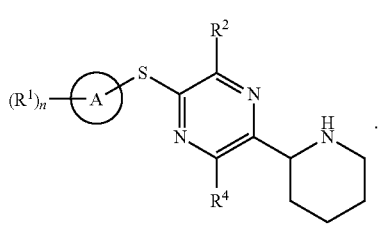

In one or more embodiments of the compounds of Formula II-B, the compound is of the Formula II-B6:

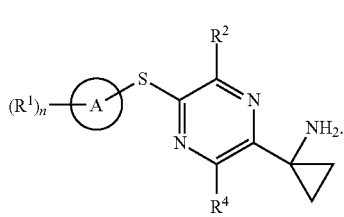

In one or more embodiments of the compounds of Formula II, the compound is of the Formula II-C:

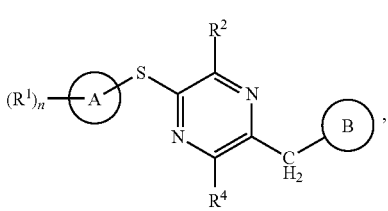

wherein:

B forms a 3- to 12-membered monocyclic or polycyclic heterocycle, wherein the heterocycle is optionally substituted with one or more —$C_1$-$C_6$alkyl, —OH, or —$NH_2$.

In one or more embodiments of the compounds of Formula II-C, the compound is of the Formula II-C1:

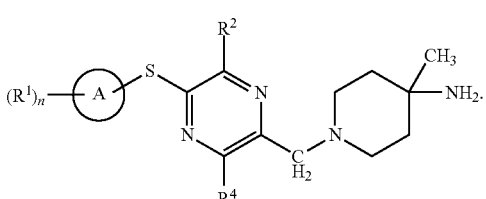

In one or more embodiments of the compounds of Formula II, the compound is of the Formula II-D:

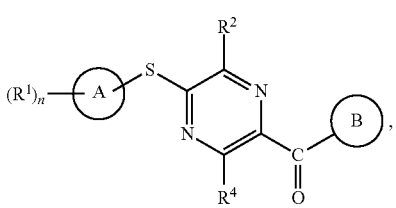

wherein:

B forms a 3- to 12-membered monocyclic or polycyclic heterocycle, wherein the heterocycle is optionally substituted with one or more —$C_1$-$C_6$alkyl, —OH, or —$NH_2$.

In one or more embodiments of the compounds of Formula II-D, the compound is of the Formula II-D1:

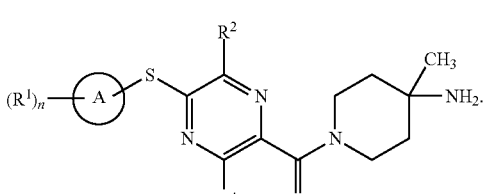

In one or more embodiments of the compounds of Formula II, the compound is of the Formula II-E:

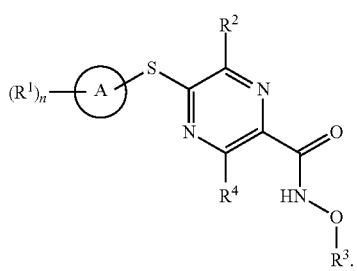
II-E

In one or more embodiments of the compounds of Formula II, the compound is of the Formula II-F:

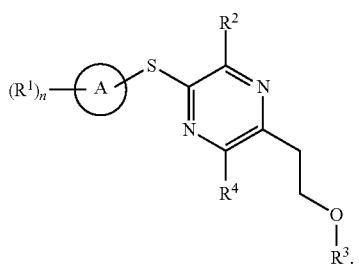
II-F

In one or more embodiments of the compounds of Formula II, the compound is of the Formula II-G:

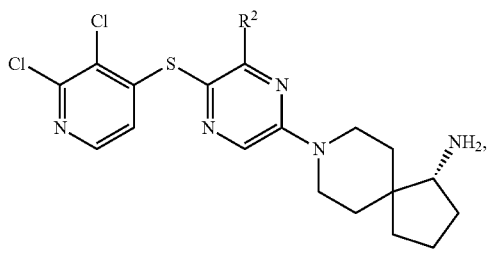
II-G wherein $R^2$ is an aryl or heteroaryl.

In one or more embodiments of the compounds of Formula III, the compound is of the Formula III-A:

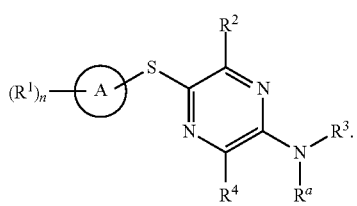
III-A

In one or more embodiments of the compounds of Formula III-A, the compound is of the Formula III-A1:

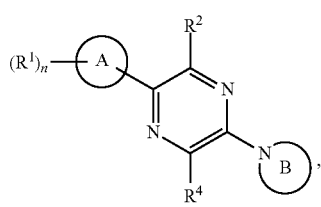
III-A1 wherein

B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with one or more —$C_1$-$C_6$alkyl, —OH, or —$NH_2$.

In one or more embodiments of the compounds of Formula III-A, the compound is of the Formula III-A2:

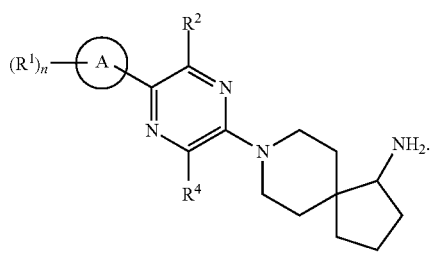
III-A2

In one or more embodiments of the compounds of Formula III-A, the compound is of the Formula III-A3:

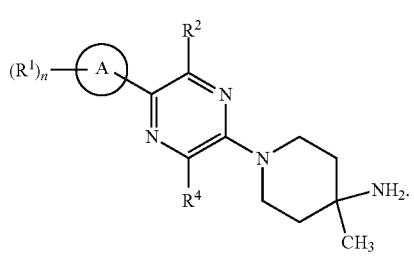
III-A3

In one or more embodiments, a compound of the present disclosure (e.g., a compound of Formula I, II, III, I-V1, I-V2, I-W, I-X, I-Y, or I-Z) can be selected from:

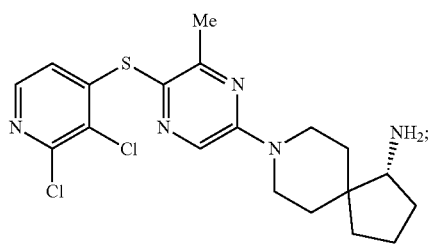
1

-continued
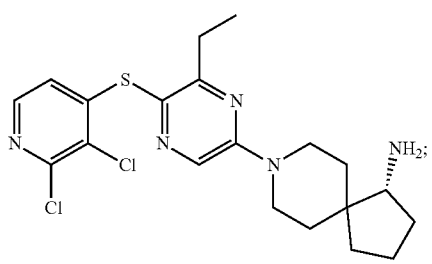
2
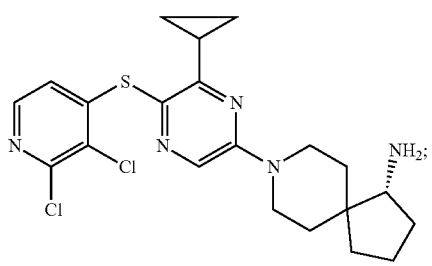
3
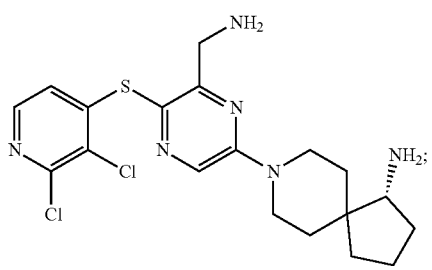
4
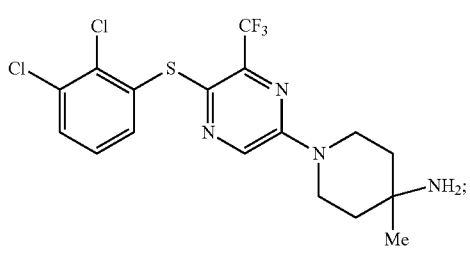
5
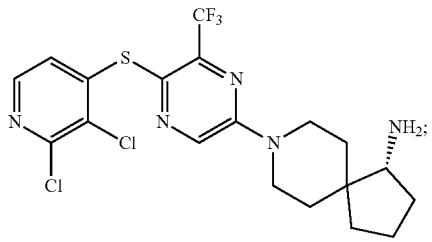
6
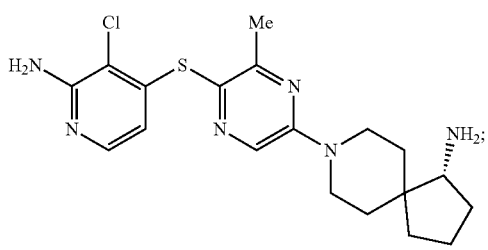
7
-continued
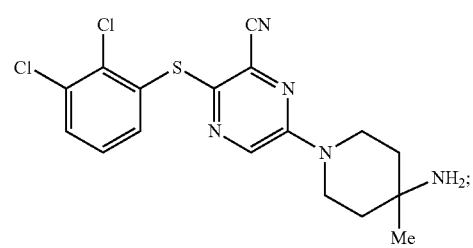
8
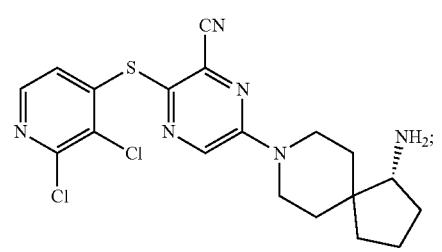
9
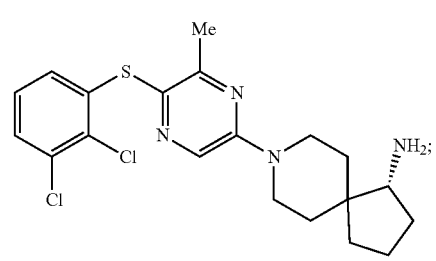
10
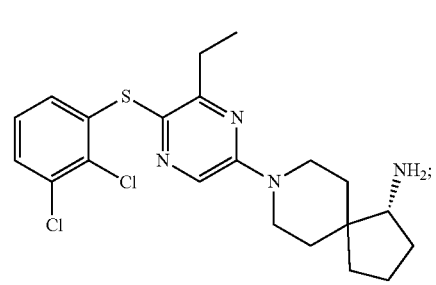
11
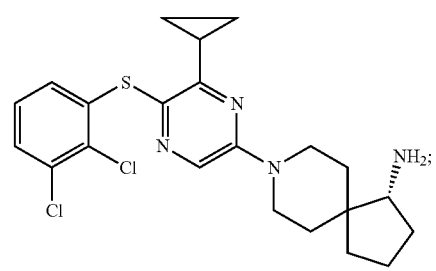
12
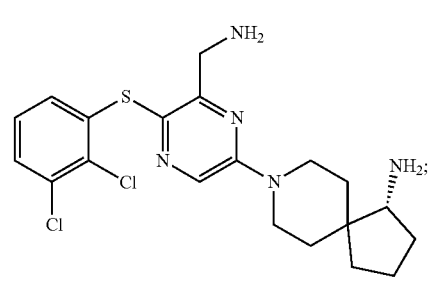
13

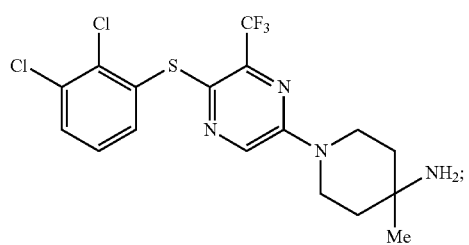
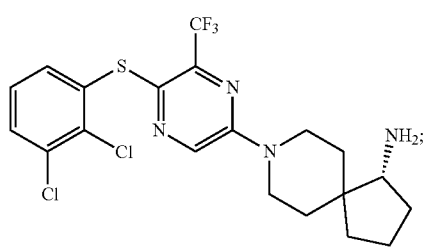
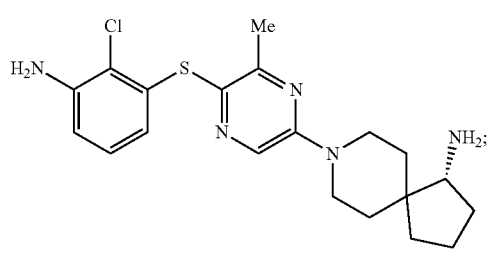
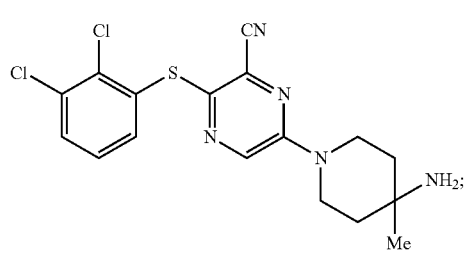
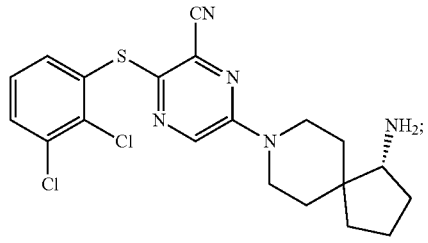
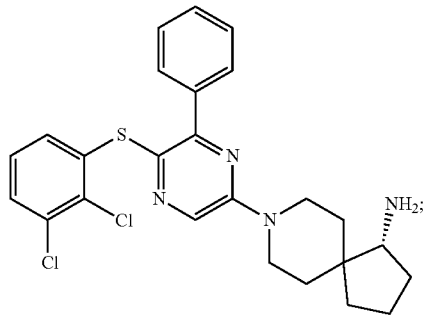
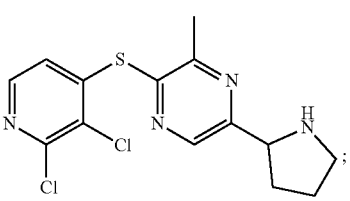
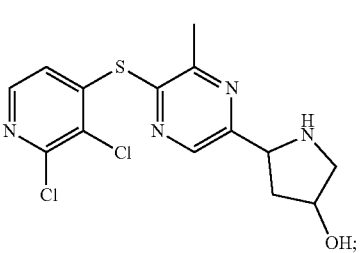
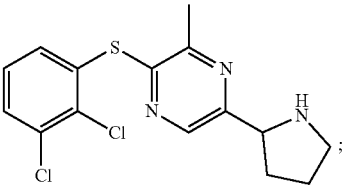
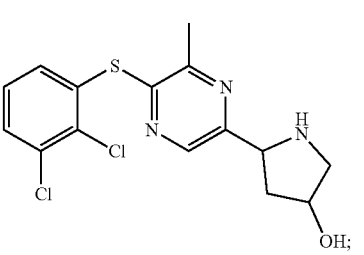
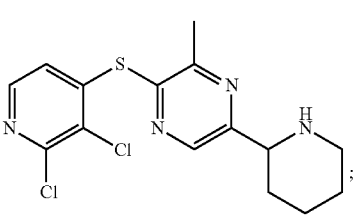
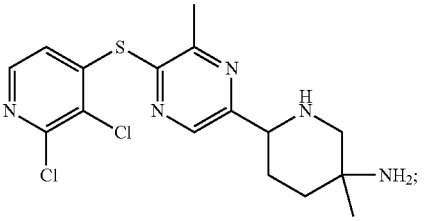
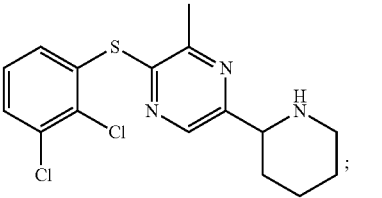

27 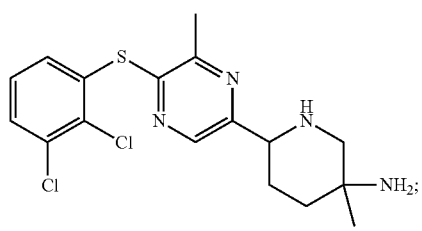
28 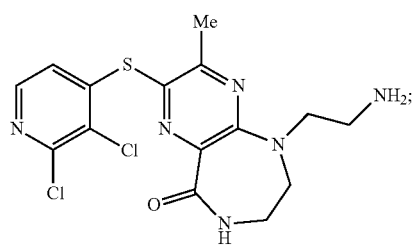
29 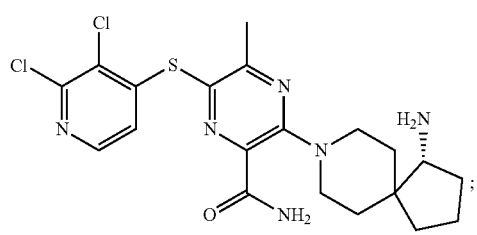
30 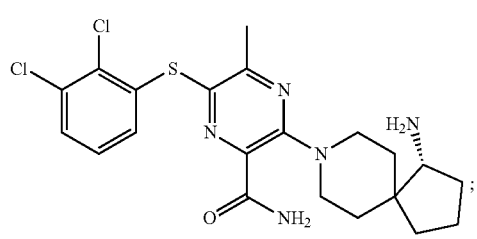
31 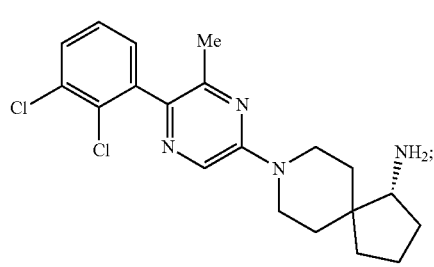
32 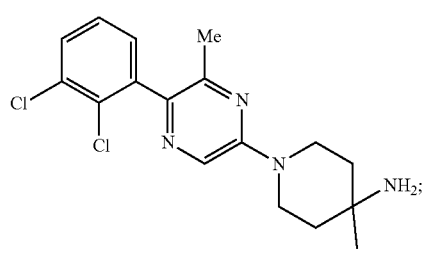
33 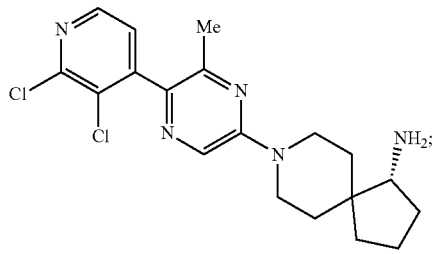
34 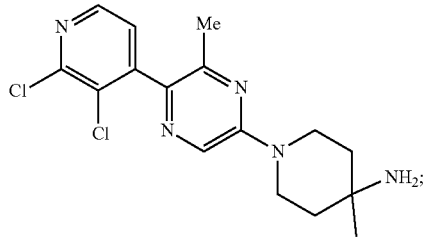
35 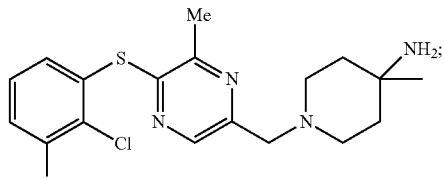
36 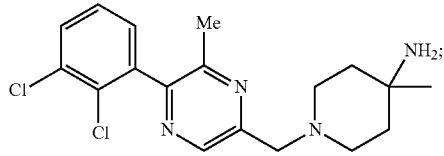
37 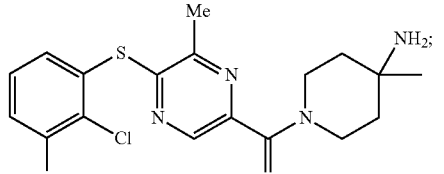
38 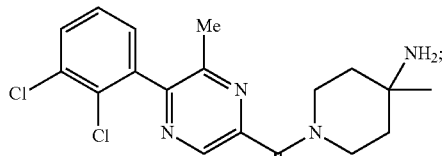
39 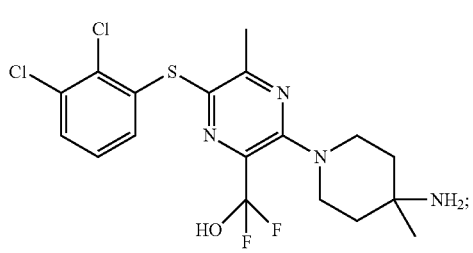

-continued
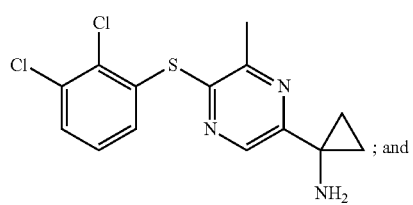
; and
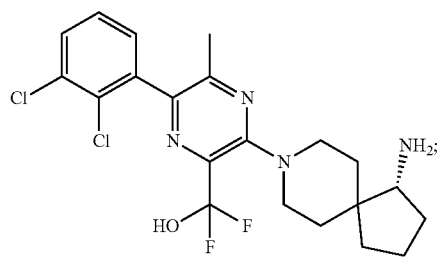
and pharmaceutically acceptable salts, prodrugs, solvates, hydrates, tautomers, or isomers thereof.
In one or more embodiments, a compound of the present disclosure (e.g., a compound of Formula I, II, III, I-V1, I-V2, I-W, I-X, I-Y, or I-Z) can be selected from:
| Compound # | Structure |
|---|---|
| A-1 | 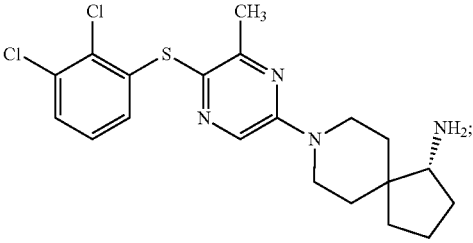 [SMILES: Cc1nc(N2CCC3(CCC[C@H]3N)CC2)cnc1Sc1cccc(Cl)c1Cl] |
| A-2 | 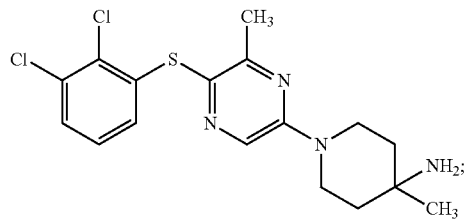 [SMILES: Cc1nc(N2CCC(C)(N)CC2)cnc1Sc1cccc(Cl)c1Cl] |
| A-3 | 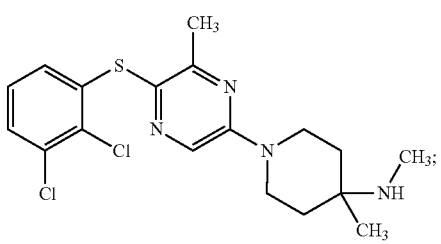 [SMILES: CNC1(C)CCN(c2cnc(Sc3cccc(Cl)c3Cl)c(C)n2)CC1] |
| A-4 | 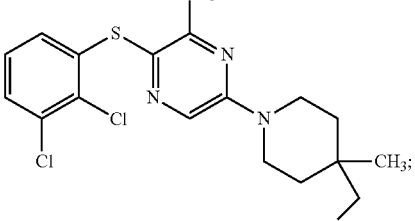 |
| A-5 | 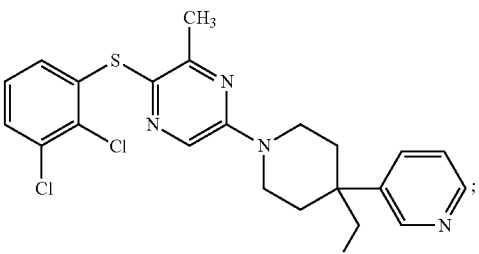 |
| A-6 | 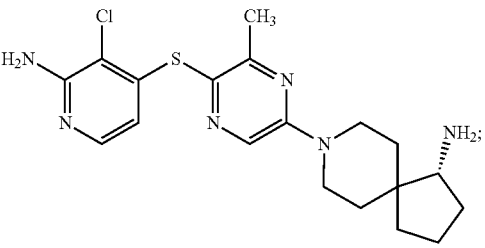 |
| A-7 | 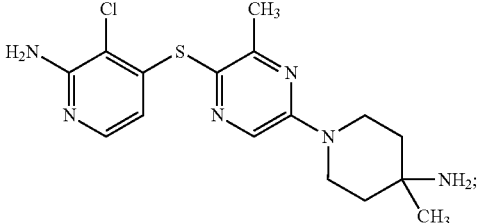 |
| A-8 | 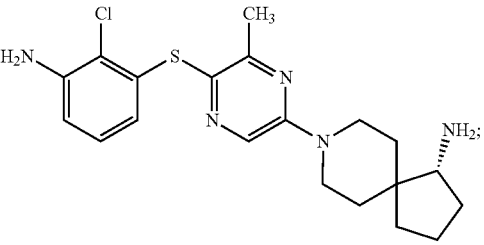 [SMILES: Cc1nc(N2CCC3(CCC[C@H]3N)CC2)cnc1Sc1cccc(N)c1Cl] |
| A-9 | 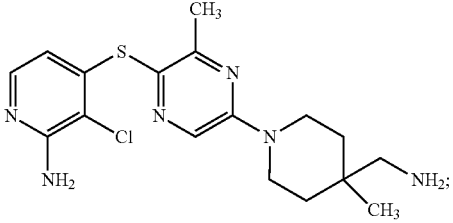 [SMILES: Cc1nc(N2CCC(C)(CN)CC2)cnc1Sc1ccnc(N)c1Cl] |

| Compound # | Structure |
|---|---|
| A-10 | 3-methyl-2-[(2,3-difluorophenyl)thio]-6-[(1S)-1-amino-8-azaspiro[4.5]decan-8-yl]pyrazine |
| A-11 | 3-methyl-2-[(2,3-difluorophenyl)thio]-6-(4-amino-4-methylpiperidin-1-yl)pyrazine |
| A-12 | 3-methyl-2-[(2,3-dichloropyridin-4-yl)thio]-6-[(1S)-1-amino-8-azaspiro[4.5]decan-8-yl]pyrazine |
| A-13 | 3-methyl-2-[(2,3-dichlorophenyl)thio]-6-(4-amino-4-methylpiperidin-1-yl)pyrazine |
| A-14 | 3-ethyl-2-[(2,3-dichlorophenyl)thio]-6-[(1S)-1-amino-8-azaspiro[4.5]decan-8-yl]pyrazine |
| A-15 | 3-phenyl-2-[(2,3-dichlorophenyl)thio]-6-[(1S)-1-amino-8-azaspiro[4.5]decan-8-yl]pyrazine |
| A-16 | 3-cyclopropyl-2-[(2,3-dichloropyridin-4-yl)thio]-6-[(1S)-1-amino-8-azaspiro[4.5]decan-8-yl]pyrazine |
| A-17 | 3-iodo-2-[(2,3-dichlorophenyl)thio]-6-[(1S)-1-amino-8-azaspiro[4.5]decan-8-yl]pyrazine |
| A-18 | 3-iodo-2-[(2,3-dichlorophenyl)thio]-6-(4-amino-4-methylpiperidin-1-yl)pyrazine |
| A-19 | 3-cyano-2-[(2,3-dichlorophenyl)thio]-6-(4-amino-4-methylpiperidin-1-yl)pyrazine |
| A-20 | 3-cyano-2-[(2,3-dichlorophenyl)thio]-6-[(1S)-1-amino-8-azaspiro[4.5]decan-8-yl]pyrazine |

*Note: Structures are shown as chemical diagrams in the original; names above are descriptive interpretations of the drawn structures.*

-continued

| Compound # | Structure |
|---|---|
| A-21 | (2,3-dichlorophenylthio)-hydroxypyrazine with 8-azaspiro[4.5]decane-1-amine substituent |
| A-22 | (2,3-dichlorophenylthio)-hydroxypyrazine with 4-methyl-4-aminopiperidine |
| A-23 | 3-(2,3-dichlorophenyl)-2-methylpyrazine with 8-azaspiro[4.5]decane-1-amine |
| A-24 | 3-(2,3-dichlorophenyl)-2-methylpyrazine with 4-methyl-4-aminopiperidine |
| A-25 | 3-(2,3-dichlorophenyl)-2-methylpyrazine with 3-methyl-3-aminoazetidine |
| A-26 | 3-(2,3-dichlorophenyl)-2-cyanopyrazine with 4-methyl-4-aminopiperidine |
| A-27 | 3-(2,3-dichlorophenyl)-2-cyanopyrazine with 8-azaspiro[4.5]decane-1-amine |
| A-28 | 3-(2,3-dichlorophenyl)-2-methylpyrazine with 4-methyl-4-(aminomethyl)piperidine |
| A-29 | 3-(2,3-dichlorophenyl)-2-methyl-hydroxypyrazine with 8-azaspiro[4.5]decane-1-amine |
| A-30 | 3-(2,3-dichlorophenyl)-2-methyl-carboxamide pyrazine with 8-azaspiro[4.5]decane-1-amine |
| A-31 | 3-(2,3-dichlorophenyl)-2-methyl-aminopyrazine with 8-azaspiro[4.5]decane-1-amine |

| Compound # | Structure |
|---|---|
| A-32 | 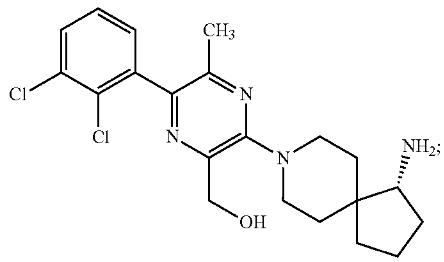 [SMILES: Cc1nc(N2CCC3(CCC[C@H]3N)CC2)c(CO)nc1-c1cccc(Cl)c1Cl] |
| A-33 | 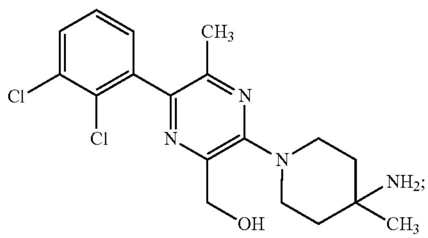 [SMILES: Cc1nc(N2CCC(C)(N)CC2)c(CO)nc1-c1cccc(Cl)c1Cl] |
| A-34 | 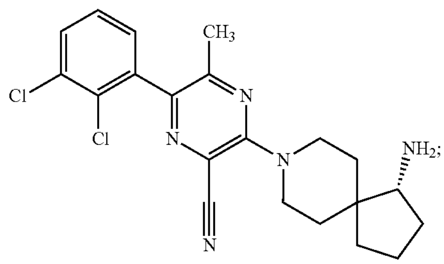 [SMILES: Cc1nc(N2CCC3(CCC[C@H]3N)CC2)c(C#N)nc1-c1cccc(Cl)c1Cl] |
| A-35 | 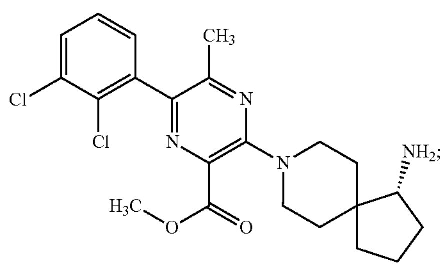 [SMILES: COC(=O)c1nc(-c2cccc(Cl)c2Cl)c(C)nc1N1CCC2(CCC[C@H]2N)CC1] |
| A-36 | 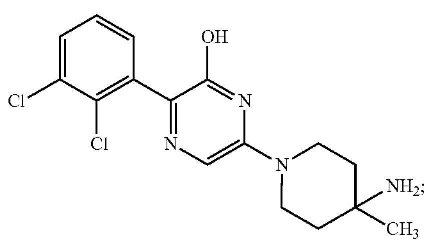 [SMILES: CC1(N)CCN(c2cnc(-c3cccc(Cl)c3Cl)c(O)n2)CC1] |
| A-37 | 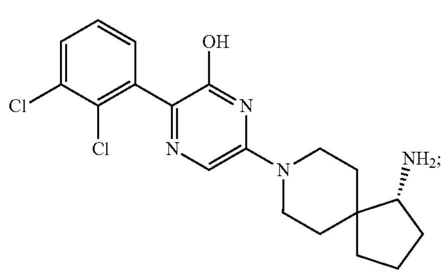 [SMILES: N[C@@H]1CCCC12CCN(c1cnc(-c3cccc(Cl)c3Cl)c(O)n1)CC2] |
| A-38 | 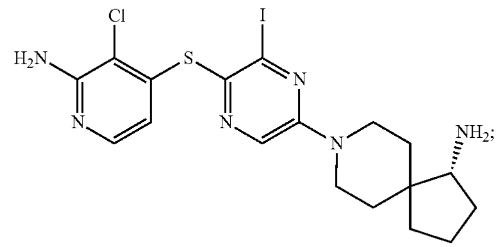 [SMILES: Nc1nccc(Sc2ncc(N3CCC4(CCC[C@H]4N)CC3)nc2I)c1Cl] |
| A-39 | 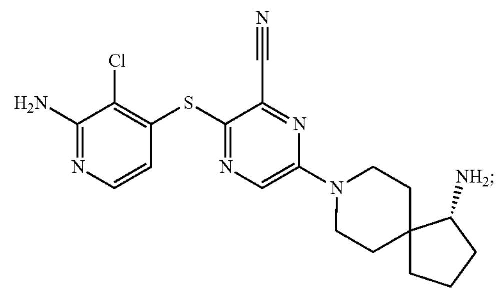 [SMILES: N#Cc1nc(N2CCC3(CCC[C@H]3N)CC2)cnc1Sc1ccnc(N)c1Cl] |
| A-40 | 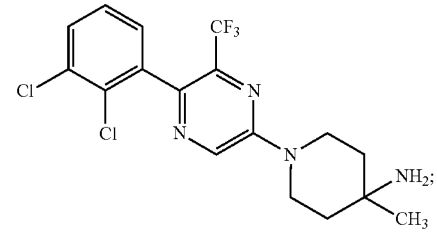 |
| A-41 | 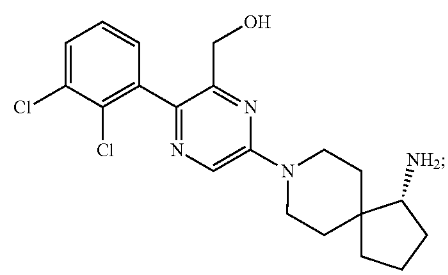 [SMILES: N[C@@H]1CCCC12CCN(c1cnc(-c3cccc(Cl)c3Cl)c(CO)n1)CC2] |
| A-42 | 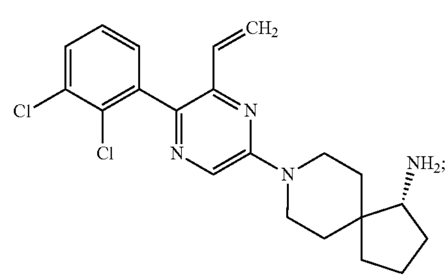 [SMILES: C=Cc1nc(N2CCC3(CCC[C@H]3N)CC2)cnc1-c1cccc(Cl)c1Cl] |

| Compound # | Structure |
|---|---|
| A-43 | 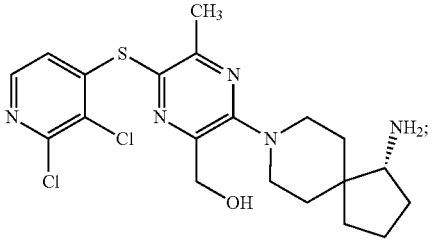 [SMILES: Cc1nc(N2CCC3(CCC[C@H]3N)CC2)c(CO)nc1Sc1ccnc(Cl)c1Cl] |
| A-44 | 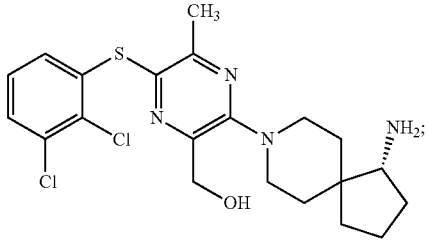 [SMILES: Cc1nc(N2CCC3(CCC[C@H]3N)CC2)c(CO)nc1Sc1cccc(Cl)c1Cl] |
| A-45 | 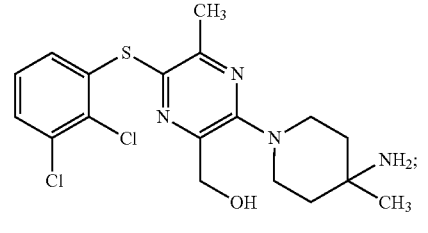 [SMILES: Cc1nc(N2CCC(C)(N)CC2)c(CO)nc1Sc1cccc(Cl)c1Cl] |
| A-46 | 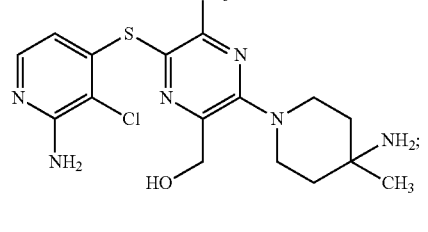 |
| A-47 | 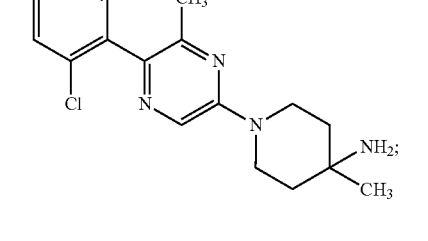 |
| A-48 | 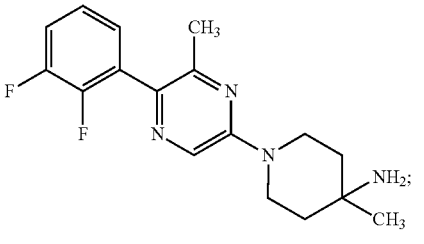 [SMILES: Cc1nc(N2CCC(C)(N)CC2)cnc1-c1cccc(F)c1F] |
| A-49 | 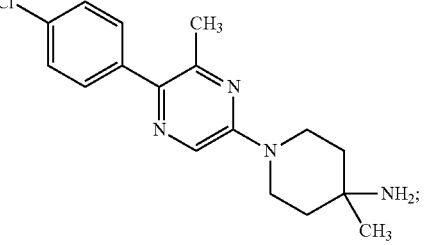 |
| A-50 | 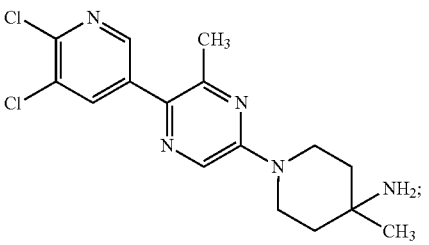 [SMILES: Cc1nc(N2CCC(C)(N)CC2)cnc1-c1cnc(Cl)c(Cl)c1] |
| A-51 | 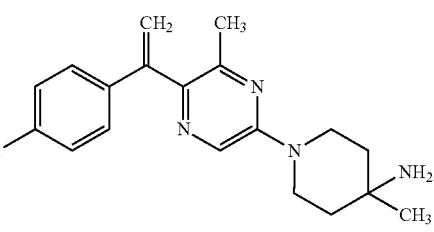 |
| A-52 | 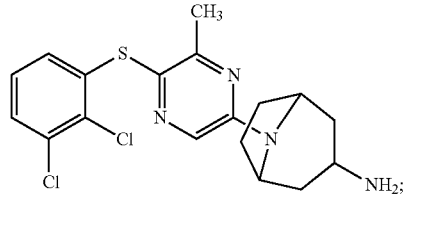 [SMILES: Cc1nc(N2C3CCC2CC(N)C3)cnc1Sc1cccc(Cl)c1Cl] |
| A-53 | 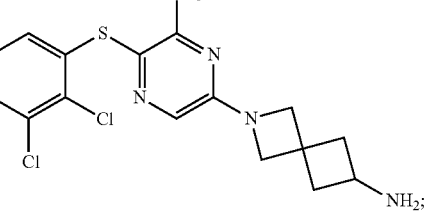 |
| A-54 | |

| Compound # | Structure |
|---|---|
| A-55 | 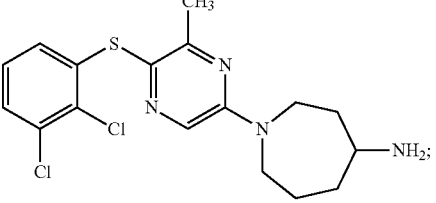 |
| A-56 | 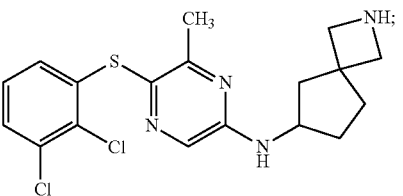 [SMILES: Cc1nc(NC2CCC3(CNC3)C2)cnc1Sc1cccc(Cl)c1Cl] |
| A-57 | 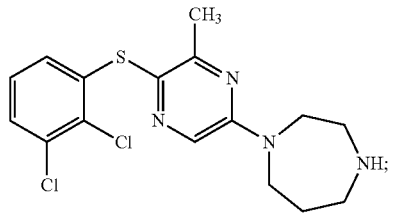 [SMILES: Cc1nc(N2CCCNCC2)cnc1Sc1cccc(Cl)c1Cl] |
| A-58 | 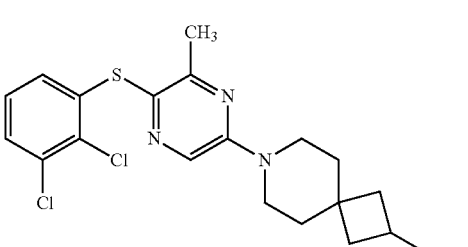 |
| A-59 | 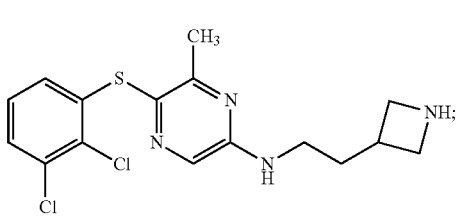 [SMILES: Cc1nc(NCCC2CNC2)cnc1Sc1cccc(Cl)c1Cl] |
| A-60 | 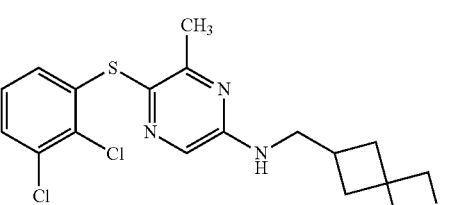 |
| A-61 | 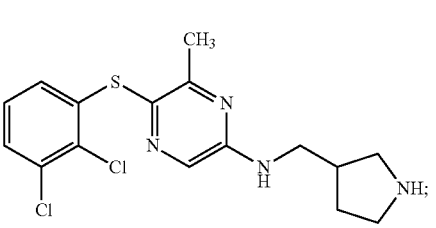 [SMILES: Cc1nc(NCC2CCNC2)cnc1Sc1cccc(Cl)c1Cl] |
| A-62 | 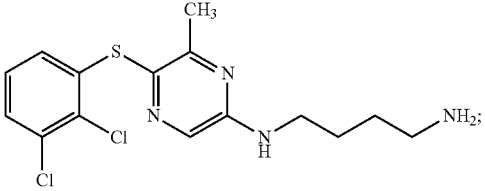 [SMILES: Cc1nc(NCCCCN)cnc1Sc1cccc(Cl)c1Cl] |
| A-63 | 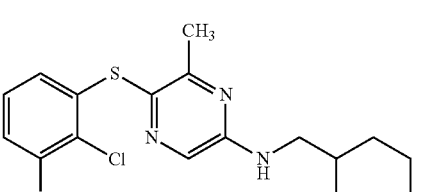 |
| A-64 | 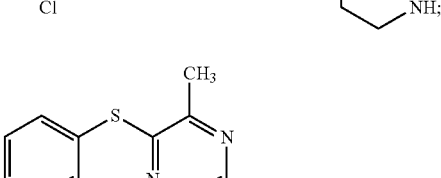 |
| A-65 | 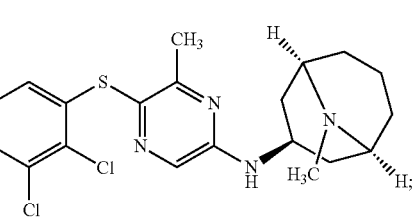 |
| A-66 | 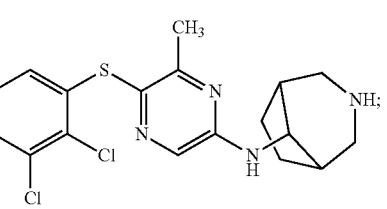 |
| A-67 | 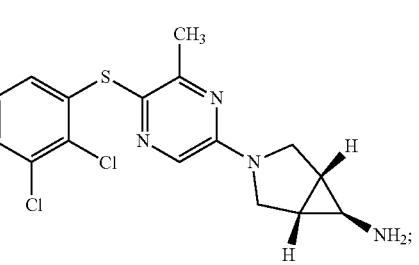 |
| A-68 | 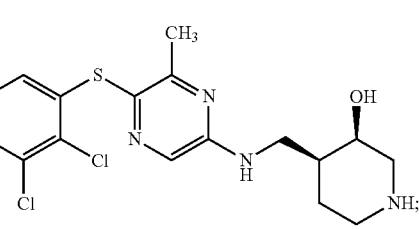 |

| Compound # | Structure |
|---|---|
| A-69 | 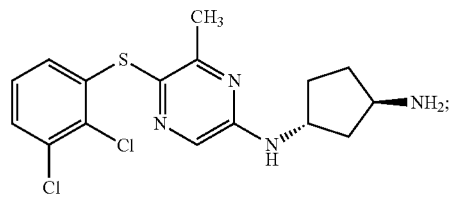 [SMILES: Cc1nc(N[C@@H]2CC[C@@H](N)C2)cnc1Sc1cccc(Cl)c1Cl] |
| A-70 | 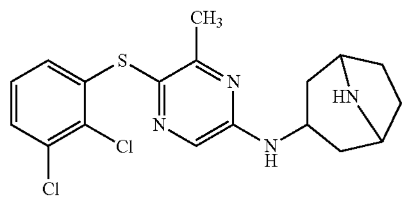 |
| A-71 | 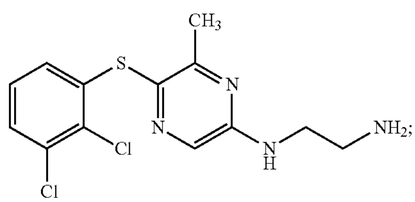 [SMILES: Cc1nc(NCCN)cnc1Sc1cccc(Cl)c1Cl] |
| A-72 | 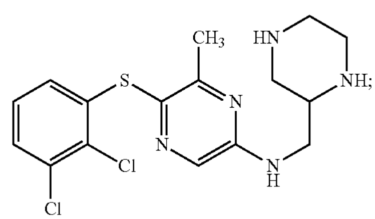 [SMILES: Cc1nc(NCC2CNCCN2)cnc1Sc1cccc(Cl)c1Cl] |
| A-73 | 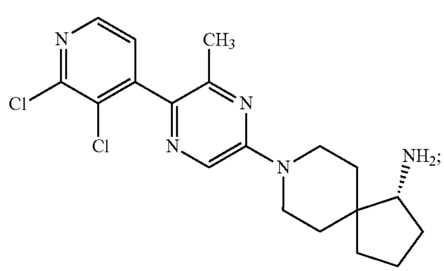 [SMILES: Cc1nc(N2CCC3(CCC[C@H]3N)CC2)cnc1-c1ccnc(Cl)c1Cl] |
| A-74 | 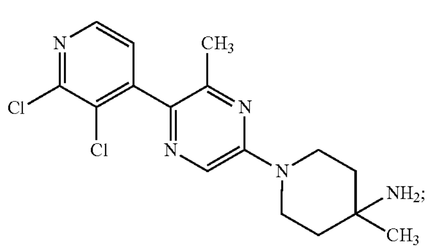 |

| Compound # | Structure |
|---|---|
| A-75 | |
| A-76 | |
| A-77 | |
| A-78 | |
| A-79 | |

| Compound # | Structure |
|---|---|
| A-80 | 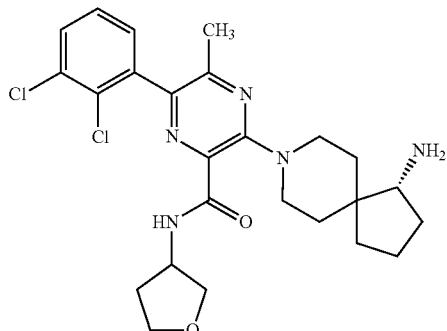 |
| A-81 | 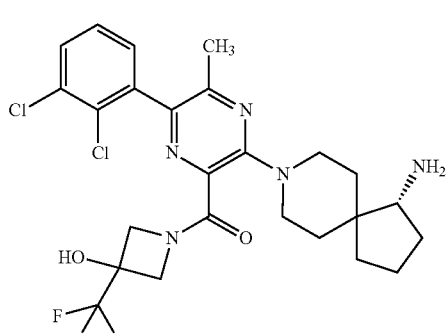 |
| A-82 | 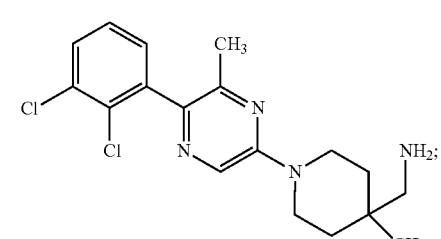 |
| A-83 | 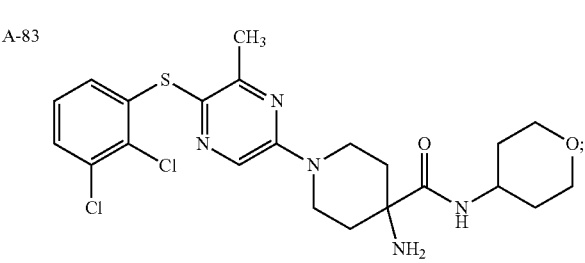 |
| A-84 | 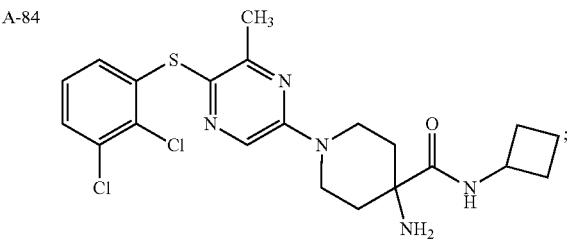 |
| A-85 | 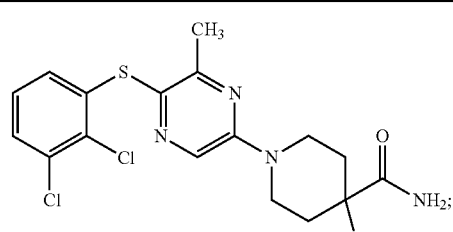 |
| A-86 | 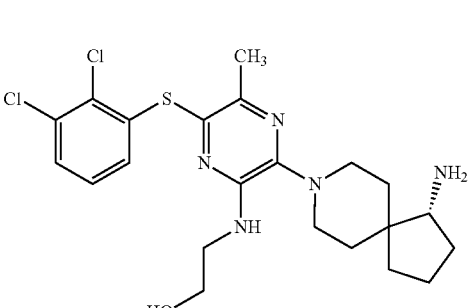 |
| A-87 | 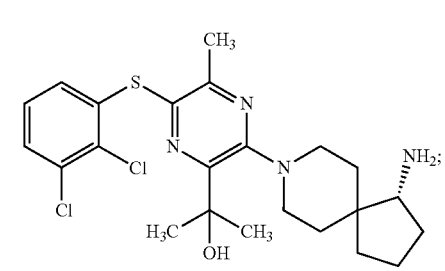 [SMILES: Cc1nc(N2CCC3(CCC[C@H]3N)CC2)c(C(C)(C)O)nc1Sc1cccc(Cl)c1Cl] |
| A-88 | 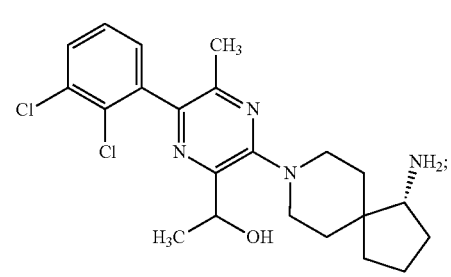 [SMILES: Cc1nc(N2CCC3(CCC[C@H]3N)CC2)c(C(C)O)nc1-c1cccc(Cl)c1Cl] |
| A-89 | 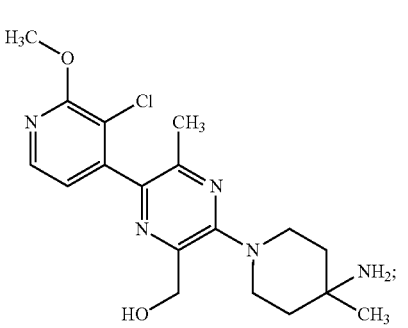 [SMILES: COc1nccc(-c2nc(CO)c(N3CCC(C)(N)CC3)nc2C)c1Cl] |

-continued

| Compound # | Structure |
|---|---|
| A-90 | (structure) |
| A-91 | (structure) |
| A-92 | (structure) |
| A-93 | (structure) |
| A-94 | (structure) |
| A-95 | (structure) |
| A-96 | (structure) |
| A-97 | (structure) |
| A-98 | (structure) |
| A-99 | (structure) |

| Compound # | Structure |
|---|---|
| A-100 | 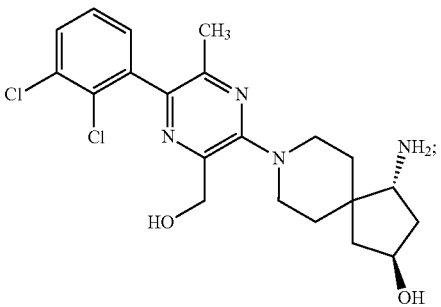 [SMILES: Cc1nc(N2CCC3(CC2)C[C@H](O)C[C@H]3N)c(CO)nc1-c1cccc(Cl)c1Cl] |
| A-101 | 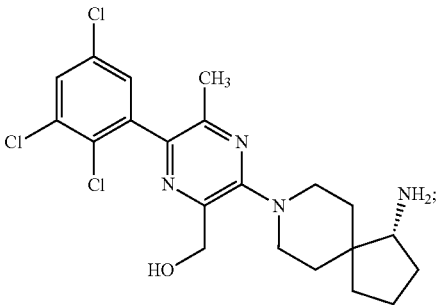 [SMILES: Cc1nc(N2CCC3(CCC[C@H]3N)CC2)c(CO)nc1-c1cc(Cl)cc(Cl)c1Cl] |
| A-102 | 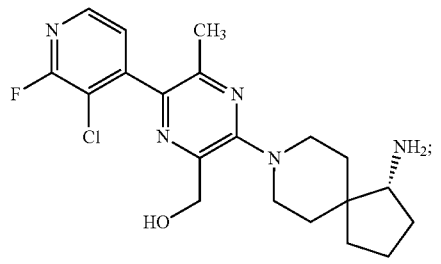 [SMILES: Cc1nc(N2CCC3(CCC[C@H]3N)CC2)c(CO)nc1-c1ccnc(F)c1Cl] |
| A-103 | 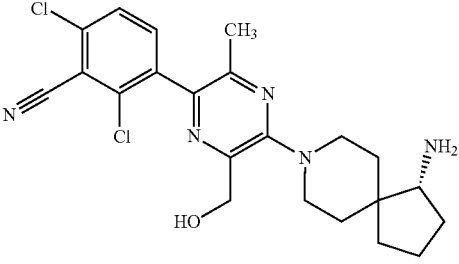 |
| A-104 | 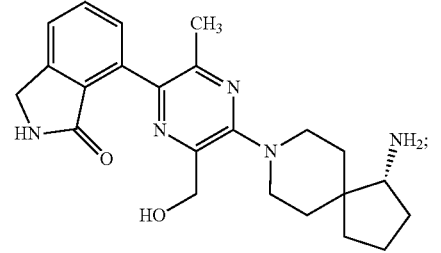 [SMILES: Cc1nc(N2CCC3(CCC[C@H]3N)CC2)c(CO)nc1-c1cccc2c1C(=O)NC2] |
| A-105 | 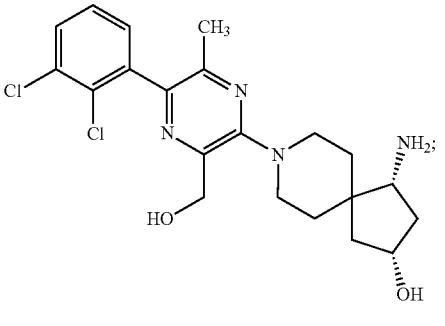 [SMILES: Cc1nc(N2CCC3(CC2)C[C@@H](O)C[C@H]3N)c(CO)nc1-c1cccc(Cl)c1Cl] |
| A-106 | 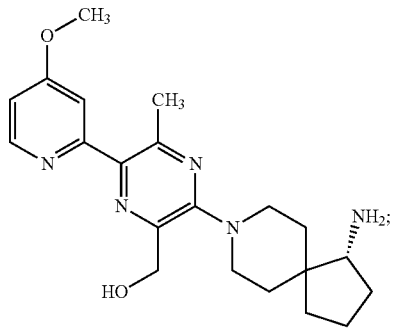 [SMILES: COc1ccnc(-c2nc(CO)c(N3CCC4(CCC[C@H]4N)CC3)nc2C)c1] |
| A-107 | 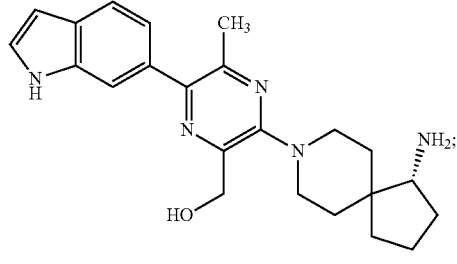 [SMILES: Cc1nc(N2CCC3(CCC[C@H]3N)CC2)c(CO)nc1-c1ccc2cc[nH]c2c1] |
| A-108 | 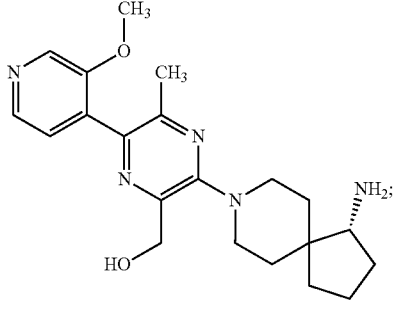 [SMILES: COc1cnccc1-c1nc(CO)c(N2CCC3(CCC[C@H]3N)CC2)nc1C] |
| A-109 | 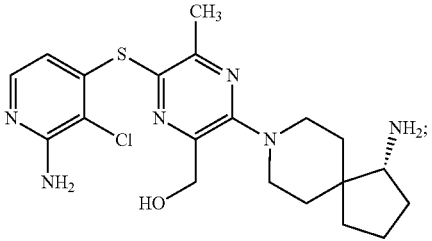 [SMILES: Cc1nc(N2CCC3(CCC[C@H]3N)CC2)c(CO)nc1Sc1ccnc(N)c1Cl] |

| Compound # | Structure |
|---|---|
| A-110 | (structure) |
| A-111 | (structure) |
| A-112 | (structure) |
| A-113 | (structure) |
| A-114 | (structure) |
| A-115 | (structure) |
| A-116 | (structure) |
| A-117 | (structure) |
| A-118 | (structure) |
| A-119 | (structure) |

-continued
| Compound # | Structure |
|---|---|
| A-120 | 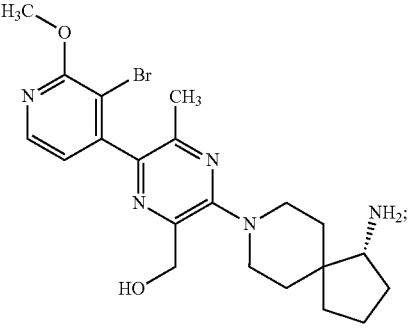 [SMILES: COc1nccc(-c2nc(CO)c(N3CCC4(CCC[C@H]4N)CC3)nc2C)c1Br] |
| A-121 | 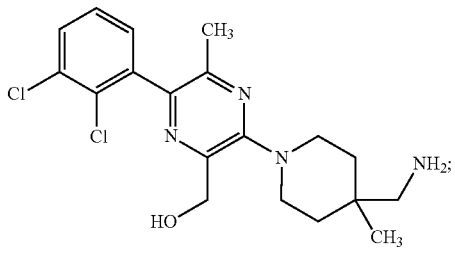 [SMILES: Cc1nc(N2CCC(C)(CN)CC2)c(CO)nc1-c1cccc(Cl)c1Cl] |
| A-122 | 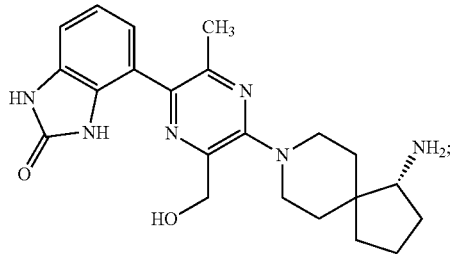 [SMILES: Cc1nc(N2CCC3(CCC[C@H]3N)CC2)c(CO)nc1-c1cccc2[nH]c(=O)[nH]c12] |
| A-123 | 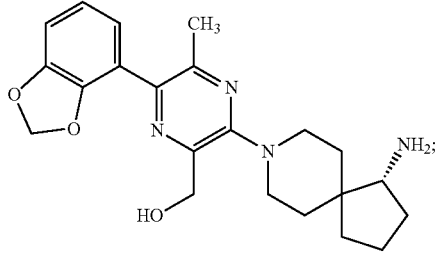 [SMILES: Cc1nc(N2CCC3(CCC[C@H]3N)CC2)c(CO)nc1-c1cccc2c1OCO2] |
| A-124 | 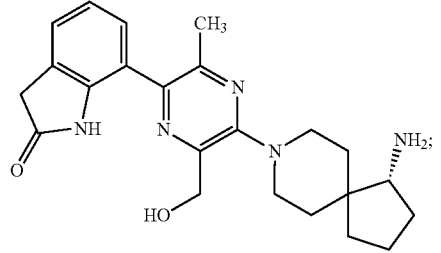 [SMILES: Cc1nc(N2CCC3(CCC[C@H]3N)CC2)c(CO)nc1-c1cccc2c1NC(=O)C2] |
-continued
| Compound # | Structure |
|---|---|
| A-125 | 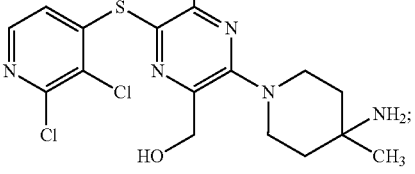 |
| A-126 | 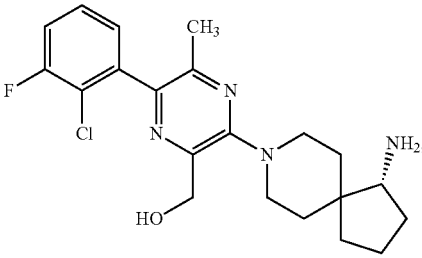 |
| A-127 | 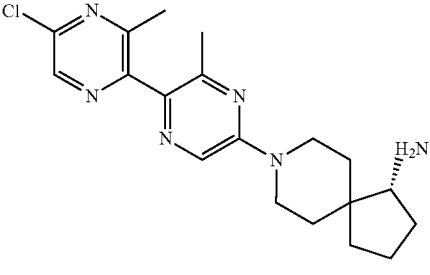 [SMILES: Cc1nc(Cl)cnc1-c1ncc(N2CCC3(CCC[C@H]3N)CC2)nc1C] |
| A-128 | 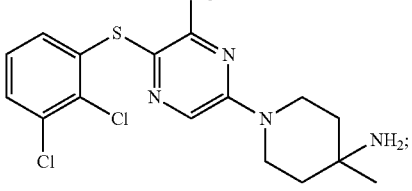 |
| A-129 | 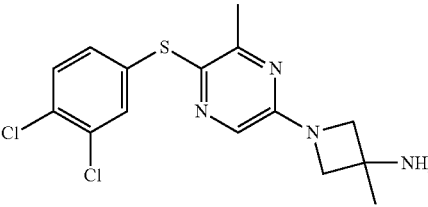 |
| A-130 | 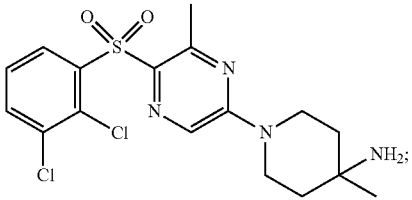 [SMILES: Cc1nc(N2CCC(C)(N)CC2)cnc1S(=O)(=O)c1cccc(Cl)c1Cl] |

| Compound # | Structure |
|---|---|
| A-131 | 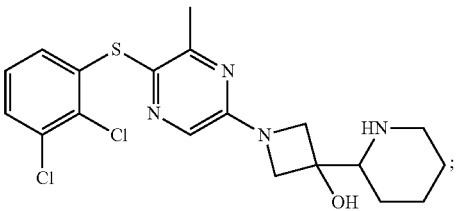 [SMILES: Cc1nc(N2CC(O)(C3CCCCN3)C2)cnc1Sc1cccc(Cl)c1Cl ; ";"] |
| A-132 | 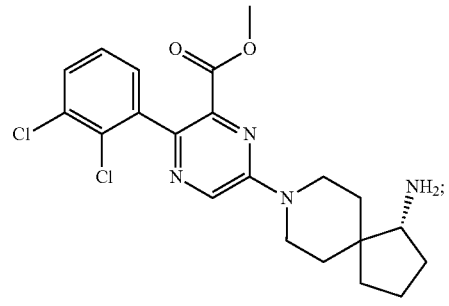 [SMILES: COC(=O)c1nc(N2CCC3(CCC[C@H]3N)CC2)cnc1-c1cccc(Cl)c1Cl] |
| A-133 | 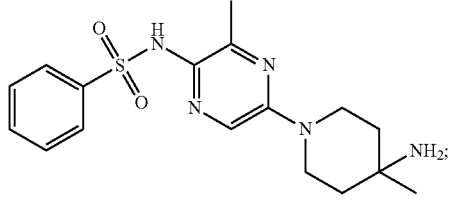 [SMILES: Cc1nc(N2CCC(C)(N)CC2)cnc1NS(=O)(=O)c1ccccc1] |
| A-134 | 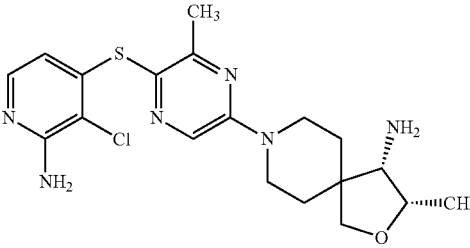 |
| A-135 | 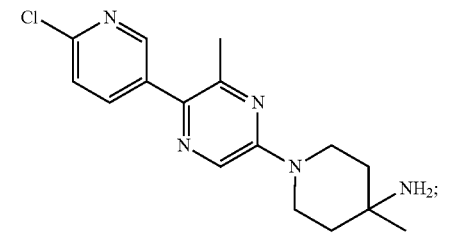 [SMILES: Cc1nc(N2CCC(C)(N)CC2)cnc1-c1ccc(Cl)nc1] |
| A-136 | 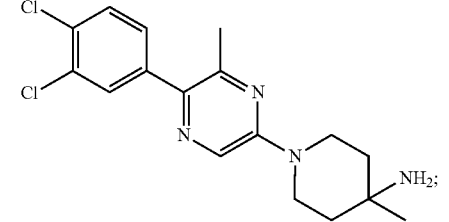 [SMILES: Cc1nc(N2CCC(C)(N)CC2)cnc1-c1ccc(Cl)c(Cl)c1] |
| A-137 | 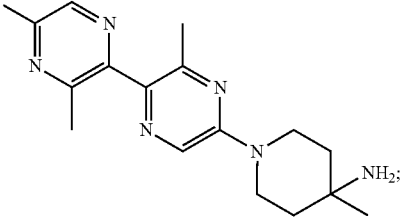 |
| A-138 | 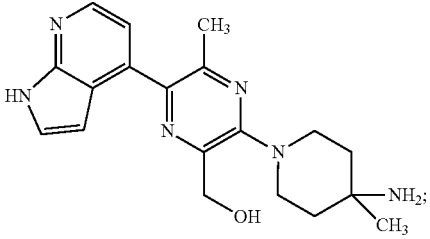 [SMILES: Cc1nc(N2CCC(C)(N)CC2)c(CO)nc1-c1ccnc2[nH]ccc12] |
| A-139 | 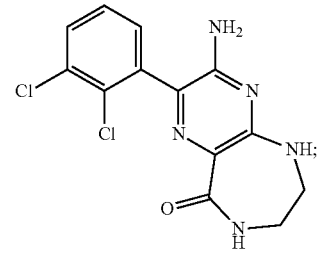 [SMILES: Nc1nc2c(nc1-c1cccc(Cl)c1Cl)C(=O)NCCN2] |
| A-140 | 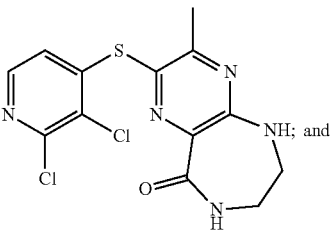 [SMILES: Cc1nc2c(nc1Sc1ccnc(Cl)c1Cl)C(=O)NCCN2 ; "and"] |
| A-141 | 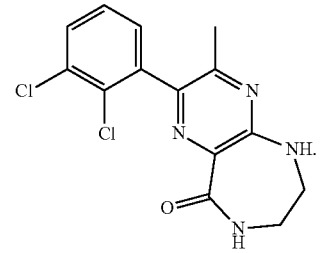 [SMILES: Cc1nc2c(nc1-c1cccc(Cl)c1Cl)C(=O)NCCN2] |
and pharmaceutically acceptable salts, prodrugs, solvates, hydrates, tautomers, or isomers thereof.
In one or more embodiments, a compound of the present disclosure (e.g., a compound of Formula I, II, III, I-V1, I-V2, I-W, I-X, I-Y, or I-Z) can be selected from:

| Compound # | Structure |
|---|---|
| A-142 | 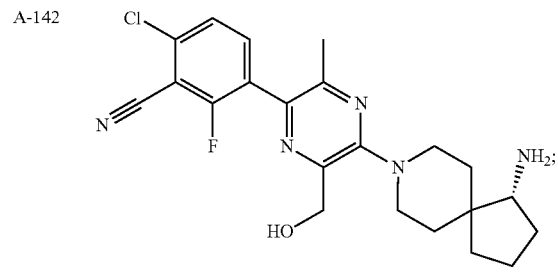 |
| A-143 | 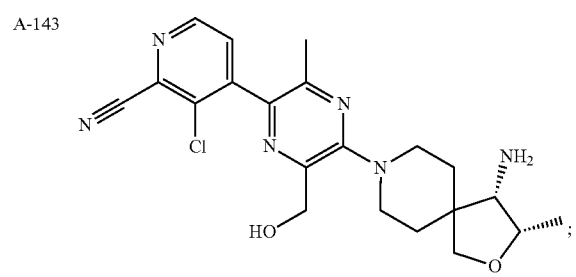 |
| A-144 | 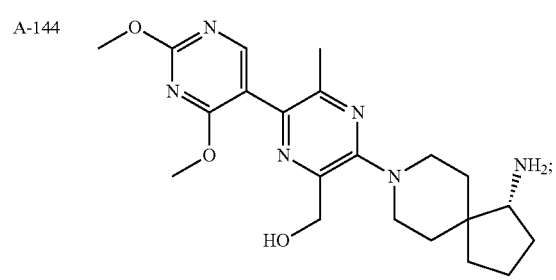 |
| A-145 | 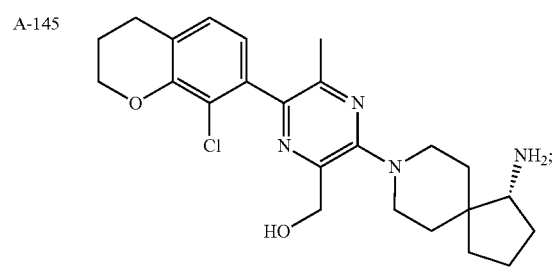 |
| A-146 | 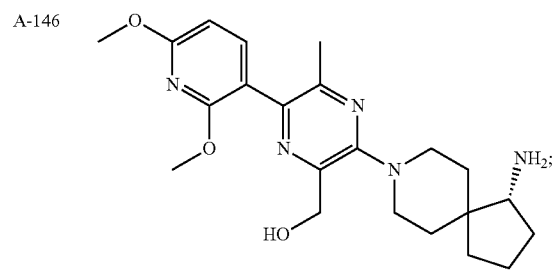 |
| A-147 | 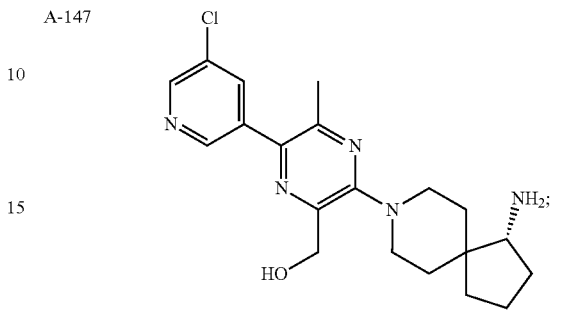 |
| A-148 | 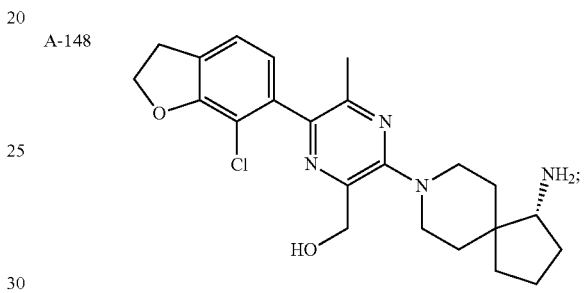 |
| A-149 | 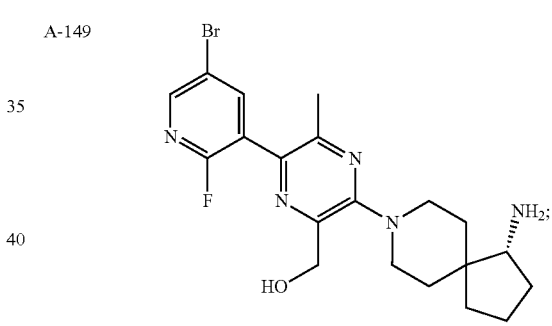 |
| A-150 | 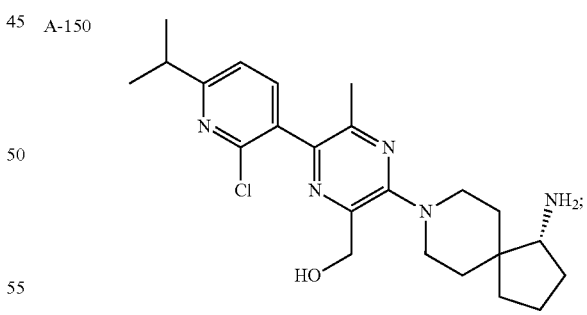 |
| A-151 | 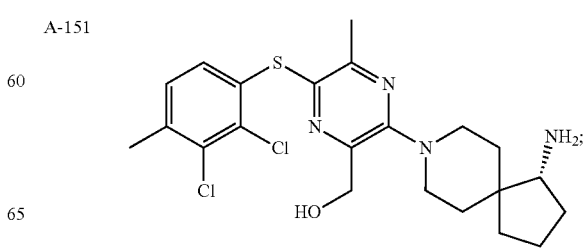 |

| Compound # | Structure |
|---|---|
| A-152 | 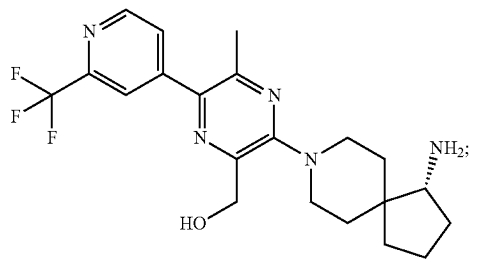 |
| A-153 | 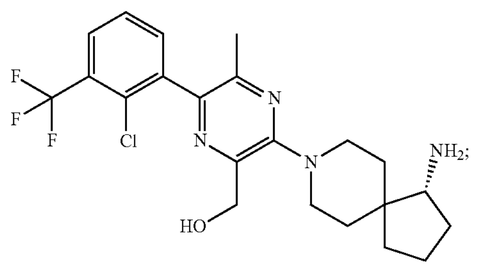 [SMILES: Cc1nc(N2CCC3(CCC[C@H]3N)CC2)c(CO)nc1-c1cccc(C(F)(F)F)c1Cl] |
| A-154 | 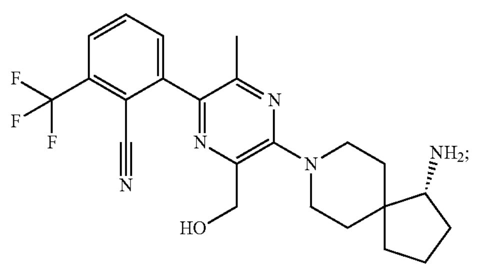 [SMILES: Cc1nc(N2CCC3(CCC[C@H]3N)CC2)c(CO)nc1-c1cccc(C(F)(F)F)c1C#N] |
| A-155 | 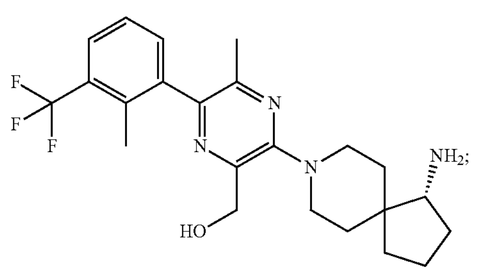 |
| A-156 | 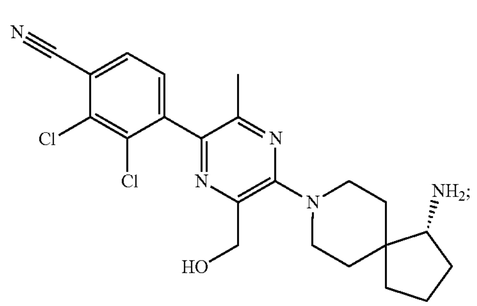 [SMILES: Cc1nc(N2CCC3(CCC[C@H]3N)CC2)c(CO)nc1-c1ccc(C#N)c(Cl)c1Cl] |
| A-157 | |
| A-158 | |
| A-159 | |
| A-160 | |
| A-161 | |

| Compound # | Structure |
|---|---|
| A-162 | 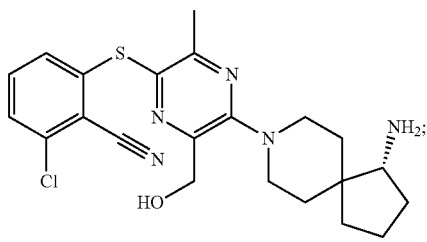 [SMILES: Cc1nc(N2CCC3(CCC[C@H]3N)CC2)c(CO)nc1Sc1cccc(Cl)c1C#N] |
| A-163 | 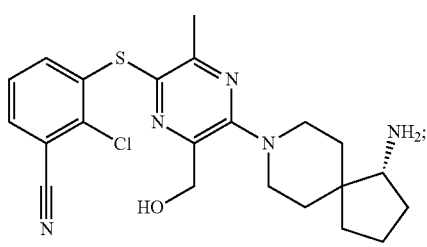 [SMILES: Cc1nc(N2CCC3(CCC[C@H]3N)CC2)c(CO)nc1Sc1cccc(C#N)c1Cl] |
| A-164 | 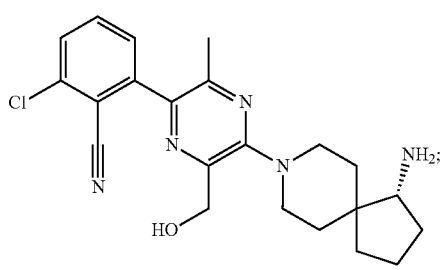 [SMILES: Cc1nc(N2CCC3(CCC[C@H]3N)CC2)c(CO)nc1-c1cccc(Cl)c1C#N] |
| A-165 | 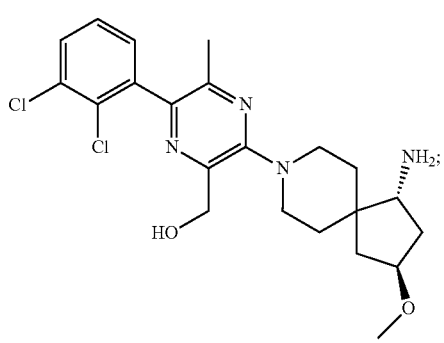 [SMILES: CO[C@@H]1C[C@@H](N)C2(CCN(c3nc(C)c(-c4cccc(Cl)c4Cl)nc3CO)CC2)C1] |
| A-166 | 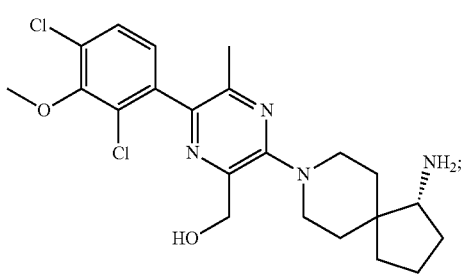 [SMILES: COc1c(Cl)ccc(-c2nc(CO)c(N3CCC4(CCC[C@H]4N)CC3)nc2C)c1Cl] |
| Compound # | Structure |
|---|---|
| A-167 | 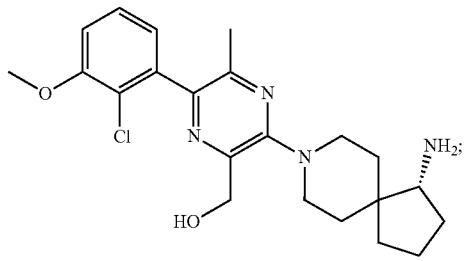 [SMILES: COc1cccc(-c2nc(CO)c(N3CCC4(CCC[C@H]4N)CC3)nc2C)c1Cl] |
| A-168 | 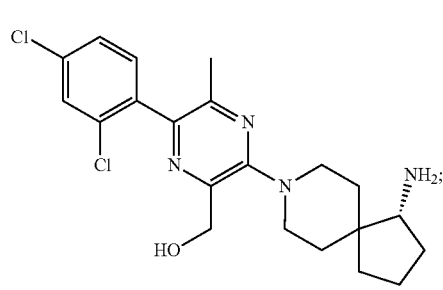 [SMILES: Cc1nc(N2CCC3(CCC[C@H]3N)CC2)c(CO)nc1-c1ccc(Cl)cc1Cl] |
| A-169 | 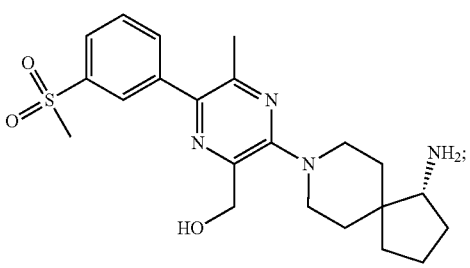 [SMILES: Cc1nc(N2CCC3(CCC[C@H]3N)CC2)c(CO)nc1-c1cccc(S(C)(=O)=O)c1] |
| A-170 | 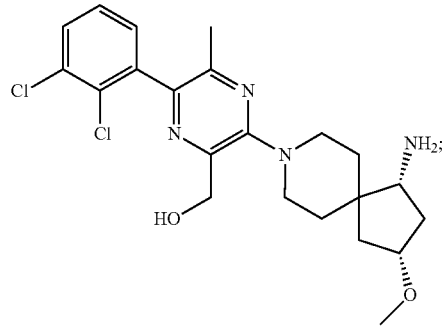 [SMILES: CO[C@H]1C[C@@H](N)C2(CCN(c3nc(C)c(-c4cccc(Cl)c4Cl)nc3CO)CC2)C1] |
| A-171 | 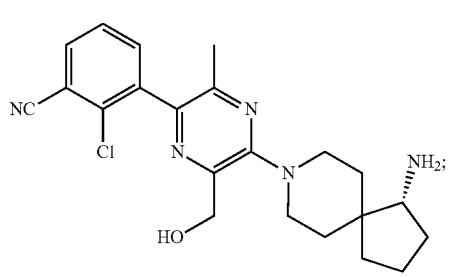 [SMILES: Cc1nc(N2CCC3(CCC[C@H]3N)CC2)c(CO)nc1-c1cccc(C#N)c1Cl] |

| Compound # | Structure |
|---|---|
| A-172 | 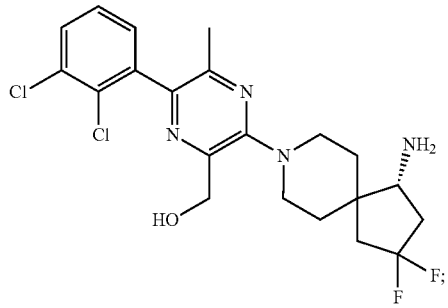 [SMILES: Cc1nc(N2CCC3(CC2)CC(F)(F)C[C@H]3N)c(CO)nc1-c1cccc(Cl)c1Cl] |
| A-173 | 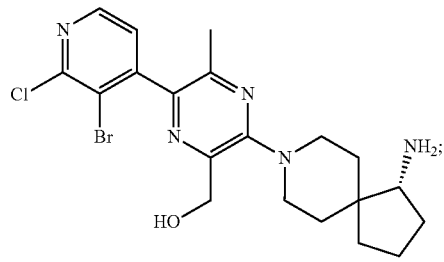 [SMILES: Cc1nc(N2CCC3(CCC[C@H]3N)CC2)c(CO)nc1-c1ccnc(Cl)c1Br] |
| A-174 | 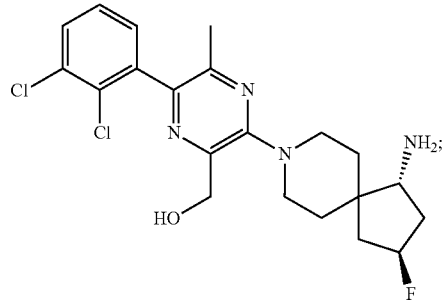 [SMILES: Cc1nc(N2CCC3(CC2)C[C@H](F)C[C@H]3N)c(CO)nc1-c1cccc(Cl)c1Cl] |
| A-175 | 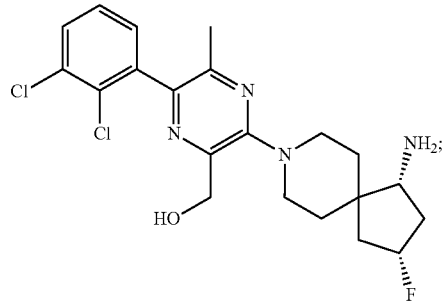 [SMILES: Cc1nc(N2CCC3(CC2)C[C@@H](F)C[C@H]3N)c(CO)nc1-c1cccc(Cl)c1Cl] |
| A-176 | 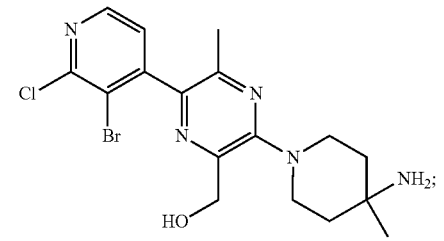 [SMILES: Cc1nc(N2CCC(C)(N)CC2)c(CO)nc1-c1ccnc(Cl)c1Br] |
| Compound # | Structure |
|---|---|
| A-177 | 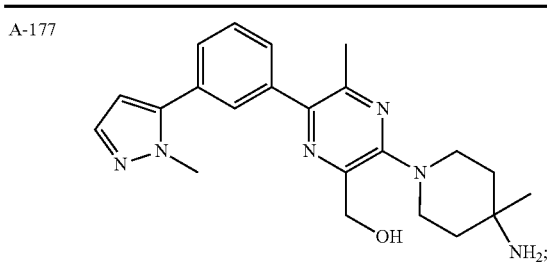 |
| A-178 | 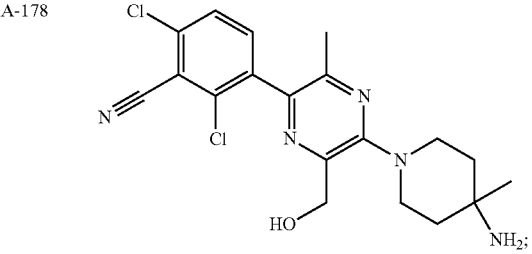 |
| A-179 | 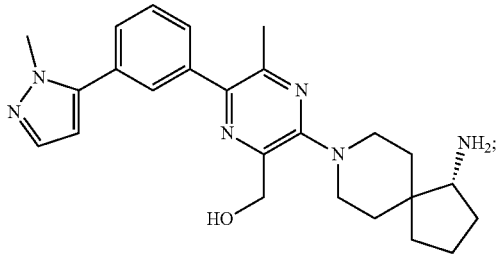 [SMILES: Cc1nc(N2CCC3(CCC[C@H]3N)CC2)c(CO)nc1-c1cccc(-c2ccnn2C)c1] |
| A-180 | 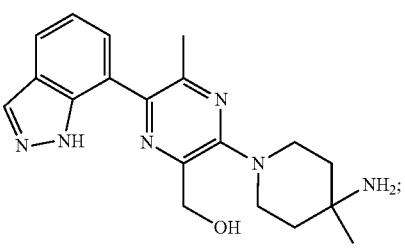 [SMILES: Cc1nc(N2CCC(C)(N)CC2)c(CO)nc1-c1cccc2cn[nH]c12] |
| A-181 | 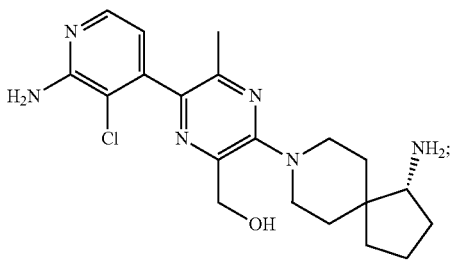 [SMILES: Cc1nc(N2CCC3(CCC[C@H]3N)CC2)c(CO)nc1-c1ccnc(N)c1Cl] |

| Compound # | Structure |
|---|---|
| A-182 | 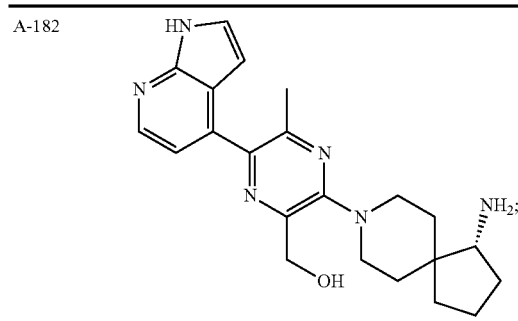 |
| A-183 | 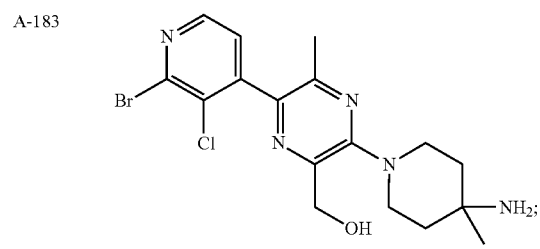 |
| A-184 | 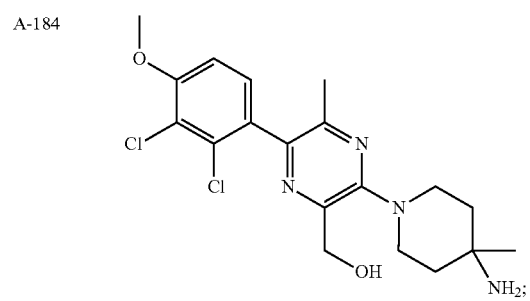 |
| A-185 | 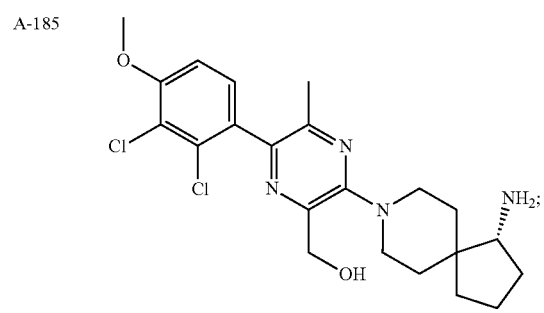 |
| A-186 | 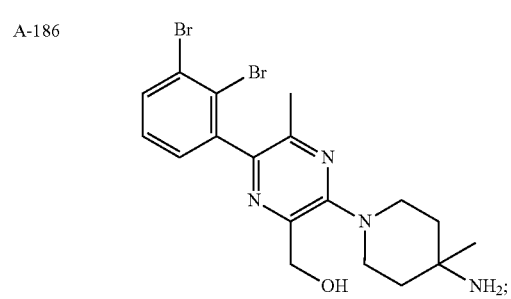 |
| A-187 | 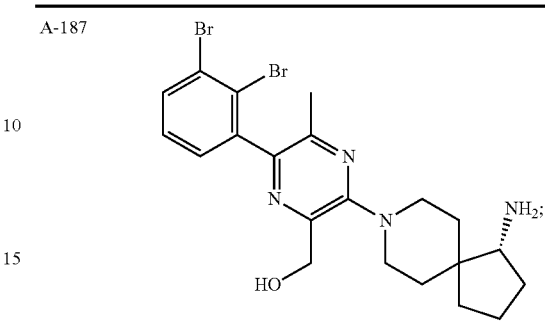 |
| A-188 | 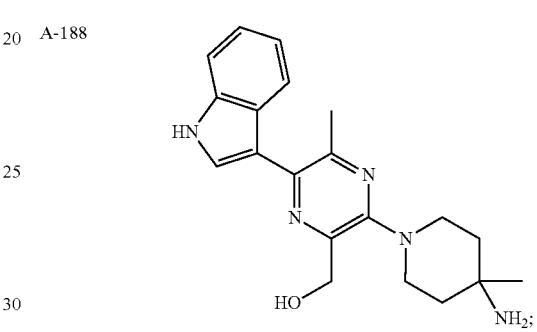 |
| A-189 | 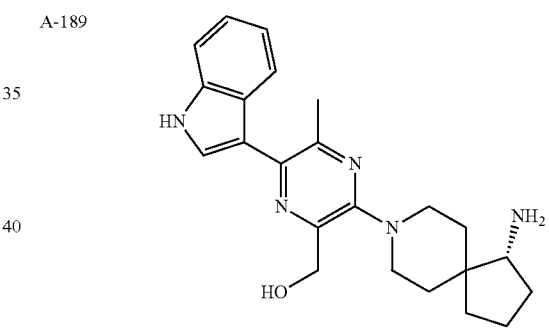 |
| A-190 | 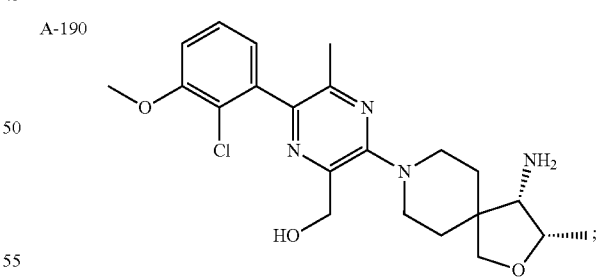 |
| A-191 | 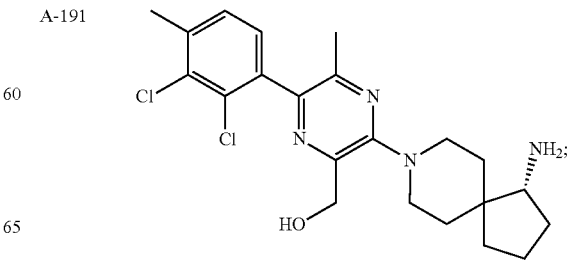 |

| Compound # | Structure |
|---|---|
| A-192 | 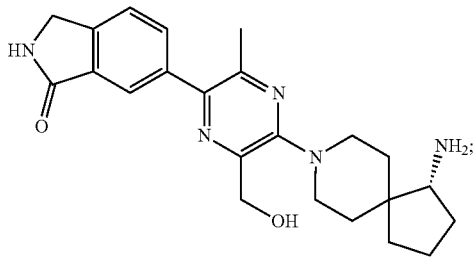 [SMILES: Cc1nc(N2CCC3(CCC[C@H]3N)CC2)c(CO)nc1-c1ccc2c(c1)C(=O)NC2] |
| A-193 | 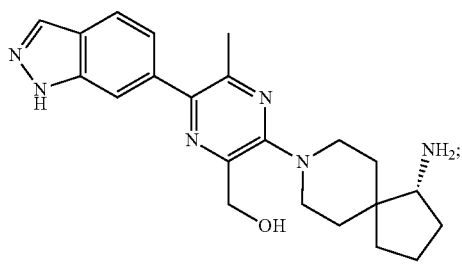 [SMILES: Cc1nc(N2CCC3(CCC[C@H]3N)CC2)c(CO)nc1-c1ccc2cn[nH]c2c1] |
| A-194 | 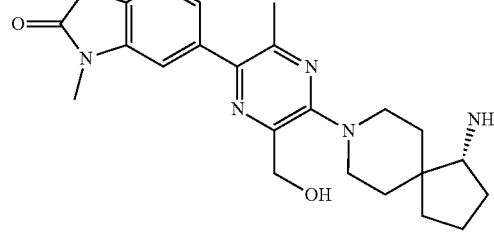 |
| A-195 | 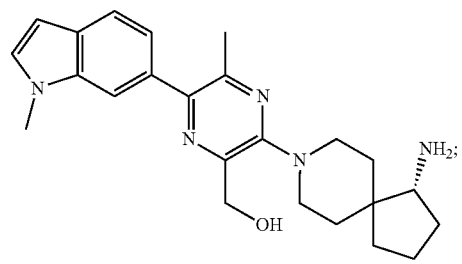 [SMILES: Cc1nc(N2CCC3(CCC[C@H]3N)CC2)c(CO)nc1-c1ccc2ccn(C)c2c1] |
| A-196 | 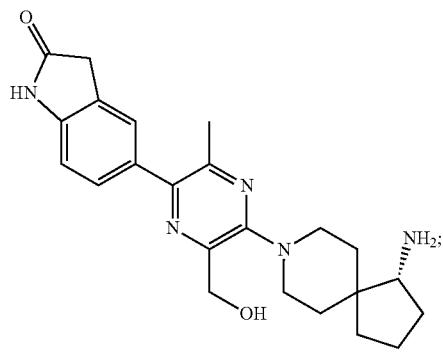 [SMILES: Cc1nc(N2CCC3(CCC[C@H]3N)CC2)c(CO)nc1-c1ccc2c(c1)CC(=O)N2] |
| A-197 | 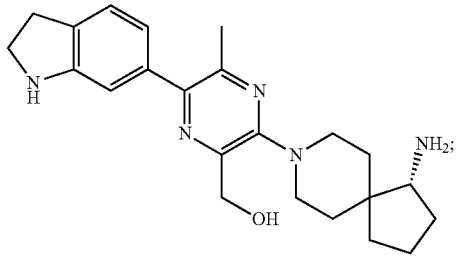 [SMILES: Cc1nc(N2CCC3(CCC[C@H]3N)CC2)c(CO)nc1-c1ccc2c(c1)NCC2] |
| A-198 | 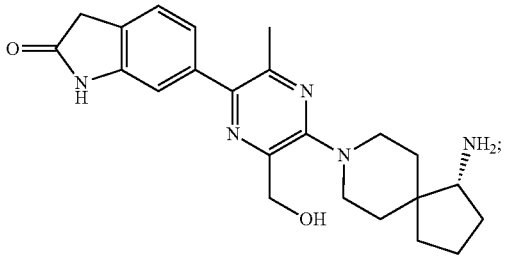 [SMILES: Cc1nc(N2CCC3(CCC[C@H]3N)CC2)c(CO)nc1-c1ccc2c(c1)NC(=O)C2] |
| A-199 | 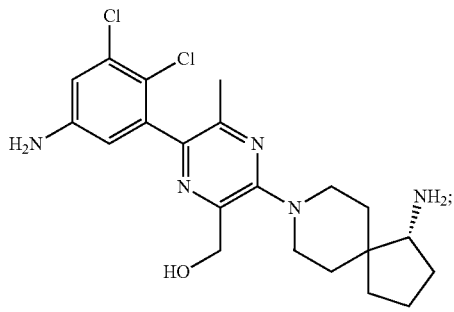 [SMILES: Cc1nc(N2CCC3(CCC[C@H]3N)CC2)c(CO)nc1-c1cc(N)cc(Cl)c1Cl] |
| A-200 | 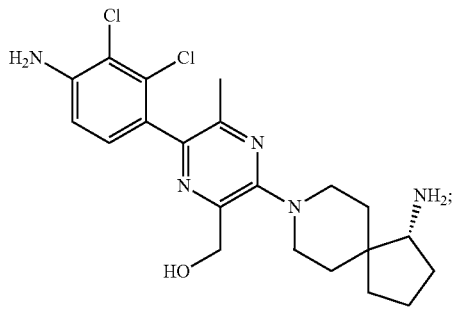 [SMILES: Cc1nc(N2CCC3(CCC[C@H]3N)CC2)c(CO)nc1-c1ccc(N)c(Cl)c1Cl] |
| A-201 | 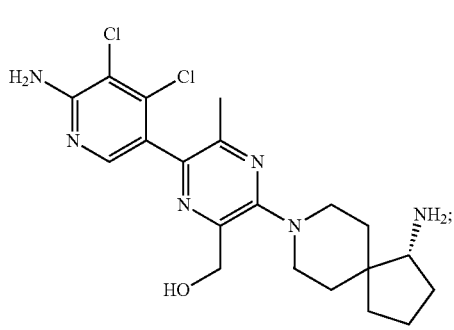 |

| Compound # | Structure |
|---|---|
| A-202 | 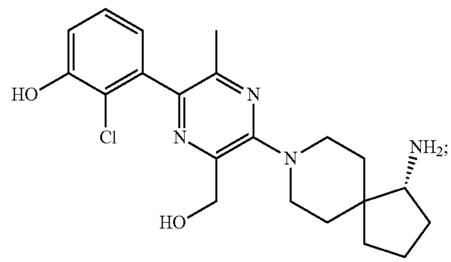 [SMILES: Cc1nc(N2CCC3(CCC[C@H]3N)CC2)c(CO)nc1-c1cccc(O)c1Cl] |
| A-203 | 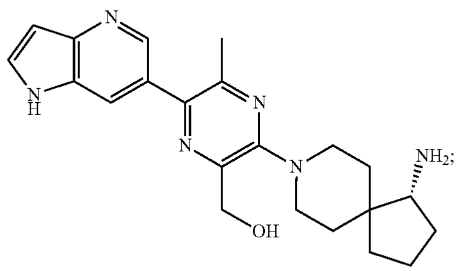 [SMILES: Cc1nc(N2CCC3(CCC[C@H]3N)CC2)c(CO)nc1-c1cnc2cc[nH]c2c1] |
| A-204 | 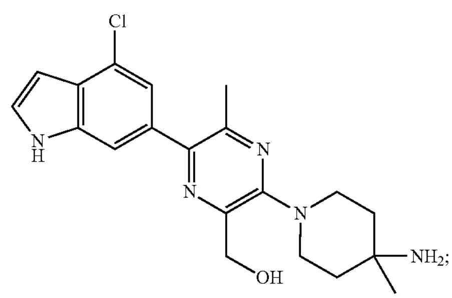 [SMILES: Cc1nc(N2CCC(C)(N)CC2)c(CO)nc1-c1cc(Cl)c2cc[nH]c2c1] |
| A-205 | 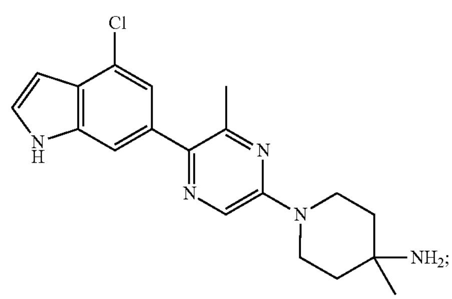 [SMILES: Cc1nc(N2CCC(C)(N)CC2)cnc1-c1cc(Cl)c2cc[nH]c2c1] |
| A-206 | 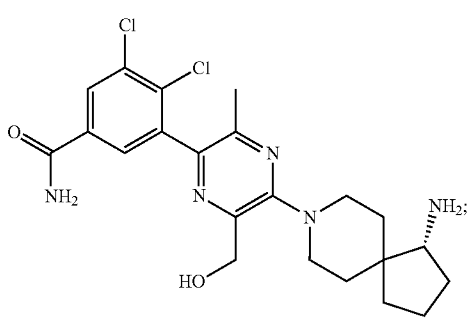 [SMILES: Cc1nc(N2CCC3(CCC[C@H]3N)CC2)c(CO)nc1-c1cc(C(N)=O)cc(Cl)c1Cl] |
| A-207 | |
| A-208 | |
| A-209 | |
| A-210 | |
| A-211 | |

| Compound # | Structure |
|---|---|
| A-212 | 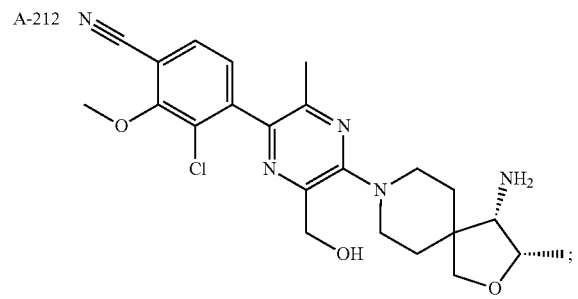 |
| A-213 | 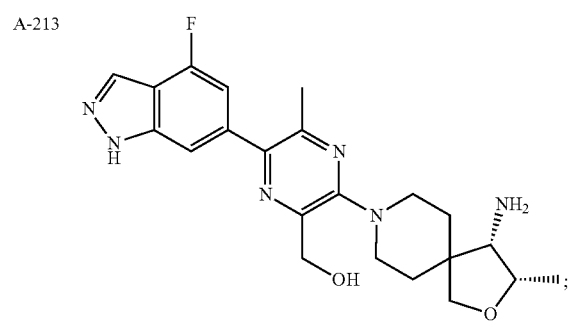 |
| A-214 | 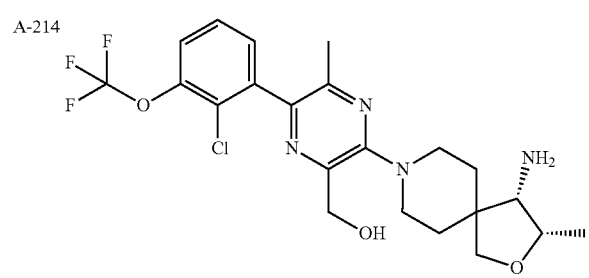 |
| A-215 | 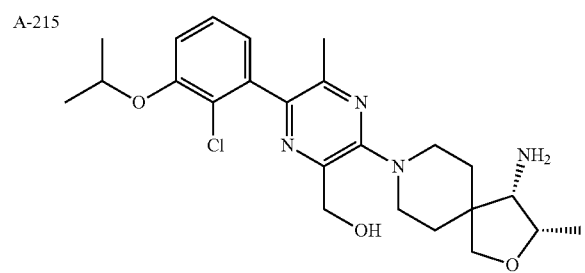 |
| A-216 | 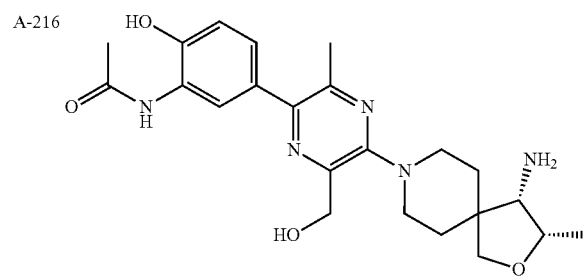 |
| A-217 | 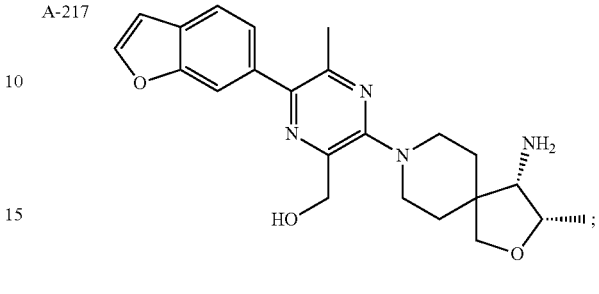 |
| A-218 | 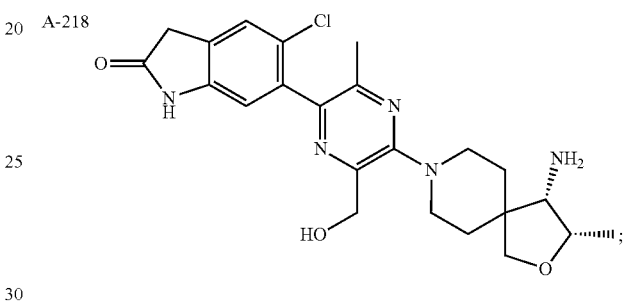 |
| A-219 | 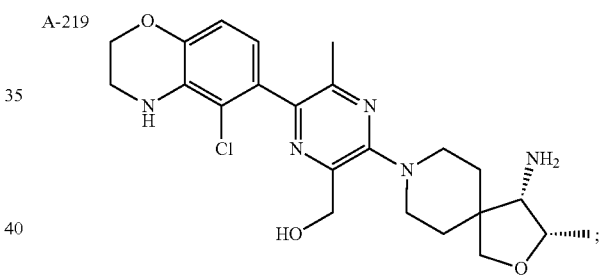 |
| A-220 | 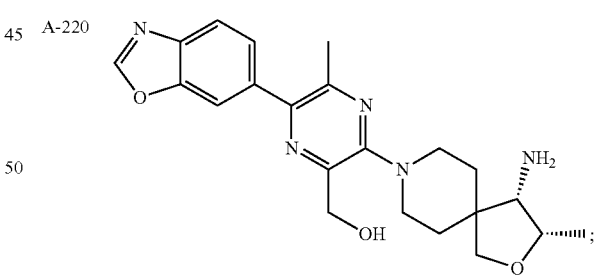 |
| A-221 |  |

| Compound # | Structure |
|---|---|
| A-222 | 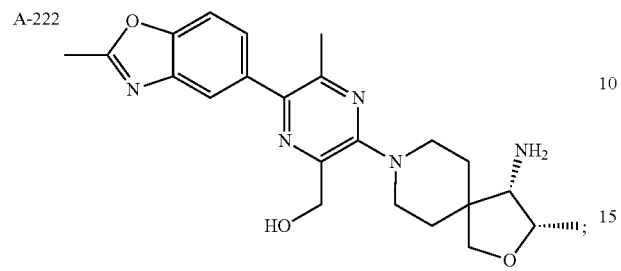 |
| A-223 | 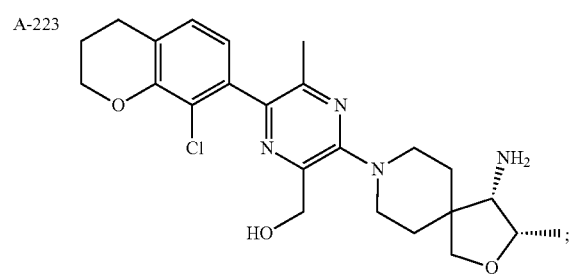 |
| A-224 | 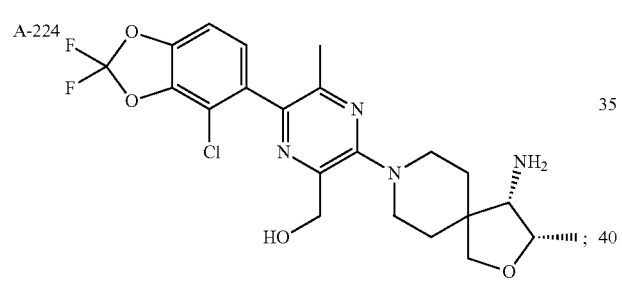 |
| A-225 | 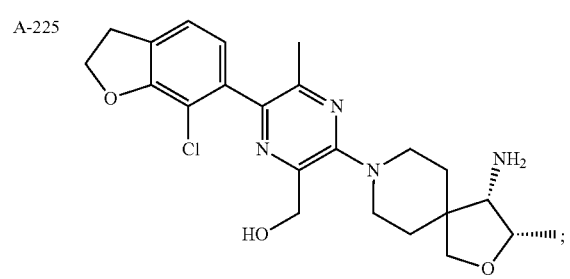 |
| A-226 | 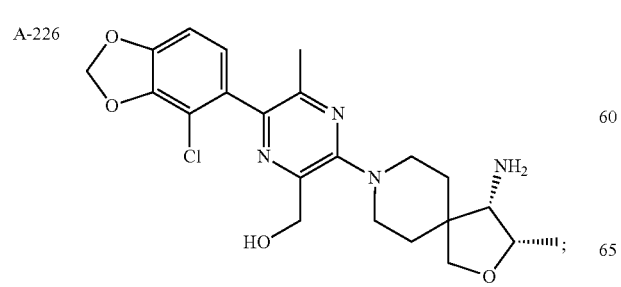 |
| Compound # | Structure |
|---|---|
| A-227 | 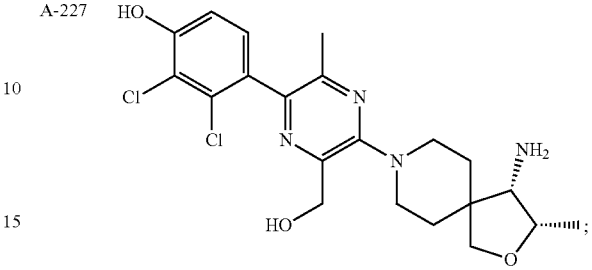 |
| A-228 | 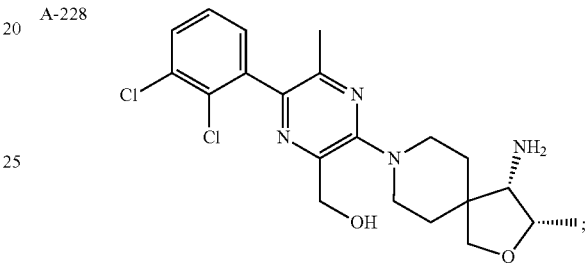 |
| A-229 | 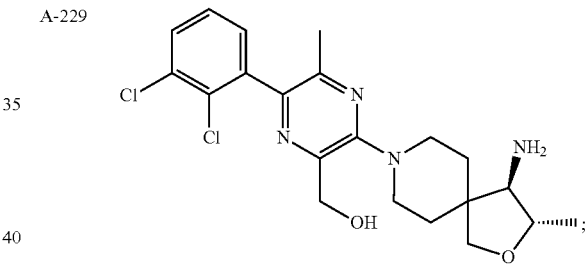 |
| A-230 | 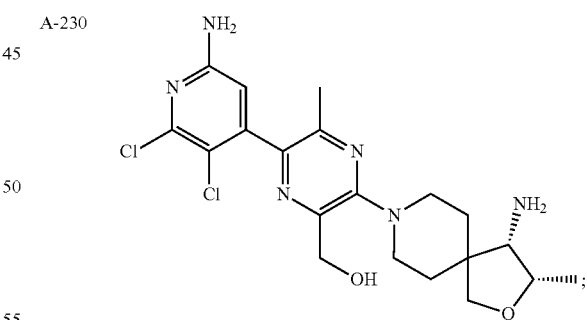 |
| A-231 | 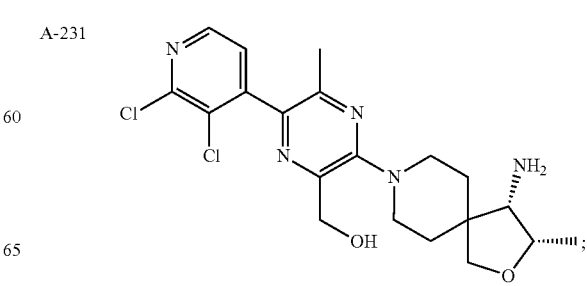 |

| Compound # | Structure |
|---|---|
| A-232 | 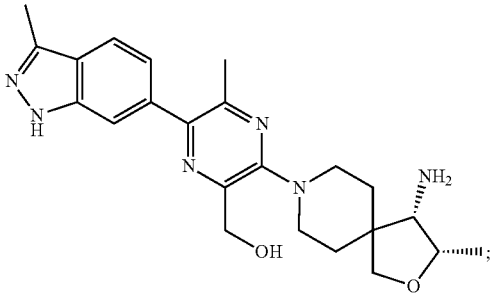 [SMILES: Cc1nc(N2CCC3(CC2)CO[C@@H](C)[C@H]3N)c(CO)nc1-c1ccc2c(C)n[nH]c2c1 ; ";"] |
| A-233 | 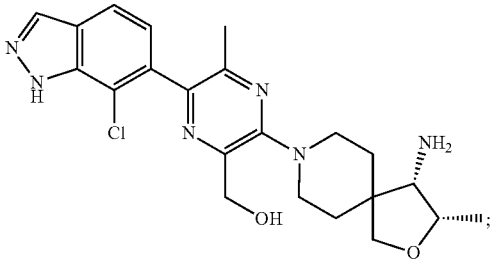 [SMILES: Cc1nc(N2CCC3(CC2)CO[C@@H](C)[C@H]3N)c(CO)nc1-c1ccc2cn[nH]c2c1Cl ; ";"] |
| A-234 | 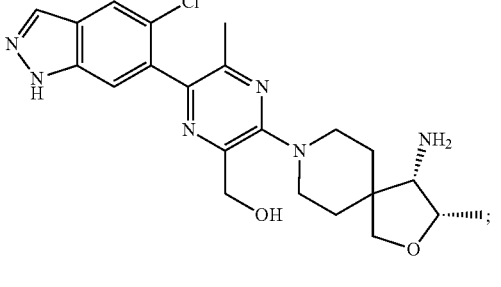 |
| A-235 | 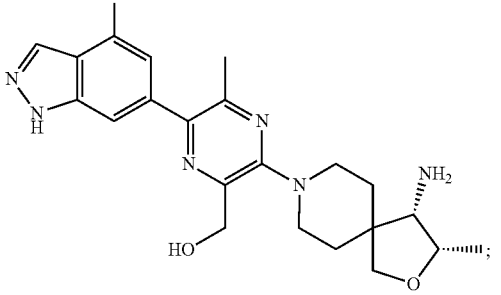 |
| A-236 | 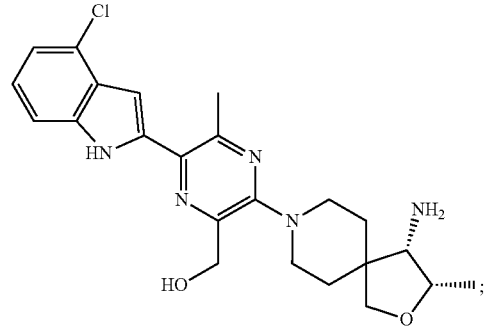 [SMILES: Cc1nc(N2CCC3(CC2)CO[C@@H](C)[C@H]3N)c(CO)nc1-c1cc2c(Cl)cccc2[nH]1 ; ";"] |
| A-237 | 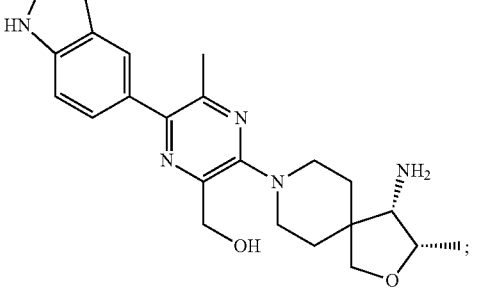 |
| A-238 | 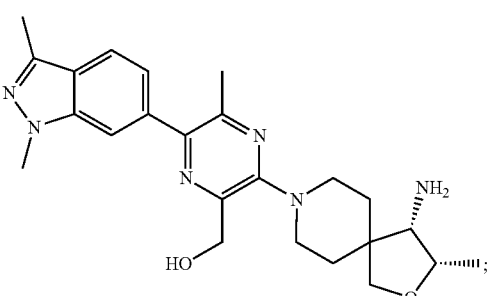 |
| A-239 | 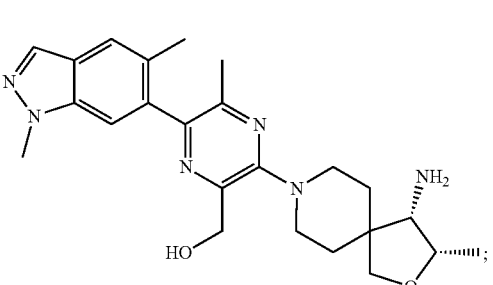 |
| A-240 | 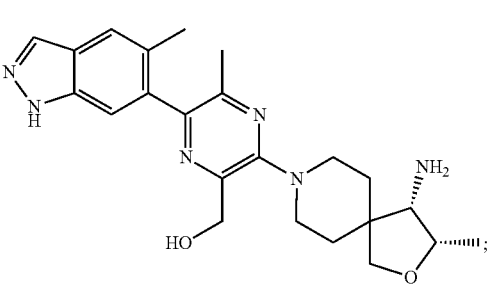 [SMILES: Cc1cc2cn[nH]c2cc1-c1nc(CO)c(N2CCC3(CC2)CO[C@@H](C)[C@H]3N)nc1C ; ";"] |
| A-241 | 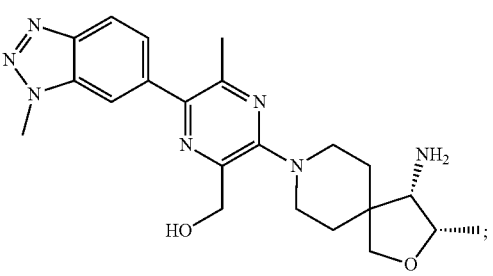 [SMILES: Cc1nc(N2CCC3(CC2)CO[C@@H](C)[C@H]3N)c(CO)nc1-c1ccc2nnn(C)c2c1 ; ";"] |

| Compound # | Structure |
|---|---|
| A-242 | 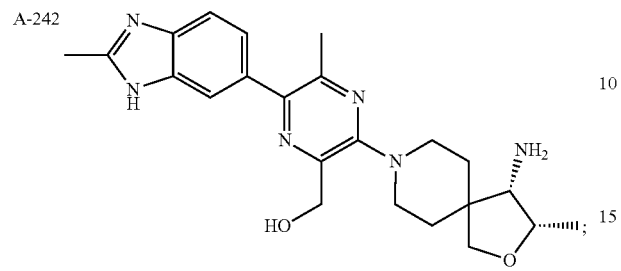 |
| A-243 | 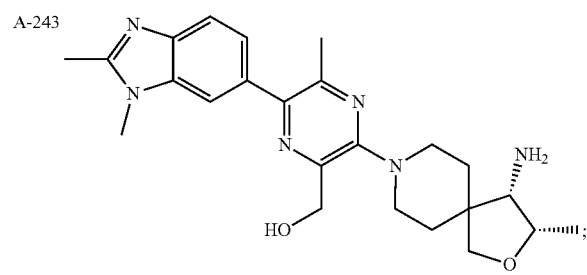 |
| A-244 | 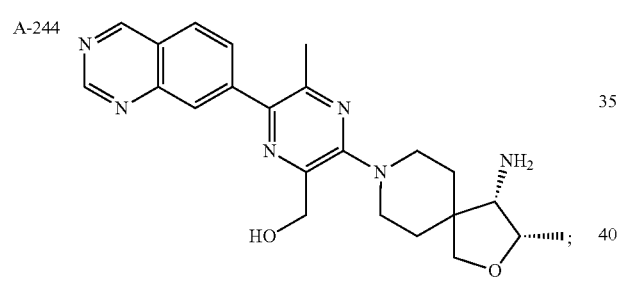 |
| A-245 | 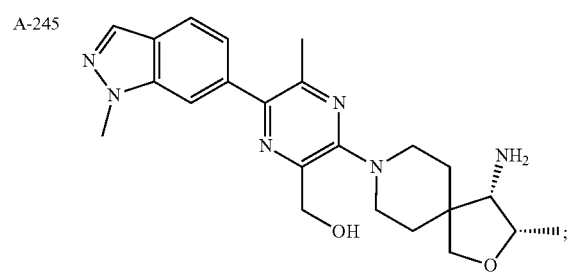 |
| A-246 | 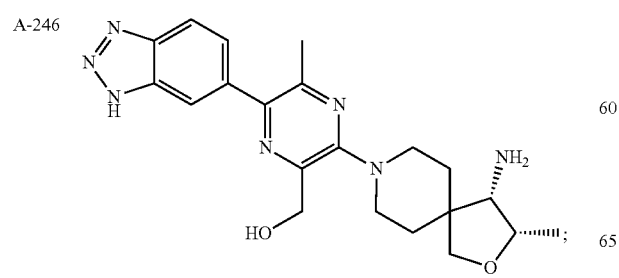 |
| A-247 |  |
| A-248 | 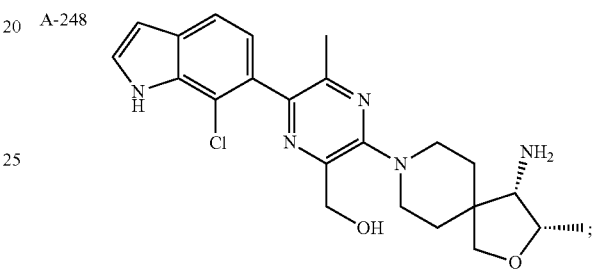 |
| A-249 |  |
| A-250 | 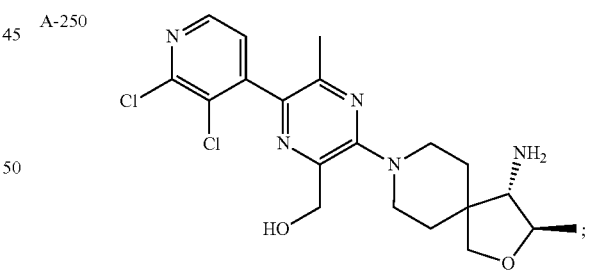 |
| A-251 | 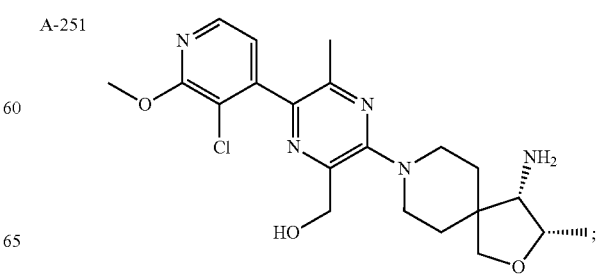 |

| Compound # | Structure |
|---|---|
| A-252 | |
| A-253 | |
| A-254 | |
| A-255 | |
| A-256 | |
| A-257 | 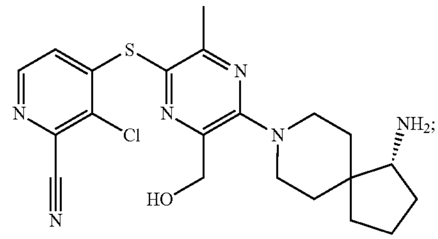 [SMILES: Cc1nc(N2CCC3(CCC[C@H]3N)CC2)c(CO)nc1Sc1ccnc(C#N)c1Cl] |
| A-258 | 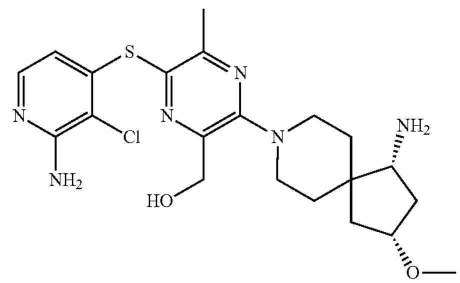 |
| A-259 | 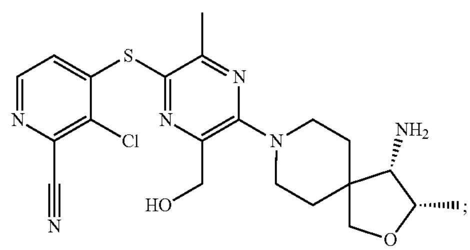 |
| A-260 | 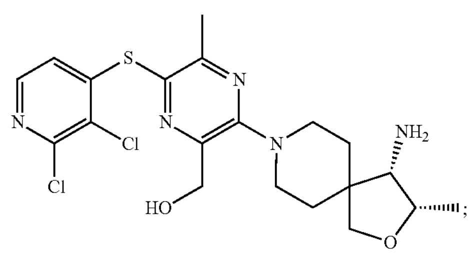 |
| A-261 | 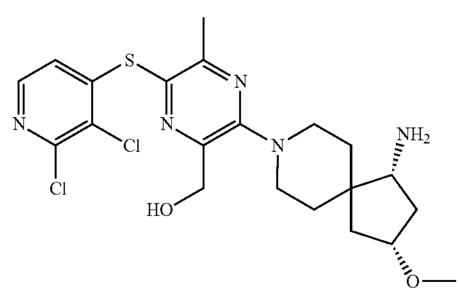 |
| A-262 | 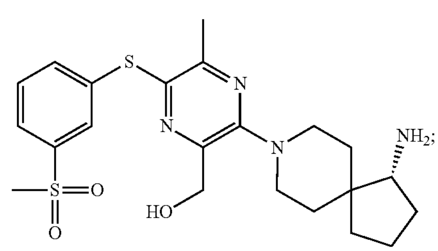 [SMILES: Cc1nc(N2CCC3(CCC[C@H]3N)CC2)c(CO)nc1Sc1cccc(S(C)(=O)=O)c1] |

| Compound # | Structure |
|---|---|
| A-263 | 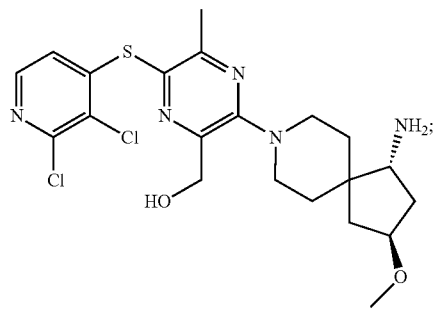 [SMILES: CO[C@@H]1C[C@@H](N)C2(CCN(c3nc(C)c(Sc4ccnc(Cl)c4Cl)nc3CO)CC2)C1] |
| A-264 | 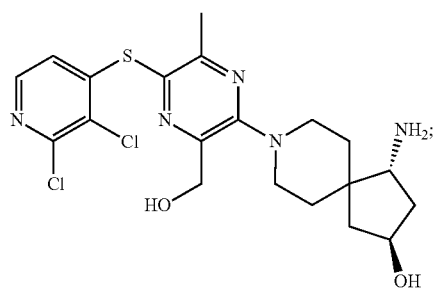 [SMILES: Cc1nc(N2CCC3(CC2)C[C@H](O)C[C@H]3N)c(CO)nc1Sc1ccnc(Cl)c1Cl] |
| A-265 | 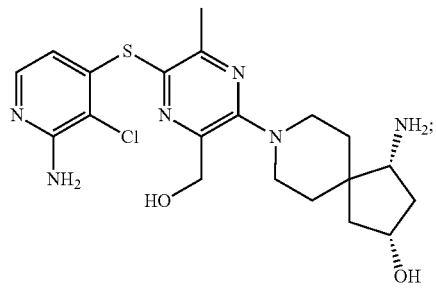 [SMILES: Cc1nc(N2CCC3(CC2)C[C@@H](O)C[C@H]3N)c(CO)nc1Sc1ccnc(N)c1Cl] |
| A-266 | 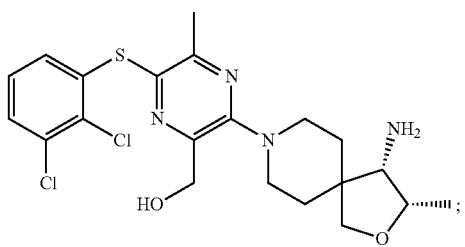 [SMILES: Cc1nc(N2CCC3(CC2)CO[C@@H](C)[C@H]3N)c(CO)nc1Sc1cccc(Cl)c1Cl ; ";"] |
| A-267 | 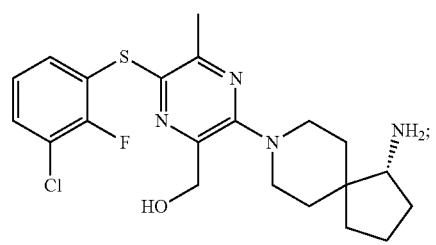 [SMILES: Cc1nc(N2CCC3(CCC[C@H]3N)CC2)c(CO)nc1Sc1cccc(Cl)c1F] |
| A-268 | 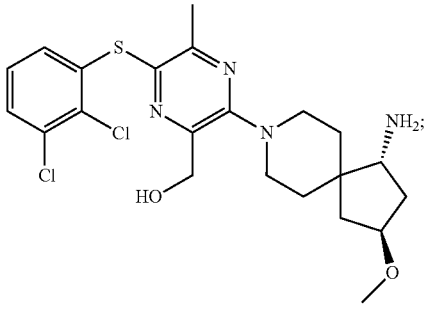 [SMILES: CO[C@@H]1C[C@@H](N)C2(CCN(c3nc(C)c(Sc4cccc(Cl)c4Cl)nc3CO)CC2)C1] |
| A-269 | 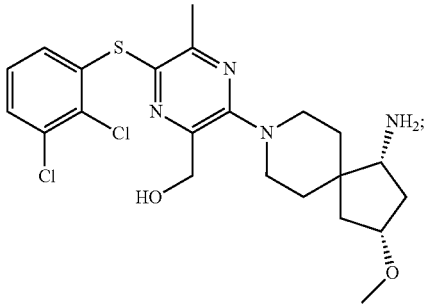 [SMILES: CO[C@H]1C[C@@H](N)C2(CCN(c3nc(C)c(Sc4cccc(Cl)c4Cl)nc3CO)CC2)C1] |
| A-270 | 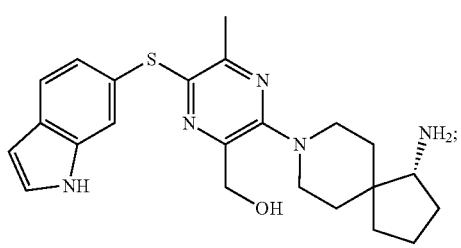 [SMILES: Cc1nc(N2CCC3(CCC[C@H]3N)CC2)c(CO)nc1Sc1ccc2cc[nH]c2c1] |
| A-271 | 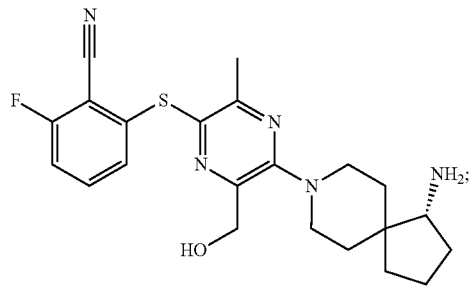 [SMILES: Cc1nc(N2CCC3(CCC[C@H]3N)CC2)c(CO)nc1Sc1cccc(F)c1C#N] |
| A-272 | 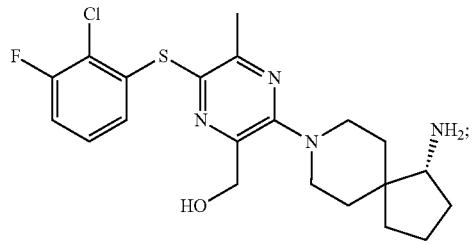 [SMILES: Cc1nc(N2CCC3(CCC[C@H]3N)CC2)c(CO)nc1Sc1cccc(F)c1Cl] |

| Compound # | Structure |
|---|---|
| A-273 | 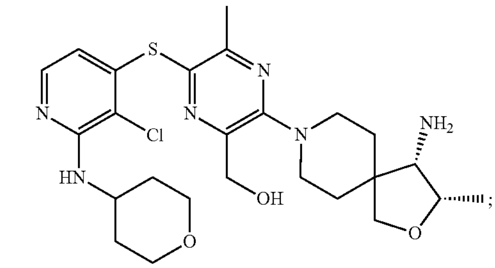 |
| A-274 | 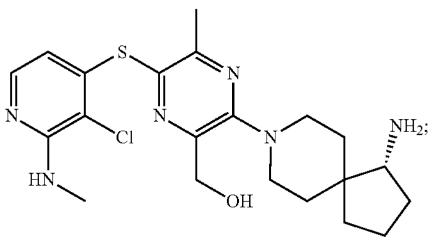 [SMILES: CNc1nccc(Sc2nc(CO)c(N3CCC4(CCC[C@H]4N)CC3)nc2C)c1Cl] |
| A-275 | 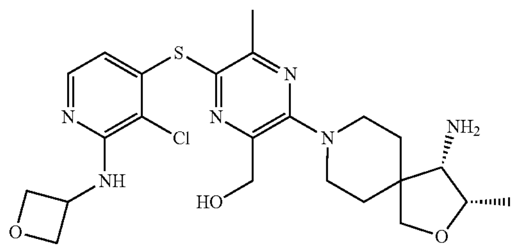 |
| A-276 | 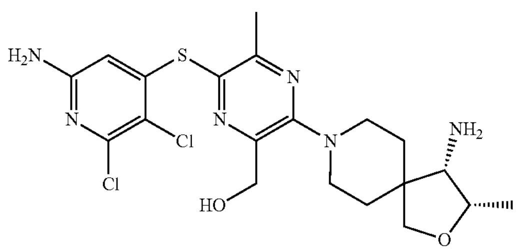 |
| A-277 | 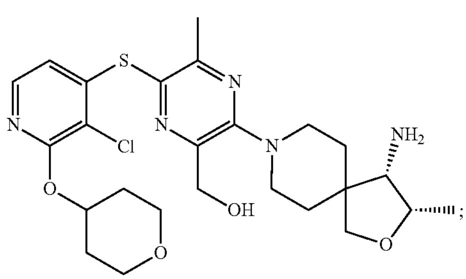 [SMILES: Cc1nc(N2CCC3(CC2)CO[C@@H](C)[C@H]3N)c(CO)nc1Sc1ccnc(OC2CCOCC2)c1Cl ; ";"] |
| A-278 | 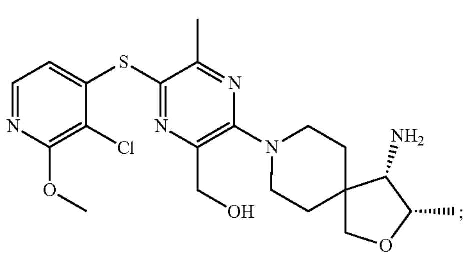 [SMILES: COc1nccc(Sc2nc(CO)c(N3CCC4(CC3)CO[C@@H](C)[C@H]4N)nc2C)c1Cl ; ";"] |
| A-279 | |
| A-280 | |
| A-281 | |
| A-282 | |
| A-283 | |

| Compound # | Structure |
|---|---|
| A-284 | 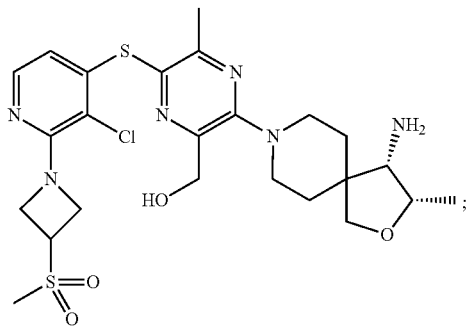 [SMILES: Cc1nc(N2CCC3(CC2)CO[C@@H](C)[C@H]3N)c(CO)nc1Sc1ccnc(N2CC(S(C)(=O)=O)C2)c1Cl ; ";"] |
| A-285 | 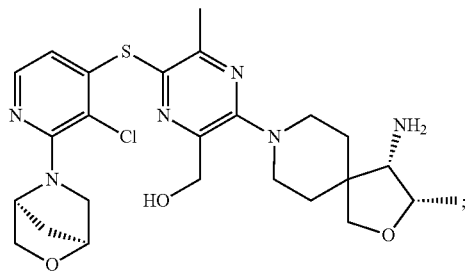 [SMILES: Cc1nc(N2CCC3(CC2)CO[C@@H](C)[C@H]3N)c(CO)nc1Sc1ccnc(N2C[C@@H]3C[C@H]2CO3)c1Cl ; ";"] |
| A-386 | 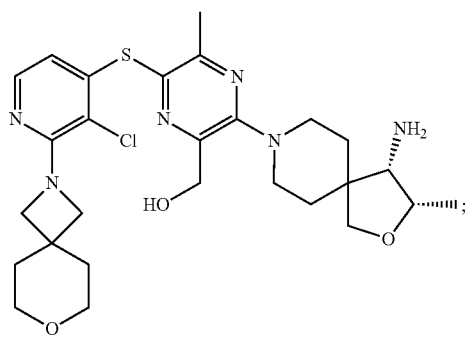 [SMILES: Cc1nc(N2CCC3(CC2)CO[C@@H](C)[C@H]3N)c(CO)nc1Sc1ccnc(N2CC3(CCOCC3)C2)c1Cl ; ";"] |
| A-287 | 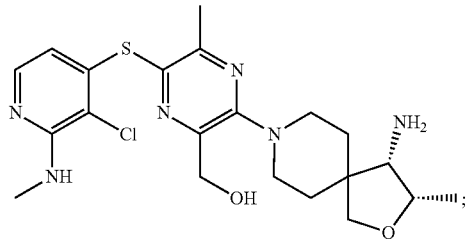 |
| A-288 | 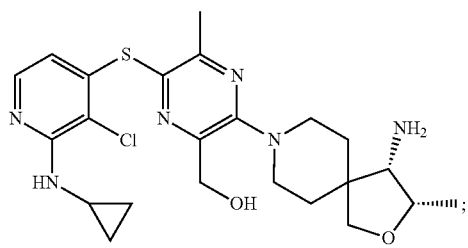 |
| A-289 | 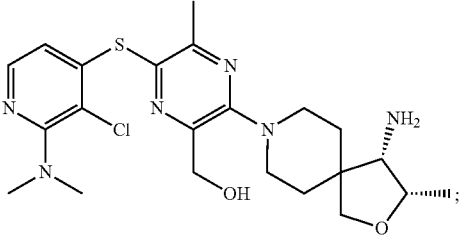 [SMILES: Cc1nc(N2CCC3(CC2)CO[C@@H](C)[C@H]3N)c(CO)nc1Sc1ccnc(N(C)C)c1Cl ; ";"] |
| A-290 | 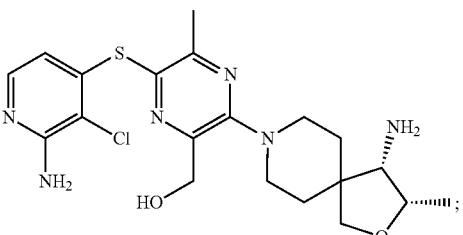 |
| A-291 | 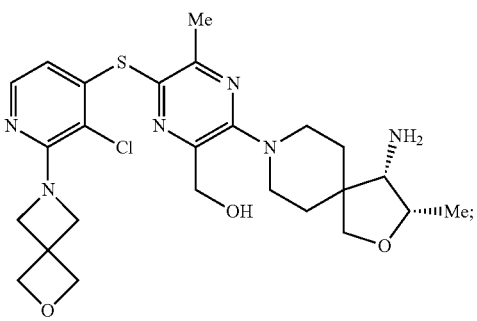 [SMILES: Cc1nc(N2CCC3(CC2)CO[C@@H](C)[C@H]3N)c(CO)nc1Sc1ccnc(N2CC3(COC3)C2)c1Cl] |
| A-292 | 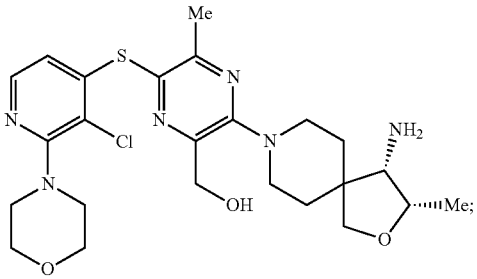 [SMILES: Cc1nc(N2CCC3(CC2)CO[C@@H](C)[C@H]3N)c(CO)nc1Sc1ccnc(N2CCOCC2)c1Cl] |
| A-293 | 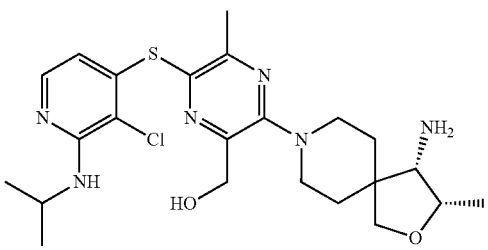 |

| Compound # | Structure |
|---|---|
| A-294 | 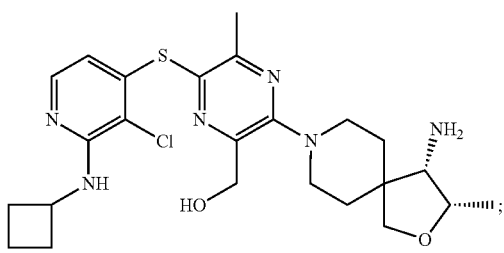 [SMILES: Cc1nc(N2CCC3(CC2)CO[C@@H](C)[C@H]3N)c(CO)nc1Sc1ccnc(NC2CCC2)c1Cl ; ";"] |
| A-295 | 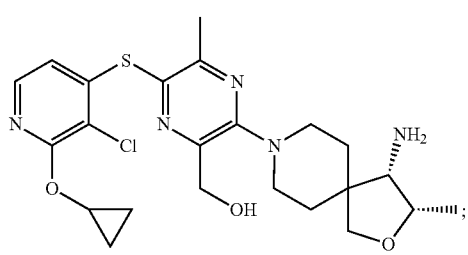 |
| A-296 | 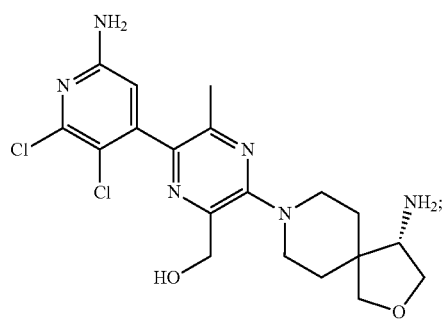 [SMILES: Cc1nc(N2CCC3(CC2)COC[C@H]3N)c(CO)nc1-c1cc(N)nc(Cl)c1Cl] |
| A-297 | 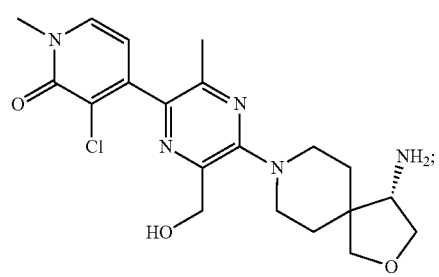 [SMILES: Cc1nc(N2CCC3(CC2)COC[C@H]3N)c(CO)nc1-c1ccn(C)c(=O)c1Cl] |
| A-298 | 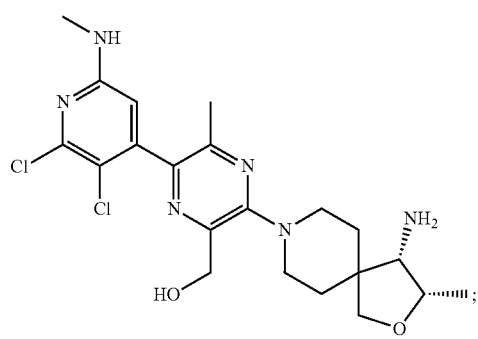 |
| A-299 | 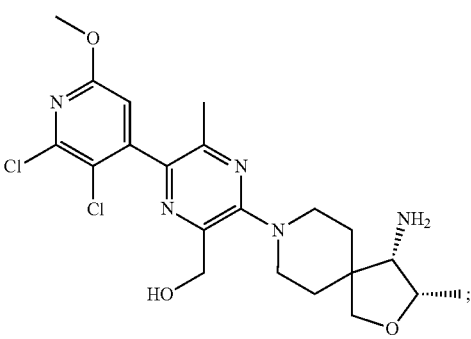 [SMILES: COc1cc(-c2nc(CO)c(N3CCC4(CC3)CO[C@@H](C)[C@H]4N)nc2C)c(Cl)c(Cl)n1 ; ";"] |
| A-300 | 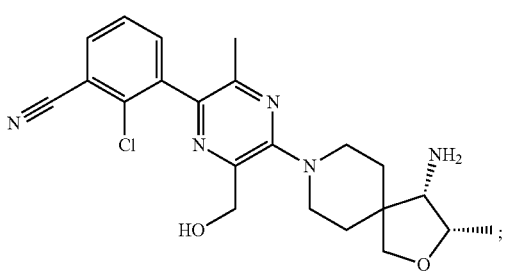 [SMILES: Cc1nc(N2CCC3(CC2)CO[C@@H](C)[C@H]3N)c(CO)nc1-c1cccc(C#N)c1Cl ; ";"] |
| A-301 | 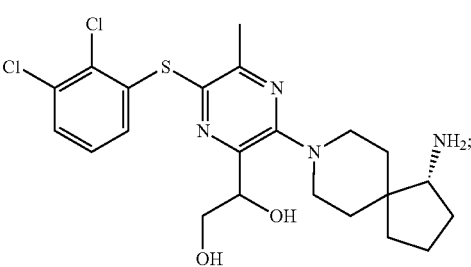 [SMILES: Cc1nc(N2CCC3(CCC[C@H]3N)CC2)c(C(O)CO)nc1Sc1cccc(Cl)c1Cl] |
| A-302 | 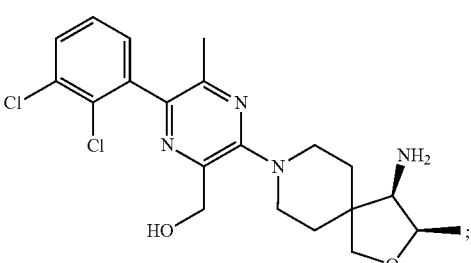 |
| A-303 | 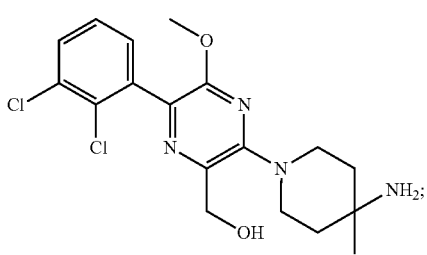 [SMILES: COc1nc(N2CCC(C)(N)CC2)c(CO)nc1-c1cccc(Cl)c1Cl] |

-continued

| Compound # | Structure |
|---|---|
| A-304 | (structure) |
| A-305 | (structure) |
| A-306 | (structure) |
| A-307 | (structure) |
| A-308 | (structure) |
| A-309 | (structure) | and pharmaceutically acceptable salts, prodrugs, solvates, hydrates, tautomers, or isomers thereof.

In one or more embodiments of Formula I, II, III, I-V1, I-V2, I-W, I-X, I-Y, or I-Z, A is a 5- to 12-membered monocyclic or polycyclic cycloalkyl. In one or more embodiments of Formula I, II, III, I-V1, I-V2, I-W, I-X, I-Y, or I-Z, A is heterocycloalkyl. In one or more embodiments of Formula I, II, III, I-V1, I-V2, I-W, I-X, I-Y, or I-Z, A is aryl. In one or more embodiments of Formula I, II, III, I-V1, I-V2, I-W, I-X, I-Y, or I-Z, A is heteroaryl. In one or more embodiments of Formula I, II, III, I-V1, I-V2, I-W, I-X, I-Y, or I-Z, A is pyridinyl.

In one or more embodiments of Formula I, I-V1, I-V2, I-W, I-X, I-Y, or I-Z, $Y^1$ is —S—. In one or more embodiments of Formula I, I-V1, I-V2, I-W, I-X, I-Y, or I-Z, $Y^1$ is a direct bond. In one or more embodiments of Formula I-V1, I-V2, I-W, or I-Z, $Y^1$ is —NH—. In one or more embodiments of Formula I-V1, I-V2, I-W, or I-Z, $Y^1$ is —C(=CH$_2$)—. In one or more embodiments of Formula I-V1, I-V2, I-W, or I-Z, $Y^1$ is —S(O$_2$)—. In one or more embodiments of Formula I-V1, I-V2, I-W, or I-Z, $Y^1$ is —S(O$_2$)—NH—.

In one or more embodiments of Formula I, II, III, I-W, I-X, I-Y, or I-Z, $Y^2$ is —NR$^a$—. In one or more embodiments of Formula I, II, III, I-W, I-X, I-Y, or I-Z, $Y^2$ is —(CR$^a{}_2$)$_m$—. In one or more embodiments of Formula I, II, III, I-W, I-X, I-Y, or I-Z, $Y^2$ is —C(O)—. In one or more embodiments of Formula I, II, III, I-W, I-X, I-Y, or I-Z, $Y^2$ is —C(R$^a$)$_2$NH— or —(CR$^a{}_2$)$_m$O—. In one or more embodiments of Formula I, II, III, I-W, I-X, I-Y, or I-Z, $Y^2$ is —C(O)N(R$^a$)—, —N(R$^a$)C(O)—, —S(O)$_2$N(R$^a$)—, —N(R$^a$)S(O)$_2$—, —N(R$^a$)C(S)—, or —C(S)N(R$^a$)—. In one or more embodiments of Formula I, II, III, I-W, I-X, I-Y, or I-Z, $Y^2$ is —N(R$^a$)C(O)N(R$^a$)—, —N(R$^a$)C(S)N(R$^a$)—, —OC(O)N(R$^a$)—, —N(R$^a$)C(O)O—, or —C(O)N(R$^a$)O—. In one or more embodiments of Formula I, II, III, I-W, I-X, or I-Y, $Y^2$ is —C(O)O—, —OC(O)—, or —OC(O)O—.

In one or more embodiments of Formula I, II, III, I-V1, I-V2, I-W, I-X, I-Y, or I-Z, $R^1$ is independently, at each occurrence, selected from —H, optionally substituted —C$_1$-C$_6$alkyl, halogen, —OH, —CN, and —NR$^5$R$^6$. In one or more embodiments of Formula I, II, III, I-V1, I-V2, I-W, I-X, I-Y, or I-Z, $R^1$ is independently, at each occurrence, selected from —H, optionally substituted —C$_1$-C$_6$alkyl, halogen, —OH, and —NR$^5$R$^6$. In one or more embodiments of Formula I, II, III, I-V1, I-V2, I-W, I-X, I-Y, or I-Z, $R^1$ is independently, at each occurrence, selected from —H, optionally substituted —C$_1$-C$_6$alkyl, halogen, and —NR$^5$R$^6$. In one or more embodiments of Formula I, II, III, I-V1, I-V2, I-W, I-X, I-Y, or I-Z, $R^1$ is independently, at each occurrence, selected from —H, methyl, fluoro, chloro, bromo, and —NH$_2$. In one or more embodiments of Formula I, II, III, I-V1, I-V2, I-W, I-X, I-Y, or I-Z, R$^1$ is independently, at each occurrence, selected from —H, methyl, fluoro, chloro, and —NH$_2$. In one or more embodiments of Formula I, II, III, I-V1, I-V2, I-W, I-X, I-Y, or I-Z, R$^1$ is —H. In some embodiments wherein R$^1$ is —C$_1$-C$_6$alkyl, the alkyl is substituted with halogen. In certain such embodiments, the halogen is fluoro.

In one or more embodiments of Formula I-V1, I-V2, or I-W, R$^1$ is oxo.

In one or more embodiments of Formula I, II, III, I-V1, I-V2, I-W, I-X, I-Y, or I-Z, R$^1$ is —S(O)$_2$R$^5$. In certain such embodiments, R$^5$ is —C$_1$-C$_6$alkyl.

In one or more embodiments of Formula I-V1, I-V2, or I-W, R$^1$ is heteroaryl. In certain such embodiments wherein R$^1$ is heteroaryl, the heteroaryl is substituted with R$^5$. In certain such embodiments, R$^5$ is —C$_1$-C$_6$alkyl.

In one or more embodiments of I-V1, I-V2, or I-W, R$^1$ is —C(O)NR$^5$R$^6$. In certain such embodiments, R$^5$ and R$^6$ are both —H.

In one or more embodiments of Formula I-V1, I-V2, or I-W, R$^1$ is optionally substituted heterocyclyl. In one or more embodiments of Formula I-V1, I-V2, or I-W, R$^1$ is optionally substituted spiroheterocyclyl.

In one or more embodiments of Formula I, II, III, I-V1, I-V2, I-W, I-X, I-Y, or I-Z, R$^1$ is —NR$^5$R$^6$. In certain such embodiments, R$^5$ is independently, at each occurrence, —H or —C$_1$-C$_6$alkyl and R$^6$ is independently, at each occurrence, —C$_1$-C$_6$alkyl, —C$_3$-C$_8$cycloalkyl, or monocyclic or polycyclic 3- to 12-membered heterocycle.

In one or more embodiments of Formula I-V1, I-V2, or I-W, R$^1$ is —OR$^6$. In certain such embodiments, R$^6$ is independently, at each occurrence, —C$_1$-C$_6$alkyl, —C$_3$-C$_8$cycloalkyl, or monocyclic or polycyclic 3- to 12-membered heterocycle. In certain such embodiments, R$^6$ is —CH$_3$.

In one or more embodiments of Formula I, II, III, I-W, I-V1, I-V2, I-X, I-Y, or I-Z, R$^2$ is —OR$^b$. In certain such embodiments when R$^2$ is —OR$^b$, R$^b$ is —H. In certain embodiments when R$^2$ is —OR$^b$, R$^b$ is optionally substituted —C$_1$-C$_6$alkyl.

In one or more embodiments of Formula I, II, III, I-V1, I-V2, I-W, I-X, I-Y, or I-Z, R$^2$ is optionally substituted —C$_1$-C$_6$alkyl. In one or more embodiments of Formula I, II, III, I-V1, I-V2, I-W, I-X, I-Y, or I-Z, R$^2$ is —CN. In one or more embodiments of Formula I, II, III, I-V1, I-V2, I-W, I-X, I-Y, or I-Z, R$^2$ is optionally substituted —C$_2$-C$_6$alkenyl. In one or more embodiments of Formula I, II, III, I-V1, I-V2, I-W, I-X, I-Y, or I-Z, R$^2$ is optionally substituted —C$_4$-C$_8$cycloalkenyl. In one or more embodiments of Formula I, II, III, I-W, I-V1, I-V2, I-X, I-Y, or I-Z, R$^2$ is optionally substituted —C$_2$-C$_6$alkynyl. In one or more embodiments of Formula I, II, III, I-V1, I-V2, I-W, I-X, I-Y, or I-Z, R$^2$ is optionally substituted —C$_3$-C$_8$cycloalkyl. In one or more embodiments of Formula I, II, III, I-V1, I-V2, I-W, I-X, I-Y, or I-Z, R$^2$ is optionally substituted aryl. In one or more embodiments of Formula I, II, III, I-V1, I-V2, I-W, I-X, I-Y, or I-Z, R$^2$ is optionally substituted heterocyclyl containing 1-5 heteroatoms selected from the group consisting of N, S, P, and O. In one or more embodiments of Formula I, II, III, I-V1, I-V2, I-W, I-X, I-Y, or I-Z, R$^2$ is optionally substituted heteroaryl containing 1-5 heteroatoms selected from the group consisting of N, S, P, and O. In one or more embodiments of Formula I, II, III, I-V1, I-V2, I-W, I-X, I-Y, or I-Z, R$^2$ is methyl. In one or more embodiments of Formula I-V1, I-V2, I-W or I-Z, R$^2$ is halogen. In one or more embodiments of Formula I-V1 or I-V2, R$^2$ is —NH$_2$.

In one or more embodiments of Formula I-V1, I-V2, I-W or I-Z, R$^2$ is —C(O)OR$^b$. In certain such embodiments, R$^b$ is optionally substituted —C$_1$-C$_6$alkyl.

In one or more embodiments of Formula I, II, III, I-W, I-X, or I-Y, R$^a$ is —H. In one or more embodiments of Formula I, II, III, I-W, I-X, or I-Y, R$^a$ is —OH. In one or more embodiments of Formula I, II, III, I-W, I-X, or I-Y, R$^a$ is optionally substituted —C$_3$-C$_8$cycloalkyl. In one or more embodiments of Formula I, II, III, I-W, I-X, or I-Y, R$^a$ is optionally substituted —C$_1$-C$_6$alkyl.

In one or more embodiments of Formula I, II, III, I-V1, I-V2, I-W, I-X, I-Y, or I-Z, R$^b$ is —H. In one or more embodiments of Formula I, II, III, I-V1, I-V2, I-W, I-X, I-Y, or I-Z, R$^b$ is optionally substituted —C$_1$-C$_6$alkyl. In one or more embodiments of Formula I, II, III, I-V1, I-V2, I-W, I-X, I-Y, or I-Z, R$^b$ is optionally substituted —C$_3$-C$_8$cycloalkyl. In one or more embodiments of Formula I, II, III, I-V1, I-V2, I-W, I-X, I-Y, or I-Z, R$^b$ is optionally substituted —C$_2$-C$_6$alkenyl. In one or more embodiments of Formula I, II, III, I-V1, I-V2, I-W, I-X, I-Y, or I-Z, R$^b$ is optionally substituted heterocyclyl containing 1-5 heteroatoms selected from the group consisting of N, S, P, and O. In one or more embodiments of I-V1, I-V2, or I-W, R$^b$ is optionally substituted heteroaryl containing 1-5 heteroatoms selected from the group consisting of N, S, P, and O. In one or more embodiments of I-V1, I-V2, or I-W, R$^b$ is optionally substituted —(CH$_2$)$_n$-aryl.

In one or more embodiments of Formula I-V1, I-V2, or I-W, R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F.

In one or more embodiments of Formula I-Y or I-Z, R$^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F.

In one or more embodiments of Formula I, II, III, I-V1, I-W, I-X, I-Y, or I-Z, R$^3$ is optionally substituted —C$_1$-C$_6$alkyl. In one or more embodiments of Formula I, II, III, I-V1, I-W, I-X, I-Y, or I-Z, R$^3$ is an optionally substituted 3- to 12-membered monocyclic or polycyclic heterocycle. In one or more embodiments of Formula I, II, III, I-V1, I-W, I-X, I-Y, or I-Z, R$^3$ is an optionally substituted 3- to 12-membered monocyclic heterocycle. In one or more embodiments of Formula I, II, III, I-V1, I-W, I-X, I-Y, or I-Z, R$^3$ is an optionally substituted 3- to 12-membered polycyclic heterocycle. In one or more embodiments of Formula I-V1 or I-W, R$^3$ is an optionally substituted 5- to 12-membered spiroheterocycle. In one or more embodiments of Formula I-V1 or I-W, R$^3$ is —C$_1$-C$_6$alkyl, which is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl.

In one or more embodiments of Formula I, II, III, I-V2, I-W, I-X, or I-Y, $R^4$ is —H. In one or more embodiments of Formula I, II, III, I-V2, I-W, I-X, or I-Y, $R^4$ is optionally substituted —$C_1$-$C_6$alkyl. In one or more embodiments of Formula or I-V2 or I-W, $R^4$ is —$C_1$-$C_6$alkyl, substituted with one or more —OH, —$NH_2$, —$OR^b$, halogen, or oxo. In one or more embodiments of Formula I, II, III, I-W, I-X, or I-Y, $R^4$ is —$C_1$-$C_6$alkyl substituted with —OH. In one or more embodiments of Formula I, II, III, I-V2, I-W, I-X, or I-Y, $R^4$ is —$CH_2$—OH. In one or more embodiments of Formula I-V2, I-W, or I-Y, $R^4$ is —CN. In one or more embodiments of Formula I-V2, I-W, I-X, or I-Y, $R^4$ is optionally substituted heteroaryl. In one or more embodiments of Formula I-V2 or I-W, $R^4$ is —$C_1$-$C_6$haloalkyl or —$C_1$-$C_6$hydroxyalkyl. In one or more embodiments of Formula I-V2 or I-W, $R^4$ is —$CF_2$OH or —CHFOH.

In one or more embodiments of Formula I-V2, I-W, or I-Y, $R^4$ is —C(O)$R^b$. In certain such embodiments, $R^b$ is optionally substituted heterocyclyl.

In one or more embodiments of Formula I-V2, I-W, or I-Y, $R^4$ is —C(O)NH($CH_2$)$_n R^b$. In certain such embodiments, $R^b$ is optionally substituted heterocyclyl and n is 0.

In one or more embodiments of Formula I-V2, I-W, or I-Y, $R^4$ is —C(O)NH($CH_2$)$_n$OH. In certain such embodiments, n is 0.

In one or more embodiments of Formula I-V2, I-W, or I-Y, $R^4$ is —NH($CH_2$)$_n$OH. In certain such embodiments, n is 2.

In one or more embodiments of Formula I-V2, I-W, I-X, or I-Y, $R^4$ is —$NHR^5$. In certain such embodiments, $R^5$ is —H.

In one or more embodiments of Formula I-V2, I-W, I-X, or I-Y, $R^4$ is —$OR^5$. In certain such embodiments, $R^5$ is —H.

In one or more embodiments of Formula I-V2, I-W, I-X, or I-Y, $R^4$ is —C(O)$OR^5$. In certain such embodiments, $R^5$ is —$C_1$-$C_6$alkyl.

In one or more embodiments of Formula I-V2, I-W, I-X, or I-Y, $R^4$ is —C(O)$NR^5 R^6$. In certain such embodiments, $R^5$ and $R^6$ are both —H.

In one or more embodiments of Formula I, II, III, I-W, I-X, or I-Y, when $Y^2$ is —$NR^a$— or —$(CR^a_2)_m$—, $R^3$ and $R^a$ together with the atom to which they are attached combine to form an optionally substituted 3- to 12-membered monocyclic heterocycle. In one or more embodiments of Formula I, II, III, I-W, I-X, or I-Y when $Y^2$ is —$NR^a$— or —$(CR^a_2)_m$—, $R^3$ and W together with the atoms to which they are attached combine to form an optionally substituted 3- to 12-membered polycyclic heterocycle. In one or more embodiments of Formula I, II, III, I-W, I-X, or I-Y when $Y^2$ is —$NR^a$— or —$(CR^a_2)_m$—, $R^3$ and $R^a$ together with the atoms to which they are attached combine to form an optionally substituted 5- to 12-membered spiroheterocycle.

In one or more embodiments of Formula I-W when $Y^2$ is —$NR^a$— or —$(CR^a_2)_m$—, $R^3$ and $R^a$ together with the atom to which they are attached combine to form 3- to 12-membered monocyclic heterocycle, which is optionally substituted with one or more —$C_1$-$C_6$alkyl, halogen, —OH, —$OR^b$, —$NH_2$, —$NHR^b$, heteroaryl, heterocyclyl, —$(CH_2)_n NH_2$, —$(CH_2)_n$OH, —$COOR^b$, —$CONHR^b$, —CONH($CH_2$)$_n COOR^b$, —$NHCOOR^b$, —$CF_3$, —$CHF_2$, —$CH_2$F, or =O. In certain such embodiments, the 3- to 12-membered monocyclic heterocycle is substituted with —$OR^b$, $R^b$ is —H, —$C_1$-$C_6$alkyl, or $C_3$-$C_8$cycloalkyl.

In one or more embodiments of Formula I-W when $Y^2$ is —$NR^a$— or —$(CR^a_2)_m$—, $R^3$ and $R^a$ together with the atoms to which they are attached combine to form a 3- to 12-membered polycyclic heterocycle, which is optionally substituted with one or more —$C_1$-$C_6$alkyl, halogen, —OH, —$OR^b$, —$NH_2$, —$NHR^b$, heteroaryl, heterocyclyl, —$(CH_2)_n NH_2$, —$(CH_2)_n$OH, —$COOR^b$, —$CONHR^b$, —CONH($CH_2$)$_n COOR^b$, —$NHCOOR^b$, —$CF_3$, —$CHF_2$, —$CH_2$F, or =O. In certain such embodiments, the 3- to 12-membered polycyclic heterocycle is substituted with —$OR^b$, $R^b$ is —H, —$C_1$-$C_6$alkyl, or $C_3$-$C_8$cycloalkyl.

In one or more embodiments of Formula I-W when $Y^2$ is —$NR^a$— or —$(CR^a_2)_m$—, $R^3$ and $R^a$ together with the atoms to which they are attached combine to form a 5- to 12-membered spiroheterocycle, which is optionally substituted with one or more —$C_1$-$C_6$alkyl, halogen, —OH, —$OR^b$, —$NH_2$, —$NHR^b$, heteroaryl, heterocyclyl, —$(CH_2)_n NH_2$, —$(CH_2)_n$OH, —$COOR^b$, —$CONHR^b$, —CONH($CH_2$)$_n COOR^b$, —$NHCOOR^b$, —$CF_3$, —$CHF_2$, —$CH_2$F, or =O. In certain such embodiments, the 5- to 12-membered spiroheterocycle is substituted with —$OR^b$, $R^b$ is —H, —$C_1$-$C_6$alkyl, or $C_3$-$C_8$cycloalkyl.

In one or more embodiments of Formula I-W when $Y^2$ is —$NR^a$— or —$(CR^a_2)_m$—, $R^3$ and $R^a$ together with the atoms to which they are attached combine to form a 10- to 12-membered spiroheterocycle, which is optionally substituted with one or more —$C_1$-$C_6$alkyl, halogen, —OH, —$OR^b$, —$NH_2$, —$NHR^b$, heteroaryl, heterocyclyl, —$(CH_2)_n NH_2$, —$(CH_2)_n$OH, —$COOR^b$, —$CONHR^b$, —CONH($CH_2$)$_n COOR^b$, —$NHCOOR^b$, —$CF_3$, —$CHF_2$, —$CH_2$F, or =O. In certain such embodiments, the 10- to 12-membered spiroheterocycle is substituted with —$OR^b$, $R^b$ is —H, —$C_1$-$C_6$alkyl, or $C_3$-$C_8$cycloalkyl.

In one or more embodiments of Formula I, II, III, I-W, I-X, or I-Y when $Y^2$ is —$NR^a$— or —$(CR^a_2)_m$—, $R^a$ and $R^4$ together with the atom to which they are attached combine to form an optionally substituted monocyclic or polycyclic 3- to 12-membered cycloalkyl. In one or more embodiments of Formula I, II, III, I-W, I-X, I-Y, or I-Z when $Y^2$ is —$NR^a$— or —$(CR^a_2)_m$—, $R^a$ and $R^4$ together with the atom to which they are attached combine to form an optionally substituted monocyclic or polycyclic 3- to 12-membered heterocycle.

In one or more embodiments of Formula I, II, III, I-W, I-X, or I-Y when $Y^2$ is —C(O)—, $R^3$ is an optionally substituted 3- to 12-membered monocyclic or polycyclic heterocycle.

In one or more embodiments of Formula I-W, I-X, or I-Y when $Y^2$ is —C($R^a$)$_2$NH—, $R^3$ is —H and and the two $R^a$s, together with the carbon atom to which they are both attached, form a 3- to 8-membered cycloalkyl.

In one or more embodiments of Formula I-W when $Y^2$ is —$NR^a$—, $R^a$ is —H, and $R^3$ is —$C_1$-$C_6$alkyl optionally substituted with one or more —$C_1$-$C_6$alkyl, —OH, —$NH_2$, —$OR^b$, —$NHR^b$, —$(CH_2)_n$OH, heterocyclyl, or spiroheterocyclyl. In certain such embodiments, $R^3$ is substituted with —$NH_2$, heterocyclyl, or spiroheterocyclyl.

In one or more embodiments of Formula I-W when $Y^2$ is —$NR^a$—, $R^a$ is —H, and $R^3$ is a 3- to 12-membered monocyclic or polycyclic heterocycle, a 5- to 12-membered spiroheterocycle, or $C_3$-$C_8$cycloalkyl, wherein the heterocycle, spiroheterocycle, and $C_3$-$C_8$cycloalkyl are optionally substituted with one or more —$C_1$-$C_6$alkyl, —OH, —$NH_2$, —$OR^b$, —$NHR^b$, —$(CH_2)_n$OH, heterocyclyl, or spiroheterocyclyl.

In one or more embodiments of Formula I, II, III, I-W, I-X, or I-Y when $Y^2$ is —$(CR^a_2)_m$—, $R^a$ is —H, m is 1, and $R^3$ is an optionally substituted 3- to 12-membered monocyclic or polycyclic heterocycle.

In one or more embodiments of Formula I, II, III, I-V1, I-V2, I-W, I-X, I-Y, or I-Z, n is independently, at each occurrence, 0, 1, 2, or 3. In one or more embodiments of Formula I, II, III, I-V1, I-V2, I-W, I-X, I-Y, or I-Z, n is 1. In one or more embodiments of Formula I, II, III, I-V1, I-V2, I-W, I-X, I-Y, or I-Z, n is 2. In one or more embodiments of Formula I, II, III, I-V1, I-V2, I-W, I-X, I-Y, or I-Z, n is 0. In one or more embodiments of Formula I, II, III, I-V1, I-V2, I-W, I-X, I-Y, or I-Z, n is 3.

In one variation of Formula I, II, III, I-W, I-X, or I-Y, $R^2$ is —$C_1$-$C_6$alkyl and $R^4$ is —H. In certain instances of Formula I, II, III, I-W, I-X, or I-Y, $R^2$ is —$C_1$-$C_6$alkyl and $R^4$ is —$C_1$-$C_6$alkyl. In certain instances of Formula I, II, III, I-W, I-X, or I-Y, $R^2$ is —$C_1$-$C_6$alkyl and $R^4$ is —$C_1$-$C_6$alkyl, substituted with one or more —OH, —$NH_2$, halogen, or oxo. In certain instances of Formula I, II, III, I-W, I-X, or I-Y, $R^2$ is —$C_1$-$C_6$alkyl and $R^4$ is —$C_1$-$C_6$alkyl, substituted with —OH.

In one variation of Formula I, II, III, I-W, I-X, or I-Y, $R^2$ is —$OR^b$ and $R^4$ is —H. In certain instances of Formula I, II, III, I-W, I-X, or I-Y, $R^2$ is —$OR^b$ and $R^4$ is —$C_1$-$C_6$alkyl. In certain instances of Formula I, II, III, I-W, I-X, or I-Y, $R^2$ is —$OR^b$ and $R^4$ is —$C_1$-$C_6$alkyl, substituted with one or more —OH, —$NH_2$, halogen, or oxo. In certain instances of Formula I, II, III, I-W, I-X, or I-Y, $R^2$ is —$OR^b$ and $R^4$ is —$C_1$-$C_6$alkyl, substituted with —OH.

In one variation of Formula I, II, III, I-V1, I-V2, I-W, I-X, I-Y, or I-Z, $Y^1$ is —S— and A is a 5- to 12-membered monocyclic or polycyclic cycloalkyl. In certain instances of Formula I, II, III, I-V1, I-V2, I-W, I-X, I-Y, or I-Z, $Y^1$ is —S— and A is heterocycloalkyl. In certain instances of Formula I, II, III, I-V1, I-V2, I-W, I-X, I-Y, or I-Z, $Y^1$ is —S— and A is aryl. In certain instances of Formula I, II, III, I-V1, I-V2, I-W, I-X, I-Y, or I-Z, $Y^1$ is —S— and A is heteroaryl.

In one variation of Formula I, II, III, I-V1, I-V2, I-W, I-X, I-Y, or I-Z, $Y^1$ is a direct bond and A is a 5- to 12-membered monocyclic or polycyclic cycloalkyl. In certain instances of Formula I, II, III, I-V1, I-V2, I-W, I-X, I-Y, or I-Z, $Y^1$ is a direct bond and A is heterocycloalkyl. In certain instances of Formula I, II, III, I-V1, I-V2, I-W, I-X, I-Y, or I-Z, $Y^1$ is a direct bond and A is aryl. In certain instances of Formula I, II, III, I-V1, I-V2, I-W, I-X, I-Y, or I-Z, $Y^1$ is a direct bond and A is heteroaryl.

Methods of Synthesizing the Disclosed Compounds

The compounds of the present disclosure may be made by a variety of methods, including standard chemistry. Suitable synthetic routes are depicted in the schemes given below.

The compounds of any of the formulae described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of the present disclosure.

Those skilled in the art will recognize if a stereocenter exists in any of the compounds of the present disclosure. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-lnterscience, 1994).

Preparation of Compounds

The compounds described herein may be made from commercially available starting materials or synthesized using known organic, inorganic, and/or enzymatic processes.

The compounds of the present disclosure can be prepared in a number of ways well known to those skilled in the art of organic synthesis. By way of example, compounds of the present disclosure can be synthesized using the methods described below, together with synthetic methods known in the art of synthetic organic chemistry, or variations thereon as appreciated by those skilled in the art. These methods include but are not limited to those methods described below.

Scheme 1. General synthesis of 2-amino-5-thioaryl-(or thioheteroaryl)-6-methylpyrazines

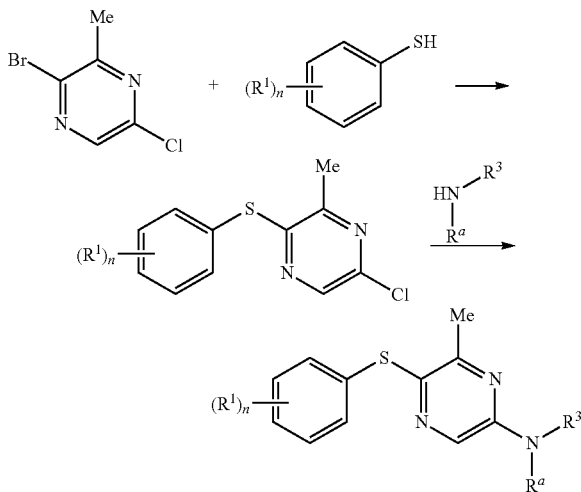

A general synthesis of 2-amino-5-thioaryl-(or thioheteroaryl)-6-methylpyrazines is outlined in Scheme 1. 2-bromo-5-chloro-3-methylpyrazine can be coupled to a substituted aryl- or heteroaryl 1-thiol in the presence of a copper catalyst (e.g., CuI). The resulting thioether can then be coupled to a substituted primary or secondary amine to give a 2-amino-5-thioaryl-(or thioheteroaryl)-6-methylpyrazine. Additional deprotection and/or functionalization steps can be required to produce the final compound.

Scheme 2. General Synthesis of 2-amino-5-aryl(or heteroaryl)-6-methylpyrazines

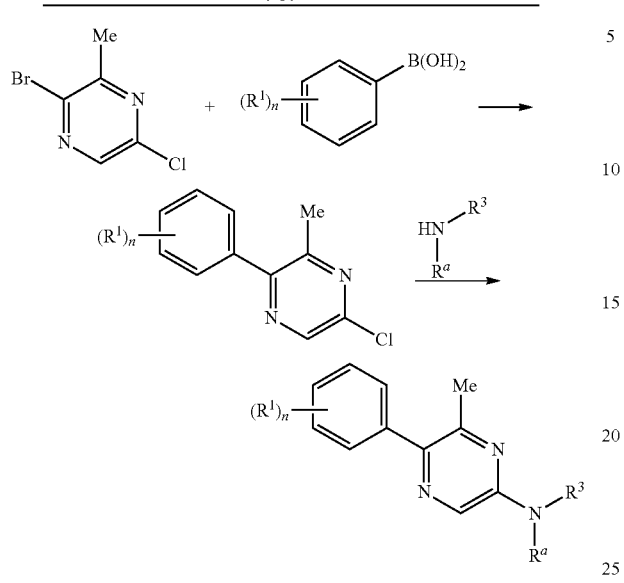

A general synthesis of 2-amino-5-aryl(or heteroaryl)-6-methylpyrazines is outlined in Scheme 2. 2-bromo-5-chloro-3-methylpyrazine can be coupled to a substituted aryl- or heteroaryl boronic acid in the presence of a palladium catalyst (e.g., Pd(dppf)Cl$_2$). The resulting biaryl intermediate can then be coupled to a substituted primary or secondary amine to give a 2-amino-5-aryl(or heteroaryl)-6-methylpyrazine. Additional deprotection and/or functionalization steps can be required to produce the final compound.

Scheme 3. General Synthesis of 3-amino-6-aryl-5-methypyrazinyl-2-methanol and 3-amino-5-methyl-6-arylsulfanyl pyrazinyl-2-methanol

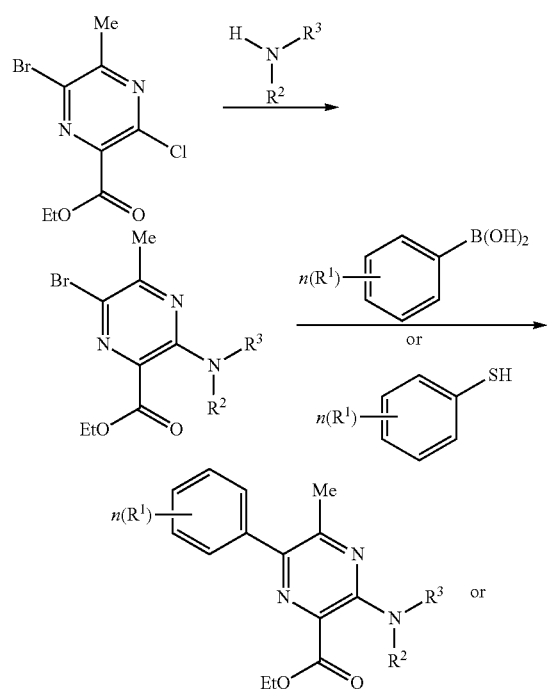

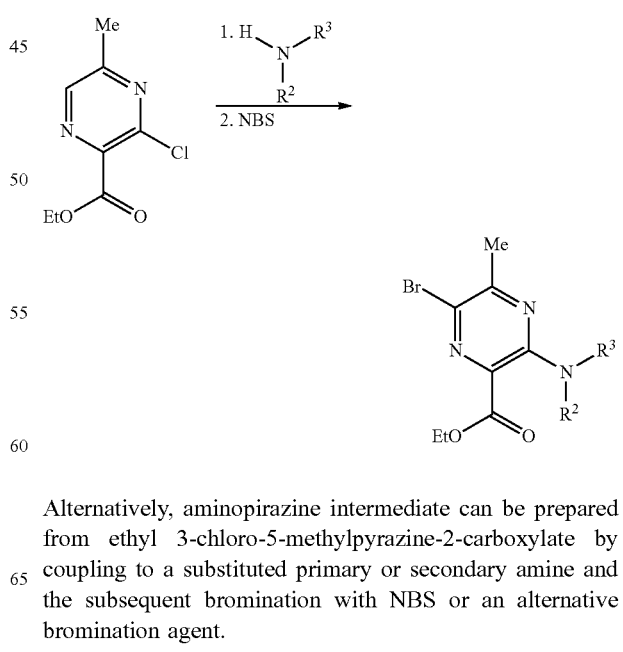

A general synthesis of 3-amino-6-aryl-5-methylpyrazinyl-2-methanol and 3-amino-5-methyl-6-arylsulfanylpyrazinyl-2-methanol is outlined in Scheme 3. Ethyl 6-bromo-3-chloro-5-methylpyrazine-2-carboxylate can be coupled to a substituted primary or secondary amine. The resulting aminopyrazine intermediate can be coupled to a substituted aryl- or heteroaryl boronic acid or a substitutes aryl thiol in the presence of a palladium catalyst (e.g., Pd(dppf)Cl$_2$), followed by a reduction step. Additional deprotection and/or functionalization steps can be required to produce the final compound.

Alternatively, aminopirazine intermediate can be prepared from ethyl 3-chloro-5-methylpyrazine-2-carboxylate by coupling to a substituted primary or secondary amine and the subsequent bromination with NBS or an alternative bromination agent.

Methods of Using the Disclosed Compounds and Compositions

Methods and Uses of the Disclosure

Another aspect of the disclosure relates to a method of treating a disease associated with SHP2 modulation in a subject in need thereof. The method involves administering to a patient in need of treatment for diseases or disorders associated with SHP2 modulation an effective amount of one or more compounds of the present disclosure (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), or of one or more pharmaceutical compositions of the present disclosure. In some embodiments, the disease can be, but is not limited to Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In addition, SHP2 plays a role in transducing signals originating from immune checkpoint molecules, including but not limited to programmed cell death protein 1 (PD-1) and cytotoxic T-lymphocyte-associated protein 4 (CTLA-4). In this context, modulation of SHP2 function can lead to immune activation, specifically anti-cancer immune responses.

Another aspect of the disclosure is directed to a method of inhibiting SHP2. The method involves administering to a patient in need thereof an effective amount of one or more compounds of the present disclosure (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), or of one or more pharmaceutical compositions of the present disclosure.

The present disclosure relates to compounds or compositions disclosed herein that are capable of modulating the activity of (e.g., inhibiting) SHP2. The present disclosure also relates to the therapeutic use of such compounds and compositions.

One or more disclosed compounds or compositions can be administered in effective amounts to treat or prevent a disorder and/or prevent the development thereof in subjects. In some embodiments, SHP2 is inhibited after treatment with less than 1000 nM of a compound of the disclosure. In some embodiments, SHP2 is inhibited after treatment with about 10 nM to about 100 nM of a compound of the disclosure. In some embodiments, SHP2 is inhibited after treatment with 10 nM to 100 nM of a compound of the disclosure. In some embodiments, SHP2 is inhibited after treatment with less than 10 nM of a compound of the disclosure.

Another aspect of the present disclosure relates to one or more compounds of the present disclosure (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), or one or more compositions of the present disclosure for use in treating or preventing a disease associated with SHP2 modulation. In some embodiments, the disease is Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In another aspect, the present disclosure relates to the use of one or more compounds of the present disclosure (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), in the manufacture of a medicament for treating or preventing a disease. In some embodiments, the disease is associated with SHP2 modulation.

In another aspect, the present disclosure relates to one or more compounds of the present disclosure (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), for use as a medicament. In some embodiments, the medicament is used for treating or preventing a disease associated with SHP2 modulation.

In one aspect, the present disclosure relates to one or more compositions comprising one or more compounds of the present disclosure (e.g., compounds of Formula I, II, III, I-V1, I-V2, I-W, I-X, I-Y, or I-Z, and pharmaceutically acceptable salts, prodrugs, solvates, hydrates, tautomers, or isomers thereof), for use as a medicament. In some embodiments, the medicament is used for treating or preventing a disease associated with SHP2 modulation.

Pharmaceutical Compositions and Modes of Administration of the Disclosure

Another aspect of the present disclosure relates to pharmaceutical compositions comprising one or more compounds of the present disclosure and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

Administration of the disclosed compounds and pharmaceutical compositions can be accomplished via any mode of administration for therapeutic agents. These modes include systemic or local administration such as oral, nasal, parenteral, intravenous, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising one or more compounds of the present disclosure and a pharmaceutically acceptable carrier, such as, but not limited to, a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, one or more disclosed compounds are dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

One or more disclosed compounds or compositions can be also formulated as a suppository that can be prepared from fatty emulsions or suspensions; using polyalkylene glycols such as propylene glycol, as the carrier.

One or more disclosed compounds or compositions can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

One or more disclosed compounds or compositions can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxy propylmethacrylamide-phenol, polyhydroxyethyl-aspanamidephenol, or polyethyleneoxide polylysine substituted with palmitoyl residues. Furthermore, the one or more disclosed compounds can be coupled to a class of biodegradable polymers useful in achieving controlled release of a drug, for example, polylactic acid, polyepsilon caprolactone, polyhydroxy butyric acid, poly orthoesters, polyacetals, polydihydropyrans, polycyanoacrylates and crosslinked or amphipathic block copolymers of hydrogels. In some embodiments, one or more disclosed compounds are not covalently bound to a polymer, e.g., a polycarboxylic acid polymer, or a polyacrylate.

One or more disclosed compounds or compositions can be delivered by parental administration. Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Dosage Regimens of the Disclosure

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In some embodiments, the compositions are in the form of a tablet that can be scored.

If desired, the effective daily dose of one or more compounds or compositions of this disclosure may be administered as one, two, three, four, five, six, or more sub-doses administered separately at appropriate intervals throughout the day, optionally, in unit dosage forms. In some embodiments of this disclosure, the one or more compounds or compositions of this disclosure, or mixtures thereof, may be administered two or three times daily. In some embodiments, the one or more compounds or compositions of this disclosure will be administered once daily.

In some embodiments, one or more compounds or compositions described herein may be used alone or together or conjointly administered, or used in combination, with another type of therapeutic agent. Conjoint administration or used in combination refers to any form of administration of two or more different therapeutic compounds or compositions such that the second compound or composition is administered while the previously administered therapeutic compound or composition is still effective in the body. For example, the different therapeutic compounds or compositions can be administered either in the same formulation or in a separate formulation, either simultaneously, sequentially, or by separate dosing of the individual components of the treatment. In some embodiments, the different therapeutic compounds or compositions can be administered within one hour, 12 hours, 24 hours, 36 hours, 48 hours, 72 hours, or a week of one another. Thus, an individual who receives such treatment can benefit from a combined effect of different therapeutic compounds or compositions.

Kits

In some embodiments, this disclosure also provides a pharmaceutical package or kit comprising one or more containers filled with at least one compound or composition of this disclosure. Optionally associated with such a container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both. In some embodiments, the kit comprises at least two containers, at least one of which contains at least one compound or composition of this disclosure. In some embodiments, the kit contains at least two containers, and each of the at least two containers contains at least one compound or composition of this disclosure.

In some embodiments, the kit includes additional materials to facilitate delivery of the subject compounds and compositions. For example, the kit may include one or more of a catheter, tubing, infusion bag, syringe, and the like. In some embodiments, the compounds and compositions are packaged in a lyophilized form, and the kit includes at least two containers: a container comprising the lyophilized compounds or compositions and a container comprising a suitable amount of water, buffer, or other liquid suitable for reconstituting the lyophilized material.

The foregoing applies to any of the compounds, compositions, methods, and uses described herein. This disclosure specifically contemplates any combination of the features of such compounds, compositions, methods, and uses (alone or in combination) with the features described for the various kits described in this section.

EXEMPLARY EMBODIMENTS

Some embodiments of this disclosure are Embodiment I, as follows:

Embodiment I-1

A compound of the Formula I:

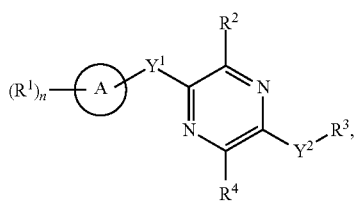

I or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a_2)_m$—, —C(O)—, —$C(R^a)_2$NH—, —$(CR^a_2)_m$O—, —C(O)N($R^a$)—, —N($R^a$)C(O)—, —S(O)$_2$N($R^a$)—, —N($R^a$)S(O)$_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, —C(O)$R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5$S(O)$_2$$NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5$S(O)$_2$$NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —S(O)$_2NR^5R^6$, —S(O)$_2R^5$, —$NR^5$S(O)$_2$$NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-2

The compound of embodiment I-1, wherein A is a 5- to 12-membered monocyclic or polycyclic cycloalkyl.

Embodiment I-3

The compound of embodiment I-1 or I-2, wherein A is heterocycloalkyl.

Embodiment I-4

The compound of any one of embodiments I-1 to I-3, wherein A is aryl.

Embodiment I-5

The compound of any one of embodiments I-1 to I-4, wherein A is heteroaryl.

Embodiment I-6

The compound of any one of embodiments I-1 to I-5, wherein $Y^1$ is —S—.

Embodiment I-7

The compound of any one of embodiments I-1 to I-6, wherein $Y^1$ is a direct bond.

Embodiment I-8

The compound of any one of embodiments I-1 to I-7, wherein $Y^2$ is —$NR^a$—.

Embodiment I-9

The compound of any one of embodiments I-1 to I-8, wherein $Y^2$ is —$(CR^a{}_2)_m$—.

Embodiment I-10

The compound of any one of embodiments I-1 to I-9, wherein $Y^2$ is —C(O)—.

Embodiment I-11

The compound of any one of embodiments I-1 to I-10, wherein $Y^2$ is —$C(R^a)_2NH$— or —$(CR^a{}_2)_mO$—.

Embodiment I-12

The compound of any one of embodiments I-1 to I-11, wherein $Y^2$ is —$C(O)N(R^a)$—, —$N(R^a)C(O)$—, —$S(O)_2N(R^a)$—, —$N(R^a)S(O)_2$—, —$N(R^a)C(S)$—, or —$C(S)N(R^a)$—.

Embodiment I-13

The compound of any one of embodiments I-1 to I-12, wherein $Y^2$ is —$N(R^a)C(O)N(R^a)$—, —$N(R^a)C(S)N(R^a)$—, —$OC(O)N(R^a)$—, —$N(R^a)C(O)O$—, or —$C(O)N(R^a)O$—.

Embodiment I-14

The compound of any one of embodiments I-1 to I-13, wherein $Y^2$ is —C(O)O—, —OC(O)—, or —OC(O)O—.

Embodiment I-15

The compound of any one of embodiments I-1 to I-14, wherein $R^2$ is —$OR^b$.

Embodiment I-16

The compound of any one of embodiments I-1 to I-15, wherein $R^2$ is —$C_1$-$C_6$alkyl.

Embodiment I-17

The compound of any one of embodiments I-1 to I-16, wherein $R^2$ is —CN.

Embodiment I-18

The compound of any one of embodiments I-1 to I-17, wherein $R^2$ is —$C_2$-$C_6$alkenyl.

Embodiment I-19

The compound of any one of embodiments I-1 to I-18, wherein $R^2$ is —$C_4$-$C_8$cycloalkenyl.

Embodiment I-20

The compound of any one of embodiments I-1 to I-19, wherein $R^2$ is —$C_2$-$C_6$alkynyl.

Embodiment I-21

The compound of any one of embodiments I-1 to I-20, wherein $R^2$ is —$C_3$-$C_8$cycloalkyl.

Embodiment I-22

The compound of any one of embodiments I-1 to I-21, wherein $R^2$ is aryl.

Embodiment I-23

The compound of any one of embodiments I-1 to I-22, wherein $R^2$ is heterocyclyl containing 1-5 heteroatoms selected from the group consisting of N, S, P, and O.

Embodiment I-24

The compound of any one of embodiments I-1 to I-23, wherein $R^2$ is or heteroaryl containing 1-5 heteroatoms selected from the group consisting of N, S, P, and O.

Embodiment I-25

The compound of any one of embodiments I-1 to I-24, wherein $R^a$ is —H.

Embodiment I-26

The compound of any one of embodiments I-1 to I-25, wherein $R^a$ is —OH.

Embodiment I-27

The compound of any one of embodiments I-1 to I-26, wherein $R^a$ is —$C_3$-$C_8$cycloalkyl.

Embodiment I-28

The compound of any one of embodiments I-1 to I-27, wherein $R^a$ is —$C_1$-$C_6$alkyl.

Embodiment I-29

The compound of any one of embodiments I-1 to I-28, wherein $R^b$ is —H.

Embodiment I-30

The compound of any one of embodiments I-1 to I-29, wherein $R^b$ is —$C_1$-$C_6$alkyl.

Embodiment I-31

The compound of any one of embodiments I-1 to I-30, wherein $R^b$ is —$C_3$-$C_8$cycloalkyl.

Embodiment I-32

The compound of any one of embodiments I-1 to I-31, wherein $R^b$ is —$C_2$-$C_6$alkenyl.

Embodiment I-33

The compound of any one of embodiments I-1 to I-32, wherein $R^b$ is heterocyclyl containing 1-5 heteroatoms selected from the group consisting of N, S, P, and O.

Embodiment I-34

The compound of any one of embodiments I-1 to I-33, wherein $R^3$ is —$C_1$-$C_6$alkyl.

Embodiment I-35

The compound of any one of embodiments I-1 to I-34, wherein $R^3$ is 3- to 12-membered monocyclic or polycyclic heterocycle.

Embodiment I-36

The compound of any one of embodiments I-1 to I-35, wherein $R^3$ is a 3- to 12-membered monocyclic heterocycle.

Embodiment I-37

The compound of any one of embodiments I-1 to I-36, wherein $R^3$ is a 3- to 12-membered polycyclic heterocycle.

Embodiment I-38

The compound of any one of embodiments I-1 to I-37, wherein $R^3$ and $R^a$ together with the atom to which they are attached combine to form a 3- to 12-membered monocyclic heterocycle.

Embodiment I-39

The compound of any one of embodiments I-1 to I-38, wherein $R^3$ and $R^a$ together with the atoms to which they are attached combine to form a 3- to 12-membered polycyclic heterocycle.

Embodiment I-40

The compound of any one of embodiments I-1 to I-39, wherein $R^3$ and $R^a$ together with the atoms to which they are attached combine to form a 5- to 12-membered spiroheterocycle.

Embodiment I-41

The compound of any one of embodiments I-1 to I-40, wherein $R^a$ and $R^4$ together with the atom to which they are attached combine to form a monocyclic or polycyclic 3- to 12-membered cycloalkyl.

Embodiment I-42

The compound of any one of embodiments I-1 to I-41, wherein $R^a$ and $R^4$ together with the atom to which they are attached combine to form a monocyclic or polycyclic 3- to 12-membered heterocycle.

Embodiment I-43

A compound of the Formula I-A:

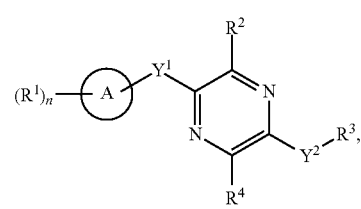

I-A or a pharmaceutically acceptable salt, prodrug, solvate, hydrate, tautomer, or isomer thereof, wherein:

A is aryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_m$O—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2$ NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is independently —ORᵇ, —CN, —C₁-C₆alkyl, —C₂-C₆alkenyl, —C₄-C₈cycloalkenyl, —C₂-C₆alkynyl, —C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

Rᵃ is independently, at each occurrence, —H, -D, —OH, —C₃-C₈cycloalkyl, or —C₁-C₆alkyl, wherein each alkyl or cycloalkyl is optionally substituted with one or more —NH₂, wherein 2 Rᵃ, together with the carbon atom to which they are both attached, can combine to form a 3- to 8-membered cycloalkyl;

Rᵇ is independently, at each occurrence, —H, -D, —C₁-C₆alkyl, —C₃-C₈cycloalkyl, —C₂-C₆alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R³ is independently —C₁-C₆alkyl or a 3- to 12-membered monocyclic or polycyclic heterocycle, wherein each alkyl or heterocycle is optionally substituted with one or more —C₁-C₆alkyl, —OH, or —NH₂; or R³ can combine with Rᵃ to form a 3- to 12-membered monocyclic or polycyclic heterocycle or a 5- to 12-membered spiroheterocycle, wherein each heterocycle or spiroheterocycle is optionally substituted with —C₁-C₆alkyl, —OH, or —NH₂;

R⁴ is independently —H, -D, or —C₁-C₆alkyl, wherein each alkyl is optionally substituted with one or more —OH, —NH₂, halogen, or oxo; or Rᵃ and R⁴, together with the atom or atoms to which they are attached, can combine to form a monocyclic or polycyclic C₃-C₁₂cycloalkyl or a monocyclic or polycyclic 3- to 12-membered heterocycle, wherein the cycloalkyl or heterocycle is optionally substituted with oxo;

R⁵ and R⁶ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, or —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-44

A compound of the Formula I-B:

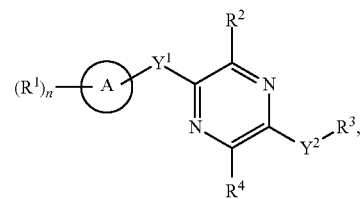

or a pharmaceutically acceptable salt, prodrug, solvate, hydrate, tautomer, or isomer thereof, wherein:

A is heteroaryl;

Y¹ is —S— or a direct bond;

Y² is —Rᵃ—, —(CRᵃ₂)ₘ—, —C(O)—, —C(Rᵃ)₂NH—, —(CRᵃ₂)ₘO—, —C(O)N(Rᵃ)—, —N(Rᵃ)C(O)—, —S(O)₂N(Rᵃ)—, —N(Rᵃ)S(O)₂—, —N(Rᵃ)C(O)N(Rᵃ)—, —N(Rᵃ)C(S)N(Rᵃ)—, —C(O)O—, —OC(O)—, —OC(O)N(Rᵃ)—, —N(Rᵃ)C(O)O—, —C(O)N(Rᵃ)O—, —N(Rᵃ)C(S)—, —C(S)N(Rᵃ)—, or —OC(O)O—; wherein the bond on the left side of Y², as drawn, is bound to the pyrazine ring and the bond on the right side of the Y² moiety is bound to R³;

R¹ is independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, —OH, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, or —CO₂R⁵, wherein each alkyl, alkenyl, cycloalkenyl, alkynyl, or cycloalkyl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R² is independently —ORᵇ, —CN, —C₁-C₆alkyl, —C₂-C₆alkenyl, —C₄-C₈cycloalkenyl, —C₂-C₆alkynyl, —C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl; and wherein the heterocyclyl or heteroaryl is not attached via a nitrogen atom;

Rᵃ is independently, at each occurrence, —H, -D, —OH, —C₃-C₈cycloalkyl, or —C₁-C₆alkyl, wherein each alkyl or cycloalkyl is optionally substituted with one or more —NH₂, wherein 2 Rᵃ, together with the carbon atom to which they are both attached, can combine to form a 3- to 8-membered cycloalkyl;

Rᵇ is independently, at each occurrence, —H, -D, —C₁-C₆alkyl, —C₃-C₈cycloalkyl, —C₂-C₆alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂

$NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl, or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-45

A compound of the Formula II:

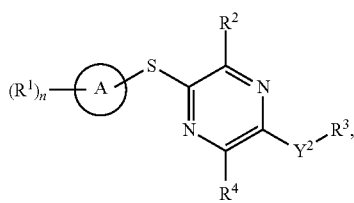

II or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^2$ is —$NR^a$—, —$(CR^a_2)_m$—, —C(O)—, —$C(R^a)_2NH$—, —$(CR^a_2)_mO$—, —C(O)N($R^a$)—, —N($R^a$)C(O)—, —$S(O)_2N(R^a)$—, —N($R^a$)S(O)$_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-46

The compound of embodiment I-45, where the compound is of the Formula II-A:

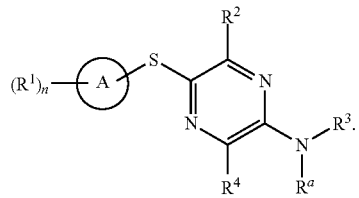

II-A

Embodiment I-47

The compound of embodiment I-46, where the compound is of the Formula II-A1:

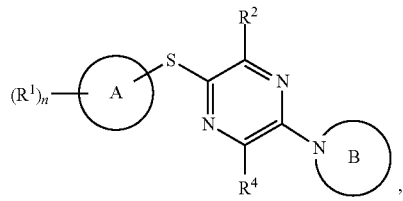

IIA-1 wherein:
B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with —$C_1$-$C_6$alkyl, —OH, or —$NH_2$.

Embodiment I-48

The compound of embodiment I-46, wherein the compound is of the Formula II-A2:

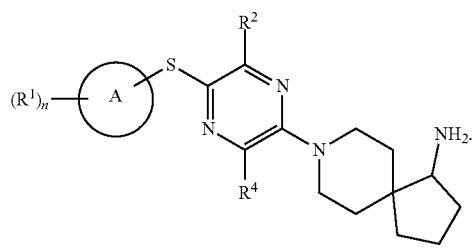

II-A2

Embodiment I-49

The compound of embodiment I-46, wherein the compound is of the Formula II-A3:

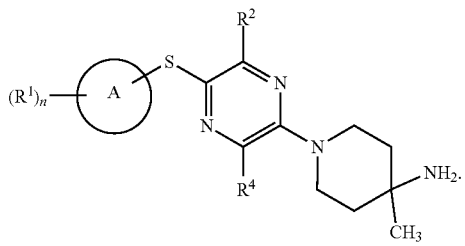

II-A3

Embodiment I-50

The compound of embodiment I-45, wherein the compound is of the Formula II-B:

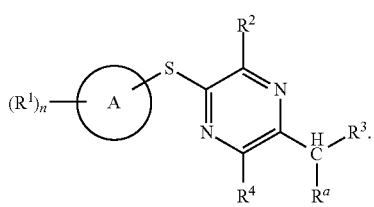

II-B

Embodiment I-51

The compound of embodiment I-50, wherein the compound is of the Formula II-B1:

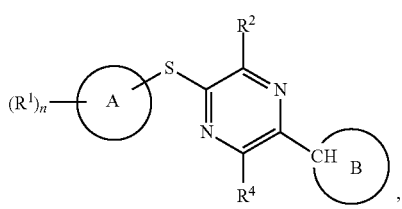

II-B1 wherein:
B forms a 3- to 12-membered monocyclic or polycyclic heterocycle or a 5- to 12-membered spiroheterocycle along with the carbon atom to which it is attached, wherein the heterocycle or spiroheterocycle is optionally substituted with —$C_1$-$C_6$alkyl, —OH, or —$NH_2$.

Embodiment I-52

The compound of embodiment I-50, wherein the compound is of the Formula II-B2:

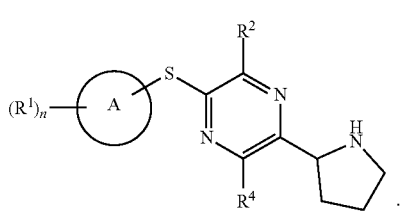

II-B2

Embodiment I-53

The compound of embodiment I-50, wherein the compound is of the Formula II-B3:

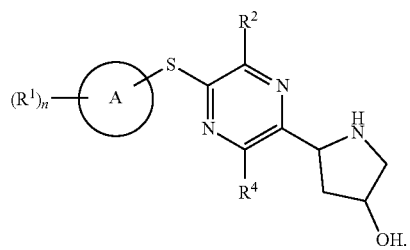

II-B3

Embodiment I-54

The compound of embodiment I-50, wherein the compound is of the Formula II-B4:

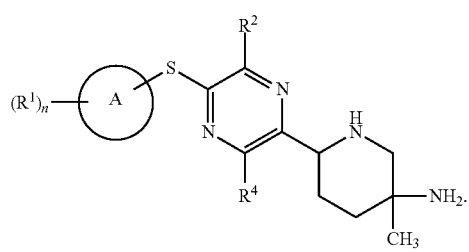

II-B4

Embodiment I-55

The compound of embodiment I-50, wherein the compound is of the Formula II-B5:

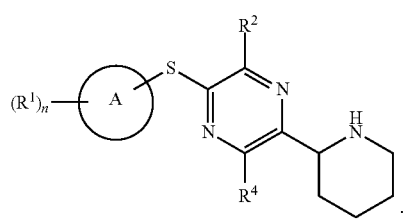

II-B5

Embodiment I-56

The compound of embodiment I-50, wherein the compound is of the Formula II-B6:

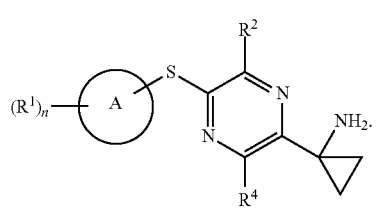

II-B6

Embodiment I-57

The compound of embodiment I-45, wherein the compound is of the Formula II-C:

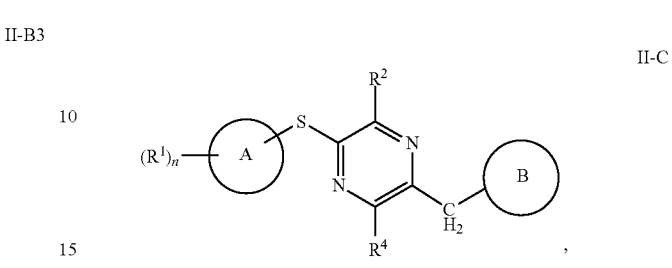

II-C wherein:

B forms a 3- to 12-membered monocyclic or polycyclic heterocycle, wherein the heterocycle is optionally substituted with —$C_1$-$C_6$alkyl, —OH, or —$NH_2$.

Embodiment I-58

The compound of embodiment I-57, wherein the compound is of the Formula II-C1:

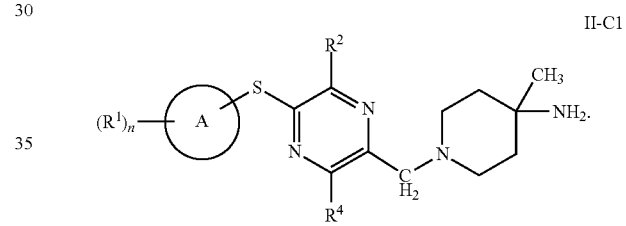

II-C1

Embodiment I-59

The compound of embodiment I-57, wherein the compound is of the Formula II-D:

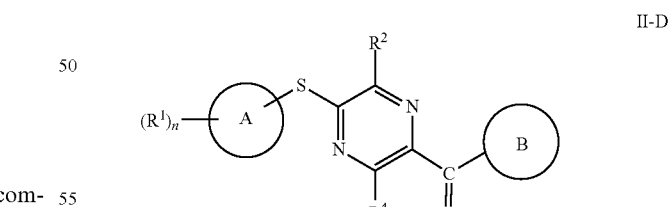

II-D wherein:

B forms a 3- to 12-membered monocyclic or polycyclic heterocycle, wherein the heterocycle is optionally substituted with —$C_1$-$C_6$alkyl, —OH, or —$NH_2$.

Embodiment I-60

The compound of embodiment I-57, wherein the compound is of the Formula II-D1:

139

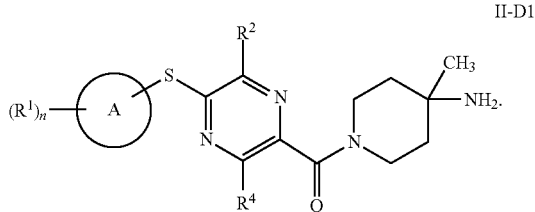

Embodiment I-61

The compound of embodiment I-45, wherein the compound is of the Formula II-E:

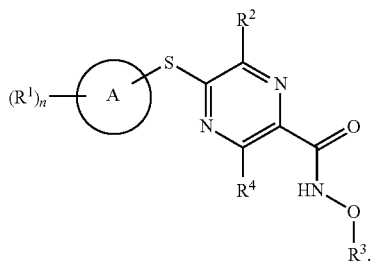

Embodiment I-62

The compound of embodiment I-45, wherein the compound is of the Formula II-F:

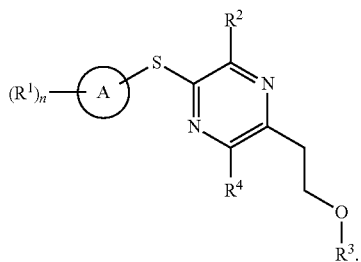

Embodiment I-63

The compound of embodiment I-45, wherein the compound is of the Formula II-G:

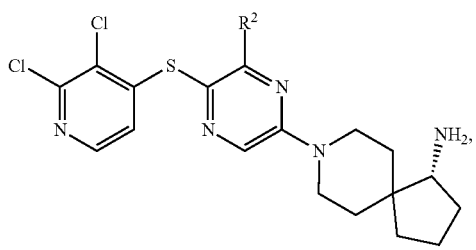

wherein $R^2$ is aryl or heteroaryl.

140

Embodiment I-64

A compound of the Formula III:

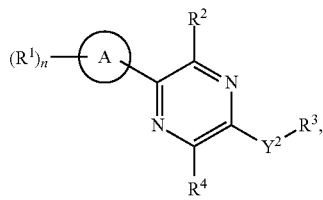

or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, and —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2$ NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R³ is independently, at each occurrence, selected from the group consisting of —C₁-C₆alkyl or a 3- to 12-membered monocyclic or polycyclic heterocycle, wherein each alkyl or heterocycle is optionally substituted with one or more —C₁-C₆alkyl, —OH, or —NH₂; or R³ can combine with Rᵃ to form a 3- to 12-membered monocyclic or polycyclic heterocycle or a 5- to 12-membered spiroheterocycle, wherein each heterocycle or spiroheterocycle is optionally substituted with —C₁-C₆alkyl, —OH, or —NH₂;

R⁴ is independently —H, -D, or —C₁-C₆alkyl, wherein each alkyl is optionally substituted with one or more —OH, —NH₂, halogen, or oxo; or Rᵃ and R⁴, together with the atom or atoms to which they are attached, can combine to form a monocyclic or polycyclic C₃-C₁₂cycloalkyl or a monocyclic or polycyclic 3- to 12-membered heterocycle, wherein the cycloalkyl or heterocycle is optionally substituted with oxo;

R⁵ and R⁶ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, or —CN;

R⁷ and R⁸ are independently, at each occurrence, —H, -D, —C₁-C₆alkyl, —C₂-C₆alkenyl, —C₄-C₈cycloalkenyl, —C₂-C₆alkynyl, —C₃-C₈cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-65

The compound of embodiment I-64, wherein the compound is of the Formula III-A:

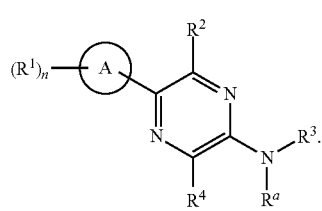

III-A

Embodiment I-66

The compound of embodiment I-65, wherein the compound is of the Formula III-A1:

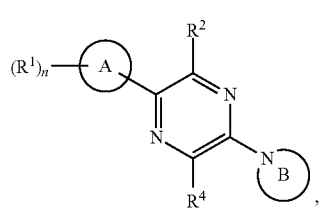

III-A1 wherein

B forms a 3- to 12-membered monocyclic or polycyclic heterocycle or a 5- to 12-membered spiroheterocycle along with the nitrogen atom to which it is attached, wherein the heterocycle or spiroheterocycle is optionally substituted with —C₁-C₆alkyl, —OH, or —NH₂.

Embodiment I-67

The compound of embodiment I-65, wherein the compound is of the Formula III-A2:

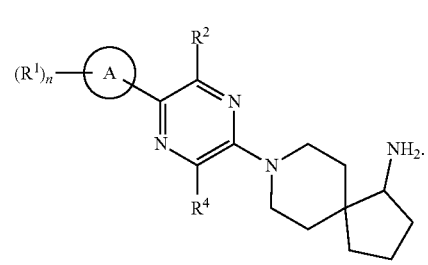

III-A2

Embodiment I-68

The compound of embodiment I-65, wherein the compound is of the Formula III-A3:

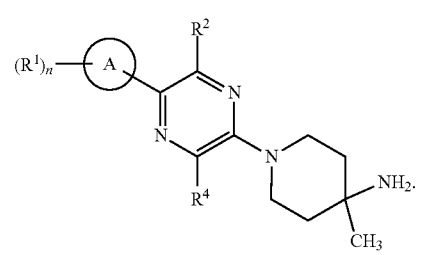

III-A3

Embodiment I-69

A compound selected from the group consisting of Compounds 1-41, or a pharmaceutically acceptable salt, prodrug, solvate, hydrate, tautomer, or isomer thereof.

Embodiment I-70

A pharmaceutical composition comprising one or more compounds of any one of embodiments I-1 to I-69 and a pharmaceutically acceptable carrier.

Embodiment I-71

A method of treating a disease associated with SHP2 modulation in a subject in need thereof, comprising administering to the subject an effective amount of one or more compounds of any one of embodiments I-1 to I-69.

Embodiment I-72

The method of embodiment I-71, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment I-73

One or more compounds of any one of embodiments I-1 to I-69 for use in treating or preventing a disease associated with SHP2 modulation.

Embodiment I-74

Use of one or more compounds of any one of embodiments I-1 to I-69 in the manufacture of a medicament for treating or preventing a disease associated with SHP2 modulation.

Embodiment I-75

A compound of the Formula I-X:

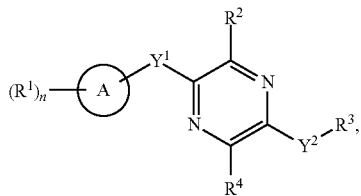

I-X or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —H, —$C_1$-$C_6$alkyl, or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with —$C_1$-$C_6$alkyl, —OH, or —$NH_2$;

$R^4$ is independently —H, -D, —$C_1$-$C_6$alkyl, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —$NHS(O)_2NHR^5$, —$S(O)_2OH$, —$C(O)OR^5$, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, halogen, or oxo; wherein each aryl or heteroaryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo wherein the heterocycle optionally comprises —$S(O)_2$— in the heterocycle;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-76

A compound of the Formula I-Y:

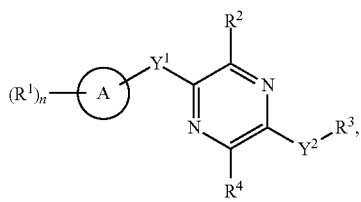

I-Y or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety, as drawn, is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, heteroaryl, —$(CH_2)_nOH$, —$C_1$-$C_6$alkyl, —$CF_3$, —$CHF_2$, or —$CH_2F$;

$R^3$ is independently —H, —$C_1$-$C_6$alkyl, a 3- to 12-membered monocyclic or polycyclic heterocycle, $C_3$-$C_8$cycloalkyl, or —$(CH_2)_n$—$R^b$, wherein each alkyl, heterocycle, or cycloalkyl is optionally substituted with one or more —$C_1$-$C_6$alkyl, —OH, —$NH_2$, —$OR^a$, —$NHR^a$, —$(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with —$C_1$-$C_6$alkyl, —OH, —$NH_2$, heteroaryl, heterocyclyl, —$(CH_2)_nNH_2$, —$COOR^b$, —$CONHR^b$, —$CONH(CH_2)_nCOOR^b$, —$NHCOOR^b$, —$CF_3$, —$CHF_2$, or —$CH_2F$;

$R^4$ is independently —H, -D, —$C_1$-$C_6$alkyl, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —NHS$(O)_2NHR^5$, —$S(O)_2OH$, —$C(O)OR^5$, —$NH(CH_2)_nOH$, —$C(O)NH(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, halogen, or oxo; wherein each aryl or heteroaryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo wherein the heterocycle optionally comprises —$S(O)_2$— in the heterocycle;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-77

A compound of the Formula I-Z:

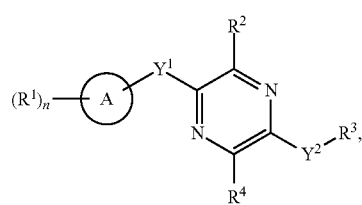

I-Z or a pharmaceutically acceptable salt, prodrug, solvate, hydrate, tautomer, or isomer thereof, wherein:

A is a 5- to 12-membered monocyclic or polycyclic cycloalkyl, heterocycloalkyl, aryl, or heteroaryl;

$Y^1$ is —S—, a direct bond, —NH—, —S(O)$_2$—, —S(O)$_2$—NH—, —C(=CH$_2$)—, —CH—, or —S(O)—;

$Y^2$ is —NR$^a$—, —(CR$^a{}_2$)$_m$—, —C(R$^a$)$_2$NH—, —(CR$^a{}_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —OC(O)N(R$^a$)—, —N(R$^a$)C(O)O—, —C(O)N(R$^a$)O—, —N(R$^a$)C(S)—, or —C(S)N(R$^a$)—; where in the bond on the left side of $Y^2$, as drawn, is bound to the pyrazine ring and the bond on the right side of the $Y^2$ moiety, as drawn, is bound to $R^3$;

$R^1$ is independently, at each occurrence, —H, -D, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ is independently —OR$^b$, —NH$_2$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

$R^a$ is independently, at each occurrence, —OH, —C$_3$-C$_8$cycloalkyl, or —C$_1$-C$_6$alkyl, wherein each alkyl or cycloalkyl is optionally substituted with one or more —NH$_2$, wherein 2R$^a$, together with the carbon atom to which they are both attached, can combine to form a 3- to 8-membered cycloalkyl;

$R^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, heteroaryl, —(CH$_2$)$_n$OH, —C$_1$-C$_6$alkyl, —CF$_3$, —CHF$_2$, or —CH$_2$F;

$R^3$ is independently, at each occurrence, —H, —C$_1$-C$_6$alkyl, a 3- to 12-membered monocyclic or polycyclic heterocycle, C$_3$-C$_8$cycloalkyl, or —(CH$_2$)$_n$—R$^b$, wherein each alkyl, heterocycle, or cycloalkyl is optionally substituted with one or more —C$_1$-C$_6$alkyl, —OH, —NH$_2$, —OR$^a$, —NHR$^a$, —(CH$_2$)$_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

$R^4$ is independently —C$_1$-C$_6$alkyl, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, halogen, or oxo; wherein each aryl or heteroaryl is optionally substituted with one or more —OH, —NH$_2$, or halogen;

$R^a$ and $R^4$, together with the atom or atoms to which they are attached, are combined to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

$R^5$ and $R^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment I-78

A compound selected from the group consisting of Compounds A-1 to A-141, or a pharmaceutically acceptable salt, prodrug, solvate, hydrate, tautomer, or isomer thereof.

Some embodiments of this disclosure are Embodiment II, as follows:

Embodiment II-1

A compound of Formula I-W:

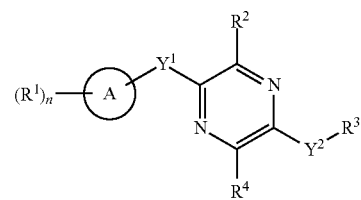

or a pharmaceutically acceptable salt, prodrug, solvate, hydrate, tautomer, and isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —S(O)$_2$—, —S(O)$_2$—NH—, —C(=CH$_2$)—, —CH—, or —S(O)—;

$Y^2$ is —NR$^a$—, —(CR$^a_2$)$_m$—, —C(O)—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the pyrazine ring and the bond on the right side of the Y$^2$ moiety, as drawn, is bound to R$^3$;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ is independently —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

$R^a$ is independently, at each occurrence, —H, -D, —OH, —C$_3$-C$_8$cycloalkyl, —C$_1$-C$_6$alkyl, 3- to 12-membered heterocyclyl, or —(CH$_2$)$_n$-aryl, wherein each alkyl or cycloalkyl is optionally substituted with one or more —NH$_2$, or wherein 2 R$^a$, together with the carbon atom to which they are both attached, can combine to form a 3- to 8-membered cycloalkyl;

$R^b$ is independently, at each occurrence, —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

$R^3$ is independently —H, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$—R$^b$, wherein each alkyl, spiroheterocycle, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or $R^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

$R^4$ is independently —H, -D, —C$_1$-C$_6$alkyl, —C$_1$-C$_6$haloalkyl, —C$_1$-C$_6$hydroxyalkyl, —CF$_2$OH, —CHFOH, —NH—NHR$^5$, —NH—OR$^5$, —O—NR$^5$R$^6$, —NHR$^5$, —OR$^5$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —CN, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen; or $R^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

$R^5$ and $R^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment II-2

The compound of embodiment II-1, wherein the compound is Formula I:

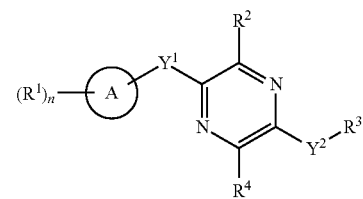

or a pharmaceutically acceptable salt, prodrug, solvate, hydrate, tautomer, or isomer thereof, wherein:

A is 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a{}_2)_m$—, —C(O)—, —$C(R^a)_2$NH—, —$(CR^a{}_2)_m$O—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N(R^a)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo;

$R^5$ and $R^6$ are each independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment II-3

The compound of embodiment II-1, wherein the compound is Formula I-W6:

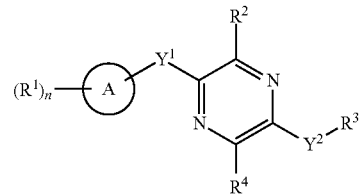

I-W6 or a pharmaceutically acceptable salt, prodrug, solvate, hydrate, tautomer, or isomer thereof, wherein:

A is a 5- to 12-membered monocyclic or polycyclic heteroaryl;

$Y^1$ is —S—;

$Y^2$ is —$NR^a$—; wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —$(CH_2)_n$$NH_2$, —$COOR^b$, —$CONHR^b$, —$CONH(CH_2)_nCOOR^b$, —$NHCOOR^b$, —$CF_3$, —$CHF_2$, or —$CH_2F$;

$R^1$ is independently, at each occurrence, —H, —$C_1$-$C_6$alkyl, —OH, halogen, —$NO_2$, —CN, —$NR^5R^6$, —$SR^5$, —$C(O)R^5$, or —$CO_2R^5$;

$R^2$ is —$C_1$-$C_6$alkyl;

$R^b$ is independently, at each occurrence, —H or —$C_1$-$C_6$alkyl;

$R^4$ is —H, —$C_1$-$C_6$alkyl, —$C_1$-$C_6$haloalkyl, —$C_1$-$C_6$hydroxyalkyl, —$CF_2OH$, —CHFOH, —$C(O)NH(CH_2)_n$OH, —$C(O)NH(CH_2)_nR^b$, —$C(O)R^b$, —$C(O)NR^5R^6$, —OH, or —CN, wherein alkyl is optionally substituted with one or more —OH, —$NH_2$, halogen, or oxo; or $R^5$ and $R^6$ are each independently, at each occurrence, —H or —$C_1$-$C_6$alkyl; and n is independently, at each occurrence, 1, 2, 3, 4, 5, 6, 7, 8, 9, or 10.

Embodiment II-4

The compound of embodiment II-1, wherein the compound is Formula I-W7:

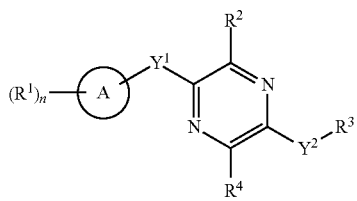

I-W7 or a pharmaceutically acceptable salt, prodrug, solvate, hydrate, tautomer, or isomer thereof, wherein:

A is a 5- to 12-membered monocyclic or polycyclic heteroaryl;

$Y^1$ is a direct bond;

$Y^2$ is —$NR^a$—; wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, —OH, —$NH_2$, heteroaryl, heterocyclyl, —$(CH_2)_n$$NH_2$, —$COOR^b$, —$CONHR^b$, —$CONH(CH_2)_nCOOR^b$, —$NHCOOR^b$, —$CF_3$, —$CHF_2$, or —$CH_2F$;

$R^1$ is independently, at each occurrence, —H, —$C_1$-$C_6$alkyl, —OH, halogen, —$NO_2$, —CN, —$NR^5R^6$, —$SR^5$, —$C(O)R^5$, or —$CO_2R^5$;

$R^2$ is —$C_1$-$C_6$alkyl;

$R^b$ is independently, at each occurrence, —H or —$C_1$-$C_6$alkyl;

$R^4$ is —H, —$C_1$-$C_6$alkyl, —$C_1$-$C_6$haloalkyl, —$C_1$-$C_6$hydroxyalkyl, —$CF_2OH$, —CHFOH, —$C(O)NH(CH_2)_nOH$, —$C(O)NH(CH_2)_nR^b$, —$C(O)R^b$, —$C(O)NR^5R^6$, —OH, or —CN, wherein alkyl is optionally substituted with one or more —OH, —$NH_2$, halogen, or oxo; or $R^5$ and $R^6$ are each independently, at each occurrence, —H or —$C_1$-$C_6$alkyl; and n is independently, at each occurrence, 1, 2, 3, 4, 5, 6, 7, 8, 9, or 10.

Embodiment II-5

A compound of Formula I-V1:

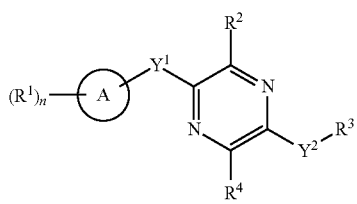

I-V1 or a pharmaceutically acceptable salt, prodrug, solvate, hydrate, tautomer, or isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —$S(O)_2$—, —$S(O)_2$—NH—, —C(=$CH_2$)—, —CH—, or —S(O)—;

$Y^2$ is —$NR^a$—, wherein the bond on the left side of $Y^2$, as drawn, is bound to the pyrazine ring and the bond on the right side of the $Y^2$ moiety, as drawn, is bound to $R^3$;

$R^a$ and $R^4$, together with the atom or atoms to which they are attached, are combined to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^b$ is independently, at each occurrence, —H, -D, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$, —$NR^5C(O)R^6$, heterocycle, aryl, heteroaryl, —$(CH_2)_nOH$, —$C_1$-$C_6$alkyl, —$CF_3$, —$CHF_2$, or —$CH_2F$;

$R^3$ is independently —H, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, spiroheterocycle, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN; and n is independently, at each occurrence, 0, 1, 2, 3, 4, 5, 6, 7, 8, 9, or 10.

Embodiment II-6

A compound of Formula I-V2:

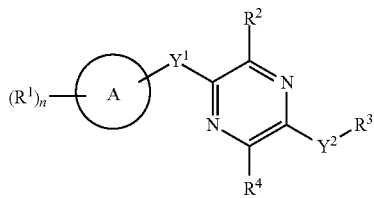

I-V2 or a pharmaceutically acceptable salt, prodrug, solvate, hydrate, tautomer, and isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —$S(O)_2$—, —$S(O)_2$—NH—, —C(=$CH_2$)—, —CH—, or —S(O)—;

$Y^2$ is —$NR^a$—, wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^1$ is independently, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —C(O)$R^5$, —$CO_2R^5$, —C(O)$NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —C(O)$OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —S(O)$NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^b$ is independently, at each occurrence, —H, -D, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —C(O)$NR^5R^6$, —$NR^5C(O)R^6$, heterocycle, aryl, heteroaryl, —$(CH_2)_nOH$, —$C_1$-$C_6$alkyl, —$CF_3$, —$CHF_2$, or —$CH_2F$;

$R^4$ is independently —H, -D, —$C_1$-$C_6$alkyl, —$C_1$-$C_6$haloalkyl, —$C_1$-$C_6$hydroxyalkyl, —$CF_2OH$, —CHFOH, —NH—$NHR^5$, —NH—$OR^5$, —O—$NR^5R^6$, —$NHR^5$, —$OR^5$, —NHC(O)$R^5$, —NHC(O)$NHR^5$, —NHS(O)$_2R^5$, —NHS(O)$_2NHR^5$, —$S(O)_2OH$, —C(O)$OR^5$, —NH($CH_2)_n$OH, —C(O)NH($CH_2)_nOH$, —C(O)NH($CH_2)_nR^b$, —C(O)$R^b$, —$NH_2$, —OH, —CN, —C(O)$NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN; and n is independently, at each occurrence, 0, 1, 2, 3, 4, 5, 6, 7, 8, 9, or 10.

Embodiment II-7

The compound of embodiment II-5 or II-6, wherein $R^2$ is —$NH_2$.

Embodiment II-8

The compound of any one of embodiments II-1 to II-2 and II-5 to II-7, wherein A is cycloalkyl.

Embodiment II-9

The compound of any one of embodiments II-1 to II-2 and II-5 to II-7, wherein A is heterocycloalkyl.

Embodiment II-10

The compound of any one of embodiments II-1 to II-2 and II-5 to II-7, wherein A is aryl.

Embodiment II-11

The compound of any one of embodiments II-1 to II-2 and II-5 to II-7, wherein A is heteroaryl.

Embodiment II-12

The compound of any one of embodiments II-1 to II-7, wherein A is pyridinyl.

Embodiment II-13

The compound of any one of embodiments II-1 to II-12, wherein n is 1 or 2.

Embodiment II-14

The compound of any one of embodiments II-1 to II-13, wherein $R^1$ is independently, at each occurrence, —$C_1$-$C_6$alkyl, halogen, or —$NR^5R^6$.

Embodiment II-15

The compound of any one of embodiments II-1 to II-13, wherein $R^1$ is independently selected from methyl, fluoro, chloro, and —$NH_2$.

Embodiment II-16

The compound of any one of embodiments II-1 to II-2 and II-5 to II-15, wherein $Y^1$ is —S—.

Embodiment II-17

The compound of any one of embodiments II-1 to II-2 and II-5 to II-15, wherein $Y^1$ is a direct bond.

Embodiment II-18

The compound of any of one of embodiments II-1 to II-6 and II-8 to II-17, wherein $R^2$ is —$OR^b$.

Embodiment II-19

The compound of embodiment 18, wherein $R^b$ is —H.

Embdoment II-20

The compound of embodiment 18, wherein $R^b$ is —$C_1$-$C_6$alkyl.

Embodiment II-21

The compound of any of one of embodiments II-1 to II-6 and II-8 to II-17, wherein $R^2$ is —CN.

Embodiment II-22

The compound of any of one of embodiments II-1 to II-6 and II-8 to II-17, wherein $R^2$ is —$C_1$-$C_6$alkyl.

Embodiment II-23

The compound of any of embodiment II-22, wherein $R^2$ is methyl.

Embodiment II-24

The compound of any of one of embodiments II-1 to II-6 and II-8 to II-17, wherein $R^2$ is —$C_2$-$C_6$alkenyl.

Embodiment II-25

The compound of any of one of embodiments II-1 to II-6 and II-8 to II-17, wherein $R^2$ is —$C_2$-$C_6$alkynyl.

Embodiment II-26

The compound of any one of embodiments II-1 to II-4 and II-6 to II-25, wherein $R^4$ is —$C_1$-$C_6$alkyl, which is optionally substituted with one or more —OH, —$NH_2$, halogen, or oxo.

Embodiment II-27

The compound of embodiment II-26, wherein $R^4$ is —$C_1$-$C_6$alkyl, which is substituted with —OH.

Embodiment II-28

The compound of embodiment II-26, wherein $R^4$ is —$CH_2$—OH.

Embodiment II-29

The compound of any one of embodiments II-1 to II-4 and II-6 to II-25, wherein $R^4$ is —H.

Embodiment II-30

The compound of any one of embodiments II-1 to II-4 and II-6 to II-25, wherein $R^4$ is —CN.

Embodiment II-31

The compound of any one of embodiments II-1 to II-4 and II-6 to II-25, wherein $R^4$ is —$CF_2OH$ or —CHFOH.

Embodiment II-32

The compound of any one of embodiments II-1 to II-2 and II-7 to II-31, wherein $Y^2$ is —$NR^a$—.

Embodiment II-33

The compound of any one of embodiments II-1 to II-2 and II-7 to II-31, wherein $Y^2$ is —$(CR^a_2)_m$—.

Embodiment II-34

The compound of any one of embodiments II-1 to II-2, II-5, and II-7 to II-33, wherein $R^3$ is —$C_1$-$C_6$alkyl, which is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl.

Embodiment II-35

The compound of any one of embodiments II-1 to II-2, II-5, and II-7 to II-34, wherein $R^a$ is —H.

Embodiment II-36

The compound of any one of embodiments II-1 to II-2, II-5, 11-7 to II-33, and 11-35, wherein $R^3$ is 3- to 12-membered monocyclic or polycyclic heterocycle.

Embodiment II-37

The compound of any one of embodiments II-1 to II-2, II-5, 11-7 to II-33, and 11-35, wherein $R^3$ is a 3- to 12-membered monocyclic heterocycle.

Embodiment II-38

The compound of any one of embodiments II-1 to II-2, II-5 to 11-33, and 11-35, wherein $R^3$ is a 3- to 12-membered polycyclic heterocycle.

Embodiment II-39

The compound of any one of embodiments II-1 to II-4 and II-7 to II-33, wherein $R^3$ and $R^a$ together with the atom to which they are attached combine to form a 3- to 12-membered monocyclic heterocycle, which is optionally substituted with —$C_1$-$C_6$alkyl, —OH, —$NH_2$, heteroaryl, heterocyclyl, —$(CH_2)_n NH_2$, —$COOR^b$, —$CONHR^b$, —$CONH(CH_2)_n COOR^b$, —$NHCOOR^b$, —$CF_3$, —$CHF_2$, or —$CH_2F$.

Embodiment II-40

The compound of any one of embodiments II-1 to II-4 and II-6 to II-33, wherein $R^3$ and $R^a$ together with the atoms to which they are attached combine to form a 3- to 12-membered polycyclic heterocycle, which is optionally substituted with —$C_1$-$C_6$alkyl, —OH, —$NH_2$, heteroaryl, heterocyclyl, —$(CH_2)_n NH_2$, —$COOR^b$, —$CONHR^b$, —$CONH(CH_2)_n COOR^b$, —$NHCOOR^b$, —$CF_3$, —$CHF_2$, or —$CH_2F$.

Embodiment II-41

The compound of any one of embodiments II-1 to II-4 and II-6 to II-33, wherein $R^3$ and $R^a$ together with the atoms to which they are attached combine to form a 5- to 12-membered spiroheterocycle, which is optionally substituted with —$C_1$-$C_6$alkyl, —OH, —$NH_2$, heteroaryl, heterocyclyl, —$(CH_2)_n NH_2$, —$COOR^b$, —$CONHR^b$, —$CONH(CH_2)_n COOR^b$, —$NHCOOR^b$, —$CF_3$, —$CHF_2$, or —$CH_2F$.

Embodiment II-42

The compound of embodiment II-41, wherein $R^3$ and $R^a$ together with the atoms to which they are attached combine to form a 10- to 12-membered spiroheterocycle, which is optionally substituted with —$C_1$-$C_6$alkyl, —OH, —$NH_2$, heteroaryl, heterocyclyl, —$(CH_2)_n NH_2$, —$COOR^b$, —$CONHR^b$, —$CONH(CH_2)_n COOR^b$, —$NHCOOR^b$, —$CF_3$, —$CHF_2$, or —$CH_2F$.

Embodiment II-43

The compound of any of embodiments II-1 to II-2, II-7 to II-25, II-32 to II-34 and II-36 to II-38, wherein $R^a$ and $R^4$ together with the atom to which they are attached combine to form a monocyclic or polycyclic 3- to 12-membered cycloalkyl.

Embodiment II-44

The compound of any of embodiments II-1 to II-2, II-7 to II-25, II-32 to II-34 and II-36 to II-38, wherein $R^a$ and $R^4$ together with the atom to which they are attached combine to form a monocyclic or polycyclic 3- to 12-membered heterocycle.

Embodiment II-45

A compound selected from the group consisting of Compounds 1-41 and Compounds A-1 to A-309, or a pharmaceutically acceptable salt, prodrug, solvate, hydrate, tautomer, or isomer thereof.

Embodiment II-46

A pharmaceutical composition comprising a compound of any one of embodiments II-1 to II-45, or a pharmaceutically acceptable salt, prodrug, solvate, hydrate, tautomer, or isomer thereof, and a pharmaceutically acceptable carrier.

Embodiment II-47

A method of treating a disease associated with SHP2 modulation in a subject in need thereof, comprising administering to the subject an effective amount of a compound of any one of embodiments II-1 to II-45, or a pharmaceutically acceptable salt, prodrug, solvate, hydrate, tautomer, or isomer thereof

Embodiment II-48

The method of embodiment II-47, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-49

A compound of any one of embodiments II-1 to II-45, or a pharmaceutically acceptable salt, prodrug, solvate, hydrate, tautomer, or isomer thereof, for use as a medicament.

Embodiment II-50

A compound of any one of embodiments II-1 to II-45, or a pharmaceutically acceptable salt, prodrug, solvate, hydrate, tautomer, or isomer thereof, for use in treating or preventing a disease associated with SHP2 modulation.

Embodiment II-51

Use of a compound of any one of embodiments II-1 to II-45, or a pharmaceutically acceptable salt, prodrug, solvate, hydrate, tautomer, or isomer thereof, in the manufacture of a medicament for treating or preventing a disease associated with SHP2 modulation.

Embodiment II-52

A method of treating a disease associated with SHP2 modulation in a subject in need thereof, comprising administering to the subject an effective amount of a pharmaceutical composition of embodiment II-48.

Embodiment II-53

The method of embodiment II-52, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-54

A pharmaceutical composition of embodiment II-48 for use as a medicament.

Embodiment II-55

A pharmaceutical composition of embodiment II-48 for use in treating or preventing a disease associated with SHP2 modulation.

Embodiment II-56

Use of a pharmaceutical composition of embodiment II-48 in the manufacture of a medicament for treating or preventing a disease associated with SHP2 modulation.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Definitions used in the following examples and elsewhere herein are:

| | |
|---|---|
| CH$_2$Cl$_2$, DCM | Methylene chloride, Dichloromethane |
| CH$_3$CN, MeCN | Acetonitrile |
| CuI | Copper (I) iodide |
| DIPEA | Diisopropylethyl amine |
| DMF | N,N-Dimethylformamide |
| equiv | Equivalent |
| ESI | Electrospray ionization |
| EtOAc | Ethyl acetate |
| hr | hour |
| H$_2$O | Water |
| HCl | Hydrochloric acid |
| HPLC | High-performance liquid chromatography |
| K$_3$PO$_4$ | Potassium phosphate (tribasic) |
| LC-MS | Liquid chromatography mass spectrometry |
| MeOH | Methanol |
| min | Minute(s) |
| Na$_2$SO$_4$ | Sodium sulfate |
| NMP | N-methyl pyrrolidone |
| NMR | Nuclear magnetic resonance |
| Pd(dppf)Cl$_2$ | [1,1'-Bis(diphenylphosphino)ferrocene]dichloropalladium(II) |
| TLC | Thin layer chromatography |

Examples 1-93

Example 1—Synthesis of (R)-8-(5-((2,3-dichlorophenyl)thio)-6-methylpyrazin-2-yl)-8-azaspiro[4.5]decan-1-amine

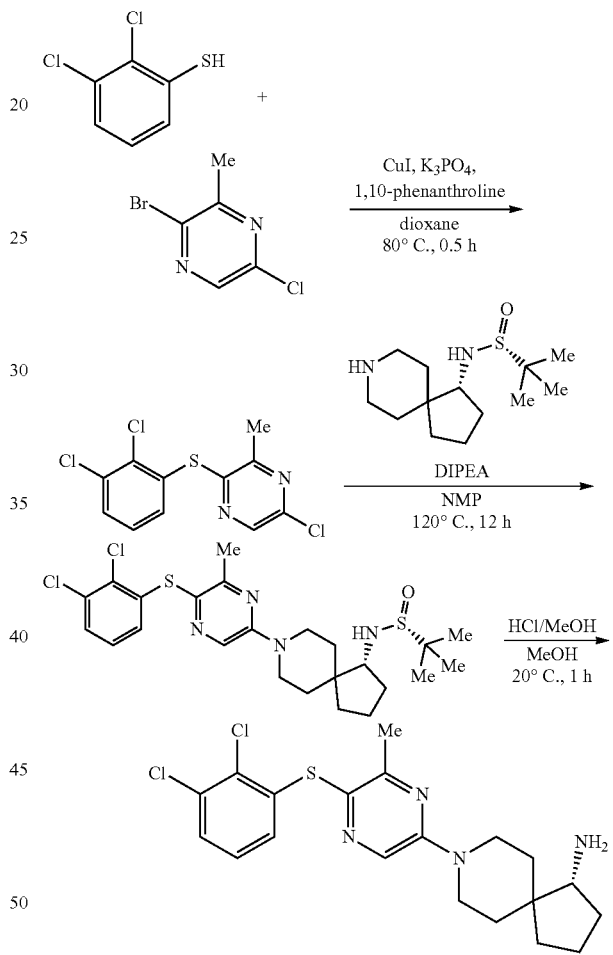

Step 1. Synthesis of 5-chloro-2-((2,3-dichlorophenyl)thio)-3-methylpyrazine

To a solution of 2-bromo-5-chloro-3-methylpyrazine (50 mg, 241.01 μmol, 1 equiv) in dioxane (3 mL) under an inert atmosphere at 20° C. was added 2,3-dichlorobenzenethiol (64.74 mg, 361.52 μmol, 1.5 equiv), CuI (9.18 mg, 48.20 μmol, 0.2 equiv), K$_3$PO$_4$ (102.32 mg, 482.02 μmol, 2 equiv), and 1,10-phenanthroline (17.37 mg, 96.40 μmol, 0.4 equiv), sequentially. The resulting mixture was stirred at 80° C. for 0.5 hours. The reaction mixture was then cooled, and H$_2$O (20 mL) was added to the solution. The resulting aqueous phase was extracted with ethyl acetate (4×10 mL), and the combined organic extracts were washed with brine (2×10 mL), dried over anhydrous Na₂SO₄, filtered, and concentrated under reduced pressure. The crude residue was purified to give 5-chloro-2-((2,3-dichlorophenyl)thio)-3-methylpyrazine (25.00 mg, 34% yield) as a light yellow solid. LC-MS (ESI): m/z: [M+H] calculated for C₁₁H₇Cl₃N₂S: 304.94; found 305.0.

Step 2. Synthesis of N—((R)-8-(5-((2,3-dichlorophenyl)thio)-6-methylpyrazin-2-yl)-8-azaspiro[4.5]decan-1-yl)-2-methylpropane-2-sulfinamide To a solution of 5-chloro-2-((2,3-dichlorophenyl)thio)-3-methylpyrazine (25 mg, 81.80 μmol, 1 equiv) and 2-methyl-N—((R)-8-azaspiro[4.5]decan-1-yl)propane-2-sulfinamide (42.28 mg, 163.61 μmol, 2 equiv) in NMP (1 mL) under an inert atmosphere at 20° C. was added DIPEA (84.58 mg, 654.43 μmol, 114.30 μL, 8 equiv). The mixture was then stirred at 120° C. for 12 hours. The reaction mixture was then cooled, and H₂O (20 mL) was added to the solution. The resulting aqueous phase was then extracted with ethyl acetate (4×10 mL). The combined organic extracts were washed with brine (2×10 mL), dried over anhydrous Na₂SO₄, filtered, and concentrated under reduced pressure to give crude N—((R)-8-(5-((2,3-dichlorophenyl)thio)-6-methylpyrazin-2-yl)-8-azaspiro[4.5]decan-1-yl)-2-methylpropane-2-sulfinamide (30 mg) as a black brown solid which was used directly in the next step without further purification. LC-MS (ESI): m/z: [M+H] calculated for C₂₄H₃₂Cl₂N₄OS₂: 527.14; found 527.1.

Step 3. Synthesis of (R)-8-(5-((2,3-dichlorophenyl)thio)-6-methylpyrazin-2-yl)-8-azaspiro[4.5]decan-1-amine To a solution of N—((R)-8-(5-((2,3-dichlorophenyl)thio)-6-methylpyrazin-2-yl)-8-azaspiro[4.5]decan-1-yl)-2-methylpropane-2-sulfinamide (30 mg, 56.86 μmol, 1 equiv) in MeOH (1 mL) under an inert atmosphere at 20° C. was added HCl in MeOH (4M, 3 mL). The resulting mixture was stirred at 20° C. for 1 hour. The reaction mixture was then concentrated under reduced pressure to give the crude product. This crude residue was purified by preparative HPLC to give (R)-8-(5-((2,3-dichlorophenyl)thio)-6-methylpyrazin-2-yl)-8-azaspiro[4.5]decan-1-amine (7.01 mg, 29.12% yield) as a solid. ¹H NMR (400 MHz, methanol-d₄) δ 8.12 (br s, 1H), 7.34 (d, J=7.72 Hz, 1H), 7.12 (t, J=7.94 Hz, 1H), 6.69 (d, J=7.72 Hz, 1H), 4.45-4.27 (m, 2H), 3.27-3.14 (m, 3H), 2.44 (s, 3H), 2.18-2.29 (m, 1H), 1.94-1.72 (m, 6H), 1.64-1.50 (m, 3H). LC-MS (ESI): m/z: [M+H] calculated for C₂₀H₂₄Cl₂N₄S: 423.11; found 423.1.

Example 2—Synthesis of 1-(5-((2,3-dichlorophenyl)thio)-6-methylpirazine-2-yl)-4-methylpiperidin-4-amine

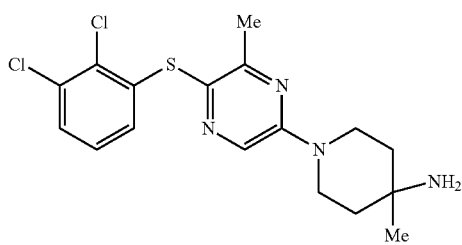 [SMILES: Cc1nc(N2CCC(C)(N)CC2)cnc1Sc1cccc(Cl)c1Cl]

1-(5-((2,3-dichlorophenyl)thio)-6-methylpirazine-2-yl)-4-methylpiperidin-4-amine was synthesized in the manner similar to Example 1, except 2-methyl-N—((R)-8-azaspiro[4.5]decan-1-yl)propane-2-sulfinamide was substituted with tert-butyl (4-methylpiperidin-4-yl)carbamate. ¹H NMR (400 MHz, DMSO-d₆) δ 8.26 (s, 4H), 7.48-7.46 (m, 1H), 7.26-7.22 (m, 1H), 6.75 (d, J=8 Hz, 1H), 4.09-4.06 (m, 2H), 3.40 (m, 2H), 2.38 (s, 3H), 1.79-1.74 (m, 4H), 1.37 (s, 3H). LC-MS (ESI): m/z: [M+H] calculated for C₁₇H₂₀Cl₂N₄S: 383.08; found 383.1.

Example 3—Synthesis of 1-(5-((2,3-dichlorophenyl)thio)-6-methylpyrazin-2-yl)-N,4-dimethylpiperidin-4-amine

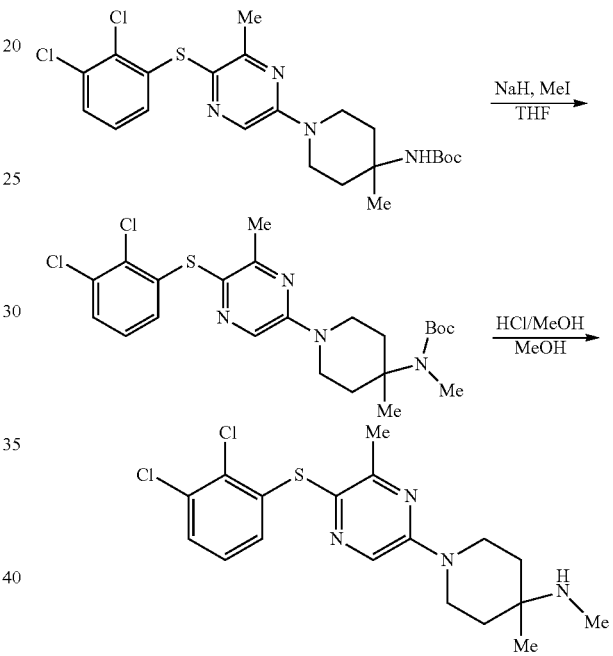

Step 1. Synthesis of tert-butyl (1-(5-((2,3-dichlorophenyl)thio)-6-methylpyrazin-2-yl)-4-methylpiperidin-4-yl)(methyl)carbamate To a solution of tert-butyl (1-(5-((2,3-dichlorophenyl)thio)-6-methylpyrazin-2-yl)-4-methylpiperidin-4-yl)carbamate (150.00 mg, 310.27 μmol, 1.00 equiv) in THF (5.00 mL) was added sodium hydride (12.41 mg, 310.27 μmol, 60% purity, 1 equiv) portionwise at 0° C. under an inert atmosphere. The mixture was stirred at 0° C. for 30 minutes, and then methyl iodide (44.04 mg, 310.27 μmol, 19.32 μL, 1 equiv) was added dropwise at 0° C. The mixture was stirred at 0° C. and stirred for 1.5 hours, after which the reaction mixture was quenched by addition water (50 mL) and extracted with EtOAc (3×20 mL). The combined organic layers were washed with brine (2×20 mL), dried over sodium sulfate, filtered, and concentrated under reduced pressure to give the methylated product as a yellow solid (110.00 mg, crude). LC-MS (ESI): m/z: [M+H] calculated for C₂₃H₃₀Cl₂N₄O₂S: 497.15; found: 497.1; RT=1.12 minutes.

Step 2. Synthesis of 1-(5-((2,3-dichlorophenyl)thio)-6-methylpyrazin-2-yl)-N,4-dimethylpiperidin-4-amine 1-(5-((2,3-dichlorophenyl)thio)-6-methylpyrazin-2-yl)-N,4-dimethylpiperidin-4-amine was synthesized in the manner similar to Example 1, except N—((R)-8-(5-((2,3-dichlorophenyl)thio)-6-methylpyrazin-2-yl)-8-azaspiro[4.5]decan-1-yl)-2-methylpropane-2-sulfinamide was substituted with tert-butyl (1-(5-((2,3-dichlorophenyl)thio)-6-methylpyrazin-2-yl)-4-methylpiperidin-4-yl)(methyl)carbamate. $^1$H NMR (400 MHz, chloroform-d) δ ppm 8.38 (s, 1H), 7.93 (s, 1H), 3.87-3.84 (m, 1H), 3.56-3.44 (m, 1H), 2.40 (s, 3H), 1.74 (br d, J=4.15 Hz, 1H), 1.35-1.29 (m, 1H). LC-MS (ESI): m/z: [M+H] calculated for $C_{18}H_{22}Cl_2N_4S$: 397.09; found: 396.9.

Example 4—Synthesis of 1-(5-((2,3-dichlorophenyl)thio)-6-methylpirazine-2-yl)-4-aminomethyl-4-methylpiperidine

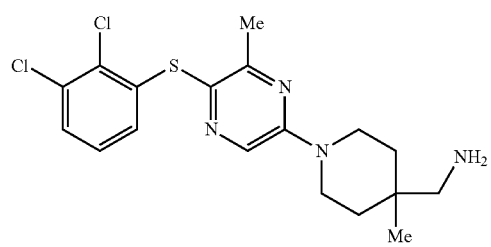 [SMILES: Cc1nc(N2CCC(C)(CN)CC2)cnc1Sc1cccc(Cl)c1Cl]

1-(5-((2,3-dichlorophenyl)thio)-6-methylpirazine-2-yl)-4-aminomethyl-4-methylpiperidine was synthesized in the manner similar to Example 1, except 2-methyl-N—((R)-8-azaspiro[4.5]decan-1-yl)propane-2-sulfinamide was substituted with tert-butyl ((4-methylpiperidin-4-yl)methyl)carbamate. 1-(5-((2,3-dichlorophenyl)thio)-6-methylpirazine-2-yl)-4-aminomethyl-4-methylpiperidine was isolated as its formate salt after HPLC purification. $^1$H NMR (500 MHz, DMSO-$d_6$) δ 8.36 (s, 1H), 8.22 (d, J=0.7 Hz, 1H), 7.46 (dd, J=8.0, 1.4 Hz, 1H), 7.23 (t, J=8.0 Hz, 1H), 6.72 (dd, J=8.0, 1.4 Hz, 1H), 3.89 (dt, J=13.5, 5.0 Hz, 2H), 3.40 (ddd, J=13.3, 9.6, 3.5 Hz, 2H), 2.57 (s, 2H), 2.38 (s, 3H), 1.49 (ddd, J=13.7, 9.6, 4.1 Hz, 2H), 1.36 (dt, J=13.5, 4.5 Hz, 2H), 1.00 (s, 3H). LC-MS (ESI): m/z: [M+H] calculated for $C_{18}H_{22}Cl_2N_4S$: 397.09; found 397.39.

Example 5—Synthesis of (1-(5-((2,3-dichlorophenyl)thio)-6-methylpyrazin-2-yl)-4-(pyridin-3-yl)piperidin-4-yl)methanamine

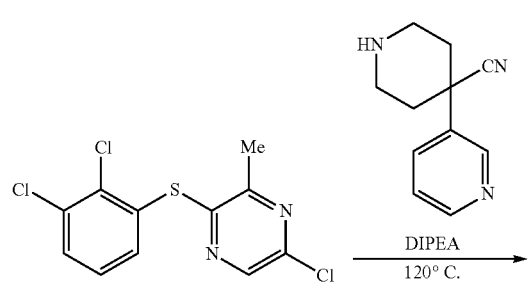

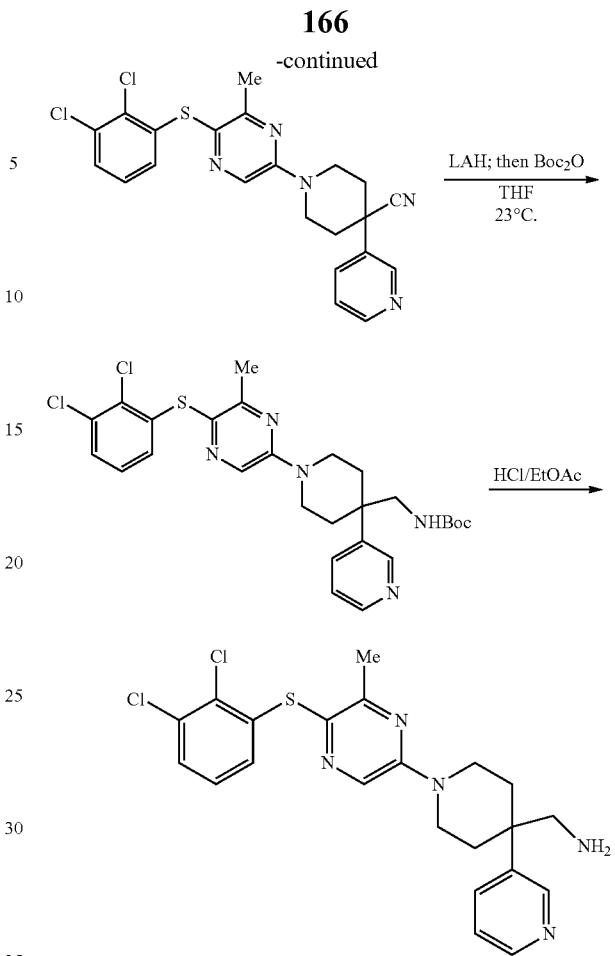

Synthesis of 4-(pyridin-3-yl)piperidine-4-carbonitrile

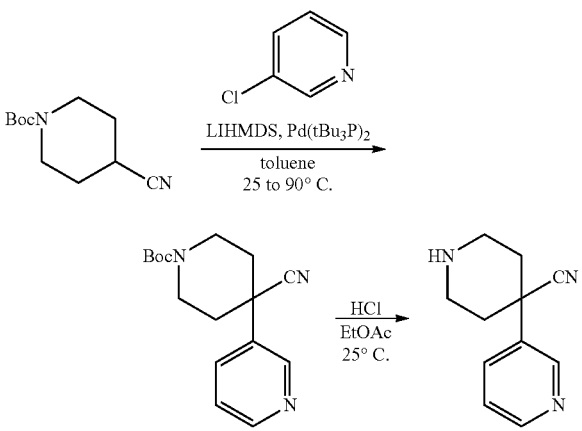

Synthesis of 4-(pyridin-3-yl)piperidine-4-carbonitrile

To a mixture of tert-butyl 4-cyanopiperidine-1-carboxylate (500 mg, 2.3 mmol, 1 equiv) and 3-chloropyridine (405 mg, 3.5 mmol, 340 µL, 1.5 equiv) in toluene (10 mL) was added LiHMDS (1M, 7.1 mL, 3 equiv) and Pd(t-Bu₃P)₂ (243 mg, 476 μmol, 0.2 equiv) in one portion at 25° C. under an inert atmosphere. The mixture was stirred at 25° C. for 2 hours, and then warmed to 90° C. for 15 hours. The reaction mixture was then poured into H₂O (5 mL), and the aqueous phase was extracted with ethyl acetate (3×10 mL). The combined organic phase was washed with brine (2 mL), dried with anhydrous sodium sulfate, filtered, and concentrated under reduced pressure. The residue was purified by column chromatography to give tert-butyl 4-cyano-4-(pyridin-3-yl)piperidine-1-carboxylate (180 mg, 626 μmol, 26% yield) as a yellow oil. ¹H NMR (400 MHz, chloroform-d) δ 8.64 (br s, 1H), 8.51 (br d, J=3.53 Hz, 1H), 7.69 (br d, J=7.94 Hz, 1H), 7.25 (dd, J=7.94, 4.85 Hz, 1H), 7.14 (s, 1H), 4.32-4.11 (m, 2H), 3.09 (br s, 2H), 2.01 (br d, J=12.8 Hz, 2H), 1.91-1.79 (m, 3H), 1.37 (s, 9H), 1.36-1.32 (m, 2H), 1.15-1.12 (m, 1H), 1.09 (s, 1H). Deprotection with HCl (4N, dioxane) produced 4-(pyridin-3-yl)piperidine-4-carbonitrile hydrochloride that was used in the next step without further purification.

Step 1. Synthesis of 1-(5-((2,3-dichlorophenyl)thio)-6-methylpyrazin-2-yl)-4-(pyridin-3-yl)piperidine-4-carbonitrile To a mixture of 4-(pyridin-3-yl)piperidine-4-carbonitrile hydrochloride (108 mg, 356 μmol, 1 equiv) in DIEA (4 mL) was added 5-chloro-2-((2,3-dichlorophenyl)thio)-3-methylpyrazine (80 mg, 427 μmol, 1.2 equiv) at 120° C. under an inert atmosphere. The mixture was stirred at 120° C. for 15 hours before it was poured into H₂O (5 mL), and the aqueous phase was then extracted with ethyl acetate (3×5 mL). The combined organic extracts were washed with brine (1 mL), dried with anhydrous sodium sulfate, filtered, and concentrated under reduced pressure. The residue was purified by column chromatography to give 1-(5-((2,3-dichlorophenyl)thio)-6-methylpyrazin-2-yl)-4-(pyridin-3-yl)piperidine-4-carbonitrile (60 mg, 131 μmol, 37% yield) as a white solid. ¹H NMR (400 MHz, chloroform-d) δ 8.80 (d, J=2.19 Hz, 1H), 8.65 (d, J=4.82 Hz, 1H), 8.07 (s, 1H), 7.85 (dd, J=8.11, 1.53 Hz, 1H), 7.40 (dd, J=7.89, 4.82 Hz, 1H), 7.30 (dd, J=8.33, 1.32 Hz, 1H), 7.06 (t, J=8.11 Hz, 1H), 6.83-6.78 (m, 1H), 5.31 (s, 1H), 4.62 (br d, J=14.03 Hz, 2H), 3.44 (br t, J=13.15 Hz, 2H), 2.53 (s, 3H), 2.31 (br d, J=12.28 Hz, 2H), 2.19-2.09 (m, 2H).

Step 2. Synthesis of tert-butyl ((1-(5-((2,3-dichlorophenyl)thio)-6-methylpyrazin-2-yl)-4-(pyridin-3-yl)piperidin-4-yl)methyl)carbamate To a solution of 1-(5-((2,3-dichlorophenyl)thio)-6-methylpyrazin-2-yl)-4-(pyridin-3-yl)piperidine-4-carbonitrile (60 mg, 131 μmol, 1 equiv) in THF (5 mL) was added lithium aluminum hydride (30 mg, 788 μmol, 6 equiv) in one portion at 0° C. under an inert atmosphere. The mixture was stirred at 0° C. for 2 hours before H₂O (0.1 mL) was added drop wise into the reaction mixture to give a turbid liquid. This mixture was then diluted with THF (10 mL) before Boc₂O (85 mg, 391 μmol, 90 μL, 3 equiv) was added at 25° C. under N₂. The mixture was stirred at 25° C. for 2 hours before the mixture was filtered and concentrated in vacuum. The residue was purified by column chromatography to give tert-butyl ((1-(5-((2,3-dichlorophenyl)thio)-6-methylpyrazin-2-yl)-4-(pyridin-3-yl)piperidin-4-yl)methyl)carbamate (27 mg, 51 μmol, 39% yield) as a white solid. ¹H NMR (400 MHz, chloroform-d) δ 8.73-8.46 (m, 2H), 8.00 (s, 1H), 7.71 (br d, J=6.58 Hz, 1H), 7.38 (br s, 1H), 7.25 (br d, J=8.33 Hz, 1H), 7.01 (t, J=7.89 Hz, 1H), 6.67 (d, J=7.89 Hz, 1H), 4.31 (br s, 1H), 3.97 (br s, 2H), 3.41 (br d, J=5.26 Hz, 3H), 2.47 (s, 3H), 2.25 (br s, 2H), 2.00 (br s, 2H), 1.40 (s, 9H), 1.31-1.23 (m, 1H).

Step 3. Synthesis of (1-(5-((2,3-dichlorophenyl)thio)-6-methylpyrazin-2-yl)-4-(pyridin-3-yl)piperidin-4-yl)methanamine Synthesis of (1-(5-((2,3-dichlorophenyl)thio)-6-methylpyrazin-2-yl)-4-(pyridin-3-yl)piperidin-4-yl)methanamine was synthesized in a manner similar to Example 1. ¹H NMR (400 MHz, methanol-d₄) δ 8.72 (s, 1H), 8.56 (d, J=4.63 Hz, 1H), 8.49 (br s, 1H), 8.08 (s, 1H), 8.03 (br d, J=8.16 Hz, 1H), 7.56 (dd, J=7.94, 4.85 Hz, 1H), 7.34 (d, J=7.94 Hz, 1H), 7.11 (t, J=8.05 Hz, 1H), 6.67 (d, J=7.72 Hz, 1H), 4.16 (br d, J=13.45 Hz, 2H), 3.35-3.33 (m, 1H), 3.28 (br s, 1H), 3.23 (s, 2H), 2.44 (s, 5H), 2.01 (br t, J=10.14 Hz, 2H). LC-MS (ESI): m/z: [M+H] calculated for C₂₂H₂₃Cl₂N₅S: 460.11; found 459.9.

Example 6—Synthesis of (R)-8-(5-((2-amino-3-chloropyridin-4-yl)thio)-6-methylpyrazin-2-yl)-8-azaspiro[4.5]decan-1-amine

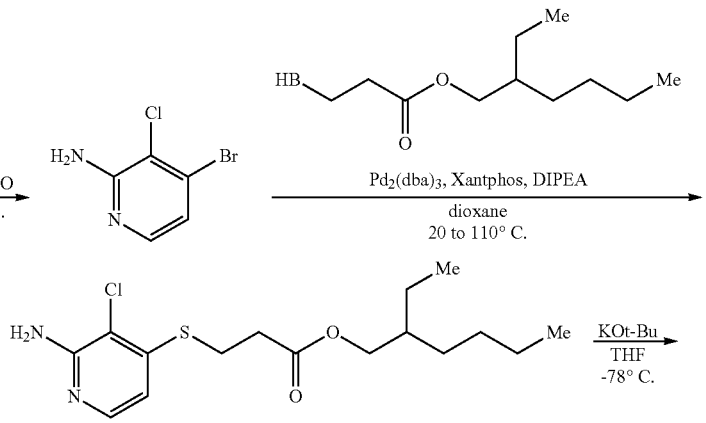

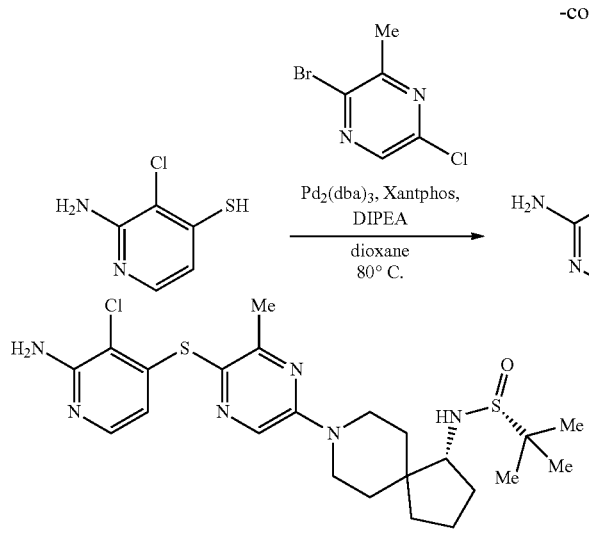
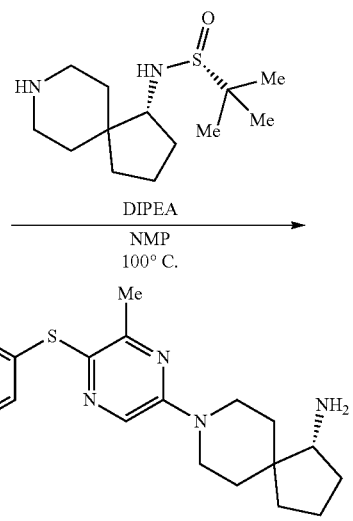

Step 1. Synthesis of 4-bromo-3-chloropyridin-2-amine

Three separate batches of 4-bromo-3-chloro-2-fluoropyridine (3×8.00 g, 3×38.02 mmol, 3×1 equiv) and NH₃·H₂O (3×60 mL) were stirred at 120° C. for 2 hours, after which the three batches were combined and concentrated to reduce the volume of the solution. The aqueous phase was then extracted with dichloromethane (3×50 mL), and the combined organic extracts were washed with brine (2×50 mL), dried over anhydrous sodium sulfate, filtered, and concentrated to give 4-bromo-3-chloropyridin-2-amine (22.06 g, 106.33 mmol, 93% yield) as a white solid. ¹H NMR (400 MHz, chloroform-d) δ 7.76 (d, J=5.26 Hz, 1H), 6.91 (d, J=5.26 Hz, 1H), 5.06 (br, 2H).

Step 2. Synthesis of 2-ethylhexyl 3-((2-amino-3-chloropyridin-4-yl)thio)propanoate To a solution of 4-bromo-3-chloropyridin-2-amine (5 g, 24.1 mmol, 1 equiv) in dioxane (50 mL) was added 2-ethylhexyl 3-sulfanylpropanoate (5.2 g, 24.1 mmol, 1 equiv), Xantphos (1.3 g, 2.4 mmol, 0.1 equiv), Pd₂(dba)₃ (831 mg, 1.4 mmol, 0.06 equiv), DIPEA (8.4 mL, 48.2 mmol, 2 equiv) at 20° C. The mixture was then warmed 110° C. and stirred for 5 hours under an inert atmosphere. After this time, the reaction was diluted with H₂O, the aqueous phase was extracted with dichloromethane (3×50 mL). The combined organic extracts were washed with brine (2×50 mL), dried over anhydrous sodium sulfate, filtered, and concentrated. The reaction mixture was beating, and then filtered to give 2-ethylhexyl 3-((2-amino-3-chloropyridin-4-yl)thio)propanoate (5 g, 14.7 mmol, 61% yield) as a light green solid. ¹H NMR (400 MHz, chloroform-d) δ ppm 7.85 (d, J=5.51 Hz, 1H), 6.50 (d, J=5.51 Hz, 1H), 4.84 (br s, 1H), 4.03 (dd, J=5.84, 1.21 Hz, 2H), 3.20 (t, J=7.50 Hz, 2H), 2.71 (t, J=7.39 Hz, 2H), 1.66-1.51 (m, 3H), 1.45-1.31 (m, 2H), 1.27 (br s, 5H), 0.87 (t, J=7.39 Hz, 6H).

Step 3. Synthesis of 2-amino-3-chloropyridine-4-thiol

To a solution of 2-ethylhexyl 3-((2-amino-3-chloropyridin-4-yl)thio)propanoate (5 g, 14.5 mmol, 1 equiv) in THF (50 mL) at −78° C. under an inert atmosphere was added potassium tert-butoxide (1M in THF, 29 mL, 29 mmol, 2 equiv). The reaction was stirred at −78° C. for 1 hour, after which the reaction mixture was filtered and concentrated. The crude residue was purified by silica gel column to give 2-amino-3-chloropyridine-4-thiol (1.9 g, 11.8 mmol, 81% yield) as a yellow solid.

Step 4. Synthesis of 3-chloro-4-((5-chloro-3-methylpyrazin-2-yl)thio)pyridin-2-amine To a solution of 2-amino-3-chloropyridine-4-thiol (4.09 g, 25.4 mmol, 1.1 equiv) in dioxane (25 mL) under an inert atmosphere was added DIEA (8.08 mL, 46.2 mmol, 2 equiv), 2-bromo-5-chloro-3-methylpyrazine (4.80 g, 23.1 mmol, 1 equiv), Xantphos (1.34 g, 2.31 mmol, 0.1 equiv) and Pd₂(dba)₃ (1.69 g, 1.85 mmol, 0.08 equiv). The reaction mixture was stirred at 80° C. for 1 hour, after which the reaction mixture was concentrated. The residue was purified by silica gel column to give 3-chloro-4-((5-chloro-3-methylpyrazin-2-yl)thio)pyridin-2-amine (3.20 g, 11.1 mmol, 48% yield) as a yellow solid. ¹H NMR (400 MHz, chloroform-d) δ 8.23 (s, 1H), 7.82 (d, J=5.29 Hz, 1H), 6.44 (d, J=5.29 Hz, 1H), 4.93 (br s, 2H), 2.56 (s, 3H).

Step 5. Synthesis of (R)—N—((R)-8-(5-((2-amino-3-chloropyridin-4-yl)thio)-6-methylpyrazin-2-yl)-8-azaspiro[4.5]decan-1-yl)-2-methylpropane-2-sulfinamide To a solution of 3-chloro-4-((5-chloro-3-methylpyrazin-2-yl)thio)pyridin-2-amine (750 mg, 2.61 mmol, 1 equiv) in DIEA (9.00 mL) and NMP (3.00 mL) was added (R)-2-methyl-N—((R)-8-azaspiro[4.5]decan-1-yl)propane-2-sulfinamide (1.01 g, 3.92 mmol, 1.5 equiv). The reaction was stirred at 100° C. for 2 hours, after which the reaction mixture was concentrated under reduced pressure. The crude residue was purified by silica gel column to give (R)—N—((R)-8-(5-((2-amino-3-chloropyridin-4-yl)thio)-6-methylpyrazin-2-yl)-8-azaspiro[4.5]decan-1-yl)-2-methylpropane-2-sulfinamide (750 mg, 1.47 mmol, 56% yield) as solid.

Step 6. Synthesis of (R)-8-(5-((2-amino-3-chloropyridin-4-yl)thio)-6-methylpyrazin-2-yl)-8-azaspiro[4.5]decan-1-amine A mixture of (R)—N—((R)-8-(5-((2-amino-3-chloropyridin-4-yl)thio)-6-methylpyrazin-2-yl)-8-azaspiro[4.5]decan- 1-yl)-2-methylpropane-2-sulfinamide (1.00 g, 1.96 mmol, 1 equiv) in HCl/MeOH (10 mL) was stirred at 20° C. for 1 hour, after which the reaction mixture was concentrated under reduced pressure. The residue was purified by HPLC to give (R)-8-(5-((2-amino-3-chloropyridin-4-yl)thio)-6-methylpyrazin-2-yl)-8-azaspiro[4.5]decan-1-amine (350 mg, 864 µmol, 44% yield) as a white solid. $^1$H NMR (400 MHz, chloroform-d) δ 8.03 (s, 1H), 7.62 (d, J=5.51 Hz, 1H), 5.88 (d, J=5.51 Hz, 1H), 5.14 (br s, 2H), 4.24 (br t, J=14.33 Hz, 2H), 3.13 (br s, 2H), 2.98 (br s, 1H), 2.44 (s, 3H), 1.26-1.92 (m, 10H). LC-MS (ESI): m/z: [M+H] calculated for $C_{19}H_{25}Cl_2N_6S$: 405.15; found 405.0.

Example 7—Synthesis of 4-((5-(4-amino-4-methyl-piperidin-1-yl)-3-methylpyrazin-2-yl)thio)-3-chloro-pyridin-2-amine

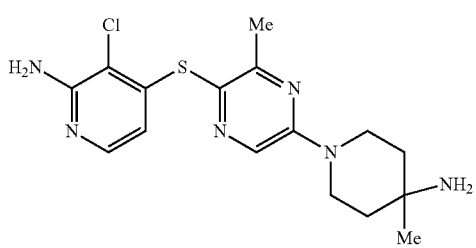 [SMILES: Cc1nc(N2CCC(C)(N)CC2)cnc1Sc1ccnc(N)c1Cl]

4-((5-(4-amino-4-methylpiperidin-1-yl)-3-methyl-pyrazin-2-yl)thio)-3-chloropyridin-2-amine was synthesized in the manner similar to Example 6, except (R)-2-methyl-N—((R)-8-azaspiro[4.5]decan-1-yl)propane-2-sulfinamide was substituted with 4-methylpiperidin-4-amine. $^1$H NMR (400 MHz, methanol-$d_4$) δ 8.52 (s, 1H), 8.18 (s, 1H), 7.57 (d, J=5.70 Hz, 1H), 5.78 (d, J=5.70 Hz, 1H), 4.31-4.15 (m, 2H), 3.60-3.40 (m, 2H), 2.46 (s, 3H), 1.97-1.79 (m, 4H), 1.49 (s, 3H). LC-MS (ESI): m/z: [M+H] calculated for $C_{16}H_{21}ClN_6S$: 365.1; found 365.1.

N-(3-bromo-2-chlorophenyl)-2,2,2-trifluoroacetamide

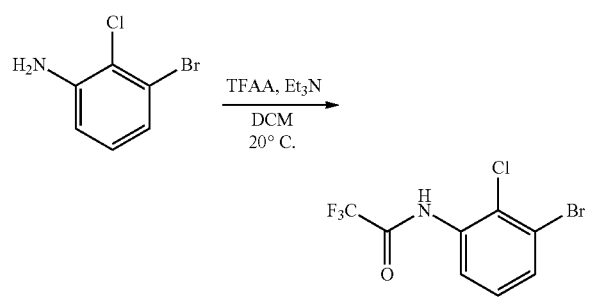

To a solution of 3-bromo-2-chloroaniline (8 g, 39 mmol, 1 equiv) in DCM (80 mL) under an inert atmosphere at 0° C. was added triethylamine (16.11 mL, 116 mmol, 3 equiv) followed by trifluoroacetic anhydride (8.1 mL, 58 mmol, 1.5 equiv). The resulting mixture was then warmed to 20° C. and stirred for 2 hours. After this time, the reaction was quenched with $H_2O$ (100 mL) and extracted with DCM (3×150 mL). The combined organic extracts were washed with brine (140 mL), dried over $Na_2SO_4$, filtered, and concentrated under reduced pressure. The crude residue was purified by silica gel chromatography to give N-(3-bromo-2-chlorophenyl)-2,2,2-trifluoroacetamide (10 g, 33 mmol, 85% yield) as white solid. $^1$H NMR (400 MHz, chloroform-d) δ 8.48 (s, 1H) 8.34-8.31 (m, 1H) 7.53-7.51 (m, 1H) 7.26-7.21 (m, 1H).

Example 8—Synthesis of (R)-8-(5-((3-amino-2-chlorophenyl)thio)-6-methylpyrazin-2-yl)-8-azaspiro[4.5]decan-1-amine

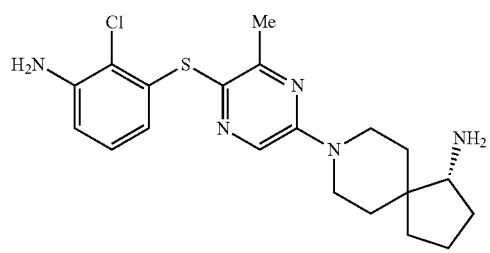 [SMILES: Cc1nc(N2CCC3(CCC[C@H]3N)CC2)cnc1Sc1cccc(N)c1Cl]

(R)-8-(5-((3-amino-2-chlorophenyl)thio)-6-methyl-pyrazin-2-yl)-8-azaspiro[4.5]decan-1-amine was synthesized in the manner similar to Example 6, except 4-bromo-3-chloropyridin-2-amine was substituted with N-(3-bromo-2-chlorophenyl)-2,2,2-trifluoroacetamide. $^1$H NMR (400 MHz, methanol-$d_4$) δ 8.54 (s, 1H), 8.65-8.47 (m, 1H), 8.02 (s, 1H), 6.85 (t, J=7.94 Hz, 1H), 6.64 (dd, J=8.05, 1.43 Hz, 1H), 5.99 (dd, J=7.72, 1.32 Hz, 1H), 4.42-4.19 (m, 2H), 3.20-3.04 (m, 2H), 2.41 (s, 2H), 2.22-2.13 (m, 1H), 2.04-2.34 (m, 8H). LC-MS (ESI): m/z: [M+H] calculated for $C_{20}H_{26}ClN_5S$: 404.16; found 404.1.

Example 9—Synthesis of 4-((5-(4-(aminomethyl)-4-methylpiperidin-1-yl)-3-methylpyrazin-2-yl)thio)-3-chloropyridin-2-amine

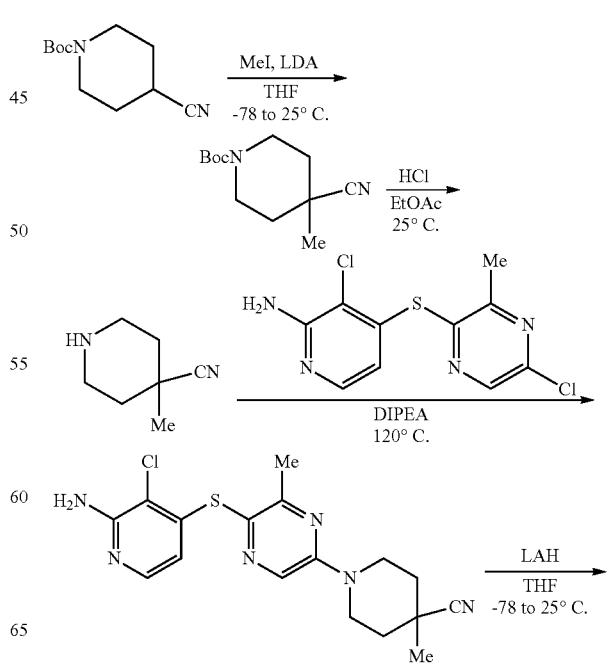

-continued

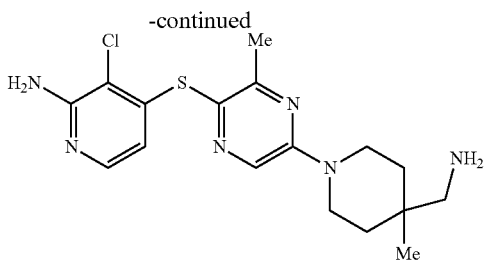

Step 1. Synthesis of tert-butyl 4-cyano-4-methylpiperidine-1-carboxylate

To a solution of tert-butyl 4-cyanopiperidine-1-carboxylate (3.00 g, 14.2 mmol, 1 equiv) in THF (60 mL) under inert atmosphere at −78° C. was added LDA (2M in THF, 7.85 mL, 1.1 equiv) in a dropwise fashion over 15 minutes. The resulting yellow solution was stirred at −78° C. for 30 minutes before iodomethane (1.33 mL, 21.4 mmol, 1.5 equiv) was added in a dropwise fashion. The reaction mixture was stirred at −78° C. for 30 minutes before it was warmed to 25° C. and stirred for 1 hour. After this time, the reaction mixture was poured into 100 mL of ice-water carefully, and the organic layer was separated. The aqueous phase was extracted with ethyl acetate (3×100 mL). The combined organic extracts were washed with brine (5 mL), dried with anhydrous $Na_2SO_4$, filtered, and concentrated under reduced pressure. The crude residue was purified by column chromatography to give tert-butyl 4-cyano-4-methylpiperidine-1-carboxylate (1.82 g, 8.11 mmol, 56% yield) as a white solid. $^1$H NMR (400 MHz, chloroform-d) δ 4.22-3.93 (m, 2H), 3.00 (br s, 2H), 1.85 (br d, J=13.23 Hz, 2H), 1.47-1.31 (m, 14H).

Step 2. Synthesis of 4-methylpiperidine-4-carbonitrile

To a solution of HCl/EtOAc (4M, 20 mL) under inert atmosphere was added tert-butyl 4-cyano-4-methylpiperidine-1-carboxylate (1.82 g, 8.11 mmol, 1 equiv) at 25° C. The mixture was stirred at 25° C. for 3 hours, after which the reaction mixture was filtered and concentrated under reduced pressure to give 4-methylpiperidine-4-carbonitrile (1.46 g, crude, HCl salt) as a white solid. $^1$H NMR (400 MHz, methanol-$d_4$) δ 3.45 (br d, J=13.67 Hz, 2H), 3.16 (td, J=13.34, 2.65 Hz, 2H), 2.19 (br d, J=14.11 Hz, 2H), 1.74-1.86 (m, 2H), 1.46 (s, 3H).

Step 3. Synthesis of 1-(5-((2-amino-3-chloropyridin-4-yl)thio)-6-methylpyrazin-2-yl)-4-methylpiperidine-4-carbonitrile The mixture of 4-methylpiperidine-4-carbonitrile (200 mg, 696 μmol, 1 equiv) and 3-chloro-4-((5-chloro-3-methylpyrazin-2-yl)thio)pyridin-2-amine (112 mg, 696 μmol, 1 equiv) in DIPEA (2.00 mL) was stirred at 120° C. under an inert atmosphere for 2 hours. The reaction mixture was then poured into $H_2O$ (5 mL), and the aqueous phase was extracted with EtOAc (3×5 mL). The combined organic extracts were washed with brine (1 mL), dried with anhydrous $Na_2SO_4$, filtered, and concentrated under reduced pressure. The crude residue was then purified by column chromatography to give 1-(5-((2-amino-3-chloropyridin-4-yl)thio)-6-methylpyrazin-2-yl)-4-methylpiperidine-4-carbonitrile (100 mg, 266 μmol, 38% yield) as a white solid. $^1$H NMR (400 MHz, chloroform-d) δ 8.05 (s, 1H), 7.67 (d, J=5.29 Hz, 1H), 5.87 (d, J=5.51 Hz, 1H), 4.84 (br s, 2H), 4.43 (br d, J=13.01 Hz, 2H), 3.26 (br t, J=12.24 Hz, 2H), 2.47 (s, 3H), 2.07 (br s, 1H), 1.41-1.47 (m, 4H).

Step 4. Synthesis of 4-((5-(4-(aminomethyl)-4-methylpiperidin-1-yl)-3-methylpyrazin-2-yl)thio)-3-chloropyridin-2-amine To a mixture of 1-(5-((2-amino-3-chloropyridin-4-yl)thio)-6-methylpyrazin-2-yl)-4-methylpiperidine-4-carbonitrile (100 mg, 266 μmol, 1.00 equiv) in THF (2.60 mL) under inert atmosphere at −78° C. was added LAH (60.7 mg, 1.60 mmol, 6 equiv) in one portion. The mixture was stirred at 25° C. for 2 hours. After this time, $H_2O$ (0.1 mL) was added dropwise into the reaction mixture. The resulting mixture was filtered, and the filtrate was concentrated under reduced pressure to give crude product. The residue was purified by HPLC to 4-((5-(4-(aminomethyl)-4-methylpiperidin-1-yl)-3-methylpyrazin-2-yl)thio)-3-chloropyridin-2-amine (500 ug, 1.32 μmol, 0.49% yield) as a white solid. $^1$H NMR (400 MHz, methanol-$d_4$) δ 8.11 (s, 1H), 7.56 (d, J=5.51 Hz, 1H), 5.77 (d, J=5.73 Hz, 1H), 4.58 (s, 2H), 4.09 (s, 2H), 3.47 (br s, 3H), 2.87 (s, 2H), 2.43 (s, 3H), 1.57 (br s, 4H), 1.27 (s, 1H), 1.17 (s, 3H). LC-MS (ESI): m/z: [M+H] calculated for $C_{17}H_{24}ClN_6S$: 379.1; found 379.2.

Example 10—Synthesis of (R)-8-(5-((2,3-difluorophenyl)thio)-6-methylpyrazin-2-yl)-8-azaspiro[4.5]decan-1-amine

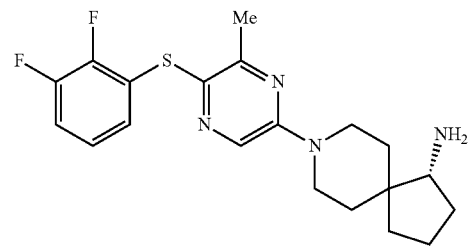 [SMILES: Cc1nc(N2CCC3(CCC[C@H]3N)CC2)cnc1Sc1cccc(F)c1F]

(R)-8-(5-((2,3-difluorophenyl)thio)-6-methylpyrazin-2-yl)-8-azaspiro[4.5]decan-1-amine was synthesized in the manner similar to Example 1, except 2,3-dichlorobenzenethiol was substituted with 2,3-difluorobenzenethiol. $^1$H NMR (400 MHz, methanol-$d_4$) δ 8.52-8.50 (m, 2H), 7.98 (s, 2H), 7.19-7.17 (m, 1H), 7.15-7.13 (m, 1H), 7.07-7.04 (m, 1H), 4.32-4.24 (m, 2H), 3.19-3.14 (m, 2H), 2.46 (s, 3H), 2.32-2.23 (m, 1H), 1.88-1.32 (m, 10H). LC-MS (ESI): m/z: [M+H] calculated for $C_{20}H_{24}F_2N_4S$: 391.17; found 391.0.

Example 11—Synthesis of 1-(5-((2,3-difluorophenyl)thio)-6-methylpyrazin-2-yl)-4-methylpiperidin-4-amine

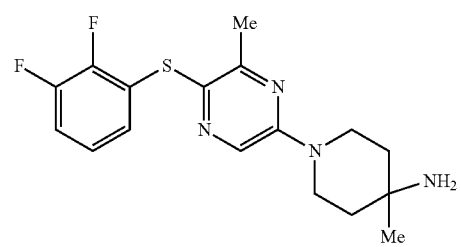 [SMILES: Cc1nc(N2CCC(C)(N)CC2)cnc1Sc1cccc(F)c1F]

1-(5-((2,3-difluorophenyl)thio)-6-methylpyrazin-2-yl)-4-methylpiperidin-4-amine was synthesized in the manner similar to Example 1, except 2,3-dichlorobenzenethiol and (R)-2-methyl-N—((R)-8-azaspiro[4.5]decan-1-yl)propane-2-sulfinamide were substituted with 2,3-difluorobenzenethiol and 4-methylpiperidin-4-amine, respectively. $^1$H NMR (400 MHz, methanol-$d_4$) δ 8.53 (s, 1H), 8.01 (s, 1H), 7.18-7.17 (m, 1H), 7.16-7.08 (m, 1H), 6.95-6.91 (m, 1H), 4.12-4.09 (m, 2H), 3.43-3.41 (m, 2H), 2.47 (s, 3H), 1.83-1.81 (m, 4H), 1.45 (s, 3H). LC-MS (ESI): m/z: [M+H] calculated for $C_{17}H_{20}F_2N_4S$: 351.14; found 351.2.

Example 12—Synthesis of 1-(5-((2,3-dichlorophenyl)thio)-6-methylpyrazin-2-yl)-4-methylpiperidin-4-amine

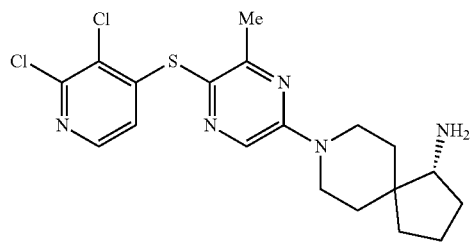 [SMILES: Cc1nc(N2CCC3(CCC[C@H]3N)CC2)cnc1Sc1ccnc(Cl)c1Cl]

1-(5-((2,3-dichlorophenyl)thio)-6-methylpyrazin-2-yl)-4-methylpiperidin-4-amine was synthesized in the manner similar to Example 6, except 4-bromo-3-chloropyridin-2-amine was substituted with 2,3-dichloro-4-iodopyridine. $^1$H NMR (400 MHz, methanol-$d_4$) δ 8.53 (s, 1H), 8.17 (s, 1H), 7.98 (d, J=5.26 Hz, 1H), 6.54 (d, J=5.26 Hz, 1H), 4.46-4.31 (m, 2H), 3.23-3.14 (m, 2H), 2.44 (s, 3H), 2.24-2.14 (m, 1H), 1.91-1.53 (m, 9H), LC-MS (ESI): m/z: [M+H] calculated for $C_{19}H_{24}Cl_2N_5S$: 424.11; found: 424.1.

Example 13—Synthesis of 5-(4-amino-4-methylpiperidin-1-yl)-N-(2,3-dichlorophenyl)-3-methylpyrazin-2-amine

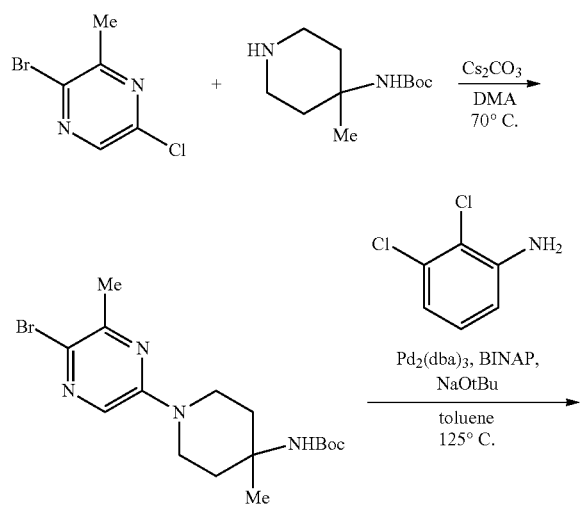

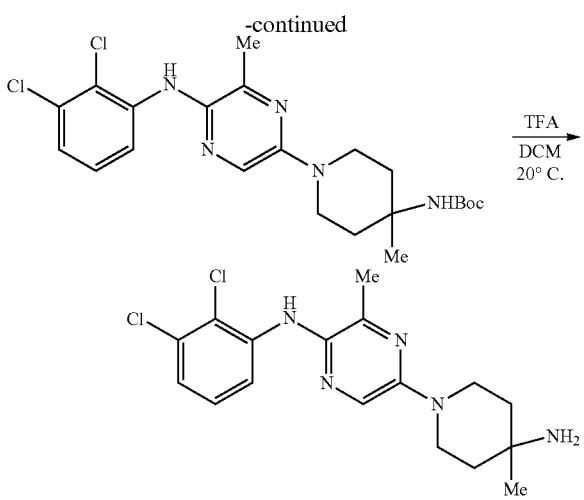

Step 1. Synthesis of tert-butyl (1-(5-bromo-6-methylpyrazin-2-yl)-4-methylpiperidin-4-yl)carbamate To a mixture of 2-bromo-5-chloro-3-methylpyrazine (300 mg, 1.5 mmol, 1 equiv) and tert-butyl(4-methylpiperidin-4-yl)carbamate (373 mg, 1.7 mmol, 1.1 equiv) in DMA (4 mL) under inert atmosphere was added $Cs_2CO_3$ (945 mg, 2.9 mmol, 1.9 equiv). The resulting mixture was warmed to 70° C. and stirred for 3 hours before the reaction mixture was cooled and concentrated under reduced pressure. The crude residue was purified by prep-TLC to give tert-butyl (1-(5-bromo-6-methylpyrazin-2-yl)-4-methylpiperidin-4-yl)carbamate (90 mg, 234 μmol, 16% yield). $^1$H NMR (400 MHz, chloroform-d) δ 7.68 (s, 1H), 4.39 (br, s, 1H), 3.83-3.78 (m, 2H), 3.31-3.25 (m, 2H), 2.48 (s, 3H), 2.10-2.07 (m, 2H), 1.66-1.61 (m, 2H), 1.43 (s, 9H), 1.38 (s, 3H).

Step 2. Synthesis of tert-butyl (1-(5-((2,3-dichlorophenyl)amino)-6-methylpyrazin-2-yl)-4-methylpiperidin-4-yl)carbamate To a solution of tert-butyl (1-(5-bromo-6-methylpyrazin-2-yl)-4-methylpiperidin-4-yl)carbamate (45 mg, 117 μmol, 1 equiv) in toluene (1.5 mL) at 20° C. under an inert atmosphere was added 2,3-dichloroaniline (21 μL, 175 μmol, 1.5 equiv), sodium tert-butoxide (22.5 mg, 234 μmol, 2 equiv), $Pd_2(dba)_3$ (10.7 mg, 11.7 μmol, 0.1 equiv), BINAP (14.5 mg, 23.4 μmol, 0.2 equiv), sequentially. The resulting mixture was warmed to 125° C. for 1.5 hours by microwave. After this time, the mixture was cooled and concentrated under reduced pressure, and the crude residue was purified by prep-TLC to give tert-butyl (1-(5-((2,3-dichlorophenyl)amino)-6-methylpyrazin-2-yl)-4-methylpiperidin-4-yl)carbamate (50 mg, 107 μmol, 46% yield) as a yellow oil. LC-MS (ESI): m/z: [M+H] calculated for $C_{22}H_{29}Cl_2N_5O_2$: 466.17; found 466.2.

Step 3. Synthesis of 5-(4-amino-4-methylpiperidin-1-yl)-N-(2,3-dichlorophenyl)-3-methylpyrazin-2-amine A solution of tert-butyl (1-(5-((2,3-dichlorophenyl)amino)-6-methylpyrazin-2-yl)-4-methylpiperidin-4-yl)carbamate (50 mg, 107 μmol, 1 equiv) in TFA (1 mL) and DCM (1 mL) was stirred at 20° C. for 2 hours. After this time, the pH of the mixture was adjusted to pH=8 with sat. $NaHCO_3$.

The resulting mixture was extracted with DCM (3×5 mL). The organic extracts were washed with brine (5 mL), dried over Na$_2$SO$_4$, filtered, and concentrated. The resulting crude residue was purified by prep-HPLC to give 5-(4-amino-4-methylpiperidin-1-yl)-N-(2,3-dichlorophenyl)-3-methyl-pyrazin-2-amine (6.5 mg, 15.8 µmol, 15% yield) as its formate salt. $^1$H NMR (400 MHz, methanol-d$_4$) δ 8.53 (s, 1H, HCOOH), 7.82 (s, 1H), 7.19-7.17 (m, 1H), 7.11-7.07 (m, 1H), 7.00-6.98 (m, 1H), 4.03-3.99 (m, 2H), 3.34-3.30 (m, 2H), 2.39 (s, 3H), 1.91-1.84 (m, 4H), 1.46 (s, 3H). LC-MS (ESI): m/z: [M+H] calculated for C$_{17}$H$_{21}$Cl$_2$N$_5$: 366.12; found 366.0.

Example 14—Synthesis of (R)-8-(5-((2,3-dichlorophenyl)thio)-6-ethylpyrazin-2-yl)-8-azaspiro[4.5]decan-1-amine

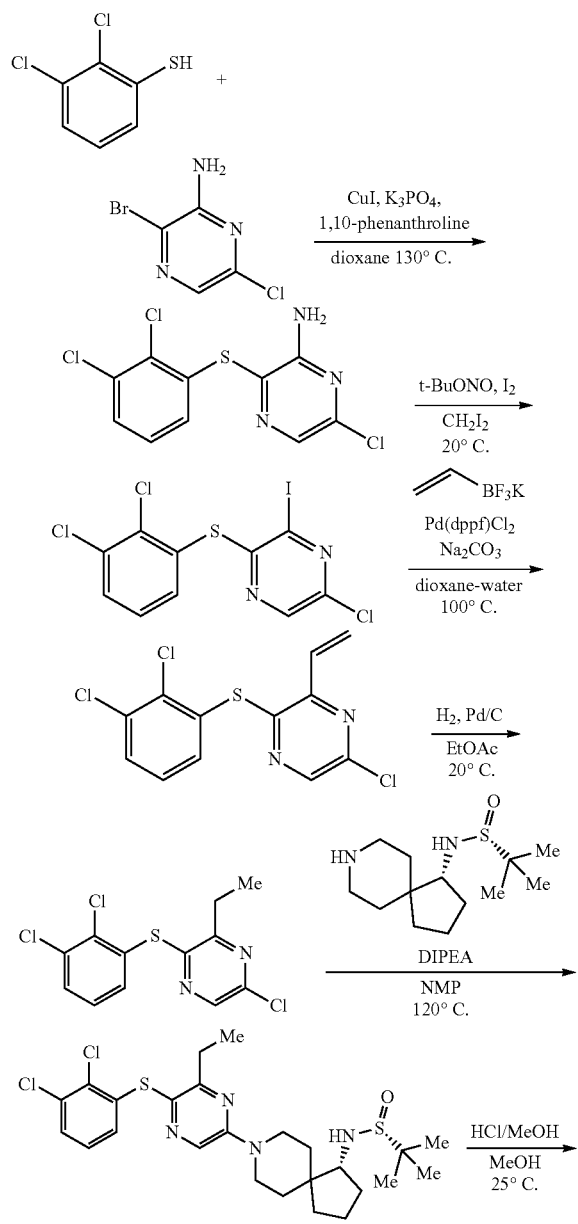

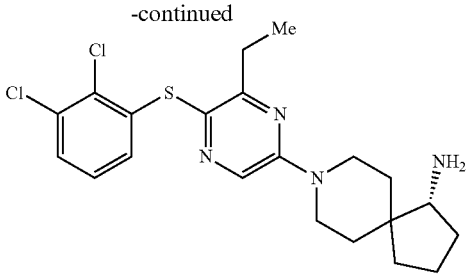

Step 1. Synthesis of 6-chloro-3-((2,3-dichlorophenyl)thio)pyrazin-2-amine

To a solution of 2,3-dichlorobenzenethiol (1.3 g, 7.2 mmol, 1.5 equiv) and 3-bromo-6-chloropyrazin-2-amine (1 g, 4.8 mmol, 1 equiv) in dioxane (10 mL) under inert atmosphere at 20° C. was added K$_3$PO$_4$ (1.0 g, 4.8 mmol, 1 equiv), 1,10-phenanthroline (86 mg, 480 µmol, 0.1 equiv) and CuI (91 mg, 480 µmol, 0.1 equiv). The resulting mixture was warmed to 130° C. using microwave radiation for 1.5 hours, after which the reaction mixture was concentrated under reduced pressure. The crude residue was purified by silica gel chromatography to give 6-chloro-3-((2,3-dichlorophenyl)thio)pyrazin-2-amine (400 mg, 1.3 mmol, 27% yield) as a yellow solid.

Step 2. Synthesis of 5-chloro-2-((2,3-dichlorophenyl)thio)-3-iodopyrazine

To a solution of 6-chloro-3-((2,3-dichlorophenyl)thio)pyrazin-2-amine (800 mg, 2.6 mmol, 1 equiv) in CH$_2$I$_2$ (15 mL) at 20° C. was added I$_2$ (795 mg, 3.1 mmol, 1.2 equiv) followed by t-BuONO (1.2 mL, 10.4 mmol, 4 equiv). The resulting mixture was stirred at 20° C. for 3 hours. After this time, the reaction was quenched with saturated aqueous Na$_2$SO$_3$ solution (15 mL). The resulting mixture was extracted with DCM (3×20 mL), and the combined organic extracts were washed with brine (20 mL), dried over Na$_2$SO$_4$, filtered, and concentrated under reduced pressure. The crude residue was purified by silica gel chromatography to give 5-chloro-2-((2,3-dichlorophenyl)thio)-3-iodopyrazine (400 mg, 958 µmol, 37% yield) as a white solid.

Step 3. Synthesis of 5-chloro-2-((2,3-dichlorophenyl)thio)-3-vinylpyrazine

To a solution of 5-chloro-2-((2,3-dichlorophenyl)thio)-3-iodopyrazine (150 mg, 359.3 µmol, 1 equiv) in a mixture of dioxane (3 mL) and H$_2$O (1 mL) at 20° C. was added potassium trifluoro(vinyl)borate (48 mg, 359.3 µmol, 1 equiv), Pd(dppf)Cl$_2$ (26.3 mg, 36 µmol, 0.1 equiv) and Na$_2$CO$_3$ (76.2 mg, 719 µmol, 2 equiv). The resulting mixture was warmed to 100° C. for 5 hours, after which the mixture was cooled and concentrated under reduced pressure. The crude residue was purified by silica gel chromatography to give 5-chloro-2-((2,3-dichlorophenyl)thio)-3-vinylpyrazine (80 mg, 252 µmol, 70% yield) as a yellow solid. $^1$H NMR (400 MHz, chloroform-d) δ 8.17 (s, H), 7.53-7.51 (m, 1H), 7.45-7.43 (m, 1H), 7.24-7.22 (m, 1H), 7.02-6.56 (m, 1H), 6.60-6.56 (m, 1H), 5.77-5.70 (m, 1H). LC-MS (ESI): m/z: [M+H] calculated for C$_{12}$H$_7$Cl$_3$N$_2$S: 316.94; found 316.9.

Step 4. Synthesis of 5-chloro-2-((2,3-dichlorophenyl)thio)-3-ethylpyrazine

To a solution of 5-chloro-2-((2,3-dichlorophenyl)thio)-3-vinylpyrazine (95 mg, 299 µmol, 1 equiv) in ethyl acetate (10 mL) was added Pd/C (10 mg), after which the resulting mixture was placed under an atmosphere of H₂ (15 psi). The mixture was stirred at 20° C. for 1 hour, after which the mixture was filtered and concentrated to give 5-chloro-2-((2,3-dichlorophenyl)thio)-3-ethylpyrazine (95 mg, crude) as a colorless oil which was used without further purification.

Step 5. Synthesis of (R)—N—((R)-8-(5-((2,3-dichlorophenyl)thio)-6-ethylpyrazin-2-yl)-8-azaspiro[4.5]decan-1-yl)-2-methylpropane-2-sulfinamide To a solution of 5-chloro-2-((2,3-dichlorophenyl)thio)-3-ethylpyrazine (100 mg, 313 μmol, 1 equiv) in DIPEA (3 mL) and NMP (1 mL) at 20° C. was added (R)-2-methyl-N—((R)-8-azaspiro[4.5]decan-1-yl)propane-2-sulfinamide (121.3 mg, 469 μmol, 1.5 equiv). The mixture was then warmed to 120° C. for 2 hours. After this time, the mixture was cooled and concentrated under reduced pressure to give crude (R)—N—((R)-8-(5-((2,3-dichlorophenyl)thio)-6-ethylpyrazin-2-yl)-8-azaspiro[4.5]decan-1-yl)-2-methylpropane-2-sulfinamide (150 mg, crude) as a brown oil which was used without further purification. LC-MS (ESI): m/z: [M+H] calculated for $C_{25}H_{34}Cl_2N_4OS_2$: 541.16; found 541.1.

Step 6. Synthesis of (R)-8-(5-((2,3-dichlorophenyl)thio)-6-ethylpyrazin-2-yl)-8-azaspiro[4.5]decan-1-amine (R)-8-(5-((2,3-dichlorophenyl)thio)-6-ethylpyrazin-2-yl)-8-azaspiro[4.5]decan-1-amine was synthesized in the manner similar to Example 1, except N—((R)-8-(5-((2,3-dichlorophenyl)thio)-6-methylpyrazin-2-yl)-8-azaspiro[4.5]decan-1-yl)-2-methylpropane-2-sulfinamide was substituted with (R)—N—((R)-8-(5-((2,3-dichlorophenyl)thio)-6-ethylpyrazin-2-yl)-8-azaspiro[4.5]decan-1-yl)-2-methylpropane-2-sulfinamide. ¹H NMR (400 MHz, chloroform-d) δ 8.47 (s, 1H, HCOOH), 8.12 (s, 1H), 7.34-7.30 (m, 1H), 7.12-7.08 (m, 1H), 6.67-6.65 (m, 1H), 4.44-4.32 (m, 2H), 3.23-3.19 (m, 2H), 2.83-2.77 (m, 2H), 1.90-1.86 (m, 1H), 1.75-1.58 (m, 9H), 1.21-1.17 (m, 2H). LC-MS (ESI): m/z: [M+H] calculated for $C_{21}H_{26}Cl_2N_4S$: 437.13; found 437.1.

Example 15—Synthesis of (R)-8-(5-((2,3-dichlorophenyl)thio)-6-phenylpyrazin-2-yl)-8-azaspiro[4.5]decan-1-amine

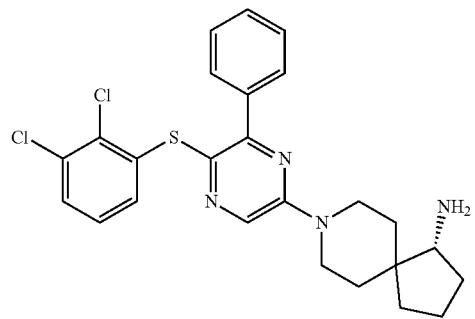 [SMILES: N[C@@H]1CCCC12CCN(c1cnc(Sc3cccc(Cl)c3Cl)c(-c3ccccc3)n1)CC2]

(R)-8-(5-((2,3-dichlorophenyl)thio)-6-phenylpyrazin-2-yl)-8-azaspiro[4.5]decan-1-amine was synthesized in the manner similar to Example 14, except potassium trifluoro(vinyl)borate was replaced with phenylboronic acid. (R)-8-(5-((2,3-dichlorophenyl)thio)-6-phenylpyrazin-2-yl)-8-azaspiro[4.5]decan-1-amine was isolated as its formate salt. ¹H NMR (400 MHz, methanol-d₄) δ 8.54 (s, 1H, HCOOH), 8.19 (s, 1H), 7.61-7.58 (m, 2H), 7.38-7.30 (m, 4H), 7.13-7.11 (m, 1H), 7.09-6.89 (m, 1H), 4.43-4.31 (m, 2H), 3.30-3.18 (m, 2H), 3.18-3.13 (m, 1H), 2.16-2.05 (m, 1H), 1.91-1.52 (m, 9H). LC-MS (ESI): m/z: [M+H] calculated for $C_{25}H_{26}Cl_2N_4S$: 485.13; found 485.2.

Example 16—Synthesis of (R)-8-(6-cyclopropyl-5-((2,3-dichloropyridin-4-yl)thio)pyrazin-2-yl)-8-azaspiro[4.5]decan-1-amine

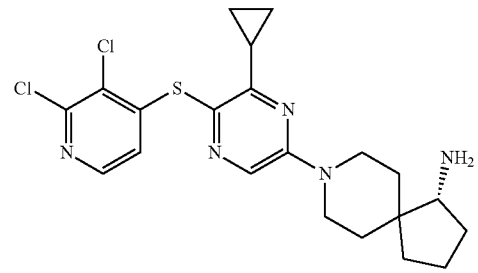 [SMILES: N[C@@H]1CCCC12CCN(c1cnc(Sc3ccnc(Cl)c3Cl)c(C3CC3)n1)CC2]

(R)-8-(6-cyclopropyl-5-((2,3-dichloropyridin-4-yl)thio)pyrazin-2-yl)-8-azaspiro[4.5]decan-1-amine was synthesized in the manner similar to Example 14, except 2,3-dichlorobenzenethiol and potassium trifluoro(vinyl)borate were replaced with 2,3-dichloropyridine-4-thiol and cyclopropylboronic acid, respectively. ¹H NMR (400 MHz, chloroform-d) δ 8.27 (s, 1H), 8.01-7.29 (m, 2H), 6.52 (d, J=5.39 Hz, 1H), 4.18 (d, J=9.03 Hz, 2H), 3.16-3.05 (m, 2H), 3.00 (t, J=6.39 Hz, 1H), 2.42-2.33 (m, 1H), 2.43-2.32 (m, 1H), 2.07 (s, 1H), 1.90-1.77 (m, 2H), 1.69 (d, J=8.40 Hz, 2H), 1.75-1.59 (m, 3H), 1.55-1.48 (m, 1H), 1.51 (br d, J=13.30 Hz, 1H), 1.38 (d, J=14.17 Hz, 1H), 1.26-1.21 (m, 1H), 1.04-0.97 (m, 1H), 1.03-0.97 (m, 1H), 0.93-0.87 (m, 1H), 0.93-0.87 (m, 1H). LC-MS (ESI): m/z: [M+H] calculated for $C_{21}H_{25}Cl_2N_5S$: 450.12; found: 450.2.

Example 17—Synthesis of (R)-8-(5-((2,3-dichlorophenyl)thio)-6-phenylpyrazin-2-yl)-8-azaspiro[4.5]decan-1-amine

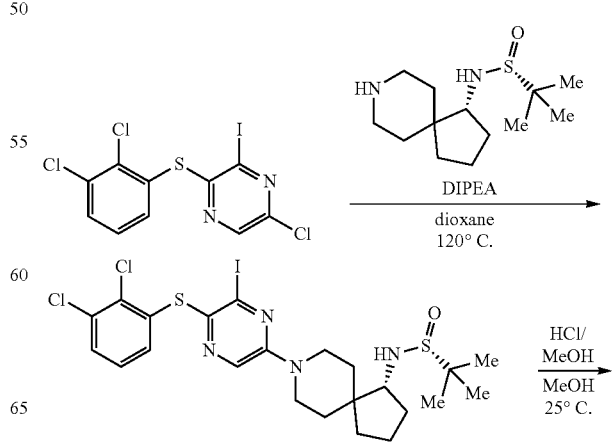

-continued

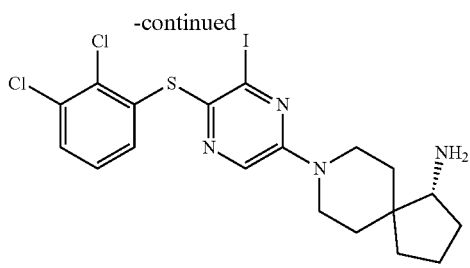

Step 1. Synthesis of (R)—N—((R)-8-(5-((2,3-dichlorophenyl)thio)-6-iodopyrazin-2-yl)-8-azaspiro[4.5]decan-1-yl)-2-methylpropane-2-sulfinamide To a solution of 5-chloro-2-((2,3-dichlorophenyl)thio)-3-iodopyrazine (300 mg, 719 μmol, 1 equiv) in dioxane (4 mL) and DIPEA (4 mL) at 20° C. was added (R)-2-methyl-N—((R)-8-azaspiro[4.5]decan-1-yl)propane-2-sulfinamide (241 mg, 934 μmol, 1.3 equiv), and the resulting mixture was warmed to 120° C. for 3 hours. After this time, the mixture was cooled and concentrated. The crude residue was purified by silica gel chromatography (R)—N—((R)-8-(5-((2,3-dichlorophenyl)thio)-6-iodopyrazin-2-yl)-8-azaspiro[4.5]decan-1-yl)-2-methylpropane-2-sulfinamide (200 mg, 313 μmol, 44% yield) as a yellow solid.

Step 2. Synthesis of (R)-8-(5-((2,3-dichlorophenyl)thio)-6-iodopyrazin-2-yl)-8-azaspiro[4.5]decan-1-amine (R)-8-(5-((2,3-dichlorophenyl)thio)-6-phenylpyrazin-2-yl)-8-azaspiro[4.5]decan-1-amine was synthesized in the manner similar to Example 1, except N—((R)-8-(5-((2,3-dichlorophenyl)thio)-6-methylpyrazin-2-yl)-8-azaspiro[4.5]decan-1-yl)-2-methylpropane-2-sulfinamide was substituted with (R)—N—((R)-8-(5-((2,3-dichlorophenyl)thio)-6-iodopyrazin-2-yl)-8-azaspiro[4.5]decan-1-yl)-2-methylpropane-2-sulfinamide.

(R)-8-(5-((2,3-dichlorophenyl)thio)-6-phenylpyrazin-2-yl)-8-azaspiro[4.5]decan-1-amine was isolated as its formate salt. $^1$H NMR (400 MHz, methanol-$d_4$) δ 8.54 (HCOOH s, 1H), 8.11 (s, 1H), 7.45-7.40 (m, 1H), 7.23-7.16 (m, 1H), 6.96 (dd, J=7.94, 1.32 Hz, 1H), 4.35-4.12 (m, 2H), 3.24-3.10 (m, 2H), 2.28-2.14 (m, 1H), 1.96-1.41 (m, 10H). LC-MS (ESI): m/z: [M+H] calculated for $C_{19}H_{21}Cl_2IN_4S$: 534.99; found 535.0.

Example 18—Synthesis of 1-(5-((2,3-dichlorophenyl)thio)-6-iodopyrazin-2-yl)-4-methylpiperidin-4-amine

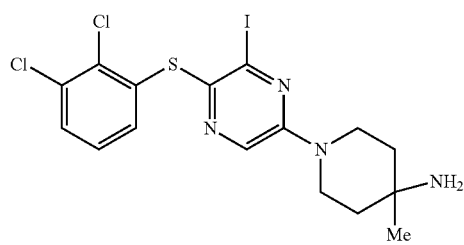 [SMILES: CC1(N)CCN(c2cnc(Sc3cccc(Cl)c3Cl)c(I)n2)CC1]

1-(5-((2,3-dichlorophenyl)thio)-6-iodopyrazin-2-yl)-4-methylpiperidin-4-amine was synthesized in a manner similar to Example 17, except (R)-2-methyl-N—((R)-8-azaspiro[4.5]decan-1-yl)propane-2-sulfinamide was replaced with tert-butyl (4-methylpiperidin-4-yl) carbamate. $^1$H NMR (400 MHz, methanol-$d_4$) δ 8.13 (s, 1H), 7.44 (dd, J=8.05, 1.43 Hz, 1H), 7.20 (t, J=7.94 Hz, 1H), 7.04 (dd, J=7.94, 1.32 Hz, 1H), 4.14-4.02 (m, 2H), 3.50-3.36 (m, 2H), 1.86-1.44 (m, 2H), 1.94-1.76 (m, 1H), 1.47 (s, 3H). LC-MS (ESI): m/z: [M+H] calculated for $C_{16}H_{17}Cl_2IN_4S$: 494.96; found 495.0.

Example 19—Synthesis of 6-(4-amino-4-methylpiperidin-1-yl)-3-((2,3-dichlorophenyl)thio)pyrazine-2-carbonitrile

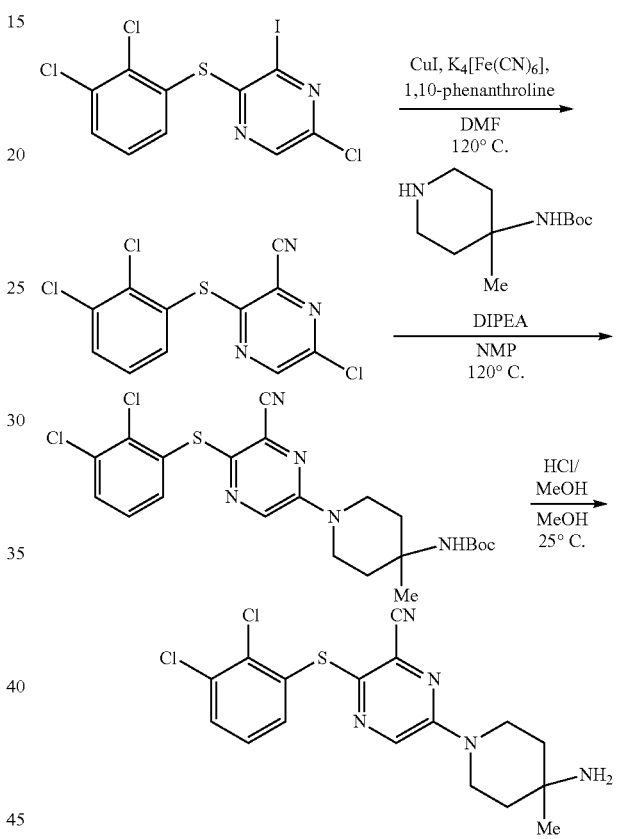

Synthesis of 6-chloro-3-((2,3-dichlorophenyl)thio)pyrazine-2-carbonitrile

To a solution of 5-chloro-2-((2,3-dichlorophenyl)thio)-3-iodopyrazine (800 mg, 1.9 mmol, 1 equiv) in DMF (10 mL) at 20° C. was added CuI (73 mg, 384 μmol), 1,10-phenanthroline (69.2 mg, 384 μmol, 202 equiv), $K_4[Fe(CN)_6]$ (1.4 g, 3.8 mmol, 202 equiv). The resulting mixture was warmed to 120° C. for 3 hours. After this time, the mixture was cooled and poured into water (5 mL). The resulting mixture was extracted with EtOAc (3×5 mL). The combined organic extracts were washed with water (5 mL) and brine (5 mL), dried over $Na_2SO_4$, filtered, and concentrated under reduced pressure. The crude residue was purified by silica gel chromatography to give 6-chloro-3-((2,3-dichlorophenyl)thio)pyrazine-2-carbonitrile (320 mg, 1.0 mmol, 52.6% yield) as a yellow solid. $^1$H NMR (400 MHz, chloroform-d) δ 8.40 (s, 1H), 7.64-7.40 (m, 2H), 7.32-7.26 (m, 1H).

6-(4-amino-4-methylpiperidin-1-yl)-3-((2,3-dichlorophenyl)thio)pyrazine-2-carbonitrile was synthesized in a manner similar to Example 1, except N—((R)-8-(5-((2,3-dichlorophenyl)thio)-6-methylpyrazin-2-yl)-8-azaspiro[4.5]decan-1-yl)-2-methylpropane-2-sulfinamide was replaced with tert-butyl (1-(6-cyano-5-((2,3-dichlorophenyl)thio)pyrazin-2-yl)-4-methylpiperidin-4-yl)carbamate. $^1$H NMR (400 MHz, methanol-$d_4$) δ 8.47 (s, 1H), 7.50-7.47 (m, 1H), 7.26-7.20 (m, 2H), 4.22-4.17 (m, 2H), 1.92-1.86 (m, 4H), 1.50 (s, 3H). LC-MS (ESI): m/z: [M+H] calculated for $C_{17}H_{17}Cl_2N_5S$: 394.06; found 394.1.

Example 20—Synthesis of (R)-6-(1-amino-8-azaspiro[4.5]decan-8-yl)-3-((2,3-dichlorophenyl)thio)pyrazine-2-carbonitrile

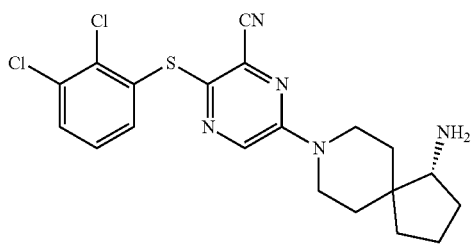 [SMILES: N#Cc1nc(N2CCC3(CCC[C@H]3N)CC2)cnc1Sc1cccc(Cl)c1Cl]

(R)-6-(1-amino-8-azaspiro[4.5]decan-8-yl)-3-((2,3-dichlorophenyl)thio)pyrazine-2-carbonitrile was synthesized in the manner similar to Example 19, except tert-butyl(4-methylpiperidin-4-yl)carbamate was replaced with (R)-2-methyl-N—((R)-8-azaspiro[4.5]decan-1-yl)propane-2-sulfinamide.

(R)-6-(1-amino-8-azaspiro[4.5]decan-8-yl)-3-((2,3-dichlorophenyl)thio)pyrazine-2-carbonitrile was isolated as its formate salt. $^1$H NMR (400 MHz, methanol-$d_4$) δ 8.5 (s, 1H, HCOOH), 8.43 (s, 1H), 7.49-7.46 (m, 1H), 7.25-7.21 (m, 1H), 7.17-7.16 (m, 1H), 4.38-4.26 (m, 2H), 3.25-3.20 (m, 2H), 2.24-2.22 (m, 1H), 1.89-1.57 (m, 10H). LC-MS (ESI): m/z: [M+H] calculated for $C_{20}H_{21}Cl_2N_5S$: 434.09; found 434.1.

Example 21—Synthesis of (R)-6-(1-amino-8-azaspiro[4.5]decan-8-yl)-3-((2,3-dichlorophenyl)thio)pyrazin-2-ol

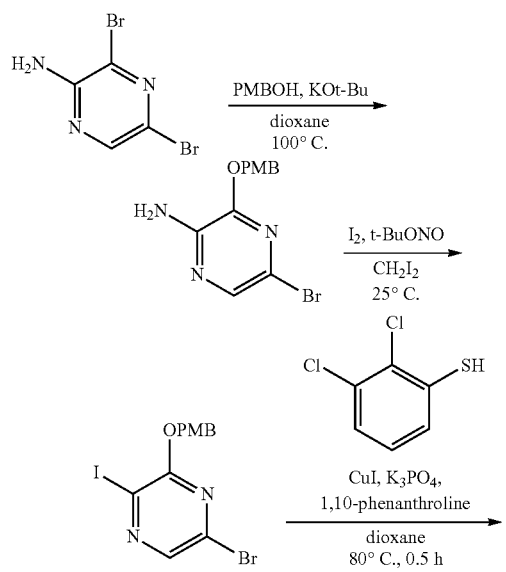

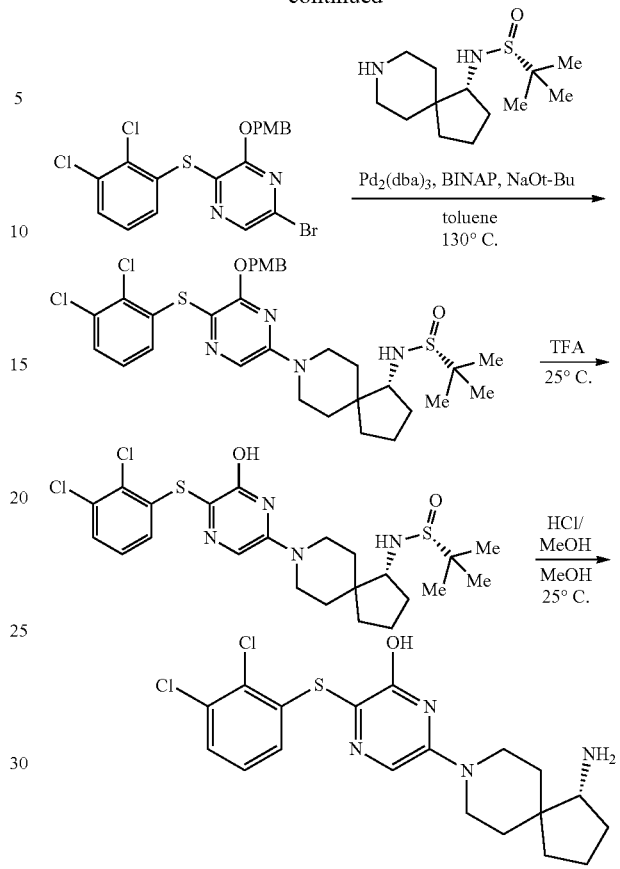

Step 1. Synthesis of 5-bromo-3-((4-methoxybenzyl)oxy)pyrazin-2-amine

To a solution of 3,5-dibromopyrazin-2-amine (15.00 g, 59.31 mmol, 1.0 equiv) and (4-methoxyphenyl)methanol (11.07 mL, 88.97 mmol, 1.5 equiv) in dioxane (70 mL) was added KOt-Bu (9.98 g, 88.97 mmol, 1.5 equiv) at 25° C. The mixture was stirred at 100° C. for 2 hours. After this time, the reaction was quenched by addition water (20 mL), and the resulting biphasic mixture was extracted with EtOAc (3×20 mL). The combined organic layers were washed with brine (50 mL), dried over $Na_2SO_4$, filtered, and concentrated under reduced pressure. The crude residue was purified by silica gel chromatography to give 5-bromo-3-((4-methoxybenzyl)oxy)pyrazin-2-amine (12 g, 38.69 mmol, 65% yield) as a red solid. $^1$H NMR (400 MHz, chlorofom-d) δ 7.67 (s, 1H), 7.42-7.40 (m, 2H), 7.33-7.28 (m, 1H), 6.96-6.91 (m, 3H), 5.34 (s, 2H), 3.85 (s, 3H).

Step 2. Synthesis of 5-bromo-2-iodo-3-((4-methoxybenzyl)oxy)pyrazine

To a solution of 5-bromo-3-((4-methoxybenzyl)oxy)pyrazin-2-amine (5.00 g, 16.1 mmol, 1 equiv) in $CH_2I_2$ (20 mL) was added t-BuONO (7.64 mL, 64.5 mmol, 4 equiv) and $I_2$ (4.91 g, 19.3 mmol, 1.2 equiv). The mixture was stirred at 25° C. for 3 hours. The reaction mixture was then diluted with saturated aqueous $Na_2S_2O_3$ (10 mL) and extracted with $CH_2Cl_2$ (3×10 mL). The combined organic layers were washed with brine (30 mL), dried over $Na_2SO_4$, filtered, and concentrated under reduced pressure. The crude residue was purified by silica gel chromatography to give 5-bromo-2-iodo-3-((4-methoxybenzyl)oxy)pyrazine (2.30 g, 5.46 mmol, 33.9% yield) as a white solid. $^1$H NMR (400 MHz, chloroform-d) δ 8.09 (s, 1H), 7.46 (d, J=8.31 Hz, 2H), 7.30-7.28 (m, 1H), 6.95 (d, J=8.44 Hz, 2H), 5.43-5.39 (m, 2H), 3.85 (s, 3H).

Step 3. Synthesis of 5-bromo-2-((2,3-dichlorophenyl)thio)-3-((4-methoxybenzyl)oxy)pyrazine To a solution of 5-bromo-2-iodo-3-((4-methoxybenzyl)oxy)pyrazine (2.30 g, 5.46 mmol, 1 equiv) and 2,3-dichlorobenzenethiol (978 mg, 5.46 mmol, 1 equiv) in dioxane (20 mL) at 25° C. was added CuI (104 mg, 546 µmol, 0.10 equiv), $K_3PO_4$ (1.39 g, 6.55 mmol, 1.2 equiv) and 1,10-phenanthroline (98.4 mg, 546 µmol, 0.10 equiv). The resulting mixture was then warmed to 70° C. and stirred for 3 hours. After this time, the reaction mixture was diluted with $H_2O$ (10 mL), and the resulting biphasic mixture was extracted with EtOAc (3×10 mL). The combined organic extracts were washed with brine (30 mL), dried over $Na_2SO_4$, filtered, and concentrated under reduced pressure. The crude residue was purified by silica gel chromatography to give 5-bromo-2-((2,3-dichlorophenyl)thio)-3-((4-methoxybenzyl)oxy) pyrazine (1.80 g, 3.81 mmol, 69.8% yield) as a white solid. $^1$H NMR (400 MHz, chloroform-d) δ 7.92 (s, 1H), 7.52-7.47 (m, 2H), 7.41-7.39 (m, 2H), 7.21-7.17 (m, 1H), 6.92-6.90 (m, 2H), 5.39 (s, 2H), 3.81 (s, 3H).

Step 4. Synthesis of (R)—N—((R)-8-(5-((2,3-dichlorophenyl)thio)-6-((4-methoxybenzyl)oxy)pyrazin-2-yl)-8-azaspiro[4.5]decan-1-yl)-2-methylpropane-2-sulfinamide To a solution of 5-bromo-2-((2,3-dichlorophenyl)thio)-3-((4-methoxybenzyl)oxy) pyrazine (1.00 g, 2.12 mmol, 1 equiv) and N-((4R)-8-azaspiro[4.5]decan-4-yl)-2-methylpropane-2-sulfinamide (822 mg, 3.18 mmol, 1.5 equiv) in toluene (10 mL) at 25° C. was added NaOt-Bu (437 mg, 4.24 mmol, 2 equiv), [1-(2-diphenylphosphanyl-1-naphthyl)-2-naphthyl]-diphenyl-phosphane (132 mg, 212 µmol, 0.10 equiv), and $Pd_2(dba)_3$ (97.1 mg, 106 µmol, 0.05 equiv). The resulting mixture warmed to 130° C. and stirred for 3 hours under microwave radiation. After this time, the reaction mixture was cooled and concentrated under reduced pressure. The residue was purified by silica gel chromatography to give (R)—N—((R)-8-(5-((2,3-dichlorophenyl)thio)-6-((4-methoxy benzyl)oxy)pyrazin-2-yl)-8-azaspiro[4.5]decan-1-yl)-2-methylpropane-2-sulfinamide (700 mg, 1.08 mmol, 50.8% yield) as a yellow solid. $^1$H NMR (400 MHz, chloroform-d) δ 7.70 (s, 1H), 7.24 (dd, J=8.01, 1.16 Hz, 1H), 7.18 (d, J=8.56 Hz, 2H), 6.97 (t, J=8.01 Hz, 1H), 6.84-6.79 (m, 3H), 5.28 (s, 2H), 4.22-4.19 (m, 2H), 3.82 (s, 3H), 3.41-3.36 (m, 1H), 3.22-3.21 (m, 1H), 3.15-3.04 (m, 2H), 3.15-3.04 (m, 2H), 2.19-2.11 (m, 1H), 1.39-1.19 (m, 10H), 1.30-1.26 (m, 1H), 1.24 (s, 9H).

Step 5. Synthesis of (R)—N—((R)-8-(5-((2,3-dichlorophenyl)thio)-6-hydroxypyrazin-2-yl)-8-azaspiro[4.5]decan-1-yl)-2-methylpropane-2-sulfinamide A solution of (R)—N—((R)-8-(5-((2,3-dichlorophenyl)thio)-6-((4-methoxybenzyl)oxy) pyrazin-2-yl)-8-azaspiro[4.5]decan-1-yl)-2-methylpropane-2-sulfinamide (300 mg, 462 µmol, 1 equiv) in TFA (10 mL) at 25° C. was stirred for 1 hour before it was concentrated under reduced pressure. The crude material so obtained was used into the next step without further purification. LC-MS (ESI): m/z: [M+H] calculated for $C_{23}H_{30}Cl_2N_4O_2S_2$: 529.12; found 529.0.

Step 6. Synthesis of (R)-6-(1-amino-8-azaspiro[4.5]decan-8-yl)-3-((2,3-dichlorophenyl)thio)pyrazin-2-ol A solution of (R)—N—((R)-8-(5-((2,3-dichlorophenyl)thio)-6-hydroxypyrazin-2-yl)-8-azaspiro[4.5]decan-1-yl)-2-methylpropane-2-sulfinamide (300 mg, 567 µmol, 1 equiv) in HCl/MeOH (10 mL) at 25° C. was stirred for 0.5 hours. After this time, the reaction mixture was concentrated. The crude residue so obtained was purified by prep-HPLC to give (R)-6-(1-amino-8-azaspiro[4.5]decan-8-yl)-3-((2,3-dichlorophenyl)thio)pyrazin-2-ol (150 mg, 353 µmol, 62.2% yield) as a white solid. $^1$H NMR (400 MHz, chloroform-d) δ 8.39 (s, 1H), 7.58 (s, 1H), 7.25-7.22 (m, 1H), 7.05-7.01 (m, 1H), 6.69-6.67 (m, 1H), 4.23-4.141 (m, 2H), 3.18-3.06 (m, 3H), 1.84-1.83 (m, 1H), 1.81-1.48 (m, 9H).

Example 22—Synthesis of 6-(4-amino-4-methylpiperidin-1-yl)-3-((2,3-dichlorophenyl)thio)pyrazin-2-ol

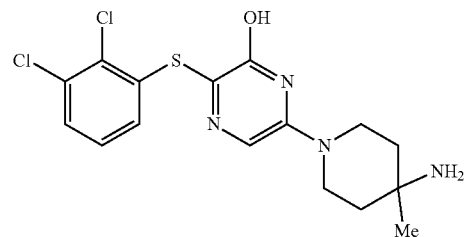 [SMILES: CC1(N)CCN(c2cnc(Sc3cccc(Cl)c3Cl)c(O)n2)CC1]

6-(4-amino-4-methylpiperidin-1-yl)-3-((2,3-dichlorophenyl)thio)pyrazin-2-ol was synthesized in the manner similar to Example 21, except (R)-2-methyl-N—((R)-8-azaspiro[4.5]decan-1-yl)propane-2-sulfinamide was substituted with tert-butyl(4-methylpiperidin-4-yl)carbamate. $^1$H NMR (400 MHz, chloroform-d) δ 7.79 (s, 1H), 7.31-7.29 (m, 1H), 7.11-7.07 (m, 1H), 6.83-6.81 (m, 1H), 4.12-4.08 (m, 2H), 3.41-3.34 (m, 2H), 1.84-1.81 (m, 4H), 1.44 (s, 3H). LC-MS (ESI): m/z: [M+H] calculated for $C_{16}H_{18}Cl_2N_4OS$: 385.06, found 385.0.

Example 23—Synthesis of (R)-8-(5-((2,3-dichlorophenyl)thio)-6-methylpyrazin-2-yl)-8-azaspiro[4.5]decan-1-amine

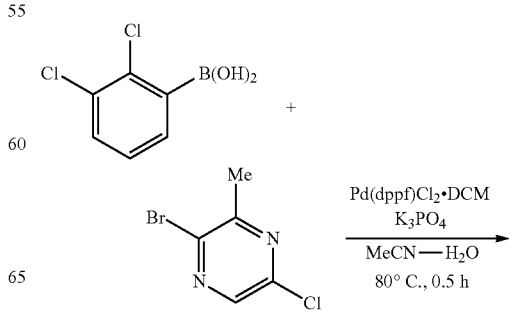

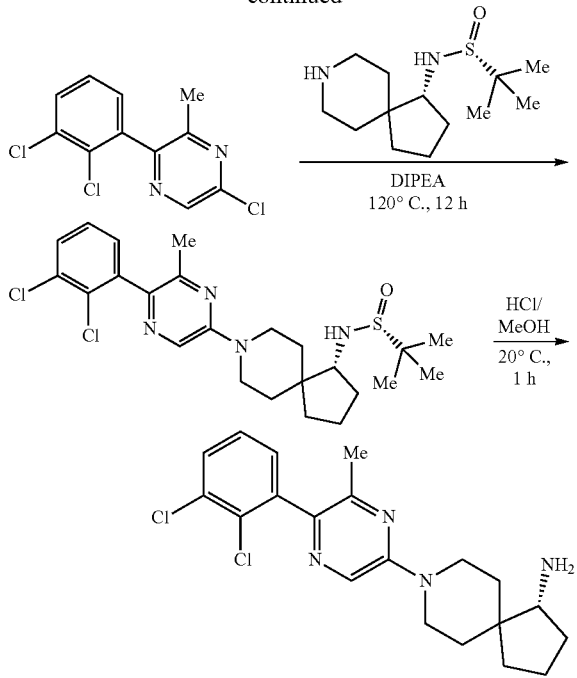

Step 1. Synthesis of 5-chloro-2-(2,3-dichlorophenyl)-3-methylpyrazine

To a degassed solution of 2-bromo-5-chloro-3-methylpyrazine (400 mg, 1.93 mmol, 1 equiv) and (2,3-dichlorophenyl)boronic acid (367.92 mg, 1.93 mmol, 1 equiv) in MeCN (60 mL) and $H_2O$ (6 mL) under an inert atmosphere was added Pd(dppf)$Cl_2$.DCM (157.45 mg, 192.81 µmol, 0.1 equiv). The reaction mixture was stirred in a microwave at 120° C. for 2 hours. After this time, TLC (2:1 petroleum ether:ethyl acetate, $R_f$=0.49) indicated complete consumption of the bromopyrazine starting material. The reaction mixture was then poured into water (500 mL), and the resulting aqueous phase was extracted with ethyl acetate (3×200 mL). The combined organic extracts were then washed with brine (500 mL), dried over anhydrous $Na_2SO_4$, filtered, and concentrated under reduced pressure to give a crude residue that was purified by silica gel chromatography to afford 5-chloro-2-(2,3-dichlorophenyl)-3-methylpyrazine (800 mg, 2.92 mmol, 75.6% yield) as a yellow solid. $^1$H NMR (400 MHz, chloroform-d): δ 8.53 (s, 1H), 7.59-7.62 (m, 1H), 7.35-7.39 (m, 1H), 7.25-7.29 (m, 1H), 2.44 (s, 3H).

Step 2. Synthesis of N—((R)-8-(5-(2,3-dichlorophenyl)-6-methylpyrazin-2-yl)-8-azaspiro[4.5]decan-1-yl)-2-methylpropane-2-sulfinamide A mixture of 5-chloro-2-(2,3-dichlorophenyl)-3-methylpyrazine (250 mg, 913.91 µmol, 1 equiv) and 2-methyl-N—((R)-8-azaspiro[4.5]decan-1-yl)propane-2-sulfinamide (259.79 mg, 1.01 mmol, 1.1 equiv) in DIPEA (1.18 g, 9.14 mmol, 1.60 mL, 10 equiv) was stirred under an inert atmosphere at 95° C. for 2 hours. After this time, LC-MS indicated complete consumption of the chloropyrazine starting material and the presence of a peak corresponding to the desired product. The reaction mixture was then cooled to 20° C. and poured into water (10 mL). The resulting aqueous phase was extracted with ethyl acetate (2×5 mL). The combined organic extracts were washed with brine (20 mL), dried over anhydrous $Na_2SO_4$ and concentrated to afford N—((R)-8-(5-(2,3-dichlorophenyl)-6-methylpyrazin-2-yl)-8-azaspiro[4.5]decan-1-yl)-2-methylpropane-2-sulfinamide (250 mg, 504.53 µmol, 27.6% yield) as a yellow oil. LC-MS (ESI): m/z: [M+H] calculated for $C_{24}H_{32}Cl_2N_4OS$: 495.17; found 495.1.

Step 3. Synthesis of (R)-8-(5-(2,3-dichlorophenyl)-6-methylpyrazin-2-yl)-8-azaspiro[4.5]decan-1-amine A mixture of N—((R)-8-(5-(2,3-dichlorophenyl)-6-methylpyrazin-2-yl)-8-azaspiro[4.5]decan-1-yl)-2-methylpropane-2-sulfinamide (250 mg, 504.53 µmol, 1 equiv) in HCl-MeOH (4M, 25 mL, 198.2 equiv) was stirred under an inert atmosphere at 20° C. for 1 hour. The mixture was then concentrated under reduced pressure and purified by preparative HPLC to afford (R)-8-(5-(2,3-dichlorophenyl)-6-methylpyrazin-2-yl)-8-azaspiro[4.5]decan-1-amine (150 mg, 383.30 µmol, 76% yield) as a yellow oil. $^1$H NMR (400 MHz, methanol-$d_4$): δ 8.07 (s, 1H), 7.64 (d, J=16 Hz 1H), 7.43 (m, 1H), 7.33 (d, J=16 Hz 1H), 4.41-4.33 (m, 2H), 3.27-3.17 (m, 3H), 2.23-2.21 (m, 1H), 2.21 (s, 3H), 1.93-1.59 (m, 9H). LC-MS (ESI): m/z: [M+H] calculated for $C_{20}H_{24}Cl_2N_4$: 391.14; found 391.1.

Example 24—Synthesis of 1-(5-(2,3-dichlorophenyl)-6-methylpyrazin-2-yl)-4-methylpiperidin-4-amine

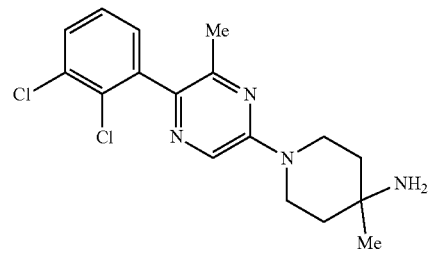 [SMILES: Cc1nc(N2CCC(C)(N)CC2)cnc1-c1cccc(Cl)c1Cl]

1-(5-(2,3-dichlorophenyl)-6-methylpyrazin-2-yl)-4-methylpiperidin-4-amine was synthesized in the manner similar to Example 23, except 2-methyl-N—((R)-8-azaspiro[4.5]decan-1-yl)propane-2-sulfinamide was substituted with tert-butyl (4-methylpiperidin-4-yl)carbamate. $^1$H NMR (400 MHz, methanol-$d_4$): δ 8.19 (s, 1H), 7.67 (m 1H), 7.42-7.46 (m, 1H), 7.35 (d, J=12 Hz 1H), 4.27-4.23 (m, 2H), 3.49-3.45 (m, 2H), 2.25 (s, 3H), 1.93-1.91 (m, 4H) 1.52 (s, 3H). LC-MS (ESI): m/z: [M+H] calculated for $C_{17}H_{20}Cl_2N_4$: 351.11; found 351.0.

Example 25—Synthesis of 1-(5-(2,3-dichlorophenyl)-6-methylpyrazin-2-yl)-3-methylazetidin-3-amine

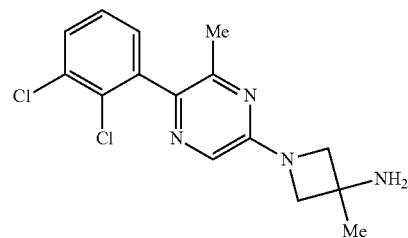 [SMILES: Cc1nc(N2CC(C)(N)C2)cnc1-c1cccc(Cl)c1Cl]

1-(5-(2,3-dichlorophenyl)-6-methylpyrazin-2-yl)-3-methylazetidin-3-amine was synthesized in the manner similar to Example 23, except 2-methyl-N—((R)-8-azaspiro[4.5]decan-1-yl)propane-2-sulfinamide was substituted with tert-butyl (3-methylazetidin-3-yl)carbamate. 1-(5-(2,3-dichlorophenyl)-6-methylpyrazin-2-yl)-3-methylazetidin-3-amine was isolated as its formate salt after HPLC purification. $^1$H NMR (500 MHz, DMSO-d$_6$) δ 8.25 (s, 1H), 7.76 (s, 1H), 7.70 (dd, J=8.0, 1.6 Hz, 1H), 7.47-7.43 (m, 1H), 7.35 (dd, J=7.6, 1.6 Hz, 1H), 3.93-3.88 (m, 2H), 3.86 (d, J=8.2 Hz, 2H), 2.12 (s, 3H), 1.44 (s, 3H). LC-MS (ESI): m/z: [M+H] calculated for $C_{15}H_{16}Cl_2N_4$: 323.08; found 323.38.

Example 26—Synthesis of 6-(4-amino-4-methylpiperidin-1-yl)-3-(2,3-dichlorophenyl)pyrazine-2-carbonitrile

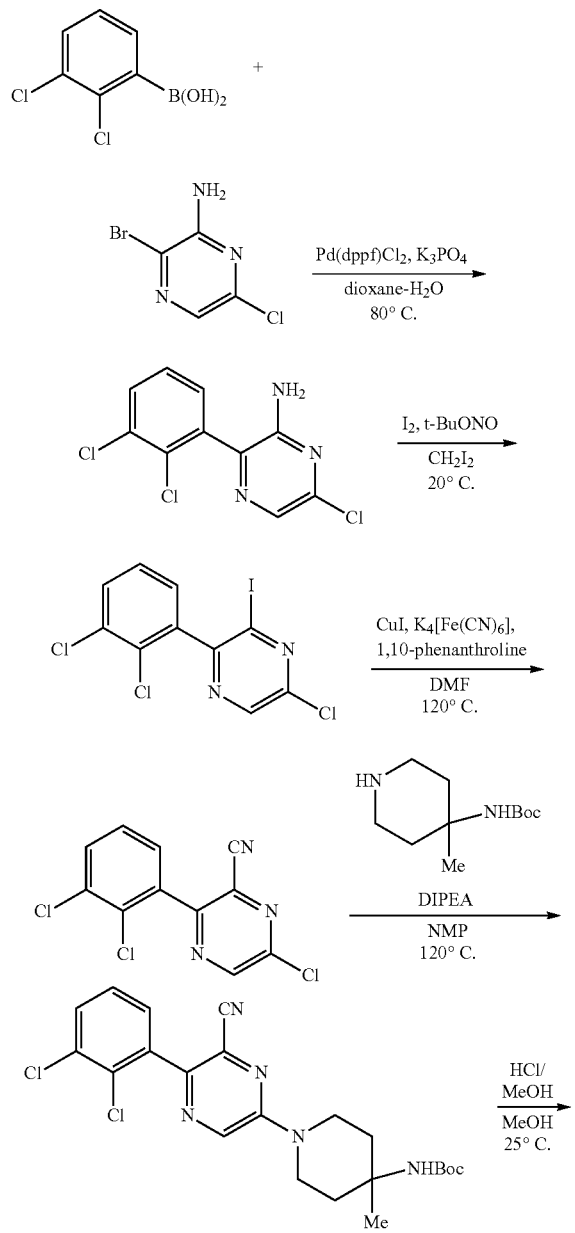

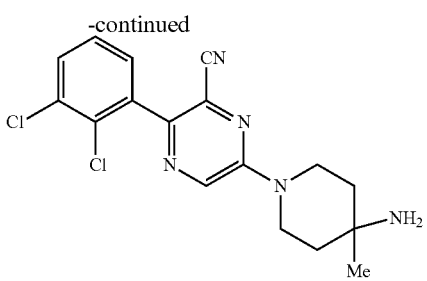

Step 1. Synthesis of 6-chloro-3-(2,3-dichlorophenyl)pyrazin-2-amine

To a solution of 3-bromo-6-chloropyrazin-2-amine (30 g, 144 mmol, 1 equiv) in dioxane (360 mL) was added (2,3-dichlorophenyl)boronic acid (33 g, 173 mmol, 1.2 equiv), a solution of K$_3$PO$_4$ (92 g, 432 mmol, 3.0 equiv) in H$_2$O (36 mL), and Pd(dppf)Cl$_2$ (11 g, 14.4 mmol, 0.1 equiv). The reaction mixture was warmed to 80° C. and stirred for 16 hours, after which the solution was concentrated under reduced pressure. The residue was purified by silica gel chromatography to give 6-chloro-3-(2,3-dichlorophenyl)pyrazin-2-amine (25 g, 91 mmol, 63% yield) as a yellow solid. $^1$H NMR (400 MHz, DMSO-d$_6$) δ 7.87-7.82 (m, 1H), 7.73 (dd, J=7.94, 1.54 Hz, 1H), 7.50-7.44 (m, 1H), 7.41-7.36 (m, 1H), 6.69 (br s, 2H).

Step 2. Synthesis of 5-chloro-2-(2,3-dichlorophenyl)-3-iodopyrazine

To a solution of 6-chloro-3-(2,3-dichlorophenyl)pyrazin-2-amine (15 g, 54 mmol, 1 equiv) in CH$_2$I$_2$ (150 mL) at 25° C. was added tert-butyl nitrite (26 mL, 219 mmol, 4 equiv) and I2 (13 mL, 66 mmol, 1.2 equiv), sequentially. The reaction mixture was stirred for 16 hours before it was quenched by addition aqueous Na$_2$S$_2$O$_3$ (150 mL) and extracted with DCM (2×100 mL). The combined organic extracts were then washed with brine (100 mL), dried over Na$_2$SO$_4$, filtered, and concentrated under reduced pressure. The residue was then purified by silica gel chromatography to give 6-chloro-3-(2,3-dichlorophenyl)pyrazine-2-carbonitrile (9.0 g, 23 mmol, 43% yield) as a yellow solid. LC-MS (ESI): m/z: [M+H] calculated for $C_{10}H_4Cl_3IN_2$: 384.85; found 384.8.

Step 3. Synthesis of 6-chloro-3-(2,3-dichlorophenyl)pyrazine-2-carbonitrile

To a solution of 6-chloro-3-(2,3-dichlorophenyl)pyrazine-2-carbonitrile (450 mg, 1.2 mmol, 1 equiv) in DMF (5 mL) at 25° C. was added 1,10-phenanthroline (42 mg, 234 μmol, 0.2 equiv), CuI (45 mg, 234 μmol, 0.2 equiv), potassium ferrocyanide (862 mg, 2.3 mmol, 2 equiv). Then the mixture was then warmed to 120° C. and stirred for 4 hours. After this time, the reaction mixture was concentrated under reduced pressure, and the crude residue so obtained was purified by silica gel chromatography to give 6-chloro-3-(2,3-dichlorophenyl)pyrazine-2-carbonitrile (170 mg, 597

μmol, 51% yield) as a white solid. ¹H NMR (400 MHz, methanol-d₄) δ 9.04 (s, 1H), 7.80-7.77 (m, 1H), 7.55-7.49 (m, 2H).

Step 4. Synthesis of tert-butyl (1-(6-cyano-5-(2,3-dichlorophenyl)pyrazin-2-yl)-4-methylpiperidin-4-yl)carbamate A mixture of 6-chloro-3-(2,3-dichlorophenyl)pyrazine-2-carbonitrile (50 mg, 176 μmol, 1 equiv) and tert-butyl(4-methylpiperidin-4-yl)carbamate (56.5 mg, 264 μmol, 1.5 equiv) in dioxane (1 mL) and DIPEA (1 mL) was warmed to 120° C. and stirred for 2 hours. The mixture was then concentrated under reduced pressure to give tert-butyl(1-(6-cyano-5-(2,3-dichlorophenyl)pyrazin-2-yl)-4-methylpiperidin-4-yl)carbamate (80 mg, crude) as a yellow oil which was used directly in the next step without further purification. LC-MS (ESI): m/z: [M+H] calculated for $C_{22}H_{25}Cl_2N_5O_2$: 462.14; found 462.0.

Step 5. Synthesis of 6-(4-amino-4-methylpiperidin-1-yl)-3-(2,3-dichlorophenyl)pyrazine-2-carbonitrile A solution of tert-butyl(1-(6-cyano-5-(2,3-dichlorophenyl)pyrazin-2-yl)-4-methylpiperidin-4-yl)carbamate (80 mg, 173 μmol, 1 equiv) in HCl/MeOH (4M, 3 mL) was stirred at 20° C. for 1 hour. After this time, the mixture was concentrated under reduced pressure, and the crude residue was purified by prep-HPLC to give 6-(4-amino-4-methylpiperidin-1-yl)-3-(2,3-dichlorophenyl)pyrazine-2-carbonitrile (9.1 mg, 21 μmol, 12% yield, 94% purity) as a yellow solid. LC-MS (ESI): m/z: [M+H] calculated for $C_{17}H_{18}Cl_2N_5$: 362.09; found 362.0; RT=0.992 minutes. 6-(4-amino-4-methylpiperidin-1-yl)-3-(2,3-dichlorophenyl)pyrazine-2-carbonitrile was isolated as its formate salt. ¹H NMR (400 MHz, chloroform-d) δ 8.59 (s, 1H, HCOOH), 7.71-7.68 (m, 1H), 7.47-7.44 (m, 2H), 4.23-4.19 (m, 2H), 3.57-3.50 (m, 2H), 1.92-1.83 (m, 4H), 1.49 (s, 3H). LC-MS (ESI): m/z: [M+H] calculated for $C_{17}H_{17}Cl_2N_5$: 362.09; found 362.1.

Example 27—Synthesis of (R)-6-(1-amino-8-azaspiro[4.5]decan-8-yl)-3-(2,3-dichloro phenyl)pyrazine-2-carbonitrile

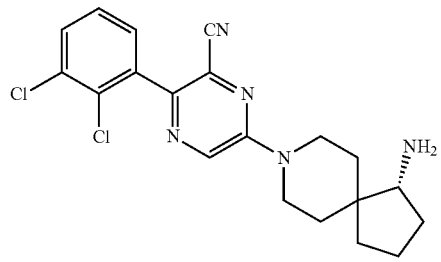

(R)-6-(1-amino-8-azaspiro[4.5]decan-8-yl)-3-(2,3-dichlorophenyl)pyrazine-2-carbonitrile was synthesized in the manner similar to Example 26, except tert-butyl(4-methylpiperidin-4-yl) carbamate was replaced with (R)-2-methyl-N—((R)-8-azaspiro[4.5]decan-1-yl)propane-2-sulfinamide.

(R)-6-(1-amino-8-azaspiro[4.5]decan-8-yl)-3-(2,3-dichlorophenyl)pyrazine-2-carbonitrile was isolated as its formate salt. LC-MS (ESI): m/z: [M+H] calculated for $C_{20}H_{21}Cl_2N_5$: 402.12; found 402.2.

Example 28—Synthesis of (1-(5-(2,3-dichlorophenyl)-6-methylpyrazin-2-yl)-4-methylpiperidin-4-yl) methanamine

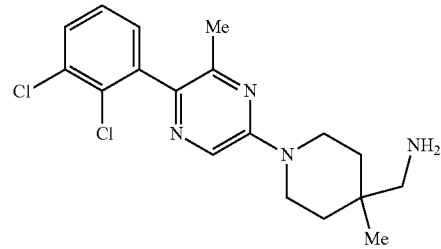 [SMILES: Cc1nc(N2CCC(C)(CN)CC2)cnc1-c1cccc(Cl)c1Cl]

(1-(5-(2,3-dichlorophenyl)-6-methylpyrazin-2-yl)-4-methylpiperidin-4-yl) methanamine was synthesized in the manner similar to Example 23, except 2-methyl-N—((R)-8-azaspiro[4.5]decan-1-yl)propane-2-sulfinamide was substituted with tert-butyl((4-methyl piperidin-4-yl)methyl)carbamate. ¹H NMR (500 MHz, DMSO-d₆) δ 8.28 (s, 1H), 7.82 (d, J=0.7 Hz, 1H), 7.51 (d, J=7.7 Hz, 1H), 7.42 (dd, J=8.0, 1.4 Hz, 1H), 7.22 (t, J=8.0 Hz, 1H), 6.65 (dd, J=8.1, 1.4 Hz, 1H), 4.11-4.00 (m, 1H), 2.78-2.56 (m, 4H), 2.35 (d, J=2.4 Hz, 6H), 1.97 (dddd, J=21.8, 10.9, 7.7, 5.0 Hz, 2H), 1.80-1.69 (m, 2H), 1.63 (dt, J=10.7, 8.8 Hz, 2H). LC-MS (ESI): m/z: [M+H] calculated for $C_{18}H_{22}Cl_2N_4$: 365.12; found 365.2.

Example 29—Synthesis of (R)-3-(1-amino-8-azaspiro[4.5]decan-8-yl)-6-(2,3-dichlorophenyl)-5-methylpyrazin-2-ol

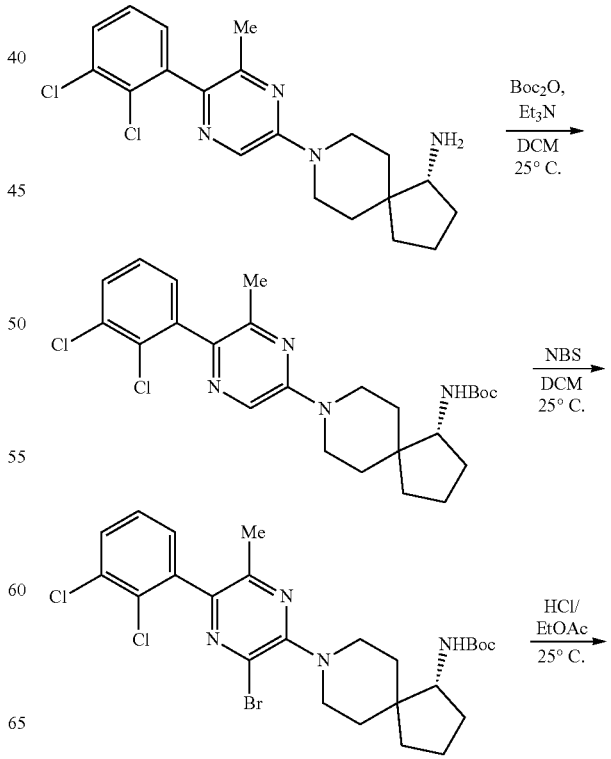

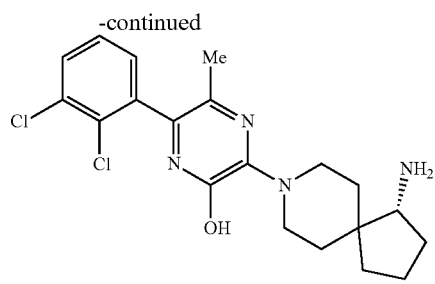

Step 1. Synthesis of (R)-tert-butyl (8-(5-(2,3-dichlorophenyl)-6-methylpyrazin-2-yl)-8-azaspiro[4.5]decan-1-yl)carbamate To a solution of (R)-8-(5-(2,3-dichlorophenyl)-6-methylpyrazin-2-yl)-8-azaspiro[4.5]decan-1-amine (4.0 g, 10 mmol, 1 equiv) in DCM (3 mL) at 25° C. was added Boc$_2$O (3.4 g, 15 mmol, 1.5 equiv) and Et$_3$N (3.1 g, 30 mmol, 3 equiv). The mixture was stirred for 2 hours before it was concentrated under reduced pressure. The crude residue was then purified by silica gel chromatography to give (R)-tert-butyl (8-(5-(2,3-dichlorophenyl)-6-methylpyrazin-2-yl)-8-azaspiro[4.5]decan-1-yl)carbamate (2.3 g, 4.6 mmol, 46% yield) as a colorless oil. $^1$H NMR (400 MHz, chloroform-d) δ 7.99 (s, 1H), 7.49 (dd, J=7.72, 1.98 Hz, 1H), 7.29-7.26 (m, 1H), 7.25-7.21 (m, 1H), 4.30-4.07 (m, 2H), 3.20-3.03 (m, 2H), 2.23 (s, 3H), 2.15-2.05 (m, 1H), 1.84-1.56 (m, 10H), 1.43 (s, 9H).

Step 2. Synthesis of (R)-tert-butyl (8-(3-bromo-5-(2,3-dichlorophenyl)-6-methylpyrazin-2-yl)-8-azaspiro[4.5]decan-1-yl)carbamate To a solution of (R)-tert-butyl(8-(5-(2,3-dichlorophenyl)-6-methylpyrazin-2-yl)-8-azaspiro[4.5]decan-1-yl)carbamate (2.3 g, 4.7 mmol, 1 equiv) in DCM (15 mL) at 0° C. was added NBS (1.2 g, 7.0 mmol, 1.5 equiv). The mixture was then warmed to 25° C. and stirred for 2 hours, after which the reaction mixture was concentrated under reduced pressure. The crude residue was then purified by silica gel chromatography to give (R)-tert-butyl (8-(3-bromo-5-(2,3-dichlorophenyl)-6-methylpyrazin-2-yl)-8-azaspiro[4.5]decan-1-yl)carbamate (1.3 g, 2.3 mmol, 48.7% yield) as a white solid. $^1$H NMR (400 MHz, chloroform-d) δ 7.52 (dd, J=7.39, 2.32 Hz, 1H), 7.28-7.26 (m, 2H), 4.45 (m, 1H), 3.91-3.85 (m, 3H), 3.12-3.05 (m, 2H), 2.24 (s, 3H), 2.16-2.01 (m, 2H), 1.92 (m, 1H), 1.82-1.63 (m, 5H), 1.55 (s, 9H).

Step 3. Synthesis of (R)-3-(1-amino-8-azaspiro[4.5]decan-8-yl)-6-(2,3-dichlorophenyl)-5-methylpyrazin-2-ol A solution of (R)-tert-butyl(8-(3-bromo-5-(2,3-dichlorophenyl)-6-methylpyrazin-2-yl)-8-azaspiro[4.5]decan-1-yl)carbamate (50.0 mg, 87.7 µmol, 1 equiv) in HCl/EtOAc (4M, 3 mL) was stirred at 25° C. for 0.5 hours, after which the reaction mixture was concentrated under reduced pressure. The residue was purified by prep-HPLC to give (R)-3-(1-amino-8-azaspiro[4.5]decan-8-yl)-6-(2,3-dichlorophenyl)-5-methylpyrazin-2-ol (20.00 mg, 39.37 µmol, 39.80% yield) as a white solid. $^1$H NMR (400 MHz, DMSO-d$_6$) δ 7.73-7.71 (m, 1H), 7.44-7.39 (m, 2H), 4.55-4.51 (m, 2H), 3.08-2.98 (m, 1H), 1.82-1.71 (m, 2H), 1.69 (s, 3H), 1.65- 1.35 (m, 9H). LC-MS (ESI): m/z: [M+H] calculated for $C_{20}H_{24}Cl_2N_4O$: 407.13; found 407.9.

Example 30—Synthesis of (R)-3-(1-amino-8-azaspiro[4.5]decan-8-yl)-6-(2,3-dichlorophenyl)-5-methylpyrazine-2-carboxamide

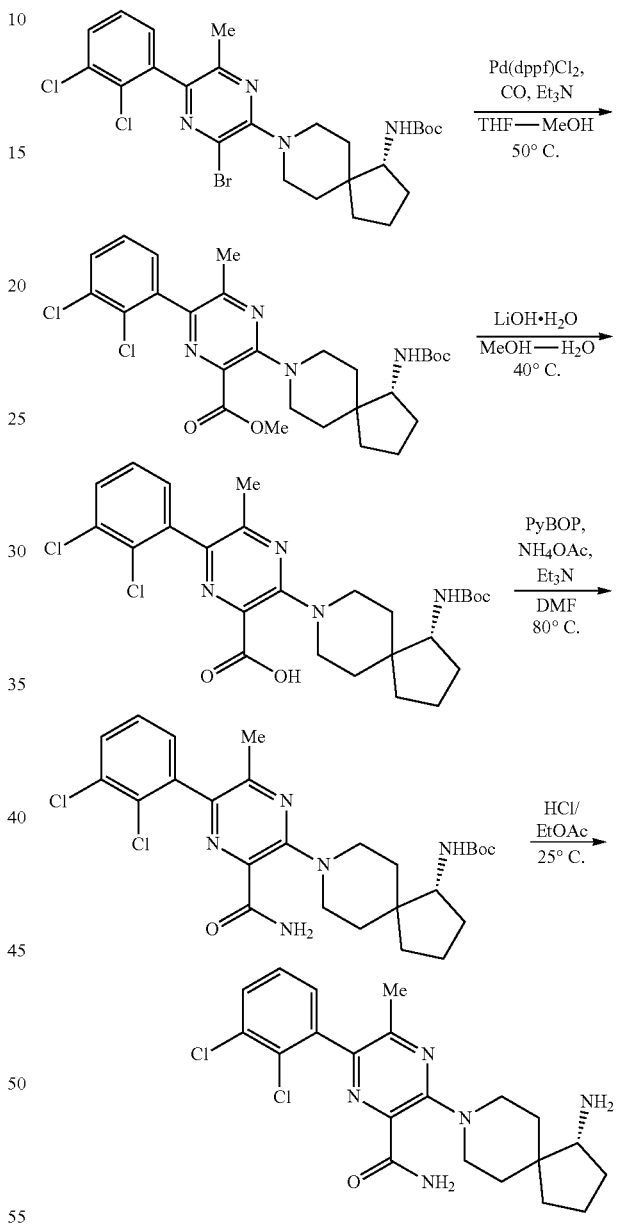

Step 1. Synthesis of (R)-methyl 3-(1-((tert-butoxycarbonyl)amino)-8-azaspiro[4.5]decan-8-yl)-6-(2,3-dichlorophenyl)-5-methylpyrazine-2-carboxylate To a solution of (R)-tert-butyl(8-(3-bromo-5-(2,3-dichlorophenyl)-6-methylpyrazin-2-yl)-8-azaspiro[4.5]decan-1-yl)carbamate (1.0 g, 1.7 mmol, 1 equiv) in THF (2.0 mL) and MeOH (2.0 mL) at 25° C. was added Et$_3$N (729 µL, 5.3 mmol, 3.1 equiv) and Pd(dppf)Cl$_2$ (128 mg, 0.17 mmol, 0.1 equiv). The suspension was degassed and purged with CO three times, and then the mixture was sealed under a CO atmosphere (50 psi), warmed to 50° C., and stirred for 2 hours. After this time, the reaction mixture was cooled and concentrated under reduced pressure. The crude residue was purified by silica gel chromatography to give compound (R)-methyl 3-(1-((tert-butoxycarbonyl)amino)-8-azaspiro [4.5]decan-8-yl)-6-(2,3-dichlorophenyl)-5-methylpyrazine-2-carboxylate (900.0 mg, 1.6 mmol, 93.6% yield) as a green solid. $^1$H NMR (400 MHz, chloroform-d) δ 7.49 (dd, J=6.84, 2.87 Hz, 1H), 7.31-7.27 (m, 2H), 3.93 (s, 3H), 3.85-3.75 (m, 2H), 3.20 (m, 2H), 2.27 (s, 3H), 2.14-2.04 (m, 1H), 1.87-1.58 (m, 8H), 1.44 (s, 9H).

Step 2. Synthesis of (R)-3-(1-((tert-butoxycarbonyl) amino)-8-azaspiro[4.5]decan-8-yl)-6-(2, 3-dichlorophenyl)-5-methylpyrazine-2-carboxylic acid To a solution of methyl(R)-methyl-3-(1-((tert-butoxycarbonyl)amino)-8-azaspiro[4.5]decan-8-yl)-6-(2,3-dichlorophenyl)-5-methylpyrazine-2-carboxylate (1.0 g, 1.8 mmol, 1 equiv) in a mixture of THF (1 mL), MeOH (3 mL), and H$_2$O (1 mL) at 25° C. was added LiOH.H$_2$O (229 mg, 5.4 mmol, 3 equiv). The resulting mixture was warmed to 40° C. and stirred for 3 hours, after which the reaction mixture was concentrated under reduced pressure. The crude residue was diluted with H$_2$O (10 mL) and extracted with MTBE (20 mL). The water phase was then adjusted to pH=4 with aqueous HCl (1M) and extracted with ethyl acetate (3×20 mL). The combined ethyl acetate extracts were washed with brine (30 mL), dried over Na$_2$SO$_4$, filtered, and concentrated under reduced pressure. The crude residue was purified by silica gel chromatography to give (R)-3-(1-((tert-butoxycarbonyl)amino)-8-azaspiro[4.5]decan-8-yl)-6-(2,3-dichlorophenyl)-5-methylpyrazine-2-carboxylic acid (900 mg, 1.6 mmol, 92% yield) as a yellow solid. $^1$H NMR (400 MHz, chloroform-d) δ 7.57-7.55 (m, 1H), 7.35-7.27 (m, 2H), 4.05-3.91 (m, 2H), 3.79-3.77 (m, 1H), 3.36-3.27 (m, 2H), 2.34 (s, 3H), 2.09 (m, 2H), 1.72-1.56 (m, 9H), 1.44 (s, 11H).

Step 3. Synthesis of (R)-tert-butyl(8-(3-carbamoyl-5-(2,3-dichlorophenyl)-6-methylpyrazin-2-yl)-8-azaspiro[4.5]decan-1-yl)carbamate To a solution of (R)-3-(1-((tert-butoxycarbonyl)amino)-8-azaspiro[4.5]decan-8-yl)-6-(2,3-dichlorophenyl)-5-methylpyrazine-2-carboxylic acid (50 mg, 93 μmol, 1 equiv) in DMF (1.0 mL) at 25° C. was added PyBOP (97 mg, 186 μmol, 2 equiv), NH$_4$OAc (18 mg, 233 μmol, 2.5 equiv) and Et$_3$N (26 μL, 187 μmol, 2 equiv). The mixture was then warmed to 80° C. and stirred for 3 hours. After this time, the reaction mixture was diluted with water (5 mL) and extracted with ethyl acetate (3×10 mL). The combined organic extracts were washed with brine (20 mL), dried over Na$_2$SO$_4$, filtered, and concentrated under reduced pressure to give (R)-tert-butyl(8-(3-carbamoyl-5-(2,3-dichlorophenyl)-6-methylpyrazin-2-yl)-8-azaspiro[4.5]decan-1-yl)carbamate (40 mg, crude) as a red oil.

Step 4. Synthesis of (R)-3-(1-amino-8-azaspiro[4.5] decan-8-yl)-6-(2,3-dichlorophenyl)-5-methylpyrazine-2-carboxamide A mixture of (R)-tert-butyl(8-(3-carbamoyl-5-(2,3-dichlorophenyl)-6-methylpyrazin-2-yl)-8-azaspiro[4.5]decan-1-yl)carbamate (40.00 mg, 74.84 μmol, 1 equiv) in HCl/ethyl acetate (4M, 5 mL) was stirred at 25° C. for 0.5 hours, after which the reaction mixture was concentrated under reduced pressure. The crude residue was adjusted to pH=7 with saturated aqueous Na$_2$HCO$_3$ (10 mL), and the resulting aqueous solution was extracted with ethyl acetate (3×10 mL). The combined organic extracts were washed with brine (20 mL), dried over Na$_2$SO$_4$, filtered, and concentrated under reduced pressure. The crude residue was purified by prep-HPLC to give (R)-3-(1-amino-8-azaspiro[4.5]decan-8-yl)-6-(2,3-dichlorophenyl)-5-methyl pyrazine-2-carboxamide (3.00 mg, 6.91 μmol, 9.23% yield) as a yellow solid. $^1$H NMR (400 MHz, chloroform-d) δ 7.55-7.53 (m, 1H), 7.33-7.29 (m, 2H), 3.98-3.88 (m, 2H), 3.17-3.06 (m, 3H), 2.34 (s, 3H), 1.83-1.78 (m, 1H), 1.74-1.43 (s, 9H). LC-MS (ESI): m/z: [M+H] calculated for C$_{21}$H$_{25}$Cl$_2$N$_5$O: 434.14; found 433.9.

Example 31—Synthesis of (R)-8-(3-amino-5-(2,3-dichlorophenyl)-6-methylpyrazin-2-yl)-8-azaspiro [4.5]decan-1-amine

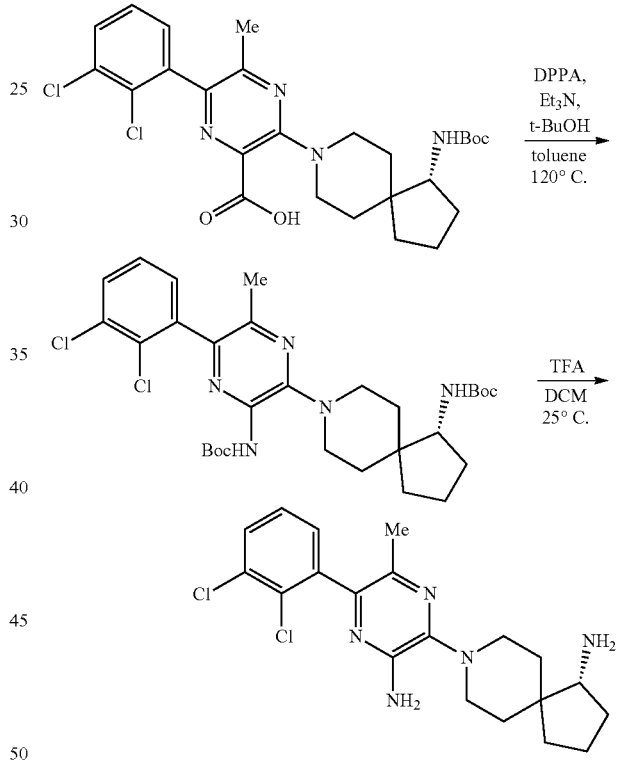

Step 1. Synthesis of tert-butyl (R)-(8-(3-((tert-butoxycarbonyl)amino)-5-(2,3-dichlorophenyl)-6-methylpyrazin-2-yl)-8-azaspiro[4.5]decan-1-yl)carbamate To a solution of (R)-3-(1-((tert-butoxycarbonyl)amino)-8-azaspiro[4.5]decan-8-yl)-6-(2,3-dichlorophenyl)-5-methylpyrazine-2-carboxylic acid (80 mg, 149 μmol, 1 equiv) in toluene at 25° C. (3.0 mL) was added DPPA (35 μL, 164 μmol, 1.1 equiv), Et$_3$N (41 μL, 299 μmol, 2 equiv) and t-BuOH (142 μL, 1.5 mmol, 10 equiv), sequentially. The mixture was then warmed to 120° C. and stirred for 3 hours. After this time, the reaction mixture was cooled and concentrated under reduced pressure. The crude residue was purified by silica gel chromatography to give tert-butyl(R)-

(8-(3-((tert-butoxycarbonyl)amino)-5-(2,3-dichlorophenyl)-6-methylpyrazin-2-yl)-8-azaspiro[4.5]decan-1-yl)carbamate (60 mg, 98 µmol, 66% yield) as a white solid. $^1$H NMR (400 MHz, chloroform-d) 7.49-7.47 (m, 1H), 7.28-7.21 (m, 3H), 4.51 (s, 2H), 4.45-4.43 (m, 1H), 3.77-3.75 (m, 1H), 3.51-3.46 (m, 2H), 2.92-2.87 (m, 2H), 2.16 (s, 3H), 2.07 (m, 1H), 1.84-1.61 (m, 9H), 1.46-1.40 (s, 18H).

Step 2. Synthesis of (R)-8-(3-amino-5-(2,3-dichlorophenyl)-6-methylpyrazin-2-yl)-8-azaspiro[4.5]decan-1-amine (R)-8-(3-amino-5-(2,3-dichlorophenyl)-6-methylpyrazin-2-yl)-8-azaspiro[4.5]decan-1-amine was synthesized in the manner similar to 5-(4-amino-4-methylpiperidin-1-yl)-N-(2,3-dichlorophenyl)-3-methylpyrazin-2-amine. $^1$H NMR (400 MHz, chloroform-d) δ 7.52-7.50 (m, 1H), 7.29-7.27 (m, 1H), 7.19-7.17 (m, 1H), 3.44-3.39 (m, 2H), 3.17-3.13 (m, 1H), 2.90-2.87 (m, 2H), 2.11 (m, 1H), 2.00 (s, 3H), 1.81-1.45 (m, 10H). LC-MS (ESI): m/z: [M+H] calculated for $C_{20}H_{25}Cl_2N_5$: 406.15; found 406.0.

Example 32—Synthesis of (R)-(3-(1-amino-8-azaspiro[4.5]decan-8-yl)-6-(2,3-dichlorophenyl)-5-methylpyrazin-2-yl)methanol

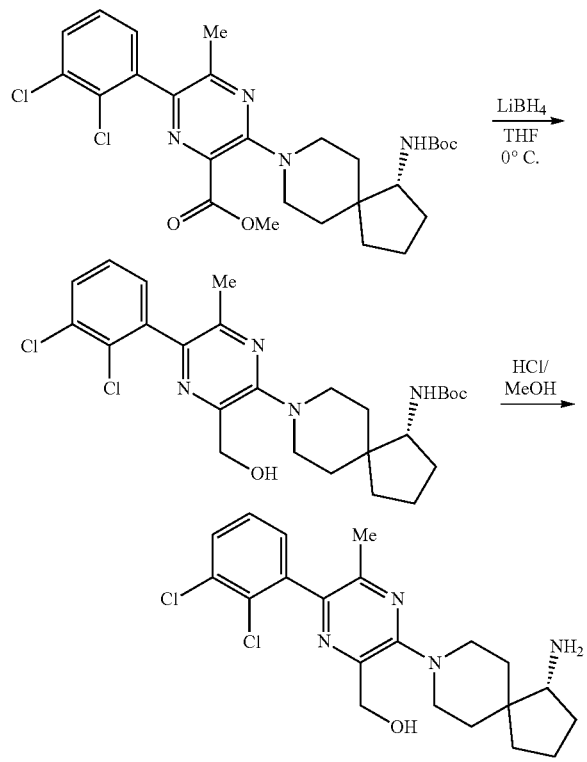

Step 1. Synthesis of (R)-tert-butyl (8-(5-(2,3-dichlorophenyl)-3-(hydroxymethyl)-6-methylpyrazin-2-yl)-8-azaspiro[4.5]decan-1-yl)carbamate To a solution of methyl (R)-3-(1-((tert-butoxycarbonyl)amino)-8-azaspiro[4.5]decan-8-yl)-6-(2,3-dichlorophenyl)-5-methylpyrazine-2-carboxylate (50 mg, 90 µmol, 1 equiv) in THF (3 mL) at 0° C. under inert atmosphere was added LiBH$_4$ (2M, 91 µL, 180 µmol, 2 equiv). The resulting mixture was stirred at 0° C. for 1 hour before it was quenched by addition of H$_2$O (3 mL). The resulting biphasic mixture was extracted with ethyl acetate (3×5 mL). The combined organic layers were washed with brine (10 mL), dried over Na$_2$SO$_4$, filtered, and concentrated under reduced pressure to give (R)-tert-butyl(8-(5-(2,3-dichlorophenyl)-3-(hydroxymethyl)-6-methylpyrazin-2-yl)-8-azaspiro[4.5]decan-1-yl)carbamate (50 mg, crude) as a yellow oil. The crude product was used in the next step without further purification.

Step 2. Synthesis of (R)-(3-(1-amino-8-azaspiro[4.5]decan-8-yl)-6-(2,3-dichlorophenyl)-5-methylpyrazin-2-yl)methanol A solution of (R)-tert-butyl(8-(5-(2,3-dichlorophenyl)-3-(hydroxymethyl)-6-methylpyrazin-2-yl)-8-azaspiro[4.5]decan-1-yl)carbamate (50.0 mg, 95.9 µmol, 1 equiv) in HCl/EtOAc (4M, 3.0 mL) at 25° C. was stirred for 0.5 hours. After this time, the reaction mixture was concentrated under reduced pressure. The residue was purified by prep-HPLC to give (R)-(3-(1-amino-8-azaspiro[4.5]decan-8-yl)-6-(2,3-dichlorophenyl)-5-methylpyrazin-2-yl) methanol (18.0 mg, 42.7 µmol, 44.6% yield) as a white solid. $^1$H NMR (400 MHz, methanol-d$_4$) δ 7.61 (dd, J=7.94, 1.32 Hz, 1H), 7.44-7.36 (m, 1H), 7.36-7.30 (m, 1H), 4.67 (s, 2H), 3.76-3.67 (m, 2H), 3.23 (m, 1H), 3.11 (m, 2H), 2.25 (s, 3H), 2.17 (m, 1H), 1.93-1.49 (m, 9H). LC-MS (ESI): m/z: [M+H] calculated for $C_{21}H_{26}Cl_2N_4O$: 421.15; found 421.2.

Example 33—Synthesis of (3-(4-amino-4-methylpiperidin-1-yl)-6-(2,3-dichlorophenyl)-5-methylpyrazin-2-yl)methanol

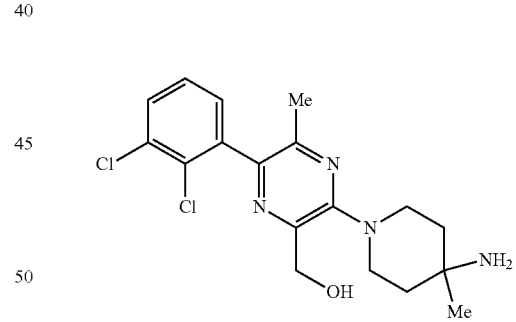

(3-(4-amino-4-methylpiperidin-1-yl)-6-(2,3-dichlorophenyl)-5-methylpyrazin-2-yl)methanol was synthesized in the manner similar to Example 29, Example 30, and Example 32, except tert-butyl(R)-(8-(5-(2,3-dichlorophenyl)-6-methylpyrazin-2-yl)-8-azaspiro[4.5]decan-1-yl)carbamate was substituted with tert-butyl(1-(5-(2,3-dichlorophenyl)-6-methylpyrazin-2-yl)-4-methylpiperidin-4-yl)carbamate. $^1$H NMR (400 MHz, methanol-d$_4$) δ 7.66 (dd, J=8.01, 1.65 Hz, 1H), 7.47-7.41 (m, 1H), 7.39-7.34 (m, 1H), 4.70 (s, 2H), 3.76 (dt, J=13.94, 4.10 Hz, 2H), 3.40-3.32 (m, 2H), 2.31-2.24 (m, 3H), 2.08-1.90 (m, 4H), 1.50 (s, 3H). LC-MS (ESI): m/z: [M+H] calculated for $C_{18}H_{22}Cl_2N_4O$: 381.12; found 381.1.

Example 34—Synthesis of (R)-3-(1-amino-8-azaspiro[4.5]decan-8-yl)-6-(2,3-dichlorophenyl)-5-methylpyrazine-2-carbonitrile

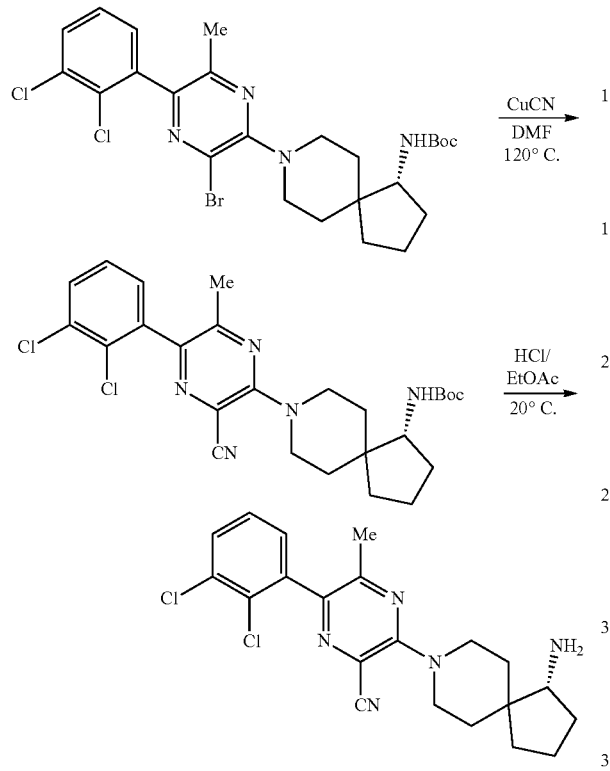

Step 1. Synthesis of (R)-tert-butyl (8-(3-cyano-5-(2,3-dichlorophenyl)-6-methylpyrazin-2-yl)-8-azaspiro[4.5]decan-1-yl) carbamate To a solution of (R)-tert-butyl(8-(3-bromo-5-(2,3-dichlorophenyl)-6-methylpyrazin-2-yl)-8-azaspiro[4.5]decan-1-yl)carbamate (30 mg, 52 μmol, 1 equiv) in DMF (1.0 mL) at 25° C. was added CuCN (9.4 mg, 105 μmol, 2 equiv). The mixture warmed to 120° C. and stirred for 2 hours, after which the reaction was cooled to 25° C. and diluted with H$_2$O (3 mL). The resulting biphasic mixture was extracted with ethyl acetate (3×3 mL). The combined organic extracts were washed with brine (5 mL), dried over Na$_2$SO$_4$, filtered, and concentrated under reduced pressure. The crude residue was purified by prep-TLC to give (R)-tert-butyl (8-(3-cyano-5-(2,3-dichlorophenyl)-6-methylpyrazin-2-yl)-8-azaspiro[4.5]decan-1-yl) carbamate (20 mg, 39 μmol, 73% yield) as a yellow oil.

Step 2. Synthesis of (R)-3-(1-amino-8-azaspiro[4.5]decan-8-yl)-6-(2,3-dichlorophenyl)-5-methylpyrazine-2-carbonitrile A solution of (R)-tert-butyl(8-(3-cyano-5-(2,3-dichlorophenyl)-6-methylpyrazin-2-yl)-8-azaspiro[4.5]decan-1-yl) carbamate (30.0 mg, 58.1 μmol, 1 equiv) in HCl/EtOAc (4M, 3 mL) was stirred at 25° C. for 0.5 hours, after which the reaction mixture was concentrated under reduced pressure. The crude residue was purified by prep-HPLC to give (R)-3-(1-amino-8-azaspiro[4.5]decan-8-yl)-6-(2,3-dichlorophenyl)-5-methylpyrazine-2-carbonitrile (12.0 mg, 28.8 μmol, 49.6% yield) as a yellow solid. $^1$H NMR (400 MHz, methanol-d$_4$) δ 8.47 (s, 1H), 7.36 (m, 1H), 7.34 (m, 1H), 7.28 (m, 1H), 4.52-4.38 (m, 2H), 3.31-3.23 (m, 2H), 2.25 (s, 3H), 2.20 (m, 1H), 1.85-1.51 (m, 9H). LC-MS (ESI): m/z: [M+H] calculated for C$_{21}$H$_{23}$Cl$_2$N$_5$: 416.13; found 416.2.

Example 35—Synthesis of methyl(R)-3-(1-amino-8-azaspiro[4.5]decan-8-yl)-6-(2,3-dichlorophenyl)-5-methylpyrazine-2-carboxylate

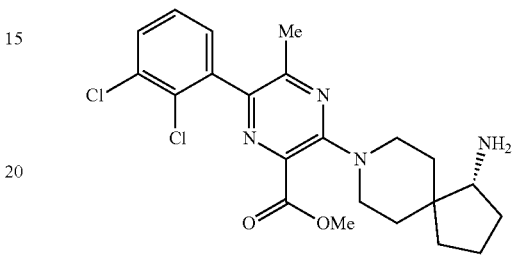

(R)-3-(1-amino-8-azaspiro[4.5]decan-8-yl)-6-(2,3-dichlorophenyl)-5-methylpyrazine-2-carboxylate was synthesized in the manner similar to Example 30. $^1$H NMR (400 MHz, chloroform-d) δ 7.56-7.59 (m, 1H), 7.29-7.29 (m, 1H), 7.27-7.29 (m, 1H), 3.83-3.90 (m, 5H), 3.11-3.17 (m, 4H), 2.19 (s, 3H), 2.13-2.18 (m, 1H), 1.46-1.84 (m, 10H). LC-MS (ESI): m/z: [M+H] calculated for C$_{22}$H$_{26}$Cl$_2$N$_4$O$_2$: 449.14; found 449.2.

Example 36—Synthesis of methyl-6-(4-amino-4-methylpiperidin-1-yl)-3-(2,3-dichlorophenyl)pyrazin-2-ol

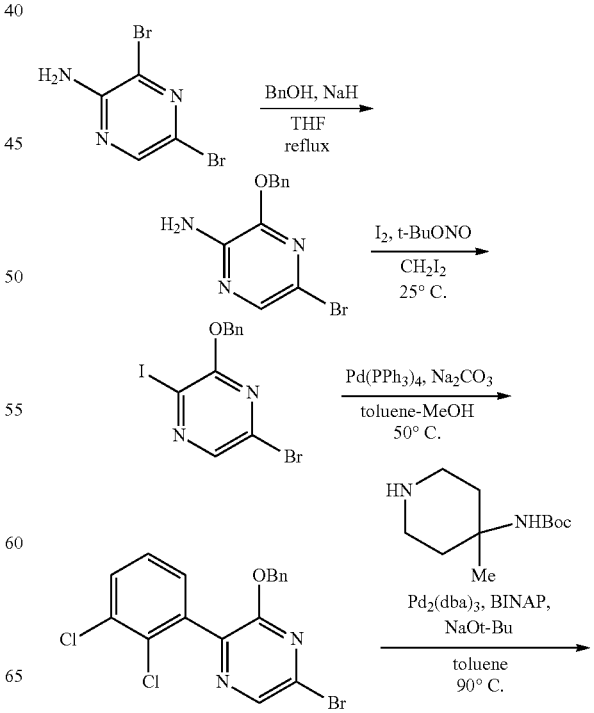

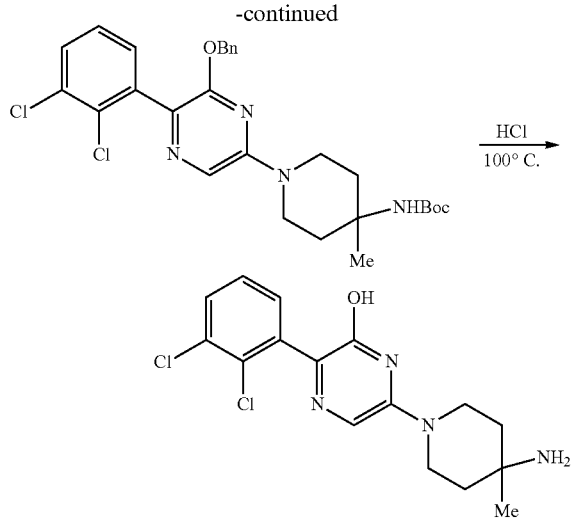

Step 1. Synthesis of 3-(benzyloxy)-5-bromopyrazin-2-amine

A suspension of NaH (427.1 mg, 17.79 mmol, 1.5 equiv) in dry THF (30 mL) at 0° C. was stirred for 10 minutes before benzyl alcohol (1.85 mL, 17.79 mmol, 1.5 equiv) was added and the mixture was stirred for 30 minutes. After this time, 3,5-dibromopyrazin-2-amine (3.00 g, 11.86 mmol, 1 equiv) was added, and the reaction was warmed to reflux and stirred for 10 hours. The mixture was then cooled to 25° C., and the residue was poured into ice water (50 mL). The aqueous phase was then extracted with ethyl acetate (3×20 mL). The combined organic phase was washed with brine (2×30 mL), dried with anhydrous $Na_2SO_4$, filtered, and concentrated under reduced pressure. The crude residue was purified by silica gel chromatography to give 3-(benzyloxy)-5-bromopyrazin-2-amine (3.30 g, 11.78 mmol, 99.33% yield) as a yellow oil.

Step 2. Synthesis of 3-(benzyloxy)-5-bromo-2-iodopyrazine

To a solution of 3-(benzyloxy)-5-bromopyrazin-2-amine (3.30 g, 11.78 mmol, 1 equiv) in $CH_2I_2$ (30 mL) was added tert-butyl nitrite (5.59 mL, 47.12 mmol, 4 equiv) and $I_2$ (3.59 g, 14.14 mmol, 1.2 equiv). The reaction mixture was then stirred at 25° C. for 16 hours, after which the reaction mixture was quenched by addition aqueous $Na_2S_2O_3$ (150 mL) and then extracted with DCM (2×100 mL). The combined organic extracts were washed with brine (100 mL), dried over $Na_2SO_4$, filtered, and concentrated under reduced pressure. The crude residue was purified by silica gel chromatography to give 3-(benzyloxy)-5-bromo-2-iodopyrazine (1.90 g, 4.86 mmol, 41.25% yield) as a yellow solid. $^1$H NMR (400 MHz, chloroform-d) δ 8.08 (s, 1H), 7.51-7.32 (m, 6H), 5.45 (s, 2H).

Step 3. Synthesis of 3-(benzyloxy)-5-bromo-2-(2,3-dichlorophenyl)pyrazine

To a solution of 3-(benzyloxy)-5-bromo-2-(2,3-dichlorophenyl)pyrazine (1.90 g, 4.86 mmol, 1 equiv) in toluene (40 mL) at 25° C. was added (2,3-dichlorophenyl)boronic acid (1.39 g, 7.29 mmol, 1.5 equiv), a solution of $Na_2CO_3$ in methanol (2M, 7.29 mL, 3 equiv), and $Pd(PPh_3)_4$ (786.1 mg, 680.4 µmol, 0.14 equiv). The reaction mixture was then warmed to 60° C. and stirred for 16 hours. The reaction mixture was filtered and concentrated. The residue was purified by silica gel chromatography to give 3-(benzyloxy)-5-bromo-2-(2,3-dichlorophenyl)pyrazine (600 mg, 1.46 mmol, 15% yield) as a yellow solid. $^1$H NMR (400 MHz, chloroform-d) δ 8.35 (s, 1H), 7.54 (dd, J=6.17, 3.53 Hz, 1H), 7.39-7.27 (m, 7H), 5.43 (s, 2H).

Step 4. Synthesis of tert-butyl(1-(6-(benzyloxy)-5-(2,3-dichlorophenyl)pyrazin-2-yl)-4-methylpiperidin-4-yl)carbamate To a solution of 3-(benzyloxy)-5-bromo-2-(2,3-dichlorophenyl)pyrazine (90.0 mg, 220 µmol, 1 equiv) in toluene (1 mL) was added tert-butyl(4-methylpiperidin-4-yl)carbamate (70.5 mg, 329 µmol, 1.5 equiv), NaOt-Bu (42.2 mg, 439 µmol, 2 equiv), [1-(2-diphenylphosphanyl-1-naphthyl)-2-naphthyl]-diphenyl-phosphane (137 mg, 219 µmol, 1 equiv) and $Pd_2(dba)_3$ (10.0 mg, 11.0 µmol, 0.05 equiv). The reaction mixture was then warmed to 90° C. and stirred for 1 hour. The reaction mixture was then filtered and concentrated under reduced pressure. The residue was purified by silica gel chromatography to give tert-butyl(1-(6-(benzyloxy)-5-(2,3-dichlorophenyl)pyrazin-2-yl)-4-methylpiperidin-4-yl)carbamate (100 mg, 184 µmol, 83.8% yield) as a white solid.

Step 5. Synthesis of 6-(4-amino-4-methylpiperidin-1-yl)-3-(2,3-dichlorophenyl)pyrazin-2-ol A mixture of tert-butyl(1-(6-(benzyloxy)-5-(2,3-dichlorophenyl)pyrazin-2-yl)-4-methylpiperidin-4-yl)carbamate (100 mg, 184 µmol, 1 equiv) in HCl (2 mL) was warmed to 100° C. and stirred for 2 hours. After this time, the reaction mixture was cooled and concentrated under reduced pressure. The crude residue was purified by pre-HPLC to give 6-(4-amino-4-methylpiperidin-1-yl)-3-(2,3-dichlorophenyl)pyrazin-2-ol (23.00 mg, 65.11 µmol, 35.39% yield) as a yellow solid. $^1$H NMR (400 MHz, DMSO-$d_6$) δ 7.71 (s, 1H), 7.58 (dd, J=7.45, 1.75 Hz, 1H), 7.40-7.27 (m, 2H), 3.83 (br d, J=14.47 Hz, 2H), 3.41 (br d, J=8.77 Hz, 2H), 1.62 (br s, 4H), 1.26 (s, 3H). LC-MS (ESI): m/z: [M+H] calculated for $C_{16}H_{18}Cl_2N_4O$: 353.09; found 353.1.

Example 37—Synthesis of (R)-6-(1-amino-8-azaspiro[4.5]decan-8-yl)-3-(2,3-dichlorophenyl)pyrazin-2-ol

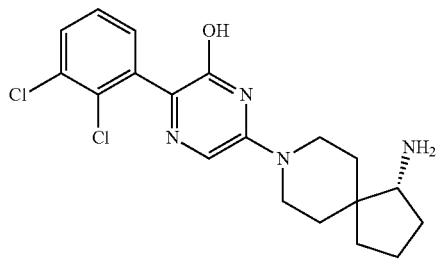 [SMILES: N[C@@H]1CCCC12CCN(c1cnc(-c3cccc(Cl)c3Cl)c(O)n1)CC2]

(R)-6-(1-amino-8-azaspiro[4.5]decan-8-yl)-3-(2,3-dichlorophenyl)pyrazin-2-ol was synthesized in the manner similar to Example 36, except tert-butyl(4-methylpiperidin-4-yl)carbamate was substituted with (R)-2-methyl-N—((R)-8-azaspiro[4.5]decan-1-yl)propane-2-sulfinamide. $^1$H NMR (400 MHz, DMSO-d$_6$) δ 8.34 (s, 1H), 7.76 (s, 1H), 7.60 (br dd, J=7.61, 1.87 Hz, 1H), 7.46-7.28 (m, 2H), 4.24-4.04 (m, 2H), 3.12-3.02 (m, 2H), 2.93 (br s, 1H), 2.03-1.89 (m, 2H), 1.85-1.39 (m, 8H). LC-MS (ESI): m/z: [M+H] calculated for C$_{19}$H$_{22}$Cl$_2$N$_4$O: 393.12; found 392.9.

Example 38—Synthesis of (R)-8-(5-((2-amino-3-chloropyridin-4-yl)thio)-6-iodopyrazin-2-yl)-8-azaspiro[4.5]decan-1-amine

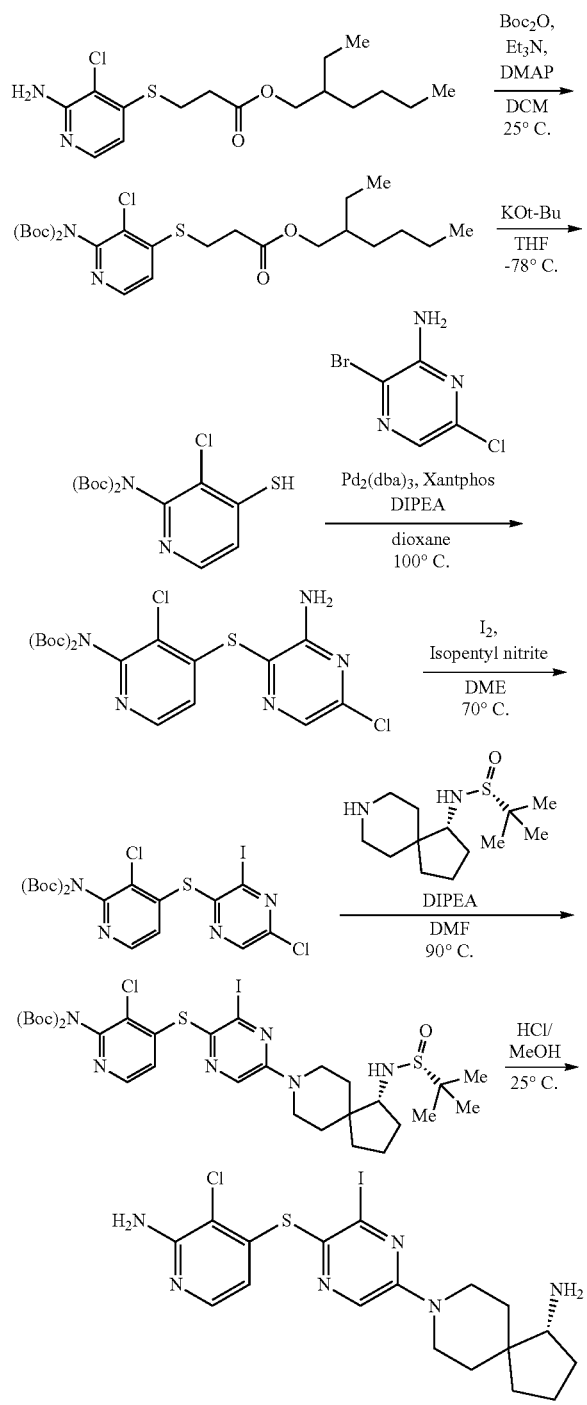

Step 1. Synthesis of 2-ethylhexyl-3-[[24bis(tert-butoxycarbonyl)amino]-3-chloro-4-pyridyl]sulfanyl]propanoate To four parallel batches of 2-ethylhexyl 3-((2-amino-3-chloropyridin-4-yl)thio)propanoate (4×2.8 g, 4×8.2 mmol, 1 equiv) and Boc$_2$O (4×9.4 mL, 4×41 mmol, 5 equiv) in DCM (4×150 mL) at 25° C. under an inert atmosphere was added DMAP (4×201 mg, 1.6 mmol, 0.2 equiv) and Et$_3$N (4×3.4 mL, 25 mmol, 3 equiv), sequentially. The resulting mixture was stirred for 12 hours, after which the four batches were combined. The combined mixture was poured into water (500 mL) and extracted with DCM (3×200 mL). The combined organic extracts were washed with brine (500 mL), dried with anhydrous Na$_2$SO$_4$, filtered, and concentrated under reduced pressure. The residue was purified by silica gel chromatography to afford 2-ethylhexyl-3-[[24bis(tert-butoxycarbonyl)amino]-3-chloro-4-pyridyl]sulfanyl] propanoate (11 g, 25 mmol, 74.7% yield) as a colorless oil. $^1$H NMR (400 MHz, chloroform-d$_6$) δ 8.27-8.26 (d, J=6.4 Hz, 1H), 7.08-7.06 (d, J=8 Hz, 1H), 4.07-4.05 (m, 2H), 3.29-3.25 (d, J=8 Hz, 1H), 2.77-2.73 (d, J=8 Hz, 1H), 1.56 (s, 3H), 1.40 (s, 18H), 1.40-1.29 (m, 6H), 0.91-0.87 (m, 6H).

Step 2. Synthesis of tert-butyl(3-chloro-4-mercapto-pyridin-2-yl)carbamate

To two parallel solutions of 2-ethylhexyl3-[[2-[bis(tert-butoxycarbonyl)amino]-3-chloro-4-pyridyl]sulfanyl]propanoate (2×5.9 g, 2×13.1 mmol, 1 equiv) in THF (2×100 mL) at −78° C. under inert atmpsphere was added KOt-Bu (1M in THF, 2×2.0 mL, 2×19.6 mmol, 1.5 equiv). The mixture was stirred at −78° C. for 10 minutes before the two batches were combined. The mixture was concentrated under reduced pressure. The crude residue was purified by silica gel chromatography to afford tert-butyl (3-chloro-4-mercaptopyridin-2-yl)carbamate (4.0 g, 15 mmol, 58.3% yield) as a yellow solid.

Step 3. Synthesis of bis tert-butyl(4-((3-amino-5-chloropyrazin-2-yl)thio)-3-chloropyridin-2-yl)carbamate To a solution of bis tert-butyl(3-chloro-4-mercaptopyridin-2-yl)carbamate (4.00 g, 15 mmol, 1 equiv) and 3-bromo-6-chloropyrazin-2-amine (3.20 g, 15.3 mmol, 1 equiv) in dioxane (100 mL) at 20° C. under inert atmosphere was added DIPEA (5.36 mL, 30.6 mmol, 2 equiv). The mixture was warmed to 60° C. and stirred for 2 hours. After this time, the mixture was cooled to 20° C. and concentrated under reduced pressure. The crude residue was purified by silica gel chromatography to afford bis tert-butyl (4-((3-amino-5-chloropyrazin-2-yl)thio)-3-chloropyridin-2-yl)carbamate (2.50 g, 6.44 mmol, 41% yield) as a yellow solid. $^1$H NMR (400 MHz, chloroform-d) δ 8.16-8.15 (d, J=5.2 Hz, 1H), 8.00 (s, 1H), 6.43-6.42 (d, J=5.2 Hz, 1H), 5.23 (s, 2H), 1.55 (s, 9H).

Step 4. Synthesis of tert-butyl(3-chloro-4-((5-chloro-3-iodopyrazin-2-yl)thio)pyridin-2-yl)carbamate To four parallel batches of bis tert-butyl(4-((3-amino-5-chloropyrazin-2-yl)thio)-3-chloropyridin-2-yl)carbamate (4×500 mg, 4×1.3 mmol, 1 equiv) and isopentyl nitrite (4×867 µL, 4×6.4 mmol, 5 equiv) in DME (4×5 mL) at 25° C. was added I2 (4×653 mg, 4×2.6 mmol, 2 equiv) in one portion. The mixture was warmed to 70° C. and stirred for 2 hours. After this time, the four batches were combined and poured into water (100 mL). The aqueous phase was then extracted with ethyl acetate (3×100 mL). The combined organic extracts were washed with brine (200 mL), dried with anhydrous Na$_2$SO$_4$, filtered, and concentrated under reduced pressure. The crude residue was the purified by silica gel chromatography to afford bis tert-butyl (3-chloro-4-((5-chloro-3-iodopyrazin-2-yl)thio)pyridin-2-yl)carbamate (1.2 g, 2.4 mmol, 46.5% yield) as a yellow solid.

Step 5. Synthesis of bis tert-butyl(4-((5-((R)-1-(((R)-tert-butylsulfinyl)amino)-8-azaspiro[4.5]decan-8-yl)-3-iodopyrazin-2-yl)thio)-3-chloropyridin-2-yl)carbamate To two parallel batches of bis tert-butyl(3-chloro-4-((5-chloro-3-iodopyrazin-2-yl)thio)pyridin-2-yl)carbamate (2×25.0 mg, 2×62.6 μmol, 1 equiv) and (R)-2-methyl-N—OR)-8-azaspiro[4.5]decan-1-yl)propane-2-sulfinamide (2×16.1 mg, 2×62.6 μmol, 1 equiv) in DMF (2×2.00 mL) at 25° C. under inert atmosphere was added DIPEA (2×109 μL, 2×626 μmol, 10 equiv). The mixture was warmed to 90° C. and stirred for 1 hour. After this time, the two batches were combined and poured into water (5 mL). The aqueous phase was then extracted with ethyl acetate (3×20 mL). The combined organic extracts were washed with brine (10 mL), dried over anhydrous Na$_2$SO$_4$, filtered, and concentrated under reduced pressure to afford bis tert-butyl (4-((5-((R)-1-(((R)-tert-butylsulfinyl)amino)-8-azaspiro[4.5]decan-8-yl)-3-iodopyrazin-2-yl)thio)-3-chloropyridin-2-yl)carbamate (100 mg, crude) as a yellow oil that was used in the next step without further purification.

Step 6. Synthesis of (R)-8-(5-((2-amino-3-chloropyridin-4-yl)thio)-6-iodopyrazin-2-yl)-8-azaspiro[4.5]decan-1-amine To a solution of bis tert-butyl (4-((5-((R)-1-(((R)-tert-butylsulfinyl)amino)-8-azaspiro[4.5]decan-8-yl)-3-iodopyrazin-2-yl)thio)-3-chloropyridin-2-yl)carbamate (150 mg, 208 μmol, 1 equiv) in MeOH (2 mL) at 20° C. under inert atmosphere was added HCl/MeOH (4M, 520 μL, 10 equiv). The mixture was then stirred at 20° C. for 2 hours. The mixture was then concentrated under reduced pressure, and the crude residue was purified by pre-HPLC to give (R)-8-(5-((2-amino-3-chloropyridin-4-yl)thio)-6-iodopyrazin-2-yl)-8-azaspiro[4.5]decan-1-amine (14.0 mg, 27.0 μmol, 13.0% yield) as a yellow solid. $^1$H NMR (400 MHz, methanol-d$_4$): δ 8.29 (s, 1H), 7.67-7.65 (d, J=6.8 Hz, 1H), 6.31-6.30 (d, J=6.8 Hz, 1H), 4.40-4.28 (m, 2H), 3.29-3.26 (m, 4H), 2.24-2.23 (m, 1H), 1.90-1.59 (m, 8H). LC-MS (ESI): m/z: [M+H] calculated for C$_{18}$H$_{22}$ClIN$_6$S: 517.04; found 517.1.

Example 39—Synthesis of (R)-3-((2-amino-3-chloropyridin-4-yl)thio)-6-(1-amino-8-azaspiro[4.5]decan-8-yl)pyrazine-2-carbonitrile

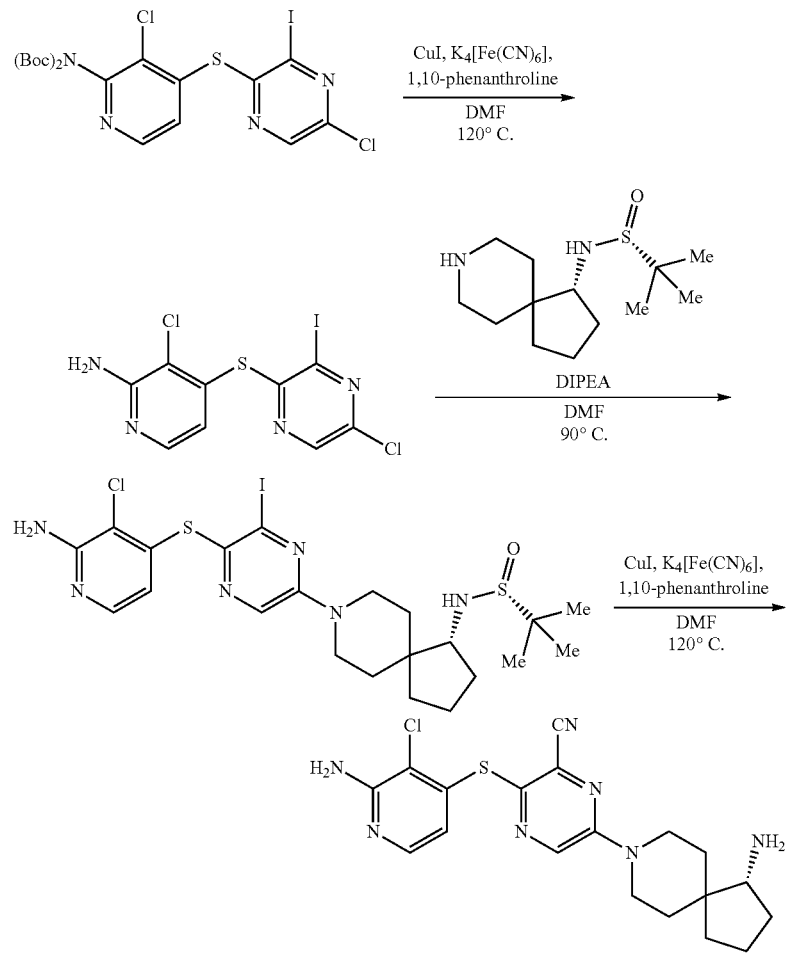

Step 1. Synthesis of 3-chloro-4-((5-chloro-3-iodopyrazin-2-yl)thio)pyridin-2-amine To a solution of tert-butyl(3-chloro-4-((5-chloro-3-iodopyrazin-2-yl)thio)pyridin-2-yl)carbamate (1.10 g, 2.20 mmol, 1 equiv) in DMF (10 mL) under inert atmosphere was added CuI (83.8 mg, 440 µmol, 0.2 equiv), 1,10-phenanthroline (79.2 mg, 440 µmol, 0.2 equiv), and K$_4$[Fe(CN)$_6$] (1.62 g, 4.40 mmol, 2 equiv), sequentially. The mixture was warmed to 120° C. and stirred for 3 hours. After this time, the residue was poured into water (50 mL) and extracted with ethyl acetate (3×20 mL). The combined organic extracts were washed with brine (50 mL), dried with anhydrous Na$_2$SO$_4$, filtered, and concentrated under reduced pressure. The residue was purified by silica gel chromatography to afford 3-chloro-4-((5-chloro-3-iodopyrazin-2-yl)thio)pyridin-2-amine (230 mg, 576 µmol, 26% yield).

Step 2. Synthesis of (R)—N—((R)-8-(5-((2-amino-3-chloropyridin-4-yl)thio)-6-iodopyrazin-2-yl)-8-azaspiro[4.5]decan-1-yl)-2-methylpropane-2-sulfinamide To two parallel batches of bis tert-butyl(3-chloro-4-((5-chloro-3-iodopyrazin-2-yl)thio)pyridin-2-yl)carbamate (2×25.0 mg, 2×62.6 µmol, 1 equiv) and (R)-2-methyl-N—OR)-8-azaspiro[4.5]decan-1-yl)propane-2-sulfinamide (2×16.1 mg, 2×62.6 µmol, 1 equiv) in DMF (2×2.00 mL) at 25° C. under inert atmosphere was added DIPEA (2×109 µL, 2×626 µmol, 10 equiv). The mixture was warmed to 90° C. and stirred for 1 hour. After this time, the two batches were combined and poured into water (5 mL). The aqueous phase was then extracted with ethyl acetate (3×20 mL). The combined organic extracts were washed with brine (10 mL), dried over anhydrous Na$_2$SO$_4$, filtered, and concentrated under reduced pressure to afford (R)—N—((R)-8-(5-((2-amino-3-chloropyridin-4-yl)thio)-6-iodopyrazin-2-yl)-8-azaspiro[4.5]decan-1-yl)-2-methylpropane-2-sulfinamide (100 mg, crude) as a yellow oil.

Step 3. Synthesis of (R)-3-((2-amino-3-chloropyridin-4-yl)thio)-6-(1-amino-8-azaspiro[4.5]decan-8-yl)pyrazine-2-carbonitrile To a solution of (R)—N—((R)-8-(5-((2-amino-3-chloropyridin-4-yl)thio)-6-iodopyrazin-2-yl)-8-azaspiro[4.5]decan-1-yl)-2-methylpropane-2-sulfinamide (100 mg, 161 µmol, 1 equiv) in DMF (1 mL) under an inert atmosphere was added CuI (6.13 mg, 32.2 µmot, 0.2 equiv), 1,10-phenanthroline (5.80 mg, 32.2 µmol, 0.2 equiv), and K$_4$[Fe (CN)$_6$] (118 mg, 322 µmol, 2 equiv), sequentially. The resulting mixture was warmed to 120° C. and stirred for 3 hours. After this time, the residue was poured into water (5 mL) and extracted with ethyl acetate (3×2 mL). The combined organic extracts were washed with brine (5 mL), dried with anhydrous Na$_2$SO$_4$, filtered, and concentrated under reduced pressure. The residue was purified by prep-HPLC to afford (R)-3-((2-amino-3-chloropyridin-4-yl)thio)-6-(1-amino-8-azaspiro[4.5]decan-8-yl) pyrazine-2-carbonitrile (4.00 mg, 9.62 µmol, 5.97% yield). $^1$H NMR (400 MHz, methanol-d$_4$): δ 8.52 (s, 1H), 7.64 (m, 1H), 6.00-6.01 (m, 1H), 4.30-4.41 (m, 3H), 3.19-3.23 (m, 2H), 2.18 (m, 1H), 1.58-1.90 (m, 9H). LC-MS (ESI): m/z: [M+H] calculated for C$_{19}$H$_{22}$ClN$_7$S: 416.13; found 416.1.

Example 40—Synthesis of 1-(5-(2,3-dichlorophenyl)-6-(trifluoromethyl)pyrazin-2-yl)-4-methylpiperidin-4-amine

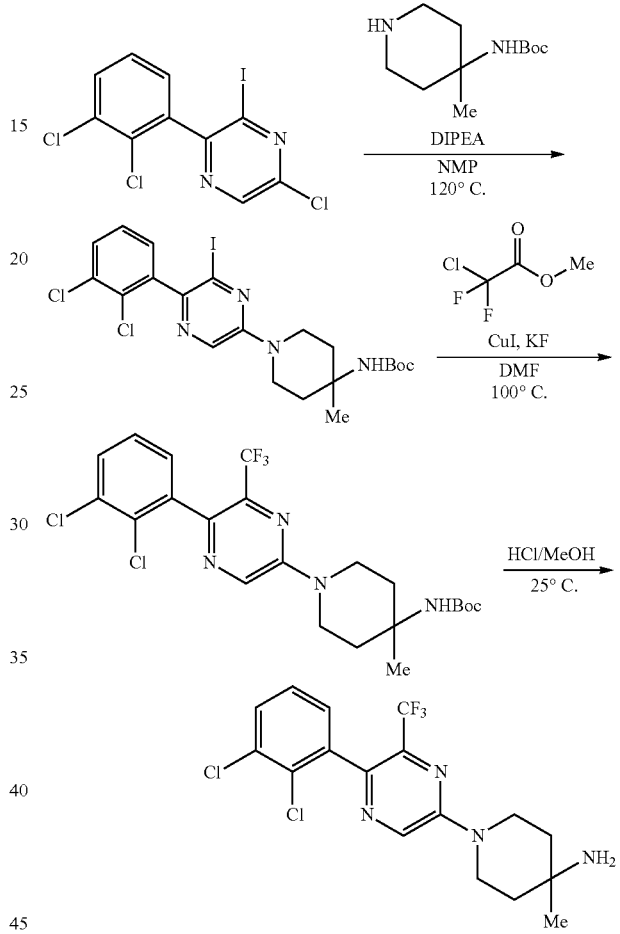

Step 1. Synthesis of tert-butyl(1-(5-(2,3-dichlorophenyl)-6-iodopyrazin-2-yl)-4-methylpiperidin-4-yl)carbamate To a solution of 5-chloro-2-(2,3-dichlorophenyl)-3-iodopyrazine (500 mg, 1.3 mmol, 1 equiv) in dioxane (3 mL) was added tert-butyl (4-methylpiperidin-4-yl)carbamate (418 mg, 2 mmol, 1.5 equiv) and DIEA (5 mL, 29 mmol, 22 equiv), sequentially. The mixture was then warmed to 90° C. and stirred for 2 hours. After this time, the reaction was concentrated under reduced pressure, and the crude residue so obtained was purified by silica gel chromatography to give tert-butyl (1-(5-(2,3-dichlorophenyl)-6-iodopyrazin-2-yl)-4-methylpiperidin-4-yl)carbamate (500 mg, 888 µmol, 68% yield) as a yellow solid. $^1$H NMR (400 MHz, methanol-d$_4$) δ 8.07 (s, 1H), 7.53-7.51 (m, 1H), 7.30-7.28 (m, 2H), 3.92-3.89 (m, 2H), 3.41-3.36 (m, 2H), 2.17-2.14 (m, 2H), 1.70-1.62 (m, 2H), 1.45 (s, 9H), 1.41 (s, 3H).

Step 2. Synthesis of tert-butyl(1-(5-(2,3-dichloro-phenyl)-6-(trifluoromethyl)pyrazin-2-yl)-4-methylpiperidin-4-yl)carbamate To a solution of tert-butyl(1-(5-(2,3-dichlorophenyl)-6-iodopyrazin-2-yl)-4-methylpiperidin-4-yl)carbamate (350 mg, 621 μmol, 1 equiv) in DMF (4 mL) at 20° C. was added methyl 2-chloro-2,2-difluoro-acetate (898 mg, 6.2 mmol, 10 equiv), CuI (118 mg, 621 μmol, 1 equiv) and KF (36 mg, 621 μmol, 1 equiv). The resulting mixture was warmed to 100° C. and stirred for 10 hours. The mixture was then purified by prep-HPLC to give tert-butyl (1-(5-(2,3-dichlorophenyl)-6-(trifluoromethyl)pyrazin-2-yl)-4-methylpiperidin-4-yl)carbamate (10 mg, 18 μmol, 2.9% yield) as a white solid.

Step 3. Synthesis of 1-(5-(2,3-dichlorophenyl)-6-(trifluoromethyl)pyrazin-2-yl)-4-methyl piperidin-4-amine A solution of tert-butyl(1-(5-(2,3-dichlorophenyl)-6-(trifluoromethyl)pyrazin-2-yl)-4-methylpiperidin-4-yl)carbamate (10 mg, 20 μmol, 1 equiv) in HCl/MeOH (4M, 2 mL) was stirred at 20° C. for 1 hour, after which the mixture was concentrated under reduced pressure. The residue was purified by prep-HPLC to give 1-(5-(2,3-dichlorophenyl)-6-(trifluoromethyl)pyrazin-2-yl)-4-methylpiperidin-4-amine (7.8 mg, 17.3 μmol, 87% yield) as a yellow solid. 1-(5-(2,3-dichlorophenyl)-6-(trifluoromethyl)pyrazin-2-yl)-4-methylpiperidin-4-amine was isolated as its formate salt. $^1$H NMR (400 MHz, methanol-$d_4$) δ 8.54 (s, 1H), 7.64-7.62 (m, 1H), 7.39-7.36 (m, 1H), 7.28-7.26 (m, 1H), 4.26-4.22 (m, 2H), 3.58-3.51 (m, 2H), 2.02-1.90 (m, 4H), 1.50 (s, 3H). LC-MS (ESI): m/z: [M+H] calculated for $C_{17}H_{17}Cl_2F_3N_4$: 405.08; found 405.0.

Example 41—Synthesis of (R)-(6-(1-amino-8-azaspiro[4.5]decan-8-yl)-3-(2,3-dichlorophenyl)pyrazin-2-yl)methanol

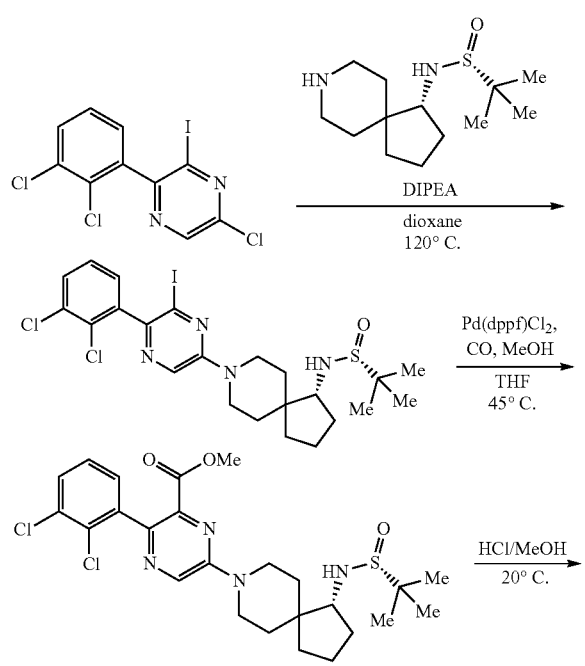

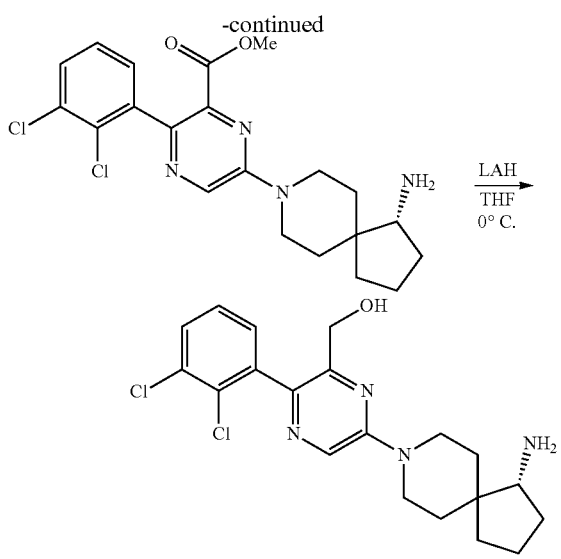

Step 1. Synthesis of (R)—N—((R)-8-(5-(2,3-dichlorophenyl)-6-iodopyrazin-2-yl)-8-azaspiro[4.5]decan-1-yl)-2-methylpropane-2-sulfinamide A mixture of 5-chloro-2-(2,3-dichlorophenyl)-3-iodopyrazine (1.5 g, 3.8 mmol, 1 equiv), (R)-2-methyl-N—((R)-8-azaspiro[4.5]decan-1-yl)propane-2-sulfinamide (1.3 g, 5 mmol, 1.3 equiv) in DIPEA (3 mL) and dioxane (3 mL) was warmed to 110° C. and stirred for 4 hours. After this time, the mixture was concentrated under reduced pressure, and the resulting crude residue was purified by silica gel chromatography to give (R)—N—((R)-8-(5-(2,3-dichlorophenyl)-6-iodopyrazin-2-yl)-8-azaspiro[4.5]decan-1-yl)-2-methylpropane-2-sulfinamide (1.8 g, crude) as a yellow oil.

Step 2. Synthesis of methyl 6-((R)-1-(((R)-tert-butylsulfinyl)amino)-8-azaspiro[4.5]decan-8-yl)-3-(2,3-dichlorophenyl)pyrazine-2-carboxylate To a solution of (R)—N—((R)-8-(5-(2,3-dichlorophenyl)-6-iodopyrazin-2-yl)-8-azaspiro[4.5]decan-1-yl)-2-methylpropane-2-sulfinamide (850 mg, 1.4 mmol, 1 equiv) in MeOH (10 mL) and THF (15 mL) at 20° C. was added Pd(dppf)Cl$_2$ (102.4 mg, 139.9 μmol 0.1 equiv) and Et$_3$N (582 μL, 4.2 mmol, 3 equiv), sequentially. The resulting mixture was placed under an atmosphere of carbon monoxide (35 psi), warmed to 45° C., and stirred for 4 hours. After this time, the reaction was concentrated under reduced pressure. The crude residue so obtained was purified by silica gel chromatography to give methyl 3-(2,3-dichlorophenyl)-6-((R)-1-((R)-1,1-dimethylethylsulfinamido)-8-azaspiro[4.5]decan-8-yl)pyrazine-2-carboxylate (600 mg, crude) as a brown solid.

Step 3. Synthesis of methyl (R)-6-(1-amino-8-azaspiro[4.5]decan-8-yl)-3-(2,3-dichlorophenyl)pyrazine-2-carboxylate A mixture of methyl 3-(2,3-dichlorophenyl)-6-((R)-1-((R)-1,1-dimethylethylsulfinamido)-8-azaspiro[4.5]decan-8-yl)pyrazine-2-carboxylate (40 mg, 74 μmol, 1 equiv) in HCl/MeOH (4M, 2 mL) was stirred at 20° C. for 2 hours. After this time, the mixture was concentrated under reduced pressure, and the resulting crude residue was purified by prep-HPLC to give methyl (R)-6-(1-amino-8-azaspiro[4.5]decan-8-yl)-3-(2,3-dichlorophenyl) pyrazine-2-carboxylate (5.8 mg, 12 μmol, 16% yield) as a yellow solid. $^1$H NMR (400 MHz, methanol-$d_4$) δ 8.41 (s, 1H), 7.58-7.56 (m, 1H), 7.38-7.36 (m, 1H), 7.34-7.30 (m, 1H), 4.48-4.35 (m, 2H), 3.73-3.67 (m, 1H), 3.65 (s, 3H), 3.24-3.21 (m, 2H), 2.26-2.21 (m, 1H), 1.93-1.57 (m, 9H). LC-MS (ESI): m/z: [M+H] calculated for $C_{21}H_{24}Cl_2N_4O_2$: 435.13; found: 435.

Step 4. Synthesis of (R)-(6-(1-amino-8-azaspiro[4.5]decan-8-yl)-3-(2,3-dichlorophenyl)pyrazin-2-yl)methanol To a solution of methyl (R)-6-(1-amino-8-azaspiro[4.5]decan-8-yl)-3-(2,3-dichlorophenyl)pyrazine-2-carboxylate (80 mg, 184 μmol, 1 equiv) in THF (2 mL) at 0° C. was added LAH (20.9 mg, 551.2 μmol, 3 equiv). The resulting mixture was stirred at 0° C. for 2 hours before the reaction was quenched with water (2 mL) and extracted with EtOAc (3×5 mL). The combined organic extracts were washed with brine (5 mL), dried over $Na_2SO_4$, filtered, and concentrated under reduced pressure. The crude residue so obtained was purified by prep-HPLC to give (R)-(6-(1-amino-8-azaspiro[4.5]decan-8-yl)-3-(2,3-dichlorophenyl)pyrazin-2-yl)methanol (10 mg, 22 μmol, 12% yield) as a yellow solid. $^1$H NMR (400 MHz, $CD_3OD$) δ ppm 8.16 (s, 1H), 7.64-7.60 (m, 1H), 7.38 (d, J=7.94 Hz, 1H), 7.31 (m, J=7.94 Hz, 1H), 4.63-4.54 (m, 2H), 4.45 (m, 1H), 4.34 (m, 2H), 3.27-3.18 (m, 2H), 2.23 (m, J=5.51 Hz, 1H), 1.92-1.53 (m, 10H). LC-MS (ESI): m/z: [M+H] calculated for $C_{20}H_{24}Cl_2N_4O_2$: 407.13; found: 407.2.

Example 42—Synthesis of (R)-8-(5-(2,3-dichlorophenyl)-6-vinylpyrazin-2-yl)-8-azaspiro[4.5]decan-1-amine

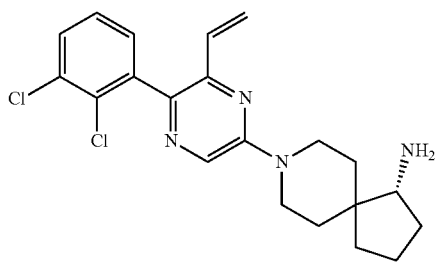 [SMILES: C=Cc1nc(N2CCC3(CCC[C@H]3N)CC2)cnc1-c1cccc(Cl)c1Cl]

(R)-8-(5-(2,3-dichlorophenyl)-6-vinylpyrazin-2-yl)-8-azaspiro[4.5]decan-1-amine was synthesized in the manner similar to Example 14, except 5-chloro-2-((2,3-dichlorophenyl)thio)-3-iodopyrazine was substituted with methyl 6-((R)-1-(((R)-tert-butylsulfinyl)amino)-8-azaspiro[4.5]decan-8-yl)-3-(2,3-dichlorophenyl)pyrazine-2-carboxylate. $^1$H NMR (400 MHz, methanol-$d_4$) δ 8.51 (s, 1H), 8.16 (s, 1H), 7.64-7.61 (m, 1H), 7.42-7.38 (m, 1H), 7.36-7.27 (m, 1H), 6.41-6.28 (m, 2H), 5.42-5.39 (m, 2H), 4.58-4.39 (m, 2H), 3.25-3.20 (m, 2H), 2.25-2.22 (m, 1H), 1.92-1.44 (m, 10H). LC-MS (ESI): m/z: [M+H] calculated for $C_{21}H_{24}Cl_2N_4$: 403.14; found: 403.1.

Example 43—Synthesis of (R)-(3-(1-amino-8-azaspiro[4.5]decan-8-yl)-6-((2,3-dichloropyridin-4-yl)thio)-5-methylpyrazin-2-yl)methanol

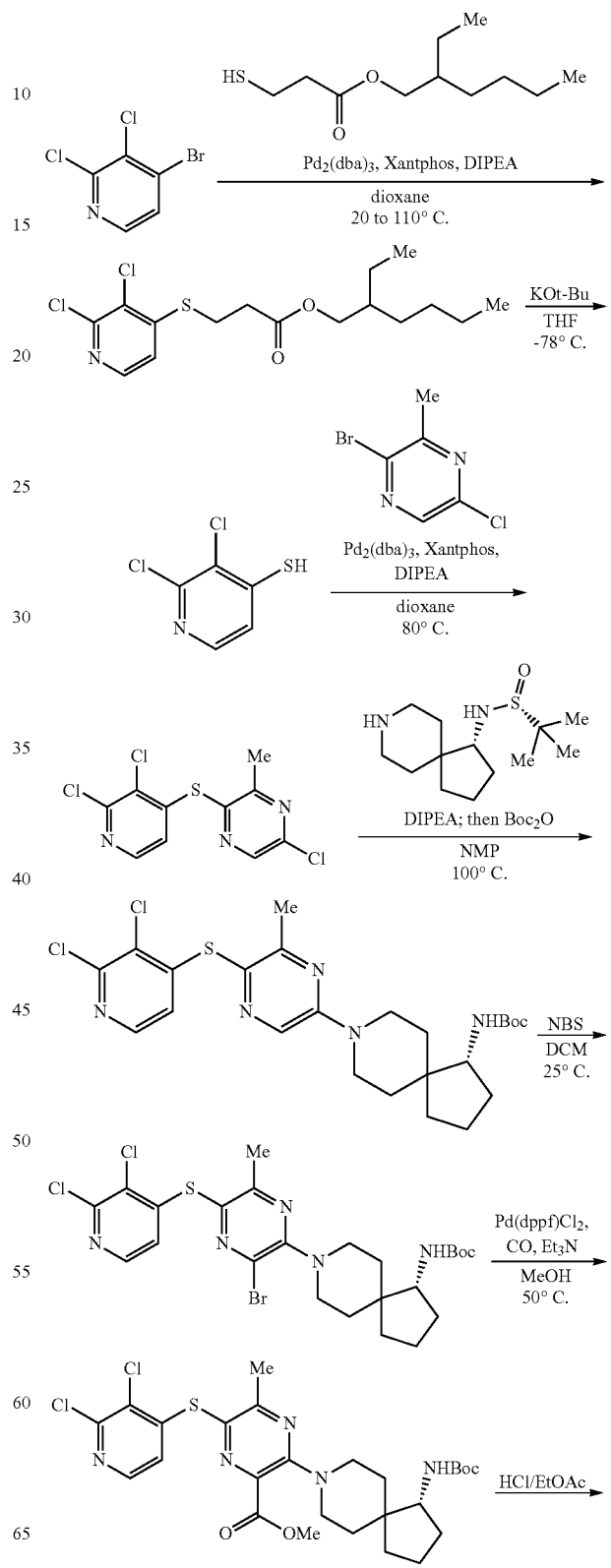

-continued

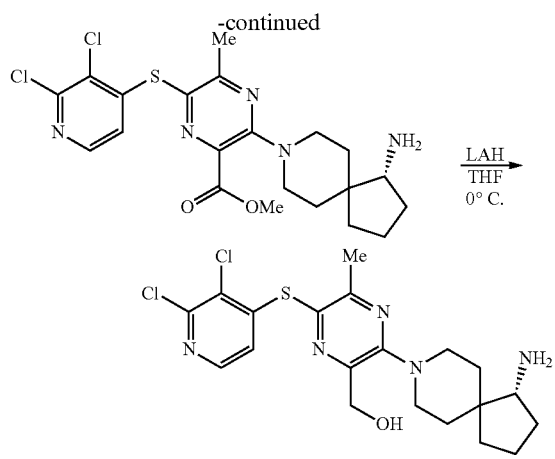

Step 1. Synthesis of 2-ethylhexyl 3-((2,3-dichloropyridin-4-yl)thio)propanoate To a solution of 2,3-dichloro-4-iodopyridine (50 g, 183 mmol, 1 equiv) in dioxane (500 mL) was added 2-ethylhexyl 3-sulfanylpropanoate (52 g, 237 mmol, 1.3 equiv), Xantphos (11 g, 18 mmol, 0.1 equiv), DIPEA (71 g, 547 mmol, 96 mL, 3 equiv) and Pd$_2$(dba)$_3$ (8.4 g, 9.1 mmol, 0.05 equiv). The reaction mixture was then warmed to 110° C. and stirred for 2 hours. After this time, the reaction mixture was filtered and concentrated under reduced pressure. The crude residue so obtained was purified by silica gel chromatography to give 2-ethylhexyl 3-((2,3-dichloropyridin-4-yl)thio)propanoate (42 g, 11 mmol, 63% yield) as a brown oil. $^1$H NMR (400 MHz, chloroform-d) δ 8.15 (d, J=5.26 Hz, 1H), 7.02 (d, J=5.26 Hz, 1H), 4.05 (d, J=5.70 Hz, 2H), 3.25 (t, J=7.45 Hz, 2H), 2.75 (t, J=7.45 Hz, 2H), 1.62-1.53 (m, 1H), 1.42-1.26 (m, 8H), 0.88 (t, J=7.45 Hz, 6H).

Step 2. Synthesis of 2,3-dichloropyridine-4-thiol

To a solution of 2-ethylhexyl 3-((2,3-dichloropyridin-4-yl)thio)propanoate (6.0 g, 16 mmol, 1.0 equiv) in THF (60 mL) at −78° C. under inert atmosphere was added KOt-Bu (1M in THF, 32 mL, 32 mmol, 2 equiv). The reaction mixture was stirred at −78° C. for 1 hour. The reaction mixture was then allowed to warm to 25° C., and ethyl acetate (20 mL) and 5% K$_2$CO$_3$ (40 mL) were added. The resulting aqueous layer was then extracted with ethyl acetate (10 mL). The aqueous phase was then adjusted to pH=3 with aqueous HCl (2M), extracted with ethyl acetate (2×40 mL). The combined organic extracts were washed with brine (40 mL), dried over Na$_2$SO$_4$, and filtered. To this filtrate was added dioxane (100 mL), and the resulting solution was concentrated under reduced pressure to leave a solution of 2,3-dichloropyridine-4-thiol (1.3 g, crude) in dioxane (40 mL) that was used in subsequent reactions without further purification.

Step 3. Synthesis of 5-chloro-2-((2,3-dichloropyridin-4-yl)thio)-3-methylpyrazine To a solution of 2-bromo-5-chloro-3-methylpyrazine (1.0 g, 4.8 mmol, 1 equiv) in dioxane (10 mL) was added DIPEA (1.7 mL, 9.6 mmol, 2 equiv), 2,3-dichloropyridine-4-thiol (1.3 g, 7.2 mmol, 1.5 equiv), Xantphos (279 mg, 482 μmol, 0.1 equiv), Pd$_2$(dba)$_3$ (353 mg, 385 μmol, 0.08 equiv). The reaction mixture was warmed to 90° C. and stirred for 1 hour. After this time, the reaction mixture was filtered and concentrated under reduced pressure. The crude residue was purified by silica gel chromatography to give 5-chloro-2-((2,3-dichloropyridin-4-yl)thio)-3-methylpyrazine (730 mg, 2.5 mmol, 53% yield) as a white solid.

Step 4. Synthesis of tert-butyl (R)-(8-(5-((2,3-dichloropyridin-4-yl)thio)-6-methylpyrazin-2-yl)-8-azaspiro[4.5]decan-1-yl)carbamate To a solution of 5-chloro-2-((2,3-dichloropyridin-4-yl)thio)-3-methylpyrazine (730 mg, 2.4 mmol, 1 equiv) in DIPEA (6 mL) was added (R)-2-methyl-N—((R)-8-azaspiro[4.5]decan-1-yl)propane-2-sulfinamide (738 mg, 2.8 mmol, 1.2 equiv) and NMP (3 mL). The reaction mixture was then warmed 130° C. under microwave irradiation and stirred for 2 hours. After this time, the reaction mixture was cooled to 25° C., and Boc$_2$O (1.3 mL, 5.6 mmol, 2 equiv) was added to the reaction. The resulting mixture was stirred at 25° C. for 16 hours. After this time, the reaction mixture was filtered and concentrated under reduced pressure. The crude residue so obtained was purified by silica gel chromatography to give tert-butyl (R)-(8-(5-((2,3-dichloropyridin-4-yl)thio)-6-methylpyrazin-2-yl)-8-azaspiro[4.5]decan-1-yl)carbamate (535 mg, 1.0 mmol, 36% yield) as a white solid.

Step 5. Synthesis of (R)-tert-butyl (8-(3-bromo-5-((2,3-dichloropyridin-4-yl)thio)-6-methylpyrazin-2-yl)-8-azaspiro[4.5]decan-1-yl)carbamate To a solution of (R)-tert-butyl (8-(5-((2,3-dichloropyridin-4-yl)thio)-6-methylpyrazin-2-yl)-8-azaspiro[4.5]decan-1-yl)carbamate (535 mg, 1.0 mmol, 1 equiv) in DCM (5 mL) was added NBS (363 mg, 2.0 mmol, 2 equiv). The reaction mixture was then stirred at 25° C. for 5 minutes before the reaction mixture was concentrated under reduced pressure. The crude residue so obtained was purified by silica gel chromatography to give (R)-tert-butyl (8-(3-bromo-5-((2,3-dichloropyridin-4-yl)thio)-6-methylpyrazin-2-yl)-8-azaspiro[4.5]decan-1-yl)carbamate (360 mg, 596 μmol, 58% yield) as a white solid.

Step 6. Synthesis of (R)-methyl 3-(1-((tert-butoxycarbonyl)amino)-8-azaspiro[4.5]decan-8-yl)-6-((2,3-dichloropyridin-4-yl)thio)-5-methylpyrazine-2-carboxylate To a solution of (R)-tert-butyl (8-(3-bromo-5-((2,3-dichloropyridin-4-yl)thio)-6-methylpyrazin-2-yl)-8-azaspiro[4.5]decan-1-yl)carbamate (360 mg, 596 μmol, 1 equiv) in MeOH (10 mL) was added Et$_3$N (165 μL, 1.2 mmol, 2 equiv) and Pd(dppf)Cl$_2$ (44 mg, 60 μmol, 0.1 equiv). The reaction mixture was then warmed to 50° C. and stirred for 16 hours under an atmosphere of CO (50 psi). After this time, the reaction mixture was filtered and concentrated under reduced pressure. The crude residue was then purified by silica gel chromatography to give (R)-methyl 3-(1-((tert-butoxycarbonyl)amino)-8-azaspiro[4.5]decan-8-yl)-6-((2,3-dichloropyridin-4-yl)thio)-5-methylpyrazine-2-carboxylate (200 mg, 343 μmol, 58% yield) as a white solid.

Step 7. Synthesis of (R)-methyl 3-(1-amino-8-azaspiro[4.5]decan-8-yl)-6-((2,3-dichloropyridin-4-yl)thio)-5-methylpyrazine-2-carboxylate A mixture of (R)-methyl 3-(1-((tert-butoxycarbonyl)amino)-8-azaspiro[4.5]decan-8-yl)-6-((2,3-dichloropyridin- 4-yl)thio)-5-methylpyrazine-2-carboxylate (100 mg, 171 µmol, 1 equiv) in HCl/EtOAc (4M, 1 mL) was stirred at 25° C. for 1 hour. After this time, the reaction was filtered and concentrated under reduced pressure. The mixture was then diluted with MeOH (3 mL) and adjusted to pH=7 with saturated aqueous NaHCO$_3$ solution. The aqueous solution was then extracted with ethyl acetate (3×3 mL), and the combined organic extracts were washed with brine, dried over Na$_2$SO$_4$, filtered, and concentrated to give (R)-methyl 3-(1-amino-8-azaspiro[4.5]decan-8-yl)-6-((2,3-dichloropyridin-4-yl)thio)-5-methylpyrazine-2-carboxylate (120 mg, 249 µmol, 72% yield) as a yellow solid that was used in the next step without further purification. LC-MS (ESI): m/z: [M+H] calculated for C$_{21}$H$_{25}$Cl$_2$N$_5$O$_2$S: 482.11; found 482.1.

Step 8. Synthesis of (R)-(3-(1-amino-8-azaspiro [4.5]decan-8-yl)-6-((2,3-dichloropyridin-4-yl)thio)-5-methylpyrazin-2-yl)methanol To a solution of (R)-methyl 3-(1-amino-8-azaspiro[4.5] decan-8-yl)-6-((2,3-dichloropyridin-4-yl)thio)-5-methyl-pyrazine-2-carboxylate (60 mg, 124 µmol, 1 equiv) in THF (1.0 mL) at 0° C. under an inert atmosphere was added LAH (14 mg, 373 µmol, 3 equiv). The reaction mixture was then warmed to 25° C. and stirred for 1 hour. After this time, the reaction was quenched by addition of MeOH (5 mL), filtered, and concentrated under reduced pressure. The crude residue was purified by prep-HPLC to give (R)-(3-(1-amino-8-azaspiro[4.5]decan-8-yl)-6-((2,3-dichloropyridin-4-yl) thio)-5-methylpyrazin-2-yl)methanol (13 mg, 28 µmol, 11% yield) as a white solid. $^1$H NMR (400 MHz, methanol-d$_4$) δ 8.67-8.42 (m, 1H), 7.99 (d, J=5.26 Hz, 1H), 6.65 (d, J=5.26 Hz, 1H), 4.63 (s, 2H), 4.00-3.87 (m, 2H), 3.23-3.14 (m, 2H), 2.49 (s, 3H), 2.21 (s, 1H), 1.97-1.51 (m, 9H). LC-MS (ESI): m/z: [M+H] calculated for C$_{20}$H$_{25}$Cl$_2$N$_5$OS: 454.12; found 454.1.

Example 44—Synthesis of (R)-(3-(1-amino-8-azaspiro[4.5]decan-8-yl)-6-((2,3-dichlorophenyl) thio)-5-methylpyrazin-2-yl)methanol

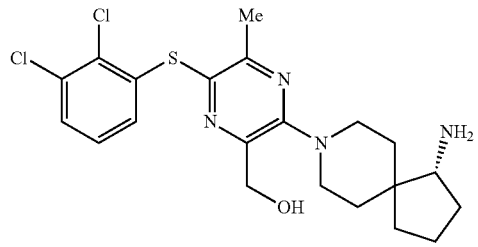 [SMILES: Cc1nc(N2CCC3(CCC[C@H]3N)CC2)c(CO)nc1Sc1cccc(Cl)c1Cl]

(R)-(3-(1-amino-8-azaspiro[4.5]decan-8-yl)-6-((2,3-dichlorophenyl)thio)-5-methylpyrazin-2-yl)methanol was synthesized in the manner similar to Example 43, except 2,3-dichloropyridine-4-thiol was substituted with 2,3-dichlorobenzenethiol. $^1$H NMR (400 MHz, methanol-d$_4$) δ 8.54 (s, 1H), 7.42 (dd, J=8.00, 1.40 Hz, 1H), 7.18 (t, J=8.06 Hz, 1H), 6.94 (dd, J=7.94, 1.46 Hz, 1H), 4.59 (s, 2H), 3.87-3.72 (m, 2H), 3.25 (t, J=6.84 Hz, 1H), 3.20-3.07 (m, 2H), 2.50 (s, 3H), 2.30-2.17 (m, 1H), 1.96-1.68 (m, 8H), 1.56 (br t, J=11.79 Hz, 2H). LC-MS (ESI): m/z: [M+H] calculated for C$_{21}$H$_{26}$Cl$_2$N$_4$OS: 453.12; found: 453.1.

Example 45—Synthesis of (3-(4-amino-4-methylpiperidin-1-yl)-6-((2,3-dichlorophenyl)thio)-5-methyl-pyrazin-2-yl)methanol

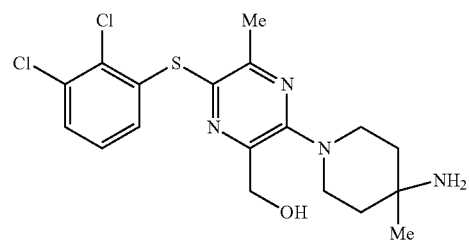 [SMILES: Cc1nc(N2CCC(C)(N)CC2)c(CO)nc1Sc1cccc(Cl)c1Cl]

(3-(4-amino-4-methylpiperidin-1-yl)-6-((2,3-dichloro-phenyl)thio)-5-methylpyrazin-2-yl)methanol was synthesized in the manner similar to Example 43, except 2,3-dichloropyridine-4-thiol and (R)-2-methyl-N—((R)-8-azaspiro[4.5]decan-1-yl)propane-2-sulfinamide were substituted with 2,3-dichlorobenzenethiol and tert-butyl (4-methylpiperidin-4-yl)carbamate, respectively. $^1$H NMR (400 MHz, methanol-d$_4$) δ 8.54 (s, 1H), 7.44 (dd, J=8.06, 1.34 Hz, 1H), 7.19 (t, J=8.00 Hz, 1H), 6.98 (dd, J=7.94, 1.34 Hz, 1H), 4.59 (s, 2H), 3.76 (dt, J=13.93, 4.15 Hz, 2H), 2.51 (s, 3H), 2.02-1.94 (m, 2H), 1.93-1.84 (m, 2H), 1.49 (s, 3H). LC-MS (ESI): m/z: [M+H] calculated for C$_{18}$H$_{22}$Cl$_2$N$_4$OS: 413.09; found: 413.1.

Example 46—Synthesis of (6-((2-amino-3-chloro-pyridin-4-yl)thio)-3-(4-amino-4-methylpiperidin-1-yl)-5-methylpyrazin-2-yl)methanol

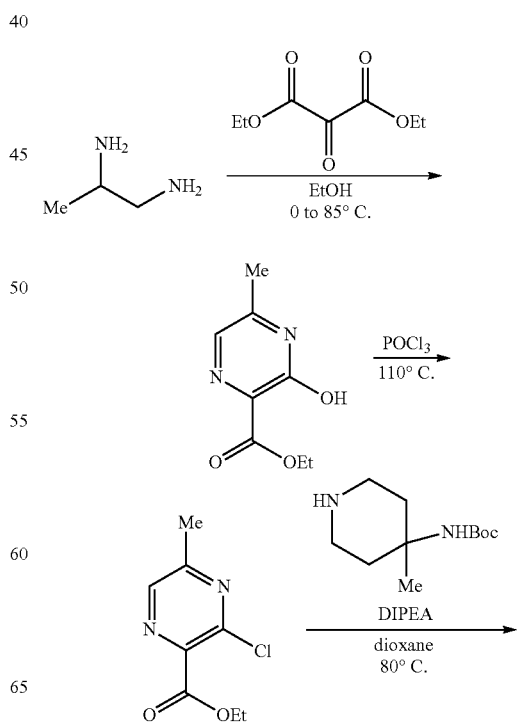

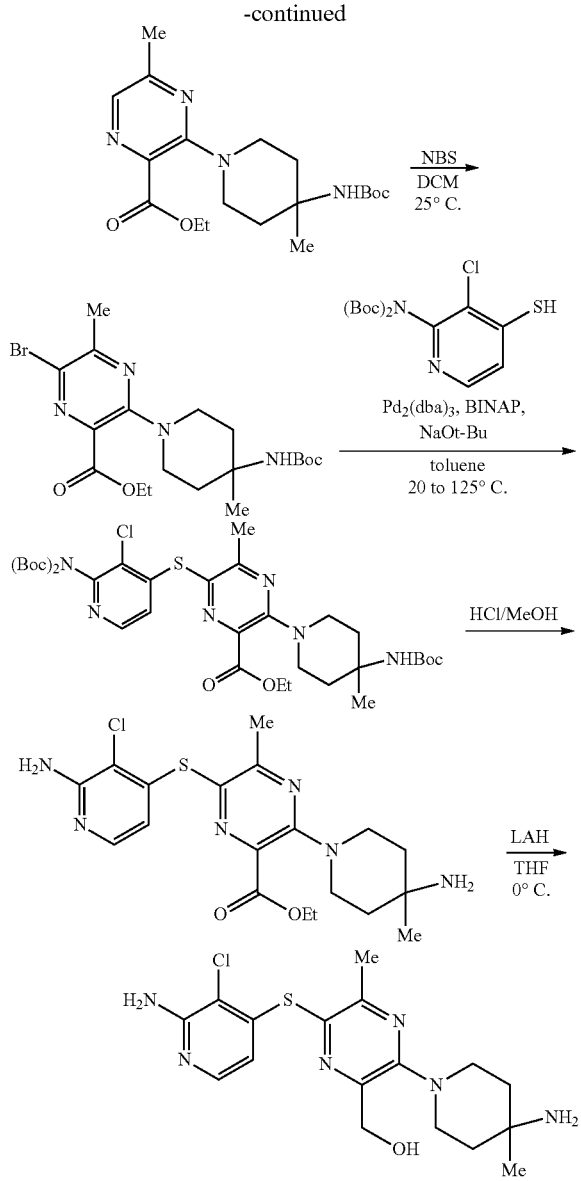

Step 1. Synthesis of ethyl 3-hydroxy-5-methylpyrazine-2-carboxylate

Diethyl 2-oxopropanedioate (221.2 mL, 1.4 mol, 1 equiv) was added to a suspension of propane-1,2-diamine (122.6 mL, 1.4 mol, 1 equiv) in EtOH (1 L) at 0° C. in a dropwise fashion, and the mixture was stirred at room temperature for 1.5 hours. The resulting milky white suspension was warmed to 85° C. and stirred for 20 hours. After this time, the reaction mixture was concentrated and purified by silica gel chromatography to give ethyl 3-hydroxy-5-methylpyrazine-2-carboxylate (47 g, 257.9 mmol, 17.9% yield) as a yellow solid.

Step 2. Synthesis of ethyl 3-chloro-5-methylpyrazine-2-carboxylate

A mixture of ethyl 3-hydroxy-5-methyl-pyrazine-2-carboxylate (5.00 g, 27.45 mmol, 1 equiv) in POCl$_3$ (50 mL) was warmed to 110° C. and stirred for 3 hours. After this time, the reaction mixture was concentrated under reduced pressure and quenched by addition of saturated aqueous NaHCO$_3$ (150 mL). The aqueous mixture was extracted with ethyl acetate (3×80 mL), and the combined organic extracts were concentrated under reduced pressure. The crude residue was purified by silica gel chromatography to give ethyl 3-chloro-5-methylpyrazine-2-carboxylate (1.10 g, 5.48 mmol, 19.96% yield) as a pale yellow oil. $^1$H NMR (400 MHz, cholorform-d) δ 8.33 (s, 1H), 4.47 (m, 2H), 2.59 (s, 3H), 1.41 (t, J=7.2 Hz, 3H).

Step 3. Synthesis of ethyl 3-(4-((tert-butoxycarbonyl)amino)-4-methylpiperidin-1-yl)-5-methylpyrazine-2-carboxylate To a solution of ethyl 3-chloro-5-methylpyrazine-2-carboxylate (3.00 g, 14 mmol, 1 equiv) in dioxane (30 mL) was added tert-butyl (4-methylpiperidin-4-yl)carbamate (4.81 g, 22.4 mmol, 1.5 equiv) and DIPEA (13 mL, 74.7 mmol, 5 equiv). The reaction mixture was then warmed to 80° C. and stirred for 16 hours. After this time, the reaction mixture was poured into water (150 mL), and the resulting aqueous mixture was extracted with ethyl acetate (3×50 mL). The combined organic extracts were washed with brine (100 mL), dried over anhydrous Na$_2$SO$_4$, filtered, and concentrated under reduced pressure. The crude residue was purified by silica gel chromatography to afford ethyl 3-(4-((tert-butoxy carbonyl)amino)-4-methylpiperidin-1-yl)-5-methylpyrazine-2-carboxylate (4.50 g, 11.8 mmol, 79% yield) as a yellow solid.

Step 4. Synthesis of ethyl 6-bromo-3-(4-((tert-butoxycarbonyl)amino)-4-methylpiperidin-1-yl)-5-methylpyrazine-2-carboxylate To four parallel batches of ethyl 3-(4-((tert-butoxycarbonyl)amino)-4-methylpiperidin-1-yl)-5-methylpyrazine-2-carboxylate (4×1.05 g, 4×2.77 mmol, 1 equiv) in DCM (4×10 mL) was added NBS (4×739 mg, 4×4.16 mmol, 1.5 equiv), and the resulting reaction mixtures were stirred at 25° C. for 1 hour. The four batches were combined, and the resulting mixture was quenched by addition of saturated aqueous Na$_2$SO$_3$ (50 mL) at 25° C. The aqueous phase was then extracted with DCM (3×50 mL). The combined organic extracts were washed with brine (100 mL), dried over anhydrous Na$_2$SO$_4$, filtered, and concentrated under reduced pressure to give 6-bromo-3-(4-((tert-butoxycarbonyl)amino)-4-methylpiperidin-1-yl)-5-methylpyrazine-2-carboxylate (3.80 g, 8.31 mmol, 75% yield) which was used in the next step without further purification.

Step 5. Synthesis of ethyl 6-((2-(bis(tert-butoxycarbonyl)amino)-3-chloropyridin-4-yl)thio)-3-(4-((tert-butoxycarbonyl)amino)-4-methylpiperidin-1-yl)-5-methylpyrazine-2-carboxylate Ethyl 6-((2-(bis(tert-butoxycarbonyl)amino)-3-chloropyridin-4-yl)thio)-3-(4-((tert-butoxy carbonyl)amino)-4-methylpiperidin-1-yl)-5-methylpyrazine-2-carboxylate was synthesized in a manner similar to 3-chloro-4-((5-chloro-3-methylpyrazin-2-yl)thio)pyridin-2-amine. $^1$H NMR (400 MHz, CDCl$_3$) δ 8.04-8.02 (m, 1H) 6.51-6.50 (m, 1H) 4.38-4.34 (m, 2H) 3.70-3.65 (m, 2H) 3.38-3.32 (m, 2H) 2.36 (s, 3H) 2.10-2.04 (m, 2H) 1.65-1.59 (m, 2H) 1.37-1.33 (m, 34H)

Step 6. Synthesis of ethyl 6-((2-amino-3-chloropyridin-4-yl)thio)-3-(4-amino-4-methylpiperidin-1-yl)-5-methylpyrazine-2-carboxylate 6-((2-amino-3-chloropyridin-4-yl)thio)-3-(4-amino-4-methylpiperidin-1-yl)-5-methylpyrazine-2-carboxylate was synthesized in a manner similar to (R)-8-(5-((2,3-dichlorophenyl)thio)-6-methylpyrazin-2-yl)-8-azaspiro[4.5]decan-1-amine. LC-MS (ESI): m/z: [M+H] calked for $C_{19}H_{26}ClN_6O_2S$: 437.14; found 437.1.

Step 7. Synthesis of (6-((2-amino-3-chloropyridin-4-yl)thio)-3-(4-amino-4-methylpiperidin-1-yl)-5-methylpyrazin-2-yl)methanol To a mixture of ethyl 6-((2-amino-3-chloropyridin-4-yl)thio)-3-(4-amino-4-methylpiperidin-1-yl)-5-methylpyrazine-2-carboxylate (1.70 g, 3.89 mmol, 1 equi) in THF (20 mL) at 0° C. under inert atmosphere was added LAH (369 mg, 9.73 mmol, 2.5 equiv) in a portionwise manner. The mixture was then warmed to 35° C. and stirred for 12 hours. After this time, the reaction was quenched by addition of water (1 mL) and stirred for 10 minutes. The aqueous phase was then extracted with ethyl acetate (3×50 mL), and the combined organic extracts were washed with brine (50 mL), dried over anhydrous $Na_2SO_4$, filtered, and concentrated under reduced pressure. The crude residue was purified by prep-HPLC to give (6-((2-amino-3-chloropyridin-4-yl)thio)-3-(4-amino-4-methylpiperidin-1-yl)-5-methylpyrazin-2-yl)methanol (200 mg, 506 μmol, 13% yield). $^1H$ NMR (400 MHz, methanol-$d_4$) δ 8.51 (s, 1H), 7.58-7.57 (m, 1H), 5.89-5.87 (m, 1H), 4.62 (s, 2H), 3.86-3.83 (m, 2H), 3.39-3.29 (m, 2H), 2.48 (s, 3H), 1.95-1.86 (m, 4H), 1.48 (s, 3H). LC-MS (ESI): m/z: [M+H] calculated for $C_{17}H_{23}ClN_6OS$: 395.13; found 395.3.

Example 47—Synthesis of 1-(5-(2-chlorophenyl)-6-methylpyrazin-2-yl)-4-methylpiperidin-4-amine

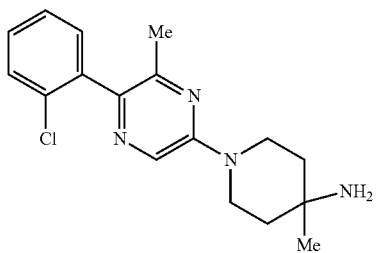 [SMILES: Cc1nc(N2CCC(C)(N)CC2)cnc1-c1ccccc1Cl]

1-(5-(2-chlorophenyl)-6-methylpyrazin-2-yl)-4-methylpiperidin-4-amine was synthesized in the manner similar to Example 23, except (2,3-dichlorophenyl)boronic acid was substituted with (2-chlorophenyl)boronic acid. 1-(5-(2-chlorophenyl)-6-methylpyrazin-2-yl)-4-methylpiperidin-4-amine was isolated as its formate salt after HPLC purification. $^1H$ NMR (500 MHz, DMSO-$d_6$) δ 8.32 (s, 1H, HCOOH), 8.22 (d, J=0.8 Hz, 1H), 7.58-7.55 (m, 1H), 7.46-7.42 (m, 2H), 7.39-7.35 (m, 1H), 3.99 (dt, J=13.8, 5.2 Hz, 2H), 3.44 (ddd, J=13.2, 8.6, 4.1 Hz, 2H), 2.15 (s, 3H), 1.72 (dt, J=11.0, 5.1 Hz, 4H), 1.34 (s, 3H). LC-MS (ESI): m/z: [M+H] calculated for $C_{17}H_{21}ClN_4$: 317.15; found 317.53.

Example 48—Synthesis of 1-(5-(2-fluorophenyl)-6-methylpyrazin-2-yl)-4-methylpiperidin-4-amine

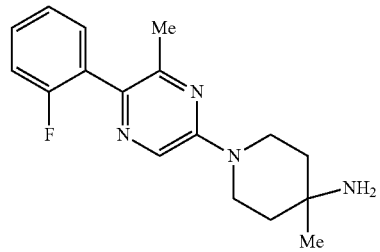 [SMILES: Cc1nc(N2CCC(C)(N)CC2)cnc1-c1ccccc1F]

1-(5-(2-fluorophenyl)-6-methylpyrazin-2-yl)-4-methylpiperidin-4-amine was synthesized in the manner similar to Example 24, except (2,3-dichlorophenyl)boronic acid was substituted with (2-fluorophenyl)boronic acid. 1-(5-(2-fluorophenyl)-6-methylpyrazin-2-yl)-4-methylpiperidin-4-amine was isolated as its formate salt after HPLC purification. $^1H$ NMR (500 MHz, DMSO-$d_6$) δ 8.32 (s, 1H, HCOOH), 8.22 (d, J=0.8 Hz, 1H), 7.58-7.55 (m, 1H), 7.46-7.42 (m, 2H), 7.39-7.35 (m, 1H), 3.99 (dt, J=13.8, 5.2 Hz, 2H), 3.44 (ddd, J=13.2, 8.6, 4.1 Hz, 2H), 2.15 (s, 3H), 1.72 (dt, J=11.0, 5.1 Hz, 4H), 1.34 (s, 3H). LC-MS (ESI): m/z: [M+H] calculated for $C_{17}H_{21}FN_4$: 301.18; found 301.47.

Example 49—Synthesis of 1-(5-(2,3-difluorophenyl)-6-methylpyrazin-2-yl)-4-methylpiperidin-4-amine

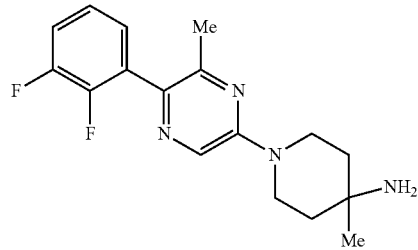 [SMILES: Cc1nc(N2CCC(C)(N)CC2)cnc1-c1cccc(F)c1F]

1-(5-(2,3-difluorophenyl)-6-methylpyrazin-2-yl)-4-methylpiperidin-4-amine 1-(5-(2,3-difluorophenyl)-6-methylpyrazin-2-yl)-4-methylpiperidin-4-amine was synthesized in the manner similar to Example 23, except (2,3-dichlorophenyl)boronic acid was substituted with (2,3-difluorophenyl)boronic acid. 1-(5-(2,3-difluorophenyl)-6-methylpyrazin-2-yl)-4-methylpiperidin-4-amine was isolated as its formate salt after HPLC purification. $^1H$ NMR (500 MHz, DMSO-$d_6$) δ 8.28 (s, 1H), 7.49 (dtd, J=10.0, 7.9, 1.8 Hz, 1H), 7.35-7.2 (m, 2H), 4.04-3.93 (m, 2H), 3.48 (dt, J=13.2, 6.3 Hz, 2H), 2.25 (d, J=1.7 Hz, 3H), 1.68 (t, J=5.8 Hz, 4H), 1.32 (s, 3H). LC-MS (ESI): m/z: [M+H] calculated for $C_{17}H_{20}F_2N_4$: 319.17; found 319.46.

Example 50—Synthesis of 1-(5-(4-chlorophenyl)-6-methylpyrazin-2-yl)-4-methylpiperidin-4-amine

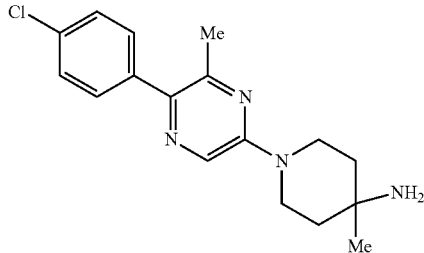 [SMILES: Cc1nc(N2CCC(C)(N)CC2)cnc1-c1ccc(Cl)cc1]

1-(5-(4-chlorophenyl)-6-methylpyrazin-2-yl)-4-methylpiperidin-4-amine was synthesized in the manner similar to Example 24, except (2,3-dichlorophenyl)boronic acid was substituted with (4-chlorophenyl)boronic acid. 1-(5-(4-chlorophenyl)-6-methylpyrazin-2-yl)-4-methylpiperidin-4-amine was isolated as its formate salt after HPLC purification. $^1$H NMR (500 MHz, DMSO-$d_6$) δ 8.24 (s, 1H, HCOOH), 7.58 (d, J=8.5 Hz, 2H), 7.49 (d, J=8.5 Hz, 2H), 3.86 (s, 2H), 3.58-3.48 (m, 3H), 2.42 (s, 3H), 1.61 (s, 4H), 1.25 (s, 3H). LC-MS (ESI): m/z: [M+H] calculated for $C_{17}H_{21}ClN_4$: 317.15; found 317.46.

Example 51—Synthesis of 1-(5-(5,6-dichloropyridin-3-yl)-6-methylpyrazin-2-yl)-4-methylpiperidin-4-amine

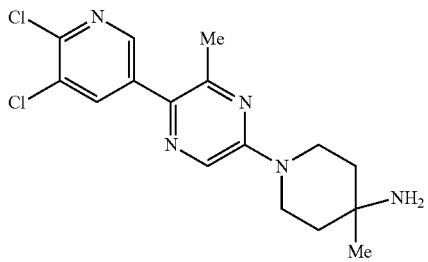 [SMILES: Cc1nc(N2CCC(C)(N)CC2)cnc1-c1cnc(Cl)c(Cl)c1]

1-(5-(5,6-dichloropyridin-3-yl)-6-methylpyrazin-2-yl)-4-methylpiperidin-4-amine was synthesized in the manner similar to Example 24, except (2,3-dichlorophenyl)boronic acid was substituted with (5,6-dichloropyridin-3-yl)boronic acid. 1-(5-(5,6-dichloropyridin-3-yl)-6-methylpyrazin-2-yl)-4-methylpiperidin-4-amine was isolated as its formate salt after HPLC purification. $^1$H NMR (500 MHz, DMSO-$d_6$) δ 8.59 (d, J=2.2 Hz, 1H), 8.30-8.28 (m, 2H), 3.93-3.83 (m, H), 3.58 (t, J=7.4 Hz, 2H), 2.46 (d, J=0.5 Hz, 3H), 1.62 (d, J 5.6 Hz, 4H), 1.26 (s, 3H). LC-MS (ESI): m/z: [M+H] calculated for $C_{16}H_{19}Cl_2N_5$: 352.10; found 352.39.

Example 52—Synthesis of 1-(5-(1-(4-chlorophenyl)vinyl)-6-methylpyrazin-2-yl)-4-methylpiperidin-4-amine

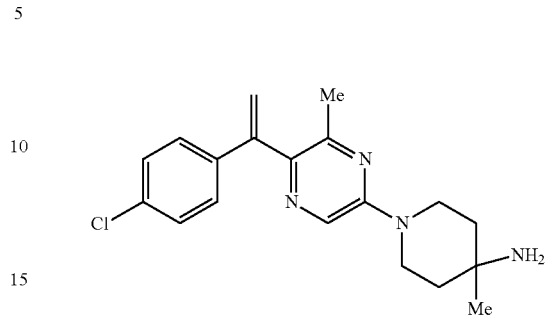

1-(5-(1-(4-chlorophenyl)vinyl)-6-methylpyrazin-2-yl)-4-methylpiperidin-4-amine was synthesized in the manner similar to Example 24, except (2,3-dichlorophenyl)boronic acid was substituted with (1-(4-chlorophenyl)vinyl)boronic acid. 1-(5-(1-(4-chlorophenyl)vinyl)-6-methylpyrazin-2-yl)-4-methylpiperidin-4-amine was isolated as its formate salt after HPLC purification. $^1$H NMR (500 MHz, DMSO-$d_6$) δ 8.42 (s, 1H), 8.13 (s, 1H), 7.41-7.37 (m, 2H), 7.28-7.24 (m, 2H), 5.88 (d, J=1.0 Hz, 1H), 5.34 (d, J=1.0 Hz, 1H), 3.69 (dt, J=12.3, 5.9 Hz, 2H), 3.60 (dt, J=12.7, 5.5 Hz, 2H), 2.16 (s, 3H), 1.54 (t, J 5.8 Hz, 4H), 1.18 (s, 3H). LC-MS (ESI): m/z: [M+H] calculated for $C_{19}H_{23}ClN_4$: 343.16; found 343.51.

Example 53—Synthesis of 8-(5-((2,3-dichlorophenyl)thio)-6-methylpyrazin-2-yl)-8-azabicyclo[3.2.1]octan-3-amine

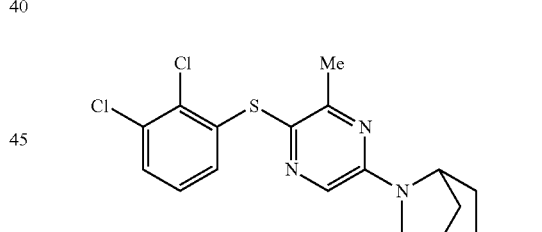

8-(5-((2,3-dichlorophenyl)thio)-6-methylpyrazin-2-yl)-8-azabicyclo[3.2.1]octan-3-amine was synthesized in the manner similar to Example 1, except 2-methyl-N—((R)-8-azaspiro[4.5]decan-1-yl)propane-2-sulfinamide was substituted with tert-butyl(8-azabicyclo[3.2.1] octan-3-yl) carbamate. 8-(5-((2,3-dichlorophenyl)thio)-6-methyl-pyrazin-2-yl)-8-azabicyclo[3.2.1]octan-3-amine was isolated as its formate salt after HPLC purification. $^1$H NMR (500 MHz, DMSO-$d_6$) δ 8.37 (s, 1H), 8.14 (d, J=0.7 Hz, 1H), 7.47 (dd, J=8.0, 1.4 Hz, 1H), 7.25 (t, J=8.0 Hz, 1H), 6.79 (dd, J=8.0, 1.4 Hz, 1H), 4.64 (s, 2H), 3.41 (tt, J=11.2, 5.6 Hz, 1H), 2.40 (d, J=0.5 Hz, 3H), 1.98 (dd, J=8.2, 4.2 Hz, 2H), 1.80 (d, J=7.3 Hz, 4H), 1.58-1.50 (m, 2H). LC-MS (ESI): m/z: [M+H] calculated for $C_{18}H_{20}Cl_2N_4S$: 395.08; found 395.4.

Example 54—Synthesis of 2-(5-((2,3-dichlorophenyl)thio)-6-methylpyrazin-2-yl)-2-azaspiro[3.3]heptan-6-amine

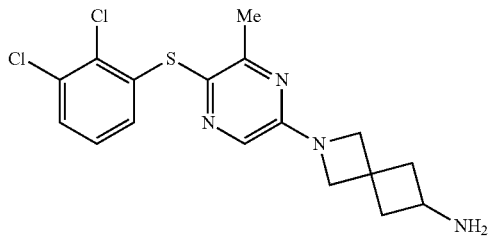 [SMILES: Cc1nc(N2CC3(CC(N)C3)C2)cnc1Sc1cccc(Cl)c1Cl]

2-(5-((2,3-dichlorophenyl)thio)-6-methylpyrazin-2-yl)-2-azaspiro[3.3]heptan-6-amine was synthesized in the manner similar to Example 1, except 2-methyl-N—((R)-8-azaspiro[4.5]decan-1-yl)propane-2-sulfinamide was substituted with tert-butyl (2-azaspiro[3.3]heptan-6-yl)carbamate. 2-(5-((2,3-dichlorophenyl)thio)-6-methylpyrazin-2-yl)-2-azaspiro[3.3]heptan-6-amine was isolated as its formate salt after HPLC purification. $^1$H NMR (500 MHz, DMSO-$d_6$) δ 8.39 (s, 1H, HCOOH), 7.92 (d, J=0.7 Hz, 1H), 7.56 (t, J=5.8 Hz, 1H), 7.43 (dt, J=8.0, 1.1 Hz, 1H), 7.22 (t, J=8.0 Hz, 1H), 6.67 (dd, J=8.1, 1.4 Hz, 1H), 3.78 (s, 2H), 3.53 (d, J=5.8 Hz, 2H), 3.52-3.43 (m, 1H), 2.37 (d, J=1.7 Hz, 3H), 2.26-2.19 (m, 2H), 1.84-1.75 (m, 2H). LC-MS (ESI): m/z: [M+H] calculated for $C_{17}H_{18}Cl_2N_4S$: 381.06; found 381.41.

Example 55—Synthesis of 1-(5-((2,3-dichlorophenyl)thio)-6-methylpyrazin-2-yl)azepan-4-amine

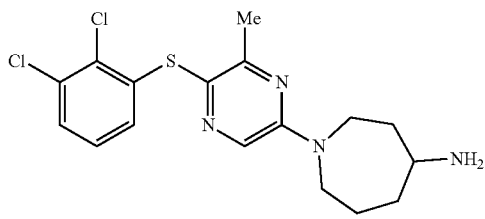 [SMILES: Cc1nc(N2CCCC(N)CC2)cnc1Sc1cccc(Cl)c1Cl]

1-(5-((2,3-dichlorophenyl)thio)-6-methylpyrazin-2-yl)azepan-4-amine was synthesized in the manner similar to Example 1, except 2-methyl-N—((R)-8-azaspiro[4.5]decan-1-yl)propane-2-sulfinamide was substituted with tert-butyl azepan-4-ylcarbamate. 1-(5-((2,3-dichlorophenyl)thio)-6-methylpyrazin-2-yl)azepan-4-amine was isolated as its formate salt after HPLC purification. $^1$H NMR (500 MHz, DMSO-$d_6$) δ 8.40 (s, 1H), 8.09 (d, J=0.7 Hz, 1H), 7.45 (dd, J=8.0, 1.4 Hz, 1H), 7.24 (t, J=8.0 Hz, 1H), 6.70 (dd, J=8.1, 1.4 Hz, 1H), 3.91-3.83 (m, 1H), 3.66 (q, J=4.9 Hz, 2H), 3.52 (ddd, J=14.6, 9.7, 3.3 Hz, 1H), 3.07 (td, J=9.8, 8.5, 5.1 Hz, 1H), 2.39 (d, J=0.5 Hz, 3H), 2.13-2.04 (m, 1H), 2.00-1.81 (m, 2H), 1.77-1.58 (m, 1H), 1.49-1.39 (m, 1H) LC-MS (ESI): m/z: [M+H] calculated for $C_{17}H_{20}Cl_2N_4S$: 383.08; found 383.33.

Example 56—Synthesis of N-(5-((2,3-dichlorophenyl)thio)-6-methylpyrazin-2-yl)-2-azaspiro[3.4]octan-6-amine

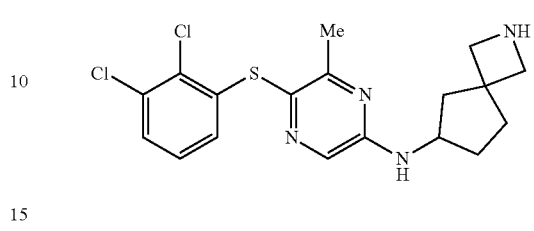

N-(5-((2,3-dichlorophenyl)thio)-6-methylpyrazin-2-yl)-2-azaspiro[3.4]octan-6-amine was synthesized in the manner similar to Example 1, except 2-methyl-N—((R)-8-azaspiro[4.5]decan-1-yl)propane-2-sulfinamide was substituted with tert-butyl 6-amino-2-azaspiro[3.4]octane-2-carboxylate. N-(5-((2,3-dichlorophenyl)thio)-6-methylpyrazin-2-yl)-2-azaspiro[3.4]octan-6-amine was isolated as its formate salt after HPLC purification. $^1$H NMR (500 MHz, DMSO-$d_6$) δ 8.44 (s, 1H), 7.82 (d, J=0.7 Hz, 1H), 7.59 (d, J=6.7 Hz, 1H), 7.43 (dd, J=8.0, 1.4 Hz, 1H), 7.23 (t, J=8.1 Hz, 1H), 6.66 (dd, J=8.1, 1.4 Hz, 1H), 4.14 (q, J 6.8 Hz, 1H), 3.80-3.64 (m, 4H), 2.36 (d, J=0.6 Hz, 3H), 2.30 (dd, J=13.4, 7.4 Hz, 1H), 2.06-1.97 (m, 2H), 1.92-1.72 (m, 2H), 1.55-1.46 (m, 1H). LC-MS (ESI): m/z: [M+H] calculated for $C_{18}H_{20}Cl_2N_4S$: 395.08; found 395.4.

Example 57—Synthesis of 1-(5-((2,3-dichlorophenyl)thio)-6-methylpyrazin-2-yl)-1,4-diazepane

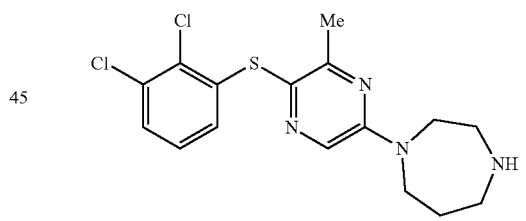

1-(5-((2,3-dichlorophenyl)thio)-6-methylpyrazin-2-yl)-1,4-diazepane was synthesized in the manner similar to Example 1, except 2-methyl-N—((R)-8-azaspiro[4.5]decan-1-yl)propane-2-sulfinamide was substituted with tert-butyl 1,4-diazepane-1-carboxylate. 1-(5-((2,3-dichlorophenyl)thio)-6-methylpyrazin-2-yl)-1,4-diazepane was isolated as its formate salt after HPLC purification. $^1$H NMR (500 MHz, DMSO-$d_6$) δ 8.32 (s, 1H), 8.09 (s, 1H), 7.45 (dd, J=8.0, 1.4 Hz, 1H), 7.2 (td, J=8.0, 1.3 Hz, 1H), 6.70 (dd, J=8.0, 1.4 Hz, 1H), 3.75 (dt, J=12.2, 5.5 Hz, 4H), 2.99 (d, J=6.5 Hz, 2H), 2.82 (d, J=5.8 Hz, 2H), 2.38 (d, J=1.2 Hz, 3H), 1.85 (d, J=7.9 Hz, 2H). LC-MS (ESI): m/z: [M+H] calculated for $C_{16}H_{18}Cl_2N_4S$: 369.06; found 369.34.

Example 58—Synthesis of 7-(5-((2,3-dichlorophenyl)thio)-6-methylpyrazin-2-yl)-7-azaspiro[3.5]nonan-2-amine

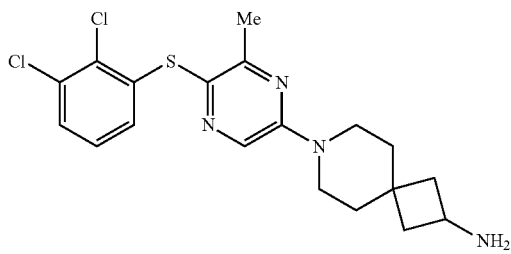 [SMILES: Cc1nc(N2CCC3(CC2)CC(N)C3)cnc1Sc1cccc(Cl)c1Cl]

7-(5-((2,3-dichlorophenyl)thio)-6-methylpyrazin-2-yl)-7-azaspiro[3.5]nonan-2-amine was synthesized in the manner similar to Example 1, except 2-methyl-N—((R)-8-azaspiro[4.5]decan-1-yl)propane-2-sulfinamide was substituted with tert-butyl (7-azaspiro[3.5]nonan-2-yl)carbamate. 7-(5-((2,3-dichlorophenyl)thio)-6-methylpyrazin-2-yl)-7-azaspiro[3.5]nonan-2-amine was isolated as its formate salt after HPLC purification. $^1$H NMR (500 MHz, DMSO-d$_6$) δ 8.40 (s, 1H), 8.23 (s, 1H), 7.46 (dd, J=8.0, 1.4 Hz, 1H), 7.23 (t, J=8.1 Hz, 1H), 6.72 (dd, J=8.0, 1.4 Hz, 1H), 3.66-3.49 (m, 5H), 2.37 (s, 3H), 2.21-2.11 (m, 2H), 1.75 (dd, J=11.5, 8.7 Hz, 2H), 1.59 (dt, J=14.2, 5.6 Hz, 4H) LC-MS (ESI): m/z: [M+H] calculated for C$_{19}$H$_{22}$C$_{12}$N$_4$S: 409.09; found 409.46.

Example 59—Synthesis of N-(2-(azetidin-3-yl)ethyl)-5-((2,3-dichlorophenyl)thio)-6-methylpyrazin-2-amine

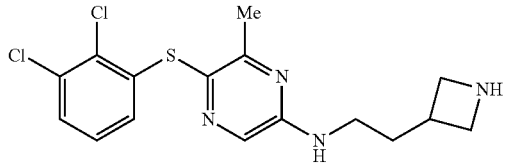 [SMILES: Cc1nc(NCCC2CNC2)cnc1Sc1cccc(Cl)c1Cl]

N-(2-(azetidin-3-yl)ethyl)-5-((2,3-dichlorophenyl)thio)-6-methylpyrazin-2-amine was synthesized in the manner similar to Example 1, except 2-methyl-N—((R)-8-azaspiro[4.5]decan-1-yl)propane-2-sulfinamide was substituted with tert-butyl 3-(2-amino ethyl)azetidine-1-carboxylate. N-(2-(azetidin-3-yl)ethyl)-5-((2,3-dichlorophenyl)thio)-6-methylpyrazin-2-amine was isolated as its formate salt after HPLC purification. $^1$H NMR (500 MHz, DMSO-d$_6$) δ 8.42 (s, 1H), 7.84 (d, J=0.8 Hz, 1H), 7.56 (t, J=5.7 Hz, 1H), 7.43 (dd, J=8.0, 1.4 Hz, 1H), 7.22 (t, J=8.0 Hz, 1H), 6.65 (dd, J=8.1, 1.4 Hz, 1H), 3.90-3.82 (m, 2H), 3.61-3.53 (m, 2H), 3.25 (q, J=6.5 Hz, 2H), 2.80 (p, J=7.7 Hz, 1H), 2.36 (d, J=0.6 Hz, 3H), 1.85 (q, J=7.1 Hz, 2H). LC-MS (ESI): m/z: [M+H] calculated for C$_{16}$H$_{18}$C$_{12}$N$_4$S: 369.06; found 369.34.

Example 60—Synthesis of N-((2-azaspiro[3.3]heptan-6-yl)methyl)-5-((2,3-dichlorophenyl)thio)-6-methylpyrazin-2-amine

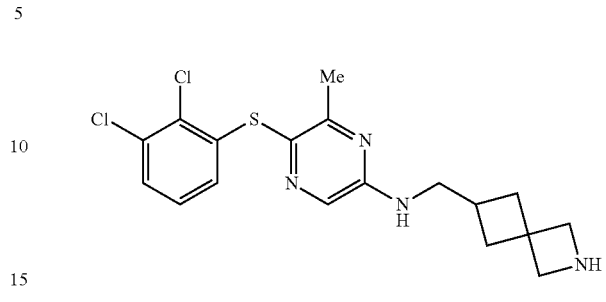

N-((2-azaspiro[3.3]heptan-6-yl)methyl)-5-((2,3-dichlorophenyl)thio)-6-methylpyrazin-2-amine was synthesized in the manner similar to Example 1, except 2-methyl-N—((R)-8-azaspiro[4.5]decan-1-yl)propane-2-sulfinamide was substituted with tert-butyl 6-(aminomethyl)-2-azaspiro[3.3]heptane-2-carboxylate. N-((2-azaspiro[3.3]heptan-6-yl)methyl)-5-((2,3-dichlorophenyl)thio)-6-methylpyrazin-2-amine was isolated as its formate salt after HPLC purification. $^1$H NMR (500 MHz, DMSO-d$_6$) δ 10.71 (s, 1H), 10.13 (d, J 0.7 Hz, 1H), 9.83 (t, J=5.6 Hz, 1H), 9.72 (dd, J=8.0, 1.4 Hz, 1H), 9.51 (t, J=8.0 Hz, 1H), 8.93 (dd, J=8.1, 1.4 Hz, 1H), 6.05 (d, J=29.9 Hz, 4H), 5.59-5.54 (m, 2H), 4.64 (d, J=0.6 Hz, 3H), 4.58-4.52 (m, 2H), 4.20 (dd, J=12.3, 7.2 Hz, 2H). LC-MS (ESI): m/z: [M+H] calculated for C$_{18}$H$_{20}$Cl$_2$N$_4$S: 395.08; found 395.4.

Example 61—Synthesis of 5-((2,3-dichlorophenyl)thio)-6-methyl-N-(pyrrolidin-3-ylmethyl)pyrazin-2-amine

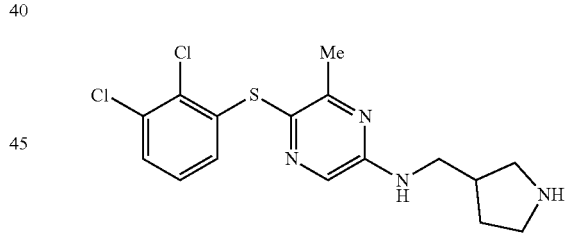

5-((2,3-dichlorophenyl)thio)-6-methyl-N-(pyrrolidin-3-ylmethyl)pyrazin-2-amine was synthesized in the manner similar to Example 1, except 2-methyl-N—((R)-8-azaspiro[4.5]decan-1-yl)propane-2-sulfinamide was substituted with tert-butyl 3-(aminomethyl)pyrrolidine-1-carboxylate. 5-((2,3-dichlorophenyl)thio)-6-methyl-N-(pyrrolidin-3-ylmethyl)pyrazin-2-amine was isolated as its formate salt after HPLC purification. $^1$H NMR (500 MHz, DMSO-d$_6$) δ 8.41 (s, 1H), 7.88 (d, J=0.7 Hz, 1H), 7.71 (t, J=5.6 Hz, 1H), 7.43 (dd, J=8.0, 1.4 Hz, 1H), 7.22 (t, J=8.0 Hz, 1H), 6.66 (dd, J=8.1, 1.4 Hz, 1H), 3.40-3.27 (m, 2H), 3.23-3.09 (m, 2H), 3.02 (q, J=9.3, 8.7 Hz, 1H), 2.81 (dd, J=11.3, 7.0 Hz, 1H), 2.36 (d, J=0.6 Hz, 3H), 1.99 (td, J=12.9, 7.4 Hz, 1H), 1.65-1.54 (m, 1H). LC-MS (ESI): m/z: [M+H] calculated for C$_{16}$H$_{18}$Cl$_2$N$_4$S: 369.06; found 369.34.

Example 62—Synthesis of $N^1$-(5-((2,3-dichlorophenyl)thio)-6-methylpyrazin-2-yl)butane-1,4-diamine

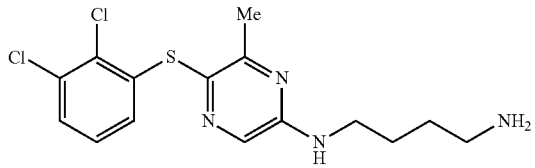 [SMILES: Cc1nc(NCCCCN)cnc1Sc1cccc(Cl)c1Cl]

$N^1$-(5-((2,3-dichlorophenyl)thio)-6-methylpyrazin-2-yl)butane-1,4-diamine was synthesized in the manner similar to Example 1, except 2-methyl-N—((R)-8-azaspiro[4.5]decan-1-yl)propane-2-sulfinamide was substituted with tert-butyl (4-aminobutyl)carbamate. $N^1$-(5-((2,3-dichlorophenyl)thio)-6-methylpyrazin-2-yl)butane-1,4-diamine was isolated as its formate salt after HPLC purification. $^1$H NMR (500 MHz, DMSO-$d_6$) δ 8.45 (s, 1H), 7.86 (d, J=0.8 Hz, 1H), 7.64 (t, J=5.5 Hz, 1H), 7.43 (dd, J=8.0, 1.4 Hz, 1H), 7.22 (t, J=8.1 Hz, 1H), 6.64 (dd, J=8.1, 1.4 Hz, 1H), 3.35-3.26 (m, 2H), 2.75 (t, J=6.7 Hz, 2H), 2.36 (d, J=0.6 Hz, 3H), 1.58 (p, J=4.1, 3.4 Hz, 4H). LC-MS (ESI): m/z: [M+H] calculated for $C_{15}H_{18}Cl_2N_4S$: 357.06; found 357.43.

Example 63—Synthesis of 5-((2,3-dichlorophenyl)thio)-6-methyl-N-(piperidin-4-ylmethyl)pyrazin-2-amine

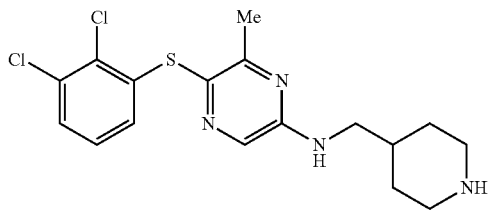 [SMILES: Cc1nc(NCC2CCNCC2)cnc1Sc1cccc(Cl)c1Cl]

5-((2,3-dichlorophenyl)thio)-6-methyl-N-(piperidin-4-ylmethyl)pyrazin-2-amine was synthesized in the manner similar to Example 1, except 2-methyl-N—((R)-8-azaspiro[4.5]decan-1-yl)propane-2-sulfinamide was substituted with tert-butyl 4-(aminomethyl)piperidine-1-carboxylate. 5-((2,3-dichlorophenyl)thio)-6-methyl-N-(piperidin-4-ylmethyl)pyrazin-2-amine was isolated as its formate salt after HPLC purification. $^1$H NMR (500 MHz, DMSO-$d_6$) δ 8.41 (s, 1H), 7.87 (d, J=0.7 Hz, 1H), 7.59 (t, J=5.7 Hz, 1H), 7.43 (dd, J=8.0, 1.4 Hz, 1H), 7.22 (t, J=8.0 Hz, 1H), 6.65 (dd, J=8.1, 1.4 Hz, 1H), 3.20 (t, J=6.0 Hz, 2H), 3.10 (d, J=12.4 Hz, 2H), 2.68-2.59 (m, 2H), 2.35 (d, J=0.6 Hz, 3H), 1.75 (d, J=12.9 Hz, 3H), 1.22 (q, J=12.7 Hz, 2H). LC-MS (ESI): m/z: [M+H] calculated for $C_{17}H_{20}Cl_2N_4S$: 383.08; found 383.41.

Example 64—Synthesis of $N^1$-(5-((2,3-dichlorophenyl)thio)-6-methylpyrazin-2-yl)propane-1,3-diamine

$N^1$-(5-((2,3-dichlorophenyl)thio)-6-methylpyrazin-2-yl)propane-1,3-diamine was synthesized in the manner similar to Example 1, except 2-methyl-N—((R)-8-azaspiro[4.5]decan-1-yl)propane-2-sulfinamide was substituted with tert-butyl (3-aminopropyl)carbamate. $N^1$-(5-((2,3-dichlorophenyl)thio)-6-methylpyrazin-2-yl)propane-1,3-diamine was isolated as its formate salt after HPLC purification. $^1$H NMR (500 MHz, DMSO-$d_6$) δ 8.42 (s, 1H), 7.86 (d, J=0.7 Hz, 1H), 7.70 (t, J=5.6 Hz, 1H), 7.44 (dd, J=8.0, 1.4 Hz, 1H), 7.22 (t, J=8.0 Hz, 1H), 6.65 (dd, J=8.1, 1.4 Hz, 1H), 3.36 (q, J=6.5 Hz, 2H), 2.81 (dd, J=8.2, 6.4 Hz, 2H), 2.37 (d, J=0.6 Hz, 3H), 1.80 (p, J=7.0 Hz, 2H). LC-MS (ESI): m/z: [M+H] calculated for $C_{14}H_{16}Cl_2N_4S$: 343.05; found 343.37.

Example 65—Synthesis of (1R,3R,5S)—N-(5-((2,3-dichlorophenyl)thio)-6-methylpyrazin-2-yl)-9-methyl-9-azabicyclo[3.3.1]nonan-3-amine

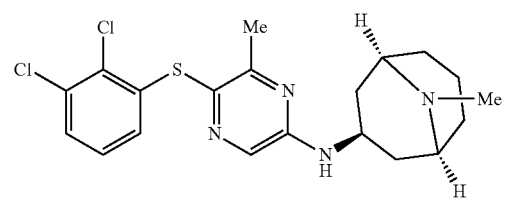 [SMILES: Cc1nc(N[C@H]2C[C@H]3CCC[C@@H](C2)N3C)cnc1Sc1cccc(Cl)c1Cl]

Synthesis of (1R,3R,5S)—N-(5-((2,3-dichlorophenyl)thio)-6-methylpyrazin-2-yl)-9-methyl-9-azabicyclo[3.3.1]nonan-3-amine was synthesized in the manner similar to Example 1, except 2-methyl-N—((R)-8-azaspiro[4.5]decan-1-yl)propane-2-sulfinamide was substituted with (1R,3R,5S)-9-methyl-9-azabicyclo[3.3.1]nonan-3-amine. Synthesis of (1R,3R,5S)—N-(5-((2,3-dichlorophenyl)thio)-6-methylpyrazin-2-yl)-9-methyl-9-azabicyclo[3.3.1]nonan-3-amine was isolated as its formate salt after HPLC purification. $^1$H NMR (500 MHz, DMSO-$d_6$) δ 8.21 (s, 1H), 7.79 (d, J=0.7 Hz, 1H), 7.42 (dd, J=8.0, 1.4 Hz, 1H), 7.32 (d, J=8.4 Hz, 1H), 7.22 (t, J=8.1 Hz, 1H), 6.65 (dd, J=8.1, 1.3 Hz, 1H), 3.00 (d, J=11.2 Hz, 2H), 2.41 (s, 3H), 2.36 (d, J=0.6 Hz, 3H), 2.34-2.26 (m, 2H), 2.01-1.85 (m, 3H), 1.46 (d, J 11.3 Hz, 1H), 1.35-1.26 (m, 2H), 0.93 (d, J=11.9 Hz, 2H). LC-MS (ESI): m/z: [M+H] calculated for $C_{20}H_{24}Cl_2N_4S$: 423.11; found 423.45.

Example 66—Synthesis of N-(5-((2,3-dichlorophenyl)thio)-6-methylpyrazin-2-yl)-3-azabicyclo[3.2.1]octan-8-amine

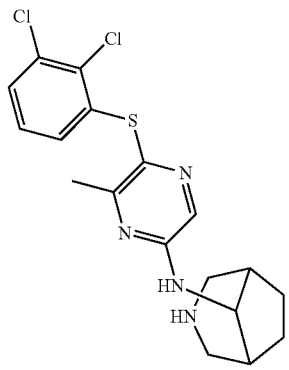 [SMILES: Cc1nc(NC2C3CCC2CNC3)cnc1Sc1cccc(Cl)c1Cl]

N-(5-((2,3-dichlorophenyl)thio)-6-methylpyrazin-2-yl)-3-azabicyclo[3.2.1]octan-8-amine was synthesized in the manner similar to Example 1, except 2-methyl-N—((R)-8-azaspiro[4.5]decan-1-yl)propane-2-sulfinamide was substituted with tert-butyl 8-amino-3-azabicyclo[3.2.1]octane-3-carboxylate. N-(5-((2,3-dichlorophenyl)thio)-6-methylpyrazin-2-yl)-3-azabicyclo[3.2.1]octan-8-amine was isolated as its formate salt after HPLC purification. $^1$H NMR (500 MHz, DMSO-$d_6$) δ 8.36 (s, 1H), 8.06 (s, 1H), 7.72 (d, J=6.0 Hz, 1H), 7.44 (dd, J=8.0, 1.4 Hz, 1H), 7.24 (d, J=8.0 Hz, 1H), 6.68 (dd, J=8.1, 1.4 Hz, 1H), 3.92-3.85 (m, 1H), 3.13 (d, J=12.7 Hz, 2H), 2.56 (d, J=14.3 Hz, 2H), 2.36 (s, 3H), 2.18 (s, 2H), 1.85-1.71 (m, 4H). LC-MS (ESI): m/z: [M+H] calculated for $C_{18}H_{20}Cl_2N_4S$: 395.08; found 395.4.

Example 67—Synthesis of (1R,5S,6S)-3-(5-((2,3-dichlorophenyl)thio)-6-methylpyrazin-2-yl)-3-azabicyclo[3.1.0]hexan-6-amine

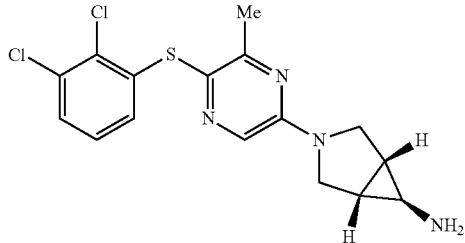 [SMILES: Cc1nc(N2C[C@@H]3[C@@H](N)[C@@H]3C2)cnc1Sc1cccc(Cl)c1Cl]

(1R,5S,6S)-3-(5-((2,3-dichlorophenyl)thio)-6-methylpyrazin-2-yl)-3-azabicyclo[3.1.0]hexan-6-amine was synthesized in the manner similar to Example 1, except 2-methyl-N—((R)-8-azaspiro[4.5]decan-1-yl)propane-2-sulfinamide was substituted with Exo-6-(boc-amino)-3-azabicyclo[3.1.0]hexane. (1R,5S,6S)-3-(5-((2,3-dichlorophenyl)thio)-6-methyl pyrazin-2-yl)-3-azabicyclo[3.1.0]hexan-6-amine was isolated as its formate salt after HPLC purification. $^1$H NMR (500 MHz, DMSO-$d_6$) δ 8.20 (s, 1H, HCOOH), 7.85 (d, J=0.7 Hz, 1H), 7.44 (dd, J=8.0, 1.4 Hz, 1H), 7.22 (t, J=8.0 Hz, 1H), 6.67 (dd, J=8.0, 1.4 Hz, 1H), 3.67 (d, J=10.9 Hz, 2H), 3.52-3.46 (m, 2H), 2.37 (d, J=0.5 Hz, 3H), 2.06 (t, J=2.2 Hz, 1H), 1.73-1.66 (m, 2H). LC-MS (ESI): m/z: [M+H] calculated for $C_{16}H_{16}Cl_2N_4S$: 367.05; found 367.35.

Example 68—Synthesis of (3R,4S)-4-(((5-((2,3-dichlorophenyl)thio)-6-methylpyrazin-2-yl)amino)methyl)piperidin-3-ol

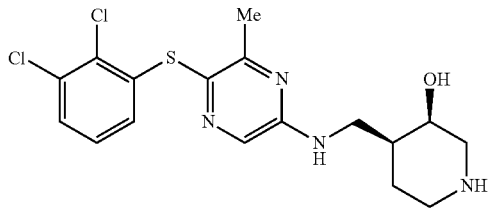 [SMILES: Cc1nc(NC[C@@H]2CCNC[C@@H]2O)cnc1Sc1cccc(Cl)c1Cl]

(3R,4S)-4-(((5-((2,3-dichlorophenyl)thio)-6-methylpyrazin-2-yl)amino)methyl) piperidin-3-ol was synthesized in the manner similar to Example 1, except 2-methyl-N—((R)-8-azaspiro[4.5]decan-1-yl)propane-2-sulfinamide was substituted with tert-butyl (3R,4S)-4-(aminomethyl)-3-hydroxypiperidine-1-carboxylate. (3R,4S)-4-(((5-((2,3-dichlorophenyl)thio)-6-methylpyrazin-2-yl)amino)methyl) piperidin-3-ol was isolated as its formate salt after HPLC purification. $^1$H NMR (500 MHz, DMSO-$d_6$) δ 8.37 (s, 1H), 7.89 (d, J=0.7 Hz, 1H), 7.66 (d, J=6.1 Hz, 1H), 7.43 (dd, J=8.0, 1.4 Hz, 1H), 7.22 (t, J=8.0 Hz, 1H), 6.66 (dd, J=8.1, 1.4 Hz, 1H), 3.84 (s, 1H), 3.34-3.19 (m, 2H), 3.11-2.99 (m, 2H), 2.84 (dd, J=12.9, 1.7 Hz, 1H), 2.71 (td, J=12.6, 3.5 Hz, 1H), 2.36 (d, J=0.6 Hz, 3H), 1.84 (dt, J=11.8, 4.4 Hz, 1H), 1.58 (dtd, J=37.2, 13.3, 3.8 Hz, 2H). LC-MS (ESI): m/z: [M+H] calculated for $C_{17}H_{20}Cl_2N_4OS$: 399.07; found 399.39.

Example 69—Synthesis of (1R,3R)—N$^1$-(5-((2,3-dichlorophenyl)thio)-6-methylpyrazin-2-yl)cyclopentane-1,3-diamine

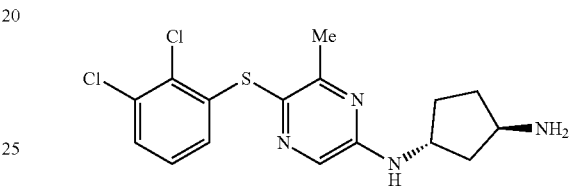

(1R,3R)—N$^1$-(5-((2,3-dichlorophenyl)thio)-6-methylpyrazin-2-yl)cyclopentane-1,3-diamine was synthesized in the manner similar to Example 1, except 2-methyl-N—((R)-8-azaspiro[4.5]decan-1-yl)propane-2-sulfinamide was substituted with tert-butyl ((1S,3S)-3-aminocyclopentyl)carbamate. (1R,3R)—N$^1$-(5-((2,3-dichlorophenyl)thio)-6-methylpyrazin-2-yl)cyclopentane-1,3-diamine was isolated as its formate salt after HPLC purification. $^1$H NMR (500 MHz, DMSO-$d_6$) δ 8.44 (s, 1H), 7.83 (d, J=0.7 Hz, 1H), 7.65 (d, J=6.9 Hz, 1H), 7.43 (dd, J=8.0, 1.4 Hz, 1H), 7.22 (t, J=8.0 Hz, 1H), 6.66 (dd, J=8.1, 1.4 Hz, 1H), 4.35 (h, J=6.6 Hz, 1H), 3.59 (p, J=6.7 Hz, 1H), 2.36 (s, 3H), 2.20-2.11 (m, 1H), 2.11-2.02 (m, 1H), 1.99-1.91 (m, 1H), 1.85 (ddd, J=13.6, 7.7, 5.8 Hz, 1H), 1.53 (td, J=13.7, 7.0 Hz, 2H). LC-MS (ESI): m/z: [M+H] calculated for $C_{16}H_{18}Cl_2N_4S$: 369.06; found 369.34.

Example 70—Synthesis of N-(5-((2,3-dichlorophenyl)thio)-6-methylpyrazin-2-yl)-8-azabicyclo[3.2.1]octan-3-amine

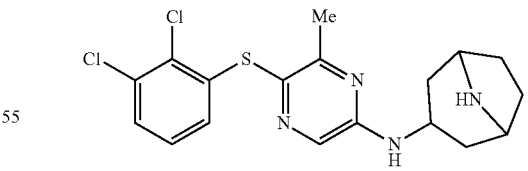

N-(5-((2,3-dichlorophenyl)thio)-6-methylpyrazin-2-yl)-8-azabicyclo[3.2.1]octan-3-amine was synthesized in the manner similar to Example 1, except 2-methyl-N—((R)-8-azaspiro[4.5]decan-1-yl)propane-2-sulfinamide was substituted with tert-Butyl 3-amino-8-azabicyclo[3.2.1]octane-8-carboxylate. N-(5-((2,3-dichlorophenyl)thio)-6-methylpyrazin-2-yl)-8-azabicyclo[3.2.1]octan-3-amine was isolated as its formate salt after HPLC purification. $^1$H NMR (500 MHz, DMSO-d6) δ 8.40 (s, 1H), 7.83 (s, 1H), 7.48 (d, J=7.3 Hz, 1H), 7.43 (ddd, J=8.0, 3.2, 1.3 Hz, 1H), 7.22 (td, J=8.0, 2.9 Hz, 1H), 6.66 (ddd, J=15.0, 8.1, 1.4 Hz, 1H), 4.14 (d, J=12.4 Hz, 1H), 3.75 (s, 2H), 2.36 (d, J=3.6 Hz, 3H), 2.18 (t, J=10.7 Hz, 2H), 2.01-1.76 (m, 6H), 1.60 (t, J=12.2 Hz, 1H). LC-MS (ESI): m/z: [M+H] calculated for $C_{18}H_{20}Cl_2N_4S$: 39508; found 395.4.

Example 71—Synthesis of $N^1$-(5-((2,3-dichlorophenyl)thio)-6-methylpyrazin-2-yl)ethane-1,2-diamine

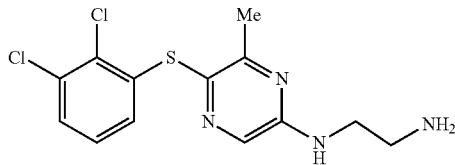 [SMILES: Cc1nc(NCCN)cnc1Sc1cccc(Cl)c1Cl]

$N^1$-(5-((2,3-dichlorophenyl)thio)-6-methylpyrazin-2-yl)ethane-1,2-diamine was synthesized in the manner similar to Example 1, except 2-methyl-N—((R)-8-azaspiro[4.5]decan-1-yl)propane-2-sulfinamide was substituted with tert-butyl (2-aminoethyl)carbamate. $N^1$-(5-((2,3-dichlorophenyl)thio)-6-methylpyrazin-2-yl)ethane-1,2-diamine was isolated as its formate salt after HPLC purification. $^1$H NMR (500 MHz, DMSO-$d_6$) δ 8.37 (s, 1H), 7.87 (d, J=0.7 Hz, 1H), 7.85 (d, J=6.1 Hz, 1H), 7.44 (dd, J=8.0, 1.4 Hz, 1H), 7.22 (t, J=8.1 Hz, 1H), 6.67 (dd, J=8.1, 1.4 Hz, 1H), 3.46 (q, J=6.0 Hz, 2H), 2.91 (t, J=6.2 Hz, 2H), 2.37 (d, J=0.6 Hz, 3H). LC-MS (ESI): m/z: [M+H] calculated for $C_{13}H_{14}Cl_2N_4S$: 329.03; found 329.3.

Example 72—Synthesis of 5-((2,3-dichlorophenyl)thio)-6-methyl-N-(piperazin-2-ylmethyl)pyrazin-2-amine

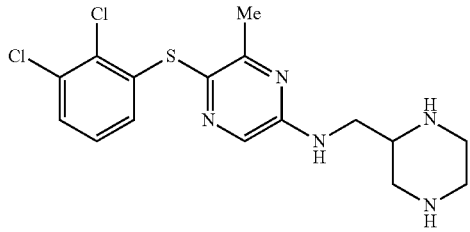 [SMILES: Cc1nc(NCC2CNCCN2)cnc1Sc1cccc(Cl)c1Cl]

5-((2,3-dichlorophenyl)thio)-6-methyl-N-(piperazin-2-ylmethyl)pyrazin-2-amine was synthesized in the manner similar to Example 1, except 2-methyl-N—((R)-8-azaspiro[4.5]decan-1-yl)propane-2-sulfinamide was substituted with di-tert-butyl 2-(aminomethyl)piperazine-1,4-dicarboxylate. 5-((2,3-dichlorophenyl)thio)-6-methyl-N-(piperazin-2-ylmethyl)pyrazin-2-amine was isolated as its formate salt after HPLC purification. $^1$H NMR (500 MHz, DMSO-$d_6$) δ 8.34 (s, 1H), 7.89 (s, 1H), 7.67 (s, 1H), 7.44 (dd, J=8.0, 1.4 Hz, 1H), 7.22 (t, J=8.0 Hz, 1H), 6.67 (dd, J=8.1, 1.4 Hz, 1H), 3.32 (td, J=6.1, 2.0 Hz, 2H), 3.11-2.90 (m, 4H), 2.80-2.65 (m, 2H), 2.37 (s, 3H). LC-MS (ESI): m/z: [M+H] calculated for $C_{16}H_{19}Cl_2N_5S$: 384.07; found 384.37.

Example 73—Synthesis of (R)-8-(5-(2,3-dichloropyridin-4-yl)-6-methylpyrazin-2-yl)-8-azaspiro[4.5]decan-1-amine

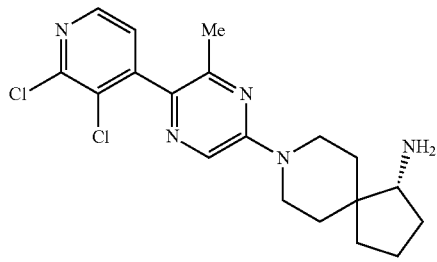 [SMILES: Cc1nc(N2CCC3(CCC[C@H]3N)CC2)cnc1-c1ccnc(Cl)c1Cl]

(R)-8-(5-(2,3-dichloropyridin-4-yl)-6-methylpyrazin-2-yl)-8-azaspiro[4.5]decan-1-amine was synthesized in the manner similar to Example 23, except (2,3-dichlorophenyl)boronic acid was substituted with (2,3-dichloropyridin-4-yl)boronic acid. (R)-8-(5-(2,3-dichloropyridin-4-yl)-6-methylpyrazin-2-yl)-8-azaspiro[4.5]decan-1-amine was isolated as its formate salt after HPLC purification. $^1$H NMR (500 MHz, DMSO-$d_6$) δ 8.45 (d, J=4.9 Hz, 1H), 8.38 (s, 1H), 8.24 (d, J=0.7 Hz, 1H), 7.52 (d, J=4.9 Hz, 1H), 4.30-4.16 (m, 2H), 3.18-3.05 (m, 2H), 2.89 (t, J=7.2 Hz, 1H), 2.17 (d, J=0.6 Hz, 3H), 1.93 (dt, J=12.9, 6.6 Hz, 1H), 1.85-1.77 (m, 1H), 1.73-1.41 (m, 5H), 1.40-1.25 (m, 2H), 1.10 (s, 2H). LC-MS (ESI): m/z: [M+H] calculated for $C_{19}H_{23}Cl_2N_5$: 392.13; found 392.44.

Example 74—Synthesis of 1-(5-(2,3-dichloropyridin-4-yl)-6-methylpyrazin-2-yl)-4-methylpiperidin-4-amine

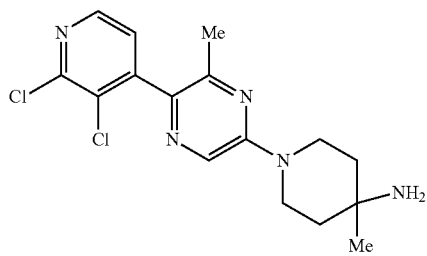 [SMILES: Cc1nc(N2CCC(C)(N)CC2)cnc1-c1ccnc(Cl)c1Cl]

1-(5-(2,3-dichloropyridin-4-yl)-6-methylpyrazin-2-yl)-4-methylpiperidin-4-amine was synthesized in the manner similar to Example 24, except except (2,3-dichlorophenyl)boronic acid was substituted with (2,3-dichloropyridin-4-yl)boronic acid. 1-(5-(2,3-dichloropyridin-4-yl)-6-methylpyrazin-2-yl)-4-methylpiperidin-4-amine was isolated as its formate salt after HPLC purification. $^1$H NMR (500 MHz, DMSO-$d_6$) δ 8.46 (d, J=4.9 Hz, 1H), 8.39 (s, 1H), 8.26 (d, J=0.8 Hz, 1H), 7.52 (d, J=4.9 Hz, 1H), 3.95 (ddd, J=13.7, 6.2, 4.3 Hz, 2H), 3.52 (ddd, J=13.0, 8.2, 4.2 Hz, 2H), 2.18 (d, J=0.5 Hz, 3H), 1.69 (qt, J=12.9, 6.4 Hz, 4H), 1.31 (s, 3H). LC-MS (ESI): m/z: [M+H] calculated for $C_{16}H_{19}Cl_2N_5$: 352.10; found 352.39.

Example 75—Synthesis of (R)-(3-(1-amino-8-azaspiro[4.5]decan-8-yl)-6-(2,3-dimethoxyphenyl)-5-methylpyrazin-2-yl)methanol

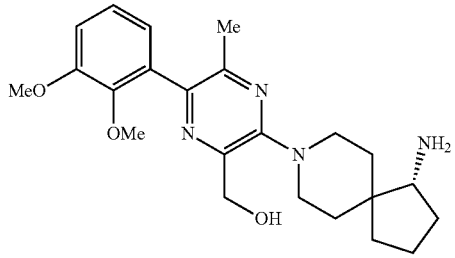 [SMILES: COc1cccc(-c2nc(CO)c(N3CCC4(CCC[C@H]4N)CC3)nc2C)c1OC]

(R)-(3-(1-amino-8-azaspiro[4.5]decan-8-yl)-6-(2,3-dimethoxy phenyl)-5-methylpyrazin-2-yl)methanol was synthesized in the manner similar to Example 29, Example 30, and Example 32, except (2,3-dichlorophenyl)boronic acid was substituted with (2,3-dimethoxyphenyl)boronic acid. (R)-(3-(1-amino-8-azaspiro[4.5]decan-8-yl)-6-(2,3-dimethoxy phenyl)-5-methylpyrazin-2-yl)methanol was isolated as its formate salt after HPLC purification. $^1$H NMR (500 MHz, Methanol-$d_4$) δ 8.57 (s, 1H), 7.19 (dd, J=8.2, 7.5 Hz, 1H), 7.14 (dd, J=8.3, 1.7 Hz, 1H), 6.90 (dd, J=7.5, 1.7 Hz, 1H), 4.70 (s, 2H), 3.93 (s, 3H), 3.72-3.61 (m, 2H), 3.61 (s, 3H), 3.21 (t, J=6.8 Hz, 1H), 3.13 (tdd, J=12.0, 2.9, 1.6 Hz, 2H), 2.29 (s, 3H), 2.27-2.14 (m, 1H), 1.98-1.76 (m, 5H), 1.72 (dt, J=12.7, 6.5 Hz, 1H), 1.63-1.52 (m, 2H). LC-MS (ESI): m/z: [M+H] calculated for $C_{23}H_{32}N_4O_3$: 413.25; found 413.60.

Example 76—Synthesis of (R)-(3-(1-amino-8-azaspiro[4.5]decan-8-yl)-6-(2-chloro-6-methoxypyridin-3-yl)-5-methylpyrazin-2-yl)methanol

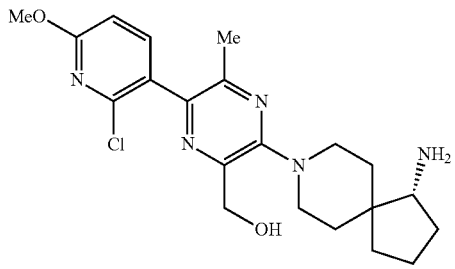 [SMILES: COc1ccc(-c2nc(CO)c(N3CCC4(CCC[C@H]4N)CC3)nc2C)c(Cl)n1]

(R)-(3-(1-amino-8-azaspiro[4.5]decan-8-yl)-6-(2-chloro-6-methoxypyridin-3-yl)-5-methylpyrazin-2-yl)methanol was synthesized in the manner similar to Example 29, Example 30, and Example 32, except (2,3-dichlorophenyl)boronic acid was substituted with (2-chloro-6-methoxypyridin-3-yl)boronic acid. (R)-(3-(1-amino-8-azaspiro[4.5]decan-8-yl)-6-(2-chloro-6-methoxypyridin-3-yl)-5-methylpyrazin-2-yl)methanol was isolated as its formate salt after HPLC purification. $^1$H NMR (500 MHz, Methanol-$d_4$) δ 8.57 (s, 1H), 7.73 (d, J=8.3 Hz, 1H), 6.90 (d, J=8.3 Hz, 1H), 4.69 (s, 2H), 3.99 (s, 3H), 3.71 (dd, J=26.0, 13.2 Hz, 2H), 3.18-3.08 (m, 3H), 2.31 (s, 3H), 2.24-2.14 (m, 1H), 1.89 (ddq, J=17.3, 9.0, 4.5 Hz, 3H), 1.84-1.72 (m, 3H), 1.71-1.61 (m, 1H), 1.54 (dd, J=24.8, 13.0 Hz, 2H). LC-MS (ESI): m/z: [M+H] calculated for $C_{21}H_{28}ClN_5O_2$: 418.19; found 418.56.

Example 77—Synthesis of (R)-(3-(1-amino-8-azaspiro[4.5]decan-8-yl)-6-(2,3-dichloropyridin-4-yl)-5-methylpyrazin-2-yl)methanol

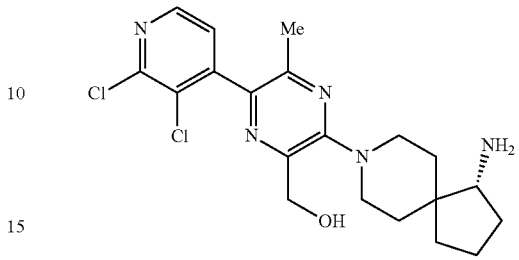

(R)-(3-(1-amino-8-azaspiro[4.5]decan-8-yl)-6-(2,3-dichloropyridin-4-yl)-5-methylpyrazin-2-yl)methanol was synthesized in the manner similar to Example 29, Example 30, and Example 32, except (2,3-dichlorophenyl)boronic acid was substituted with (2,3-dichloropyridin-4-yl)boronic acid. (R)-(3-(1-amino-8-azaspiro[4.5]decan-8-yl)-6-(2,3-dichloro pyridin-4-yl)-5-methylpyrazin-2-yl)methanol was isolated as its formate salt after HPLC purification. $^1$H NMR (500 MHz, Methanol-$d_4$) δ 8.57 (s, 1H), 8.43 (d, J=4.8 Hz, 1H), 7.47 (d, J=4.8 Hz, 1H), 4.70 (s, 2H), 3.84 (t, J=6.8 Hz, 1H), 3.78 (d, J=13.5 Hz, 1H), 3.23 (t, J=6.9 Hz, 1H), 3.20-3.12 (m, 2H), 2.30 (s, 3H), 2.27-2.19 (m, 1H), 1.96-1.68 (m, 7H), 1.65-1.51 (m, 2H), 1.20 (s, 1H). LC-MS (ESI): m/z: [M+H] calculated for $C_{20}H_{25}Cl_2N_5O$: 422.14; found 422.41.

Example 78—Synthesis of (R)-3-(1-amino-8-azaspiro[4.5]decan-8-yl)-6-(2,3-dichlorophenyl)-N-hydroxy-5-methylpyrazine-2-carboxamide

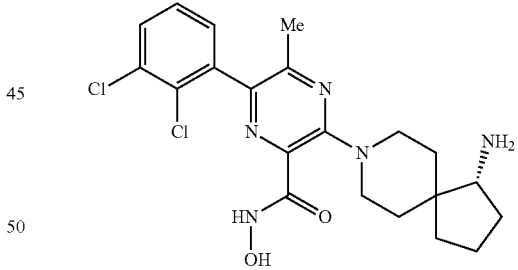

(R)-3-(1-amino-8-azaspiro[4.5]decan-8-yl)-6-(2,3-dichlorophenyl)-N-hydroxy-5-methylpyrazine-2-carboxamide was synthesized in the manner similar to Example 30, except ammonium acetate was substituted with hydroxylamine. (R)-3-(1-amino-8-azaspiro[4.5]decan-8-yl)-6-(2,3-dichlorophenyl)-N-hydroxy-5-methylpyrazine-2-carboxamide was isolated as its formate salt after HPLC purification. $^1$H NMR (500 MHz, DMSO-$d_6$) δ 8.39 (s, 1H), 7.72 (dd, J=8.0, 1.6 Hz, 1H), 7.47 (t, J=7.8 Hz, 1H), 7.41 (dd, J=7.6, 1.6 Hz, 1H), 4.01-3.86 (m, 2H), 3.17-3.06 (m, 2H), 2.91 (t, J=6.9 Hz, 1H), 2.18 (s, 3H), 2.02-1.89 (m, 1H), 1.83-1.73 (m, 1H), 1.73-1.41 (m, 5H), 1.31 (dd, J=36.2, 13.3 Hz, 3H). LC-MS (ESI): m/z: [M+H] calculated for $C_{21}H_{25}Cl_2N_5O_2$: 450.14; found 450.53.

Example 79—Synthesis of (3-((R)-1-amino-8-azaspiro[4.5]decan-8-yl)-6-(2,3-dichlorophenyl)-5-methylpyrazin-2-yl)(2-(hydroxymethyl)pyrrolidin-1-yl)methanone

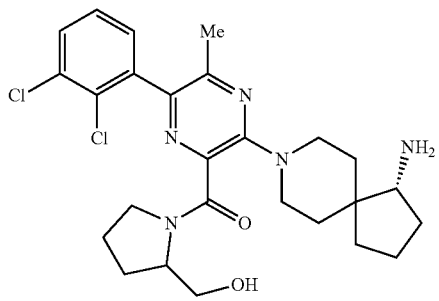 [SMILES: Cc1nc(N2CCC3(CCC[C@H]3N)CC2)c(C(=O)N2CCCC2CO)nc1-c1cccc(Cl)c1Cl]

(3-((R)-1-amino-8-azaspiro[4.5]decan-8-yl)-6-(2,3-dichlorophenyl)-5-methylpyrazin-2-yl)(2-(hydroxymethyl)pyrrolidin-1-yl)methanone was synthesized in the manner similar to Example 30, except ammonium acetate was substituted with pyrrolidin-2-ylmethanol. (3-((R)-1-amino-8-azaspiro[4.5]decan-8-yl)-6-(2,3-dichlorophenyl)-5-methylpyrazin-2-yl)(2-(hydroxyl methyl)pyrrolidin-1-yl)methanone was isolated as its formate salt after HPLC purification. $^1$H NMR (500 MHz, DMSO-$d_6$) δ 8.37 (s, 1H), 7.72 (dt, J=7.9, 1.4 Hz, 1H), 7.47 (td, J=7.8, 3.8 Hz, 1H), 7.44-7.38 (m, 1H), 4.12-3.94 (m, 2H), 3.88 (dd, J=26.8, 13.4 Hz, 1H), 3.67 (dd, J=10.3, 3.7 Hz, 1H), 3.44-3.32 (m, 3H), 3.17-3.03 (m, 2H), 2.87 (q, J=6.6 Hz, 1H), 2.18 (d, J=1.2 Hz, 3H), 1.92 (dq, J=13.5, 5.5, 4.7 Hz, 5H), 1.77 (dt, J=12.7, 8.6 Hz, 2H), 1.71-1.52 (m, 1H), 1.52-1.38 (m, 1H), 1.30 (dd, J=32.6, 13.2 Hz, 2H). LC-MS (ESI): m/z: [M+H] calculated for $C_{26}H_{33}Cl_2N_5O_2$: 518.20; found 518.55.

Example 80—Synthesis of 3-((R)-1-amino-8-azaspiro[4.5]decan-8-yl)-6-(2,3-dichlorophenyl)-5-methyl-N-(tetrahydrofuran-3-yl)pyrazine-2-carboxamide

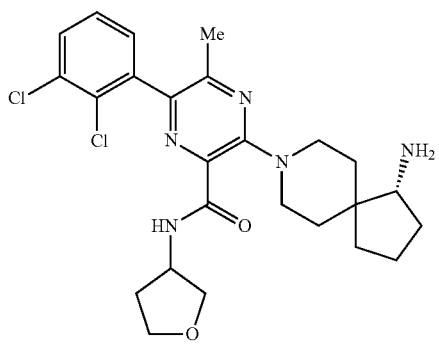 [SMILES: Cc1nc(N2CCC3(CCC[C@H]3N)CC2)c(C(=O)NC2CCOC2)nc1-c1cccc(Cl)c1Cl]

3-((R)-1-amino-8-azaspiro[4.5]decan-8-yl)-6-(2,3-dichlorophenyl)-5-methyl-N-(tetrahydrofuran-3-yl)pyrazine-2-carboxamide was synthesized in the manner similar to Example 30, except ammonium acetate was substituted with tetrahydrofuran-3-ol. 3-((R)-1-amino-8-azaspiro[4.5]decan-8-yl)-6-(2,3-dichlorophenyl)-5-methyl-N-(tetrahydrofuran-3-yl)pyrazine-2-carboxamide was isolated as its formate salt after HPLC purification. $^1$H NMR (500 MHz, DMSO-$d_6$) δ 10.95 (d, J=6.6 Hz, 1H), 10.66 (s, 1H), 10.01 (dd, J=7.9, 1.7 Hz, 1H), 9.76 (t, J=7.8 Hz, 1H), 9.72 (dd, J=7.6, 1.7 Hz, 1H), 6.70-6.59 (m, 1H), 6.21-6.03 (m, 5H), 5.97 (td, J=8.1, 5.8 Hz, 1H), 5.84 (ddd, J=8.9, 4.2, 1.7 Hz, 1H), 5.39 (t, J=12.7 Hz, 2H), 5.17 (t, J=7.0 Hz, 1H), 4.47 (s, 3H), 4.41 (dq, J=12.6, 7.7 Hz, 1H), 4.28-4.11 (m, 2H), 4.10-4.01 (m, 1H), 4.01-3.66 (m, 4H), 3.59 (dd, J=32.2, 13.4 Hz, 2H). LC-MS (ESI): m/z: [M+H] calculated for $C_{25}H_{31}Cl_2N_5O_2$: 504.19; found 504.56.

Example 81—Synthesis of (R)-(3-(1-amino-8-azaspiro[4.5]decan-8-yl)-6-(2,3-dichlorophenyl)-5-methylpyrazin-2-yl)(3-hydroxy-3-(trifluoromethyl)azetidin-1-yl)methanone

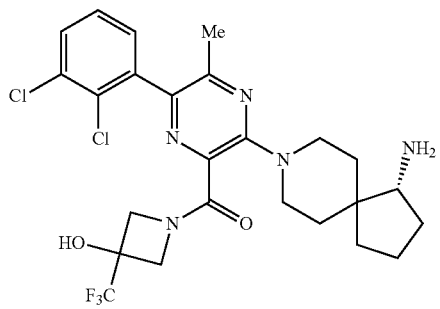 [SMILES: Cc1nc(N2CCC3(CCC[C@H]3N)CC2)c(C(=O)N2CC(O)(C(F)(F)F)C2)nc1-c1cccc(Cl)c1Cl]

(R)-(3-(1-amino-8-azaspiro[4.5]decan-8-yl)-6-(2,3-dichlorophenyl)-5-methylpyrazin-2-yl)(3-hydroxy-3-(trifluoromethyl)azetidin-1-yl)methanone was synthesized in the manner similar to Example 30, except ammonium acetate was substituted with 3-(trifluoromethyl)azetidin-3-ol. (R)-(3-(1-amino-8-azaspiro[4.5]decan-8-yl)-6-(2,3-dichlorophenyl)-5-methylpyrazin-2-yl)(3-hydroxy-3-(trifluoromethyl)azetidin-1-yl)methanone was isolated as its formate salt after HPLC purification. $^1$H NMR (500 MHz, DMSO-$d_6$) δ 8.38 (s, 1H), 7.73 (dd, J=7.3, 2.3 Hz, 1H), 7.51-7.44 (m, 2H), 4.34 (dd, J=10.6, 6.0 Hz, 1H), 4.27 (dt, J=11.2, 1.3 Hz, 1H), 4.23 (d, J=10.7 Hz, 1H), 4.04 (d, J=11.2 Hz, 1H), 3.82 (dt, J=47.5, 15.2 Hz, 2H), 3.19-3.04 (m, 2H), 2.91 (t, J=7.0 Hz, 1H), 2.20 (s, 3H), 1.93 (dt, J=16.6, 6.7 Hz, 1H), 1.83-1.40 (m, 5H), 1.40-1.25 (m, 2H). LC-MS (ESI): m/z: [M+H] calculated for $C_{25}H_{28}Cl_2F_3N_5O_2$: 558.16; found 558.51.

Example 82—Synthesis of 6-(4-(aminomethyl)-4-methylpiperidin-1-yl)-3-(2,3-dichlorophenyl)pyrazine-2-carbonitrile

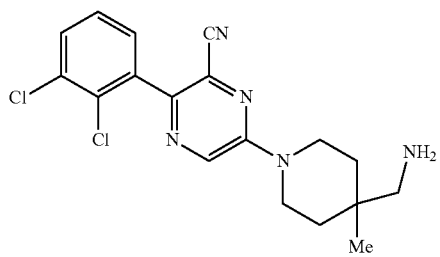 [SMILES: CC1(CN)CCN(c2cnc(-c3cccc(Cl)c3Cl)c(C#N)n2)CC1]

6-(4-(aminomethyl)-4-methylpiperidin-1-yl)-3-(2,3-dichlorophenyl)pyrazine-2-carbonitrile was synthesized in the manner similar to Example 26, except tert-butyl (4-methylpiperidin-4-yl)carbamate was substituted with tert-butyl ((4-methylpiperidin-4-yl)methyl)carbamate hydrochloride. $^1$H NMR (500 MHz, chloroform-d) δ 8.37 (s, 1H), 7.60 (dd, J=7.6, 2.0 Hz, 1H), 7.42-7.30 (m, 2H), 4.07-4.02 (m, 2H), 3.54-3.48 (m, 2H), 2.89 (s, 2H), 1.77-1.55 (m, 4H), 1.27 (s, 3H). LC-MS (ESI): m/z: [M+H] calculated for $C_{18}H_{19}Cl_2N_5$: 376.10; found 376.38.

Example 83—Synthesis of 4-amino-1-(5-((2,3-dichlorophenyl)thio)-6-methylpyrazin-2-yl)-N-(tetrahydro-2H-pyran-4-yl)piperidine-4-carboxamide

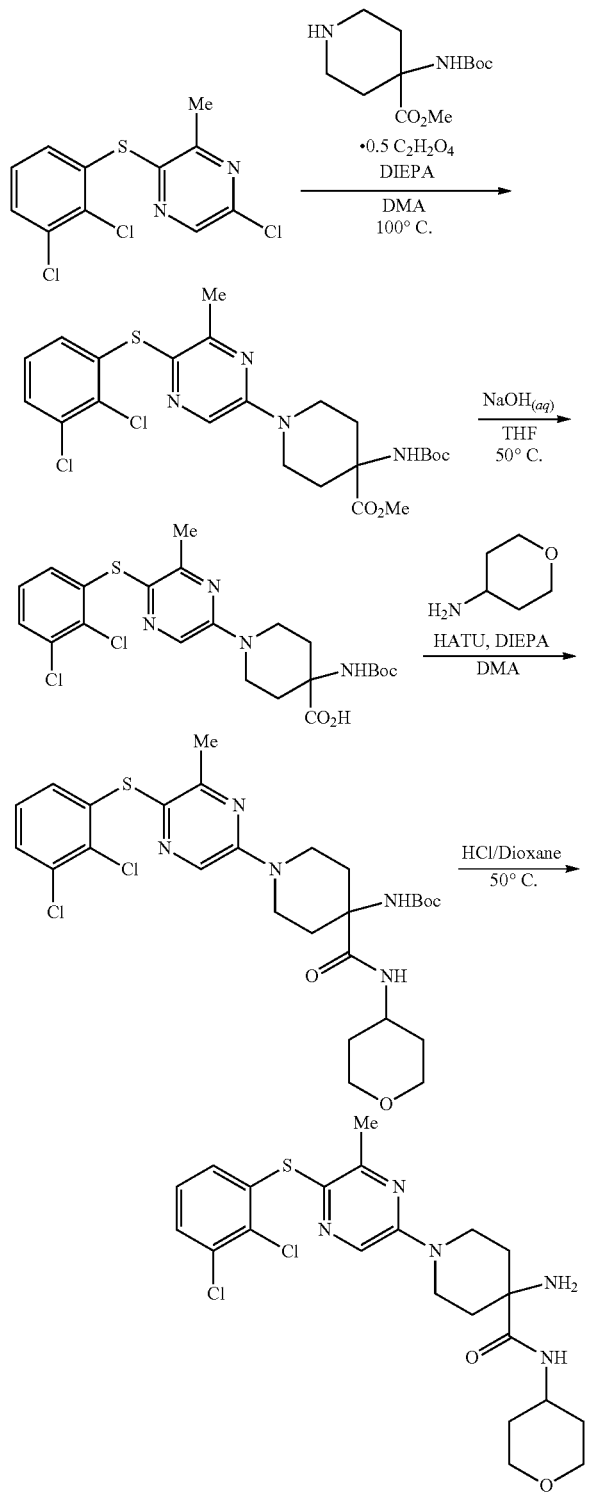

Step 1. Synthesis of methyl 4-((tert-butoxycarbonyl)amino)-1-(5-((2,3-dichlorophenyl)thio)-6-methylpyrazin-2-yl)piperidine-4-carboxylate A vial was charged with 5-chloro-2-((2,3-dichlorophenyl)thio)-3-methylpyrazine (450 mg, 1.47 mmol, 1 equiv), 4-N-Boc-aminopiperidine-4-carboxylic acid methyl ester hemioxalate (667 mg, 2.20 mmol, 1.5 equiv), diisopropylethylamine (894 µL, 5.14 mmol, 3.5 equiv), DMA (7.35 mL), and a stir bar to give a heterogeneous mixture. The vial was placed in heating block at 100° C. and stirred for 16 hours, after which the cooled reaction mixture was poured into ethyl acetate (15 mL) and water (15 mL). The separated organic phase was washed with water (1×15 mL), and the combined aqueous phases were back extracted with ethyl acetate (1×10 mL). The combined organic portions were washed with citric acid (0.2N, 3×20 mL), water (1×20 mL), and brine (1×20 mL), sequentially. The washed organic solution was dried over $MgSO_4$, filtered, and concentrated under reduced pressure to give methyl 4-((tert-butoxycarbonyl)amino)-1-(5-((2,3-dichlorophenyl)thio)-6-methylpyrazin-2-yl)piperidine-4-carboxylate (739 mg, 95%) of as a yellow foam which was used directly in the next step without further purification. LC-MS (ESI): m/z: [M+H] calculated for $C_{23}H_{28}Cl_2N_4O_4S$: 527.12; found 527.35.

Step 2. Synthesis of 4-((tert-butoxycarbonyl)amino)-1-(5-((2,3-dichlorophenyl)thio)-6-methylpyrazin-2-yl)piperidine-4-carboxylic acid To a solution of methyl 4-((tert-butoxycarbonyl)amino)-1-(5-((2,3-dichlorophenyl)thio)-6-methylpyrazin-2-yl)piperidine-4-carboxylate (737 mg, 1.39 mmol, 1 equiv) in tetrahydrofuran (7.2 mL) was added sodium hydroxide (2N, 2.08 mL, 4.17 mmol, 3 equiv). The resulting solution was stirred at room temperature for one hour before it was warmed to 50° C. and stirred for 3.5 hours. After this time, the pH of the reaction mixture was carefully adjusted to pH=4 by the dropwise addition of 1N HCl, and then water (25 mL) and ethyl acetate (25 mL) were added. The layers were separated, and the aqueous phase was extracted with ethyl acetate (2×15 mL) and dichloromethane (2×15 mL), sequentially. The combined organic extracts were dried over $MgSO_4$, filtered, and concentrated under reduced pressure to give 4-((tert-butoxycarbonyl)amino)-1-(5-((2,3-dichlorophenyl)thio)-6-methyl pyrazin-2-yl)piperidine-4-carboxylic acid (600 mg, 84%) as a light tan solid which was used in the next step without further purification. LC-MS (ESI): m/z: [M+H] calculated for $C_{22}H_{26}Cl_2N_4O_4S$: 513.11; found 513.44.

Step 3. Synthesis of tert-butyl (1-(5-((2,3-dichlorophenyl)thio)-6-methylpyrazin-2-yl)-4-((tetrahydro-2H-pyran-4-yl)carbamoyl)piperidin-4-yl)carbamate A vial was charged with tetrahydro-2H-pyran-4-amine (14.4 mg, 0.1427 mmol, 1.2 equiv), 4-((tert-butoxy carbonyl)amino)-1-(5-((2,3-dichlorophenyl)thio)-6-methylpyrazin-2-yl) piperidine-4-carboxylic acid (61.1 mg, 0.1190 mmol, 1.0 equiv), diisopropylethylamine (45.5 µL, 0.2618 mmol, 2.2 equiv), DMA (1.19 mL), and a stir bar. To this solution was added HATU (54.2 mg, 0.1427 mmol, 1.2 equiv), and the resulting mixture was stirred for 6 hours. After this time, the reaction mixture was diluted with water (15 mL) and ethyl acetate (15 mL). The layers were separated, and the organic phase was washed with 0.2N HCl (3×10 mL), water (1×10 mL), and brine (3×10 mL), sequentially. The washed solution was then dried over MgSO$_4$, filtered, and concentrated to give tert-butyl (1-(5-((2,3-dichlorophenyl)thio)-6-methylpyrazin-2-yl)-4-((tetrahydro-2H-pyran-4-yl)carbamoyl)piperidin-4-yl)carbamate (63 mg, 88%) as a clear film which was used directly in the next step without further purification. LC-MS (ESI): m/z: [M+H] calculated for C$_{27}$H$_{35}$Cl$_2$N$_5$O$_4$S: 596.18; found 596.55.

Step 4. Synthesis of 4-amino-1-(5-((2,3-dichlorophenyl)thio)-6-methylpyrazin-2-yl)-N-(tetrahydro-2H-pyran-4-yl)piperidine-4-carboxamide To a solution of tert-butyl (1-(5-((2,3-dichlorophenyl)thio)-6-methylpyrazin-2-yl)-4-((tetrahydro-2H-pyran-4-yl)carbamoyl)piperidin-4-yl)carbamate (63 mg, 0.1056 mmol, 1 equiv) in dioxane (1 mL) was added HCl in dioxane (4N, 2 mL). The resulting solution was warmed to 50° C. and stirred for 30 minutes. The mixture was then concentrated under reduced pressure, and the crude product was purified by prep-HPLC to afford 4-amino-1-(5-((2,3-dichlorophenyl)thio)-6-methylpyrazin-2-yl)-N-(tetrahydro-2H-pyran-4-yl)piperidine-4-carboxamide (20 mg, 38%). $^1$H NMR (500 MHz, DMSO-d$_6$) δ 8.25 (s, 1H), 7.89 (d, J=8.0 Hz, 1H), 7.47 (dd, J=8.0, 1.4 Hz, 1H), 7.25 (t, J=8.0 Hz, 1H), 6.74 (dd, J=8.0, 1.4 Hz, 1H), 4.15 (dt, J=13.4, 4.0 Hz, 2H), 3.83 (m, 2H), 3.78-3.69 (m, 1H), 3.43-3.35 (m, 4H), 2.39 (s, 3H), 1.93 (m, 2H), 1.71-1.63 (m, 2H), 1.53-1.33 (m, 4H). LC-MS (ESI): m/z: [M+H] calculated for C$_{22}$H$_{27}$Cl$_2$N$_5$O$_2$S: 496.13; found 496.56.

Example 84—Synthesis of 4-amino-N-cyclobutyl-1-(5-((2,3-dichlorophenyl)thio)-6-methylpyrazin-2-yl)piperidine-4-carboxamide

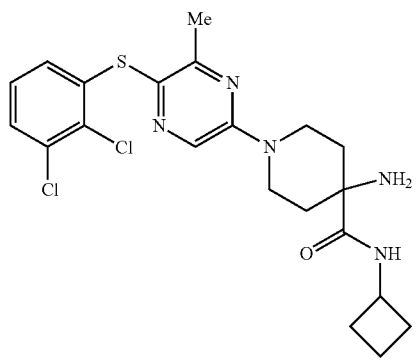 [SMILES: Cc1nc(N2CCC(N)(C(=O)NC3CCC3)CC2)cnc1Sc1cccc(Cl)c1Cl]

4-amino-N-cyclobutyl-1-(5-((2,3-dichlorophenyl)thio)-6-methylpyrazin-2-yl)piperidine-4-carboxamide was synthesized in a manner similar to Example 83, except tetrahydro-2H-pyran-4-amine was substituted with cyclobutanamine hydrochloride. $^1$H NMR (500 MHz, DMSO-d$_6$) δ 8.24 (s, 1H), 8.13 (d, J=8.1 Hz, 1H), 7.47 (dd, J=8.0, 1.4 Hz, 1H), 7.25 (t, J=8.0 Hz, 1H), 6.74 (dd, J=8.0, 1.4 Hz, 1H), 4.22-4.07 (m, 3H), 3.37 (m, 2H), 2.39 (s, 3H), 2.15 (m, 2H), 2.02-1.79 (m, 4H), 1.69-1.55 (m, 2H), 1.39 (d, J=13.4 Hz, 2H). LC-MS (ESI): m/z: [M+H] calculated for C$_{21}$H$_{25}$Cl$_2$N$_5$OS: 466.12; found 466.52.

Example 85—Synthesis of 4-amino-1-(5-((2,3-dichlorophenyl)thio)-6-methylpyrazin-2-yl)piperidine-4-carboxamide

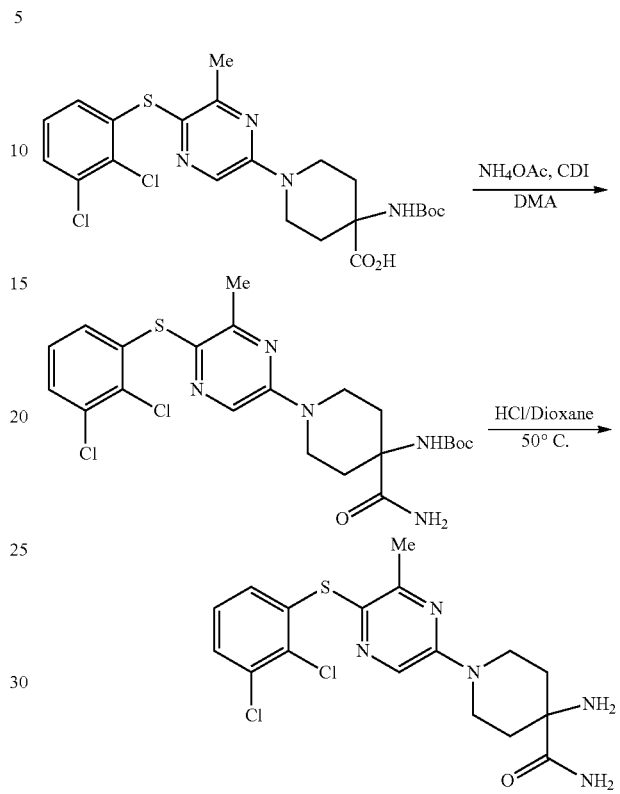

Step 1. Synthesis of tert-butyl (4-carbamoyl-1-(5-((2,3-dichlorophenyl)thio)-6-methylpyrazin-2-yl)piperidin-4-yl)carbamate A vial was charged with 4-((tert-butoxycarbonyl)amino)-1-(5-((2,3-dichlorophenyl)thio)-6-methylpyrazin-2-yl)piperidine-4-carboxylic acid (100 mg, 0.1947 mmol, 1 equiv), DMA (1.94 mL), and a stir bar. The resulting solution was cooled in an ice bath and 1,1'-carbonyldiimidazole (47.3 mg, 0.2920 mmol, 1.5 equiv) was added. After 30 minutes, ammonium acetate (75.0 mg, 0.9735 mmol, 5 equiv) was added and the solution was allowed to warm to room temperature. Additional CDI (31 mg, 0.194 mmol, 1 equiv) and ammonium acetate (38 mg, 0.4930 mmol, 2.5 equiv) were added after 3.5 hours. After 72 hours, the reaction mixture was diluted with water (15 mL) and ethyl acetate (15 mL). The layers were separated, and the organic phase was washed with 0.2N HCl (3×10 mL), water (1×10 mL), sat NaHCO$_3$ (1×10 mL), and brine (1×10 mL), sequentially. The washed organic solution was then dried over MgSO$_4$, filtered, and concentrated under reduced pressure. The crude residue was then purified by silica gel chromatography to afford tert-butyl (4-carbamoyl-1-(5-((2,3-dichlorophenyl)thio)-6-methylpyrazin-2-yl)piperidin-4-yl)carbamate (51 mg, 51%) as a white solid. LC-MS (ESI): m/z: [M+H] calculated for C$_{22}$H$_{27}$Cl$_2$N$_5$O$_3$S: 512.12; found 512.40.

Step 2. Synthesis of 4-amino-1-(5-((2,3-dichlorophenyl)thio)-6-methylpyrazin-2-yl)piperidine-4-carboxamide To a solution of tert-butyl (4-carbamoyl-1-(5-((2,3-dichlorophenyl)thio)-6-methylpyrazin-2-yl)piperidin-4-yl)

carbamate (51 mg, 0.09952 mmol, 1 equiv) in dioxane (1 mL) was added HCl in dioxane (4N, 2 mL). The resulting solution was then warmed to 50° C. and stirred for 30 minutes. The mixture was then cooled and concentrated under reduced pressure. The crude residue was then purified by prep-HPLC to afford 4-amino-1-(5-((2,3-dichlorophenyl) thio)-6-methylpyrazin-2-yl)piperidine-4-carboxamide (26 mg, 64%) as its formate salt. $^1$H NMR (500 MHz, DMSO-$d_6$) δ 8.25 (s, 1H), 8.20 (s, 1H), 7.50-7.40 (m, 2H), 7.25 (t, J=8.0 Hz, 1H), 7.02 (s, 1H), 6.74 (dd, J=8.0, 1.4 Hz, 1H), 4.16-4.03 (m, 2H), 3.46-3.31 (m, 2H), 2.39 (s, 3H), 1.92 (ddd, J=13.4, 11.6, 4.4 Hz, 2H), 1.45 (d, J=13.5 Hz, 2H). LC-MS (ESI): m/z: [M+H] calculated for $C_{17}H_{19}Cl_2N_5OS$: 412.07; found 412.42.

Example 86—Synthesis of (R)-2-((3-(1-amino-8-azaspiro[4.5]decan-8-yl)-6-((2,3-dichlorophenyl) thio)-5-methylpyrazin-2-yl)amino)ethan-1-ol

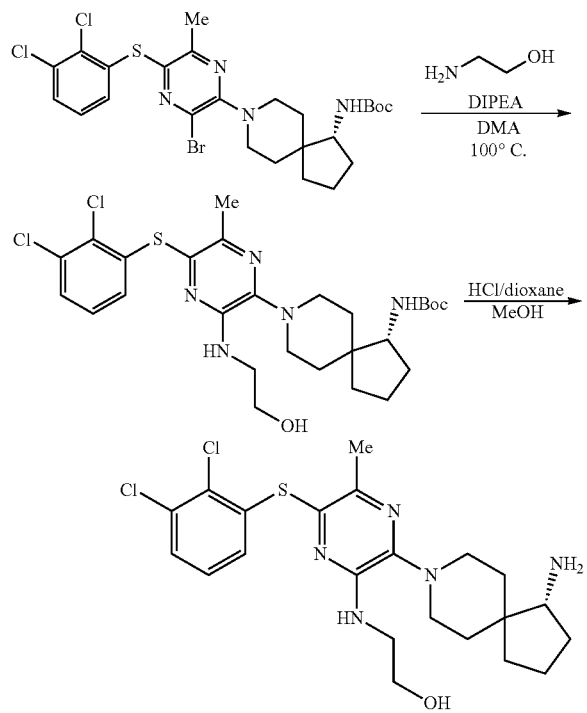

Step 1. Synthesis of tert-butyl (R)-(8-(5-((2,3-dichlorophenyl)thio)-3-((2-hydroxyethyl)amino)-6-methylpyrazin-2-yl)-8-azaspiro[4.5]decan-1-yl)carbamate To a solution of tert-butyl (R)-(8-(3-bromo-5-((2,3-dichlorophenyl)thio)-6-methylpyrazin-2-yl)-8-azaspiro[4.5] decan-1-yl)carbamate (50 mg, 0.08299 mmol, 1 equiv) in N,N-dimethylacetamide (2 mL) at 20° C. under an inert atmosphere was added DIPEA (13.7 μL, 0.08299 mmol, 1 equiv). The resulting mixture was then warmed to 120° C. and stirred for 12 hours. After this time, the reaction was cooled and concentrated under reduced pressure to provide tert-butyl (R)-(8-(5-((2,3-dichlorophenyl)thio)-3-((2-hydroxyethyl)amino)-6-methyl pyrazin-2-yl)-8-azaspiro[4.5] decan-1-yl)carbamate (40 mg, 0.0687 mmol) as a light yellow solid that was used in the next step without further purification. LC-MS (ESI): m/z: [M+H] calculated for $C_{27}H_{37}Cl_2N_5O_3S$: 582.20; found 582.63.

Step 2. Synthesis of (R)-2-((3-(1-amino-8-azaspiro [4.5]decan-8-yl)-6-((2,3-dichlorophenyl)thio)-5-methylpyrazin-2-yl)amino)ethan-1-ol To a solution of tert-butyl (R)-(8-(5-((2,3-dichlorophenyl) thio)-3-((2-hydroxy ethyl)amino)-6-methylpyrazin-2-yl)-8-azaspiro[4.5]decan-1-yl)carbamate (40 mg, 0.0687 mmol, 1 equiv) in MeOH (2 mL) was added HCl (4.0M in dioxane, 1 mL). The resulting mixture was stirred at 20° C. for 1 hour. The reaction mixture was then concentrated under reduced pressure, and the crude residue so obtained was purified by prep-HPLC to give (R)-2-((3-(1-amino-8-azaspiro[4.5]decan-8-yl)-6-((2,3-dichlorophenyl)thio)-5-methylpyrazin-2-yl)amino)ethan-1-ol (3.0 mg 7.5% yield) as a solid. $^1$H NMR (500 MHz, DMSO-$d_6$) δ 8.44 (s, 1H), 7.82 (d, J=0.7 Hz, 1H), 7.59 (d, J=6.7 Hz, 1H), 7.43 (dd, J=8.0, 1.4 Hz, 1H), 3.72-3.61 (m, 2H), 3.61 (m, 2H), 3.56 (t, J=6.8 Hz, 1H), 3.45 (tdd, J=12.0, 2.9, 1.6 Hz, 2H), 2.29 (s, 3H), 2.27-2.14 (m, 1H), 1.98-1.76 (m, 5H), 1.72 (dt, J=12.7, 6.5 Hz, 1H), 1.63-1.52 (m, 2H). LC-MS (ESI): m/z: [M+H] calculated for $C_{22}H_{29}Cl_2N_5OS$: 482.15; found 482.53.

Example 87—Synthesis of (R)-2-(3-(1-amino-8-azaspiro[4.5]decan-8-yl)-6-((2,3-dichlorophenyl) thio)-5-methylpyrazin-2-yl)propan-2-ol

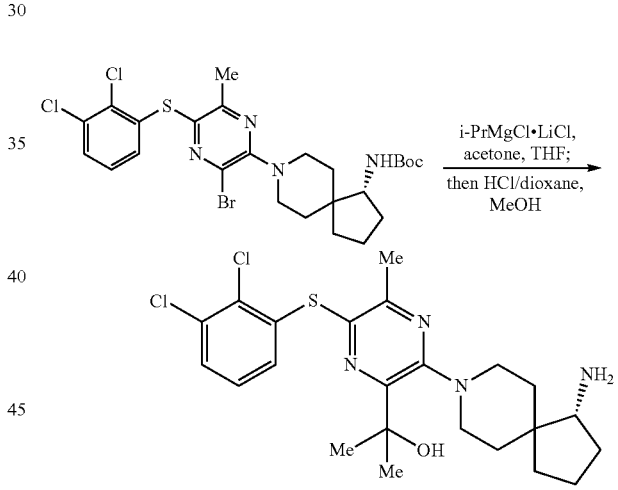

A solution of tert-butyl (8-(3-bromo-5-((2,3-dichlorophenyl)thio)-6-methylpyrazin-2-yl)-8-azaspiro[4.5]decan-1-yl) carbamate (22 mg, 36.5 μmol, 1 equiv) was dissolved in THF (0.3 ml) and cooled to −25° C., and isopropylmagnesium chloride lithium chloride complex (1.3M in THF, 56.1 μL, 73.0 μmol, 2 equiv) was added dropwise. Upon completion of this addition, the reaction was warmed to 0° C. over 2.5 hours. After this time, the solution was cooled to to −25° C., and another portion of isopropylmagnesium chloride lithium chloride complex (1.3M in THF, 56.1 μL, 73.0 μmol, 2 equiv) was added. The resulting mixture was warmed to −15° C. over 1 hour, after acetone (26.7 μL, 365 μmol, 10 equiv) was added, and the reaction was warmed to 0° C. After 1 hour, the mixture was poured into aqueous NaHCO$_3$ (5 mL) and extracted with EtOAc (5×2 mL). The combined organic extracts were passed through a plug of silica gel (eluted with EtOAc), and the filtrate was concentrated under reduced pressure. The resulting crude residue was dissolved in MeOH (2 mL), and HCl (4M in dioxane, 1 mL) was added. The reaction was stirred at room temperature for 2 hours. After this time, the solvent was removed under reduced pressure, and the crude product was purified by prep-HPLC to give (R)-2-(3-(1-amino-8-azaspiro[4.5]decan-8-yl)chlorophenyl)thio)-5-methylpyrazin-2-yl)propan-2-ol (3.9 mg, 22% yield) as a white amorphous solid. (R)-2-(3-(1-amino-8-azaspiro[4.5]decan-8-yl)-6-((2,3-dichlorophenyl)thio)-5-methylpyrazin-2-yl)propan-2-ol was isolated as its formate salt. $^1$H NMR (500 MHz, Methanol-$d_4$) δ 8.60 (s, 1H), 7.66 (dd, J=8.1, 1.5 Hz, 1H), 7.61 (dd, J=7.8, 1.5 Hz, 1H), 7.37 (t, J=7.9 Hz, 1H), 3.24-3.14 (m, 3H), 3.05-2.96 (m, 2H), 2.56 (s, 3H), 2.23 (t, J=7.5 Hz, 1H), 2.10-2.02 (m, 1H), 1.93-1.52 (m, 8H), 1.26 (d, J=1.2 Hz, 6H). LC-MS (ESI): m/z: [M+H] calculated for $C_{23}H_{30}Cl_2N_4OS$: 481.15; found 481.47.

Example 88—Synthesis of 1-(3-((R)-1-amino-8-azaspiro[4.5]decan-8-yl)-6-(2,3-dichlorophenyl)-5-methylpyrazin-2-yl)ethan-1-ol

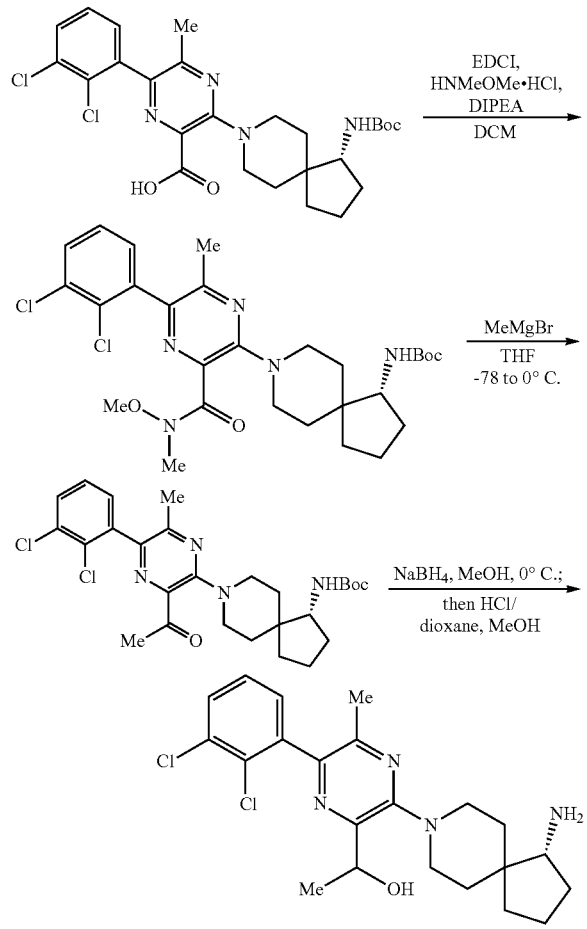

Step 1. Synthesis of tert-butyl (R)-(8-(5-(2,3-dichlorophenyl)-3-(methoxy(methyl)carbamoyl)-6-methylpyrazin-2-yl)-8-azaspiro[4.5]decan-1-yl)carbamate To a solution of (R)-3-(1-((tert-butoxycarbonyl)amino)-8-azaspiro[4.5]decan-8-yl)-6-(2,3-dichlorophenyl)-5-methylpyrazine-2-carboxylic acid (66 mg, 123 μmol, 1 equiv) in DCM (0.5 mL) at 23° C. was added N,O-dimethylhydroxylamine hydrochloride (13.9 mg, 143 μmol, 1.2 equiv), 1-[bis (dimethylamino)methylene]-1H-1,2,3-triazolo[4,5-b]pyridinium 3-oxide hexafluorophosphate (54.3 mg, 143 μmol, 1.2 equiv), and diisopropylethylamine (64.3 μL, 369 μmol, 3 equiv), sequentially. The resulting mixture was stirred for 40 minutes before water (3 mL) and brine (3 mL) were added, and the aqueous phase was extracted with EtOAc (5×2 mL). The combined organic extracts were passed through a plug of silica gel, and the filtrate was concentrated under reduced pressure. The resulting crude material (75 mg) was used in the next step without further purification. LC-MS (ESI): m/z: [M+H] calculated for $C_{28}H_{37}Cl_2N_5O_4$: 578.22; found 578.56.

Step 2. Synthesis of tert-butyl (R)-(8-(3-acetyl-5-(2,3-dichlorophenyl)-6-methylpyrazin-2-yl)-8-azaspiro[4.5]decan-1-yl)carbamate A solution of crude tert-butyl (8-(5-(2,3-dichlorophenyl)-3-(methoxy(methyl)carbamoyl)-6-methylpyrazin-2-yl)-8-azaspiro[4.5]decan-1-yl)carbamate (75 mg, 129 μmol, 1 equiv) in tetrahydrofuran (2 mL) was cooled to −78° C. Once cool, methylmagnesium bromide (3M in diethyl ether, 215 μL, 645 μmol, 5 equiv) was added dropwise, and the reaction was warmed to 0° C. After stirring for 45 minutes, aqueous ammonium chloride (10 mL) was added, and the resulting biphasic mixture was extracted with EtOAc (5×3 mL). The combined organic fractions were passed through a plug of silica gel and concentrated under reduced pressure. The crude material so obtained (13 mg) was used in the next step without further purification. LC-MS (ESI): m/z: [M+H] calculated for $C_{27}H_{34}Cl_2N_4O_3$: 533.20; found 533.57.

Step 3. Synthesis of 1-(3-((R)-1-amino-8-azaspiro[4.5]decan-8-yl)-6-(2,3-dichlorophenyl)-5-methylpyrazin-2-yl)ethan-1-ol A solution of (R)-tert-butyl (8-(3-acetyl-5-((2,3-dichlorophenyl)thio)-6-methylpyrazin-2-yl)-8-azaspiro[4.5]decan-1-yl)carbamate (13 mg, 22.9 μmol, 1 equiv) in MeOH (0.45 mL) was cooled to 0° C. Once cool, sodium borohydride (2.59 mg, 68.6 μmol, 3 equiv) was added in one portion, and the resulting mixture was stirred for 15 minutes. After this time, saturated aqueous NaHCO$_3$ (5 mL) was added, and the resulting biphasic mixture was extracted with EtOAc (5×2 mL). The combined organic extracts were passed through a plug of silica gel (eluted with EtOAc), and the filtrate was concentrated under reduced pressure. The resulting residue was dissolved in MeOH (2 mL), and HCl (4M in dioxane, 1 mL) was added. The resulting mixture was stirred at room temperature for 2 hours, after which the solvent was removed under reduced pressure. The crude residue so obtained was purified by prep-HPLC to give 1-(3-((R)-1-amino-8-azaspiro[4.5]decan-8-yl)-6-(2,3-dichlorophenyl)-5-methylpyrazin-2-yl)ethan-1-ol (2.0 mg, 4% yield over three steps) as a white amorphous solid. 1-(3-((R)-1-amino-8-azaspiro[4.5]decan-8-yl)-6-(2,3-dichlorophenyl)-5-methylpyrazin-2-yl)ethan-1-ol was isolated as its formate salt. $^1$H NMR (500 MHz, methanol-$d_4$) δ 8.58 (s, 1H), 7.66 (dd, J=7.9, 1.5 Hz, 1H), 7.44 (t, J=7.8 Hz, 1H), 7.37 (dd, J=7.6, 1.6 Hz, 1H), 5.16 (q, J=6.4 Hz, 1H), 3.74 (dd, J=24.3, 10.8 Hz, 1H), 3.57-3.47 (m, 1H), 3.29-3.25 (m, 1H), 3.24-3.18 (m, 1H), 3.11 (s, 1H), 2.29 (s, 3H), 2.28-2.20 (m, 2H), 2.01-1.71 (m, 6H), 1.61 (q, J=14.8, 13.7 Hz, 2H), 1.53 (d, J=6.3 Hz, 3H). LC-MS (ESI): m/z: [M+H] calculated for C$_{22}$H$_{28}$Cl$_2$N$_4$O: 435.16; found 435.51.

Example 89—Synthesis of (3-(4-amino-4-methylpiperidin-1-yl)-6-(3-chloro-2-methoxypyridin-4-yl)-5-methylpyrazin-2-yl)methanol

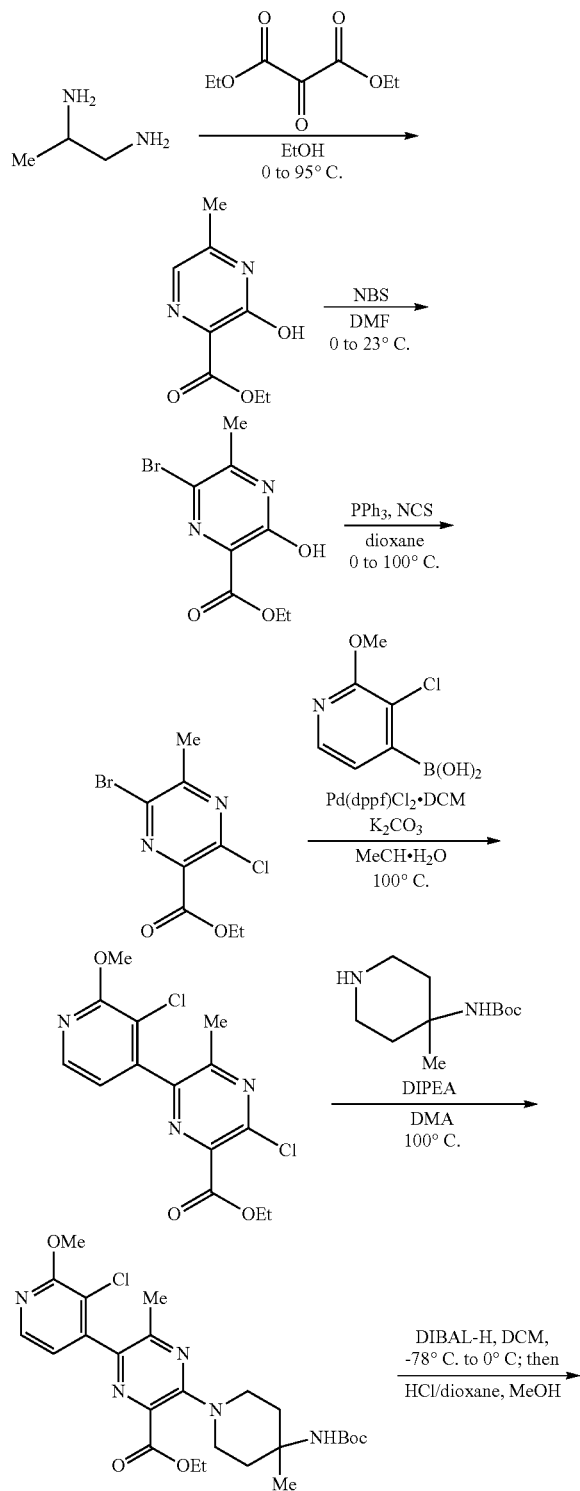

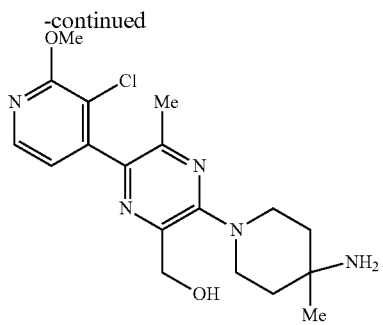

Step 1. Synthesis of ethyl 5-methyl-3-oxo-3,4-dihydropyrazine-2-carboxylate

A 500 mL flask was charged with ethanol (216 mL) and propane-1,2-diamine (11.1 mL, 131 mmol, 1.01 equiv), and the resulting clear, colorless solution was cooled to 0° C. Once cool, diethyl 2-oxomalonate (20 mL, 130 mmol, 1.0 equiv) was added to the solution in a dropwise fashion, the cooling bath was removed, and the reaction was allowed to warm to room temperature. After stirring for 2 hours, the clear, colorless solution had become a thick, milky white mixture. At this time, the flask was fitted with a reflux condenser, and the reaction was warmed to 95° C. The reaction mixture was then left to stir for 24 hours, after which the solution was cooled to room temperature and concentrated under reduced pressure to give a dark orange oil. This oil was then diluted with a minimal amount of DCM and passed through a silica gel plug, and the filtrate containing the desired product was concentrated under reduced pressure to give a bright orange solid. This solid was triturated with MTBE to give ethyl 5-methyl-3-oxo-3,4-dihydropyrazine-2-carboxylate (4.27 g, 23.4 mmol, 18%) as a salmon-colored solid. $^1$H NMR (500 MHz, DMSO-d$_6$) δ 7.35 (br s, 1H), 4.26 (q, J=7.1 Hz, 2H), 2.24 (s, 3H), 1.27 (t, J=7.1 Hz, 3H).

Step 2. Synthesis of ethyl 6-bromo-5-methyl-3-oxo-3,4-dihydropyrazine-2-carboxylate A 500 mL flask was charged with ethyl 5-methyl-3-oxo-3,4-dihydropyrazine-2-carboxylate (3 g, 16.4 mmol, 1 equiv) and DMF (65.6 mL) under an inert atmosphere, and the resulting solution was cooled to 0° C. Once cool, NBS (3.06 g, 17.2 mmol, 1.05 equiv) was added in one portion, and the cooling bath was removed. After stirring for 1 hour, the reaction was diluted with water (150 mL) and ethyl acetate (200 mL). The layers were separated, and the resulting organic solution was then washed with water (150 mL), ½ saturated brine (2×150 mL), and brine (2×150 mL), sequentially. The organic solution was then dried over magnesium sulfate, filtered, and concentrated to give ethyl 6-bromo-5-methyl-3-oxo-3,4-dihydropyrazine-2-carboxylate (3.77 g, 14.4 mmol, 88.0%) as a pale yellow solid. $^1$H NMR (500 MHz, DMSO-d$_6$) δ 4.30 (q, J=7.1 Hz, 2H), 2.49-2.41 (br s, 3H), 1.29 (t, J=7.1 Hz, 3H).

Step 3. Synthesis of ethyl 6-bromo-3-chloro-5-methylpyrazine-2-carboxylate

A 500 mL flask was charged with triphenylphosphine (18.0 g, 68.7 mmol, 3 equiv) and 1,4-dioxane (228 mL), giving a clear, colorless solution. N-chlorosuccinimide (9.32 g, 69.8 mmol, 3.05 equiv) was then added to this solution, and the resulting mixture was left to stir for 30 minutes. After this time, the solution had become a thick, white slurry. Ethyl 6-bromo-5-methyl-3-oxo-3,4-dihydropyrazine-2-carboxylate (6 g, 22.9 mmol, 1 equiv) was then added to this slurry in one portion, and the resulting mixture was warmed to 100° C. and left to stir for 1 hour. After this time, the mixture had turned brown/black. The reaction was then cooled to room temperature, triethylamine (57 mL) was added, and the resulting mixture was concentrated to a thick black oil. This crude material was dissolved in DCM and passed through a silica gel plug, producing an oily brown solid. This solid was further purified by silica gel chromatography to give ethyl 6-bromo-3-chloro-5-methylpyrazine-2-carboxylate (5.20 g, 18.6 mmol, 81.2%) as an orange oil that slowly crystallized to give an orange solid. $^1$H NMR (500 MHz, chloroform-d) δ 4.50-4.45 (m, 2H), 2.72 (s, 3H), 1.43 (t, J=7.1 Hz, 3H).

Step 4. Synthesis of ethyl 3-chloro-6-(3-chloro-2-methoxypyridin-4-yl)-5-methylpyrazine-2-carboxylate (3-chloro-2-methoxypyridin-4-yl)boronic acid (209 mg, 1.12 mmol, 1.5 equiv), potassium carbonate (415 mg, 3.01 mmol, 4 equiv), [1,1'-bis(diphenylphosphino)ferrocene]dichloropalladium(II), complex with dichloromethane (122 mg, 150 μmol, 0.2 equiv) and methyl 6-bromo-3-chloro-5-methylpyrazine-2-carboxylate (200 mg, 753 μmol, 1 equiv) were weighed into a 40 mL vial equipped with a stir bar and screw-cap septum. The reaction vessel was then placed under inert atmosphere, and degassed MeCN (7.52 mL) and water (50 μL) were added to the vial. The mixture was placed into a heating block preheated at 100° C. and stirred vigorously for 1 hour. After this time, the crude reaction mixture was filtered through a silica gel plug (eluting with EtOAc). The filtrate was concentrated under reduced pressure to give crude ethyl 3-chloro-6-(3-chloro-2-methoxypyridin-4-yl)-5-methylpyrazine-2-carboxylate (555 mg), which was used directly in the next step without further purification. LC-MS (ESI): m/z: [M+H] calculated for $C_{14}H_{13}Cl_2N_3O_3$: 342.03; found 342.22.

Step 5. Synthesis of ethyl 3-(4-((tert-butoxycarbonyl)amino)-4-methylpiperidin-1-yl)-6-(3-chloro-2-methoxypyridin-4-yl)-5-methylpyrazine-2-carboxylate To a solution of tert-butyl (4-methylpiperidin-4-yl)carbamate (555 mg, 2.59 mmol, 5 equiv) in DMA (4 mL) was added ethyl 3-chloro-6-(3-chloro-2-methoxypyridin-4-yl)-5-methylpyrazine-2-carboxylate (170 mg, 518 μmol, 1 equiv) and diisopropylethylamine (45.1 μL, 259 μmol, 0.5 equiv), sequentially. The mixture was then warmed to 100° C. and stirred for 30 minutes. After this time, the reaction mixture was diluted with EtOAc (10 mL) and washed with saturated aqueous NaHCO$_3$ (15 mL), water (10 mL), and brine (10 mL), sequentially. The combined aqueous washes were extracted with EtOAc (3×15 mL). The combined organic extracts were passed through a plug of silica, and filtrate was concentrated under reduced pressure to give crude ethyl 3-(4-((tert-butoxy carbonyl)amino)-4-methylpiperidin-1-yl)-6-(3-chloro-2-methoxypyridin-4-yl)-5-methylpyrazine-2-carboxylate (411 mg), which was used without further purification in the next step. LC-MS (ESI): m/z: [M+H] calculated for $C_{25}H_{34}ClN_5O_5$: 520.22; found 520.62.

Step 6. Synthesis of (3-(4-amino-4-methylpiperidin-1-yl)-6-(3-chloro-2-methoxypyridin-4-yl)-5-methylpyrazin-2-yl)methanol A solution of ethyl 3-(4-((tert-butoxycarbonyl)amino)-4-methylpiperidin-1-yl)-6-(3-chloro-2-methoxypyridin-4-yl)-5-methylpyrazine-2-carboxylate (411 mg, 790 μmol, 1 equiv) in DCM (12 mL) was cooled to −78° C. To this cooled solution was added diisobutylaluminium hydride (2.37 mL, 2.37 mmol, 3 equiv) in a dropwise fashion. The resulting mixture was stirred at −78° C. for 10 min before it was warmed to 0° C. and stirred for 20 minutes. After this time, the reaction mixture was cooled to −78° C. and poured into cold, saturated, aqueous Rochelle's salt (150 mL). The mixture was stirred vigorously for 1 hour at room temperature and then extracted with EtOAc (5×15 mL). The combined extracts were filtered through a plug of silica gel, and the filtrate was concentrated under reduced pressure. The crude residue so obtained was dissolved in MeOH (2 mL), and HCl (4M in dioxane, 1 mL) was added. The reaction was stirred at room temperature for 2 hours before the solvent was removed under reduced pressure. The crude residue was then purified by prep-HPLC to give (3-(4-amino-4-methylpiperidin-1-yl)-6-(3-chloro-2-methoxypyridin-4-yl)-5-methylpyrazin-2-yl)methanol (30.0 mg, 7% yield over three steps) as a white amorphous solid. (3-(4-amino-4-methylpiperidin-1-yl)-6-(3-chloro-2-methoxypyridin-4-yl)-5-methylpyrazin-2-yl)methanol was isolated as its formate salt. $^1$H NMR (500 MHz, DMSO-d$_6$) δ 8.39 (s, 1H), 8.25 (d, J=5.1 Hz, 1H), 7.12 (d, J=5.0 Hz, 1H), 4.54 (s, 2H), 4.04 (s, 3H), 3.61 (dd, J=12.8, 6.2 Hz, 2H), 3.39-3.34 (m, 2H), 2.24 (s, 3H), 1.74 (d, J=5.7 Hz, 4H), 1.30 (s, 3H). LC-MS (ESI): m/z: [M+H] calculated for $C_{18}H_{24}ClN_5O_2$: 378.16; found 378.30.

Example 90—Synthesis of (R)-(3-(1-amino-8-azaspiro[4.5]decan-8-yl)-6-(3-chloro-2-methoxypyridin-4-yl)-5-methylpyrazin-2-yl)methanol

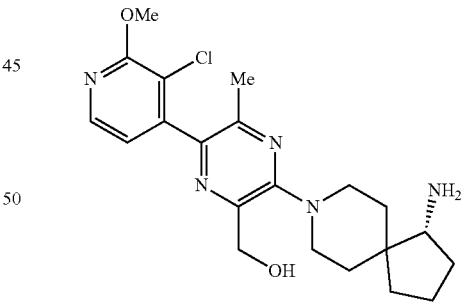

(R)-(3-(1-amino-8-azaspiro[4.5]decan-8-yl)-6-(3-chloro-2-methoxypyridin-4-yl)-5-methylpyrazin-2-yl)methanol was synthesized in the manner similar to Example 89, except of tert-butyl (4-methylpiperidin-4-yl)carbamate was substituted with (R)-2-methyl-N—((R)-8-azaspiro[4.5]decan-1-yl)propane-2-sulfinamide. (R)-(3-(1-amino-8-azaspiro[4.5]decan-8-yl)-6-(3-chloro-2-methoxypyridin-4-yl)-5-methylpyrazin-2-yl)methanol was isolated as its formate salt after HPLC purification. $^1$H NMR (500 MHz, DMSO-d$_6$) δ 8.40 (s, 1H), 8.25 (d, J=5.1 Hz, 1H), 7.13 (d, J=5.1 Hz, 1H), 4.54 (s, 2H), 4.03 (s, 3H), 3.81-3.72 (m, 2H), 3.10-3.03 (m, 2H), 2.93 (t, J=7.1 Hz, 1H), 2.23 (s, 3H), 2.03-1.27 (m, 10H). LC-MS (ESI): m/z: [M+H] calculated for $C_{21}H_{28}ClN_5O_2$: 418.19; found 418.56.

Example 91—Synthesis of (R)-(3-(1-amino-8-azaspiro[4.5]decan-8-yl)-6-(2-methoxypyridin-3-yl)-5-methylpyrazin-2-yl)methanol

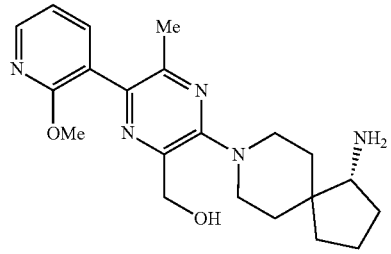 [SMILES: COc1ncccc1-c1nc(CO)c(N2CCC3(CCC[C@H]3N)CC2)nc1C]

(R)-(3-(1-amino-8-azaspiro[4.5]decan-8-yl)-6-(2-methoxypyridin-3-yl)-5-methylpyrazin-2-yl)methanol was synthesized in the manner similar to Example 89, except of tert-butyl (4-methylpiperidin-4-yl)carbamate and (3-chloro-2-methoxypyridin-4-yl)boronic acid and were substituted with (R)-2-methyl-N—((R)-8-azaspiro[4.5]decan-1-yl)propane-2-sulfinamide(2-methoxypyridin-3-yl)boronic acid, respectively. $^1$H NMR (500 MHz, DMSO-d$_6$) δ 8.29 (dd, J=5.0, 2.0 Hz, 1H), 7.78 (dd, J=7.3, 1.9 Hz, 1H), 7.16 (dd, J=7.3, 5.0 Hz, 1H), 4.54 (s, 2H), 3.90 (s, 3H), 3.67 (dd, J=21.2, 13.4 Hz, 2H), 3.02 (t, J=12.6 Hz, 2H), 2.93-2.89 (m, 1H), 2.23 (s, 3H), 1.94 (s, 1H), 1.84-1.30 (m, 9H). LC-MS (ESI): [M+H] calculated for $C_{21}H_{29}N_5O_2$: 384.24; found 384.29.

Example 92—Synthesis of (R)-(3-(1-amino-8-azaspiro[4.5]decan-8-yl)-6-(6-chloro-2-methoxypyridin-3-yl)-5-methylpyrazin-2-yl)methanol

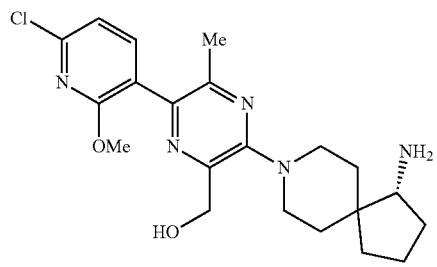 [SMILES: COc1nc(Cl)ccc1-c1nc(CO)c(N2CCC3(CCC[C@H]3N)CC2)nc1C]

(R)-(3-(1-amino-8-azaspiro[4.5]decan-8-yl)-6-(6-chloro-2-methoxypyridin-3-yl)-5-methylpyrazin-2-yl)methanol was synthesized in the manner similar to Example 89, except of tert-butyl (4-methylpiperidin-4-yl)carbamate and (3-chloro-2-methoxypyridin-4-yl)boronic acid were substituted with (R)-2-methyl-N—((R)-8-azaspiro[4.5]decan-1-yl)propane-2-sulfinamide and (6-chloro-2-methoxypyridin-3-yl)boronic acid, respectively. (R)-(3-(1-amino-8-azaspiro[4.5]decan-8-yl)-6-(6-chloro-2-methoxypyridin-3-yl)-5-methylpyrazin-2-yl)methanol was isolated as its formate salt after HPLC purification. $^1$H NMR (500 MHz, DMSO-d$_6$) δ 8.37 (s, 1H), 7.82 (d, J=7.7 Hz, 1H), 7.25 (d, J=7.7 Hz, 1H), 4.50 (s, 2H), 3.88 (s, 3H), 3.66 (dd, J=24.2, 13.1 Hz, 2H), 2.99 (t, J=12.5 Hz, 3H), 2.95-2.90 (m, 1H), 2.20 (s, 3H), 1.93 (d, J=18.5 Hz, 1H), 1.81-1.26 (m, 8H). LC-MS (ESI): m/z: [M+H] calculated for $C_{21}H_{28}ClN_5O_2$: 418.19; found 418.49.

Example 93—Synthesis of (R)-8-(5-((2,3-dichlorophenyl)thio)-6-(trifluoromethyl)pyrazin-2-yl)-8-azaspiro[4.5]decan-1-amine

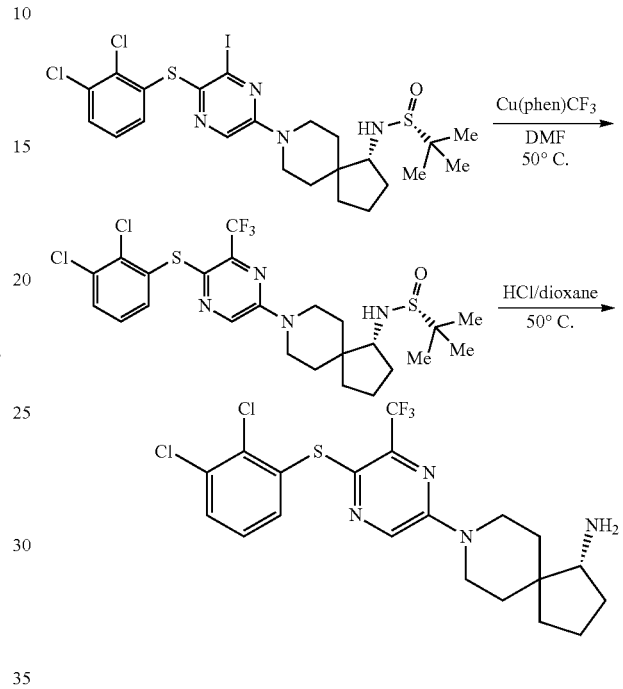

Step 1. Synthesis of (R)—N—((R)-8-(5-((2,3-dichlorophenyl)thio)-6-(trifluoromethyl)pyrazin-2-yl)-8-azaspiro[4.5]decan-1-yl)-2-methylpropane-2-sulfinamide A vial was charged with (R)—N—((R)-8-(5-((2,3-dichlorophenyl)thio)-6-iodopyrazin-2-yl)-8-azaspiro[4.5]decan-1-yl)-2-methylpropane-2-sulfinamide (69.5 mg, 0.1086 mmol, 1 equiv), (1,10-Phenanthroline)(trifluoromethyl)copper(I) (67.9 mg, 0.2172 mmol, 2 equiv), and a stir bar. DMF (543 μL) was added, and the vial was placed into a 50° C. oil bath overnight The reaction mixture was then diluted with ethyl ether (10 mL) and filtered through a pad of Celite. The filtrate was concentrated, and the resulting residue was re-dissolved in ethyl acetate (15 mL) and washed with water (1×10 mL) and brine (1×10 mL), dried over MgSO$_4$, filtered, and concentrated under reduced pressure to give 50 mg of (R)—N—((R)-8-(5-((2,3-dichlorophenyl)thio)-6-(trifluoromethyl)pyrazin-2-yl)-8-azaspiro[4.5]decan-1-yl)-2-methyl propane-2-sulfinamide, which was used directly in the next step. LC-MS (ESI): m/z: [M+H] calculated for $C_{24}H_{29}Cl_2F_3N_4OS$: 581.11; found 581.45.

Step 2. Synthesis of (R)-8-(5-((2,3-dichlorophenyl)thio)-6-(trifluoromethyl)pyrazin-2-yl)-8-azaspiro[4.5]decan-1-amine To a solution of (R)—N—((R)-8-(5-((2,3-dichlorophenyl)thio)-6-(trifluoromethyl)pyrazin-2-yl)-8-azaspiro[4.5]decan-1-yl)-2-methylpropane-2-sulfinamide in dioxane (1 mL) was added HCl in dioxane (4M, 3 mL). The resulting solution was stirred for 45 minutes at 50° C. The mixture was then concentrated under reduced pressure, and the crude product was purified by prep-HPLC to afford (R)-8-(5-((2,3-dichlorophenyl)thio)-6-(trifluoromethyl)pyrazin-2-yl)-8-azaspiro[4.5]decan-1-amine (1.6 mg, 3% over two steps) as its formate salt. $^1$H NMR (500 MHz, Methanol-$d_4$) δ 8.57 (s, 1H), 8.40 (s, 1H), 7.45 (dd, J=8.0, 1.4 Hz, 1H), 7.20 (t, J=8.0 Hz, 1H), 7.01 (dd, J=8.0, 1.4 Hz, 1H), 4.37 (dd, J=34.8, 13.6 Hz, 2H), 3.30-3.20 (m, 2H), 3.06 (m, 1H), 2.17 (m, 1H), 2.01-1.71 (m, 5H), 1.71-1.41 (m, 3H). LC-MS (ESI): m/z: [M+H] calculated for $C_{20}H_{21}Cl_2F_3N_4S$: 477.08; found 477.40.

TABLE 1

Examples 94-141

| Example | Structure | M + 1 found |
|---|---|---|
| EXAMPLE 94 | | 457.1 |
| EXAMPLE 95 | | 363.2 |
| EXAMPLE 96 | | 417.04 |
| EXAMPLE 97 | | 469.1 |
| EXAMPLE 98 | | 397.4 |
| EXAMPLE 99 | 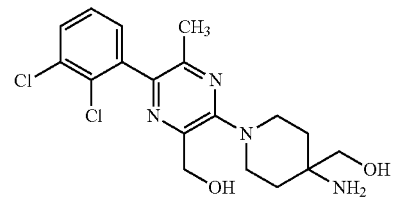 [SMILES: Cc1nc(N2CCC(N)(CO)CC2)c(CO)nc1-c1cccc(Cl)c1Cl] | 397.3 |
| EXAMPLE 100 | 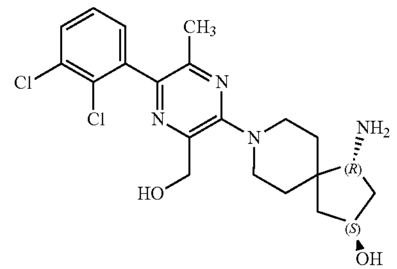 | 437.1 |
| EXAMPLE 101 | 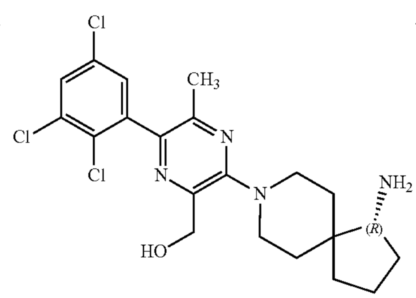 | 455.4 |
| EXAMPLE 102 | 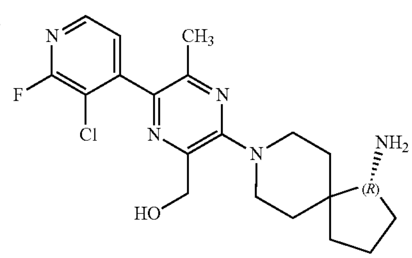 | 406.3 |
| EXAMPLE 103 | 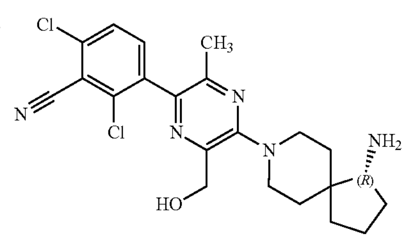 | 446.4 |
| EXAMPLE 104 | 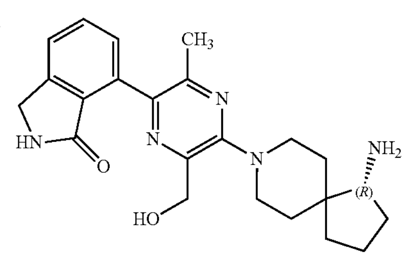 | 408.5 |

TABLE 1-continued

Examples 94-141

| Example | Structure | M + 1 found |
|---|---|---|
| EXAMPLE 105 | 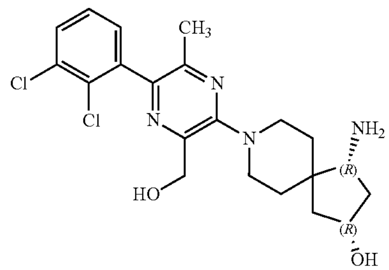 | 437.1 |
| EXAMPLE 106 | 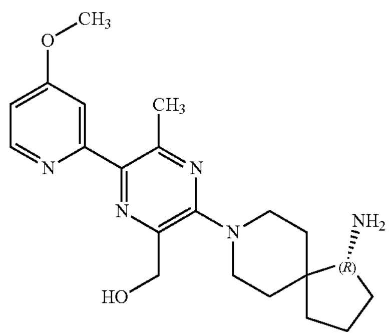 | 384.2 |
| EXAMPLE 107 | 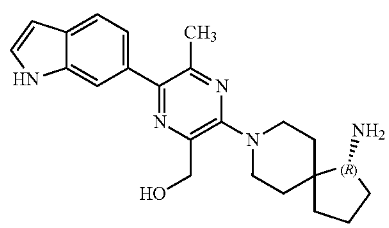 | 392.2 |
| EXAMPLE 108 | 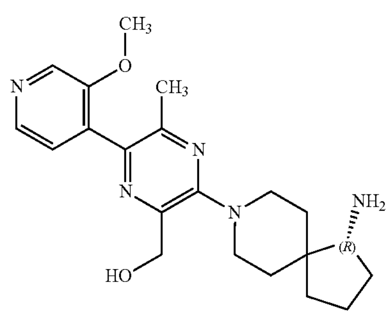 | 384.2 |
| EXAMPLE 109 | 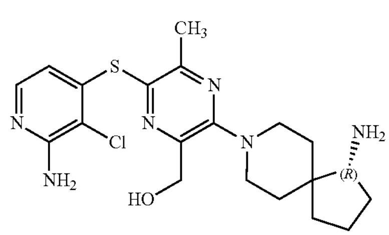 | 435.4 |
| EXAMPLE 110 | 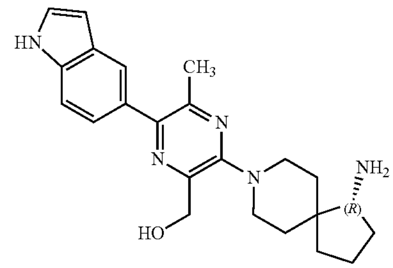 | 392.3 |
| EXAMPLE 111 | 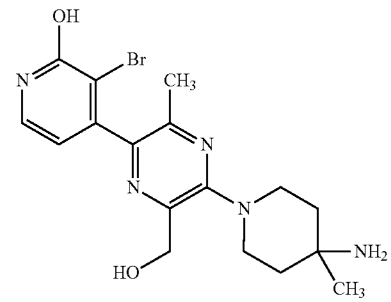 [SMILES: Cc1nc(N2CCC(C)(N)CC2)c(CO)nc1-c1ccnc(O)c1Br] | 408.4 |
| EXAMPLE 112 | 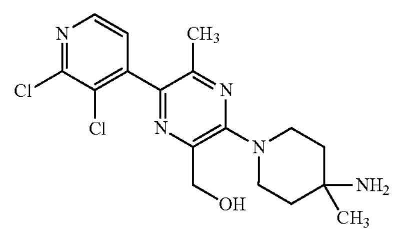 [SMILES: Cc1nc(N2CCC(C)(N)CC2)c(CO)nc1-c1ccnc(Cl)c1Cl] | 382.3 |
| EXAMPLE 113 | 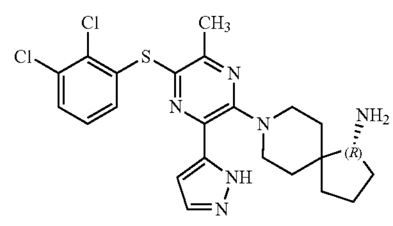 | 489.4 |
| EXAMPLE 114 | 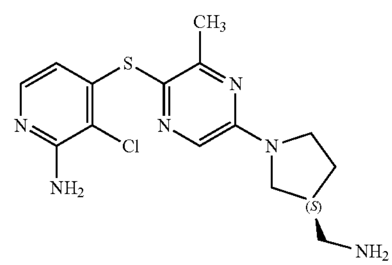 | 351.4 |

TABLE 1-continued

Examples 94-141

| Example | Structure | M + 1 found |
|---|---|---|
| EXAMPLE 115 | | 351.2 |
| EXAMPLE 116 | | 396.4 |
| EXAMPLE 117 | | 352.1 |
| EXAMPLE 118 | | 352.1 |
| EXAMPLE 119 | | 422.1 |
| EXAMPLE 120 | 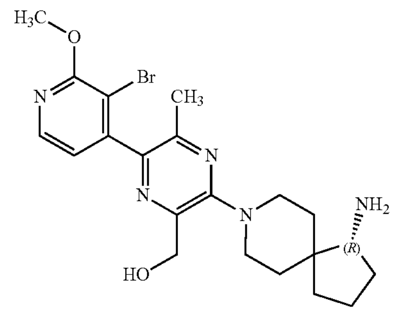 | 462.6 |
| EXAMPLE 121 | 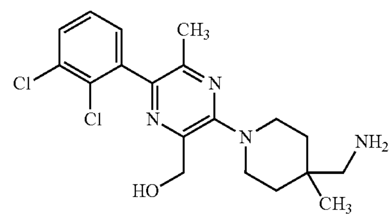 [SMILES: Cc1nc(N2CCC(C)(CN)CC2)c(CO)nc1-c1cccc(Cl)c1Cl] | 397.2 |
| EXAMPLE 122 | 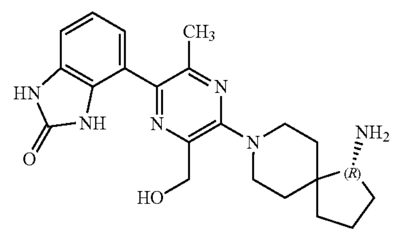 | 409.5 |
| EXAMPLE 123 | 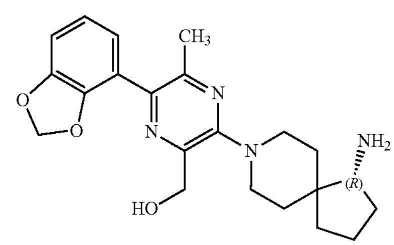 | 397.5 |
| EXAMPLE 124 | 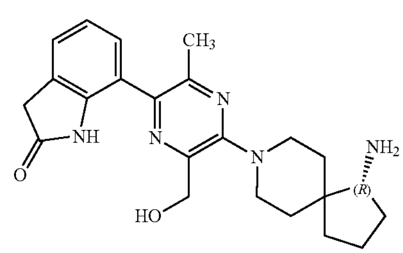 | 408.4 |
| EXAMPLE 125 | 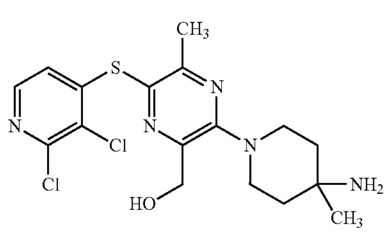 [SMILES: Cc1nc(N2CCC(C)(N)CC2)c(CO)nc1Sc1ccnc(Cl)c1Cl] | 414.2 |

TABLE 1-continued
Examples 94-141
| Example | Structure | M + 1 found |
|---|---|---|
| EXAMPLE 126 | 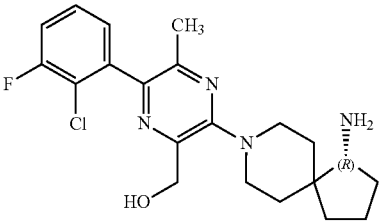 | 405.4 |
| EXAMPLE 127 | 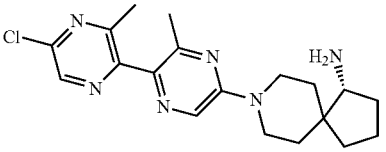 [SMILES: Cc1nc(Cl)cnc1-c1ncc(N2CCC3(CCC[C@H]3N)CC2)nc1C] | 333.1 |
| EXAMPLE 128 | 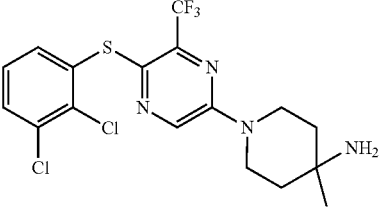 [SMILES: CC1(N)CCN(c2cnc(Sc3cccc(Cl)c3Cl)c(C(F)(F)F)n2)CC1] | 437.2 |
| EXAMPLE 129 | 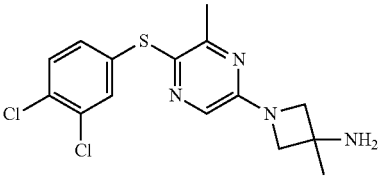 [SMILES: Cc1nc(N2CC(C)(N)C2)cnc1Sc1ccc(Cl)c(Cl)c1] | 355.6 |
| EXAMPLE 130 | 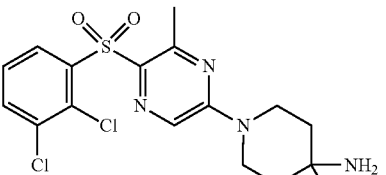 | 415.1 |
| EXAMPLE 131 | 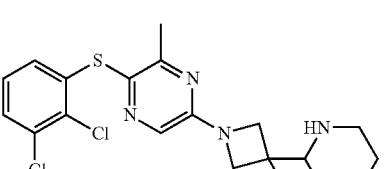 | 425.4 |
| EXAMPLE 132 | 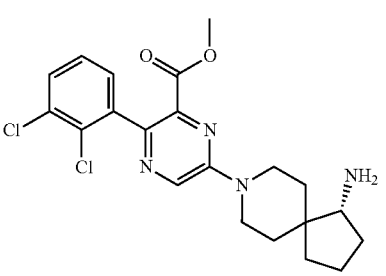 [SMILES: COC(=O)c1nc(N2CCC3(CCC[C@H]3N)CC2)cnc1-c1cccc(Cl)c1Cl] | 435.2 |
| EXAMPLE 133 | 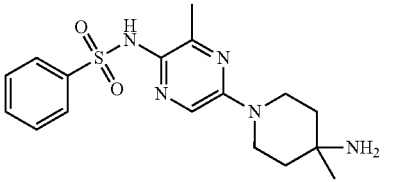 [SMILES: Cc1nc(N2CCC(C)(N)CC2)cnc1NS(=O)(=O)c1ccccc1] | 362.1 |
| EXAMPLE 134 | 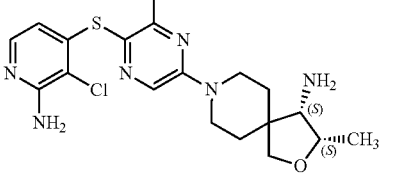 | 421.1 |
| EXAMPLE 135 | 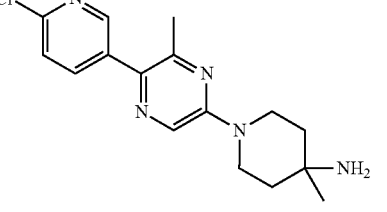 | 318.5 |
| EXAMPLE 136 | 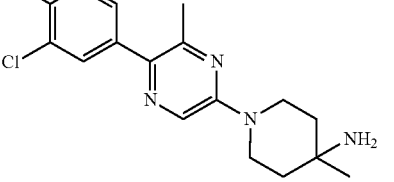 | 351.4 |
| EXAMPLE 137 | 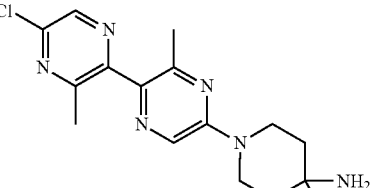 | 333.5 |
| EXAMPLE 138 | 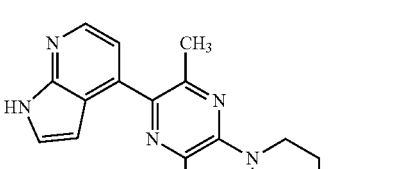 | 353.5 |
| EXAMPLE 139 | 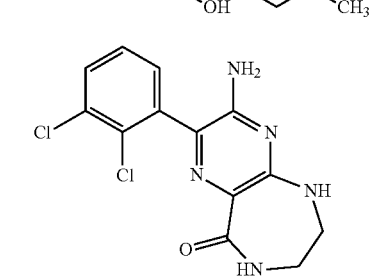 | 324.1 |

TABLE 1-continued

Examples 94-141

| Example | Structure | M + 1 found |
|---|---|---|
| EXAMPLE 140 | 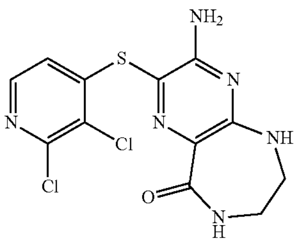 [SMILES: Nc1nc2c(nc1Sc1ccnc(Cl)c1Cl)C(=O)NCCN2] | 356.0 |
| EXAMPLE 141 | 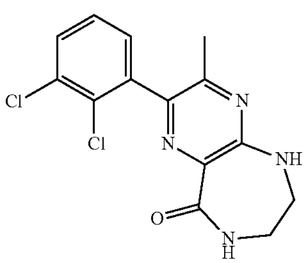 [SMILES: Cc1nc2c(nc1-c1cccc(Cl)c1Cl)C(=O)NCCN2] | 322.9 |

Synthesis of Examples 113 and 139-141

Example 113—Synthesis of (R)-8-(5-((2,3-dichlorophenyl)thio)-6-methyl-3-(1H-pyrazol-5-yl)pyrazin-2-yl)-8-azaspiro[4.5]decan-1-amine

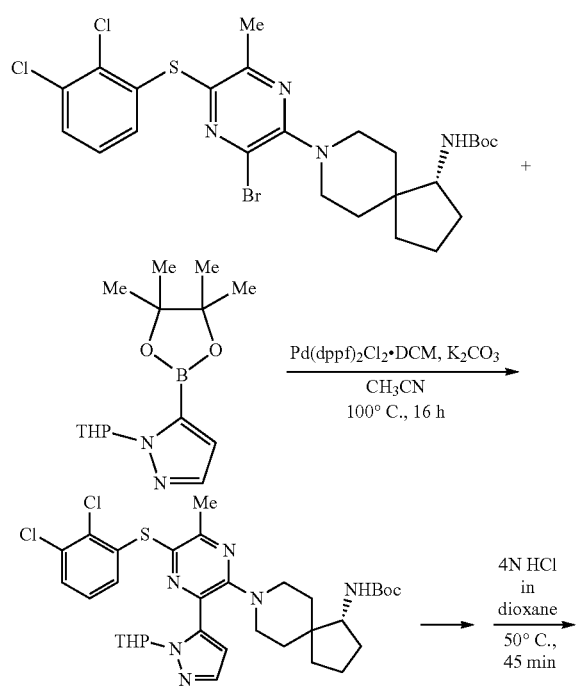

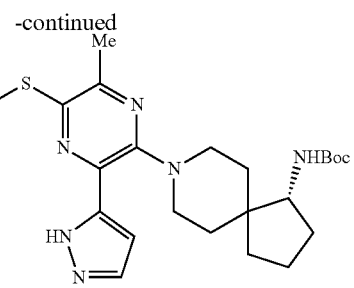

Step 1. Synthesis of tert-butyl ((1R)-8-(5-((2,3-dichlorophenyl)thio)-6-methyl-3-(1-(tetrahydro-2H-pyran-2-yl)-1H-pyrazol-5-yl)pyrazin-2-yl)-8-azaspiro[4.5]decan-1-yl)carbamate A vial was charged with (R)-tert-butyl (8-(3-bromo-5-((2,3-dichlorophenyl)thio)-6-methylpyrazin-2-yl)-8-azaspiro[4.5]decan-1-yl)carbamate (55 mg, 0.0913 mmol) (synthesized in the manner similar to Example 43), 1-(tetrahydro-2H-pyran-2-yl)-5-(4,4,5,5-tetramethyl-1,3,2-dioxaborolan-2-yl)-1H-pyrazole (51 mg, 0.183 mmol), Pd(dppf)Cl$_2$·DCM (14.9 mg, 0.0183 mmol, 0.2 equiv), potassium carbonate (50.4 mg, 0.365 mmol) and CH$_3$CN (912 μL). The resulting slurry was degassed and heated to 100° C. overnight. The reaction mixture was filtered and concentrated under reduced pressure. The crude product was purified by column chromatography to afford 18 mg (29%) of tert-butyl((1R)-8-(5-((2,3-dichlorophenyl)thio)-6-methyl-3-(1-(tetrahydro-2H-pyran-2-yl)-1H-pyrazol-5-yl)pyrazin-2-yl)-8-azaspiro[4.5]decan-1-yl)carbamate. LC-MS (ESI): m/z: [M+H] calculated for C$_{33}$H$_{42}$Cl$_2$N$_6$O$_3$S: 673.2; found 673.7.

Step 2. Synthesis of (R)-8-(5-((2,3-dichlorophenyl)thio)-6-methyl-3-(1H-pyrazol-5-yl)pyrazin-2-yl)-8-azaspiro[4.5]decan-1-amine To a solution of tert-butyl ((1R)-8-(5-((2,3-dichlorophenyl)thio)-6-methyl-3-(1-(tetrahydro-2H-pyran-2-yl)-1H-pyrazol-5-yl)pyrazin-2-yl)-8-azaspiro[4.5]decan-1-yl)carbamate (18 mg, 0.0267 mmol, 1 equiv) in dioxane (1 mL) was added HCl in dioxane (4N, 3 mL). The resulting solution was stirred for 1.5 hours at 50° C. and concentrated under reduced pressure. The crude product purified by preparative HPLC to afford (R)-8-(5-((2,3-dichlorophenyl)thio)-6-methyl-3-(1H-pyrazol-5-yl)pyrazin-2-yl)-8-azaspiro[4.5]decan-1-amine, (7.3 mg, 56%) as its formate salt. $^1$H NMR (500 MHz, DMSO-d$_6$) δ 8.40 (s, 1H), 7.70 (br s, 1H), 7.51 (dd, J=8.0, 1.4 Hz, 1H), 7.27 (t, J=8.0 Hz, 1H), 6.91 (dd, J=8.0, 1.4 Hz, 1H), 6.62 (br s, 1H), 3.00-2.78 (m, 3H), 2.46 (s, 3H), 1.91 (m, 1H), 1.78-1.60 (m, 4H), 1.59-1.47 (m, 1H), 1.48-1.37 (m, 2H), 1.28 (d, J=13.0 Hz, 1H), 1.21 (d, J=13.0 Hz, 1H). LC-MS (ESI): m/z: [M+H] calculated for C$_{23}$H$_{26}$Cl$_2$N$_6$S: 489.1; found 489.4.

Example 139—Synthesis of compound 3-amino-2-(2,3-dichlorophenyl)-5,6,7,8-tetrahydro-9H-pyrazino[2,3-e][1,4]diazepin-9-one

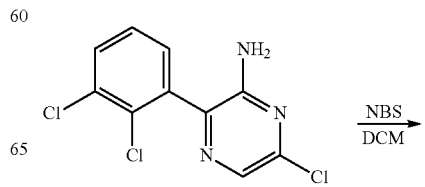

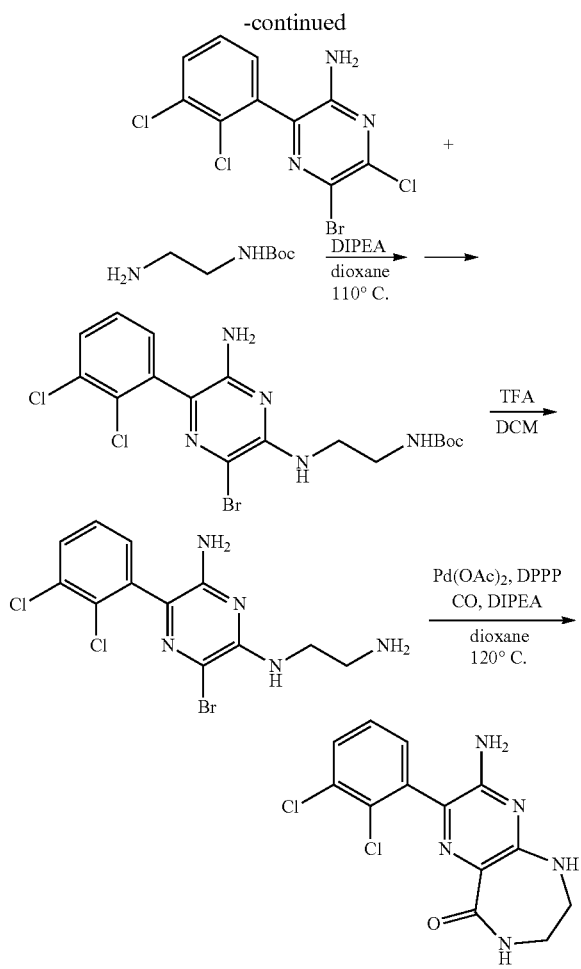

Step 1. Synthesis of 5-bromo-6-chloro-3-(2,3-dichlorophenyl)pyrazin-2-amine

To a solution of 6-chloro-3-(2,3-dichlorophenyl)pyrazin-2-amine (6 g, 21.8 mmol, 1 equiv) in DCM (15 mL) was added NBS (7.7 g, 43.7 mmol, 2 equiv). The mixture was stirred at 25° C. for 1 hour at which time TLC (Petroleum ether:Ethyl acetate=1/1) showed the reaction was complete. The reaction mixture was concentrated and the residue was passed through silica gel column (petroleum ether/ethyl acetate from 5/1 to 1/1) to give impure 5-bromo-6-chloro-3-(2,3-dichlorophenyl)pyrazin-2-amine (9.00 g, crude) as brown solid which was used without further purification. $^1$H NMR (400 MHz, CDCl$_3$) δ 7.61 (m, 1H) 7.40-7.33 (m, 2H) 4.83 (br, 2H).

Step 2. Synthesis of tert-butyl (2-((6-amino-3-bromo-5-(2,3-dichlorophenyl)pyrazin-2-yl)amino)ethyl)carbamate To a solution of impure 5-bromo-6-chloro-3-(2,3-dichlorophenyl)pyrazin-2-amine (1 g, 2.8 mmol) in dioxane (5.00 mL) was added compound tert-butyl (2-aminoethyl)carbamate (1.3 g, 8.4 mmol, 1.3 mL, 3 equiv) and DIPEA (1.4 g, 11.3 mmol, 1.9 mL, 4 equiv). The mixture was stirred at 110° C. for 4 hours, at which time LC-MS showed the reaction was complete. The reaction mixture was concentrated and the crude product was purified by silica gel chromatography (petroleum ether/ethyl acetate, 5:1) to give tert-butyl (2-((6-amino-3-bromo-5-(2,3-dichlorophenyl)pyrazin-2-yl)amino)ethyl)carbamate (600 mg, 1.26 mmol, 44% yield) as brown solid. $^1$H NMR (400 MHz, CDCl$_3$) δ 7.42 (dd, J=7.60 Hz, 1H) 7.25-7.19 (m, 2H) 4.83 (br, 2H) 3.46-3.57 (m, 2H) 3.46-3.34 (m, 2H) 1.39 (S, 9H). LC-MS (ESI): m/z: [M+H] calculated for C$_{17}$H$_{20}$BrCl$_2$N$_5$O$_2$: 476.0; found 476.0.

Step 3. Synthesis of N$^2$-(2-aminoethyl)-3-bromo-5-(2,3-dichlorophenyl)pyrazine-2,6-diamine To a solution of compound tert-butyl (2-((6-amino-3-bromo-5-(2,3-dichlorophenyl)pyrazin-2-yl)amino)ethyl)carbamate (600 mg, 1.2 mmol, 1 equiv) in DCM (6 mL) was added TFA (3 mL). The mixture was stirred at 25° C. for 2 hours, at which time TLC (Petroleum ether:Ethyl acetate=1/1) showed the reaction was complete. The reaction mixture was concentrated, MeOH (5 mL) added to the residue, and the pH adjusted to 7 by the addition of saturated aqueous NaHCO$_3$ (20 mL). The aqueous phase was extracted with ethyl acetate (3×5 mL). The combined organic phase was washed with brine (2×5 mL), dried (Na$_2$SO$_4$), filtered and concentrated to give N$^2$-(2-aminoethyl)-3-bromo-5-(2,3-dichlorophenyl)pyrazine-2,6-diamine (200 mg, 0.530 mmol, 42% yield) as brown solid which was used directly in the next reaction.

Step 4. Synthesis of 3-amino-2-(2,3-dichlorophenyl)-5,6,7,8-tetrahydro-9H-pyrazino[2,3-e][1,4]diazepin-9-one To a solution of compound N$^2$-(2-aminoethyl)-3-bromo-5-(2,3-dichlorophenyl)pyrazine-2,6-diamine (200 mg, 0.530 mmol, 1 equiv) in dioxane (80 mL) was added DIPEA (685 mg, 5.30 mmol, 926 μL, 10 equiv), 1,3-bis(diphenylphosphino)propane (218 mg, 0.530 mmol, 1 equiv), and Pd(OAc)$_2$ (59.5 mg, 0.265 mmol, 0.5 equiv). The reaction mixture was stirred at 120° C. under a CO environment at 2 MPa for 5 hours, at which time LC-MS analysis showed the reaction was complete. The reaction mixture was concentrated and the crude product purified by preparative HPLC to give compound 3-amino-2-(2,3-dichlorophenyl)-5,6,7,8-tetrahydro-9H-pyrazino[2,3-e][1,4]diazepin-9-one (2.3 mg, 0.007 mmol, 1.3% yield) as its formate salt. $^1$H NMR (400 MHz, CDCl$_3$) δ 9.02 (s, 1H) 7.54 (d, J=7.50 Hz, 1H) 7.38-7.30 (m, 2H) 4.78 (br s, 1H) 4.34 (br s, 1H) 4.12 (t, J=7.94 Hz, 2H) 3.62 (t, J=8.05 Hz, 2H). LC-MS (ESI) m/z: [M+H] calculated for C$_{13}$H$_{12}$Cl$_2$N$_5$O: 324.0; found 324.1.

Example 140—Synthesis of of 2-((2,3-dichloropyridin-4-yl)thio)-3-methyl-5,6,7,8-tetrahydro-9H-pyrazino[2,3-e][1,4]diazepin-9-one

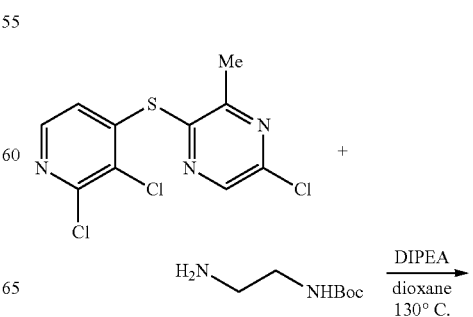

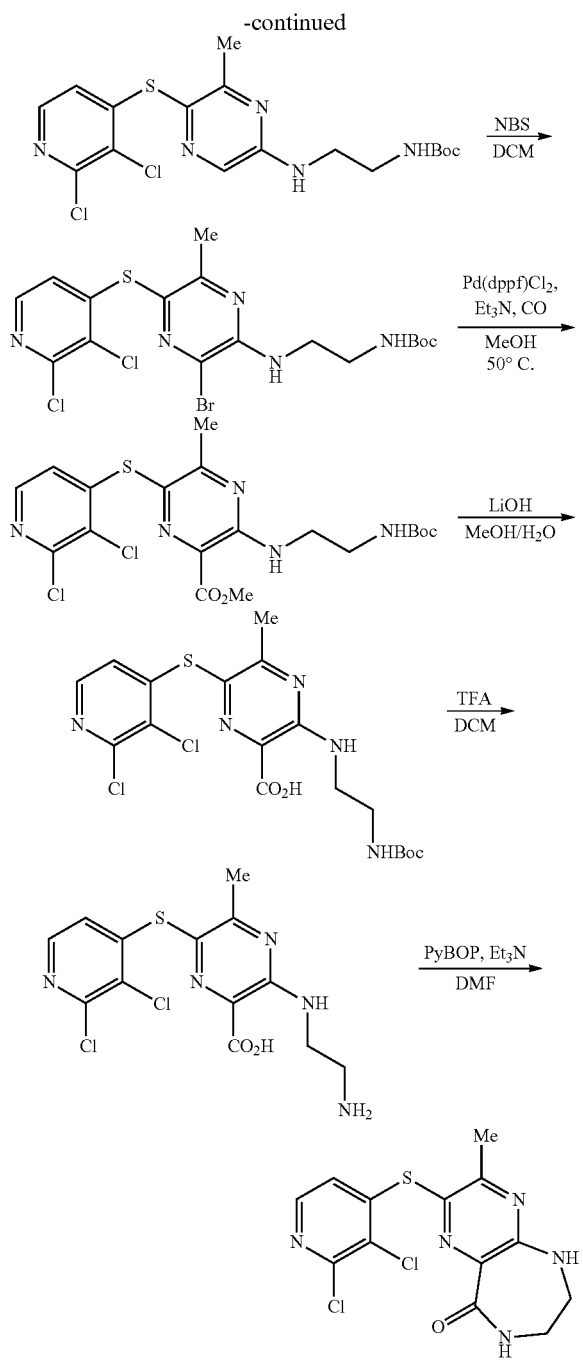

Step 1. Synthesis of tert-butyl (2-((5-((2,3-dichloropyridin-4-yl)thio)-6-methylpyrazin-2-yl)amino)ethyl)carbamate A mixture of 5-chloro-2-((2,3-dichloropyridin-4-yl)thio)-3-methylpyrazine (1.5 g, 4.9 mmol, 1 equiv) and tert-butyl (2-aminoethyl)carbamate (4.7 g, 29.3 mmol, 4.6 mL, 6 equiv) in DIPEA (6.0 mL, 33.6 mmol, 7 equiv) and dioxane (6.0 mL) was heated to 130° C. for 8 hours. TLC (Petroleum ether/EtOAc=1/1) showed the reaction was complete. The mixture was concentrated to give a residue which was purified by silica gel column (DCM/MeOH, 30:1) to give tert-butyl (2-((5-((2,3-dichloropyridin-4-yl)thio)-6-methylpyrazin-2-yl)amino)ethyl) carbamate (1.6 g, 76% yield) as a yellow oil.

Step 2. Synthesis of tert-butyl (2-((3-bromo-5-((2,3-dichloropyridin-4-yl)thio)-6-methylpyrazin-2-yl)amino)ethyl)carbamate To a solution of compound tert-butyl (2-((5-((2,3-dichloropyridin-4-yl)thio)-6-methylpyrazin-2-yl)amino)ethyl)carbamate (1.6 g, 3.7 mmol, 1 equiv) in DCM (20.0 mL) was added NBS (1.3 g, 7.4 mmol, 2 equiv) and the resulting mixture was stirred at room temperature for 1 hour at which time TLC (petroleum ether/EtOAc=2/1) showed the reaction was complete. The reaction mixture was concentrated to give a residue, the residue was purified by silica gel column (Petroleum ether/EtOAc=8/1) to give tert-butyl (2-((3-bromo-5-((2,3-dichloropyridin-4-yl)thio)-6-methylpyrazin-2-yl)amino)ethyl)carbamate (1.6 g, 3.1 mmol, 84% yield) as a yellow solid.
$^1$H NMR (400 MHz, CDCl$_3$) δ 7.99 (d, J=5.6 Hz, 1H), 6.47 (d, J=5.6 Hz, 1H), 6.34 (br, s, 1H), 4.96 (br s, 1H), 3.60-3.46 (m, 4H), 2.45 (s, 3H), 1.45 (s, 9H).

Step 3. Synthesis of methyl 3-((2-((tert-butoxycarbonyl)amino)ethyl)amino)-6-((2,3-dichloropyridin-4-yl)thio)-5-methylpyrazine-2-carboxylate To a solution of compound tert-butyl (2-((3-bromo-5-((2,3-dichloropyridin-4-yl)thio)-6-methylpyrazin-2-yl)amino)ethyl)carbamate (1.5 g, 3.0 mmol, 1 equiv) in THF (5.0 mL) and MeOH (5.0 mL) was added Pd(dppf)Cl$_2$ (109 mg, 0.147 mmol, 0.05 equiv), triethylamine (894 mg, 8.8 mmol, 1.2 mL, 2.9 equiv). The resulting mixture was stirred at 50° C. under a CO environment (50 psi) for 15 hours, at which time TLC (Petroleum ether/EtOAc=2/1) showed the reaction was complete. The mixture was concentrated to give a residue, the residue was purified by silica gel column chromatography (Petroleum ether:Ethyl acetate=5:1) to give methyl 3-((2-((tert-butoxycarbonyl)amino)ethyl)amino)-6-((2,3-dichloropyridin-4-yl)thio)-5-methylpyrazine-2-carboxylate (700 mg, 1.4 mmol, 48% yield) as a yellow solid.

Step 4. Synthesis of 3-((2-((tert-butoxycarbonyl)amino)ethyl)amino)-6-((2,3-dichloropyridin-4-yl)thio)-5-methylpyrazine-2-carboxylic acid To a solution of compound methyl 3-((2-((tert-butoxycarbonyl)amino)ethyl)amino)-6-((2,3-dichloropyridin-4-yl)thio)-5-methylpyrazine-2-carboxylate (700 mg, 1.4 mmol) in MeOH (10.0 mL) and water (2.0 mL) was added LiOH.H$_2$O (180 mg, 4.3 mmol, 3 equiv). The mixture was stirred at room temperature for 4 hours, at which time LC-MS analysis showed the reaction was complete. The pH of the mixture was adjusted with 1N HCl to approximately 4 and extracted with EtOAc (3×10 mL). The combined organic extracts were washed with brine (1×10 mL), dried (Na$_2$SO$_4$), filtered and concentrated to give 3-((2-((tert-butoxycarbonyl)amino)ethyl)amino)-6-((2,3-dichloropyridin-4-yl)thio)-5-methylpyrazine-2-carboxylic acid (500 mg, 1.1 mmol, 74% yield) as a yellow solid. LC-MS (ESI): m/z: [M-56+H] calculated for C$_{14}$H$_{13}$Cl$_2$N$_5$O$_4$S: 418.0; found 417.9 (M-56+H).

Step 5. Synthesis of 3-((2-aminoethyl)amino)-6-((2,3-dichloropyridin-4-yl)thio)-5-methylpyrazine-2-carboxylic acid A mixture of compound 3-((2-((tert-butoxycarbonyl)amino)ethyl)amino)-6-((2,3-dichloropyridin-4-yl)thio)-5- methylpyrazine-2-carboxylic acid (500 mg, 1.1 mmol, 1 equiv) in TFA (1.0 mL) and DCM (2.0 mL) was stirred at room temperature for 1 hour, at which time TLC (DCM/MeOH, 10:1) showed the reaction was complete. The mixture was concentrated to give 3-((2-aminoethyl)amino)-6-((2,3-dichloropyridin-4-yl)thio)-5-methylpyrazine-2-carboxylic acid (500 mg, 1.0 mmol, 98% yield, TFA salt) as a yellow solid.

Step 6. Synthesis of 2-((2,3-dichloropyridin-4-yl)thio)-3-methyl-5,6,7,8-tetrahydro-9H-pyrazino[2,3-e][1,4]diazepin-9-one To a solution of compound 3-((2-aminoethyl)amino)-6-((2,3-dichloropyridin-4-yl)thio)-5-methylpyrazine-2-carboxylic acid (50 mg, 0.102 mmol, 1 equiv) in DMF (5.0 mL) was added trimethylamine (62.2 mg, 0.614 mmol, 85 μL, 6 equiv) and PYBOP (107 mg, 0.205 mmol, 2 equiv). The resulting mixture was stirred at room temperature for 2 hours, at which time LC-MS analysis showed the reaction was complete. The mixture was poured into water (5 mL), and the product extracted with EtOAc (3×5 mL) The combined organic extracts were washed with water (1×5 mL), brine (1×5 mL), dried ($Na_2SO_4$), and concentrated to give the crude product which was purified by preparative HPLC to give 2-((2,3-dichloropyridin-4-yl)thio)-3-methyl-5,6,7,8-tetrahydro-9H-pyrazino[2,3-e][1,4]diazepin-9-one (1.7 mg, 0.0042 mmol, 4.1% yield, HCOOH) as its formate salt. $^1$H NMR (400 MHz, $CDCl_3$) δ 7.98 (d, J=5.6 Hz, 1H), 6.71 (d, J=5.6 Hz, 1H), 5.59-3.50 (m, 4H), 2.44 (s, 3H). LC-MS (ESI) m/z: [M+H] calculated for $C_{13}H_{12}Cl_2N_5OS$: 356.01; found 356.0.

Example 141—Synthesis of 2-(2,3-dichlorophenyl)-3-methyl-5,6,7,8-tetrahydro-9H-pyrazino[2,3-e][1,4]diazepin-9-one

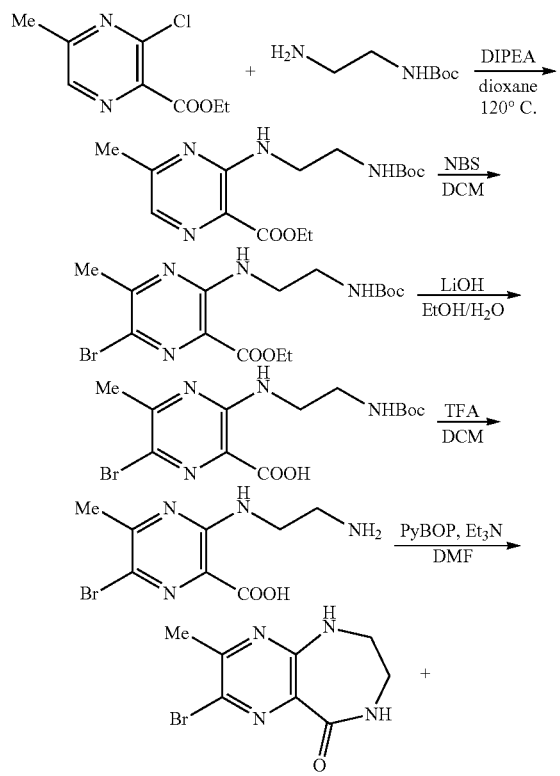

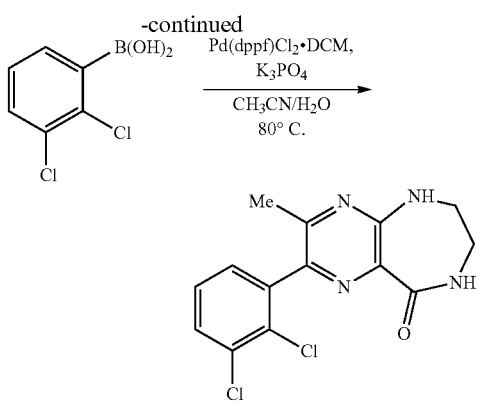

Step 1. Synthesis of ethyl 3-((2-((tert-butoxycarbonyl)amino)ethyl)amino)-5-methylpyrazine-2-carboxylate To a solution of ethyl 3-chloro-5-methylpyrazine-2-carboxylate (3.00 g, 14.95 mmol, 1.00 equiv) in dioxane (30.00 mL) was added tert-butyl (2-aminoethyl)carbamate (5.99 g, 37.38 mmol, 5.87 mL, 2.50 equiv) and DIPEA (5.80 g, 44.85 mmol, 7.83 mL, 3.00 equiv) at 20° C. The mixture was stirred at 120° C. for 1.5 hours. TLC (Petroleum ether/EtOAc=3/1) showed the reaction was complete. The mixture was concentrated to give the crude product which was purified by silica gel column (petroleum ether/EtOAc=6/1) to give ethyl 3-((2-((tert-butoxycarbonyl)amino)ethyl)amino)-5-methylpyrazine-2-carboxylate (2.20 g, 45%) as a yellow solid. $^1$H NMR (400 MHz, $CDCl_3$) δ 8.14 (s, 1H), 7.79 (s, 1H), 5.14 (s, 1H), 4.40-4.45 (m, 2H), 3.63-3.67 (m, 2H), 3.37-3.39 (m, 2H), 2.40 (s, 3H), 1.41 (s, 12H). LC-CMS (ESI) m/z: [M+H] calculated for $C_{15}H_{25}N_4O_4$: 325.1; found 325.1.

Step 2. Synthesis of ethyl 6-bromo-3-((2-((tert-butoxycarbonyl)amino)ethyl)amino)-5-methylpyrazine-2-carboxylate To a solution of ethyl 3-((2-((tert-butoxycarbonyl)amino)ethyl)amino)-5-methylpyrazine-2-carboxylate (1.00 g, 3.08 mmol, 1.00 equiv) in DCM (10.00 mL) was added NBS (822 mg, 4.62 mmol, 1.50 equiv) at 20° C., the mixture was stirred at 35° C. for 1 hour. TLC (Petroleum ether/EtOAc=3/1, $R_f$=0.7) showed the reaction was complete. The mixture was concentrated to give a residue. The residue was purified by silica gel column (petroleum ether/EtOAc=10/1) to give ethyl 6-bromo-3-((2-((tert-butoxycarbonyl)amino)ethyl)amino)-5-methylpyrazine-2-carboxylate (1.10 g, 88% yield) as a yellow solid. $^1$H NMR (400 MHz, $CDCl_3$) δ 8.09 (s, 1H), 4.94 (s, 1H), 4.39-4.44 (m, 2H), 3.62-3.63 (s, 1H), 3.37-3.38 (m, 1H), 2.56 (s, 3H), 1.42 (s, 12H). LC-MS (ESI): m/z: [M+H] calculated for $C_{15}H_{24}BrN_4O_4$: 403.1; found 403.1.

Step 3. Synthesis of 6-bromo-3-((2-((tert-butoxycarbonyl)amino)ethyl)amino)-5-methylpyrazine-2-carboxylic acid To a solution of ethyl 6-bromo-3-((2-((tert-butoxycarbonyl)amino)ethyl)amino)-5-methylpyrazine-2-carboxylate (600 mg, 1.49 mmol, 1.00 equiv) in ethanol (5.00 mL) was added LiOH.H₂O (187 mg, 4.47 mmol, 3.00 equiv) and H₂O (1.50 mL) at 10° C. The mixture was stirred at 35° C. for 1 hour. TLC (Petroleum ether/EtOAc=3/1) showed the reaction was complete. The pH of the mixture was adjusted with 2M HCl to about 4 and extracted with EtOAc (3×15 mL). The combined organic extract was washed with brine (15 mL), dried over Na₂SO₄, and concentrated to give 6-bromo-3-((2-((tert-butoxycarbonyl)amino)ethyl)amino)-5-methyl-pyrazine-2-carboxylic acid (400 mg, 71%) as a white solid.

Step 4. Synthesis of 3-((2-aminoethyl)amino)-6-bromo-5-methylpyrazine-2-carboxylic acid A solution of 6-bromo-3-((2-((tert-butoxycarbonyl)amino)ethyl)amino)-5-methylpyrazine-2-carboxylic acid (300 mg, 0.799 mmol, 1.00 equiv) in TFA (3.00 mL) and DCM (3.00 mL) was stirred at 20° C. for 2 hours. HPLC showed the reaction was complete. The mixture was concentrated to give 3-((2-aminoethyl)amino)-6-bromo-5-methylpyrazine-2-carboxylic acid (300 mg, 0.770 mmol, 96%) as a white solid. ¹H NMR (400 MHz, MeOH-d₄) δ 3.80-3.82 (m, 2H), 3.18-3.21 (m, 2H), 2.58 (s, 3H).

Step 5. Synthesis of 2-bromo-3-methyl-5,6,7,8-tetrahydro-9H-pyrazino[2,3-e][1,4]diazepin-9-one To a solution of 3-((2-aminoethyl)amino)-6-bromo-5-methylpyrazine-2-carboxylic acid (2.00 g, 7.27 mmol, 1.00 equiv) in DMF (200 mL) was added triethylamine (3.68 g, 36.35 mmol, 5.04 mL, 5.00 equiv), then PYBOP (7.57 g, 14.54 mmol, 2.00 equiv) was added to the mixture at 15° C., the mixture was stirred at 35° C. for 6 hours. LC-MS showed the reaction was complete. The mixture was concentrated and the residue was purified by silica gel column (DCM:MeOH=40:1) to give 2-bromo-3-methyl-5,6,7,8-tetrahydro-9H-pyrazino[2,3-e][1,4]diazepin-9-one (450 mg, 1.75 mmol, 24%) as a yellow solid. LC-MS (ESI) m/z: [M+H] calculated for C₈H₁₀BrN₄O: 257.0; found 257.0.

Step 6. Synthesis of 2-(2,3-dichlorophenyl)-3-methyl-5,6,7,8-tetrahydro-9H-pyrazino[2,3-e][1,4]diazepin-9-one To a solution of 2-bromo-3-methyl-5,6,7,8-tetrahydro-9H-pyrazino[2,3-e][1,4]diazepin-9-one (150 mg, 0.583 mmol, 1.00 equiv) in acetonitrile (4.00 mL) and water (1.00 mL) was added 2,3-dichlorophenylboronic acid (167 mg, 0.875 mmol, 1.50 equiv), Pd(dppf)Cl₂.DCM (47.65 mg, 0.058 mmol, 0.10 equiv) and K₃PO₄ (371 mg, 1.75 mmol, 3.00 equiv) under N₂. The mixture was heated by microwave to 80° C. for 1.5 hours, at which time LC-MS analysis showed the reaction was complete. The mixture was extracted with EtOAc (3×10 mL), the organic portion was washed with brine (1×10 mL), dried over Na₂SO₄, and concentrated to give a residue. The residue was purified by preparative HPLC to give 2-(2,3-dichlorophenyl)-3-methyl-5,6,7,8-tetrahydro-9H-pyrazino[2,3-e][1,4]diazepin-9-one (63 mg, 0.195 mmol, 33% yield) as the parent. ¹H NMR (400 MHz, CDCl₃) δ 7.62-7.59 (m, 1H), 7.39-7.38 (m, 1H), 3.60-3.55 (m, 4H), 2.21 (s, 3H). LC-MS (ESI) m/z: [M+H] calculated for C₁₄H₁₃Cl₂N₄O: 323.04; found 323.0.

Examples 142-309

Example 142—Synthesis of 3-{5-[(1R)-1-amino-8-azaspiro[4.5]decan-8-yl]-6-(hydroxymethyl)-3-methylpyrazin-2-yl}-6-chloro-2-fluorobenzonitrile

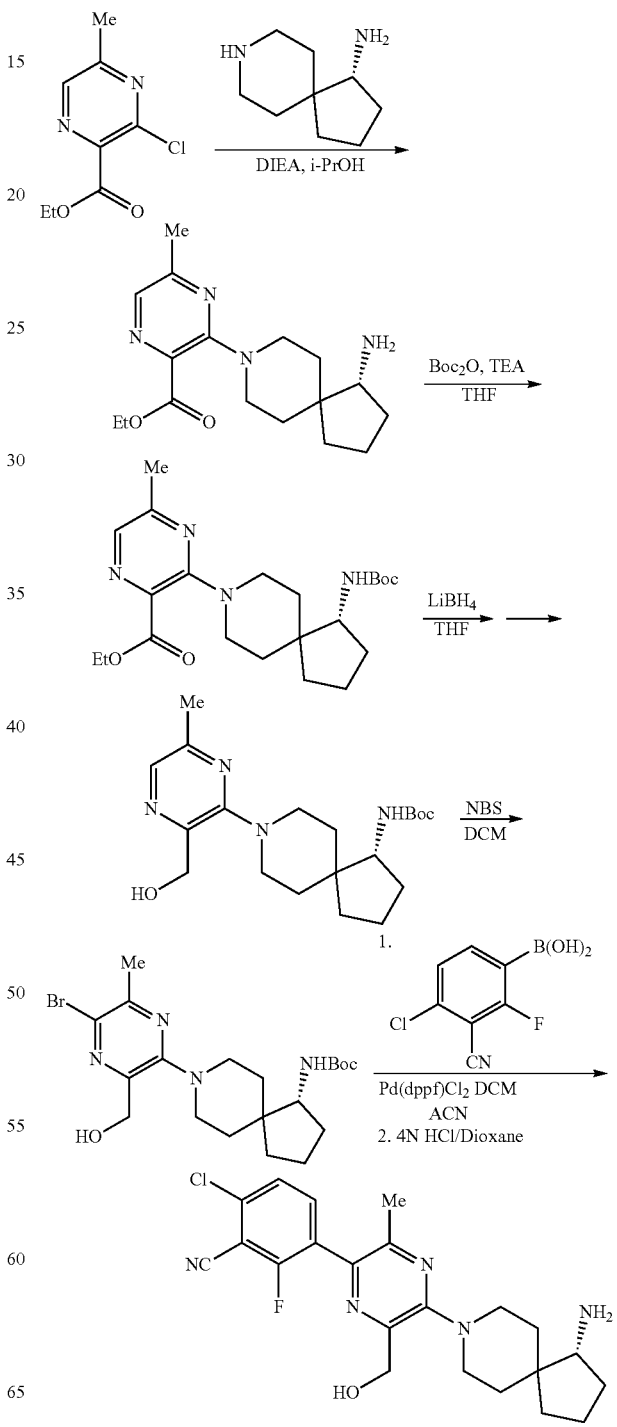

Step 1. Ethyl (R)-3-(1-((tert-butoxycarbonyl) amino)-8-azaspiro[4.5]decan-8-yl)-5-methylpyrazine-2-carboxylate To a solution of compound (R)-8-azaspiro[4.5]decan-1-amine mono HCl salt (31 g, 200.9 mmol) in i-PrOH (300 mL) was added compound ethyl 3-chloro-5-methylpyrazine-2-carboxylate (40.3 g, 200.9 mmol), and DIPEA (181.8 g, 1.4 mol, 245.0 mL). The resulting mixture was stirred at 85° C. for 16 hours. Upon completion, reaction mixture was concentrated to give compound ethyl (R)-3-(1-((tert-butoxycarbonyl)amino)-8-azaspiro[4.5]decan-8-yl)-5-methylpyrazine-2-carboxylate (64 g, crude) as a yellow oil. The resulting product was used submitted to the next step without further purification.

Step 2. Ethyl (R)-3-(1-((tert-butoxycarbonyl) amino)-8-azaspiro[4.5]decan-8-yl)-5-methylpyrazine-2-carboxylate To a solution of compound ethyl (R)-3-(1-amino-8-azaspiro[4.5]decan-8-yl)-5-methylpyrazine-2-carboxylate (64 g, 201.0 mmol) in THF (300 mL) was added Boc$_2$O (87.74 g, 401.99 mmol, 92.35 mL) and TEA (20.3 g, 201.0 mmol, 27.9 mL). The resulting mixture was stirred at at 25° C. for 2 hours, and concentrated under reduced pressure. The residue was purified by column chromatography to give ethyl (R)-3-(1-((tert-butoxycarbonyl)amino)-8-azaspiro[4.5]decan-8-yl)-5-methylpyrazine-2-carboxylate (66 g, crude) as a yellow oil. $^1$H NMR (400 MHz, CDCl$_3$) δ ppm 7.89-7.69 (m, 1H) 4.40 (q, J=7.20 Hz, 3H) 3.87-3.66 (m, 4H) 3.18-3.04 (m, 2H) 2.67-2.58 (m, 1H) 2.39 (s, 3H) 2.12-1.98 (m, 2H) 1.81-1.58 (m, 6H) 1.51 (s, 9H) 1.40-1.36 (m, 3H). LC-MS (ESI) m/z: [M+H] calculated for C$_{22}$H$_{35}$N$_4$O$_4$: 419.26; found 419.4.

Step 3. tert-butyl (R)-(8-(3-(hydroxymethyl)-6-methylpyrazin-2-yl)-8-azaspiro[4.5]decan-1-yl)carbamate To a solution of ethyl (R)-3-(1-((tert-butoxycarbonyl) amino)-8-azaspiro[4.5]decan-8-yl)-5-methylpyrazine-2-carboxylate (48 g, 114.6 mmol) in THF (500 mL) was added LiBH$_4$ (2M, 114.6 mL) at 0° C., the resulting mixture was stirred at 40° C. for 2 hours, and 30 mL of water and 100 mL of MeOH were added to the reaction mixture, followed by concentration under reduced pressure. The residue was purified by column chromatography to give tert-butyl (R)-(8-(3-(hydroxymethyl)-6-methylpyrazin-2-yl)-8-azaspiro[4.5]decan-1-yl)carbamate (25.8 g, 68.5 mmol, 59.7% yield) as a yellow oil. $^1$H NMR (400 MHz, CDCl$_3$) δ ppm 8.01-7.79 (m, 1H) 4.65-4.60 (m, 2H) 4.46-4.39 (m, 1H) 4.10 (q, J=7.06 Hz, 1H) 3.80-3.69 (m, 1H) 3.46 (s, 3H) 3.40-3.30 (m, 2H) 3.01-2.87 (m, 2H) 2.66-2.52 (m, 1H) 2.46-2.29 (m, 3H) 2.10-1.99 (m, 2H) 1.86-1.61 (m, 7H) 1.44-1.42 (m, 9H). LC-MS (ESI) m/z: [M+H] calculated for C$_{20}$H$_{33}$N$_4$O$_3$: 377.25; found 377.1.

Step 4. Synthesis of (R)-tert-butyl(8-(5-bromo-3-(hydroxymethyl)-6-methylpyrazin-2-yl)-8-azaspiro[4.5]decan-1-yl)carbamate To a solution of tert-butyl (R)-(8-(3-(hydroxymethyl)-6-methylpyrazin-2-yl)-8-azaspiro[4.5]decan-1-yl)carbamate (9 g, 23.9 mmol) in DCM (120 mL) was added NBS (5.11 g, 28.69 mmol) at 0° C. for period of 5 minutes. Upon completion, reaction mixture was warmed up to room temperature, quenched with saturated Na$_2$SO$_3$ (50 mL), extracted by EtOAc (100 mL×2), and concentrated under reduced pressure. The residue was purified by silica gel chromatography to afford (R)-tert-butyl(8-(5-bromo-3-(hydroxymethyl)-6-methylpyrazin-2-yl)-8-azaspiro[4.5]decan-1-yl)carbamate (6.8 g, 62.9%) as a yellow oil. $^1$H NMR (400 MHz, CDCl$_3$) δ ppm 4.62 (s, 2H) 4.40 (br d, J=8.82 Hz, 1H) 3.76 (br d, J=8.38 Hz, 1H) 3.59 (br s, 1H) 3.36 (br t, J=12.46 Hz, 2H) 3.07-2.87 (m, 2H) 2.59-2.44 (m, 3H) 2.14-1.98 (m, 1H) 1.82 (td, J=12.57, 3.97 Hz, 1H) 1.77-1.56 (m, 5H) 1.45 (s, 9H). LC-MS (ESI) m/z: [M+H] calculated for C$_{20}$H$_{32}$BrN$_4$O$_3$: 455.16; found 455.1.

Step 5. Synthesis of (R)-3-(5-(1-amino-8-azaspiro[4.5]decan-8-yl)-6-(hydroxymethyl)-3-methylpyrazin-2-yl)-6-chloro-2-fluorobenzonitrile A mixture of (R)-tert-butyl(8-(5-bromo-3-(hydroxymethyl)-6-methylpyrazin-2-yl)-8-azaspiro[4.5]decan-1-yl) carbamate (11 mg, 0.22 mmol), (4-chloro-3-cyano-2-fluorophenyl) boronic acid (53 mg, 0.26 mmol), and potassium carbonate (121 mg, 0.88 mmol) in acetonitrile (5 mL) was degassed and Pd(dppf)Cl$_2$.DCM (18 mg, 0.021 mmol) was added. The reaction mixture was stirred at 100° C. for 1 hour in a sealed vessel, filtered, and concentrated under reduced pressure. The residue was dissolved in 5 mL of 4N HCl/Dioxane, heated to 50° C. for 1 hour, and concentrated under reduced pressure. Purification by prep-HPLC resulted in (R)-3-(5-(1-amino-8-azaspiro[4.5]decan-8-yl)-6-(hydroxymethyl)-3-methylpyrazin-2-yl)-6-chloro-2-fluorobenzo nitrile (12 mg, 13% yield). $^1$H NMR (500 MHz, MeOH-d$_4$) δ 8.57 (s, 1H), 7.88 (t, J=8.2 Hz, 1H), 7.64 (dd, J=8.4, 0.9 Hz, 1H), 4.70 (s, 2H), 3.79 (dd, J=29.1, 13.5 Hz, 2H), 3.16 (ddd, J=14.2, 12.0, 3.7 Hz, 3H), 2.36 (d, J=2.2 Hz, 3H), 2.26-2.13 (m, 1H), 1.97-1.74 (m, 6H), 1.68 (dt, J=15.1, 7.9 Hz, 1H), 1.54 (dd, J=24.1, 13.0 Hz, 2H). LC-MS (ESI): m/z: [M+H] calculated for C$_{22}$H$_{25}$ClFN$_5$O: 430.9; found 430.4.

The following examples were synthesized in the manner similar to Examples 43 and 142.

TABLE 2

Examples 143-190

| Example | Structure | M + 1 found |
|---|---|---|
| EXAMPLE 143 | 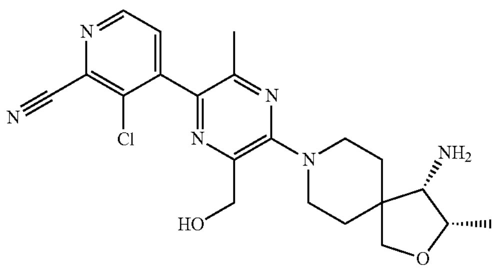 [SMILES: Cc1nc(N2CCC3(CC2)CO[C@@H](C)[C@H]3N)c(CO)nc1-c1ccnc(C#N)c1Cl] | 429.17 |
| EXAMPLE 144 | 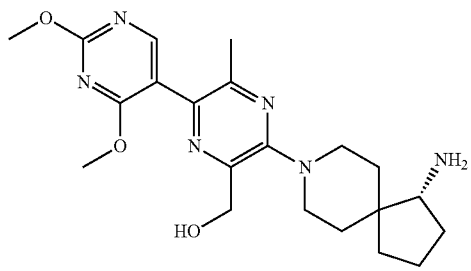 [SMILES: COc1ncc(-c2nc(CO)c(N3CCC4(CCC[C@H]4N)CC3)nc2C)c(OC)n1] | 415.24 |
| EXAMPLE 145 | 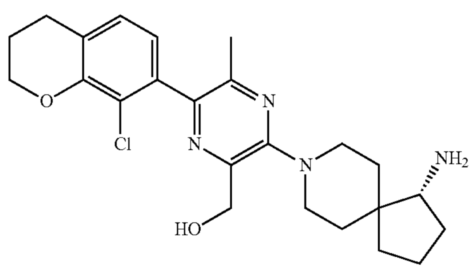 [SMILES: Cc1nc(N2CCC3(CCC[C@H]3N)CC2)c(CO)nc1-c1ccc2c(c1Cl)OCCC2] | 484.1 |
| EXAMPLE 146 | 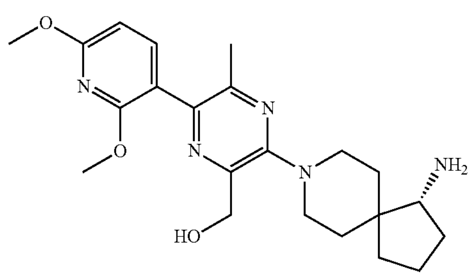 [SMILES: COc1ccc(-c2nc(CO)c(N3CCC4(CCC[C@H]4N)CC3)nc2C)c(OC)n1] | 414.24 |
| EXAMPLE 147 | 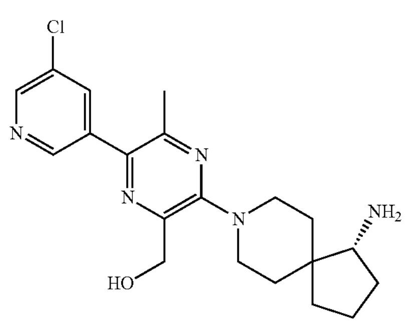 [SMILES: Cc1nc(N2CCC3(CCC[C@H]3N)CC2)c(CO)nc1-c1cncc(Cl)c1] | 388.18 |

TABLE 2-continued

Examples 143-190

| Example | Structure | M + 1 found |
|---|---|---|
| EXAMPLE 148 | 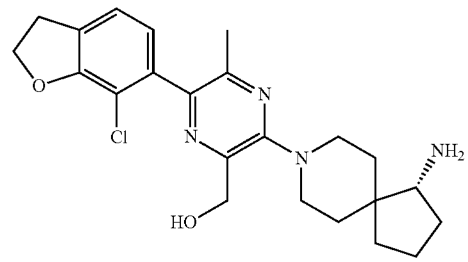 [SMILES: Cc1nc(N2CCC3(CCC[C@H]3N)CC2)c(CO)nc1-c1ccc2c(c1Cl)OCC2] | 429.2 |
| EXAMPLE 149 | 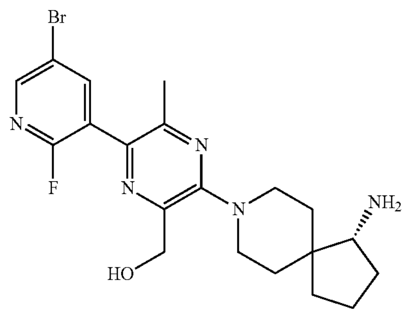 [SMILES: Cc1nc(N2CCC3(CCC[C@H]3N)CC2)c(CO)nc1-c1cc(Br)cnc1F] | 450.12 |
| EXAMPLE 150 | 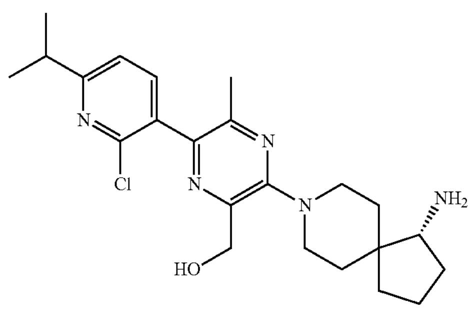 [SMILES: Cc1nc(N2CCC3(CCC[C@H]3N)CC2)c(CO)nc1-c1ccc(C(C)C)nc1Cl] | 430.23 |
| EXAMPLE 151 | 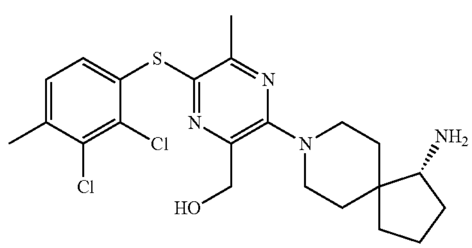 [SMILES: Cc1ccc(Sc2nc(CO)c(N3CCC4(CCC[C@H]4N)CC3)nc2C)c(Cl)c1Cl] | 467.14 |
| EXAMPLE 152 | 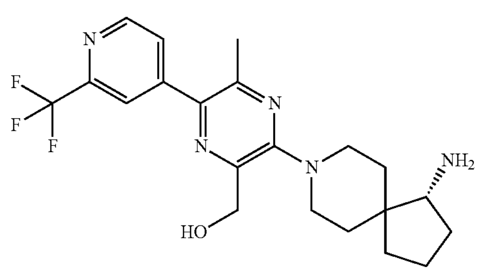 [SMILES: Cc1nc(N2CCC3(CCC[C@H]3N)CC2)c(CO)nc1-c1ccnc(C(F)(F)F)c1] | 422.21 |

TABLE 2-continued

Examples 143-190

| Example | Structure | M + 1 found |
|---|---|---|
| EXAMPLE 153 | 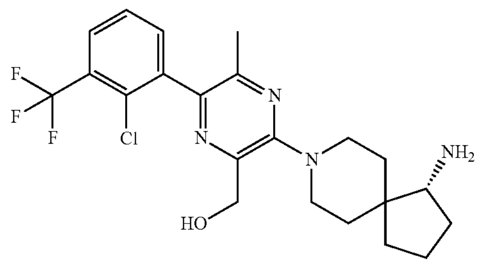 [SMILES: Cc1nc(N2CCC3(CCC[C@H]3N)CC2)c(CO)nc1-c1cccc(C(F)(F)F)c1Cl] | 455.17 |
| EXAMPLE 154 | 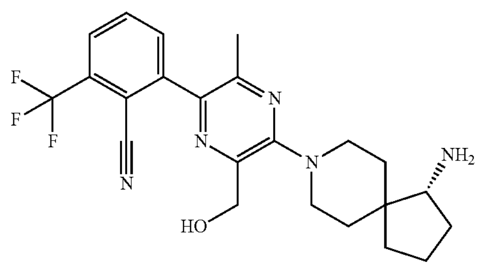 [SMILES: Cc1nc(N2CCC3(CCC[C@H]3N)CC2)c(CO)nc1-c1cccc(C(F)(F)F)c1C#N] | 446.21 |
| EXAMPLE 155 | 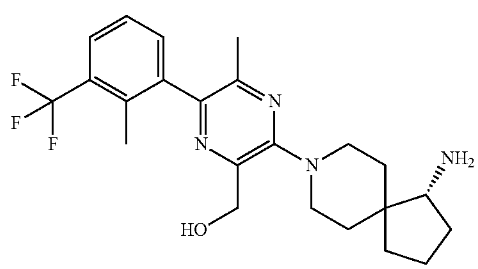 [SMILES: Cc1nc(N2CCC3(CCC[C@H]3N)CC2)c(CO)nc1-c1cccc(C(F)(F)F)c1C] | 435.23 |
| EXAMPLE 156 | 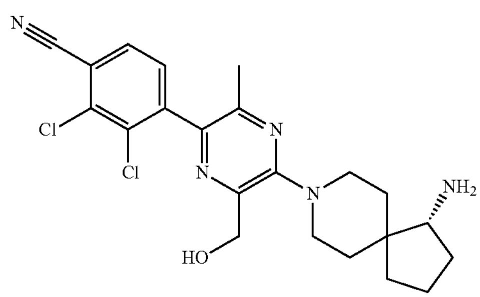 [SMILES: Cc1nc(N2CCC3(CCC[C@H]3N)CC2)c(CO)nc1-c1ccc(C#N)c(Cl)c1Cl] | 446.15 |
| EXAMPLE 157 | 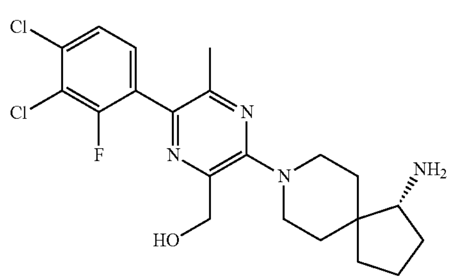 [SMILES: Cc1nc(N2CCC3(CCC[C@H]3N)CC2)c(CO)nc1-c1ccc(Cl)c(Cl)c1F] | 439.28 |

TABLE 2-continued

Examples 143-190

| Example | Structure | M + 1 found |
|---|---|---|
| EXAMPLE 158 | 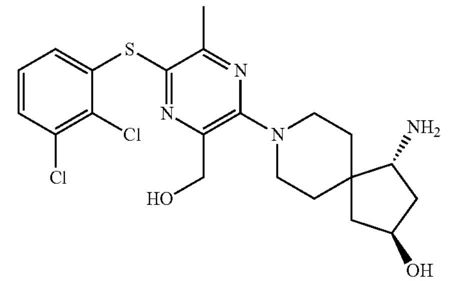 [SMILES: Cc1nc(N2CCC3(CC2)C[C@H](O)C[C@H]3N)c(CO)nc1Sc1cccc(Cl)c1Cl] | 469.12 |
| EXAMPLE 159 | 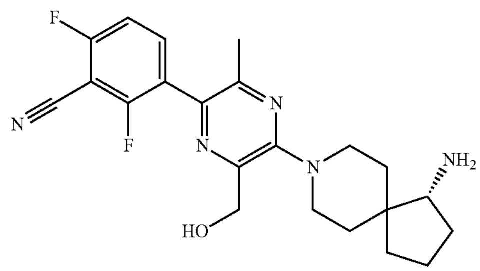 [SMILES: Cc1nc(N2CCC3(CCC[C@H]3N)CC2)c(CO)nc1-c1ccc(F)c(C#N)c1F] | 414.2 |
| EXAMPLE 160 | 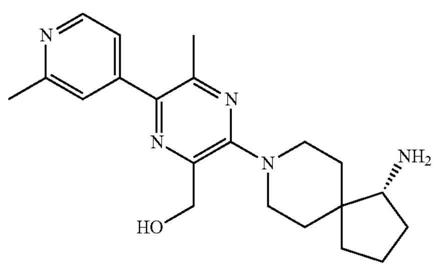 [SMILES: Cc1cc(-c2nc(CO)c(N3CCC4(CCC[C@H]4N)CC3)nc2C)ccn1] | 368.24 |
| EXAMPLE 161 | 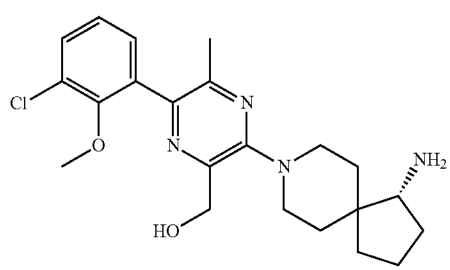 [SMILES: COc1c(Cl)cccc1-c1nc(CO)c(N2CCC3(CCC[C@H]3N)CC2)nc1C] | 417.2 |
| EXAMPLE 162 | 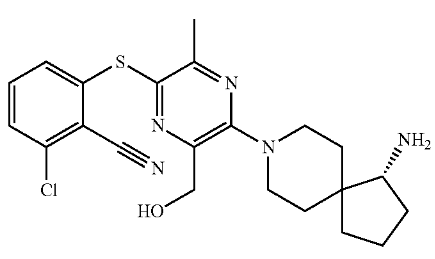 [SMILES: Cc1nc(N2CCC3(CCC[C@H]3N)CC2)c(CO)nc1Sc1cccc(Cl)c1C#N] | 444.15 |

TABLE 2-continued

Examples 143-190

| Example | Structure | M + 1 found |
|---|---|---|
| EXAMPLE 163 | 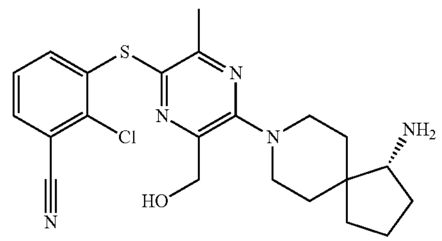 [SMILES: Cc1nc(N2CCC3(CCC[C@H]3N)CC2)c(CO)nc1Sc1cccc(C#N)c1Cl] | 444.15 |
| EXAMPLE 164 | 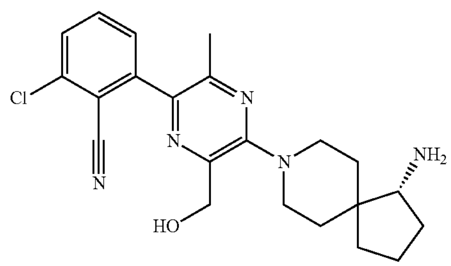 [SMILES: Cc1nc(N2CCC3(CCC[C@H]3N)CC2)c(CO)nc1-c1cccc(Cl)c1C#N] | 412.18 |
| EXAMPLE 165 | 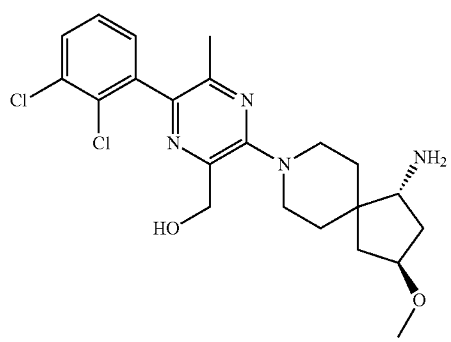 [SMILES: CO[C@@H]1C[C@@H](N)C2(CCN(c3nc(C)c(-c4cccc(Cl)c4Cl)nc3CO)CC2)C1] | 451.2 |
| EXAMPLE 166 | 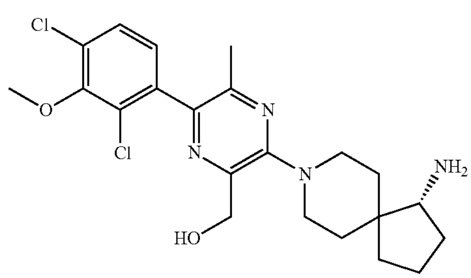 [SMILES: COc1c(Cl)ccc(-c2nc(CO)c(N3CCC4(CCC[C@H]4N)CC3)nc2C)c1Cl] | 451.16 |
| EXAMPLE 167 | 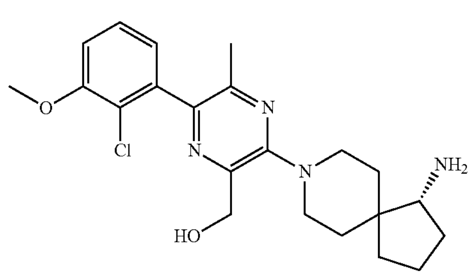 [SMILES: COc1cccc(-c2nc(CO)c(N3CCC4(CCC[C@H]4N)CC3)nc2C)c1Cl] | 417.2 |

TABLE 2-continued

Examples 143-190

| Example | Structure | M + 1 found |
|---|---|---|
| EXAMPLE 168 | 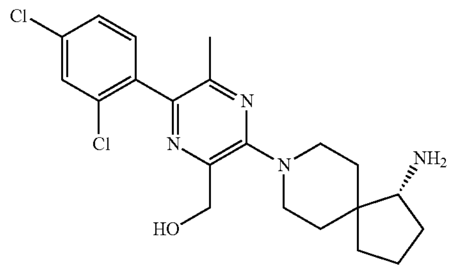 [SMILES: Cc1nc(N2CCC3(CCC[C@H]3N)CC2)c(CO)nc1-c1ccc(Cl)cc1Cl] | 421.15 |
| EXAMPLE 169 | 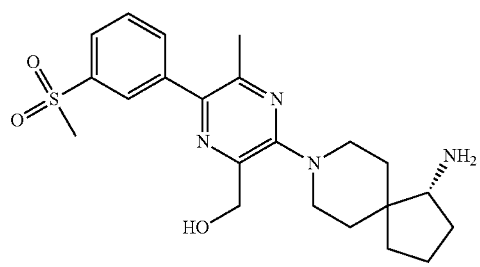 [SMILES: Cc1nc(N2CCC3(CCC[C@H]3N)CC2)c(CO)nc1-c1cccc(S(C)(=O)=O)c1] | 431.2 |
| EXAMPLE 170 | 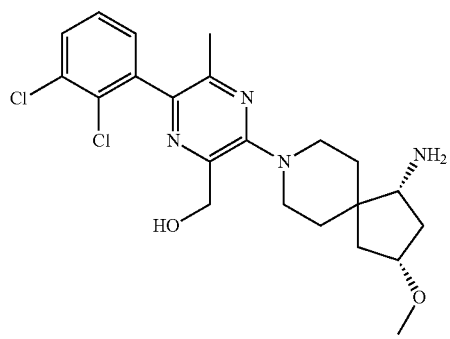 [SMILES: CO[C@H]1C[C@@H](N)C2(CCN(c3nc(C)c(-c4cccc(Cl)c4Cl)nc3CO)CC2)C1] | 451.16 |
| EXAMPLE 171 | 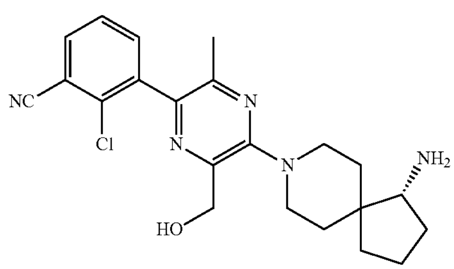 [SMILES: Cc1nc(N2CCC3(CCC[C@H]3N)CC2)c(CO)nc1-c1cccc(C#N)c1Cl] | 412.18 |
| EXAMPLE 172 | 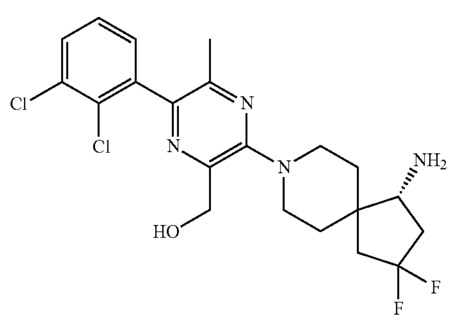 [SMILES: Cc1nc(N2CCC3(CC2)CC(F)(F)C[C@H]3N)c(CO)nc1-c1cccc(Cl)c1Cl] | 457.13 |

TABLE 2-continued

Examples 143-190

| Example | Structure | M + 1 found |
|---|---|---|
| EXAMPLE 173 | 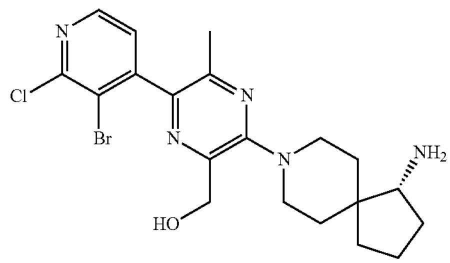 [SMILES: Cc1nc(N2CCC3(CCC[C@H]3N)CC2)c(CO)nc1-c1ccnc(Cl)c1Br] | 466.09 |
| EXAMPLE 174 | 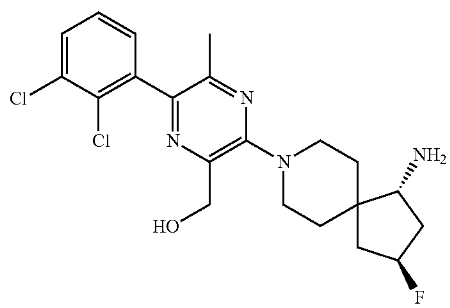 [SMILES: Cc1nc(N2CCC3(CC2)C[C@H](F)C[C@H]3N)c(CO)nc1-c1cccc(Cl)c1Cl] | 439.14 |
| EXAMPLE 175 | 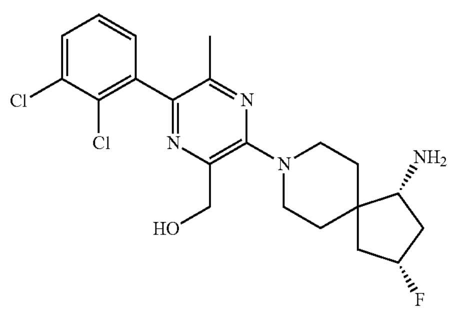 [SMILES: Cc1nc(N2CCC3(CC2)C[C@@H](F)C[C@H]3N)c(CO)nc1-c1cccc(Cl)c1Cl] | 439.14 |
| EXAMPLE 176 | 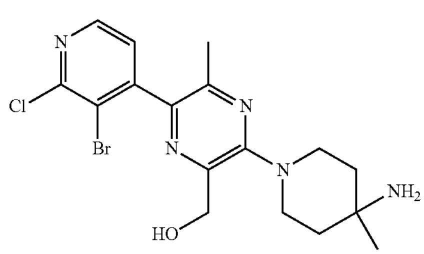 [SMILES: Cc1nc(N2CCC(C)(N)CC2)c(CO)nc1-c1ccnc(Cl)c1Br] | 426.06 |
| EXAMPLE 177 | 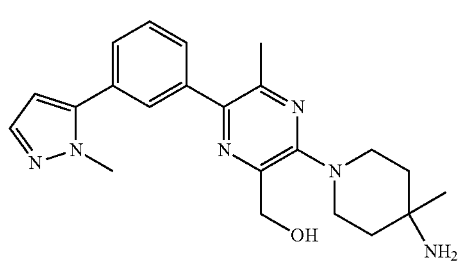 [SMILES: Cc1nc(N2CCC(C)(N)CC2)c(CO)nc1-c1cccc(-c2ccnn2C)c1] | 393.23 |

TABLE 2-continued

Examples 143-190

| Example | Structure | M + 1 found |
|---|---|---|
| EXAMPLE 178 | 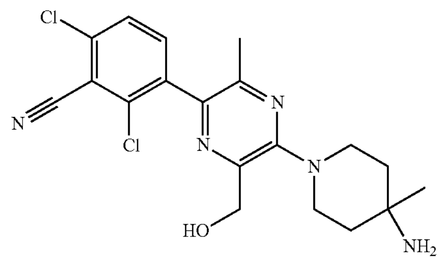 [SMILES: Cc1nc(N2CCC(C)(N)CC2)c(CO)nc1-c1ccc(Cl)c(C#N)c1Cl] | 406.11 |
| EXAMPLE 179 | 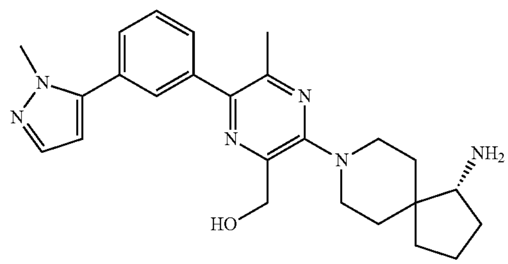 [SMILES: Cc1nc(N2CCC3(CCC[C@H]3N)CC2)c(CO)nc1-c1cccc(-c2ccnn2C)c1] | 433.26 |
| EXAMPLE 180 | 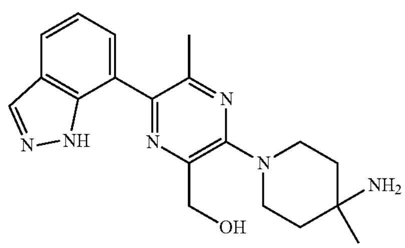 [SMILES: Cc1nc(N2CCC(C)(N)CC2)c(CO)nc1-c1cccc2cn[nH]c12] | 353.1 |
| EXAMPLE 181 | 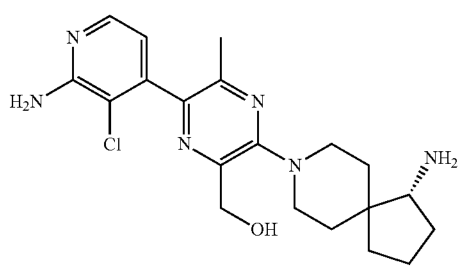 [SMILES: Cc1nc(N2CCC3(CCC[C@H]3N)CC2)c(CO)nc1-c1ccnc(N)c1Cl] | 403.19 |
| EXAMPLE 182 | 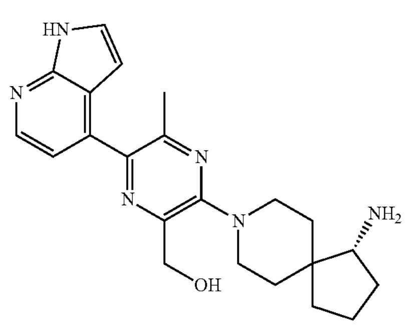 [SMILES: Cc1nc(N2CCC3(CCC[C@H]3N)CC2)c(CO)nc1-c1ccnc2[nH]ccc12] | 394.23 |

TABLE 2-continued

Examples 143-190

| Example | Structure | M + 1 found |
|---|---|---|
| EXAMPLE 183 | 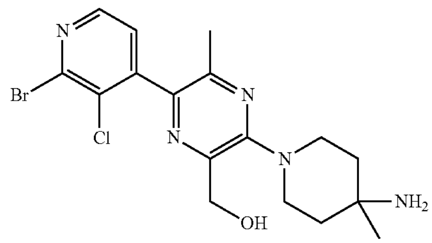 [SMILES: Cc1nc(N2CCC(C)(N)CC2)c(CO)nc1-c1ccnc(Br)c1Cl] | 426.06 |
| EXAMPLE 184 | 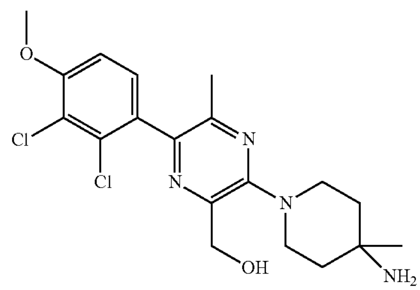 [SMILES: COc1ccc(-c2nc(CO)c(N3CCC(C)(N)CC3)nc2C)c(Cl)c1Cl] | 411.13 |
| EXAMPLE 185 | 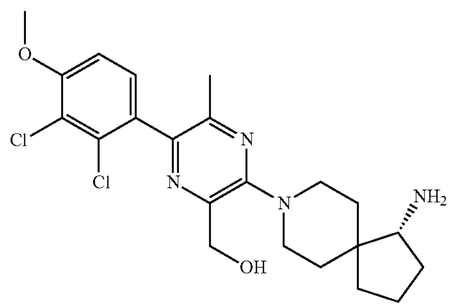 [SMILES: COc1ccc(-c2nc(CO)c(N3CCC4(CCC[C@H]4N)CC3)nc2C)c(Cl)c1Cl] | 451.16 |
| EXAMPLE 186 | 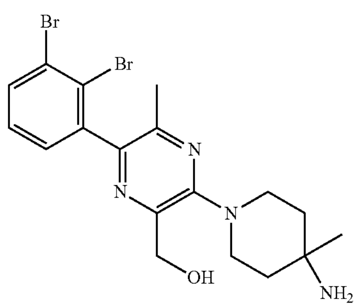 [SMILES: Cc1nc(N2CCC(C)(N)CC2)c(CO)nc1-c1cccc(Br)c1Br] | 469.02 |
| EXAMPLE 187 | 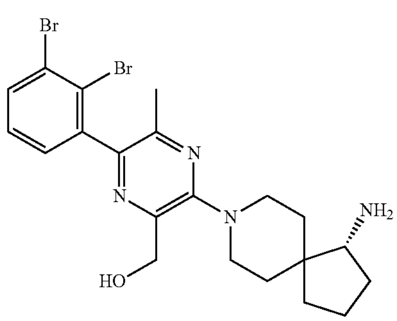 [SMILES: Cc1nc(N2CCC3(CCC[C@H]3N)CC2)c(CO)nc1-c1cccc(Br)c1Br] | 509.05 |

TABLE 2-continued

Examples 143-190

| Example | Structure | M + 1 found |
|---|---|---|
| EXAMPLE 188 | 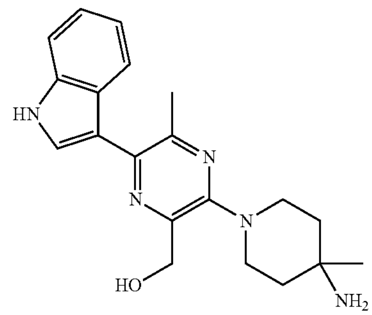 [SMILES: Cc1nc(N2CCC(C)(N)CC2)c(CO)nc1-c1c[nH]c2ccccc12] | 351.454 |
| EXAMPLE 189 | 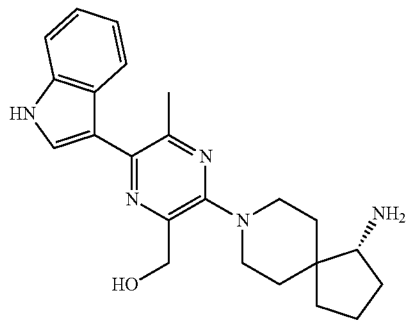 [SMILES: Cc1nc(N2CCC3(CCC[C@H]3N)CC2)c(CO)nc1-c1c[nH]c2ccccc12] | 392.24 |
| EXAMPLE 190 | 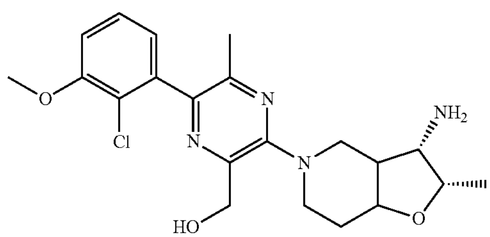 | 433.3 |

Example 191—Synthesis of {3-[(1R)-1-amino-8-azaspiro[4.5]decan-8-yl]-6-(2,3-dichloro-4-methylphenyl)-5-methylpyrazin-2-yl}methanol

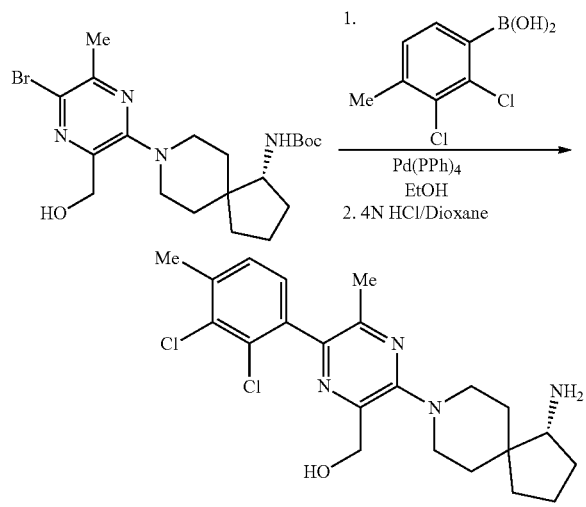

A mixture of (R)-tert-butyl(8-(5-bromo-3-(hydroxymethyl)-6-methylpyrazin-2-yl)-8-azaspiro[4.5]decan-1-yl) carbamate (50 mg, 0.11 mmol), (2,3-dichloro-4-methylphenyl)boronic acid (34 mg, 0.16 mmol), and potassium carbonate (45 mg, 0.33 mmol) in ethanol (2 mL) was degassed and Pd(PPh$_3$)$_4$ (6.3 mg, 0.005 mmol) was added. The reaction mixture was stirred at 80° C. for 4 hours in a sealed vessel, filtered, and concentrated under reduced pressure. The residue was dissolved in 5 mL of 4N HCl/Dioxane, heated to 40° C. for 1 hour, and concentrated under reduced pressure. Purification by prep-HPLC resulted in {3-[(1R)-1-amino-8-azaspiro[4.5]decan-8-yl]-6-(2,3-dichloro-4-methylphenyl)-5-methylpyrazin-2-yl}methanol (12 mg, 24.5% yield). $^1$H NMR (400 MHz, MeOH-d$_4$) δ 8.57 (s, 1H), 7.40 (dt, J=7.8, 0.8 Hz, 1H), 7.26 (d, J=7.7 Hz, 1H), 4.69 (s, 2H), 3.72 (dd, J=26.3, 13.3 Hz, 2H), 3.19-3.08 (m, 3H), 2.52 (d, J=0.7 Hz, 3H), 2.26 (d, J=1.3 Hz, 3H), 2.23-2.13 (m, 1H), 1.89 (dt, J=12.2, 3.9 Hz, 2H), 1.85-1.72 (m, 3H), 1.68 (dt, J=15.1, 7.7 Hz, 1H), 1.54 (dd, J=24.1, 13.0 Hz, 2H). LC-MS (ESI): m/z: [M+H] calculated for C$_{22}$H$_{28}$Cl$_2$N$_4$O: 435.1; found 435.4.

The following examples were synthesized in the manner similar to Example 191.

TABLE 3
Examples 192-203
| Example | Structure | M + 1 found |
|---|---|---|
| EXAMPLE 192 | 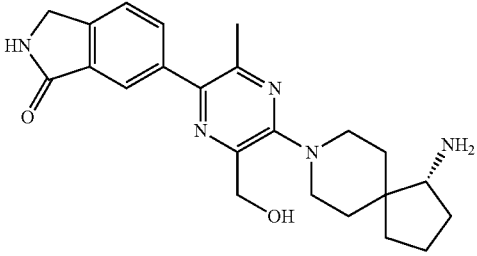 [SMILES: Cc1nc(N2CCC3(CCC[C@H]3N)CC2)c(CO)nc1-c1ccc2c(c1)C(=O)NC2] | 408.2 |
| EXAMPLE 193 | 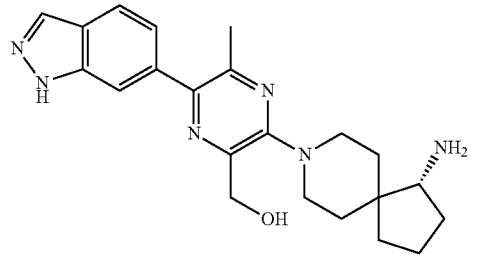 [SMILES: Cc1nc(N2CCC3(CCC[C@H]3N)CC2)c(CO)nc1-c1ccc2cn[nH]c2c1] | 393.3 |
| EXAMPLE 194 | 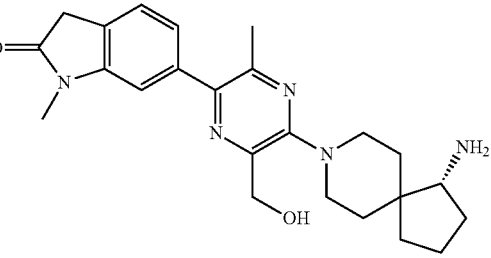 | 422.3 |
| EXAMPLE 195 | 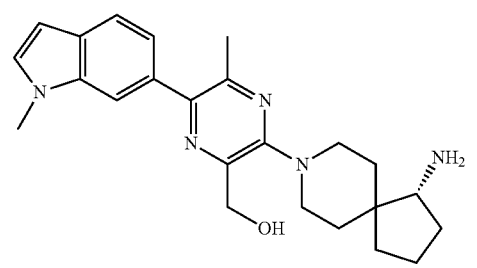 [SMILES: Cc1nc(N2CCC3(CCC[C@H]3N)CC2)c(CO)nc1-c1ccc2ccn(C)c2c1] | 406.2 |
| EXAMPLE 196 | 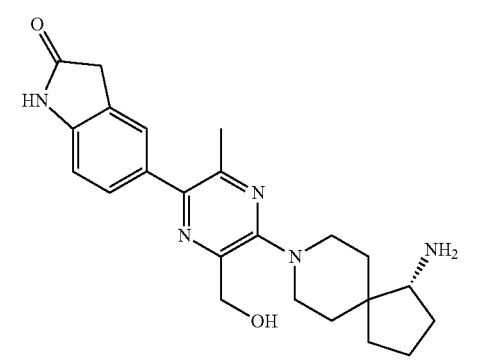 [SMILES: Cc1nc(N2CCC3(CCC[C@H]3N)CC2)c(CO)nc1-c1ccc2c(c1)CC(=O)N2] | 408.1 |

TABLE 3-continued

Examples 192-203

| Example | Structure | M + 1 found |
|---|---|---|
| EXAMPLE 197 | 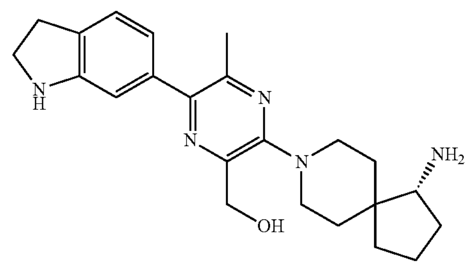 [SMILES: Cc1nc(N2CCC3(CCC[C@H]3N)CC2)c(CO)nc1-c1ccc2c(c1)NCC2] | 394.4 |
| EXAMPLE 198 | 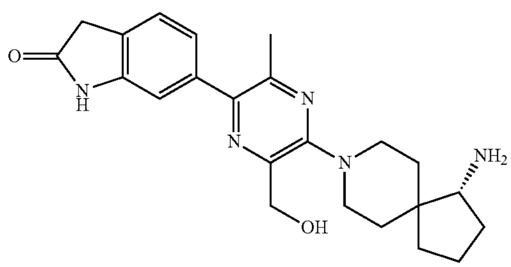 [SMILES: Cc1nc(N2CCC3(CCC[C@H]3N)CC2)c(CO)nc1-c1ccc2c(c1)NC(=O)C2] | 408.1 |
| EXAMPLE 199 | 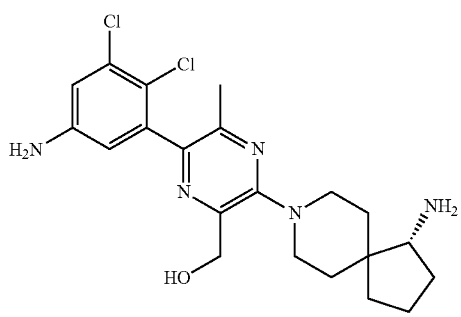 [SMILES: Cc1nc(N2CCC3(CCC[C@H]3N)CC2)c(CO)nc1-c1cc(N)cc(Cl)c1Cl] | 436.1 |
| EXAMPLE 200 | 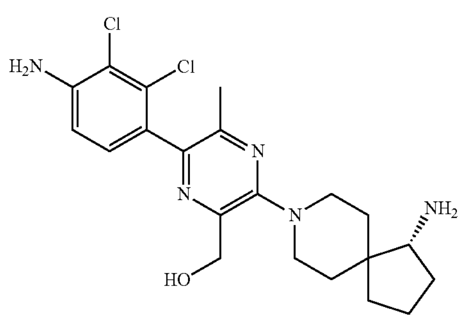 [SMILES: Cc1nc(N2CCC3(CCC[C@H]3N)CC2)c(CO)nc1-c1cnc(N)c(Cl)c1Cl] | 436.3 |
| EXAMPLE 201 | 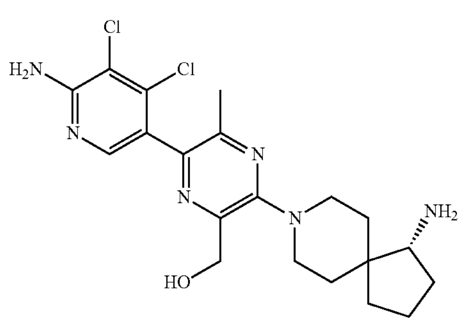 | 437.1 |

TABLE 3-continued
Examples 192-203
| Example | Structure | M + 1 found |
|---|---|---|
| EXAMPLE 202 | 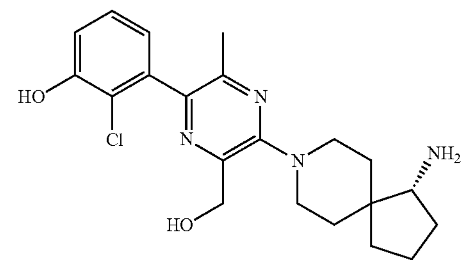 [SMILES: Cc1nc(N2CCC3(CCC[C@H]3N)CC2)c(CO)nc1-c1cccc(O)c1Cl] | 437.4 |
| EXAMPLE 203 | 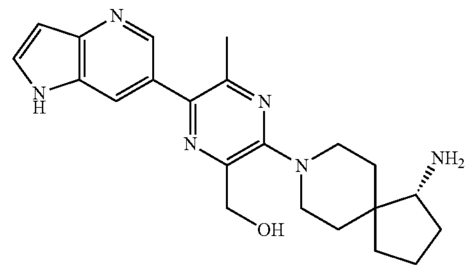 [SMILES: Cc1nc(N2CCC3(CCC[C@H]3N)CC2)c(CO)nc1-c1cnc2cc[nH]c2c1] | 393.1 |
Examples 204 and 205—Synthesis of (3-(4-amino-4-methylpiperidin-1-yl)-6-(4-chloro-1H-indol-6-yl)-5-methylpyrazin-2-yl)methanol and 1-(5-(4-chloro-1H-indol-6-yl)-6-methylpyrazin-2-yl)-4-methylpiperidin-4-amine
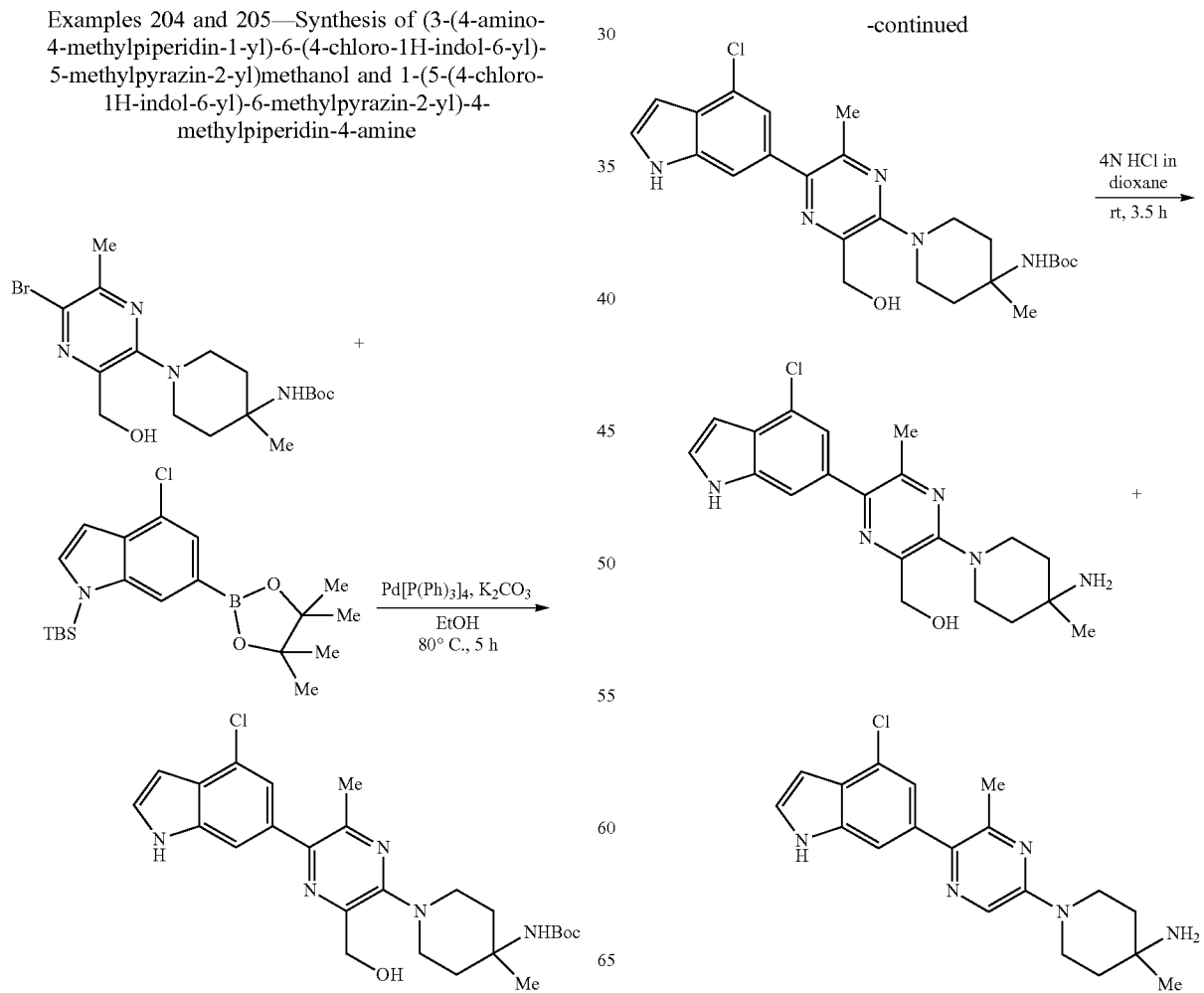

Step 1. Synthesis of tert-butyl (1-(5-(4-chloro-1H-indol-6-yl)-3-(hydroxymethyl)-6-methylpyrazin-2-yl)-4-methylpiperidin-4-yl)carbamate A vial was charged with tert-butyl (1-(5-bromo-3-(hydroxymethyl)-6-methylpyrazin-2-yl)-4-methylpiperidin-4-yl)carbamate (50 mg, 0.120 mmol, 1 equiv), 1-(tert-butyldimethylsilyl)-4-chloro-6-(4,4,5,5-tetramethyl-1,3,2-dioxaborolan-2-yl)-1H-indole (71 mg, 0.180 mmol, 1.5 equiv), tetrakis(triphenylphosphine)palladium (7 mg, 0.00602 mmol, 0.05 equiv), potassium carbonate (50 mg, 0.361 mmol, 3 equiv), and a stir bar. Degassed ethanol (800 μL) was added, the vial capped, and the headspace evacuated and filled with nitrogen three times. The vial was placed in an 80° C. oil bath for 5 hours. The reaction mixture was filtered through a pad of Celite and the filtrate concentrated. The crude product was purified by column chromatography to afford 50 mg (86%) of tert-butyl(1-(5-(4-chloro-1H-indol-6-yl)-3-(hydroxymethyl)-6-methylpyrazin-2-yl)-4-methylpiperidin-4-yl)carbamate. LC-MS (ESI): m/z: [M+H] calculated for $C_{25}H_{32}ClN_5O_3$: 486.2; found 486.2.

Step 2. Synthesis of (3-(4-amino-4-methylpiperidin-1-yl)-6-(4-chloro-1H-indol-6-yl)-5-methylpyrazin-2-yl)methanol and 1-(5-(4-chloro-1H-indol-6-yl)-6-methylpyrazin-2-yl)-4-methylpiperidin-4-amine To a solution of tert-butyl(1-(5-(4-chloro-1H-indol-6-yl)-3-(hydroxymethyl)-6-methylpyrazin-2-yl)-4-methylpiperidin-4-yl)carbamate (50 mg, 0.103 mmol, 1 equiv) in dioxane (1 mL) was added HCl in dioxane (4N, 3 mL). The resulting solution was stirred for 3.5 hours at room temperature and concentrated. The resulting mixture was purified by preparative HPLC to afford two products. Compound 1: (3-(4-amino-4-methylpiperidin-1-yl)-6-(4-chloro-1H-indol-6-yl)-5-methylpyrazin-2-yl)methanol as its formate salt. $^1$H NMR (500 MHz, MeOH-d$_4$) δ 8.58 (s, 1H), 7.56 (s, 1H), 7.41 (d, J=3.2 Hz, 1H), 7.31 (d, J=1.3 Hz, 1H), 6.59 (dd, J=3.2, 0.9 Hz, 1H), 4.72 (s, 2H), 3.62 (m, 2H), 3.30 (m, 2H), 2.56 (s, 3H), 1.93 (m 4H), 1.45 (s, 3H). LC-MS (ESI): m/z: [M+H] calculated for $C_{20}H_{24}ClN_5O$: 386.2; found 386.3. Compound 2: 1-(5-(4-chloro-1H-indol-6-yl)-6-methylpyrazin-2-yl)-4-methylpiperidin-4-amine as its formate salt. $^1$H NMR (500 MHz, MeOH-d$_4$) δ 8.58 (s, 1H), 8.09 (s, 1H), 7.46 (m, 1H), 7.40 (d, J=3.2 Hz, 1H), 7.19 (d, J=1.3 Hz, 1H), 6.58 (dd, J=3.2, 0.9 Hz, 1H), 4.03 (m, 2H), 3.55 (m, 2H), 2.49 (3, 3H), 1.79 (m, 4H), 1.41 (s, 3H). LC-MS (ESI): m/z: [M+H] calculated for $C_{19}H_{22}ClN_5$: 356.2; found 356.3.

The following example was synthesized in the manner similar to Examples 204 and 206.

TABLE 4

Example 206

| Example | Structure | M + 1 found |
|---|---|---|
| EXAMPLE 206 | ![structure] | 464.4 |

Example 207—Synthesis of {3-[(3S,4S)-4-amino-3-methyl-2-oxa-8-azaspiro[4.5]decan-8-yl]-5-methyl-6-(2-methyl-1,3-benzoxazol-6-yl)pyrazin-2-yl}methanol

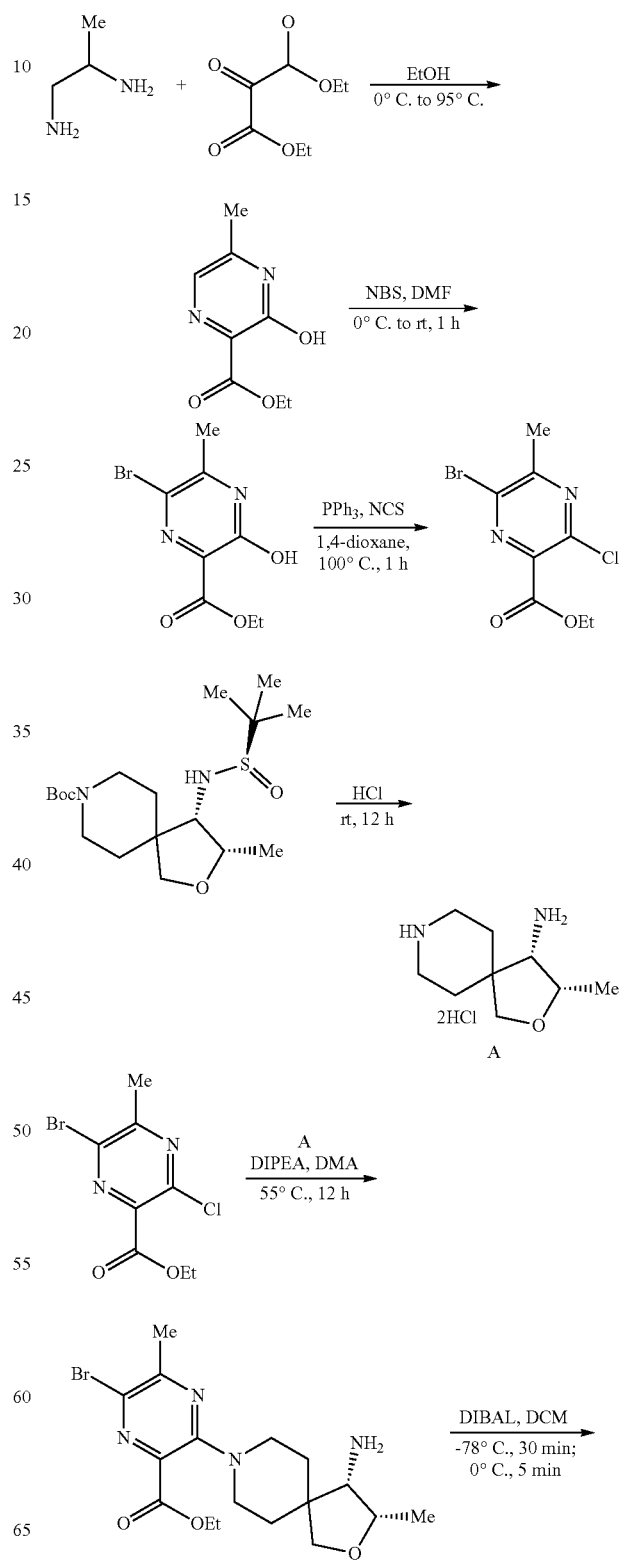

-continued

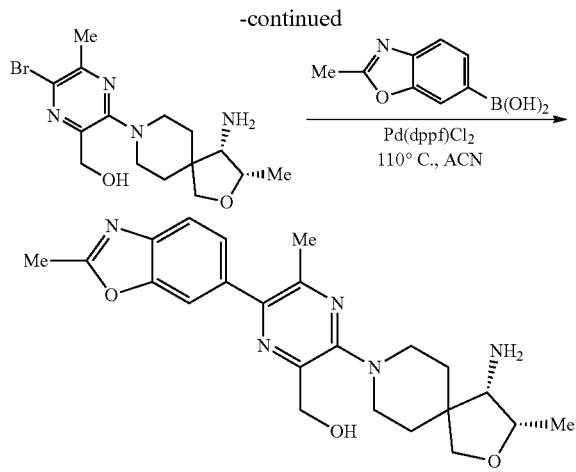

Step 1. Synthesis of ethyl 3-hydroxy-5-methylpyrazine-2-carboxylate

A 500 mL flask was charged with ethanol (216 mL) and propane-1,2-diamine (11.1 mL, 131 mmol, 1.01 equiv), and the resulting clear, colorless solution was cooled to 0° C. Once cool, diethyl 2-oxomalonate (20 mL, 130 mmol, 1.0 equiv) was added to the solution in a dropwise fashion, the cooling bath was removed, and the reaction was allowed to warm to room temperature. After stirring for 2 hours, the reaction was warmed to 95° C. and allowed to stir for 24 hours. The resulting mixture was cooled to room temperature and concentrated under reduced pressure to give a dark orange oil. Purification by column chromatography and trituration with MTBE yielded ethyl 3-hydroxy-5-methyl-pyrazine-2-carboxylate (4.27 g, 23.4 mmol, 18.0%) as a salmon-colored solid. $^1$H NMR (500 MHz, DMSO-d$_6$) δ 7.35 (br s, 1H), 4.26 (q, J=7.1 Hz, 2H), 2.24 (s, 3H), 1.27 (t, J=7.1 Hz, 3H).

Step 2. Synthesis of ethyl 6-bromo-3-hydroxy-5-methylpyrazine-2-carboxylate

A 500 mL flask was charged with ethyl 3-hydroxy-5-methylpyrazine-2-carboxylate (3 g, 16.4 mmol, 1 equiv) and DMF (65.6 mL) under a nitrogen atmosphere, and the resulting solution was cooled to 0° C., followed by addition of NBS (3.06 g, 17.2 mmol, 1.05 equiv). The resulting mixture was allowed to stir for 1 hour at room temperature, then diluted with water (150 mL) and ethyl acetate (200 mL). The layers were separated, and the resulting organic solution was then washed with water (150 mL), ½ saturated brine (2×150 mL), and brine (2×150 mL) sequentially. The organic solution was then dried over magnesium sulfate, filtered, and concentrated under reduced pressure to afford ethyl 6-bromo-3-hydroxy-5-methylpyrazine-2-carboxylate (3.77 g, 14.4 mmol, 88.0%) as a pale yellow solid. $^1$H NMR (500 MHz, DMSO-d$_6$) δ 4.30 (q, J=7.1 Hz, 2H), 2.49-2.41 (br s, 3H), 1.29 (t, J=7.1 Hz, 3H).

Step 3. Synthesis of ethyl 6-bromo-3-chloro-5-methylpyrazine-2-carboxylate

A 500 mL flask was charged with triphenylphosphine (18.0 g, 68.7 mmol, 3 equiv) and 1,4-dioxane (228 mL). N-Chlorosuccinimide (9.32 g, 69.8 mmol, 3.05 equiv) was then added to this solution, and the resulting mixture was left to stir for 30 min at room temperature. Ethyl 6-bromo-3-hydroxy-5-methylpyrazine-2-carboxylate (6 g, 22.9 mmol, 1 equiv) was added in one portion, and the resulting mixture was warmed to 100° C. and allowed to stir for 1 hour. The reaction was then cooled to room temperature, triethylamine (57 mL) was added to the reaction mixture. This crude material was dissolved in DCM and passed through a silica gel plug (elution with 5 to 10% EtOAc-Heptane) This solid was further purified by column chromatography to give ethyl 6-bromo-3-chloro-5-methylpyrazine-2-carboxylate (5.20 g, 18.6 mmol, 81.2%) as an orange solid. $^1$H NMR (500 MHz, chloroform-d) δ 4.48 (q, J=5.0, 10.0 Hz, 2H), 2.72 (s, 3H), 1.43 (t, J=7.5 Hz, 3H). LC-MS (ESI): calculated for $C_8H_9BrClN_2O_2$ [M+H] m/z 278.9, found 278.9.

Step 4. Synthesis of (3S,4S)-3-methyl-2-oxa-8-azaspiro[4.5]decan-4-amine bis HCl salt To a stirred solution of tert-butyl (3S,4S)-4-(((R)-tert-butylsulfinyl)amino)-3-methyl-2-oxa-8-azaspiro[4.5]decane-8-carboxylate (1520 mg, 4.05 mmol, 1 equiv) in anhydrous MeOH (20 mL) was added HCl (4M in 1,4-dioxane, 10.1 mL, 40.4 mmol, 10 equiv) at room temperature. This was stirred at room temperature overnight. The reaction was concentrated under reduced pressure and the resulting material was dried under high vacuum (~1 Torr) for 5 hours to afford (3S,4S)-3-methyl-2-oxa-8-azaspiro[4.5]decan-4-amine bis HCl salt (assumed quantitative yield) which was used without further purification. $^1$H NMR (500 MHz, MeOH-d$_4$) δ 4.29 (qd, J=6.5, 4.1 Hz, 1H), 3.95 (d, J=9.4 Hz, 1H), 3.83-3.78 (m, 1H), 3.56 (d, J=4.1 Hz, 1H), 3.48-3.42 (m, 1H), 3.41-3.36 (m, 1H), 3.17-3.04 (m, 2H), 2.08 (tt, J=11.9, 3.8 Hz, 2H), 2.03-1.97 (m, 1H), 1.87-1.81 (m, 1H), 1.32 (d, J=6.6 Hz, 3H).

Step 5. Synthesis of ethyl 3-((3S,4S)-4-amino-3-methyl-2-oxa-8-azaspiro[4.5]decan-8-yl)-6-bromo-5-methylpyrazine-2-carboxylate To a solution of ethyl 6-bromo-3-chloro-5-methylpyrazine-2-carboxylate (2.82 g, 10.1 mmol, 1 equiv) and (3S,4S)-3-methyl-2-oxa-8-azaspiro[4.5]decan-4-amine bis HCl salt (2.7 g, 11.2 mmol, 1.1 equiv) in DMA (50.4 mL) was added DIPEA (8.85 mL, 50.9 mmol, 5 equiv). The reaction was stirred and heated at 55° C. overnight. The reaction was then cooled and diluted with ethyl acetate (100 mL) and this organic phase was washed with 10% aqueous ammonium hydroxide (2×100 mL) and then with saturated aqueous sodium chloride (2×50 mL). The ammonium hydroxide aqueous layer was extracted with ethyl acetate (2×50 mL). The combined organic phases were dried over anhydrous magnesium sulfate, filtered, and concentrated under reduced pressure to afford ethyl 3-((3S,4S)-4-amino-3-methyl-2-oxa-8-azaspiro[4.5]decan-8-yl)-6-bromo-5-methylpyrazine-2-carboxylate as a crude material which was used without further purification. LC-MS (ESI): calculated for $C_{17}H_{26}BrN_4O_3$ [M+H] m/z: 413.1, found 412.8.

Step 6. Synthesis of (3-((3S,4S)-4-amino-3-methyl-2-oxa-8-azaspiro[4.5]decan-8-yl)-6-bromo-5-methylpyrazin-2-yl)methanol To a solution of crude ethyl 3-((3S,4S)-4-amino-3-methyl-2-oxa-8-azaspiro[4.5]decan-8-yl)-6-bromo-5-methylpyrazine-2-carboxylate (4.17 g, 10.0 mmol, 1 equiv) in DCM (100 mL) at −78° C. was added DIBAL-H (1M in DCM, 40.0 mL, 40.0 mmol, 4 equiv) dropwise. The solution was then stirred at −78° C. for 30 minutes. The solution was placed in an ice bath and allowed to warm up over 20 minutes to fully reduce the intermediate aldehyde, before being cooled back to −78° C. The resulting mixture was poured into a saturated aqueous solution of Rochelle's salt (250 mL), which had been previously cooled to 0° C. This solution was then allowed to warm to room temperature and stirred overnight. The layers were separated and the aqueous layer was extracted with DCM (3×50 mL). The combined organic layers were dried over anhydrous magnesium sulfate, filtered, and concentrated in vacuo. The crude material was purified by normal phase chromatography (0% to 20% MeOH (v/v) in DCM) to afford (3-((3S,4S)-4-amino-3-methyl-2-oxa-8-azaspiro[4.5]decan-8-yl)-6-bromo-5-methylpyrazin-2-yl)methanol as a yellow solid (1.515 g, 4.07 mmol, 41% yield over two steps). $^1$H NMR (500 MHz, MeOH-$d_4$) δ 4.59 (d, J=0.6 Hz, 2H), 4.22 (qd, J=6.4, 4.9 Hz, 1H), 3.83 (d, J=8.7 Hz, 1H), 3.69 (d, J=8.6 Hz, 1H), 3.53-3.42 (m, 2H), 3.10 (ddd, J=13.3, 10.1, 3.1 Hz, 1H), 3.05-2.97 (m, 2H), 2.51 (s, 3H), 1.88 (dddd, J=29.7, 13.9, 10.2, 3.8 Hz, 2H), 1.74-1.64 (m, 2H), 1.21 (d, J=6.5 Hz, 3H). LC-MS (ESI): calculated for calculated for $C_{15}H_{24}BrN_4O_2$ [M+H] m/z: 371.11, found 371.33.

Step 6. Synthesis of {3-[(3S,4S)-4-amino-3-methyl-2-oxa-8-azaspiro[4.5]decan-8-yl]-5-methyl-6-(2-methyl-1,3-benzoxazol-6-yl)pyrazin-2-yl}methanol (2-methylbenzo[d]oxazol-6-yl)boronic acid (30.7 mg, 174 μmol), [1,1′-bis(diphenylphosphino)ferrocene]dichloropalladium(II), complex with DCM (21.8 mg, 26.8 μmol), potassium carbonate (73.9 mg, 536 μmol) and (3-((3S,4S)-4-amino-3-methyl-2-oxa-8-azaspiro[4.5]decan-8-yl)-6-bromo-5-methylpyrazin-2-yl)methanol (50 mg, 134 μmol) were weighed into a 2 dram vial. The reaction vessel was flushed 3 times with $N_2$. MeCN (1.34 mL, degassed by sparging with $N_2$ for 1 hour) was added against $N_2$ and the headspace of the reaction vessel was flushed 3 times with $N_2$. The mixture was placed into a heating block preheated to 100° C. and stirred vigorously for 1.5 hours. The reaction mixture was cooled to room temperature and filtered through a plug of celite. The filtrate was evaporated to dryness and purified by preparative HPLC to give 15.8 mg (19%) of the desired product. $^1$H NMR (500 MHz, MeOH-$d_4$) δ 7.84 (dd, J=1.6, 0.6 Hz, 1H), 7.71 (dd, J=8.2, 0.6 Hz, 1H), 7.62 (dd, J=8.2, 1.6 Hz, 1H), 4.75-4.70 (m, 2H), 4.31-4.23 (m, 1H), 3.88 (d, J=8.6 Hz, 1H), 3.75 (d, J=8.6 Hz, 1H), 3.57 (dd, J=8.6, 4.4 Hz, 2H), 3.20-3.13 (m, 1H), 3.13-3.03 (m, 2H), 2.70 (s, 4H), 2.53 (s, 3H), 2.02-1.88 (m, 2H), 1.81-1.72 (m, 2H), 1.25 (d, J=6.5 Hz, 3H). LC-MS (ESI) m/z: [M+H] calculated for $C_{23}H_{28}ClN_5O_3$: 424.24; found 424.1.

The following example was synthesized in the manner similar to Example 207.

TABLE 5

Example 208

| Example | Structure | M + 1 found |
|---|---|---|
| EXAMPLE 208 | 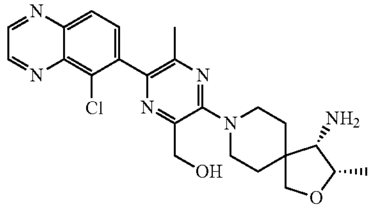 [SMILES: Cc1nc(N2CCC3(CC2)CO[C@@H](C)[C@H]3N)c(CO)nc1-c1ccc2nccnc2c1Cl] | 455.4 |

Example 209—Synthesis of {3-[(3S,4S)-4-amino-3-methyl-2-oxa-8-azaspiro[4.5]decan-8-yl]-5-methyl-6-(1-methyl-1H-indol-2-yl)pyrazin-2-yl}methanol

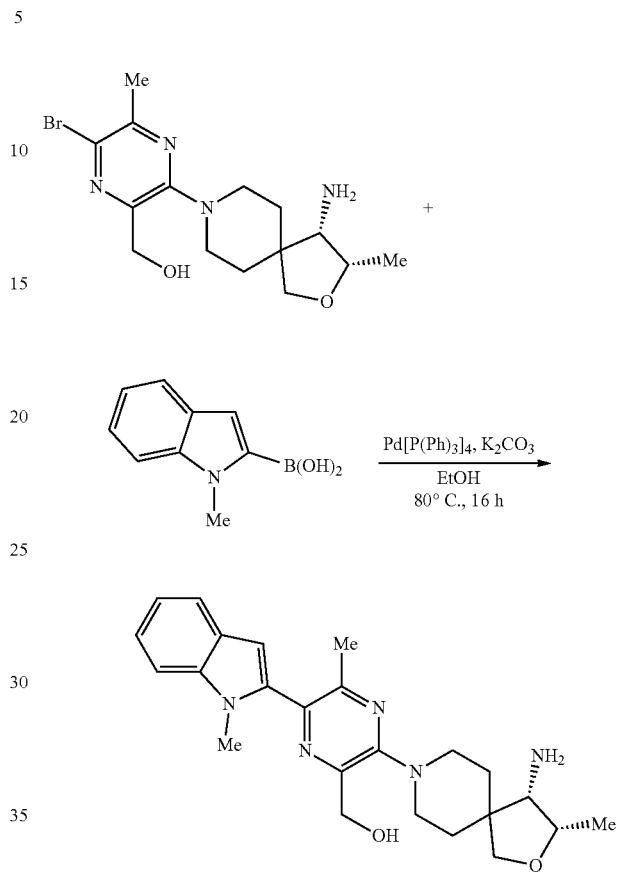

A vial was charged with (3-((3S,4S)-4-amino-3-methyl-2-oxa-8-azaspiro[4.5]decan-8-yl)-6-bromo-5-methylpyrazin-2-yl)methanol (96 mg, 0.259 mmol, 1 equiv), (1-methyl-1H-indol-2-yl)boronic acid (68 mg, 0.388 mmol, 1.5 equiv), tetrakis(triphenylphosphine)palladium (60 mg, 0.0519 mmol, 0.2 equiv), potassium carbonate (107 mg, 0.776 mmol, 3 equiv), and a stir bar. Degassed ethanol (1.72 mL) was added, the vial capped, and the headspace evacuated and filled with nitrogen three times. The vial was placed in an 80° C. oil bath overnight. The reaction mixture was filtered through a pad of Celite and the filtrate concentrated. The crude product was purified by preparative HPLC to afford (3-((3S,4S)-4-amino-3-methyl-2-oxa-8-azaspiro[4.5]decan-8-yl)-5-methyl-6-(1-methyl-1H-indol-2-yl)pyrazin-2-yl)methanol (26 mg, 24%) as its formate salt. $^1$H NMR (500 MHz, MeOH-$d_4$) δ 8.57 (s, 1H), 7.60 (m, 1H), 7.45 (m, 1H), 7.25 (m 1H), 7.11 (m 1H), 6.62 (S, 1H) 4.73 (s, 2H), 4.38-4.18 (m, 1H), 3.94 (d, J=8.8 Hz, 1H), 3.82 (d, J=8.8 Hz, 1H), 3.74 (s, 3H), 3.71-3.64 (m, 2H), 3.26-2.96 (m, 3H), 2.52 (s, 3H), 2.08-1.91 (m, 2H), 1.85 (d, J=13.4 Hz, 1H), 1.76 (d, J=12.4 Hz, 1H), 1.30 (d, J=6.5 Hz, 3H). LC-MS (ESI): m/z: [M+H] calculated for $C_{24}H_{31}N_5O_2$: 422.3; found: 422.5.

The following examples were synthesized in the manner similar to Example 209.

TABLE 6

Examples 210-227

| Example | Structure | M + 1 found |
|---|---|---|
| EXAMPLE 210 | 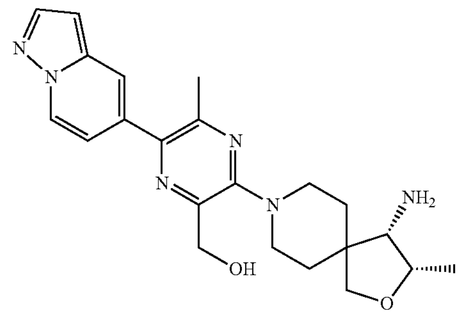 [SMILES: Cc1nc(N2CCC3(CC2)CO[C@@H](C)[C@H]3N)c(CO)nc1-c1ccn2nccc2c1] | 409.5 |
| EXAMPLE 211 | 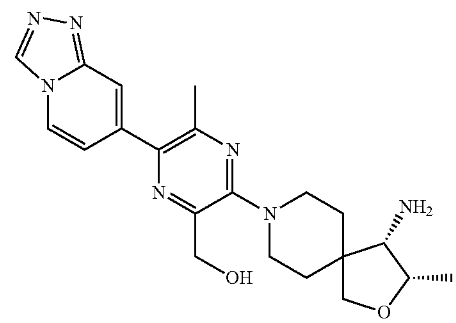 [SMILES: Cc1nc(N2CCC3(CC2)CO[C@@H](C)[C@H]3N)c(CO)nc1-c1ccn2cnnc2c1] | 410.3 |
| EXAMPLE 212 | 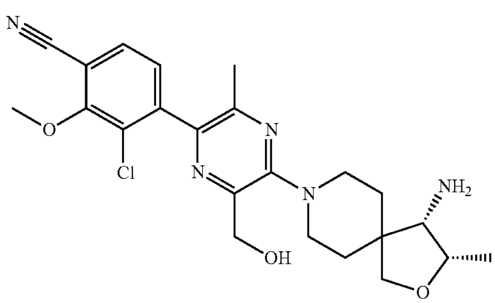 [SMILES: COc1c(C#N)ccc(-c2nc(CO)c(N3CCC4(CC3)CO[C@@H](C)[C@H]4N)nc2C)c1Cl] | 458.5 |
| EXAMPLE 213 | 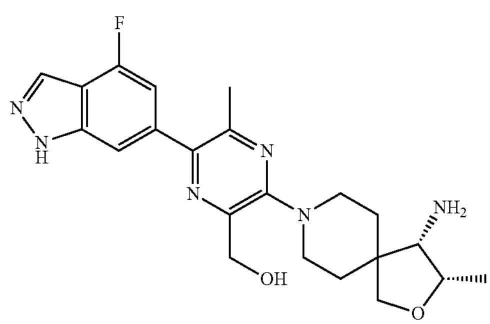 [SMILES: Cc1nc(N2CCC3(CC2)CO[C@@H](C)[C@H]3N)c(CO)nc1-c1cc(F)c2cn[nH]c2c1] | 427.1 |
| EXAMPLE 214 | 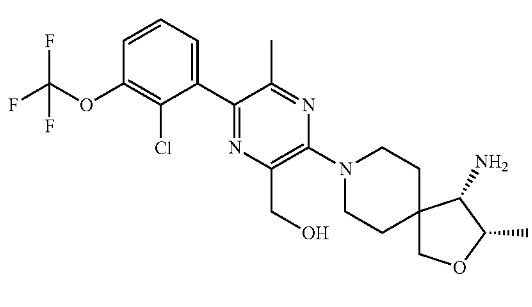 [SMILES: Cc1nc(N2CCC3(CC2)CO[C@@H](C)[C@H]3N)c(CO)nc1-c1cccc(OC(F)(F)F)c1Cl] | 487.4 |

TABLE 6-continued

Examples 210-227

| Example | Structure | M + 1 found |
|---|---|---|
| EXAMPLE 215 | 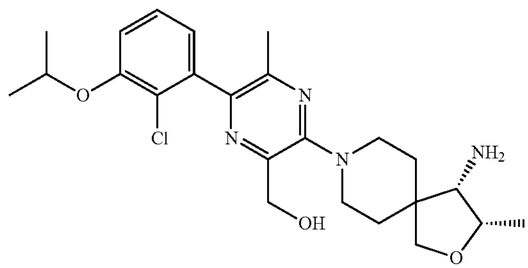 [SMILES: Cc1nc(N2CCC3(CC2)CO[C@@H](C)[C@H]3N)c(CO)nc1-c1cccc(OC(C)C)c1Cl] | 461.4 |
| EXAMPLE 216 | 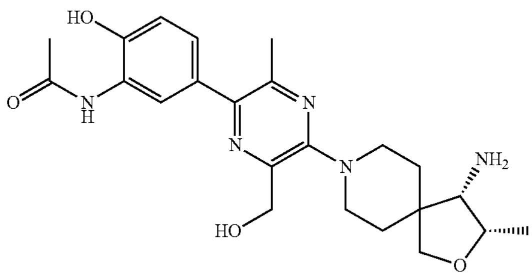 [SMILES: CC(=O)Nc1cc(-c2nc(CO)c(N3CCC4(CC3)CO[C@@H](C)[C@H]4N)nc2C)ccc1O] | 442.01 |
| EXAMPLE 217 | 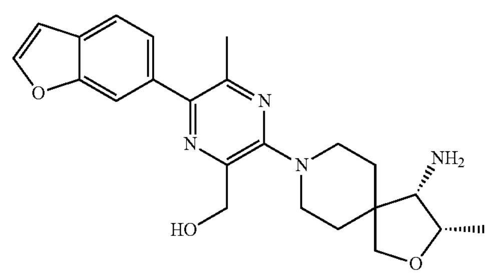 [SMILES: Cc1nc(N2CCC3(CC2)CO[C@@H](C)[C@H]3N)c(CO)nc1-c1ccc2ccoc2c1] | 409.1 |
| EXAMPLE 218 | 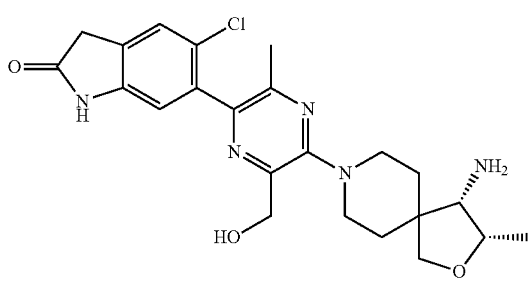 [SMILES: Cc1nc(N2CCC3(CC2)CO[C@@H](C)[C@H]3N)c(CO)nc1-c1cc2c(cc1Cl)CC(=O)N2] | 458.7 |
| EXAMPLE 219 | 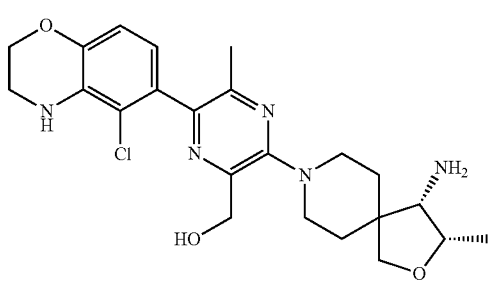 [SMILES: Cc1nc(N2CCC3(CC2)CO[C@@H](C)[C@H]3N)c(CO)nc1-c1ccc2c(c1Cl)NCCO2] | 460.1 |

TABLE 6-continued

Examples 210-227

| Example | Structure | M + 1 found |
|---|---|---|
| EXAMPLE 220 | 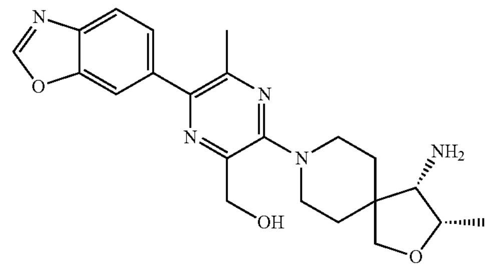 [SMILES: Cc1nc(N2CCC3(CC2)CO[C@@H](C)[C@H]3N)c(CO)nc1-c1ccc2ncoc2c1] | 410.27 |
| EXAMPLE 221 | 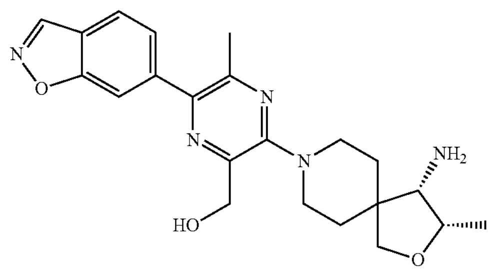 [SMILES: Cc1nc(N2CCC3(CC2)CO[C@@H](C)[C@H]3N)c(CO)nc1-c1ccc2cnoc2c1] | 410.35 |
| EXAMPLE 222 | 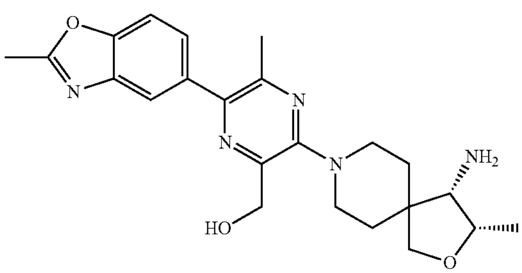 | 424.2 |
| EXAMPLE 223 | 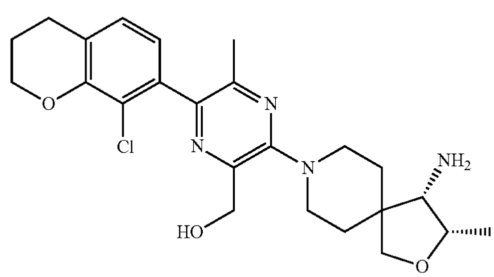 [SMILES: Cc1nc(N2CCC3(CC2)CO[C@@H](C)[C@H]3N)c(CO)nc1-c1ccc2c(c1Cl)OCCC2] | 459.34 |
| EXAMPLE 224 | 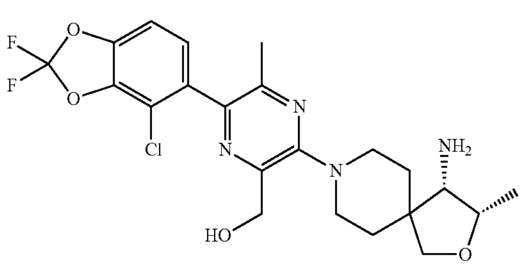 [SMILES: Cc1nc(N2CCC3(CC2)CO[C@@H](C)[C@H]3N)c(CO)nc1-c1ccc2c(c1Cl)OC(F)(F)O2] | 483.1 |

TABLE 6-continued
Examples 210-227
| Example | Structure | M + 1 found |
|---|---|---|
| EXAMPLE 225 | 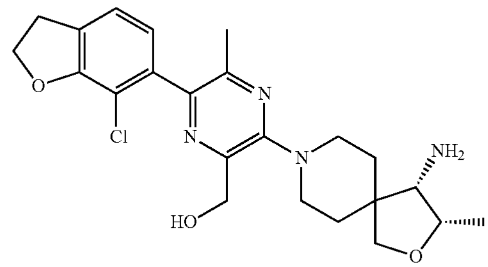 [SMILES: Cc1nc(N2CCC3(CC2)CO[C@@H](C)[C@H]3N)c(CO)nc1-c1ccc2c(c1Cl)OCC2] | 445.35 |
| EXAMPLE 226 | 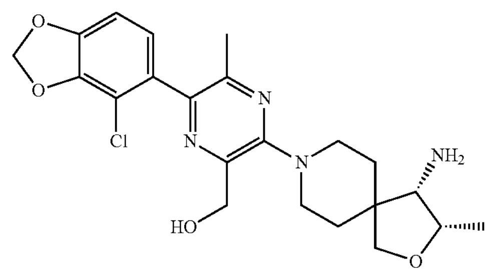 [SMILES: Cc1nc(N2CCC3(CC2)CO[C@@H](C)[C@H]3N)c(CO)nc1-c1ccc2c(c1Cl)OCO2] | 447.4 |
| EXAMPLE 227 | 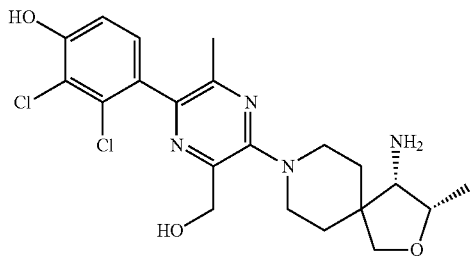 [SMILES: Cc1nc(N2CCC3(CC2)CO[C@@H](C)[C@H]3N)c(CO)nc1-c1ccc(O)c(Cl)c1Cl] | 453.01 |
Example 228—Synthesis of {3-[(3S,4S)-4-amino-3-methyl-2-oxa-8-azaspiro[4.5]decan-8-yl]-6-(2,3-dichlorophenyl)-5-methylpyrazin-2-yl}methanol
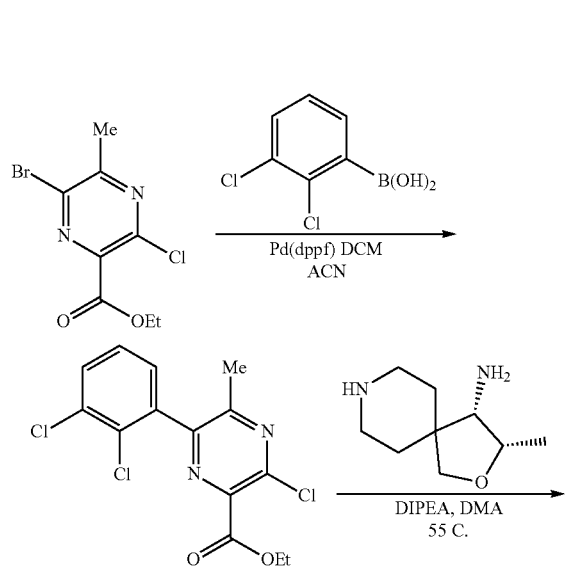
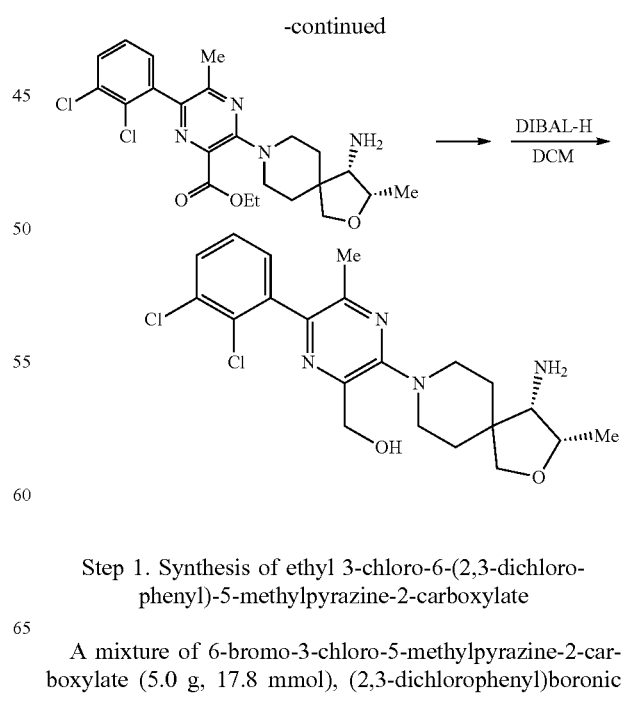
Step 1. Synthesis of ethyl 3-chloro-6-(2,3-dichlorophenyl)-5-methylpyrazine-2-carboxylate
A mixture of 6-bromo-3-chloro-5-methylpyrazine-2-carboxylate (5.0 g, 17.8 mmol), (2,3-dichlorophenyl)boronic acid (4.1 g, 21.3 mmol), and potassium carbonate (9.8 g, 71.2 mmol) in acetonitrile (178 mL) was degassed and Pd(dppf)Cl$_2$ DCM (2.9 g, 3.56 mmol) was added. The reaction mixture was stirred at 100° C. for 1 hour, filtered, and concentrated under reduced pressure. Purification by column chromatography resulted in ethyl 3-chloro-6-(2,3-dichlorophenyl)-5-methylpyrazine-2-carboxylate (4.2 g, 12.1 mmol, 68.2%). LC-MS (ESI): calculated for $C_{14}H_{11}Cl_3N_2O_2$ [M+H] m/z: 344.9, found 345.1.

Step 2. Synthesis of ethyl 3-((3S,4S)-4-amino-3-methyl-2-oxa-8-azaspiro[4.5]decan-8-yl)-6-(2,3-dichlorophenyl)-5-methylpyrazine-2-carboxylate To a solution of ethyl 3-chloro-6-(2,3-dichlorophenyl)-5-methylpyrazine-2-carboxylate (1.2 g, 3.47 mmol) and (3S,4S)-3-methyl-2-oxa-8-azaspiro[4.5]decan-4-amine bis HCl salt (0.92 g, 3.81 mmol) in DMA (17 mL) was added DIPEA (2.85 mL, 17.2 mmol). The reaction was heated to 55° C. overnight. The reaction was then cooled and diluted with ethyl acetate (100 mL) and this organic phase was washed with 10% aqueous ammonium hydroxide (50 mL), dried over anhydrous magnesium sulfate, filtered, and concentrated to afford crude ethyl-3-((3S,4S)-4-amino-3-methyl-2-oxa-8-azaspiro[4.5]decan-8-yl)-6-(2,3-dichlorophenyl)-5-methylpyrazine-2-carboxylate (2.0 g). The resulting material was submitted to the next step without further purification. LC-MS (ESI): calculated for $C_{23}H_{28}Cl_2N_4O_3$ [M+H] m/z: 479.1, found 479.3.

Step 3. Synthesis of {3-[(3S,4S)-4-amino-3-methyl-2-oxa-8-azaspiro[4.5]decan-8-yl]-6-(2,3-dichlorophenyl)-5-methylpyrazin-2-yl}methanol To a solution of ethyl-3-((3S,4S)-4-amino-3-methyl-2-oxa-8-azaspiro[4.5]decan-8-yl)-6-(2,3-dichlorophenyl)-5-methylpyrazine-2-carboxylate (2 g, 4.2 mmol) in DCM (40 mL) at −78° C. was added DIBAL-H (1M in DCM, 16.6 mmol) dropwise. The solution was then stirred at −78° C. for 30 minutes. The solution was placed in an ice bath and allowed to warm up over 20 minutes to fully reduce the intermediate aldehyde, before being cooled back to −78° C. The solution was poured into a saturated aqueous cold solution of Rochelle's salt (100 mL). This solution was then allowed to warm to room temperature and stirred for an additional 3 hours. The layers were separated and the aqueous layer was extracted with DCM (2×40 mL). The combined organic layers were dried over anhydrous magnesium sulfate, filtered, and concentrated under reduced pressure. Purification by preparative HPLC afforded {3-[(3S,4S)-4-amino-3-methyl-2-oxa-8-azaspiro[4.5]decan-8-yl]-6-(2,3-dichlorophenyl)-5-methylpyrazin-2-yl}methanol (0.83 g, 45.8%). $^1$H NMR (500 MHz, MeOH-d$_4$) δ 8.53 (s, 1H), 7.66 (dd, J=8.1, 1.6 Hz, 1H), 7.44 (t, J=7.8 Hz, 1H), 7.37 (dd, J=7.7, 1.6 Hz, 1H), 4.70 (s, 2H), 4.32 (qd, J=6.5, 4.2 Hz, 1H), 3.98 (d, J=9.0 Hz, 1H), 3.87 (d, J=9.0 Hz, 1H), 3.81-3.67 (m, 2H), 3.41 (d, J=4.2 Hz, 1H), 3.11 (dddd, J=35.0, 13.7, 11.1, 2.8 Hz, 2H), 2.28 (s, 3H), 2.06-1.95 (m, 3H), 1.94-1.87 (m, 1H), 1.76 (ddd, J=10.5, 4.6, 2.3 Hz, 1H), 1.33 (d, J=6.5 Hz, 3H). LC-MS (ESI): calculated for $C_{21}H_{27}Cl_2N_4O_2$ [M+H] m/z: 437.1, found 437.36.

The following examples were synthesized in the manner similar to Example 228.

TABLE 7

Examples 229-231

| Example | Structure | M + 1 found |
|---|---|---|
| EXAMPLE 229 | 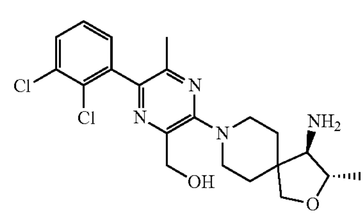 [SMILES: Cc1nc(N2CCC3(CC2)CO[C@@H](C)[C@@H]3N)c(CO)nc1-c1cccc(Cl)c1Cl] | 437.4 |
| EXAMPLE 230 | 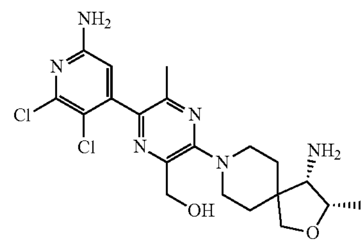 [SMILES: Cc1nc(N2CCC3(CC2)CO[C@@H](C)[C@H]3N)c(CO)nc1-c1cc(N)nc(Cl)c1Cl] | 453.35 |
| EXAMPLE 231 | 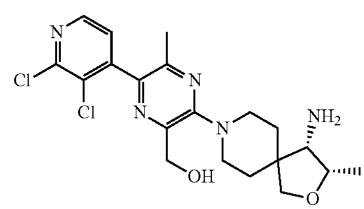 [SMILES: Cc1nc(N2CCC3(CC2)CO[C@@H](C)[C@H]3N)c(CO)nc1-c1ccnc(Cl)c1Cl] | 438.32 |

Example 232—Synthesis of {3-[(3S,4S)-4-amino-3-methyl-2-oxa-8-azaspiro[4.5]decan-8-yl]-5-methyl-6-(3-methyl-2H-indazol-6-yl)pyrazin-2-yl}methanol

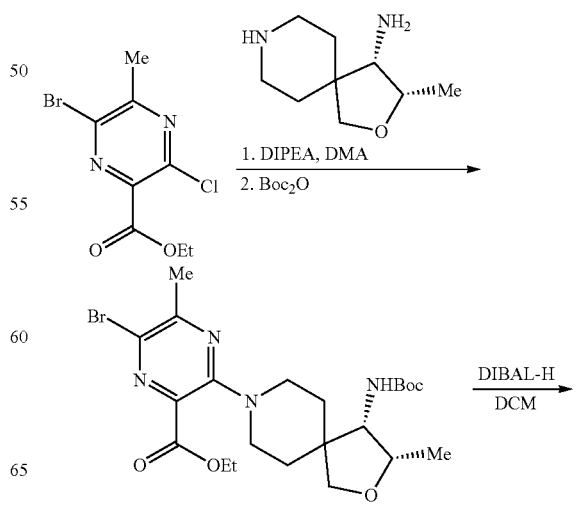

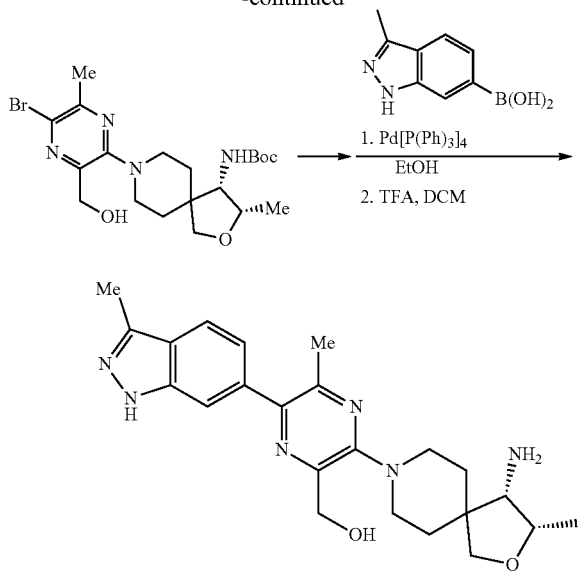

Step 1. Synthesis of ethyl 6-bromo-3-((3S,4S)-4-((tert-butoxycarbonyl)amino)-3-methyl-2-oxa-8-azaspiro[4.5]decan-8-yl)-5-methylpyrazine-2-carboxylate A 200 mL flask was charged with ethyl 6-bromo-3-chloro-5-methylpyrazine-2-carboxylate (2.5 g, 8.94 mmol, 1 equiv) and (3S,4S)-3-methyl-2-oxa-8-azaspiro[4.5]decan-4-amine dihydrochloride (2.60 g, 10.7 mmol, 1.2 equiv), and the flask was flushed with nitrogen. DMA (89.3 mL) was then added to the flask, followed by DIPEA (9.32 mL, 53.6 mmol, 6 equiv). The resulting orange solution was then warmed to 85° C. After stirring for 23 hours, the reaction was cooled to room temperature, Boc$_2$O (7.76 g, 35.6 mmol, 4 equiv) was added to the reaction solution, and the resulting orange solution was left to stir at 23° C. for 1 hour, diluted with EtOAc (200 mL) and water (50 mL). The layers were separated, and the organic phase was washed with water (2×50 mL) and brine (50 mL). The washed organic phase was then dried over sodium sulfate, filtered, and concentrated under reduced pressure to a yellow residue. The crude residue was purified by column chromatography to give ethyl 6-bromo-3-((3S,4S)-4-((tert-butoxy carbonyl)amino)-3-methyl-2-oxa-8-azaspiro[4.5]decan-8-yl)-5-methylpyrazine-2-carboxylate as a bright yellow solid (2.67 g, 58% yield). LC-MS (ESI): m/z: [M+Na] calculated for $C_{22}H_{33}BrN_4O_5$: 535.1; found 535.3.

Step 2. Synthesis of tert-butyl ((3S,4S)-8-(5-bromo-3-(hydroxymethyl)-6-methylpyrazin-2-yl)-3-methyl-2-oxa-8-azaspiro[4.5]decan-4-yl)carbamate A dry 100 mL flask was charged with ethyl 6-bromo-3-((3S,4S)-4-((tert-butoxycarbonyl)amino)-3-methyl-2-oxa-8-azaspiro[4.5]decan-8-yl)-5-methylpyrazine-2-carboxylate (1.15 g, 2.23 mmol, 1 equiv) and DCM (22.3 mL). The resulting yellow solution was cooled to −78° C. before DIBAL-H (11.5 mL, 11.15 mmol, 5 equiv) was added dropwise. After stirring for 1 hour, the reaction was warmed to −40° C. After 1 hour, the reaction was cooled to −78° C. and quenched by addition of saturated aqueous Rochelle's salt (20 mL), and the resulting mixture was allowed to warm to 23° C. The biphasic mixture was filtered through a pad of Celite and transferred to a separatory funnel. The layers were separated, and the aqueous phase was extracted with DCM (2×20 mL). The combined organic extracts were then dried over sodium sulfate. The dried solution was filtered, and the filtrate was concentrated under reduced pressure. The crude residue so obtained was purified by column chromatography to give both tert-butyl ((3S,4S)-8-(5-bromo-3-(hydroxymethyl)-6-methylpyrazin-2-yl)-3-methyl-2-oxa-8-azaspiro[4.5]decan-4-yl)carbamate (466 mg, 44% yield) and tert-butyl ((3S,4S)-8-(5-bromo-3-formyl-6-methylpyrazin-2-yl)-3-methyl-2-oxa-8-azaspiro[4.5]decan-4-yl)carbamate (253 mg, 24% yield). LC-MS (ESI): m/z: [M+H] calculated for $C_{20}H_{31}BrN_4O_4$: 471.2; found 471.1.

Step 3. Synthesis of tert-butyl ((3S,4S)-8-(3-(hydroxymethyl)-6-methyl-5-(3-methyl-1H-indazol-6-yl)pyrazin-2-yl)-3-methyl-2-oxa-8-azaspiro[4.5]decan-4-yl)carbamate A vial was charged with tert-butyl ((3S,4S)-8-(5-bromo-3-(hydroxymethyl)-6-methylpyrazin-2-yl)-3-methyl-2-oxa-8-azaspiro[4.5]decan-4-yl)carbamate (88 mg, 0.187 mmol, 1 equiv), (3-methyl-1H-indazol-6-yl)boronic acid (49 mg, 0.280 mmol, 1.5 equiv), tetrakis(triphenylphosphine)palladium (43.1 mg, 0.0373 mmol, 0.2 equiv), potassium carbonate (77 mg, 0.560 mmol, 3 equiv), and a stir bar. Degassed ethanol (1.24 mL) was added, the vial capped, and the headspace evacuated and filled with nitrogen three times. The vial was placed in an 80° C. oil bath overnight. The reaction mixture was diluted with ethyl acetate, filtered through a pad of Celite and the filtrate concentrated under reduced pressure. Purification by column chromatography afforded tert-butyl ((3S,4S)-8-(3-(hydroxymethyl)-6-methyl-5-(3-methyl-1H-indazol-6-yl)pyrazin-2-yl)-3-methyl-2-oxa-8-azaspiro[4.5]decan-4-yl)carbamate (65 mg, 66%). LC-MS (ESI): m/z: [M+H] calculated for $C_{28}H_{38}N_6O_4$: 523.3; found 523.2.

Step 4. Synthesis of (3-((3S,4S)-4-amino-3-methyl-2-oxa-8-azaspiro[4.5]decan-8-yl)-5-methyl-6-(3-methyl-1H-indazol-6-yl)pyrazin-2-yl)methanol To a solution of tert-butyl ((3S,4S)-8-(3-(hydroxymethyl)-6-methyl-5-(3-methyl-1H-indazol-6-yl)pyrazin-2-yl)-3-methyl-2-oxa-8-azaspiro[4.5]decan-4-yl)carbamate (65 mg, 0.124 mmol, 1 equiv) in DCM (3 mL) was added TFA (500 µL). The resulting solution was allowed to stir for one hour at room temperature and concentrated under reduced pressure. The crude product was purified by preparative HPLC to afford of (3-((3S,4S)-4-amino-3-methyl-2-oxa-8-azaspiro[4.5]decan-8-yl)-5-methyl-6-(3-methyl-1H-indazol-6-yl)pyrazin-2-yl)methanol (31.6 mg, 60%). $^1$H NMR (500 MHz, MeOH-d$_4$) δ 7.82 (dd, J=8.3, 0.8 Hz, 1H), 7.66 (t, J=1.1 Hz, 1H), 7.37 (dd, J=8.3, 1.4 Hz, 1H), 4.74 (s, 2H), 4.32 (m, 1H), 3.99 (d, J=9.1 Hz, 1H), 3.88 (d, J=9.1 Hz, 1H), 3.80-3.63 (m, 2H), 3.46 (d, J=4.2 Hz, 1H), 3.08 (m, 2H), 2.62 (s, 3H), 2.53 (s, 3H), 2.08-1.97 (m, 2H), 1.93 (d, J=13.2 Hz, 1H), 1.77 (d, J=13.2 Hz, 1H), 1.35 (d, J=6.5 Hz, 3H). LC-MS (ESI): m/z: [M+H] calculated for $C_{23}H_{30}N_6O_2$: 423.2; found 423.1.

Example 233—Synthesis of {3-[(3S,4S)-4-amino-3-methyl-2-oxa-8-azaspiro[4.5]decan-8-yl]-6-(7-chloro-2H-indazol-6-yl)-5-methylpyrazin-2-yl}methanol

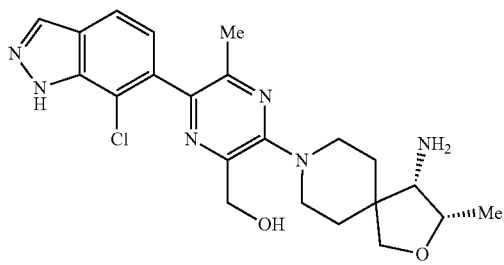 [SMILES: Cc1nc(N2CCC3(CC2)CO[C@@H](C)[C@H]3N)c(CO)nc1-c1ccc2cn[nH]c2c1Cl]

Synthesis of {3-[(3S,4S)-4-amino-3-methyl-2-oxa-8-azaspiro[4.5]decan-8-yl]-6-(7-chloro-2H-indazol-6-yl)-5-methylpyrazin-2-yl}methanol was synthesized in the manner similar to Example 232, except (3-methyl-1H-indazol-6-yl)boronic acid was replaced with 7-chloro-6-(4,4,5,5-tetramethyl-1,3,2-dioxaborolan-2-yl)-1H-indazole as its formate salt. $^1$H NMR (500 MHz, MeOH-$d_4$) δ 8.54 (s, 1H), 8.22 (s, 1H), 7.85 (d, J=8.2 Hz, 1H), 7.19 (d, J=8.2 Hz, 1H), 4.73 (s, 2H), 4.32 (m, 1H), 3.97 (d, J=8.9 Hz, 1H), 3.86 (d, J=8.9 Hz, 1H), 3.74 (m, 2H), 3.23-3.00 (m, 2H), 2.31 (s, 3H), 2.01 (m, 2H), 1.90 (m, 1H), 1.77 (m, 1H), 1.33 (d, J=6.5 Hz, 3H). LC-MS (ESI): m/z: [M+H] calculated for $C_{22}H_{27}ClN_6O_2$: 443.1; found 443.1.

Synthesis of 7-chloro-6-(4,4,5,5-tetramethyl-1,3,2-dioxaborolan-2-yl)-1H-indazole

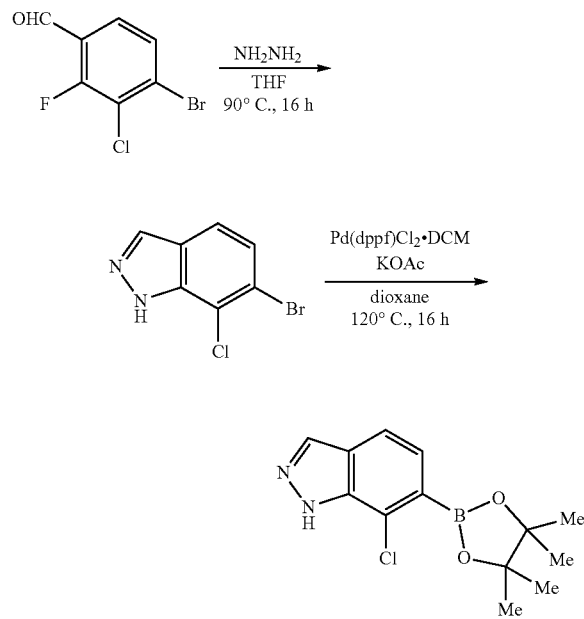

Step 1. Synthesis of 6-bromo-7-chloro-1H-indazole

To a solution of 4-bromo-3-chloro-2-fluorobenzaldehyde (1.15 g, 4.84 mmol, 1 equiv) in THF (4.8 mL) was added neat hydrazine (4.8 mL). The resulting two phase mixture was vigorously stirred for 16 hours at 90° C. The cooled reaction mixture was added dropwise to a stirred solution of water (25 mL) to precipitate a solid. The white solid was collected by filtration, washed with water, and dried under vacuum to a constant mass to afford 6-bromo-7-chloro-1H-indazole (1.0 g. 89%) and used without further purification. LC-MS (ESI): m/z: [M+H] calculated for $C_7H_4BrClN_2$: 230.9; found: 230.6.

Step 2. Synthesis of 7-chloro-6-(4,4,5,5-tetramethyl-1,3,2-dioxaborolan-2-yl)-1H-indazole To a vial containing 6-bromo-7-chloro-1H-indazole (346 mg, 1.49 mmol, 1 equiv), bis(pinacolato)diboron (566 mg, 2.23, 1.5 equiv), Pd(dppf)Cl$_2$.DCM (60.8 mg, 0.0745 mmol, 0.05 equiv), potassium acetate (438 mg, 4.47 mmol, 3 equiv), and a stir bar was added degassed dioxane (14.9 mL). The vial was sealed and the headspace evacuated and filled with nitrogen three times. The vial was heated in reaction block at 120° C. for 16 hours. The cooled reaction mixture was diluted with ethyl acetate and filtered through a pad of Celite. The filtrate was concentrated under reduced pressure to give to the crude product which was purified by column chromatography to afford 7-chloro-6-(4,4,5,5-tetramethyl-1,3,2-dioxaborolan-2-yl)-1H-indazole (186 mg, 45%) as a white solid. LC-MS (ESI): m/z: [M+H] calculated for $C_{13}H_{16}BClN_2O_2$: 279.1; found: 279.1.

Example 234—Synthesis of {3-[(3S,4S)-4-amino-3-methyl-2-oxa-8-azaspiro[4.5]decan-8-yl]-6-(5-chloro-2H-indazol-6-yl)-5-methylpyrazin-2-yl}methanol

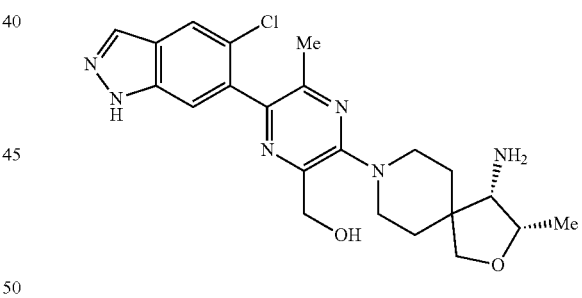

Synthesis of {3-[(3S,4S)-4-amino-3-methyl-2-oxa-8-azaspiro[4.5]decan-8-yl]-6-(5-chloro-2H-indazol-6-yl)-5-methylpyrazin-2-yl}methanol was synthesized in the manner similar to Example 233, except 6-bromo-7-chloro-1H-indazole was substituted with 6-bromo-5-chloro-1H-indazole as its formate salt. $^1$H NMR (500 MHz, MeOH-$d_4$) δ 8.50 (s, 1H), 8.13 (d, J=1.0 Hz, 1H), 7.99 (d, J=1.0 Hz, 1H), 7.60 (s, 1H), 4.73 (s, 2H), 4.39-4.22 (m, 1H), 3.99 (d, J=9.1 Hz, 1H), 3.89 (d, J=9.1 Hz, 1H), 3.75 (m, 2H), 3.22-2.97 (m, 2H), 2.31 (m, 3H), 2.08-1.98 (m, 2H), 1.93 (d, J=12.5 Hz, 1H), 1.78 (d, J=12.5 Hz, 1H), 1.34 (d, J=6.5 Hz, 3H). LC-MS (ESI): m/z: [M+H] calculated for $C_{22}H_{27}ClN_6O_2$: 443.1; found 443.4.

The following examples were synthesized in the manner similar to Example 232.

TABLE 8

Examples 235-253

| Example | Structure | M + 1 found |
|---|---|---|
| EXAMPLE 235 | 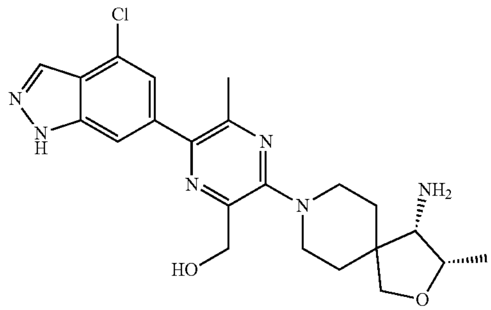 [SMILES: Cc1nc(N2CCC3(CC2)CO[C@@H](C)[C@H]3N)c(CO)nc1-c1cc(Cl)c2cn[nH]c2c1] | 443.1 |
| EXAMPLE 236 | 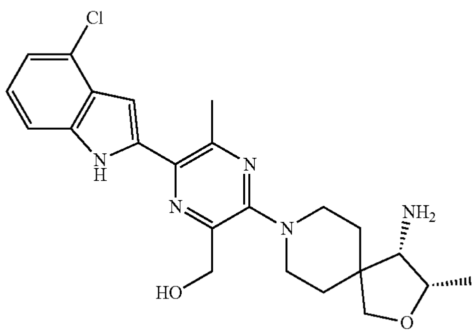 [SMILES: Cc1nc(N2CCC3(CC2)CO[C@@H](C)[C@H]3N)c(CO)nc1-c1cc2c(Cl)cccc2[nH]1] | 442.2 |
| EXAMPLE 237 | 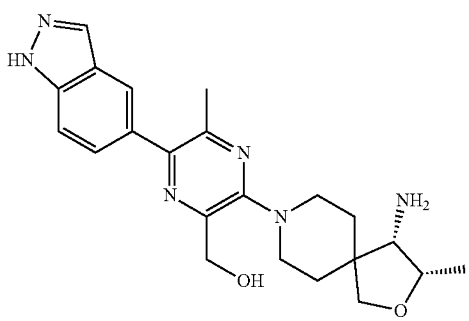 [SMILES: Cc1nc(N2CCC3(CC2)CO[C@@H](C)[C@H]3N)c(CO)nc1-c1ccc2[nH]ncc2c1] | 409.3 |
| EXAMPLE 238 | 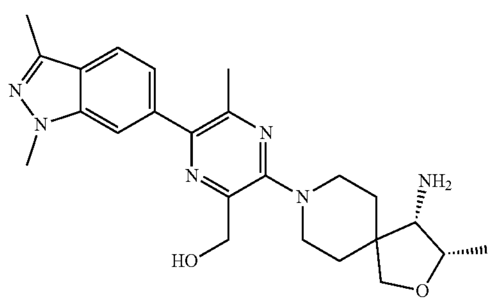 [SMILES: Cc1nc(N2CCC3(CC2)CO[C@@H](C)[C@H]3N)c(CO)nc1-c1ccc2c(C)nn(C)c2c1] | 437.3 |
| EXAMPLE 239 | 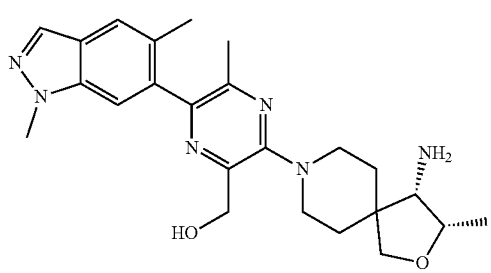 [SMILES: Cc1cc2cnn(C)c2cc1-c1nc(CO)c(N2CCC3(CC2)CO[C@@H](C)[C@H]3N)nc1C] | 437.1 |

TABLE 8-continued

Examples 235-253

| Example | Structure | M + 1 found |
|---|---|---|
| EXAMPLE 240 | 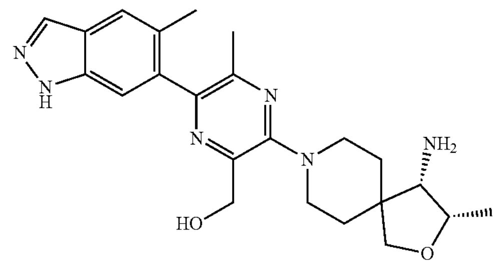 [SMILES: Cc1cc2cn[nH]c2cc1-c1nc(CO)c(N2CCC3(CC2)CO[C@@H](C)[C@H]3N)nc1C] | 423.4 |
| EXAMPLE 241 | 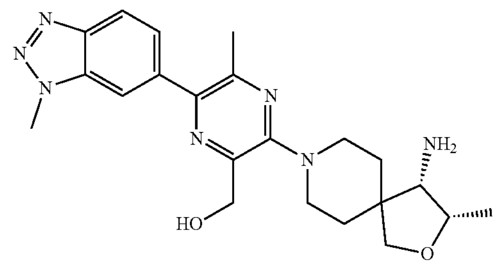 [SMILES: Cc1nc(N2CCC3(CC2)CO[C@@H](C)[C@H]3N)c(CO)nc1-c1ccc2nnn(C)c2c1] | 424.5 |
| EXAMPLE 242 | 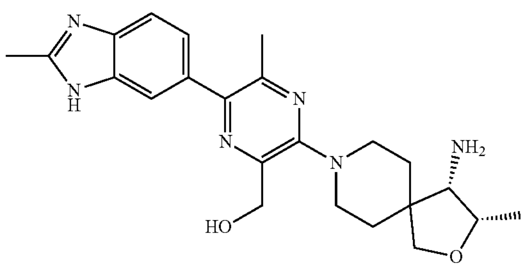 | 423.3 |
| EXAMPLE 243 | 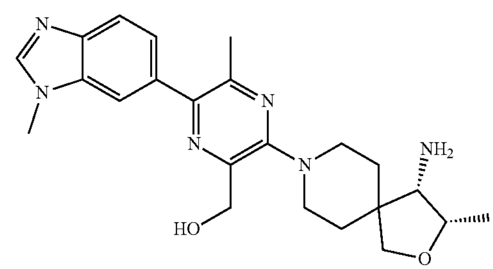 [SMILES: Cc1nc(N2CCC3(CC2)CO[C@@H](C)[C@H]3N)c(CO)nc1-c1ccc2ncn(C)c2c1] | 423.3 |
| EXAMPLE 244 | 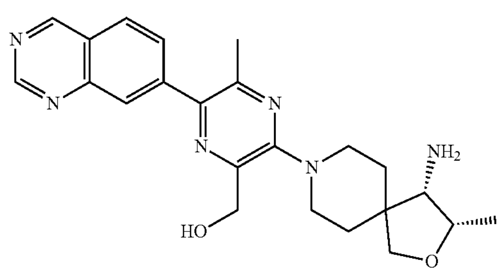 [SMILES: Cc1nc(N2CCC3(CC2)CO[C@@H](C)[C@H]3N)c(CO)nc1-c1ccc2cncnc2c1] | 421.4 |

TABLE 8-continued

Examples 235-253

| Example | Structure | M + 1 found |
|---|---|---|
| EXAMPLE 245 | 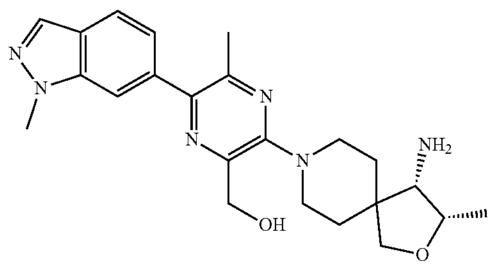 [SMILES: Cc1nc(N2CCC3(CC2)CO[C@@H](C)[C@H]3N)c(CO)nc1-c1ccc2cnn(C)c2c1] | 423.3 |
| EXAMPLE 246 | 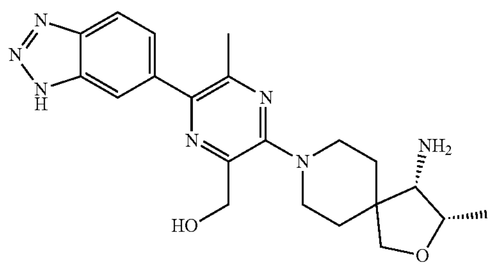 [SMILES: Cc1nc(N2CCC3(CC2)CO[C@@H](C)[C@H]3N)c(CO)nc1-c1ccc2nn[nH]c2c1] | 410.2 |
| EXAMPLE 247 | 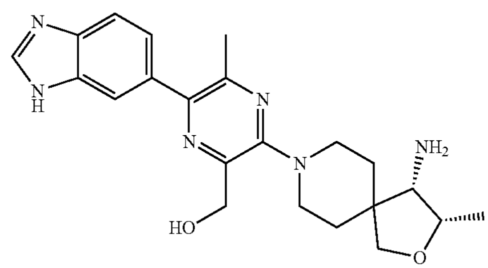 [SMILES: Cc1nc(N2CCC3(CC2)CO[C@@H](C)[C@H]3N)c(CO)nc1-c1ccc2nc[nH]c2c1] | 409.3 |
| EXAMPLE 248 | 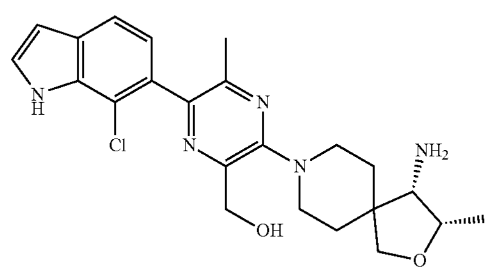 [SMILES: Cc1nc(N2CCC3(CC2)CO[C@@H](C)[C@H]3N)c(CO)nc1-c1ccc2cc[nH]c2c1Cl] | 442.5 |
| EXAMPLE 249 | 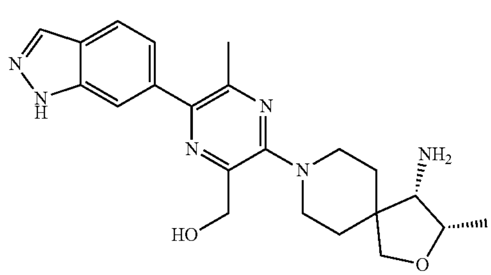 [SMILES: Cc1nc(N2CCC3(CC2)CO[C@@H](C)[C@H]3N)c(CO)nc1-c1ccc2cn[nH]c2c1] | 409.2 |

TABLE 8-continued

Examples 235-253

| Example | Structure | M + 1 found |
|---|---|---|
| EXAMPLE 250 | 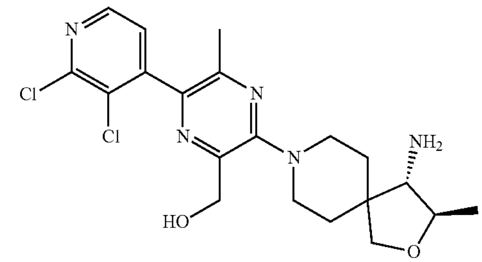 [SMILES: Cc1nc(N2CCC3(CC2)CO[C@H](C)[C@H]3N)c(CO)nc1-c1ccnc(Cl)c1Cl] | 438.2 |
| EXAMPLE 251 | 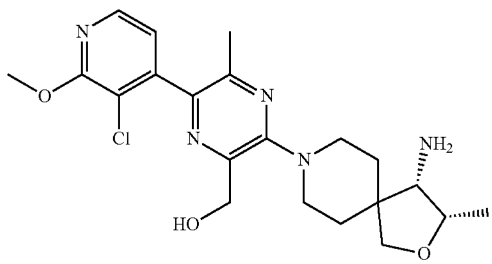 | 434.4 |
| EXAMPLE 252 | 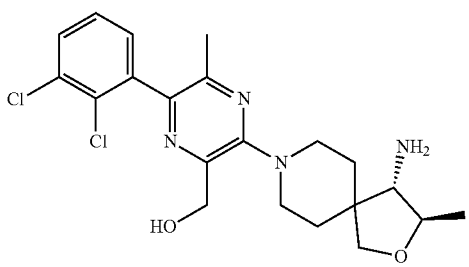 [SMILES: Cc1nc(N2CCC3(CC2)CO[C@H](C)[C@H]3N)c(CO)nc1-c1cccc(Cl)c1Cl] | 437.1 |
| EXAMPLE 253 | 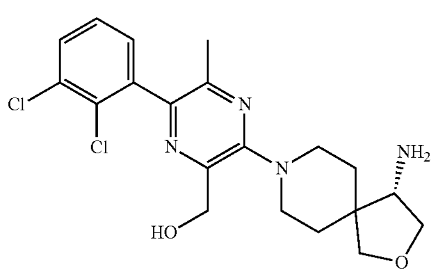 [SMILES: Cc1nc(N2CCC3(CC2)COC[C@H]3N)c(CO)nc1-c1cccc(Cl)c1Cl] | 423.13 |

Example 254—Synthesis of {3-[(1R)-1-amino-8-azaspiro[4.5]decan-8-yl]-5-methyl-6-[(1-methyl-1H-indol-7-yl)sulfanyl]pyrazin-2-yl}methanol

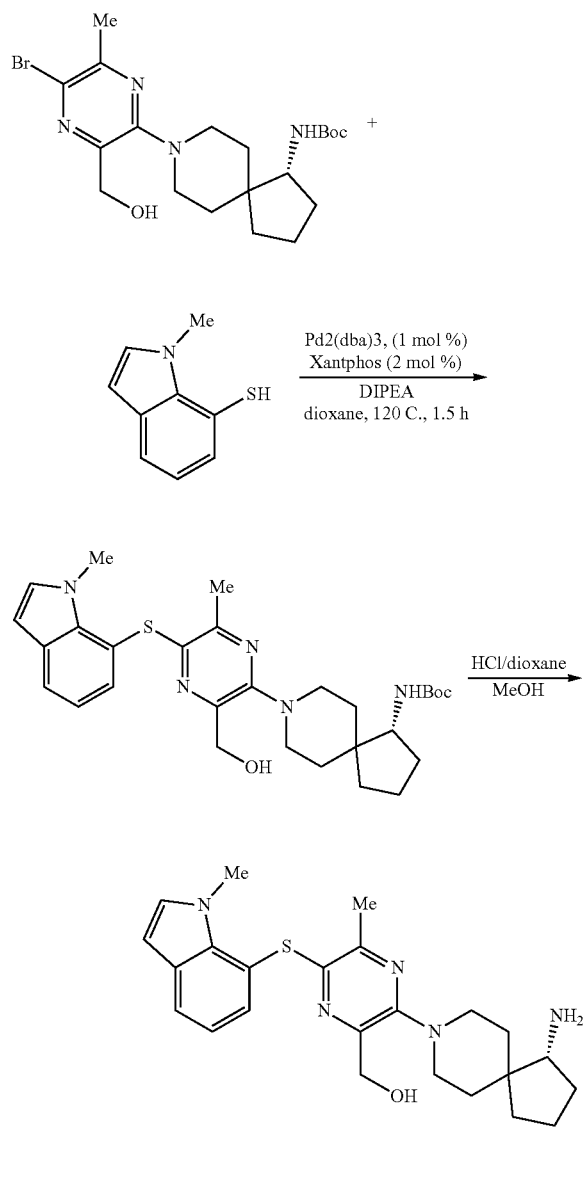

Step 1. Synthesis of (R)-tert-butyl (8-(3-(hydroxymethyl)-6-methyl-5-((1-methyl-1H-indol-7-yl)thio)pyrazin-2-yl)-8-azaspiro[4.5]decan-1-yl)carbamate To a microwave vial was added tert-butyl ((3S,4S)-8-(5-bromo-3-(hydroxymethyl)-6-methylpyrazin-2-yl)-3-methyl-2-oxa-8-azaspiro[4.5]decan-4-yl)carbamate (30 mg, 65.8 μmol), 1-methyl-1H-indole-7-thiol (22.4 mg, 131 μmol), Pd$_2$(dba)$_3$ (6.02 mg, 6.58 μmol), Xantphos (7.57 mg, 13.1 μmol), and DIPEA (22.7 μL, 131 μmol). The vial was evacuated under house vacuum for 10 minutes. Then was added degassed 1,4-dioxane (658 μL). The mixture was purged with N$_2$ and evacuated three times. The reaction mixture was stirred under microwave conditions at 120° C. for 2 hours. The resulting reaction mixture was filtered and concentrated under reduced pressure. The residue was purified by column chromatography to yield the desired product (R)-tert-butyl (8-(3-(hydroxymethyl)-6-methyl-5-((1-methyl-1H-indol-7-yl)thio)pyrazin-2-yl)-8-azaspiro[4.5]decan-1-yl)carbamate (30.0 mg, 55.7 μmol, 84.9%). LC-MS (ESI) m/z: [M+H] calculated for $C_{29}H_{39}N_5O_3S$: 538.28; found 538.5.

Step 2. Synthesis of {3-[(1R)-1-amino-8-azaspiro[4.5]decan-8-yl]-5-methyl-6-[(1-methyl-1H-indol-7-yl)sulfanyl]pyrazin-2-yl}methanol To a solution of (R)-tert-butyl (8-(3-(hydroxymethyl)-6-methyl-5-((1-methyl-1H-indol-7-yl)thio)pyrazin-2-yl)-8-azaspiro[4.5]decan-1-yl)carbamate (30 mg, 55.7 μmol) in MeOH (2 mL) was added 4M HCl in dioxane (1 mL, 4.00 mmol). The mixture was stirred in a capped vial for 3 hours. The resulting reaction mixture was concentrated under reduced pressure. The residue was purified by preparative HPLC to yield the desired product {3-[(1R)-1-amino-8-azaspiro[4.5]decan-8-yl]-5-methyl-6-[(1-methyl-1H-indol-7-yl)sulfanyl]pyrazin-2-yl}methanol (19.0 mg, 43.4 μmol, 78.1%) as the formic acid salt. $^1$H NMR (500 MHz, MeOH-d$_4$) δ 8.55 (s, 2H, formic acid), 7.65 (dd, J=7.9, 1.1 Hz, 1H), 7.24 (dd, J=7.4, 1.2 Hz, 1H), 7.12 (d, J=3.2 Hz, 1H), 7.06-6.97 (m, 1H), 6.51 (d, J=3.2 Hz, 1H), 4.36 (s, 2H), 4.02 (s, 3H), 3.53-3.36 (m, 3H), 3.29-3.17 (m, 2H), 3.02 (m, 2H), 2.54 (s, 3H), 1.93-1.64 (m, 6H), 1.51 (t, J=14.3 Hz, 2H). LC-MS (ESI) m/z: [M+H] calculated for $C_{24}H_{31}N_5OS$: 438.22; found 438.47.

Example 255—{3-[(3S,4S)-4-amino-3-methyl-2-oxa-8-azaspiro[4.5]decan-8-yl]-5-methyl-6-{[2-(trifluoromethyl)pyridin-3-yl]sulfanyl}pyrazin-2-yl}methanol

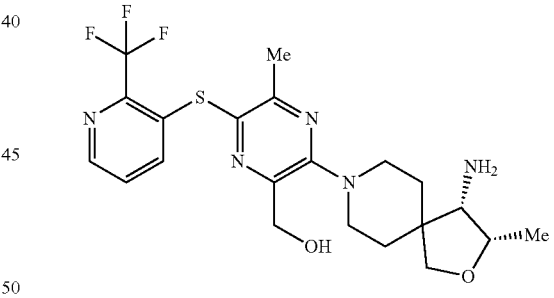

{3-[(3S,4S)-4-amino-3-methyl-2-oxa-8-azaspiro[4.5]decan-8-yl]-5-methyl-6-{[2-(trifluoromethyl)pyridin-3-yl]sulfanyl}pyrazin-2-yl}methanol was synthesized in the manner similar to Example 254, except tert-butyl (R)-(8-(5-bromo-3-(hydroxymethyl)-6-methylpyrazin-2-yl)-8-azaspiro[4.5]decan-1-yl)carbamate was replaced with tert-butyl ((3S,4S)-8-(5-bromo-3-(hydroxymethyl)-6-methylpyrazin-2-yl)-3-methyl-2-oxa-8-azaspiro[4.5]decan-4-yl)carbamate and 1-methyl-1H-indole-7-thiol was replaced with 2-(trifluoromethyl)pyridine-3-thiol. $^1$H NMR (500 MHz, MeOH-d$_4$) δ 8.60-8.48 (m, 2H), 7.76 (dd, J=8.3, 1.3 Hz, 1H, formic acid), 7.52 (dd, J=8.1, 4.6 Hz, 1H), 4.58 (s, 2H), 4.34-4.21 (m, 1H), 3.92-3.63 (m, 5H), 3.11 (m, 2H), 2.50 (s, 3H), 2.10-1.63 (m, 4H), 1.29 (d, J=6.5 Hz, 3H). LC-MS (ESI) m/z: [M+H] calculated for $C_{21}H_{26}F_3N_5O_2S$: 470.18; found 470.4.

The following examples were synthesized in the manner similar to Example 254.

TABLE 9

Examples 256-272

| Example | Structure | M + 1 found |
|---|---|---|
| EXAMPLE 256 | 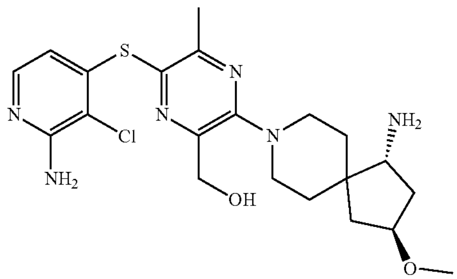 [SMILES: CO[C@@H]1C[C@@H](N)C2(CCN(c3nc(C)c(Sc4ccnc(N)c4Cl)nc3CO)CC2)C1] | 465.2 |
| EXAMPLE 257 | 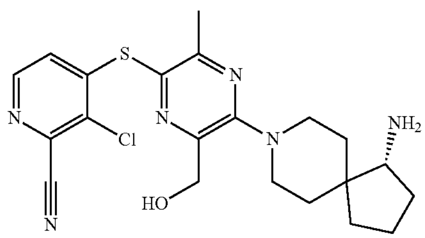 [SMILES: Cc1nc(N2CCC3(CCC[C@H]3N)CC2)c(CO)nc1Sc1ccnc(C#N)c1Cl] | 445.15 |
| EXAMPLE 258 | 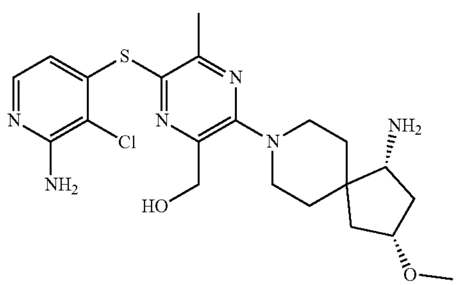 [SMILES: CO[C@H]1C[C@@H](N)C2(CCN(c3nc(C)c(Sc4ccnc(N)c4Cl)nc3CO)CC2)C1] | 465.1 |
| EXAMPLE 259 | 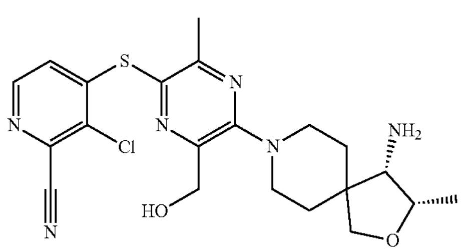 [SMILES: Cc1nc(N2CCC3(CC2)CO[C@@H](C)[C@H]3N)c(CO)nc1Sc1ccnc(C#N)c1Cl] | 461.1 |
| EXAMPLE 260 | 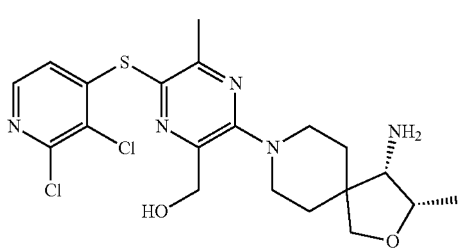 [SMILES: Cc1nc(N2CCC3(CC2)CO[C@@H](C)[C@H]3N)c(CO)nc1Sc1ccnc(Cl)c1Cl] | 470.1 |

TABLE 9-continued

Examples 256-272

| Example | Structure | M + 1 found |
|---|---|---|
| EXAMPLE 261 | 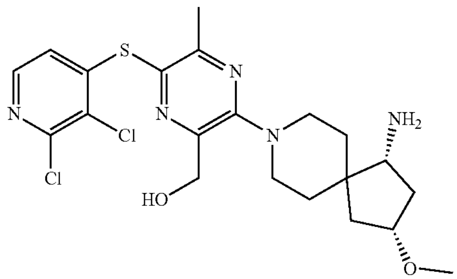 [SMILES: CO[C@H]1C[C@@H](N)C2(CCN(c3nc(C)c(Sc4ccnc(Cl)c4Cl)nc3CO)CC2)C1] | 484.1 |
| EXAMPLE 262 | 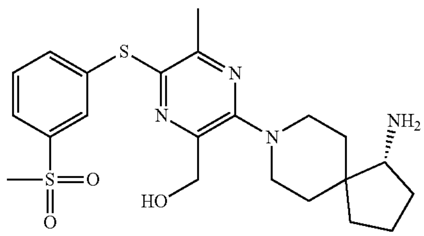 [SMILES: Cc1nc(N2CCC3(CCC[C@H]3N)CC2)c(CO)nc1Sc1cccc(S(C)(=O)=O)c1] | 463.1 |
| EXAMPLE 263 | 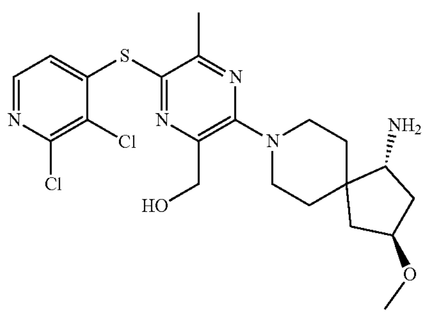 [SMILES: CO[C@@H]1C[C@@H](N)C2(CCN(c3nc(C)c(Sc4ccnc(Cl)c4Cl)nc3CO)CC2)C1] | 484.1 |
| EXAMPLE 264 | 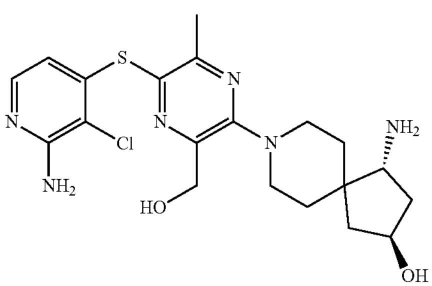 [SMILES: Cc1nc(N2CCC3(CC2)C[C@H](O)C[C@H]3N)c(CO)nc1Sc1ccnc(N)c1Cl] | 451 |
| EXAMPLE 265 | 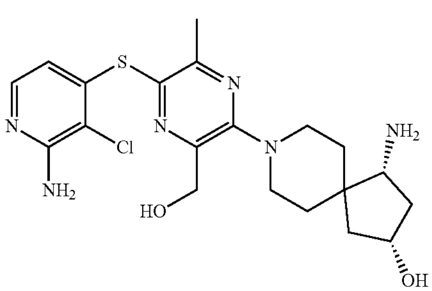 [SMILES: Cc1nc(N2CCC3(CC2)C[C@@H](O)C[C@H]3N)c(CO)nc1Sc1ccnc(N)c1Cl] | 451.2 |

TABLE 9-continued

Examples 256-272

| Example | Structure | M + 1 found |
|---|---|---|
| EXAMPLE 266 | 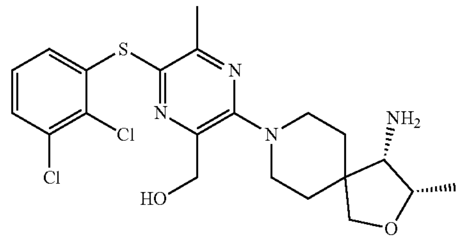 [SMILES: Cc1nc(N2CCC3(CC2)CO[C@@H](C)[C@H]3N)c(CO)nc1Sc1cccc(Cl)c1Cl] | 469.1 |
| EXAMPLE 267 | 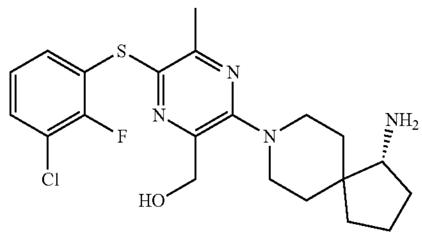 [SMILES: Cc1nc(N2CCC3(CCC[C@H]3N)CC2)c(CO)nc1Sc1cccc(Cl)c1F] | 437.15 |
| EXAMPLE 268 | 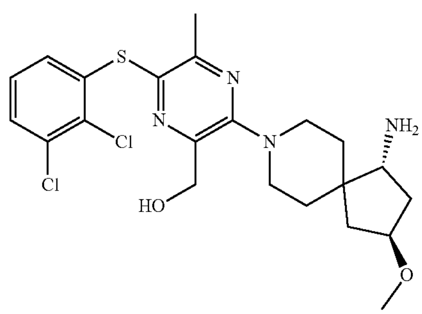 [SMILES: CO[C@@H]1C[C@@H](N)C2(CCN(c3nc(C)c(Sc4cccc(Cl)c4Cl)nc3CO)CC2)C1] | 483.1 |
| EXAMPLE 269 | 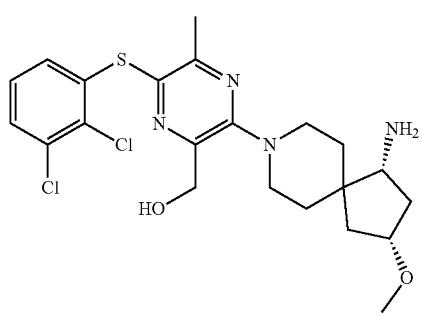 [SMILES: CO[C@H]1C[C@@H](N)C2(CCN(c3nc(C)c(Sc4cccc(Cl)c4Cl)nc3CO)CC2)C1] | 483.1 |
| EXAMPLE 270 | 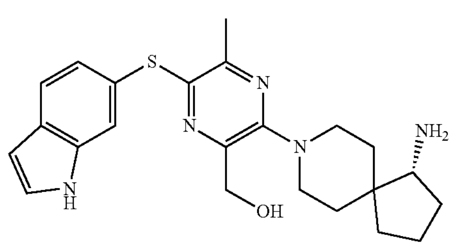 [SMILES: Cc1nc(N2CCC3(CCC[C@H]3N)CC2)c(CO)nc1Sc1ccc2cc[nH]c2c1] | 424.2 |

TABLE 9-continued

Examples 256-272

| Example | Structure | M + 1 found |
|---|---|---|
| EXAMPLE 271 | 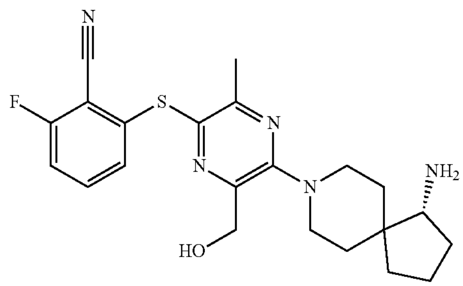 [SMILES: Cc1nc(N2CCC3(CCC[C@H]3N)CC2)c(CO)nc1Sc1cccc(F)c1C#N] | 428.1 |
| EXAMPLE 272 | 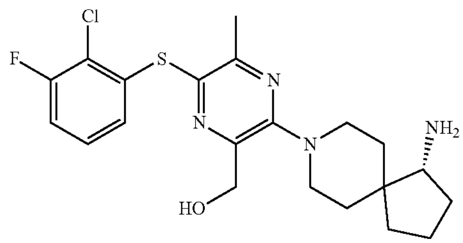 [SMILES: Cc1nc(N2CCC3(CCC[C@H]3N)CC2)c(CO)nc1Sc1cccc(F)c1Cl] | 437.1 |

Example 273—Synthesis of (3-((3S,4S)-4-amino-3-methyl-2-oxa-8-azaspiro[4.5]decan-8-yl)-6-((3-chloro-2-((tetrahydro-2H-pyran-4-yl)amino)pyridin-4-yl)thio)-5-methylpyrazin-2-yl)methanol

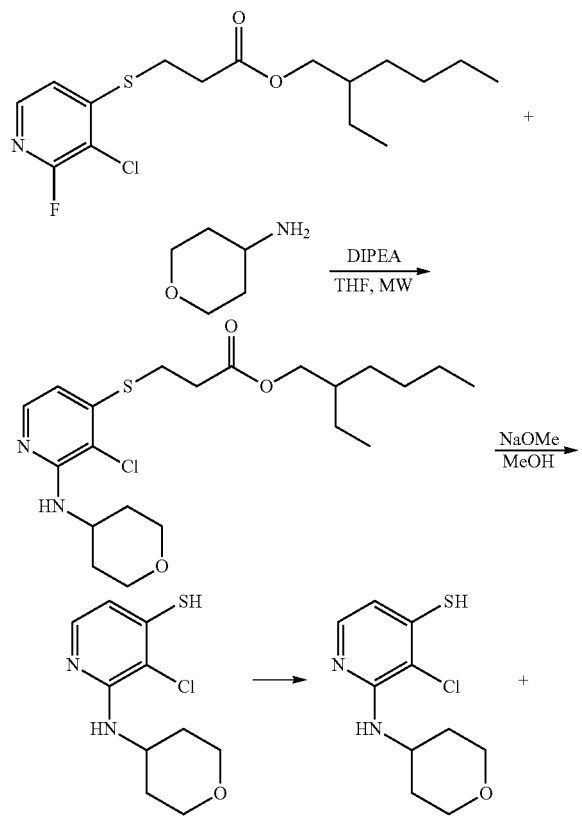

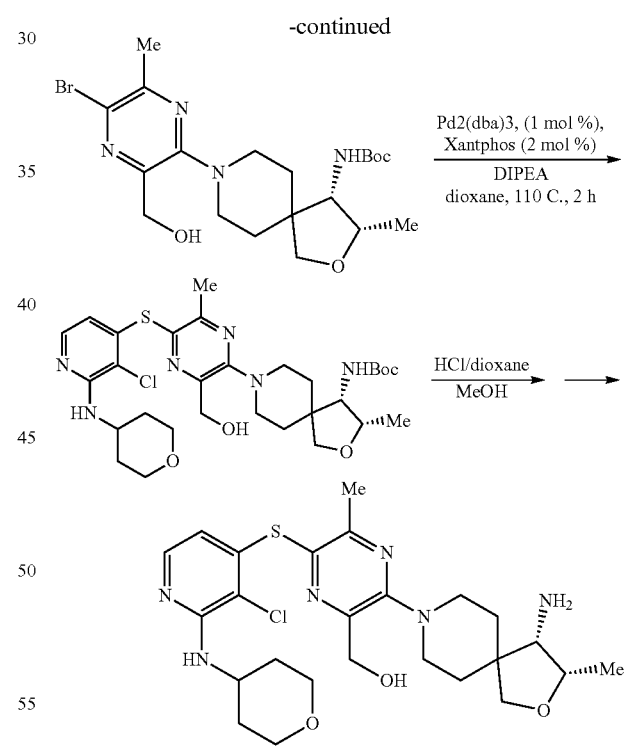

Step 1. Synthesis of 2-ethylhexyl 3-((3-chloro-2-((tetrahydro-2H-pyran-4-yl)amino)pyridin-4-yl)thio) propanoate To a solution of 2-ethylhexyl 3-((3-chloro-2-fluoropyridin-4-yl)thio)propanoate (200 mg, 574 µmol) in THF (2 mL) was added tetrahydro-2H-pyran-4-amine (173 mg, 1.72 mmol), and DIPEA (497 µL, 2.86 mmol). The reaction mixture was stirred under microwave conditions at 140° C. for 6 hours. The resulting reaction mixture was concentrated under reduced pressure and the residue was purified by column chromatography to yield the desired product 2-ethylhexyl 3-((3-chloro-2-((tetrahydro-2H-pyran-4-yl)amino)pyridin-4-yl)thio)propanoate (95.0 mg, 221 µmol, 38.6%). LC-MS (ESI) m/z: [M+H] calculated for $C_{21}H_{33}ClN_2O_3S$: 429.19; found 429.2.

Step 2. Synthesis of 2-ethylhexyl 3-((3-chloro-2-((tetrahydro-2H-pyran-4-yl)oxy)pyridin-4-yl)thio) propanoate To a suspension of 2-ethylhexyl 3-((3-chloro-2-((tetrahydro-2H-pyran-4-yl)amino)pyridin-4-yl)thio)propanoate (92 mg, 214 µmol) in MeOH (2.14 mL) was added sodium methoxide (23.1 mg, 428 µmol). Reaction mixture was stirred in a capped vial at room temperature for 30 minutes. The resulting reaction was concentrated in vacuo and the residue was purified by column chromatography using 0-20% MeOH/DCM to yield the desired product 3-chloro-2-((tetrahydro-2H-pyran-4-yl)amino)pyridine-4-thiol (27.0 mg, 110 µmol, 51.6%). LC-MS (ESI) m/z: [M+H] calculated for $C_{10}H_{13}ClN_2OS$: 245.04; found 245.0.

Step 3. Tert-butyl ((3S,4S)-8-(5-((3-chloro-2-((tetrahydro-2H-pyran-4-yl)amino)pyridin-4-yl)thio)-3-(hydroxymethyl)-6-methylpyrazin-2-yl)-3-methyl-2-oxa-8-azaspiro[4.5]decan-4-yl)carbamate To a microwave vial was added tert-butyl ((3S,4S)-8-(5-bromo-3-(hydroxymethyl)-6-methylpyrazin-2-yl)-3-methyl-2-oxa-8-azaspiro[4.5]decan-4-yl)carbamate (45 mg, 95.4 µmol), 3-chloro-2-((tetrahydro-2H-pyran-4-yl)amino)pyridine-4-thiol (26.7 mg, 104 µmol), $Pd_2(dba)_3$ (8.73 mg, 9.54 µmol), Xantphos (11.0 mg, 19.0 µmol), and DIPEA (33.0 µL, 190 µmol). The vial was evacuated under house vacuum for 10 minutes then was added degassed 1,4-dioxane (954 µL). The reaction mixture was purged with $N_2$ and evacuated three times and then stirred at 120° C. under microwave conditions for 1.5 hours. The resulting reaction mixture was filtered and the filtrate was concentrated in vacuo. The residue was purified by column chromatography to yield the desired product tert-butyl ((3S,4S)-8-(5-((3-chloro-2-((tetrahydro-2H-pyran-4-yl)amino)pyridin-4-yl)thio)-3-(hydroxymethyl)-6-methylpyrazin-2-yl)-3-methyl-2-oxa-8-azaspiro[4.5]decan-4-yl)carbamate (36.0 mg, 56.6 µmol, 59.5%). LC-MS (ESI) m/z: [M+H] calculated for $C_{30}H_{43}ClN_6O_5S$: 635.27; found 635.4.

Step 4. Synthesis of (3-((3S,4S)-4-amino-3-methyl-2-oxa-8-azaspiro[4.5]decan-8-yl)-6-((3-chloro-2-((tetrahydro-2H-pyran-4-yl)amino)pyridin-4-yl)thio)-5-methylpyrazin-2-yl)methanol To a solution of tert-butyl ((3S,4S)-8-(5-((3-chloro-2-((tetrahydro-2H-pyran-4-yl)amino)pyridin-4-yl)thio)-3-(hydroxymethyl)-6-methylpyrazin-2-yl)-3-methyl-2-oxa-8-azaspiro[4.5]decan-4-yl)carbamate (35 mg, 55.0 µmol) in MeOH (1 mL) was added 4M hydrogen chloride in dioxane (196 µL, 785 µmol). The reaction mixture was stirred at 50° C. for 30 minutes. The resulting reaction mixture was concentrated in vacuo. The residue was purified by preparative HPLC to yield (3-((3S,4S)-4-amino-3-methyl-2-oxa-8-azaspiro[4.5]decan-8-yl)-6-((3-chloro-2-((tetrahydro-2H-pyran-4-yl)amino)pyridin-4-yl)thio)-5-methylpyrazin-2-yl)methanol (15.0 mg, 28.0 µmol, 51.0%) as the formic acid salt. $^1$H NMR (500 MHz, MeOH-$d_4$) δ 8.55 (s, 1H) (formic acid), 7.68 (d, J=5.5 Hz, 1H), 5.86 (d, J=5.5 Hz, 1H), 4.65 (s, 2H), 4.33-4.25 (m, 1H), 4.13 (m, 1H), 3.97 (m, 4H), 3.90-3.77 (m, 2H), 3.55 (m, 2H), 3.27-3.11 (m, 1H), 2.50 (s, 3H), 2.03-1.84 (m, 6H), 1.77-1.59 (m, 2H), 1.29 (d, J=6.5 Hz, 3H). LC-MS (ESI) m/z: [M+H] calculated for $C_{30}H_{42}ClN_5O_6S$: 535.22; found 535.4.

Example 274—{3-[(1R)-1-amino-8-azaspiro[4.5]decan-8-yl]-6-{[3-chloro-2-(methylamino)pyridin-4-yl]sulfanyl}-5-methylpyrazin-2-yl}methanol

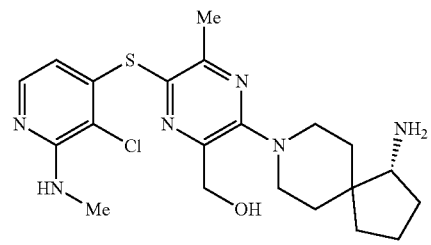 [SMILES: CNc1nccc(Sc2nc(CO)c(N3CCC4(CCC[C@H]4N)CC3)nc2C)c1Cl]

{3-[(1R)-1-amino-8-azaspiro[4.5]decan-8-yl]-6-{[3-chloro-2-(methylamino)pyridin-4-yl]sulfanyl}-5-methylpyrazin-2-yl}methanol was synthesized in the manner similar to Example 273, except tetrahydro-2H-pyran-4-amine and tert-butyl ((3S,4S)-8-(5-bromo-3-(hydroxymethyl)-6-methylpyrazin-2-yl)-3-methyl-2-oxa-8-azaspiro[4.5]decan-4-yl)carbamate were substituted with methanamine and tert-butyl (R)-(8-(5-bromo-3-(hydroxymethyl)-6-methylpyrazin-2-yl)-8-azaspiro[4.5]decan-1-yl)carbamate respectively. $^1$H NMR (500 MHz, MeOH-$d_4$) δ 8.54 (s, 1H, formic acid), 7.68 (d, J=5.6 Hz, 1H), 5.84 (d, J=5.6 Hz, 1H), 4.65 (s, 2H), 3.92 (m, 3H), 3.29-3.13 (m, 4H), 2.97 (s, 3H), 2.50 (s, 3H), 1.97-1.68 (m, 6H), 1.58 (t, J=13.1 Hz, 2H). LC-MS (ESI) m/z: [M+H] calculated for $C_{21}H_{29}ClN_6OS$: 449.18; found 449.35.

Example 275—{3-[(3S,4S)-4-amino-3-methyl-2-oxa-8-azaspiro[4.5]decan-8-yl]-6-({3-chloro-2-[(oxetan-3-yl)amino]pyridin-4-yl}sulfanyl)-5-methylpyrazin-2-yl}methanol

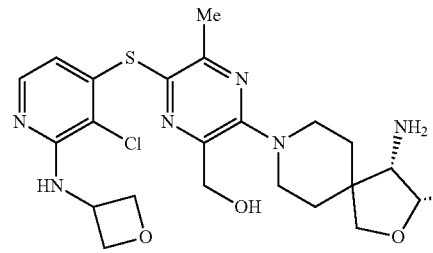

{3-[(3S,4S)-4-amino-3-methyl-2-oxa-8-azaspiro[4.5]decan-8-yl]-6-({3-chloro-2-[(oxetan-3-yl)amino]pyridin-4-yl}sulfanyl)-5-methylpyrazin-2-yl}methanol was synthesized in the manner similar to Example 273, except tetrahydro-2H-pyran-4-amine was substituted with oxetan-3-amine. $^1$H NMR (500 MHz, MeOH-$d_4$) δ 8.53 (s, 4H, formic acid), 7.79 (d, J=7.0 Hz, 1H), 6.25 (d, J=7.0 Hz, 1H), 4.66 (s, 2H), 4.82-4.71 (m, 1H) 4.62-4.54 (m, 2H), 4.49 (ddd, J=10.6, 6.5, 3.3 Hz, 1H), 4.34-4.23 (m, 1H), 4.01-3.67

(m, 6H), 3.31-3.13 (m, 2H), 2.51 (s, 3H), 2.02-1.65 (m, 4H), 1.30 (d, J=6.5 Hz, 3H). LC-MS (ESI) m/z: [M+H] calculated for $C_{23}H_{31}ClN_6O_3S$: 507.19; found 507.5.

The following example was synthesized in the manner similar to Example 273.

TABLE 10

Example 276

| Example | Structure | M + 1 found |
|---|---|---|
| EXAMPLE 276 | 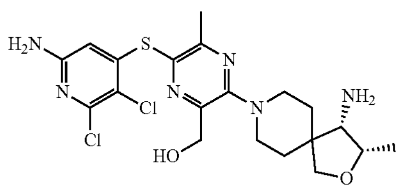 [SMILES: Cc1nc(N2CCC3(CC2)CO[C@@H](C)[C@H]3N)c(CO)nc1Sc1cc(N)nc(Cl)c1Cl] | 485 |

Example 277—Synthesis of (3-((3S,4S)-4-amino-3-methyl-2-oxa-8-azaspiro[4.5]decan-8-yl)-6-((3-chloro-2-((tetrahydro-2H-pyran-4-yl)oxy)pyridin-4-yl)thio)-5-methylpyrazin-2-yl)methanol

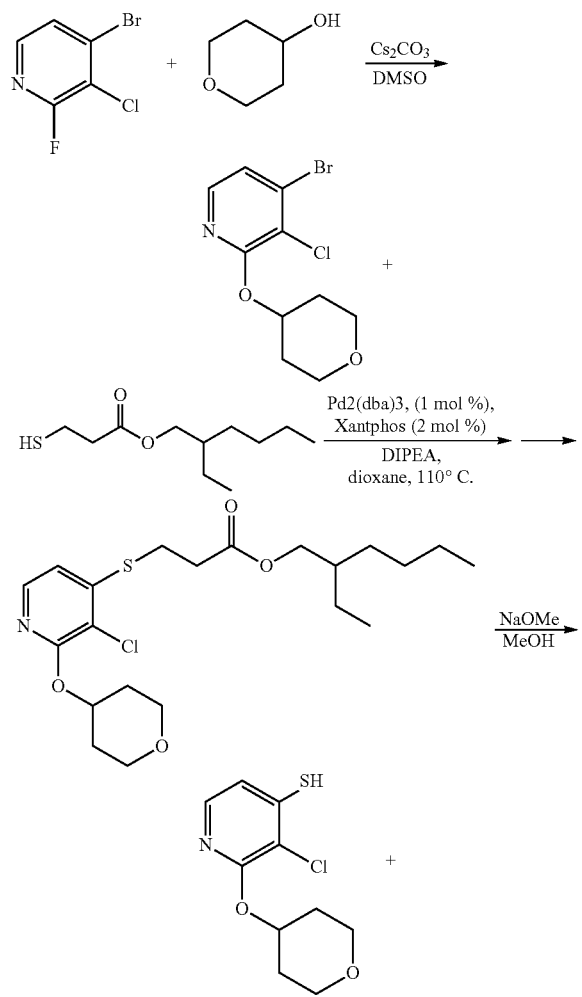

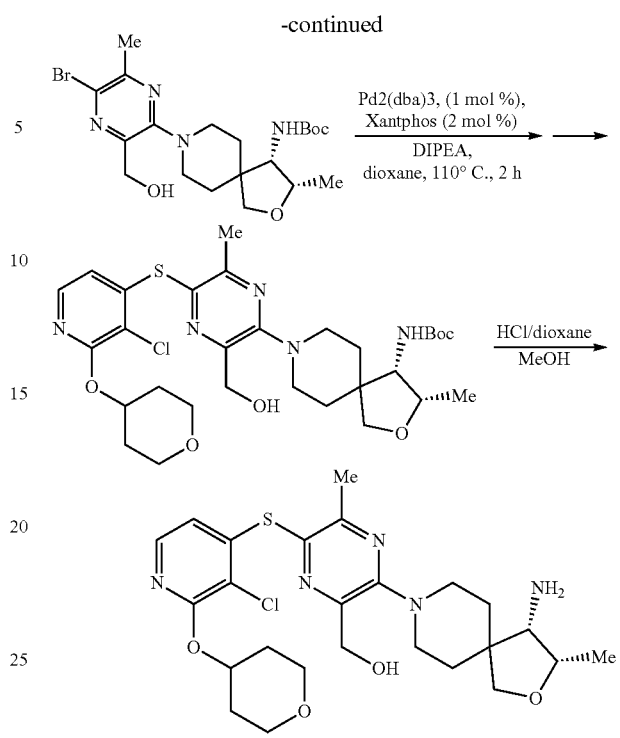

Step 1. Synthesis of 4-bromo-3-chloro-2-((tetrahydro-2H-pyran-4-yl)oxy)pyridine

To a suspension of 4-bromo-3-chloro-2-fluoropyridine (200 mg, 950 µmol) in DMSO (2 mL) was added tetrahydro-2H-pyran-4-ol (194 mg, 1.90 mmol) and cesium carbonate (772 mg, 2.37 mmol). Reaction mixture was stirred in a capped vial at 100° C. for 90 minutes. The resulting reaction mixture was diluted with EtOAc and H₂O. The aqueous layer was extracted two more times with EtOAc. The combined organic layers were dried over MgSO₄, filtered, and concentrated in vacuo. The residue was purified by column chromatography to yield the desired product 4-bromo-3-chloro-2-((tetrahydro-2H-pyran-4-yl)oxy)pyridine (91.0 mg, 344 µmol, 36.2%). LC-MS (ESI) m/z: [M+H] calculated for $C_{10}H_{11}BrClNO_2$: 291.97; found 291.7.

Step 2. Synthesis of 2-ethylhexyl 3-((3-chloro-2-((tetrahydro-2H-pyran-4-yl)oxy)pyridin-4-yl)thio) propanoate To a solution of 4-bromo-3-chloro-2-((tetrahydro-2H-pyran-4-yl)oxy)pyridine (157 mg, 536 µmol) in 1,4-dioxane (5.36 mL) was added 2-ethylhexyl 3-mercaptopropanoate (130 mg, 589 µmol), Pd₂(dba)₃ (29.3 mg, 32.1 µmol), Xantphos (31.0 mg, 53.6 µmol), and DIPEA (185 µL, 1.07 mmol). The reaction mixture was stirred at 110° C. under N₂ atmosphere for 5 hours. The resulting reaction mixture was diluted with H₂O 2O and DCM. The organic layer was separated, dried over MgSO₄, filtered, and concentrated in vacuo. The residue was purified by column chromatography using 0-33% EtOAc/heptane to yield the desired product 2-ethylhexyl 3-((3-chloro-2-((tetrahydro-2H-pyran-4-yl)oxy)pyridin-4-yl)thio)propanoate (224 mg, 520 µmol, 97.3%). LC-MS (ESI) m/z: [M+H] calculated for $C_{21}H_{32}ClNO_4S$: 430.17; found 430.4.

Step 3. Synthesis of 3-chloro-2-((tetrahydro-2H-pyran-4-yl)oxy)pyridine-4-thiol To a suspension of 2-ethylhexyl 3-((3-chloro-2-((tetrahydro-2H-pyran-4-yl)oxy)pyridin-4-yl)thio)propanoate (224 mg, 520 μmol) in MeOH (5.19 mL) was added sodium methoxide (55.6 mg, 1.03 mmol). Reaction mixture was stirred in a capped vial at room temperature for 30 minutes. The resulting reaction mixture was concentrated in vacuo and the residue was purified by column chromatography to yield the desired product 3-chloro-2-((tetrahydro-2H-pyran-4-yl)oxy)pyridine-4-thiol (95.0 mg, 386 μmol, 74.8%). LC-MS (ESI) m/z: [M+H] calculated for $C_{10}H_{12}ClNO_2S$: 246.03; found 246.0.

Step 4. Synthesis of tert-butyl ((3S,4S)-8-(5-((3-chloro-2-((tetrahydro-2H-pyran-4-yl)oxy)pyridin-4-yl)thio)-3-(hydroxymethyl)-6-methylpyrazin-2-yl)-3-methyl-2-oxa-8-azaspiro[4.5]decan-4-yl)carbamate To a microwave vial was added tert-butyl ((3S,4S)-8-(5-bromo-3-(hydroxymethyl)-6-methylpyrazin-2-yl)-3-methyl-2-oxa-8-azaspiro[4.5]decan-4-yl)carbamate (45 mg, 95.4 μmol), 3-chloro-2-((tetrahydro-2H-pyran-4-yl)oxy)pyridine-4-thiol (26.8 mg, 104 μmol), $Pd_2(dba)_3$ (8.73 mg, 9.54 μmol), Xantphos (11.0 mg, 19.0 μmol), and DIPEA (33.0 μL, 190 μmol). The vial was evacuated under house vacuum for 10 minutes then 1,4-dioxane (954 μL) was added. The mixture was purged with $N_2$ and evacuated three times and then stirred at 120° C. for 1.5 hours under microwave conditions. The resulting reaction mixture was filtered through a pad of celite and the filtrate was concentrated in vacuo. The residue was purified by column chromatography using 0-100% EtOAc/Heptanes. The clean fractions were combined and concentrated in vacuo to yield the desired product tert-butyl ((3S,4S)-8-(5-((3-chloro-2-((tetrahydro-2H-pyran-4-yl)oxy)pyridin-4-yl)thio)-3-(hydroxymethyl)-6-methylpyrazin-2-yl)-3-methyl-2-oxa-8-azaspiro[4.5]decan-4-yl)carbamate (55.0 mg, 86.4 μmol, 90.7%). LC-MS (ESI): m/z: [M+H] calculated for $C_{30}H_{42}ClN_5O_6S$: 636.25; found 636.5.

Step 5. Synthesis of (3-((3S,4S)-4-amino-3-methyl-2-oxa-8-azaspiro[4.5]decan-8-yl)-6-((3-chloro-2-((tetrahydro-2H-pyran-4-yl)oxy)pyridin-4-yl)thio)-5-methylpyrazin-2-yl)methanol To a solution of tert-butyl ((3S,4S)-8-(5-((3-chloro-2-((tetrahydro-2H-pyran-4-yl)oxy)pyridin-4-yl)thio)-3-(hydroxymethyl)-6-methylpyrazin-2-yl)-3-methyl-2-oxa-8-azaspiro[4.5]decan-4-yl)carbamate (50 mg, 78.5 μmol) in MeOH (1 mL) was added hydrogen chloride in dioxane (196 μL, 785 μmol). The reaction mixture was stirred at 50° C. for 30 minutes. The resulting reaction mixture was concentrated in vacuo. The residue was purified by reverse phase HPLC to yield the desired product (3-((3S,4S)-4-amino-3-methyl-2-oxa-8-azaspiro[4.5]decan-8-yl)-6-((3-chloro-2-((tetrahydro-2H-pyran-4-yl)oxy)pyridin-4-yl)thio)-5-methylpyrazin-2-yl)methanol (17.0 mg, 31.7 μmol, 40.4%) as the formic acid salt. $^1H$ NMR (500 MHz, MeOH-$d_4$) δ 8.55 (s, 1H, formic acid), 7.68 (d, J=5.5 Hz, 1H), 5.86 (d, J=5.5 Hz, 1H), 4.65 (s, 2H), 4.33-4.24 (m, 1H), 4.12 (m, 1H), 3.97 (m, 4H), 3.91-3.76 (m, 2H), 3.55 (m, 2H), 3.23-3.09 (m, 1H), 2.50 (s, 3H), 2.02-1.80 (m, 6H), 1.78-1.59 (m, 2H), 1.29 (d, J=6.5 Hz, 3H). LC-MS (ESI): m/z: [M+H] calculated for $C_{25}H_{34}ClN_5O_4S$: 536.20; found 536.4.

Example 278—{3-[(3S,4S)-4-amino-3-methyl-2-oxa-8-azaspiro[4.5]decan-8-yl]-6-[(3-chloro-2-methoxypyridin-4-yl)sulfanyl]-5-methylpyrazin-2-yl}methanol

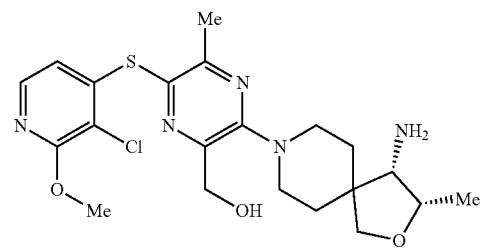 [SMILES: COc1nccc(Sc2nc(CO)c(N3CCC4(CC3)CO[C@@H](C)[C@H]4N)nc2C)c1Cl]

{3-[(3S,4S)-4-amino-3-methyl-2-oxa-8-azaspiro[4.5]decan-8-yl]-6-[(3-chloro-2-methoxypyridin-4-yl)sulfanyl]-5-methylpyrazin-2-yl}methanol was synthesized in the manner similar to Example 277, except tetrahydro-2H-pyran-4-ol was substituted with MeOH. $^1H$ NMR (500 MHz, MeOH-$d_4$) δ 8.56 (s, 1H, formic acid), 7.80 (d, J=5.5 Hz, 1H), 6.25 (d, J=5.5 Hz, 1H), 4.65 (s, 2H), 4.28 (m, 1H), 4.00 (s, 3H), 3.85 (m, 3H), 3.40-3.14 (m, 4H), 2.49 (s, 3H), 2.04-1.67 (m, 4H), 1.27 (d, J=6.5 Hz, 3H). LC-MS (ESI) m/z: [M+H] calculated for $C_{21}H_{28}ClN_5O_3S$: 466.16; found 466.37.

Example 279—{3-[(3S,4S)-4-amino-3-methyl-2-oxa-8-azaspiro[4.5]decan-8-yl]-6-{[3-chloro-2-(oxetan-3-yloxy)pyridin-4-yl]sulfanyl}-5-methylpyrazin-2-yl}methanol

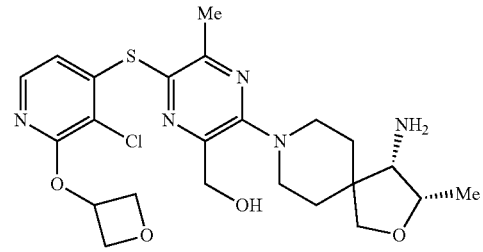 [SMILES: Cc1nc(N2CCC3(CC2)CO[C@@H](C)[C@H]3N)c(CO)nc1Sc1ccnc(OC2COC2)c1Cl]

{3-[(3S,4S)-4-amino-3-methyl-2-oxa-8-azaspiro[4.5]decan-8-yl]-6-{[3-chloro-2-(oxetan-3-yloxy)pyridin-4-yl]sulfanyl}-5-methylpyrazin-2-yl}methanol was synthesized in the manner similar to Example 277, except tetrahydro-2H-pyran-4-ol was substituted with oxetan-3-ol. $^1H$ NMR (500

MHz, MeOH-d$_4$) δ 8.46 (s, 4H, formic acid), 8.18 (d, J=7.0 Hz, 1H), 6.83 (d, J=6.9 Hz, 1H), 5.69-5.48 (m, 1H), 5.05-4.77 (m, 4H), 4.67 (s, 2H), 4.31 (dd, J=6.6, 4.3 Hz, 1H), 4.17-3.83 (m, 5H), 3.45-3.34 (m, 2H), 3.29-3.12 (m, 1H), 2.52 (s, 2H), 2.01-1.72 (m, 4H), 1.33 (d, J=6.5 Hz, 3H). LC-MS (ESI) m/z: [M+H] calculated for C$_{21}$H$_{28}$ClN$_5$O$_3$S: 508.17; found 508.4.

Example 280—1-(4-((5-((3S,4S)-4-amino-3-methyl-2-oxa-8-azaspiro[4.5]decan-8-yl)-6-(hydroxymethyl)-3-methylpyrazin-2-yl)thio)-3-chloropyridin-2-yl)azetidine-3-carbonitrile

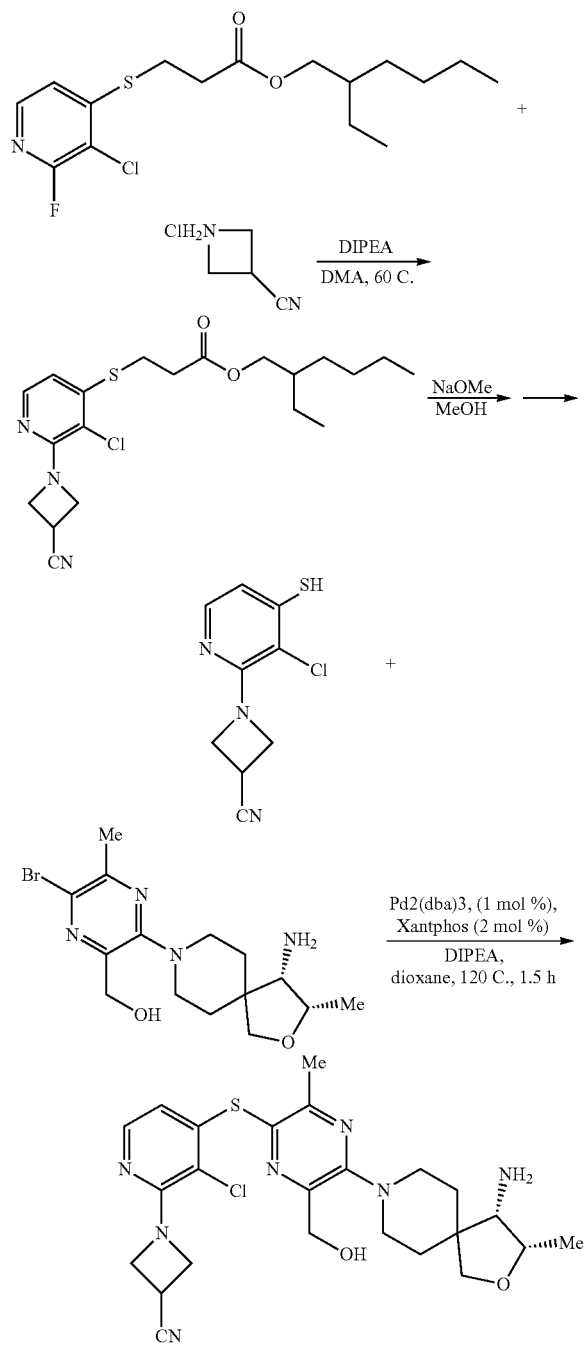

Step 1. Synthesis of octan-3-yl 3-((3-chloro-2-(3-cyanoazetidin-1-yl)pyridin-4-yl)thio)propanoate To a solution of octan-3-yl 3-((3-chloro-2-fluoropyridin-4-yl)thio)propanoate in DMA (862 μL), was added 3-azetidinecarbonitrile hydrochloride (152 mg, 1.29 mmol) and DIPEA (298 μL, 1.72 mmol). Reaction mixture was stirred in a capped vial at 60° C. for 6 hours. The resulting reaction mixture was concentrated in vacuo and the residue, octan-3-yl 3-((3-chloro-2-(3-cyanoazetidin-1-yl)pyridin-4-yl)thio)propanoate, was carried onto the next step without any further purification and assuming quantitative yield. LC-MS (ESI) m/z: [M+H] calculated for C$_{20}$H$_{28}$ClN$_3$O$_2$S: 410.17; found 409.9.

Step 2. Synthesis of 1-(3-chloro-4-mercaptopyridin-2-yl)azetidine-3-carbonitrile To a suspension of octan-3-yl 3-((3-chloro-2-(3-cyanoazetidin-1-yl)pyridin-4-yl)thio)propanoate (176 mg, 429 μmol) in MeOH (4.28 mL) was added sodium methoxide (44.7 mg, 828 μmol). The mixture was stirred at room temperature for 30 minutes. The resulting reaction was concentrated in vacuo and the residue was purified by column chromatography to yield the desired product 1-(3-chloro-4-mercaptopyridin-2-yl)azetidine-3-carbonitrile (89.0 mg, 394 μmol, 91.9%). LC-MS (ESI) m/z: [M+H] calculated for C$_9$H$_8$ClN$_3$S: 226.01; found 225.7.

Step 3. Synthesis of 1-(4-((5-((3S,4S)-4-amino-3-methyl-2-oxa-8-azaspiro[4.5]decan-8-yl)-6-(hydroxymethyl)-3-methylpyrazin-2-yl)thio)-3-chloropyridin-2-yl)azetidine-3-carbonitrile 1-(3-chloro-4-mercaptopyridin-2-yl)azetidine-3-carbonitrile (81.9 mg, 363 μmol), (3-((3S,4S)-4-amino-3-methyl-2-oxa-8-azaspiro[4.5]decan-8-yl)-6-bromo-5-methylpyrazin-2-yl)methanol (90 mg, 242 μmol), Xantphos (28.0 mg, 48.4 μmol) and Pd$_2$(dba)$_3$ (22.1 mg, 24.2 μmol) were weighed into a microwave vial. The reaction vessel was flushed 3 times with N$_2$ and dioxane (degassed) (2.42 mL) was added, followed by DIPEA (84.0 μL, 484 μmol). The headspace of the reaction was flushed 3 more times with N$_2$ and the mixture was heated to 120° C. in a microwave for 2 hours. After cooling to room temperature the mixture was filtered over celite, the filtrate was evaporated to dryness and the crude residue was purified by preparative HPLC to give the desired product 1-(4-((5-((3S,4S)-4-amino-3-methyl-2-oxa-8-azaspiro[4.5]decan-8-yl)-6-(hydroxymethyl)-3-methylpyrazin-2-yl)thio)-3-chloropyridin-2-yl) azetidine-3-carbonitrile (32.0 mg, 62 μmol, 25.8%). LC-MS (ESI) m/z: [M+H] calculated for C$_{24}$H$_{30}$ClN$_7$O$_2$S: 516.20; found 516.1. 1H NMR (500 MHz, MeOH-d$_4$) δ 8.38 (s, 1H), 7.79 (d, J=5.4 Hz, 1H), 6.09 (d, J=5.4 Hz, 1H), 4.66 (s, 2H), 4.54 (t, J=8.6 Hz, 2H), 4.40-4.35 (m, 3H), 4.35-4.29 (m, 1H), 4.02-3.85 (m, 3H), 3.72 (tt, J=8.7, 6.0 Hz, 1H), 3.47 (d, J=4.1 Hz, 1H), 3.22-3.15 (m, 1H), 3.12 (ddd, J=13.7, 11.2, 2.7 Hz, 1H), 2.50 (s, 3H), 2.03-1.94 (m, 2H), 1.91 (d, J=13.5 Hz, 1H), 1.78-1.71 (m, 1H), 1.34 (d, J=6.5 Hz, 3H).

Example 281—{3-[(3S,4S)-4-amino-3-methyl-2-oxa-8-azaspiro[4.5]decan-8-yl]-6-{[3-chloro-2-(1H-imidazol-1-yl)pyridin-4-yl]sulfanyl}-5-methylpyrazin-2-yl}methanol

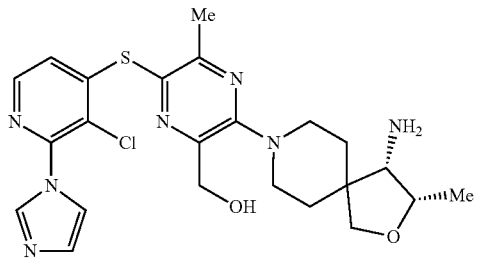 [SMILES: Cc1nc(N2CCC3(CC2)CO[C@@H](C)[C@H]3N)c(CO)nc1Sc1ccnc(-n2ccnc2)c1Cl]

{3-[(3S,4S)-4-amino-3-methyl-2-oxa-8-azaspiro[4.5]decan-8-yl]-6-{[3-chloro-2-(1H-imidazol-1-yl)pyridin-4-yl]sulfanyl}-5-methylpyrazin-2-yl}methanol was synthesized in the manner similar to Example 280, except 3-azetidinecarbonitrile was substituted with imidazole. $^1$H NMR (500 MHz, MeOH-$d_4$) δ 8.53 (s, 1H, formic acid), 8.29-8.09 (m, 2H), 7.67 (t, J=1.4 Hz, 1H), 7.18 (dd, J=1.5, 1.0 Hz, 1H), 6.81 (d, J=5.4 Hz, 1H), 4.67 (s, 2H), 4.36-4.24 (m, 1H), 4.00-3.78 (m, 4H), 3.28-3.11 (m, 3H), 2.55 (s, 3H), 2.02-1.83 (m, 4H), 1.31 (d, J=6.5 Hz, 3H). LC-MS (ESI) m/z: [M+H] calculated for $C_{21}H_{28}ClN_5O_3S$: 502.17; found 502.3.

Example 282—6-[4-({5-[(3S,4S)-4-amino-3-methyl-2-oxa-8-azaspiro[4.5]decan-8-yl]-6-(hydroxymethyl)-3-methylpyrazin-2-yl}sulfanyl)-3-chloropyridin-2-yl]-1λ$^6$-thia-6-azaspiro[3.3]heptane-1,1-dione

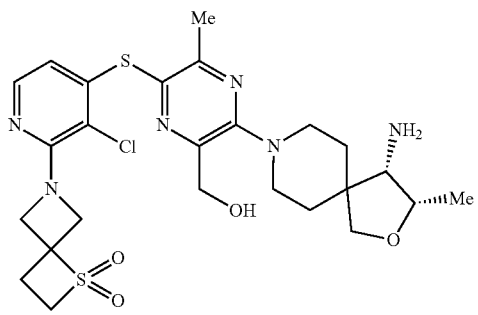 [SMILES: Cc1nc(N2CCC3(CC2)CO[C@@H](C)[C@H]3N)c(CO)nc1Sc1ccnc(N2CC3(CCS3(=O)=O)C2)c1Cl]

6-[4-({5-[(3S,4S)-4-amino-3-methyl-2-oxa-8-azaspiro[4.5]decan-8-yl]-6-(hydroxymethyl)-3-methylpyrazin-2-yl}sulfanyl)-3-chloropyridin-2-yl]-1λ$^6$-thia-6-azaspiro[3.3]heptane-1,1-dione was synthesized in the manner similar to Example 280, except 3-azetidine carbonitrile was substituted with 1-thia-6-azaspiro[3.3]heptan-6-ium 1,1-dioxide. $^1$H NMR (500 MHz, MeOH-$d_4$) δ 8.53 (s, 1H, formic acid), 7.79 (d, J=5.4 Hz, 1H), 6.09 (d, J=5.4 Hz, 1H), 4.81-4.71 (m, 2H), 4.65 (s, 2H), 4.45-4.35 (m, 2H), 4.35-4.25 (m, 1H), 4.14-4.03 (m, 3H), 4.00-3.77 (m, 4H), 3.27-3.06 (m, 2H), 2.49 (s, 3H), 2.46-2.38 (m, 2H), 2.02-1.68 (m, 4H), 1.31 (d, J=6.5 Hz, 3H). LC-MS (ESI) m/z: [M+H] calculated for $C_{25}H_{33}ClN_6O_4S_2$: 581.17; found 581.4.

Example 283—Synthesis of 1-[4-({5-[(3S,4S)-4-amino-3-methyl-2-oxa-8-azaspiro[4.5]decan-8-yl]-6-(hydroxymethyl)-3-methylpyrazin-2-yl}sulfanyl)-3-chloropyridin-2-yl]azetidin-3-ol

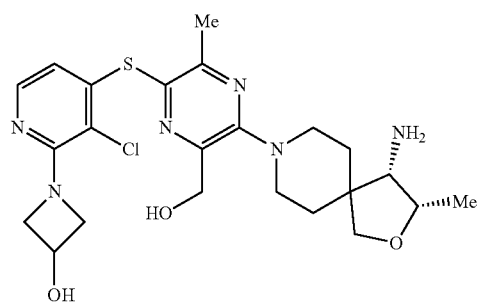 [SMILES: Cc1nc(N2CCC3(CC2)CO[C@@H](C)[C@H]3N)c(CO)nc1Sc1ccnc(N2CC(O)C2)c1Cl]

1-[4-({5-[(3S,4S)-4-amino-3-methyl-2-oxa-8-azaspiro[4.5]decan-8-yl]-6-(hydroxymethyl)-3-methylpyrazin-2-yl}sulfanyl)-3-chloropyridin-2-yl]azetidin-3-ol was synthesized in the manner similar to Example 280, except 3-azetidinecarbonitrile was substituted with 3-hydroxyazetidine (HCl salt). $^1$H NMR (500 MHz, MeOH-$d_4$) δ 8.55 (s, 1H), 7.73 (d, J=5.5 Hz, 1H), 5.98 (d, J=5.4 Hz, 1H), 4.65 (s, 2H), 4.65-4.60 (m, 1H), 4.52-4.46 (m, 2H), 4.33-4.27 (m, 1H), 4.02 (ddd, J=9.1, 4.7, 1.2 Hz, 2H), 3.95 (d, J=8.9 Hz, 1H), 3.91-3.79 (m, 5H), 3.28 (d, J=4.5 Hz, 1H), 3.23 (ddd, J=13.8, 10.7, 3.0 Hz, 1H), 3.15 (ddd, J=13.5, 10.8, 2.8 Hz, 1H), 2.50 (s, 3H), 2.00-1.90 (m, 2H), 1.85 (d, J=13.7 Hz, 1H), 1.74 (d, J=12.8 Hz, 1H), 1.30 (d, J=6.5 Hz, 3H). LC-MS (ESI) m/z: [M+H] calculated for $C_{23}H_{31}ClN_6O_3S$: 507.20; found 507.1.

Example 284—Synthesis of {3-[(3S,4S)-4-amino-3-methyl-2-oxa-8-azaspiro[4.5]decan-8-yl]-6-{[3-chloro-2-(3-methanesulfonylazetidin-1-yl)pyridin-4-yl]sulfanyl}-5-methylpyrazin-2-yl}methanol

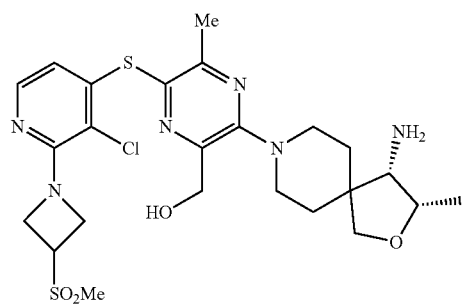 [SMILES: Cc1nc(N2CCC3(CC2)CO[C@@H](C)[C@H]3N)c(CO)nc1Sc1ccnc(N2CC(S(C)(=O)=O)C2)c1Cl]

{3-[(3S,4S)-4-amino-3-methyl-2-oxa-8-azaspiro[4.5]decan-8-yl]-6-{[3-chloro-2-(3-methanesulfonylazetidin-1-yl)pyridin-4-yl]sulfanyl}-5-methylpyrazin-2-yl}methanol was synthesized in the manner similar to Example 280, except 3-azetidinecarbonitrile was substituted with 3-methylsulfonylazetidine (HCl salt). $^1$H NMR (500 MHz, MeOH-$d_4$) δ 8.55 (s, 1H), 7.79 (d, J=5.4 Hz, 1H), 6.07 (d, J=5.4 Hz, 1H), 4.65 (s, 2H), 4.59-4.49 (m, 4H), 4.35-4.27 (m, 2H), 3.95 (d, J=9.0 Hz, 1H), 3.91-3.80 (m, 3H), 3.29 (d, J=4.4 Hz, 1H), 3.23 (ddd, J=13.6, 10.7, 3.1 Hz, 1H), 3.15 (ddd, J=13.6, 10.9, 2.9 Hz, 1H), 3.04 (s, 3H), 2.50 (s, 3H), 2.02-1.89 (m, 2H), 1.85 (d, J=13.4 Hz, 1H), 1.77-1.69 (m, 1H), 1.30 (d, J=6.5 Hz, 3H). LC-MS (ESI) m/z: [M+H] calculated for $C_{24}H_{33}ClN_6O_4S_2$: 569.18; found 569.1.

Example 285—{3-[(3S,4S)-4-amino-3-methyl-2-oxa-8-azaspiro[4.5]decan-8-yl]-6-({3-chloro-2-[(1S,4S)-2-oxa-5-azabicyclo[2.2.1]heptan-5-yl]pyridin-4-yl}sulfanyl)-5-methylpyrazin-2-yl}methanol

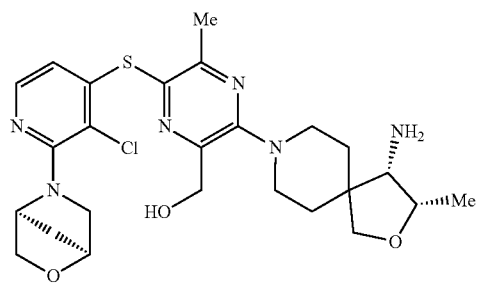 [SMILES: Cc1nc(N2CCC3(CC2)CO[C@@H](C)[C@H]3N)c(CO)nc1Sc1ccnc(N2C[C@@H]3C[C@H]2CO3)c1Cl]

{3-[(3S,4S)-4-amino-3-methyl-2-oxa-8-azaspiro[4.5]decan-8-yl]-6-({3-chloro-2-[(1S,4S)-2-oxa-5-azabicyclo[2.2.1]heptan-5-yl]pyridin-4-yl}sulfanyl)-5-methylpyrazin-2-yl}methanol was synthesized in the manner similar to Example 280, except 3-azetidinecarbonitrile was substituted with (1S,4S)-2-Oxa-5-azabicyclo[2.2.1]heptane (HCl salt). $^1$H NMR (500 MHz, MeOH-$d_4$) δ 8.50 (s, 1H), 7.76 (d, J=5.4 Hz, 1H), 6.03 (d, J=5.3 Hz, 1H), 4.66 (s, 2H), 4.65-4.63 (m, 2H), 4.32 (qd, J=6.5, 4.2 Hz, 1H), 4.08 (dd, J=7.6, 0.8 Hz, 1H), 4.01-3.83 (m, 6H), 3.46-3.40 (m, 2H), 3.19 (ddd, J=13.8, 11.0, 3.0 Hz, 1H), 3.12 (ddd, J=13.8, 11.2, 2.7 Hz, 1H), 2.51 (s, 3H), 2.03-1.86 (m, 5H), 1.79-1.71 (m, 1H), 1.34 (d, J=6.5 Hz, 3H). LC-MS (ESI) m/z: [M+H] calculated for $C_{25}H_{33}ClN_6O_3S$: 533.21; found 533.3.

The following example was synthesized in the manner similar to Example 280.

TABLE 11

Example 286

| Example | Structure | M + 1 found |
|---------|-----------|-------------|
| EXAMPLE 286 | 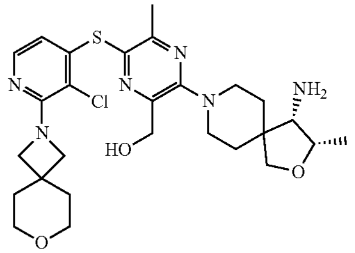 [SMILES: Cc1nc(N2CCC3(CC2)CO[C@@H](C)[C@H]3N)c(CO)nc1Sc1ccnc(N2CC3(CCOCC3)C2)c1Cl] | 561.1 |

Example 287—Synthesis of {3-[(3S,4S)-4-amino-3-methyl-2-oxa-8-azaspiro[4.5]decan-8-yl]-6-{[3-chloro-2-(methylamino)pyridin-4-yl]sulfanyl}-5-methylpyrazin-2-yl}methanol

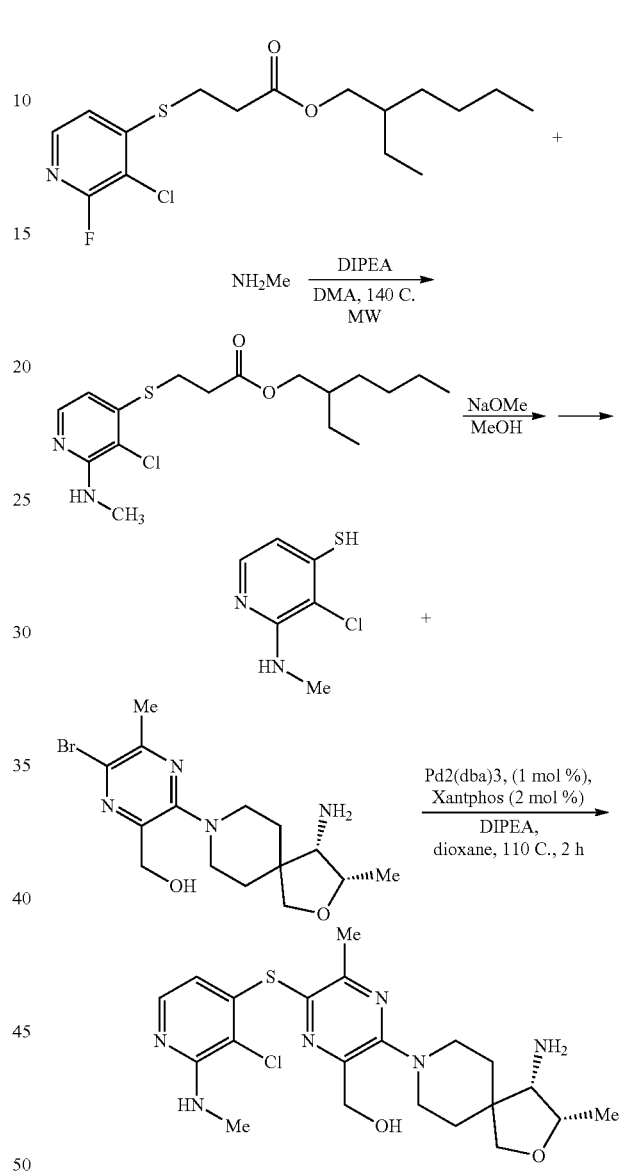

Step 1. Synthesis of 2-ethylhexyl 3-((3-chloro-2-(methylamino)pyridin-4-yl)thio)propanoate To a solution of 2-ethylhexyl 3-((3-chloro-2-fluoropyridin-4-yl)thio)propanoate (230 mg, 661 μmol) in THF (6.60 mL) was added 2M solution of methanamine (1 mL, 2.00 mmol) in THF. Reaction mixture was stirred under microwave conditions at 140° C. for 8 hours. The resulting reaction was concentrated in vacuo and the residue was purified by column chromatography using 0-20% EtOAc/Hex to yield the desired product 2-ethylhexyl 3-((3-chloro-2-(methylamino)pyridin-4-yl)thio)propanoate (180 mg, 501 μmol, 75.9%). LC-MS (ESI) m/z: [M+H] calculated for $C_{17}H_{27}ClN_2O_2S$: 359.15; found 359.4.

Step 2. Synthesis of 3-chloro-2-(methylamino)pyridine-4-thiol

To a suspension of 2-ethylhexyl 3-((3-chloro-2-(methylamino)pyridin-4-yl)thio)propanoate (180 mg, 501 μmol) in MeOH (5.00 mL) was added sodium methoxide (85.2 mg, 1.50 mmol). Reaction mixture was stirred in a sealed vial at room temperature for 30 minutes. The resulting mixture was concentrated under reduced pressure, and the residue was purified by column chromatography to yield 3-chloro-2-(methylamino)pyridine-4-thiol (60.0 mg, 343 μmol, 68.7%). LC-MS (ESI) m/z: [M+H] calculated for $C_6H_7ClN_2S$: 175.00; found 174.9.

Step 3. Synthesis of {3-[(3S,4S)-4-amino-3-methyl-2-oxa-8-azaspiro[4.5]decan-8-yl]-6-{[3-chloro-2-(methylamino)pyridin-4-yl]sulfanyl}-5-methyl-pyrazin-2-yl}methanol To a microwave vial was added (3-((3S,4S)-4-amino-3-methyl-2-oxa-8-azaspiro[4.5]decan-8-yl)-6-bromo-5-methylpyrazin-2-yl)methanol (50 mg, 134 μmol), 3-chloro-2-(methylamino)pyridine-4-thiol (35.1 mg, 201 μmol), $Pd_2(dba)_3$ (12.2 mg, 13.4 μmol), Xantphos (15.5 mg, 26.8 μmol), and DIPEA (69.9 μL, 402 μmol). The mixture was evacuated under house vacuum for 10 minutes then was added degassed 1,4-dioxane (1.34 mL). The reaction mixture was degasses, and stirred at 120° C. under microwave conditions for 2 hours. The resulting reaction mixture was filtered through a pad of celite and the filtrate was concentrated under reduced pressure. The residue was purified by preparative HPLC to yield the desired product {3-[(3S,4S)-4-amino-3-methyl-2-oxa-8-azaspiro[4.5]decan-8-yl]-6-{[3-chloro-2-(methylamino)pyridin-4-yl]sulfanyl}-5-methyl-pyrazin-2-yl}methanol (26.0 mg, 55.9 μmol, 41.7%) as the formic acid salt. $^1$H NMR (500 MHz, MeOH-$d_4$) δ 8.42 (s, 2H, formic acid), 7.68 (d, J=5.6 Hz, 1H), 5.84 (d, J=5.6 Hz, 1H), 4.65 (s, 2H), 4.35-4.26 (m, 1H), 4.02-3.78 (m, 4H), 3.44 (d, J=4.2 Hz, 1H), 3.25-3.07 (m, 2H), 2.96 (s, 3H), 2.49 (s, 3H), 2.03-1.87 (m, 4H), 1.33 (d, J=6.5 Hz, 3H). LC-MS (ESI) m/z: [M+H] calculated for $C_{21}H_{29}ClN_6O_2S$: 465.18; found 465.34.

Example 288—{3-[(3S,4S)-4-amino-3-methyl-2-oxa-8-azaspiro[4.5]decan-8-yl]-6-{[3-chloro-2-(cyclopropylamino)pyridin-4-yl]sulfanyl}-5-methyl-pyrazin-2-yl}methanol

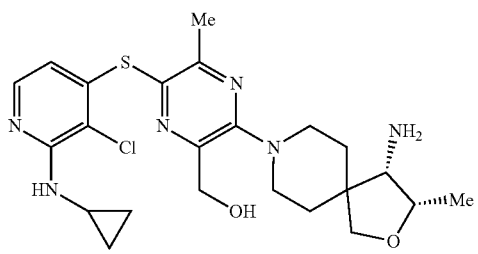 [SMILES: Cc1nc(N2CCC3(CC2)CO[C@@H](C)[C@H]3N)c(CO)nc1Sc1ccnc(NC2CC2)c1Cl]

{3-[(3S,4S)-4-amino-3-methyl-2-oxa-8-azaspiro[4.5]decan-8-yl]-6-{[3-chloro-2-(cyclopropylamino)pyridin-4-yl]sulfanyl}-5-methylpyrazin-2-yl}methanol was synthesized in the manner similar Example 287, except methanamine was substituted with cyclopropylamine. $^1$H NMR (500 MHz, MeOH-$d_4$) δ 8.55 (s, 1H, formic acid), 7.73 (d, J=5.6 Hz, 1H), 5.92 (d, J=5.6 Hz, 1H), 4.65 (s, 2H), 4.29 (m, 1H), 3.97-3.77 (m, 3H), 3.27-3.11 (m, 4H), 2.74-2.66 (m, 1H), 2.49 (s, 3H), 2.02-1.65 (m, 4H), 1.29 (d, J=6.5 Hz, 3H), 0.82 (m, 2H), 0.63-0.54 (m, 2H). LC-MS (ESI) m/z: [M+H] calculated for $C_{23}H_{31}ClN_6O_2S$: 491.19; found 491.46.

Example 289—{3-[(3S,4S)-4-amino-3-methyl-2-oxa-8-azaspiro[4.5]decan-8-yl]-6-{[3-chloro-2-(dimethylamino)pyridin-4-yl]sulfanyl}-5-methylpyrazin-2-yl}methanol

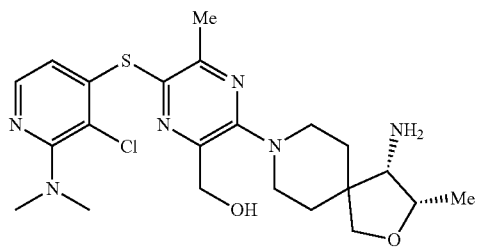 [SMILES: Cc1nc(N2CCC3(CC2)CO[C@@H](C)[C@H]3N)c(CO)nc1Sc1ccnc(N(C)C)c1Cl]

{3-[(3S,4S)-4-amino-3-methyl-2-oxa-8-azaspiro[4.5]decan-8-yl]-6-{[3-chloro-2-(dimethylamino)pyridin-4-yl]sulfanyl}-5-methylpyrazin-2-yl}methanol was synthesized in the manner similar to Example 287, except methylamine was substituted with dimethylamine. $^1$H NMR (500 MHz, MeOH-$d_4$) δ 8.42 (s, 1H, formic acid), 7.82 (d, J=5.4 Hz, 1H), 6.16 (d, J=5.4 Hz, 1H), 4.65 (s, 2H), 4.35-4.26 (m, 1H), 4.02-3.81 (m, 4H), 3.44 (d, J=4.2 Hz, 1H), 3.15 (m, 2H), 2.97 (s, 6H), 2.49 (s, 3H), 2.03-1.86 (m, 4H), 1.33 (d, J=6.5 Hz, 3H). LC-MS (ESI) m/z: [M+H] calculated for $C_{22}H_{31}ClN_6O_2S$: 479.19; found 479.40.

Example 290—{6-[(2-amino-3-chloropyridin-4-yl)sulfanyl]-3-[(3S,4S)-4-amino-3-methyl-2-oxa-8-azaspiro[4.5]decan-8-yl]-5-methylpyrazin-2-yl}methanol

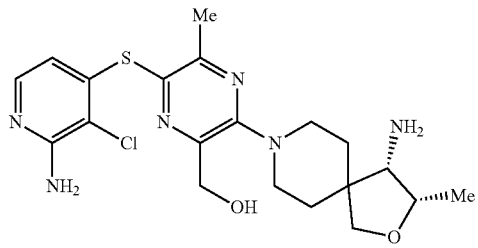 [SMILES: Cc1nc(N2CCC3(CC2)CO[C@@H](C)[C@H]3N)c(CO)nc1Sc1ccnc(N)c1Cl]

{3-[(3S,4S)-4-amino-3-methyl-2-oxa-8-azaspiro[4.5]decan-8-yl]-6-[(3-chloro-2-{2-oxa-6-azaspiro[3.3]heptan-6-yl}pyridin-4-yl)sulfanyl]-5-methylpyrazin-2-yl}methanol was synthesized in the manner similar to Example 287, except 3-chloro-2-(methylamino)pyridine-4-thiol was substituted with 2-amino-3-chloropyridine-4-thiol. $^1$H NMR (500 MHz, MeOH-$d_4$) δ 6 7.59 (d, J=5.6 Hz, 1H), 5.89 (d, J=5.5 Hz, 1H), 4.64 (s, 2H), 4.30 (qd, J=6.5, 4.1 Hz, 1H), 3.99-3.82 (m, 4H), 3.44 (d, J=4.1 Hz, 1H), 3.13 (dddd, J=34.4, 13.8, 11.1, 2.9 Hz, 2H), 2.49 (s, 3H), 2.00-1.84 (m, 3H), 1.76-1.69 (m, 1H), 1.32 (d, J=6.5 Hz, 3H). LC-MS (ESI) m/z: [M+H] calculated for $C_{20}H_{28}ClN_6O_2S$: 451.16; found 451.35.

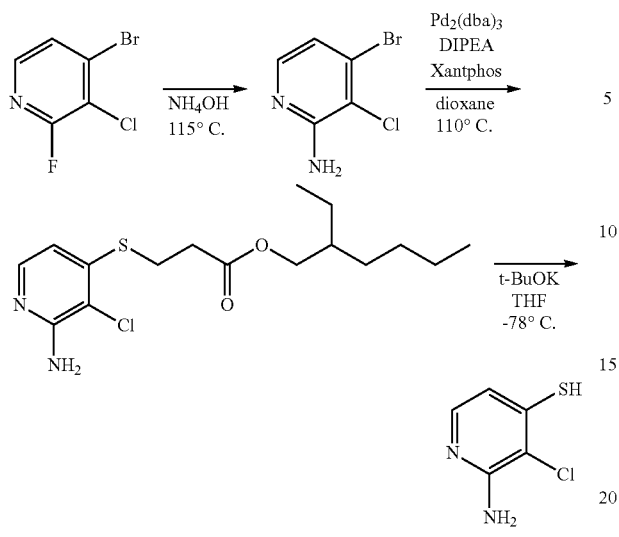

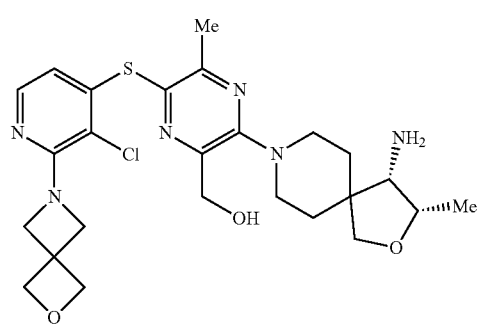 [SMILES: Cc1nc(N2CCC3(CC2)CO[C@@H](C)[C@H]3N)c(CO)nc1Sc1ccnc(N2CC3(COC3)C2)c1Cl]

Synthesis of 2-amino-3-chloropyridine-4-thiol

Step 1. 4-bromo-3-chloro-2-fluoropyridine (2 g, 9.50 mmol, 1 equiv) was suspended in ammonium hydroxide (10.4 mL, 269 mmol, 28 equiv) in a sealed vessel. The reaction was heated at 115° C. for 6 hours, cooled to room temperature, diluted with ethyl acetate, washed with brine, dried over $Na_2SO_4$, filtered, and concentrated under reduced pressure to afford the product as a white solid (1.85 g, 8.91 mmol, 95% yield). LC-MS (ESI) m/z: [M+H] calc. for $C_5H_4BrClN_2$: 206.92; found 206.6.

Step 2. 4-bromo-3-chloropyridin-2-amine (1.83 g, 8.82 mmol, 1 equiv), $Pd_2(dba)_3$ (1.04 g, 1.14 mmol, 0.13 equiv), and xantphos (1.52 g, 2.64 mmol, 0.3 equiv) were placed in a sealed pressure vessel and suspended in degassed 1,4-dioxane (44.0 mL). Next, 2-ethylhexyl 3-mercaptopropanoate (5.00 mL, 22.0 mmol, 2.5 equiv) and DIPEA (6.11 mL, 35.2 mmol, 4 equiv) were added. The reaction was degassed for ten minutes then sealed. The reaction was heated at 100° C. for 3 hours, then cooled and filtered. The filtrate was concentrated under reduced pressure to afford a yellow solid. The solid was suspended in heptane (150 mL) and stirred for 15 minutes. The solids were filtered off and suspended in heptane (150 mL) and stirred for 15 minutes. The solids were filtered off and dried under reduced pressure to afford the product as a yellow solid (2.97 g, 8.61 mmol, 98% yield). LC-MS (ESI) m/z: [M+H] calc. for $C_{16}H_{25}ClN_2O_2S$: 345.13; found 345.2. $^1$H NMR (500 MHz, Chloroform-d) δ 7.84 (d, J=5.4 Hz, 1H), 6.50 (d, J=5.5 Hz, 1H), 5.06-4.80 (m, 2H), 4.02 (dd, J=5.8, 2.4 Hz, 2H), 3.20 (t, J=7.4 Hz, 2H), 2.71 (t, J=7.4 Hz, 2H), 1.65-1.49 (m, 1H), 1.39-1.18 (m, 8H), 0.99-0.78 (m, 6H).

Step 3. 2-ethylhexyl 3-((2-amino-3-chloropyridin-4-yl)thio)propanoate (3 g, 8.69 mmol, 1 equiv) was dissolved in THF (49.9 mL). The reaction was cooled to −78° C. and placed under nitrogen. Next potassium tert-butoxide (11.2 mL, 11.2 mmol, 1.3 equiv) was added. The reaction stirred at −78° C. for 2 hours. The reaction went from a clear yellow to a thick slurry. The slurry was filtered cold and the solid was washed with THF to yield a white solid. Purification by column chromatography (0-20% gradient of MeOH/dichloromethane) afforded the product as a white solid (0.92 g, 5.72 mmol, 66% yield). LC-MS (ESI) m/z: [M+H] calc. for $C_5H_5ClN_2S$: 160.99; found 160.6. $^1$H NMR (500 MHz, DMSO-$d_6$) δ 7.03 (d, J=5.3 Hz, 1H), 6.47 (d, J=5.4 Hz, 1H).

Example 291—{3-[(3S,4S)-4-amino-3-methyl-2-oxa-8-azaspiro[4.5]decan-8-yl]-6-[(3-chloro-2-{2-oxa-6-azaspiro[3.3]heptan-6-yl}pyridin-4-yl)sulfanyl]-5-methylpyrazin-2-yl}methanol

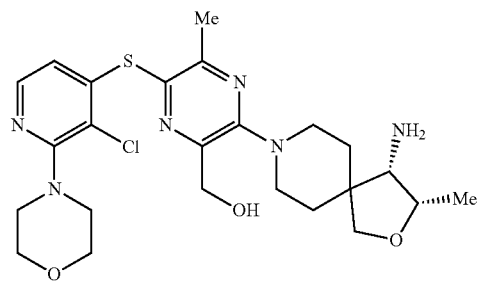 [SMILES: Cc1nc(N2CCC3(CC2)CO[C@@H](C)[C@H]3N)c(CO)nc1Sc1ccnc(N2CCOCC2)c1Cl]

{3-[(3S,4S)-4-amino-3-methyl-2-oxa-8-azaspiro[4.5]decan-8-yl]-6-[(3-chloro-2-{2-oxa-6-azaspiro[3.3]heptan-6-yl}pyridin-4-yl)sulfanyl]-5-methylpyrazin-2-yl}methanol was synthesized in the manner similar to Example 287, except methanamine was substituted with 2-oxa-6-azaspiro[3.3]heptane. $^1$H NMR (500 MHz, MeOH-$d_4$) δ 8.57 (s, 1H, formic acid), 7.74 (d, J=5.4 Hz, 1H), 6.01 (d, J=5.4 Hz, 1H), 4.66 (s, 2H), 4.87 (s, 4H) 4.43 (s, 4H), 4.30 (m, 1H), 3.97-3.76 (m, 4H), 3.32-3.11 (m, 3H), 2.50 (s, 3H), 2.03-1.65 (m, 4H), 1.30 (d, J=6.5 Hz, 3H). LC-MS (ESI) m/z: [M+H] calculated for $C_{25}H_{33}ClN_6O_3S$: 533.20; found 533.42.

Example 292—{3-[(3S,4S)-4-amino-3-methyl-2-oxa-8-azaspiro[4.5]decan-8-yl]-6-{[3-chloro-2-(morpholin-4-yl)pyridin-4-yl]sulfanyl}-5-methylpyrazin-2-yl}methanol {3-[(3S,4S)-4-amino-3-methyl-2-oxa-8-azaspiro[4.5]decan-8-yl]-6-{[3-chloro-2-(morpholin-4-yl)pyridin-4-yl]sulfanyl}-5-methylpyrazin-2-yl}methanol was synthesized in the manner similar to Example 287, except methanamine was substituted with morpholine. $^1$H NMR (500 MHz, MeOH-$d_4$) δ 7.90 (d, J=5.4 Hz, 1H), 6.29 (d, J=5.4 Hz, 1H), 4.65 (s, 2H), 4.39-4.23 (m, 1H), 4.02-3.74 (m, 10H), 3.48-3.41 (m, 1H), 3.36 (s, 2H), 3.15 (m, 2H), 2.50 (s, 3H), 2.08-1.67 (m, 4H), 1.40-1.27 (m, 3H). LC-MS (ESI) m/z: [M+H] calculated for $C_{24}H_{33}ClN_6O_3S$: 521.20; found 521.1.

The following examples were synthesized in the manner similar to Example 287.

TABLE 12

Examples 293-294

| Example | Structure | M + 1 found |
|---|---|---|
| EXAMPLE 293 | 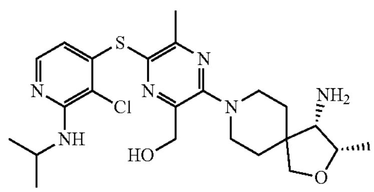 [SMILES: Cc1nc(N2CCC3(CC2)CO[C@@H](C)[C@H]3N)c(CO)nc1Sc1ccnc(NC(C)C)c1Cl] | 493.5 |
| EXAMPLE 294 | 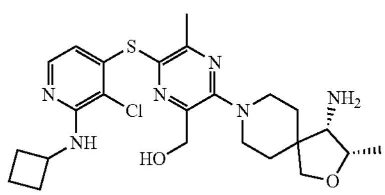 [SMILES: Cc1nc(N2CCC3(CC2)CO[C@@H](C)[C@H]3N)c(CO)nc1Sc1ccnc(NC2CCC2)c1Cl] | 505.4 |

Example 295—Synthesis of (3-((3S,4S)-4-amino-3-methyl-2-oxa-8-azaspiro[4.5]decan-8-yl)-6-((3-chloro-2-cyclopropoxypyridin-4-yl)thio)-5-methyl-pyrazin-2-yl)methanol

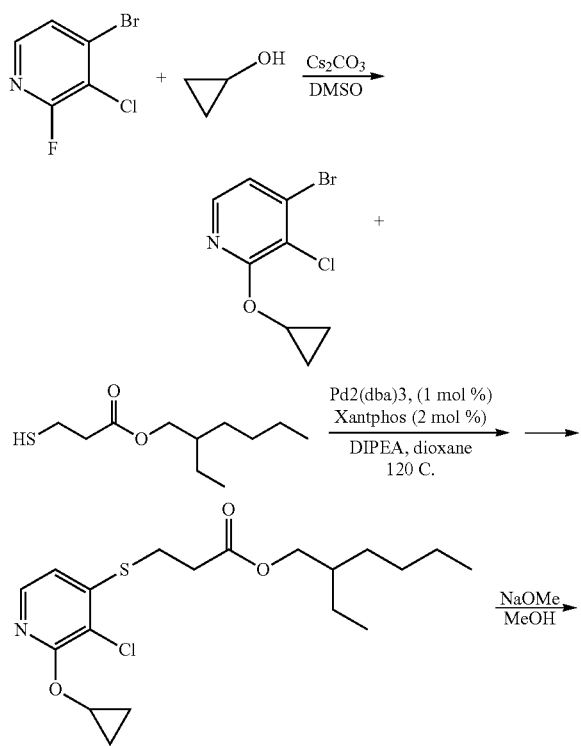

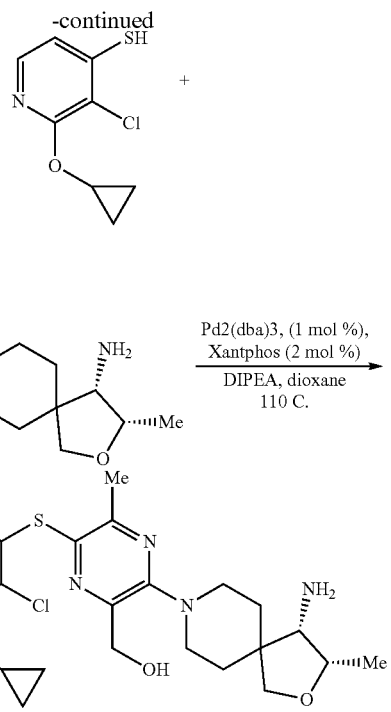

Step 1. Synthesis of 4-bromo-3-chloro-2-cyclopropoxypyridine

To a suspension of 4-bromo-3-chloro-2-fluoropyridine (200 mg, 950 μmol) in DMSO (1 mL) was added cyclopropanol (82.4 mg, 1.42 mmol) and cesium carbonate (619 mg, 1.90 mmol). Reaction mixture was stirred in a capped vial at 100° C. for 90 minutes. The resulting reaction mixture was diluted with EtOAc and $H_2O$. The aqueous layer was extracted two more times with EtOAc. The combined organic layers were dried over $MgSO_4$, filtered, and concentrated in vacuo. The residue was purified by column chromatography 0-25% EtOAc/Heptane to yield the desired product 4-bromo-3-chloro-2-cyclopropoxypyridine (50.0 mg, 201 μmol, 21.1%). LC-MS (ESI) m/z: [M+H] calculated for $C_8H_7BrClNO$: 247.94; found 249.0.

Step 2. Synthesis of tert-butyl ((3S,4S)-8-(5-((3-chloro-2-((tetrahydro-2H-pyran-4-yl)oxy)pyridin-4-yl)thio)-3-(hydroxymethyl)-6-methylpyrazin-2-yl)-3-methyl-2-oxa-8-azaspiro[4.5]decan-4-yl)carbamate To a microwave vial was added 4-bromo-3-chloro-2-cyclopropoxypyridine (50 mg, 201 μmol), 2-ethylhexyl 3-mercaptopropanoate (49.1 mg, 221 μmol), $Pd_2(dba)_3$ (5.36 mg, 12.0 μmol), Xantphos (11.6 mg, 20.1 μmol), and DIPEA (51.9 mg, 402 μmol). The mixture was evacuated under house vacuum for 10 minutes, then was added degassed 1,4-dioxane (2.01 mL). The reaction mixture was purged with $N_2$ and evacuated three times and then 120° C. for 1.5 hours under microwave conditions. The resulting reaction mixture was filtered through a pad of celite and the filtrate was concentrated in vacuo. The residue was purified by column chromatography using 0-100% EtOAc/Heptanes. The clean fractions were combined and concentrated in vacuo to yield the desired product tert-butyl ((3S,4S)-8-(5-((3-chloro-2-((tetrahydro-2H-pyran-4-yl)oxy)pyridin-4-yl)thio)-3-(hydroxymethyl)-6-methylpyrazin-2-yl)-3-methyl- 2-oxa-8-azaspiro[4.5]decan-4-yl)carbamate (55.0 mg, 86.4 µmol, 90.7%). LC-MS (ESI) m/z: [M+H] calculated for $C_{19}H_{28}ClNO_3S$: 386.15; found 386.30.

Step 3. Synthesis of 3-chloro-2-cyclopropoxypyridine-4-thiol

To a suspension of 2-ethylhexyl 3-((3-chloro-2-cyclopropoxypyridin-4-yl)thio)propanoate (40 mg, 103 µmol) in MeOH (1.02 mL) was added sodium methoxide (11.1 mg, 206 µmol). Reaction mixture was stirred in a capped vial at room temperature for 1 hour. The resulting reaction mixture was concentrated in vacuo. The residue was purified by column chromatography using 0-10% MeOH/DCM to yield the desired product 3-chloro-2-cyclopropoxypyridine-4-thiol (18.6 mg, 92.2 µmol, 89.8%). LC-MS (ESI) m/z: [M+H] calculated for $C_8H_8ClNOS$: 202.00; found 202.1.

Step 4. Synthesis of {3-[(3S,4S)-4-amino-3-methyl-2-oxa-8-azaspiro[4.5]decan-8-yl]-6-[(3-chloro-2-cyclopropoxypyridin-4-yl)sulfanyl]-5-methyl-pyrazin-2-yl}methanol To a microwave vial was added (3-((3S,4S)-4-amino-3-methyl-2-oxa-8-azaspiro[4.5]decan-8-yl)-6-bromo-5-methylpyrazin-2-yl)methanol (25 mg, 67.6 µmol), 3-chloro-2-cyclopropoxypyridine-4-thiol (21.3 mg, 101 µmol), Pd$_2$(dba)$_3$ (3.02 mg, 6.76 µmol), Xantphos (7.83 mg, 13.5 µmol), and DIPEA (23.4 µL, 135 µmol). The mixture was evacuated under house vacuum for 10 minutes, then was added degassed 1,4-dioxane (675 µL). The reaction mixture was purged with N$_2$ and evacuated three times and then stirred at 110° C. under microwave conditions for 2 hours. The reaction was complete according to the LC-MS. The resulting reaction mixture was filtered and then the filtrate was concentrated in vacuo. The residue was purified by prep HPLC to yield the desired product (3-((3S,4S)-4-amino-3-methyl-2-oxa-8-azaspiro[4.5]decan-8-yl)-6-((3-chloro-2-cyclopropoxypyridin-4-yl)thio)-5-methylpyrazin-2-yl)methanol (14.0 mg, 28.4 µmol, 42.1%) as the formic acid salt. $^1$H NMR (500 MHz, MeOH-d$_4$) δ 8.55 (s, 1H) (formic acid), 7.82 (d, J=5.5 Hz, 1H), 6.29 (d, J=5.5 Hz, 1H), 4.65 (s, 2H), 4.38-4.26 (m, 2H), 3.88 (m, 2H), 3.30-3.10 (m, 4H), 2.68 (s, 1H), 2.49 (s, 3H), 2.02-1.65 (m, 4H), 1.29 (d, J=6.5 Hz, 3H), 0.86-0.70 (m, 4H). LC-MS (ESI) m/z: [M+H] calculated for $C_{23}H_{30}ClN_5O_3S$: 492.18; found 492.42.

Example 296—Synthesis of (R)-(6-(6-amino-2,3-dichloropyridin-4-yl)-3-(1-amino-8-azaspiro[4.5]decan-8-yl)-5-methylpyrazin-2-yl)methanol

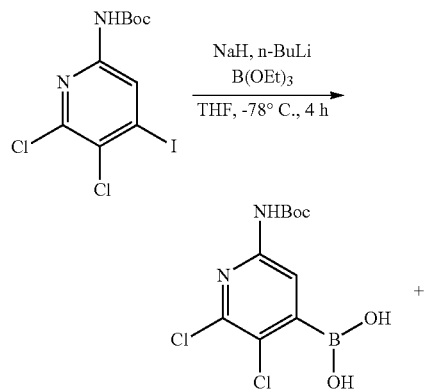

Step 1. Synthesis of (6-((tert-butoxycarbonyl)amino)-2,3-dichloropyridin-4-yl)boronic acid A mixture of tert-butyl (5,6-dichloro-4-iodopyridin-2-yl)carbamate (2 g, 5.14 mmol) in THF (25.6 mL) was cooled to 0° C. under N$_2$. Sodium hydride (240 mg, 10.0 mmol) was added in portions. When hydrogen evolution stopped, the reaction mixture was cooled at −78° C. and n-butyl lithium (4.28 mL, 10.7 mmol) was added over a period of 5 minutes. Triethyl borate (1.91 mL, 11.3 mmol) was added and the mixture was stirred at −78° C. for an additional 4 hours. Water was then added and the mixture was allowed to warm to 0° C. EtOAc and saturated ammonium chloride were added and the phases were separated. The organic phase was washed with additional saturated ammonium chloride and brine and dried over Na$_2$SO$_4$ and the solvent was evaporated. Purification by column chromatography afforded 890 mg (56%) of the desired product. LC-MS (ESI) m/z: [M+H-Boc] calculated for $C_{10}H_{13}BCl_2N_2O_4$: 206.99, found 206.9.

Step 2. Synthesis of (R)-(6-(6-amino-2,3-dichloropyridin-4-yl)-3-(1-amino-8-azaspiro[4.5]decan-8-yl)-5-methylpyrazin-2-yl)methanol

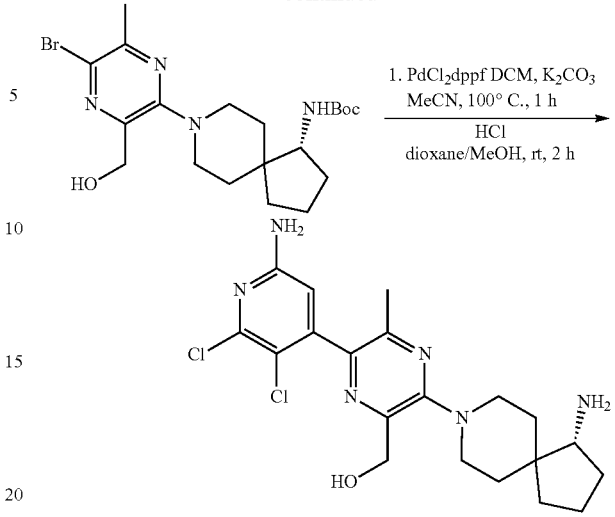

(6-((tert-butoxy carbonyl)amino)-2,3-dichloropyridin-4-yl)boronic acid (90.5 mg, 295 µmol), potassium carbonate (108 mg, 788 µmol), [1,1'-bis(diphenylphosphino) ferrocene]dichloropalladium(II), complex with DCM (32.1 mg, 39.4 µmol) and (R)-tert-butyl (8-(5-bromo-3-(hydroxymethyl)-6-methylpyrazin-2-yl)-8-azaspiro[4.5]decan-1-yl)carbamate (90 mg, 197 µmot) were weighed into a vial equipped with a stir bar and a septum screw cap. The reaction vessel was flushed 3 times with N$_2$. MeCN (1.97 mL, degassed by sparging with N$_2$ for 1 hour) was added against N$_2$ and the headspace of the reaction vessel was flushed 3 times with N$_2$. The mixture was placed into a heating block preheated to 100° C. and stirred vigorously for 1 hour. The reaction mixture was cooled to room temperature and filtered through a plug of celite. The filtrate was evaporated to dryness and purified by column chromatography (0%→99% EtOAc/heptanes). The purified product was dissolved in MeOH (2 mL). The solution was treated with HCl (4M in dioxane, 1 mL) at room temperature for 2 hours. Concentration under reduced pressure and purification by preparative HPLC to give 32 mg (37%) of the desired product. $^1$H NMR (500 MHz, MeOH-d$_4$) δ 8.56 (s, 1H), 6.50 (s, 1H), 4.68 (s, 2H), 3.76 (dd, J=30.5, 13.6 Hz, 2H), 3.26 (t, J=6.9 Hz, 1H), 3.19-3.11 (m, 2H), 2.32 (s, 3H), 2.28-2.19 (m, 1H), 1.94-1.69 (m, 6H), 1.62-1.54 (m, 3H). LC-MS (ESI) m/z: [M+H] calculated for $C_{20}H_{26}O_2N_6O$: 437.16; found 437.1.

Example 297—Synthesis of (R)-4-(5-(1-amino-8-azaspiro[4.5]decan-8-yl)-6-(hydroxymethyl)-3-methylpyrazin-2-yl)-3-chloro-1-methylpyridin-2(1H)-one

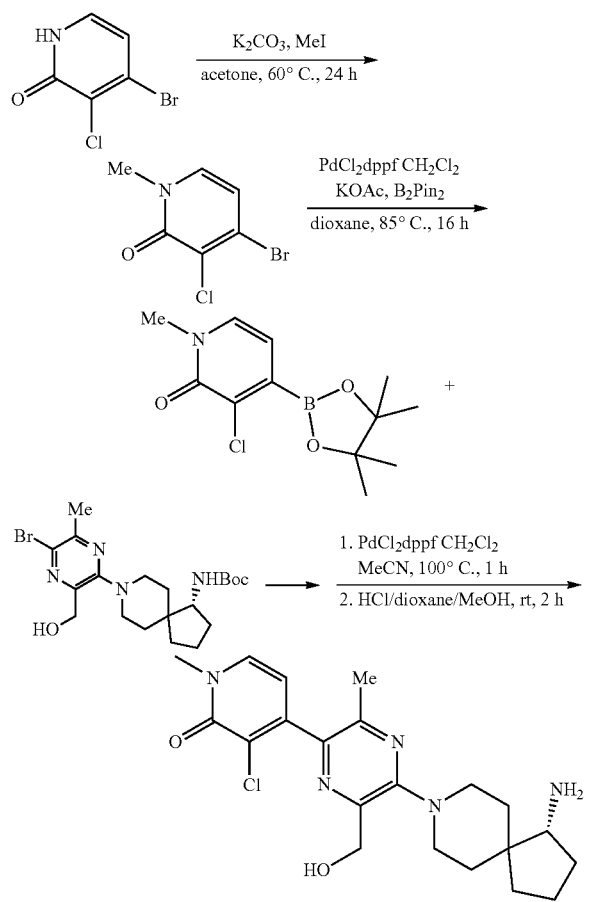

Step 1. Synthesis of 4-bromo-3-chloro-1-methylpyridin-2(1H)-one

In a 40 mL septum screw capped vial 4-bromo-3-chloropyridin-2(1H)-one (600 mg, 2.87 mmol) was dissolved in acetone (2.87 mL) and potassium carbonate (1.57 g, 11.4 mmol) was added, followed by iodomethane (706 μL, 11.4 mmol). The mixture was heated to 60° C. for 24 hours. After cooling to room temperature and filtration over celite the solvent was removed under reduced pressure and the crude product was purified by column chromatography (0-99% EtOAc/heptanes) to give 423 mg (66%) of the desired product. LC-MS (ESI) m/z: [M+H] calculated for $C_6H_5BrClNO$: 221.93, found 221.9.

Step 2. Synthesis of 3-chloro-1-methyl-4-(4,4,5,5-tetramethyl-1,3,2-dioxaborolan-2-yl)pyridin-2(1H)-one 4-bromo-3-chloro-1-methylpyridin-2(1H)-one (250 mg, 1.12 mmol), [1,1'-bis(diphenylphosphino)ferrocene]dichloropalladium(II), complex with DCM (56.6 mg, 69.4 μmol), bis(pinacolateo)diboron (426 mg, 1.68 mmol) and potassium acetate (340 mg, 3.47 mmol) were weighed into a 40 mL glass vial equipped with a screw-on septum cap and a stir bar. The reaction vessel was purged 3 times with N$_2$ and dioxane (degassed) (7.46 mL) was added against N$_2$. The headspace of the reaction was sparged 3 times with N$_2$ and the mixture was placed into a preheated heating block (85° C.). After stirring overnight the mixture was filtered over celite and then evaporated to dryness. The crude product was purified by column chromatography (1%→15% MeOH/DCM) and then triturated with a small amount of MeOH to give 120 mg (40%) of the desired product as an off-white solid. LC-MS (ESI) m/z: [M(boronic acid)-1] calculated for $C_6H_7BClNO_3$: 187.02, found 187.6.

Step 3. Synthesis of (R)-4-(5-(1-amino-8-azaspiro[4.5]decan-8-yl)-6-(hydroxymethyl)-3-methylpyrazin-2-yl)-3-chloro-1-methylpyridin-2(1H)-one (R)-tert-butyl (8-(5-bromo-3-(hydroxymethyl)-6-methylpyrazin-2-yl)-8-azaspiro[4.5]decan-1-yl)carbamate (100 mg, 219 μmol), potassium carbonate (121 mg, 876 μmol), [1,1'-bis(diphenylphosphino)ferrocene]dichloropalladium (II), complex with DCM (35.7 mg, 43.8 μmol) and 6-chloro-1-methyl-5-(4,4,5,5-tetramethyl-1,3,2-dioxaborolan-2-yl)pyridin-2(1H)-one (76.5 mg, 284 μmol) were weighed into a 2 dram vial equipped with a stir bar and a septum screw cap. The reaction vessel was flushed 3 times with N$_2$. MeCN (2.57 mL, degassed by sparging with N$_2$ for 1 hour) was added against N$_2$ and the headspace of the reaction vessel was purged 3 times with N$_2$. This mixture was placed into a heating block preheated to 100° C. and stirred vigorously for 1 hour. The reaction mixture was cooled to room temperature and filtered through a plug of celite followed by concentration under reduced pressure and purification by column chromatography (0%→99% EtOAc/heptanes). The purified product was dissolved in MeOH (2 mL). The solution was treated with HCl (4M in dioxane, 1 mL) at room temperature for 2 hours. After removal of the solvent under reduced pressure the deprotected product was purified by preparative HPLC to give 17 mg (14%) of the desired product. $^1$H NMR (500 MHz, MeOH-d$_4$) δ 8.53 (s, 1H), 7.74 (dd, J=7.0, 1.0 Hz, 1H), 6.44 (d, J=6.9 Hz, 1H), 4.69 (s, 2H), 3.86-3.74 (m, 2H), 3.71 (d, J=1.0 Hz, 3H), 3.31-3.25 (m, 1H), 3.17 (ddt, J=13.4, 11.5, 2.4 Hz, 2H), 2.34 (s, 3H), 2.31-2.20 (m, 1H), 1.95-1.71 (m, 6H), 1.59 (t, J=13.8 Hz, 2H). LC-MS (ESI) m/z: [M+H] calculated for $C_{21}H_{28}ClN_5O_2$: 418.20, found 418.3.

Example 298—Synthesis of {3-[(3S,4S)-4-amino-3-methyl-2-oxa-8-azaspiro[4.5]decan-8-yl]-6-[2,3-dichloro-6-(methylamino)pyridin-4-yl]-5-methyl-pyrazin-2-yl}methanol

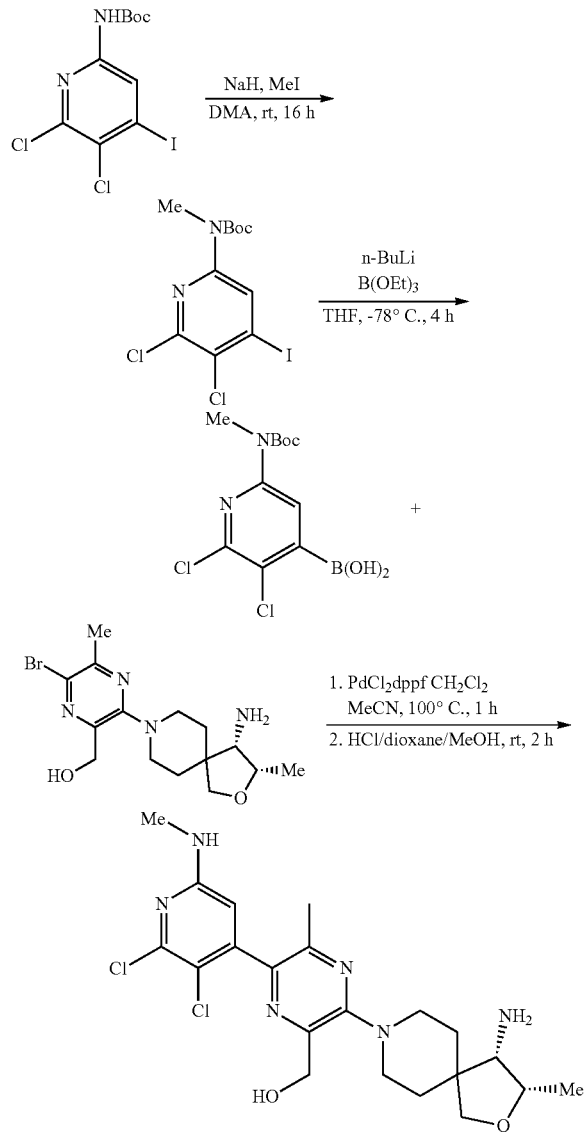

Step 1. Synthesis of tert-butyl (5,6-dichloro-4-iodopyridin-2-yl)(methyl)carbamate Sodium hydride (149 mg, 6.16 mmol) was suspended in DMA (10.2 mL) and the mixture was cooled to 0° C. At 0° C. a solution of tert-butyl (5,6-dichloro-4-iodopyridin-2-yl)carbamate (2 g, 5.14 mmol) in DMA (5.14 mL) was added over a period of 5 minutes. After the addition was completed, the reaction mixture was stirred at 0° C. for 5 minutes and then for 1 hour at room temperature. Methyl iodide (425 µL, 6.83 mmol) was added in one portion and the reaction mixture was stirred at room temperature overnight. The reaction mixture was diluted with EtOAc and washed with sodium bicarbonate and brine. The organic phase was separated, dried over $Na_2SO_4$, filtered and the solvent was removed under reduced pressure. The residue was purified by column chromatography.

Step 2. Synthesis of (6-((tert-butoxycarbonyl)(methyl)amino)-2,3-dichloropyridin-4-yl)boronic acid A mixture of tert-butyl (5,6-dichloro-4-iodopyridin-2-yl)(methyl)carbamate (500 mg, 1.24 mmol) in THF (6.19 mL) was cooled to −78° C. under $N_2$. n-Butyl lithium (1.04 mL, 2.60 mmol) was added over a period of 5 minutes and the mixture was left to stir at −78° C. for 25 minutes. Triethyl borate (462 µL, 2.72 mmol) was then added and the mixture was stirred at −78° C. for further 4 hours. Water was added and the mixture was allowed to warm to 0° C. EtOAc and saturated ammonium chloride were added and the phases were separated. The organic phase was washed with additional saturated ammonium chloride and brine and dried over $Na_2SO_4$. After filtration the solvent was evaporated and the crude product was purified by column chromatography (0-10% MeOH/DCM) to give 310 mg (79%) of the desired product. LC-MS (ESI) m/z: [M+H] calculated for $C_{11}H_{15}BCl_2N_2O_4$: 321.06, found 321.2.

Step 3. Synthesis of {3-[(3S,4S)-4-amino-3-methyl-2-oxa-8-azaspiro[4.5]decan-8-yl]-6-[2,3-dichloro-6-(methylamino)pyridin-4-yl]-5-methylpyrazin-2-yl}methanol (3-((3S,4S)-4-amino-3-methyl-2-oxa-8-azaspiro[4.5]decan-8-yl)-6-bromo-5-methylpyrazin-2-yl)methanol (100 mg, 269 µmol), [1,1'-bis(diphenylphosphino)ferrocene]dichloropalladium(II), complex with DCM (43.9 mg, 53.8 µmol), potassium carbonate (147 mg, 1.07 mmol) and (6-((tert-butoxycarbonyl)(methyl)amino)-2,3-dichloropyridin-4-yl)boronic acid (112 mg, 349 µmol) were weighed into a microwave vial equipped with a stir bar. The reaction vessel was purged 3 times with $N_2$. MeCN (2.68 mL, degassed by sparging with $N_2$ for 1 hour) was added against $N_2$ and the headspace of the reaction vessel was flushed 3 times with $N_2$. The mixture was placed into a heating block preheated to 100° C. and stirred vigorously for 3 hours. The reaction mixture was cooled to room temperature and filtered through a plug of celite, followed by concentration under reduced pressure and purification by column chromatography (0%→99% EtOAc/heptanes). After evaporation of the solvent the purified coupling product was taken up in MeOH (2 mL) and HCl in dioxane (1.00 mL, 4.03 mmol) was added. After stirring for 4 hours at room temperature the solvent was removed under reduced pressure and the crude product was purified by preparative HPLC to give 17 mg (14%) of the desired product. $^1$H NMR (500 MHz, MeOH-$d_4$) δ 8.56 (s, 1H), 6.44 (s, 1H), 4.69 (s, 2H), 4.34-4.27 (m, 1H), 3.93 (d, J=8.9 Hz, 1H), 3.82 (d, J=8.8 Hz, 1H), 3.73-3.64 (m, 2H), 3.27 (d, J=4.5 Hz, 1H), 3.21-3.13 (m, 1H), 3.12-3.04 (m, 1H), 2.90 (s, 3H), 2.32 (s, 3H), 1.97 (dt, J=13.9, 9.9 Hz, 2H), 1.85 (d, J=13.3 Hz, 1H), 1.75 (d, J=12.9 Hz, 1H), 1.30 (d, J=6.5 Hz, 3H). LC-MS (ESI) m/z: [M+H] calculated for $C_{21}H_{28}C_{12}N_6O_2$: 467.18, found 467.3.

Example 299—Synthesis of {3-[(3S,4S)-4-amino-3-methyl-2-oxa-8-azaspiro[4.5]decan-8-yl]-6-(2,3-dichloro-6-methoxypyridin-4-yl)-5-methylpyrazin-2-yl}methanol

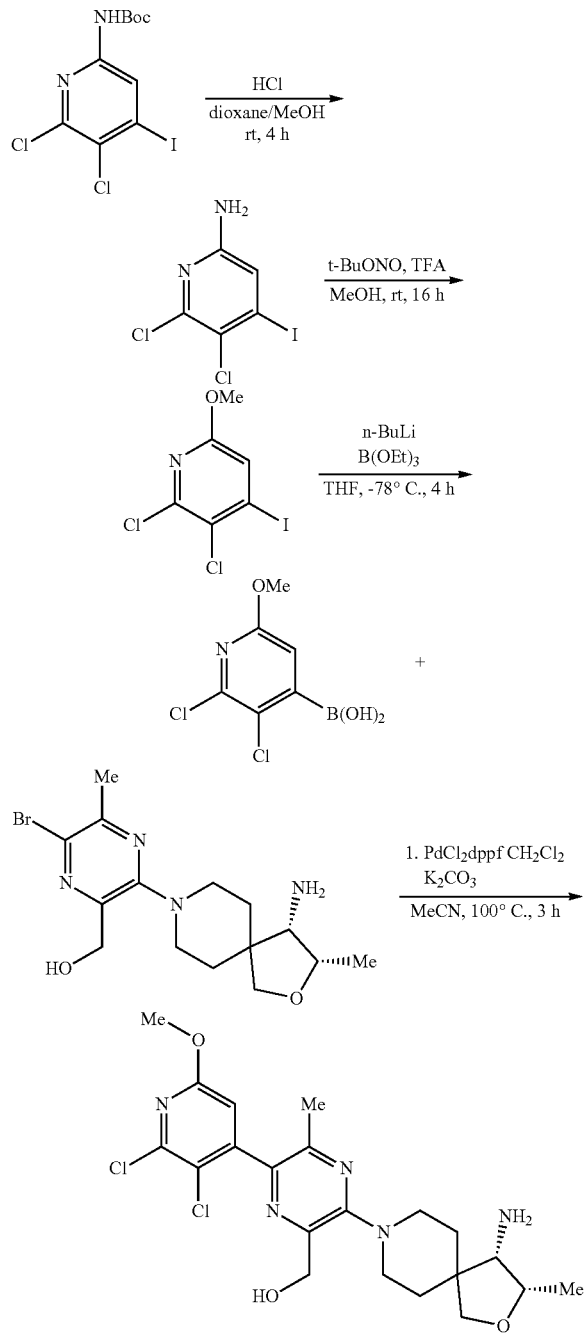

Step 1. Synthesis of 5,6-dichloro-4-iodopyridin-2-amine

Tert-butyl (5,6-dichloro-4-iodopyridin-2-yl)carbamate (2 g, 5.14 mmol) was dissolved in MeOH (20 mL) and HCl (4M in dioxane) (L) was added. The mixture was stirred at room temperature for 4 hours. The solvent was removed under reduced pressure to give the desired product pure by NMR (yield 1.5 g, quantitative). LC-MS (ESI) m/z: [M+H] calculated for $C_5H_3Cl_2IN_2$: 288.88, found 288.9.

Step 2. Synthesis of 2,3-dichloro-4-iodo-6-methoxypyridine

To a 0° C. solution of 5,6-dichloro-4-iodopyridin-2-amine (550 mg, 1.90 mmol) in MeOH (8.33 mL) and TFA (435 µL, 5.70 mmol) was added t-butyl nitrite (1.18 mL, 10.0 mmol) so as to maintain a temperature under 5° C. The resultant mixture was stirred at room temperature overnight. The reaction was quenched by the careful addition of water and then concentrated to dryness. The crude mixture was purified by column chromatography to give 381 mg (67%) of the desired product. LC-MS (ESI) m/z: [M+H] calculated for $C_6H_4Cl_2INO$: 303.88, found 304.0.

Step 3. Synthesis of (2,3-dichloro-6-methoxypyridin-4-yl)boronic acid

A mixture of 2,3-dichloro-4-iodo-6-methoxypyridine (215 mg, 707 mmol) in THF (3.53 mL) was cooled to −78° C. under $N_2$. n-Butyl lithium (592 µL, 1.48 mmol) was added over a period of 5 minutes and the mixture was left to stir at −78° C. for 25 minutes. Triethyl borate (263 µL, 1.55 mmol) was then added and the mixture was stirred at −78° C. for 4 hours. Water was then added and the mixture was allowed to warm to 0° C. EtOAc and saturated ammonium chloride were added and the phases were separated. The organic phase was washed with additional saturated ammonium chloride and brine and dried over $Na_2SO_4$ and the solvent was evaporated. The crude product was purified by column chromatography to give 124 mg (79%) of the desired product. LC-MS (ESI) m/z: [M+H] calculated for $C_6H_6BCl_2NO_3$: 220.98, found 221.0.

Step 4. Synthesis of {3-[(3S,4S)-4-amino-3-methyl-2-oxa-8-azaspiro[4.5]decan-8-yl]-6-(2,3-dichloro-6-methoxypyridin-4-yl)-5-methylpyrazin-2-yl}methanol (2,3-dichloro-6-methoxypyridin-4-yl)boronic acid (63.0 mg, 284 µmol), potassium carbonate (121 mg, 876 µmol), [1,1'-bis(diphenylphosphino)ferrocene]dichloropalladium (II), complex with DCM (35.7 mg, 43.8 and (R)-tert-butyl (8-(5-bromo-3-(hydroxymethyl)-6-methylpyrazin-2-yl)-8-azaspiro[4.5]decan-1-yl)carbamate (100 mg, 219 µmol) were weighed into a 2 dram vial equipped with a screw cap septum and a stir bar. The reaction vessel was flushed 3 times with $N_2$. MeCN (2.18 mL, degassed by sparging with $N_2$ for 1 hour) was added against $N_2$ and the headspace of the reaction vessel was flushed 3 times with $N_2$. The mixture was placed into a heating block preheated to 100° C. and stirred vigorously for 3 hours. The reaction mixture was cooled to room temperature and filtered through a plug of celite. The filtrate was evaporated to dryness and purified by preparative HPLC to give 15.8 mg (17%) of the desired product. $^1$H NMR (500 MHz, MeOH-$d_4$) δ 8.57 (s, 1H), 6.86 (s, 1H), 4.69 (s, 2H), 4.32-4.25 (m, 1H), 3.98 (s, 3H), 3.91 (d, J=8.8 Hz, 1H), 3.79 (d, J=8.7 Hz, 1H), 3.69 (t, J=14.2 Hz, 2H), 3.26-3.04 (m, 3H), 2.30 (s, 3H), 1.96 (dt, J=21.2, 10.2

Hz, 2H), 1.81 (d, J=13.6 Hz, 1H), 1.74 (d, J=12.8 Hz, 1H), 1.28 (d, J=6.5 Hz, 3H). LC-MS (ESI) m/z: [M+H] calculated for $C_{21}H_{27}Cl_2N_5O_3$: 468.16, found 468.4.

Example 300—Synthesis of 3-{5-[(3S,4S)-4-amino-3-methyl-2-oxa-8-azaspiro[4.5]decan-8-yl]-6-(hydroxymethyl)-3-methylpyrazin-2-yl}-2-chlorobenzonitrile

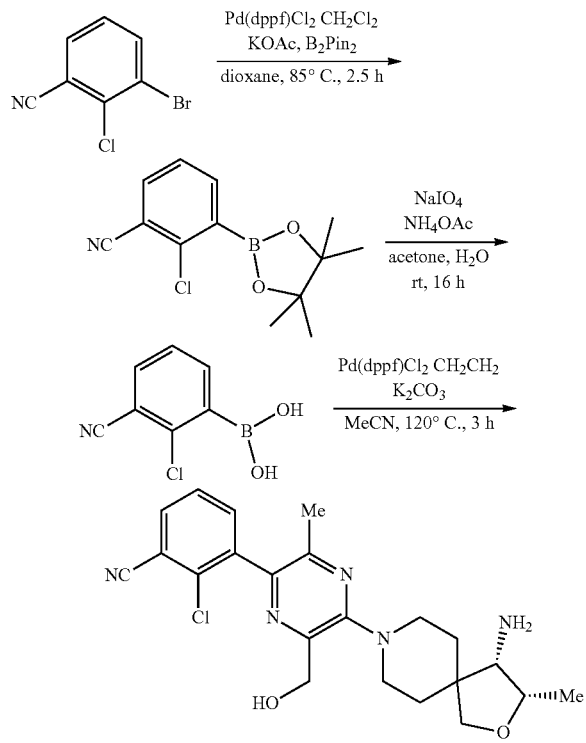

Step 1. Synthesis of 2-chloro-3-(4,4,5,5-tetramethyl-1,3,2-dioxaborolan-2-yl)benzonitrile 3-bromo-2-chlorobenzonitrile (500 mg, 2.30 mmol), bis(pinacolato)diboron (741 mg, 2.92 mmol), [1,1'-bis(diphenylphosphino)ferrocene]dichloropalladium(II), complex with DCM (93.9 mg, 115 µmol) and potassium acetate (689 mg, 7.03 mmol) were weighed into a 40 ml vial equipped with a teflon/rubber screw cap and a stir bar. The reaction vessel was purged 3 times with $N_2$, dioxane (degassed) (18.4 mL) was added against $N_2$ and the headspace of the reaction was purged 3 more times with $N_2$. The reaction was placed into a heating block preheated at 85° C. and stirred vigorously at this temperature for 2.5 hours. After cooling to room temperature the mixture was filtered over celite, the filtrate was evaporated to dryness and the crude product was purified by column chromatography (0-99% EtOAc/heptanes) to give 370 mg (61%) of the desired product. LC-MS (ESI) m/z: [M+H] calculated for $C_{13}H_{15}BClNO_2$: 264.10, found 263.8.

Step 2. Synthesis of (2-chloro-3-cyanophenyl)boronic acid

Sodium periodate (375 mg, 1.76 mmol) and ammonium acetate (135 mg, 1.76 mmol) were added to a stirred solution of 2-chloro-3-(4,4,5,5-tetramethyl-1,3,2-dioxaborolan-2-yl)benzonitrile (155 mg, 588 µmol) in acetone (3.92 mL) and water (1.96 mL). The resulting suspension was stirred overnight at room temperature. The mixture was diluted with water and extracted exhaustively with EtOAc. After removal of the solvent under reduced pressure the crude product was purified by column chromatography (0-25% MeOH/DCM) to give 281 mg (69%) of the desired product. LC-MS (ESI) m/z: [M−H] calculated for $C_7H_5BClNO_2$: 180.00, found 180.2.

Step 3. Synthesis of 3-{5-[(3S,4S)-4-amino-3-methyl-2-oxa-8-azaspiro[4.5]decan-8-yl]-6-(hydroxymethyl)-3-methylpyrazin-2-yl}-2-chlorobenzonitrile (3-((3S,4S)-4-amino-3-methyl-2-oxa-8-azaspiro[4.5]decan-8-yl)-6-bromo-5-methylpyrazin-2-yl)methanol (100 mg, 269 µmol), potassium carbonate (147 mg, 1.07 mmol), [1,1'-bis(diphenylphosphino)ferrocene]dichloropalladium (II), complex with DCM (43.9 mg, 53.8 µmol) and (2-chloro-3-cyanophenyl)boronic acid (63.3 mg, 349 µmol) were weighed into a 2 dram vial equipped with a screw cap septum and a stirbar. The reaction vessel was sparged 3 times with $N_2$. MeCN (2.68 mL, degassed by sparging with $N_2$ for 1 hour) was added against $N_2$ and the headspace of the reaction vessel was flushed 3 times with $N_2$. The mixture was placed into a heating block preheated at 120° C. and stirred vigorously for 3 hours. The reaction mixture was cooled to room temperature and filtered through a plug of celite. The filtrate was evaporated to dryness and purified by preparative HPLC to give 33.7 mg (29%) of the desired product. $^1$H NMR (500 MHz, MeOH-d$_4$) δ 8.55 (s, 1H), 7.93 (dd, J=7.7, 1.6 Hz, 1H), 7.75 (dd, J=7.7, 1.7 Hz, 1H), 7.64 (t, J=7.7 Hz, 1H), 4.70 (s, 2H), 4.34-4.28 (m, 1H), 3.95 (d, J=8.9 Hz, 1H), 3.84 (d, J=9.0 Hz, 1H), 3.78-3.68 (m, 3H), 3.22-3.13 (m, 1H), 3.10 (t, J=10.9 Hz, 1H), 2.28 (d, J=7.7 Hz, 3H), 2.03-1.95 (m, 2H), 1.87 (d, J=13.7 Hz, 1H), 1.76 (d, J=13.3 Hz, 1H), 1.31 (d, J=6.5 Hz, 3H). LC-MS (ESI) m/z: [M+H] calculated for $C_{22}H_{26}ClN_5O_2$: 428.19, found 428.1.

Example 301—Synthesis of 1-(3-((R)-1-amino-8-azaspiro[4.5]decan-8-yl)-6-((2,3-dichlorophenyl)thio)-5-methylpyrazin-2-yl)ethane-1,2-diol

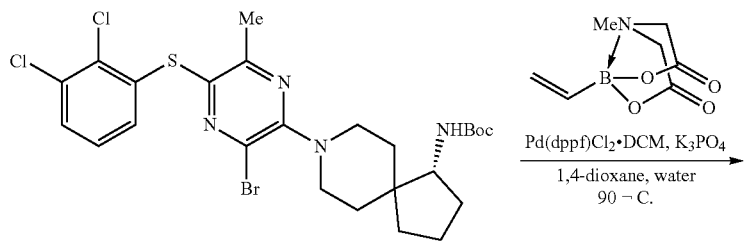

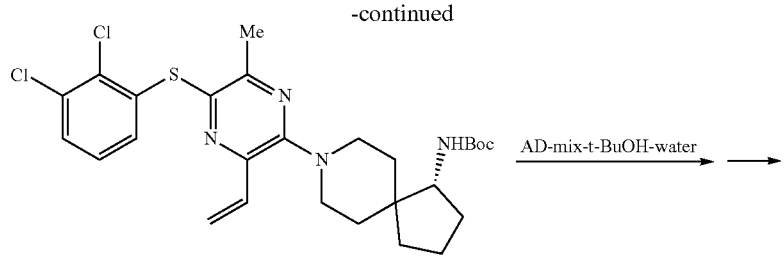

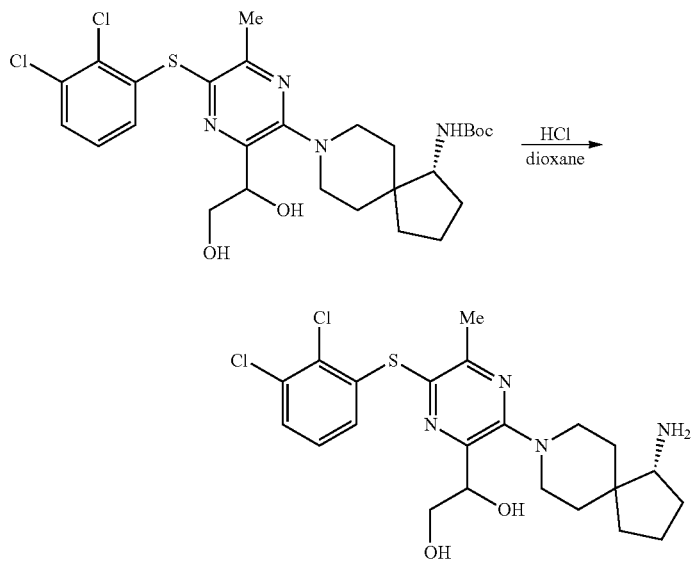

Step 1. Synthesis of tert-butyl (R)-(8-(5-((2,3-dichlorophenyl)thio)-6-methyl-3-vinylpyrazin-2-yl)-8-azaspiro[4.5]decan-1-yl)carbamate A 4 mL vial was charged with (R)-tert-butyl (8-(3-bromo-5-((2,3-dichlorophenyl)thio)-6-methylpyrazin-2-yl)-8-azaspiro[4.5]decan-1-yl)carbamate (100 mg, 0.1659 mmol, Examples 43 and 44), vinylboronic acid MIDA ester (45.5 mg, 0.2488 mmol), and [1,1'-Bis(diphenylphosphino)ferrocene]dichloropalladium(II), complex with DCM (13.5 mg, 0.01658 mmol). The vial was then flushed with nitrogen before degassed 1,4-dioxane (1.65 mL) was added to the vial, and the resulting mixture was stirred at room temperature for 10 minutes. After this time, a solution of potassium phosphate (211 mg, 0.9954 mmol, 6 equiv) in water (3304) was added to the vial, which was then placed in a heating bath at 90° C. and left to stir. After 2 hours, the reaction was cooled to room temperature and diluted with EtOAc (20 mL) and water (5 mL). The layers were separated, and the organic phase was washed with water (5 mL) and brine (5 mL), sequentially. The washed organic phase was then dried over sodium sulfate. The dried solution was then filtered, and the filtrate was concentrated to give an orange oil. This oil was purified by column chromatography to give tert-butyl (R)-(8-(5-((2,3-dichlorophenyl)thio)-6-methyl-3-vinylpyrazin-2-yl)-8-azaspiro[4.5]decan-1-yl)carbamate as a neon yellow oil (46.5 mg, 51% yield). LC-MS (ESI): m/z: [M+H] calculated for $C_{27}H_{34}Cl_2N_4O_2S$: 549.2; found 549.5.

Step 2. Synthesis of tert-butyl ((1R)-8-(5-((2,3-dichlorophenyl)thio)-3-(1,2-dihydroxyethyl)-6-methylpyrazin-2-yl)-8-azaspiro[4.5]decan-1-yl)carbamate A 4 mL vial was charged with AD-mix-beta (118 mg), t-BuOH (0.5 mL) and water (0.5 mL). The resulting orange solution was cooled to 0° C., and a solution of (R)-tert-butyl (8-(5-((2,3-dichlorophenyl)thio)-6-methyl-3-vinylpyrazin-2-yl)-8-azaspiro[4.5]decan-1-yl)carbamate (46.5 mg, 0.08461 mmol, 1 equiv) in t-BuOH (0.5 mL) was added to the vial. The resulting mixture was left to stir at 4° C. After stirring for 96 hours, the reaction was partitioned between EtOAc (10 mL) and water (5 mL). The layers were separated, and the organic phase was washed with water (5 mL) and brine (5 mL) sequentially. The washed organic solution was dried over sodium sulfate, filtered, and concentrated to an orange-brown oil. This crude material was carried into the next step without further characterization or purification.

Step 3. Synthesis of 1-(3-((R)-1-amino-8-azaspiro[4.5]decan-8-yl)-6-((2,3-dichlorophenyl)thio)-5-methylpyrazin-2-yl)ethane-1,2-diol A 2 mL vial was charged with tert-butyl ((1R)-8-(5-((2,3-dichlorophenyl)thio)-3-(1,2-dihydroxyethyl)-6-methyl-pyrazin-2-yl)-8-azaspiro[4.5]decan-1-yl)carbamate (24.5 mg, 0.042 mmol, 1 equiv), dioxane (2 mL), and HCl in dioxane (4M, 2 mL). After stirring for 2 hours, the reaction mixture was concentrated under reduced pressure to a yellow-orange solid. This crude residue was purified by preparative HPLC to give 1-(3-((R)-1-amino-8-azaspiro[4.5]decan-8-yl)-6-((2,3-dichlorophenyl)thio)-5-methylpyrazin-2-yl)ethane-1,2-diol (2.1 mg, 11% yield). LC-MS (ESI): m/z: [M+H] calculated for $C_{22}H_{28}Cl_2N_4O_2S$: 483.1; found 483.3.

Example 302—Synthesis of (3-((3R,4R)-4-amino-3-methyl-2-oxa-8-azaspiro[4.5]decan-8-yl)-6-(2,3-dichlorophenyl)-5-methylpyrazin-2-yl)methanol

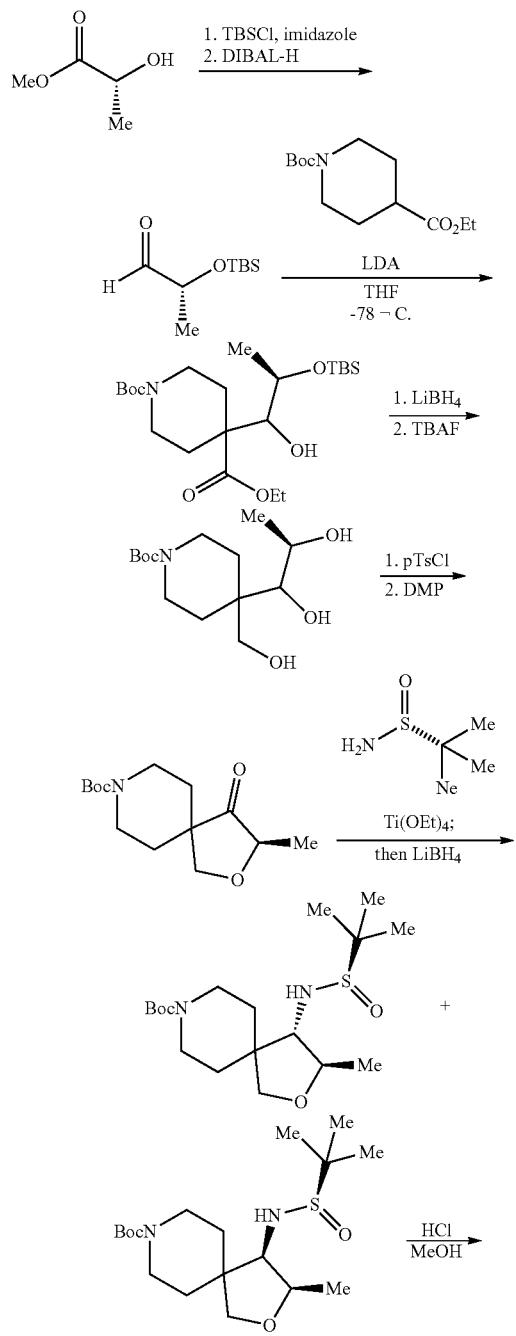

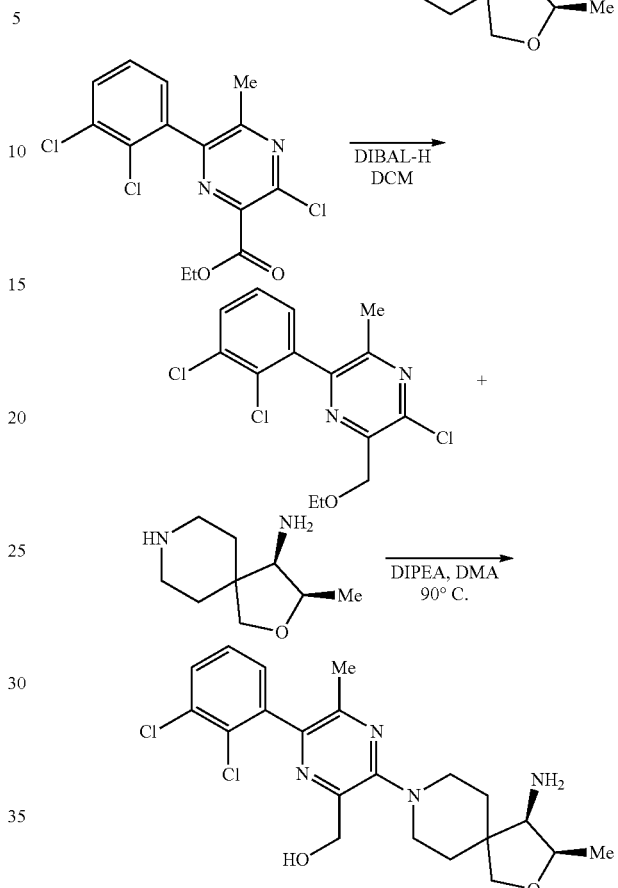

Step 1. Synthesis of methyl (R)-2-((tert-butyldimethylsilyl)oxy)propanoate

A dry 500 mL flask was charged with imidazole (6.53 g, 96.0 mmol, 2 equiv) and DCM (240 mL) before it was cooled to 0° C. Once cool, (R)-methyl 2-hydroxypropanoate (5 g, 48.0 mmol, 1 equiv) and TBSCl (9.40 g, 62.4 mmol, 1.3 equiv) were added to the solution sequentially, and the resulting mixture was allowed to warm to room temperature. After stirring for 21 hours, the reaction mixture was filtered, and the solid residue was washed with DCM. The combined filtrate was washed with 1M HCl (100 mL), saturated aqueous sodium bicarbonate (100 mL), and brine (100 mL), sequentially. The washed organic solution was then dried over sodium sulfate, filtered, and concentrated to give methyl (R)-2-((tert-butyldimethylsilyl)oxy)propanoate as a clear, colorless oil (10.4 g, 100% yield). This material was carried into the next step without further characterization or purification.

Step 2. Synthesis of (R)-2-((tert-butyldimethylsilyl)oxy)propanal

A dry 200 mL flask was charged with (R)-methyl 2-((tert-butyldimethylsilyl)oxy)propanoate (1 g, 4.57 mmol, 1 equiv) and DCM (45.6 mL), and the resulting solution was cooled to −78° C. Once cool, diisobutylaluminum hydride (1M in DCM, 6.85 mL, 6.85 mmol, 1.5 equiv) was added dropwise to the clear solution, which was then left to stir at −78° C. After stirring for 3 hours, the reaction was quenched by addition of saturated aqueous Rochelle's salt solution (40 mL) at −78° C., and the solution was then allowed to warm to room temperature over 1 hour. After this time, the reaction was transferred to a separatory funnel, and the layers were separated. The aqueous phase was then washed with DCM (2×40 mL), and the combined organic extracts were washed with brine. The washed organic solution was then dried over sodium sulfate, filtered, and concentrated to a clear, colorless oil. This oil was carried into the next step without further characterization or purification.

Step 3. Synthesis of 1-(tert-butyl) 4-ethyl 4-((2R)-2-((tert-butyldimethylsilyl)oxy)-1-hydroxypropyl) piperidine-1,4-dicarboxylate A dry 50 mL flask was charged with THF (15.2 mL) and cooled to 0° C. Once cool, LDA (6.84 mL, 6.84 mmol, 1.5 equiv) was added to the flask, producing a cloudy yellow solution. To this solution was added 1-tert-butyl 4-ethyl piperidine-1,4-dicarboxylate (1.17 mL, 4.78 mmol, 1.05 equiv) in a dropwise fashion. After this addition was complete, the reaction was left to stir at 0° C. for 30 minutes. After this time, (R)-2-((tert-butyldimethylsilyl)oxy)propanal (860 mg, 4.56 mmol, 1 equiv) in THF (2 mL+2 mL rinse) was added to the reaction in a dropwise fashion, and the resulting mixture was left to stir for 1 hour at 0° C. The reaction mixture was then warmed to 23° C. and stirred for 1 hour. After this time, the reaction was quenched by addition of saturated aqueous $NaHCO_3$:water (1:4, 10 mL) at 23° C. The resulting biphasic mixture was transferred to a separatory funnel, and the layers were separated. The aqueous phase was then extracted with EtOAc (3×10 mL), and the combined organic extracts were dried over sodium sulfate, filtered, and concentrated to a yellow oil. This oil was purified by column chromatography to give 1-(tert-butyl) 4-ethyl 4- ((2R)-2-((tert-butyldimethylsilyl)oxy)-1-hydroxypropyl)piperidine-1,4-dicarboxylate (1.17 g, 58% yield over 3 steps). LC-MS (ESI): m/z: [M+Na] calculated for $C_{22}H_{43}NO_6Si$: 468.3; found 468.4.

Step 4. Synthesis of tert-butyl 4-((2R)-2-((tert-butyldimethylsilyl)oxy)-1-hydroxypropyl)-4-(hydroxymethyl)piperidine-1-carboxylate A dry 50 mL flask was charged with 1-tert-butyl 4-ethyl 4-((2R)-2-((tert-butyldimethylsilyl)oxy)-1-hydroxypropyl) piperidine-1,4-dicarboxylate (1.17 g, 2.62 mmol, 1 equiv) and THF (13.1 mL) to give a clear, colorless solution. To this solution was added lithium borohydride (2M in THF, 1.96 mL, 3.93 mmol, 1.5 equiv) at room temperature, and the resulting clear, colorless solution was left to stir. After 72 hours, the reaction mixture was cooled to 0° C., and saturated aqueous sodium bicarbonate:water (1:2, 3.25 mL) was added to quench the reaction. Gas evolution was observed, and stirring was continued until gas evolution had stopped. After this time, the reaction was diluted with EtOAc (10 mL), and the layers were separated. The aqueous phase was then extracted with EtOAc (3×10 mL). The combined organic extracts were dried over sodium sulfate, filtered, and concentrated to a colorless, partly cloudy oil that was used directly in the next step without further purification.

Step 5. Synthesis of tert-butyl 4-((2R)-1,2-dihydroxypropyl)-4-(hydroxymethyl)piperidine-1-carboxylate A plastic 20 mL vial was charged with tert-butyl 4-((2R)-2-((tert-butyldimethylsilyl)oxy)-1-hydroxypropyl)-4-(hydroxy methyl)piperidine-1-carboxy late (1.05 g, 2.60 mmol, 1 equiv), THF (8.66 mL), and tetrabutylammonium fluoride (3.90 mL, 3.90 mmol, 1.5 equiv) sequentially at room temperature. After stirring for 3 hours, the reaction was quenched by addition of saturated aqueous sodium bicarbonate:water (1:2, 2.5 mL). The mixture was then diluted with EtOAc (10 mL), and the layers were separated. The aqueous phase was then extracted with EtOAc (3×10 mL), and the combined organic extracts were washed with brine, dried over sodium sulfate, filtered, and concentrated to give a crude oil. This oil was purified by column chromatography to give tert-butyl 4-((2R)-1,2-dihydroxypropyl)-4-(hydroxymethyl)piperidine-1-carboxylate (625 mg, 2.16 mmol, 83% yield over 2 steps) as a clear, sticky oil.

Step 6. Synthesis of tert-butyl (3R)-4-hydroxy-3-methyl-2-oxa-8-azaspiro[4.5]decane-8-carboxylate A dry 50 mL flask was charged with sodium hydride (300 mg, 7.52 mmol, 3.5 equiv) and flushed with nitrogen. THF (10 mL) was then added to the flask, and the resulting slurry was cooled to 0° C. Once cool, a solution of tert-butyl 4-((2R)-1,2-dihydroxypropyl)-4-(hydroxymethyl)piperidine-1-carboxylate (625.5 mg, 2.15 mmol, 1 equiv) in THF (4 mL+2 mL rinse) was added dropwise to the slurry. Immediately after this addition, a solution of 4-methylbenzene-1-sulfonyl chloride (409 mg, 2.15 mmol, 1 equiv) in THF (1 mL+1 mL rinse) was added dropwise to the slurry. The resulting mixture was left to stir for 1 hour at 0° C., after which the reaction mixture was cooled to −20° C. and quenched by addition of saturated aqueous ammonium chloride (1 mL). The resulting mixture was stirred vigorously for 10 minutes before additional saturated aqueous ammonium chloride (5 mL) and brine (5 mL) were added to the flask. The resulting mixture was diluted with EtOAc (10 mL), and the layers were separated. The aqueous phase was then extracted with EtOAc (3×10 mL). The combined organic extracts were then dried over sodium sulfate, filtered, and concentrated to an oil mixed with a white solid. This mixture was dissolved in DCM and filtered, and the oil so obtained was concentrated and used directly in the next step without further purification.

Step 7. Synthesis of tert-butyl (R)-3-methyl-4-oxo-2-oxa-8-azaspiro[4.5]decane-8-carboxylate A dry 25 mL flask was charged with tert-butyl (3R)-4-hydroxy-3-methyl-2-oxa-8-azaspiro[4.5]decane-8-carboxylate (570 mg, 2.13 mmol, 1 equiv) and DCM (5.32 mL), and the resulting solution was cooled to 0° C. Once cool, Dess-Martin periodinane (1.17 g, 2.76 mmol, 1.3 equiv) was added as a solid in one portion, and the resulting mixture was left to stir at 0° C. After stirring for 2 hours, the reaction was concentrated, and the crude material was diluted with DCM. The resulting mixture was filtered, and the filtrate was concentrated. The crude residue was purified by column chromatography to give tert-butyl (R)-3-methyl-4-oxo-2-oxa-8-azaspiro[4.5]decane-8-carboxylate (439 mg, 1.63 mmol, 77% yield over 2 steps) as a clear, colorless oil. LC-MS (ESI): m/z: [M+Na] calculated for $C_{14}H_{23}NO_4$: 292.2; found 292.2.

Step 8. Synthesis of tert-butyl (3R,4S)-4-(((R)-tert-butylsulfinyl)amino)-3-methyl-2-oxa-8-azaspiro[4.5] decane-8-carboxylate and tert-butyl (3R,4R)-4-(((R)-tert-butylsulfinyl)amino)-3-methyl-2-oxa-8-azaspiro[4.5]decane-8-carboxylate A dry 15 mL pressure vessel was charged with titanium (IV) ethanolate (1.35 mL, 6.48 mmol, 4 equiv), followed by addition of a solution of tert-butyl (R)-3-methyl-4-oxo-2-oxa-8-azaspiro[4.5]decane-8-carboxylate (439 mg, 1.62 mmol, 1 equiv) in THF (5.40 mL) and (R)-2-methylpropane-2-sulfinamide (392 mg, 3.24 mmol, 2 equiv), sequentially. The pressure vessel was then sealed with a screw-top cap, and the pale yellow solution was warmed to 90° C. After stirring for 23 hours, the reaction mixture was cooled to −10° C., and MeOH (540 μL) was added dropwise to the yellow solution. Lithium borohydride (810 μL, 1.62 mmol, 1 equiv) was then added in a dropwise fashion, and the resulting cloudy yellow solution was left to stir at −10° C. After stirring for 1 hour, the reaction was then quenched at −5° C. by addition of saturated aqueous ammonium chloride solution (~2 mL), followed by dilution with EtOAc (10 mL). The diluted milky white mixture was then warmed to room temperature with vigorous stirring over 30 minutes. After this time, the mixture was filtered through a pad of Celite, and the clear, colorless filtrate was concentrated to a pale yellow oil with some solids present. This crude material was purified by column chromatography to give tert-butyl (3R,4S)-4-4(((R)-tert-butylsulfinyl)amino)-3-methyl-2-oxa-8-azaspiro[4.5]decane-8-carboxylate (235.8 mg, 39% yield) and tert-butyl (3R,4R)-4-(((R)-tert-butylsulfinyl)amino)-3-methyl-2-oxa-8-azaspiro[4.5]decane-8-carboxylate (190.1 mg, 31% yield) as a white solid and a clear oil, respectively. LC-MS (ESI): m/z: [M+Na] calculated for $C_{18}H_{34}N_2O_4S$: 397.2; found 397.2.

Step 9. Synthesis of (3R,4R)-3-methyl-2-oxa-8-azaspiro[4.5]decan-4-amine

A 20 mL vial was charged with (3R,4R)-4-4(R)-tert-butylsulfinyl)amino)-3-methyl-2-oxa-8-azaspiro[4.5]decane-8-carboxylate (190.1 mg, 0.5072 mmol, 1 equiv) and MeOH (1.01 mL). To this solution was added HCl in dioxane (4M, 1.26 mL, 5.07 mmol, 10 equiv), and the vial was then sealed and warmed to 50° C. After stirring for 2 hours, the solution was concentrated and used directly in the next reaction without further purification.

Step 10. Synthesis of (3-chloro-6-(2,3-dichlorophenyl)-5-methylpyrazin-2-yl)methanol A solution of ethyl 3-chloro-6-(2,3-dichlorophenyl)-5-methylpyrazine-2-carboxylate (1.59 g, 4.61 mmol, 1 equiv) in THF (14 mL) was cooled to 0° C. Once cool, DIBAL-H (1M in hexane, 13.8 mL, 13.8 mmol, 3 equiv) was added dropwise, and the reaction mixture was allowed to warm to room temperature. After 30 minutes, the reaction mixture was diluted with diethyl ether and cooled 0° C. The reaction was then quenched by addition of water (0.55 mL), 15% aqueous NaOH (0.55 mL), and water (1.4 mL), sequentially. The resulting mixture was stirred for 30 minutes before the mixture was filtered, and the filtrate was concentrated. The crude residue so obtained was dissolved in DCM (30 ml) and washed with water (20 mL) and brine (50 mL), sequentially. The aqueous washes were back-extracted with DCM, and the combined organic layers were concentrated under reduced pressure. The crude residue so obtained was purified by column chromatography to give (3-chloro-6-(2,3-dichlorophenyl)-5-methylpyrazin-2-yl)methanol (0.99 g, 71% yield). $^1$H NMR (300 MHz, DMSO-$d_6$) δ 7.82 (dd, J=7.8, 1.8 Hz, 1H), 7.55 (t, J=7.7 Hz, 1H), 7.49 (dd, J=7.6, 1.8 Hz, 1H), 5.50 (t, J=6.0 Hz, 1H), 4.69 (d, J=6.0 Hz, 2H), 2.32 (s, 3H).

Step 11. Synthesis of (3-((3R,4R)-4-amino-3-methyl-2-oxa-8-azaspiro[4.5]decan-8-yl)-6-(2,3-dichlorophenyl)-5-methylpyrazin-2-yl)methanol A 20 mL vial was charged with (3R,4R)-3-methyl-2-oxa-8-azaspiro[4.5]decan-4-amine (86.3 mg, 0.5068 mmol, 1.5 equiv), (3-chloro-6-(2,3-dichlorophenyl)-5-methylpyrazin-2-yl)methanol (102 mg, 0.3378 mmol, 1 equiv), DMA (3.37 mL), and N,N-Diisopropylethylamine (557 μL, 3.37 mmol, 10 equiv), sequentially. The vial was then sealed, and the reaction mixture was warmed to 90° C. After stirring for 36 hours, the reaction mixture was concentrated, and the crude residue was purified by preparative HPLC to give (3-((3R,4R)-4-amino-3-methyl-2-oxa-8-azaspiro[4.5]decan-8-yl)-6-(2,3-dichlorophenyl)-5-methylpyrazin-2-yl)methanol (24 mg, 16% yield over 2 steps). (3-((3R,4R)-4-amino-3-methyl-2-oxa-8-azaspiro[4.5]decan-8-yl)-6-(2,3-dichlorophenyl)-5-methylpyrazin-2-yl)methanol was isolated as its formate salt. $^1$H NMR (500 MHz, MeOH-$d_4$) δ 8.53 (s, 1H), 7.64 (dd, J=8.1, 1.6, 0.7 Hz, 1H), 7.42 (t, J=7.9, 0.6 Hz, 1H), 7.34 (dd, J=7.6, 1.7, 0.7 Hz, 1H), 4.68 (s, 2H), 4.29 (qd, J=6.5, 4.2 Hz, 1H), 3.94 (d, J=9.0 Hz, 1H), 3.83 (d, J=9.0 Hz, 1H), 3.76-3.63 (m, 2H), 3.35 (d, J=4.3 Hz, 1H), 3.12 (ddd, J=13.7, 10.9, 2.9 Hz, 1H), 3.05 (ddd, J=13.6, 10.8, 2.7 Hz, 1H), 2.25 (s, 3H), 2.02-1.92 (m, 2H), 1.90-1.83 (m, 1H), 1.77-1.71 (m, 1H), 1.30 (d, J=6.5 Hz, 3H). LC-MS (ESI): m/z: [M+H] calculated for $C_{21}H_{26}Cl_2N_4O_2$: 437.1; found 437.3.

Example 303—Synthesis of [3-(4-amino-4-methyl-piperidin-1-yl)-6-(2,3-dichlorophenyl)-5-methoxy-pyrazin-2-yl]methanol

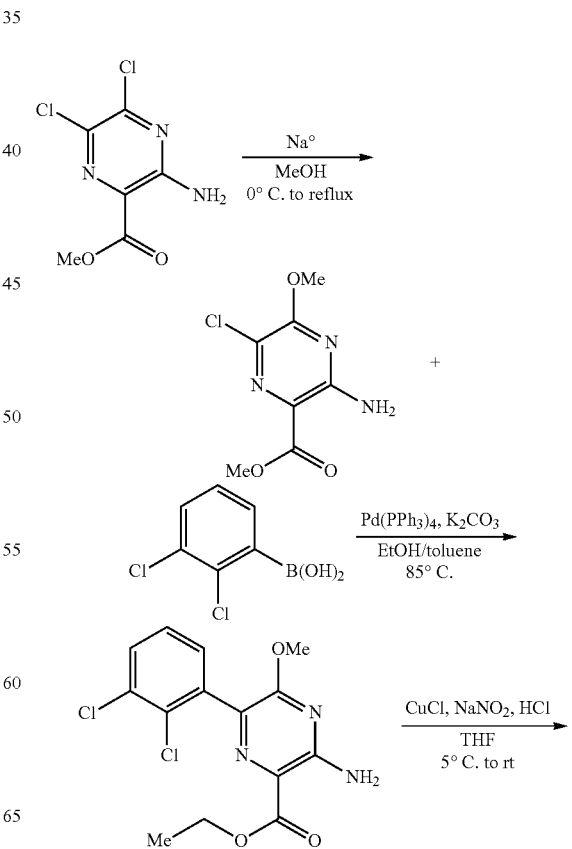

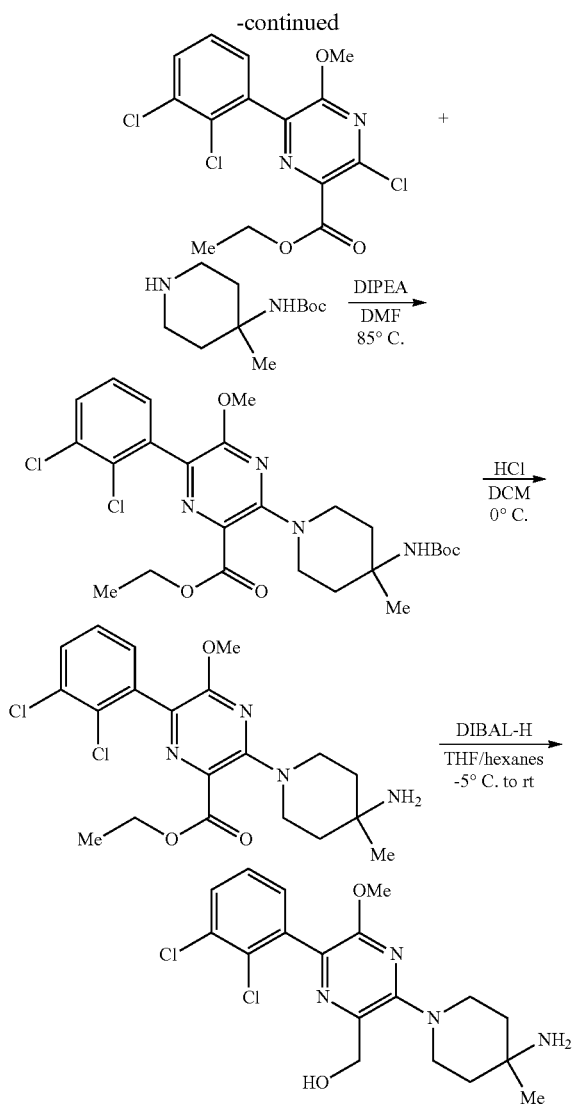

Step 1. Synthesis of methyl 3-amino-6-chloro-5-methoxypyrazine-2-carboxylate Sodium metal (0.31 g, 13.5 mmol, 1 equiv) was carefully added to anhydrous MeOH (300 mL) at 0° C. and stirred at room temperature until full dissolution was observed. Methyl 3-amino-5,6-dichloropyrazine-2-carboxylate (3.00 g, 13.5 mmol, 1 equiv) was added and the mixture was stirred at reflux for 3 hours. The mixture was cooled to room temperature and product filtered to obtain methyl 3-amino-6-chloro-5-methoxypyrazine-2-carboxylate (2.45 g, 83%) used without further purification. $^1$H NMR (400 MHz, DMSO-$d_6$) δ 7.63 (s 2H), 3.97 (s 3H), 3.80 (s 3H).

Step 2. Synthesis of ethyl 3-amino-6-(2,3-dichlorophenyl)-5-methoxypyrazine-2-carboxylate A reaction tube was charged with 3-amino-6-chloro-5-methoxypyrazine-2-carboxylate (1.06 g, 4.87 mmol, 1 equiv), 2,3-dichlorophenyl boronic acid (1.39 g, 7.26 mmol, 1.5 equiv) and $K_2CO_3$ (3.34 g, 24.2 mmol, 4.96 equiv). Toluene (26.5 mL) and ethanol (35 mL) were added, the mixture was purged with argon, and Pd(PPh$_3$)$_4$ (281 mg, 0.24 mmol, 0.05 equiv) added. The tube was sealed and reaction was stirred at 85° C. overnight. The reaction mixture was concentrated under educed pressure and crude was extracted with ethyl acetate. The organic layers were concentrated and product was purified via column chromatography (SiO$_2$, 5-20% ethyl acetate in hexane) to afford ethyl 3-amino-6-(2,3-dichlorophenyl)-5-methoxypyrazine-2-carboxylate (703 mg, 42%). $^1$H NMR (400 MHz, DMSO-$d_6$) δ 7.71 (m, 1H), 7.67 (s 1H), 7.48-7.39 (m, 2H), 4.33-4.21 (m, 2H), 3.88 (s 3H), 1.27 (t, J=7.1 Hz, 3H).

Step 3. Synthesis of ethyl 3-chloro-6-(2,3-dichlorophenyl)-5-methoxypyrazine-2-carboxylate Ethyl 3-amino-6-(2,3-dichlorophenyl)-5-methoxypyrazine-2-carboxylate (379 mg, 1.11 mmol, 1 equiv) was dissolved in THF (4.7 mL) and cooled to 5° C. 12M HCl (1.40 mL) was added dropwise and resulting solution stirred for 20 minutes at 5° C. followed by addition of NaNO$_2$ (305 mg, 4.43 mmol, 4 equiv). The reaction was stirred for 1 hour at 5° C. and then CuCl (219 mg, 2.22 mmol, 2 equiv) was added portion wise. THF (1 mL) was added and the reaction was warmed to room temperature and stirred overnight. The product was extracted with ethyl acetate and purified by column chromatography (SiO$_2$, 5% ethyl acetate in hexane) to afford ethyl 3-chloro-6-(2,3-dichlorophenyl)-5-methoxypyrazine-2-carboxylate (158 mg, 39%). $^1$H NMR (400 MHz, DMSO-$d_6$) δ 7.88-7.62 (m, 1H), 7.54 (s 1H), 7.53 (m, 1H), 4.37 (q, J=7.1 Hz, 2H), 3.99 (s 3H), 1.32 (t, J=7.1 Hz, 3H).

Step 4. Synthesis of ethyl 3-{4-[(tert-butoxycarbonyl)amino]-4-methylpiperidin-1-yl}-6-(2,3-dichlorophenyl)-5-methoxypyrazine-2-carboxylate Ethyl 3-chloro-6-(2,3-dichlorophenyl)-5-methoxy pyrazine-2-carboxylate (158 mg, 0.44 mmol, 1 equiv), tert-butyl (4-methylpeperidin-4-yl)carbamate (141 mg, 0.7 mmol, 1.5 equiv) and DIPEA (0.15 mL, 0.9 mmol, 2 equiv) were dissolved in DMF (3.16 mL) in glass sealed reactor. The reaction mixture was stirred at 85° C. overnight. After cooling to room temperature, water was added and product was purified via column chromatography (SiO$_2$, 0-20% ethyl acetate in hexane) to afford ethyl 3-{4-[(tert-butoxycarbonyl)amino]-4-methylpiperidin-1-yl}-6-(2,3-dichlorophenyl)-5-methoxy pyrazine-2-carboxylate (210 mg, 89%). $^1$H NMR (400 MHz, DMSO-$d_6$) δ 7.70 (dd, J=6.9, 2.7 Hz, 1H), 7.48-7.40 (m, 2H), 6.65 (s 1H), 4.27 (q, J=7.0 Hz, 2H), 3.88 (s 3H), 3.61 (m, 2H), 2.14 (m, 2H), 1.57-1.48 (m, 2H), 1.41 (s, 9H), 1.32-1.25 (m, 6H)

Step 5. Synthesis of ethyl 3-(4-amino-4-methylpiperidin-1-yl)-6-(2,3-dichlorophenyl)-5-methoxypyrazine-2-carboxylate A solution of ethyl 3-{4-[(tert-butoxy carbonyl)amino]-4-methylpiperidin-1-yl}-6-(2,3-dichlorophenyl)-5-methoxypyrazine-2-carboxylate (214 mg, 0.40 mmol, 1 equiv) in DCM (4 mL) was cooled to 0° C. and then HCl gas was bubbled through the solution. After 40 minutes, the reaction mixture was warmed to room temperature and the solvent evaporated to give the crude product. Water (10 mL) was added to the residue and the resulting solution cooled. A saturated solution of NaHCO$_3$ was added to adjust the pH to about 9. The product was extracted with ethyl acetate and combined organic extracts concentrated under educed pressure to afford ethyl 3-(4-amino-4-methylpiperidin-1-yl)-6-(2,3-dichlorophenyl)-5-methoxypyrazine-2-carboxylate (178 mg, 100%) as a light orange oil used without further purification. $^1$H NMR (400 MHz, DMSO-$d_6$) δ 7.70 (m, 1H), 7.44-7.43 (m, 2H), 4.27 (q, J=7.1 Hz, 2H), 3.88 (s 3H), 3.53 (m, 4H), 1.63-1.42 (m, 4H), 1.28 (t, J=7.1 Hz, 3H), 1.11 (s 3H).

Step 6. Synthesis of [3-(4-amino-4-methylpiperidin-1-yl)-6-(2,3-dichlorophenyl)-5-methoxypyrazin-2-yl]methanol A solution of ethyl 3-(4-amino-4-methylpiperidin-1-yl)-6-(2,3-dichlorophenyl)-5-methoxypyrazine-2-carboxylate (172 mg, 0.39 mmol, 1 equiv) in THF (3 mL) was cooled to −5° C. and a 1M solution of DIBAL-H (1M in hexanes, 1.17 mL, 1.17 mmol, 3 equiv) was added dropwise. Following addition, the reaction mixture warmed to room temperature. After 20 minutes, the reaction was diluted with Et$_2$O (5 mL) and cooled. The reaction was quenched by the sequential addition of H$_2$O (0.05 mL), 15% solution of NaOH (0.05 mL), and H$_2$O (0.12 mL). The resulting suspension was stirred at room temperature for 20 minutes and then filtered and the filter cake washed with Et$_2$O. The filtrate was concentrated under reduced pressure to give the crude product which was purified by column chromatography to afford [3-(4-amino-4-methylpiperidin-1-yl)-6-(2,3-dichlorophenyl)-5-methoxypyrazin-2-yl]methanol (76 mg, 49%). $^1$H NMR (400 MHz, DMSO-$d_6$) δ 7.67 (dd, J=6.9, 2.6 Hz, 1H), 7.46-7.42 (m, 2H), 5.23 (t, J=5.5 Hz, 1H), 4.47 (d, J=5.2 Hz, 2H), 3.85 (s, 3H), 3.60-3.45 (m, 4H), 1.63-1.45 (m, 4H), 1.12 (s 3H). LC-MS (ESI) m/z: [M+H] calculated for $C_{18}H_{22}Cl_2N_4O_2$: 397.1; found 397.6.

Example 304—Synthesis of {6-[(2-amino-3-chloropyridin-4-yl)sulfanyl]-3-[(1R,3R)-1-amino-3-cyclopropoxy-8-azaspiro[4.5]decan-8-yl]-5-methylpyrazin-2-yl}methanol

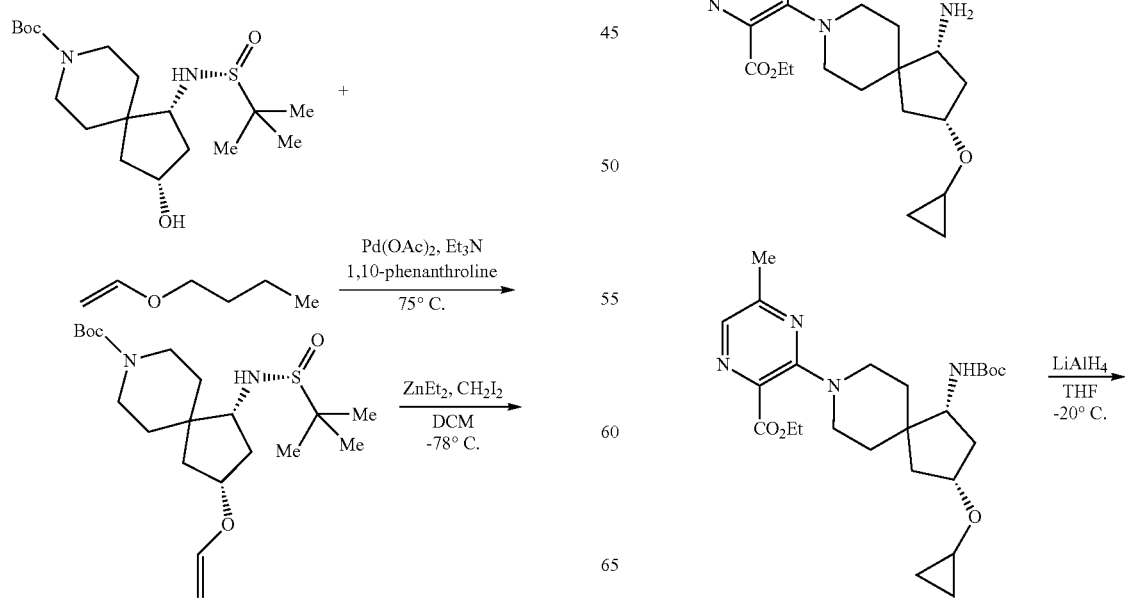

-continued

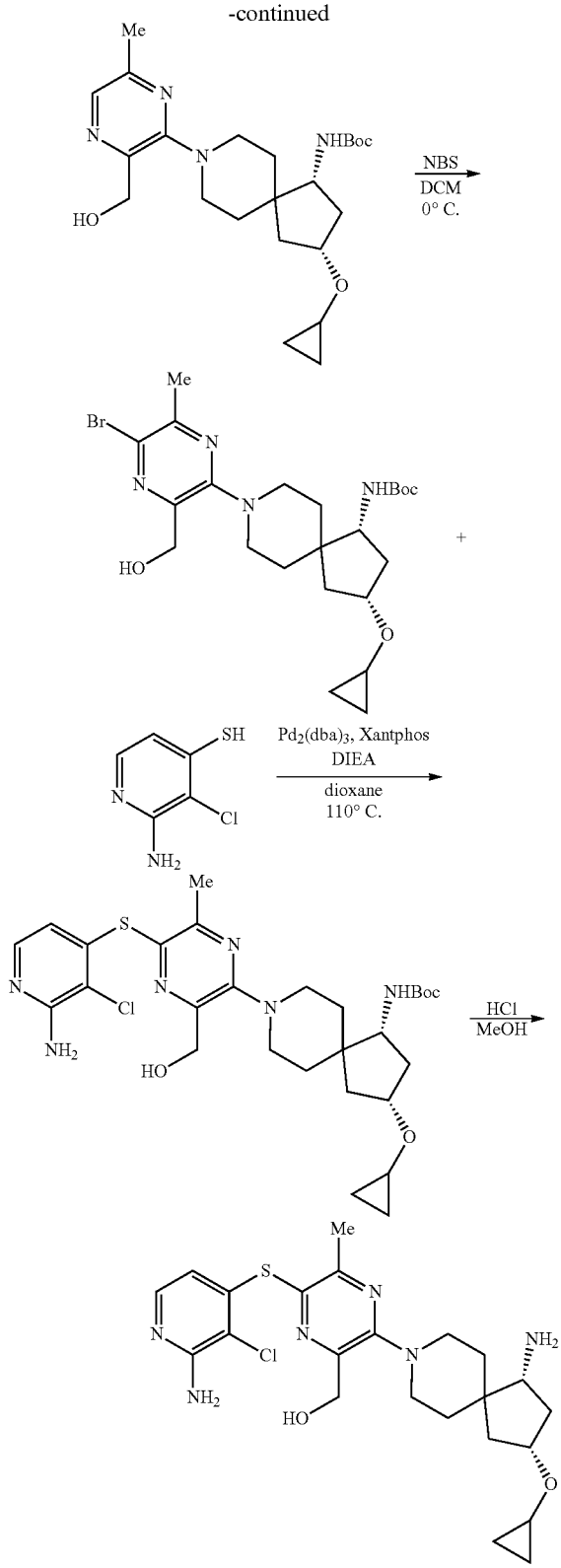

Step 1. Synthesis of tert-butyl (1R,3R)-1-(((R)-tert-butylsulfinyl)amino)-3-(vinyloxy)-8-azaspiro[4.5]decane-8-carboxylate Under a $N_2$ environment, 1,10-phenanthroline (289 mg, 1.60 mmol, 0.12 equiv) and Pd(OAc)$_2$ (299 mg, 1.33 mmol, 0.1 equiv) were stirred in 1-vinyloxybutane (53 g, 534 mmol, 68.6 mL, 40 equiv) for 10 minutes. tert-Butyl (1R,3R)-1-(((R)-tert-butylsulfinyl)amino)-3-hydroxy-8-azaspiro[4.5]decane-8-carboxylate (5 g, 13.3 mmol, 1 equiv) and triethylamine (1.35 g, 13.3 mmol, 1.86 mL, 1 equiv) were then added. The resulting reaction mixture was heated to 75° C. for 20 hours. The reaction was concentrated in vacuo to give the crude product. The crude product was purified by flash silica gel chromatography column (petroleum ether/ethyl acetate from 1:0 to 0:1) to give tert-butyl (1R,3R)-1-(((R)-tert-butylsulfinyl)amino)-3-(vinyloxy)-8-azaspiro[4.5]decane-8-carboxylate (4 g, 9.99 mmol, 75% yield) as a yellow oil. LC-MS (ESI): m/z: [M+H] calculated for $C_{20}H_{37}N_2O_4S$: 401.2; found 401.1.

Step 2. Synthesis of tert-butyl (1R,3R)-1-(((R)-tert-butylsulfinyl)amino)-3-cyclopropoxy-8-azaspiro[4.5]decane-8-carboxylate Two equivalent batches were set up in parallel. To the solution of diethylzinc (1M, 14.98 mL, 3 equiv) in dry DCM (20 mL) was added diiodomethane (8.02 g, 29.96 mmol, 2.42 mL, 6 equiv) in dry DCM (5 mL) at 0° C. for 10 minutes, then followed by tert-butyl (1R,3R)-1-(((R)-tert-butylsulfinyl)amino)-3-(vinyloxy)-8-azaspiro[4.5]decane-8-carboxylate (2 g, 4.99 mmol, 1 equiv) in dry DCM (5 mL) under $N_2$ at 0° C., then stirred 20° C. for 14 hours. Saturated $NH_4Cl$ (20 mL) was added to the reaction mixture, and the product extracted with DCM (2×10 mL). To the aqueous phase was added di-tert-butyl dicarbonate (1.09 g, 4.99 mmol, 1.15 mL, 1 equiv), and NaHCO$_3$ (629 mg, 7.49 mmol, 291 μL, 1.5 equiv), then the resulting mixture was allowed to stir at 20° C. for 15 hours. Two parallel batches were combined. The mixture was extracted with ethyl acetate (20 mL×3), combined all the organic phase, washed with brine, ddried over $Na_2SO_4$, then filtered, the filtrate was concentrate under reduced pressure to give crude product. The product was purified by column chromatography (petroleum ether: ethyl acetate=1:0 to 0:1 to give tert-butyl (1R,3R)-1-(((R)-tert-butylsulfinyl)amino)-3-cyclopropoxy-8-azaspiro[4.5]decane-8-carboxylate (1.6 g, 3.27 mmol, 33% yield, 84% purity) as colorless oil. LC-MS (ESI): m/z: [M+H] calculated for $C_{16}H_{30}N_2O_2S$: 315.2; found 315.1.

Step 3. Synthesis of (1R,3R)-3-cyclopropoxy-8-azaspiro[4.5]decan-1-amine hydrochloride To a solution of tert-butyl (1R,3R)-1-(((R)-tert-butylsulfinyl)amino)-3-cyclopropoxy-8-azaspiro[4.5]decane-8-carboxylate (1.5 g, 3.62 mmol, 1 equiv) in EtOAc (20 mL) was added HCl/EtOAc (20 mL) and the resulting reaction mixture was stirred at 25° C. for 2 hours. The reaction was concentrated under reduced pressure to give (1R,3R)-3-cyclopropoxy-8-azaspiro[4.5]decan-1-amine hydrochloride (0.892 g, 2.49 mmol, 100% yield, HCl) as a white solid and used directly in the next step without further purification. LC-MS (ESI) m/z: [M+H] calculated for $C_{12}H_{22}N_2O$: 211.2; found: 211.2.

Step 4. Synthesis of ethyl 3-((1R,3R)-1-amino-3-cyclopropoxy-8-azaspiro[4.5]decan-8-yl)-5-methyl-pyrazine-2-carboxylate To a solution of (1R,3R)-3-cyclopropoxy-8-azaspiro[4.5]decan-1-amine hydrochloride (0.89 g, 3.61 mmol, 1 equiv) in isopropyl alcohol (10 mL) was added ethyl 3-chloro-5-methyl-pyrazine-2-carboxylate (725 mg, 3.61 mmol, 1 equiv) and DIPEA (3.27 g, 25.3 mmol, 4.41 mL, 7 equiv). The reaction mixture was stirred at 90° C. for 16 hours, concentrated under reduced pressure to give ethyl 3-((1R,3R)-1-amino-3-cyclopropoxy-8-azaspiro[4.5]decan-8-yl)-5-methylpyrazine-2-carboxylate (1.36 g, crude) as a yellow oil. LC-MS (ESI): m/z: [M+H] calculated for $C_{20}H_{30}N_4O_3$: 375.2; found: 375.1.

Step 5. Synthesis of ethyl 3-((1R,3R)-1-((tert-butoxycarbonyl)amino)-3-cyclopropoxy-8-azaspiro[4.5]decan-8-yl)-5-methylpyrazine-2-carboxylate To a solution of ethyl 3-((1R,3R)-1-amino-3-cyclopropoxy-8-azaspiro[4.5]decan-8-yl)-5-methylpyrazine-2-carboxylate (1.35 g, 3.61 mmol, 1 equiv) in THF (20 mL) was added di-tert-butyl dicarbonate (1.57 g, 7.21 mmol, 1.66 mL, 2 equiv) and triethylamine (368 mg, 3.61 mmol, 501 µL, 1 equiv). The resulting mixture was stirred at 25° C. for 2 hours. The reaction mixture was concentrated under reduced pressure and product was purified by column chromatography (Petroleum ether/Ethyl acetate=1:0 to 0:1) to give ethyl 3-((1R,3R)-1-((tert-butoxy carbonyl)amino)-3-cyclopropoxy-8-azaspiro[4.5]decan-8-yl)-5-methylpyrazine-2-carboxylate (0.6 g, 1.26 mmol, 35% yield) as a yellow oil. LC-MS (ESI) m/z: [M+H] calculated for $C_{25}H_{38}N_4O_5$; 475.3; found: 475.2.

Step 6. Synthesis of tert-butyl ((1R,3R)-3-cyclopropoxy-8-(3-(hydroxymethyl)-6-methylpyrazin-2-yl)-8-azaspiro[4.5]decan-1-yl)carbamate To a solution of ethyl 3-((1R,3R)-1-((tert-butoxycarbonyl)amino)-3-cyclopropoxy-8-azaspiro[4.5]decan-8-yl)-5-methylpyrazine-2-carboxylate (0.6 g, 1.26 mmol, 1 equiv) in THF (10 mL) was added LiAlH$_4$ (2.5M, 5.06 mL, 10 equiv) at −20° C. The reaction solution was stirred at −20° C. for 2 hours. The reaction was quenched with water (10 mL) and the reaction pH adjusted to 3 with 1M HCl. The product was extracted with EtOAc (3×30 mL) and the combined organic extracts were washed with brine (1×20 mL) and dried over sodium sulfate. Filtration and concentration under reduced pressure, followed by purification by column chromatography resulted in ((1R,3R)-3-cyclopropoxy-8-(3-(hydroxymethyl)-6-methylpyrazin-2-yl)-8-azaspiro[4.5]decan-1-yl)carbamate (0.435 g, 1.01 mmol, 79% yield) as a yellow oil.

Step 7. Synthesis of tert-butyl ((1R,3R)-8-(5-bromo-3-(hydroxymethyl)-6-methylpyrazin-2-yl)-3-cyclopropoxy-8-azaspiro[4.5]decan-1-yl)carbamate To a solution of tert-butyl ((1R,3R)-3-cyclopropoxy-8-(3-(hydroxymethyl)-6-methylpyrazin-2-yl)-8-azaspiro[4.5]decan-1-yl)carbamate (435 mg, 1.01 mmol, 1 equiv) in DCM (5 mL) was added NBS (197 mg, 1.11 mmol, 1.1 equiv) at 0° C. The reaction mixture was stirred at 0° C. for 5 minutes, and quenched by the addition Na$_2$SO$_3$ (10 mL) at 25° C. The reaction mixture was concentrated under reduced pressure and purified by column chromatography (petroleum ether/ethyl acetate, 1:0 to 0:1) to give tert-butyl ((1R,3R)-8-(5-bromo-3-(hydroxymethyl)-6-methylpyrazin-2-yl)-3-cyclopropoxy-8-azaspiro[4.5]decan-1-yl)carbamate (0.4 g, 0.782 mmol, 77%) as a yellow solid. $^1$H NMR (400 MHz, Chloroform-d) δ 4.91 (d, J=9.48 Hz, 1H) 4.61 (s, 2H) 4.10-4.04 (m, 1H) 3.90-3.81 (m, 1H) 3.54 (br s, 1H) 3.43-3.30 (m, 2H) 3.24 (d, J=3.09 Hz, 1H) 3.04-2.89 (m, 2H) 2.53 (s, 3H) 2.30-2.16 (m, 1H) 1.89-1.68 (m, 6H) 1.60 (d, J=14.33 Hz, 1H) 1.44 (s, 9H) 0.56 (s, 2H) 0.47 (d, J=5.73 Hz, 2H).

Step 8. Synthesis of tert-butyl ((1R,3R)-8-(5-((2-amino-3-chloropyridin-4-yl)thio)-3-(hydroxymethyl)-6-methylpyrazin-2-yl)-3-cyclopropoxy-8-azaspiro[4.5]decan-1-yl)carbamate To a solution of tert-butyl ((1R,3R)-8-(5-bromo-3-(hydroxymethyl)-6-methylpyrazin-2-yl)-3-cyclopropoxy-8-azaspiro[4.5]decan-1-yl)carbamate (0.3 g, 0.586 mmol, 1 equiv) in dioxane (6 mL) was added 2-amino-3-chloropyridine-4-thiol (188 mg, 1.17 mmol, 2 equiv), Xantphos (67.9 mg, 0.117 mmol, 0.2 equiv), DIPEA (152 mg, 1.17 mmol, 204 mL, 2 equiv) and Pd$_2$(dba)$_3$ (53.7 mg, 0.0586 mmol, 0.1 equiv) under N$_2$. The reaction was stirred at 110° C. for 1 hour under inert atmosphere, diluted with water (6 mL) and extracted with EtOAc (3×20 mL). The combined organic extracts were washed with brine (1×10 mL), dried over sodium sulfate, filtered and concentrated under reduced pressure to give a crude product. Purification by column chromatography (petroleum ether/ethyl acetate, 1:0 to 0:1) resulted in tert-butyl ((1R,3R)-8-(5-((2-amino-3-chloropyridin-4-yl)thio)-3-(hydroxymethyl)-6-methylpyrazin-2-yl)-3-cyclopropoxy-8-azaspiro[4.5]decan-1-yl)carbamate (0.3 g, 0.507 mmol, 86%) as a yellow solid. LC-MS (ESI): m/z: [M+H] calculated for $C_{28}H_{39}ClN_6O_4S$: 591.2; found 591.1.

Step 9. Synthesis of (6-((2-amino-3-chloropyridin-4-yl)thio)-3-((1R,3R)-1-amino-3-cyclopropoxy-8-azaspiro[4.5]decan-8-yl)-5-methylpyrazin-2-yl)methanol A solution of tert-butyl ((1R,3R)-8-(5-((2-amino-3-chloropyridin-4-yl)thio)-3-(hydroxymethyl)-6-methylpyrazin-2-yl)-3-cyclopropoxy-8-azaspiro[4.5]decan-1-yl)carbamate (0.34 g, 0.575 mmol, 1 equiv) in HCl/MeOH (10 mL) was stirred at 25° C. for 30 minutes. The reaction mixture was concentrated under reduced pressure and purified by preparative HPLC to give {6-[(2-amino-3-chloropyridin-4-yl)sulfanyl]-3-[(1R,3R)-1-amino-3-cyclopropoxy-8-azaspiro[4.5]decan-8-yl]-5-methylpyrazin-2-yl}methanol (0.127 g, 0.247 mmol, 43%) as formate salt. $^1$H NMR (400 MHz, MeOH-d$_4$) δ 8.53 (s, 1H), 7.61 (d, J=5.62 Hz, 1H), 5.90 (d, J=5.50 Hz, 1H), 4.62 (s, 2H), 4.24-4.21 (m, 1H), 4.04-3.85 (m, 2H), 3.39 (m, 1H), 3.17-3.14 (m, 2H), 2.48-2.44 (m, 4H), 2.08-2.07 (m, 2H), 1.82-1.76 (m, 4H), 1.56 (d, J=11.98 Hz, 1H), 0.57-0.49 (m, 4H). LC-MS (ESI): m/z: [M+H] calculated for $C_{23}H_{31}ClN_6O_2S$: 491.2; found 491.1.

Example 305-Synthesis of {3-[(1R,3R)-1-amino-3-cyclopropoxy-8-azaspiro[4.5]decan-8-yl]-6-(2,3-dichlorophenyl)-5-methylpyrazin-2-yl}methanol

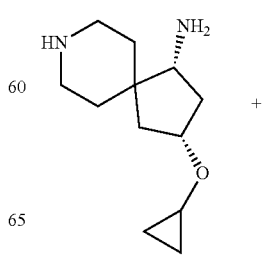

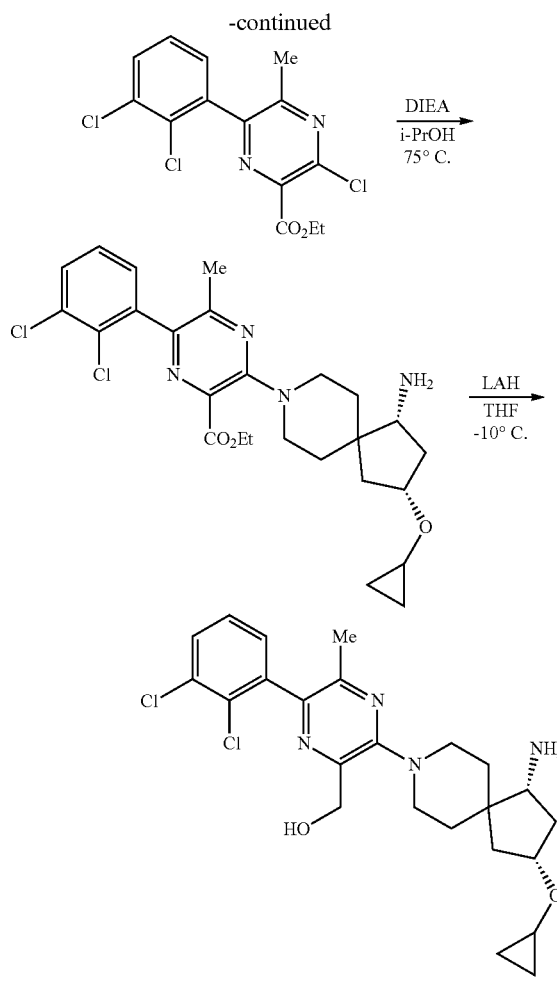

Step 1. Synthesis of ethyl 3-((1R,3R)-1-amino-3-cyclopropoxy-8-azaspiro[4.5]decan-8-yl)-6-(2,3-dichlorophenyl)-5-methylpyrazine-2-carboxylate A mixture of ethyl 3-chloro-6-(2,3-dichlorophenyl)-5-methylpyrazine-2-carboxylate (83.4 mg, 0.241 mmol, 1 equiv) and (1R,3R)-3-cyclopropoxy-8-azaspiro[4.5]decan-1-amine (59.5 mg, 0.241 mmol, 1 equiv) and DIPEA (93.51 mg, 0.723 mmol, 126.03 µL, 3.0 equiv) in isopropyl alcohol (3 mL) was heated to 75° C. for 10 hours. The reaction mixture was diluted with EtOAc (20 mL) and washed with saturated NH$_4$Cl (3×10 mL). The combined aqueous phase was back extracted with EtOAc (3×20 mL) and the combined organic extracts were washed with brine, dried (Na$_2$SO$_4$), filtered, and concentrated in vacuo to give the crude product. The crude product was purified by column chromatography (petroleum ether/EtOAc, 1:0 to 0:1) to give ethyl 3-((1R,3R)-1-amino-3-cyclopropoxy-8-azaspiro[4.5]decan-8-yl)-6-(2,3-dichlorophenyl)-5-methylpyrazine-2-carboxylate (60 mg, 41%) as a yellow oil. LC-MS (ESI) m/z: [M+H] calculated for C$_{26}$H$_{32}$Cl$_2$N$_4$O$_3$: 519.2; found 519.1.

Step 2. Synthesis of {3-[(1R,3R)-1-amino-3-cyclopropoxy-8-azaspiro[4.5]decan-8-yl]-6-(2,3-dichlorophenyl)-5-methylpyrazin-2-yl}methanol Two equivalent batches were set up in parallel. To the solution of ethyl 3-((1R,3R)-1-amino-3-cyclopropoxy-8-azaspiro[4.5]decan-8-yl)-6-(2,3-dichlorophenyl)-5-methylpyrazine-2-carboxylate (30 mg, 0.058 mmol, 1 equiv) in THF (1 mL) at −10° C. was added LiAlH$_4$ (2.5M in THF, 231 µL, 10 equiv). In 5 minutes the reaction was quenched with the slow addition of water (2 mL). Two parallel batches were combined, filtered, and the solid cake washed with MeOH (2 mL) to give a solution. The solution was purified by preparative HPLC and then by SFC to give {3-[(1R,3R)-1-amino-3-cyclopropoxy-8-azaspiro[4.5]decan-8-yl]-6-(2,3-dichlorophenyl)-5-methylpyrazin-2-yl}methanol (9.9 mg, 17%) as the parent. $^1$H NMR (400 MHz, MeOH-d$_4$) δ 7.62 (d, J=7.94 Hz, 1H), 7.38-7.44 (m, 1H), 7.32-7.35 (m, 1H), 4.66 (s, 2H), 4.17 (m, 1H), 3.62-3.79 (m, 2H), 2.99-3.15 (m, 3H), 2.42 (m, 1H), 2.25 (s, 3H), 2.01 (m, 2H), 1.75-1.91 (m, 3H), 1.70 (d, J=13.2 Hz, 1H), 1.46 (d, J=12.1 Hz, 1H), 0.40-0.61 (m, 4H). LC-MS (ESI): m/z: [M+H] calculated for C$_{24}$H$_{30}$Cl$_2$N$_4$O$_2$: 477.2; found 477.1.

Example 306—Synthesis of (4S)-4-amino-8-[5-(2,3-dichlorophenyl)-3-(hydroxymethyl)-6-methylpyrazin-2-yl]-2λ$^6$-thia-8-azaspiro[4.5]decane-2,2-dione

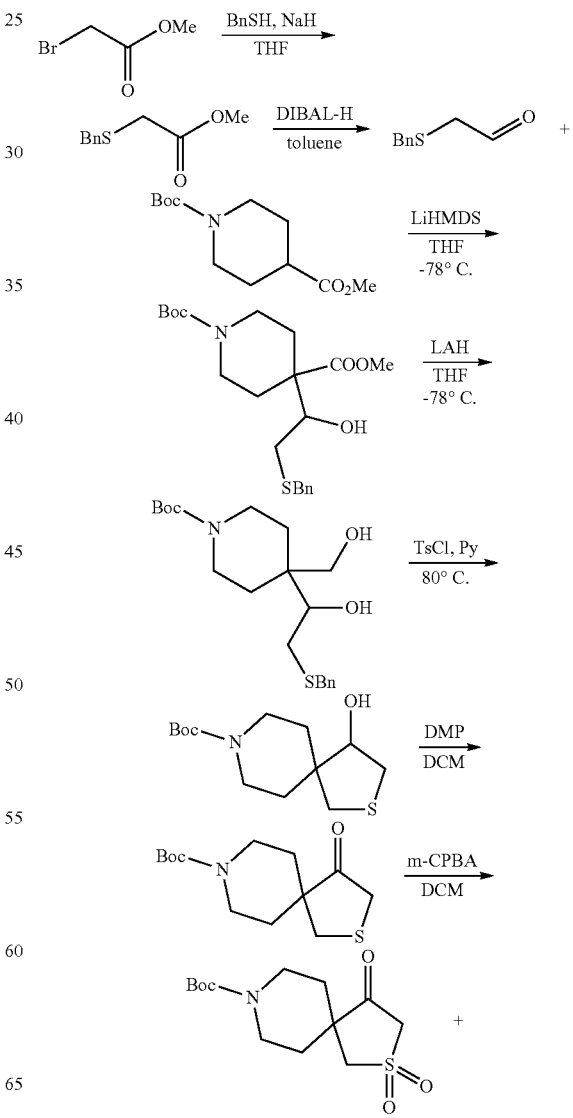

-continued

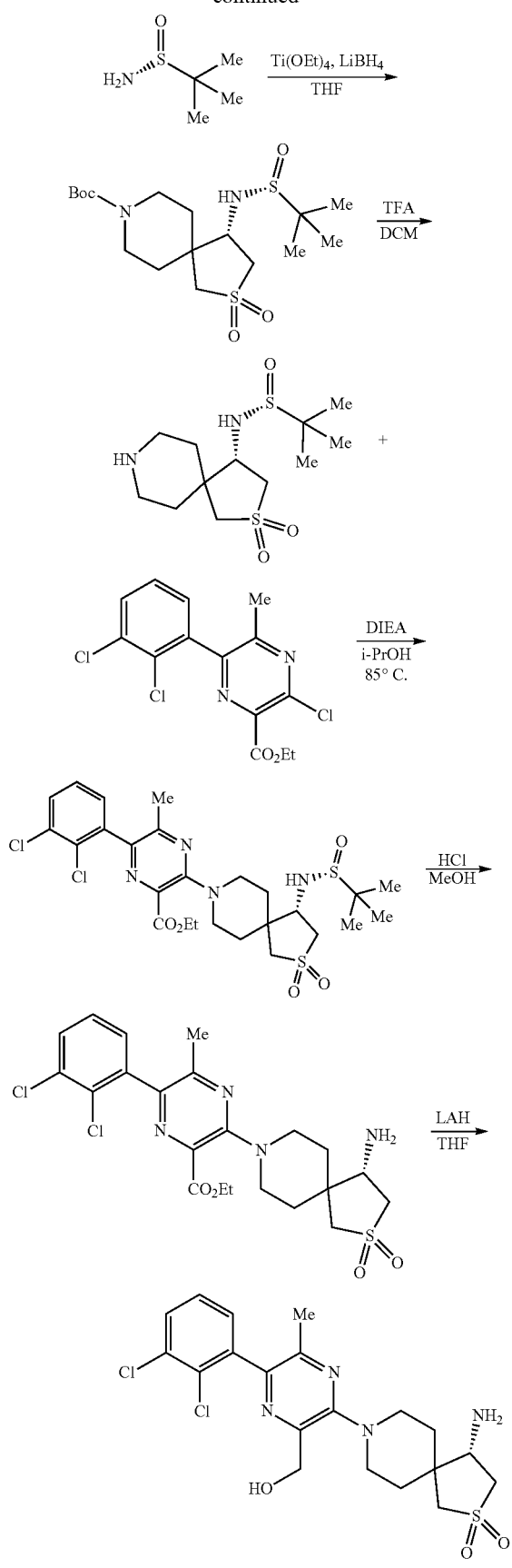

Step 1. Synthesis of methyl 2-(benzylthio)acetate

To a solution of phenylmethanethiol (33.85 g, 272.4 mmol, 31.9 mL, 1 equiv) and NaH (32.7 g, 817.15 mmol, 60% purity, 3 equiv) in THF (1000 mL) was added methyl 2-bromoacetate (50 g, 326.85 mmol, 30.85 mL, 1.2 equiv) in one portion at 0° C. under $N_2$. The mixture was stirred at 20° C. for 2 hours. The reaction was quenched with the dropwise addition of water (400 mL). The product was extracted with ethyl acetate (2×800 mL). The combined organic phase was washed with brine (1×50 mL), dried ($Na_2SO_4$), filtered and concentrated. The residue was purified by column chromatography ($SiO_2$, petroleum ether/ethyl acetate, 10:1 to 1:1) to give methyl 2-(benzylthio)acetate (38 g, 193.62 mmol, 71%) as a colorless oil. $^1$H NMR (400 MHz, Chloroform-d) δ 7.33-7.26 (m, 4H) 7.25-7.20 (m, 1H) 3.80 (s, 2H) 3.69 (s, 3H) 3.06 (s, 2H).

Step 2. Synthesis of 2-(benzylthio)acetaldehyde

To a solution of methyl 2-(benzylthio)acetate (38 g, 193.62 mmol, 1 equiv) in toluene (1000 mL) was added DIBAL-H (1M, 232.32 mL, 1.2 equiv) in one portion at −78° C. under $N_2$. The mixture was stirred at −78° C. for 30 minutes. The reaction was quenched with saturated aqueous solution of Rochelle's salt (20 mL), diluted with ethyl acetate (50 mL), and stirred at 20° C. for 3 hours. The quenched reaction mixture was filtered through Celite, dried over $MgSO_4$, filtered a second time through Celite, and concentrated to give 2-(benzylthio)acetaldehyde (32 g, crude) as a colorless oil.

Step 3. Synthesis of 1-(tert-butyl) 4-methyl 4-(2-(benzylthio)-1-hydroxyethyl)piperidine-1,4-dicarboxylate To a solution of 1-(tert-butyl) 4-methyl piperidine-1,4-dicarboxylate (29.14 g, 113.23 mmol, 1.00 equiv) was added LiHMDS (1M, 169.85 mL, 1.5 equiv) in THF (500 mL) at −78° C. and the resulting solution stirred at 20° C. for 1 hour. Then 2-(benzylthio)acetaldehyde (32 g, 192.49 mmol, 10.87 mL, 1.7 equiv) was added in one portion at −78° C. under $N_2$. The mixture was stirred at 20° C. for 15 hours. The reaction mixture was poured into water (400 mL) and the aqueous phase was extracted with ethyl acetate (3×300 mL). The combined organic phase was washed with brine (40 mL), dried ($Na_2SO_4$), filtered, and concentrated. The residue was purified by column chromatography ($SiO_2$, petroleum ether/ethyl acetate, 10:1 to 3:1) to give 1-(tert-butyl) 4-methyl 4-(2-(benzylthio)-1-hydroxyethyl)piperidine-1,4-dicarboxylate (27 g, 64 mmol, 56%) as a light yellow oil.

Step 4. Synthesis of tert-butyl 4-(2-(benzylthio)-1-hydroxyethyl)-4-(hydroxymethyl)piperidine-1-carboxylate To a solution of 1-(tert-butyl) 4-methyl 4-(2-(benzylthio)-1-hydroxyethyl)piperidine-1,4-dicarboxylate (27 g, 64 mmol, 1.00 equiv) in THF (750 mL) was added $LiAlH_4$ (3.75 g, 98.9 mmol, 1.5 equiv) in one portion at 0° C. under $N_2$. The mixture was stirred at 0° C. for 3 hours. The reaction mixture was poured into 300 mL of 1M HCl (300 mL) and the aqueous phase was extracted with ethyl acetate (3×500 mL). The combined organic phase was washed with brine (3×10 mL), dried ($Na_2SO_4$), and filtered. The residue was purified by column chromatography ($SiO_2$, petroleum ether/ethyl acetate, 5:1 to 0:1) to give tert-butyl 4-(2-(benzylthio)-

1-hydroxyethyl)-4-(hydroxymethyl)piperidine-1-carboxylate (4.33 g, 11.35 mmol, 17%) as a colorless oil.

Step 5. Synthesis of tert-butyl 4-hydroxy-2-thia-8-azaspiro[4.5]decane-8-carboxylate The solution of tert-butyl 4-(2-(benzylthio)-1-hydroxyethyl)-4-(hydroxymethyl)piperidine-1-carboxylate (2.8 g, 7.34 mmol, 1 equiv) in pyridine (80 mL) was added tosyl chloride (3.50 g, 18.35 mmol, 2.5 equiv) in one portion at 20° C. under $N_2$. The mixture was then stirred at 80° C. for 15 hours. The reaction was concentrated in vacuum. The residue was purified by column chromatography ($SiO_2$, petroleum ether/ethyl acetate, 6:1 to 1:1) to give tert-butyl 4-hydroxy-2-thia-8-azaspiro[4.5]decane-8-carboxylate (0.91 g, 3.33 mmol, 45% yield) as a light yellow oil. $^1$H NMR (400 MHz, Chloroform-d) δ 3.98 (m, 1H), 3.84 (m, 2H), 3.12-2.92 (m, 3H), 2.81-2.73 (m, 3H), 1.81-1.60 (m, 3H), 1.46 (s, 9H).

Step 6. Synthesis of tert-butyl 4-oxo-2-thia-8-azaspiro[4.5]decane-8-carboxylate To a solution of tert-butyl 4-hydroxy-2-thia-8-azaspiro[4.5]decane-8-carboxylate (0.9 g, 3.29 mmol, 1.00 equiv) and Dess-Martin (1.95 g, 4.61 mmol, 1.43 mL, 1.4 equiv) in DCM (40 mL) was added $NaHCO_3$ (940.26 mg, 11.19 mmol, 435.31 µL, 3.4 equiv) in one portion at 20° C. under $N_2$. The mixture was stirred at 20° C. for 2 hours. The residue was poured into saturated $Na_2S_2O_3$ (50 mL) and stirred for 10 minutes. The aqueous phase was extracted with DCM (2×100 mL). The combined organic phase was washed with brine (10 mL), dried ($Na_2SO_4$), and concentrated. The residue was purified by column chromatography ($SiO_2$, petroleum ether/ethyl acetate, 5/1) to give tert-butyl 4-oxo-2-thia-8-azaspiro[4.5]decane-8-carboxylate (0.39 g, 1.44 mmol, 44%) as a colorless oil. $^1$H NMR (400 MHz, Chloroform-d) δ 3.91 (m, 2H), 3.34 (s, 2H), 3.09-3.00 (m, 2H), 2.98 (s, 2H), 1.82-1.73 (m, 2H), 1.63-1.54 (m, 2H), 1.46 (s, 9H).

Step 7. Synthesis of tert-butyl 4-oxo-2-thia-8-azaspiro[4.5]decane-8-carboxylate 2,2-dioxide To a solution of tert-butyl 4-oxo-2-thia-8-azaspiro[4.5]decane-8-carboxylate (0.39 g, 1.44 mmol, 1 equiv) in DCM (30 mL) was added mCPBA (1.42 g, 5.75 mmol, 70% purity, 4 equiv) in one portion at 0° C. under $N_2$. The mixture was stirred at 20° C. for 2 hours. The residue was poured into saturated $Na_2S_2O_3$ (30 mL) and stirred for 10 minutes. The aqueous phase was extracted with DCM (2×50 mL). The combined organic phase was washed with brine (10 mL), dried ($Na_2SO_4$), filtered and concentrated. The residue was purified by column chromatography ($SiO_2$, petroleum ether/ethyl acetate, 5:1 to 1:1) to give tert-butyl 4-oxo-2-thia-8-azaspiro[4.5]decane-8-carboxylate 2,2-dioxide (0.27 g, 0.889 mmol, 61%) as a white solid. $^1$H NMR (400 MHz, Chloroform-d) δ 3.95 (m, 2H), 3.87 (s, 2H), 3.50 (s, 2H), 3.04 (m, 2H), 2.07-1.97 (m, 2H), 1.78 (m, 2H), 1.47 (s, 9H).

Step 8. Synthesis of tert-butyl (S)-4-4(R)-tert-butylsulfinyl)amino)-2-thia-8-azaspiro[4.5]decane-8-carboxylate 2,2-dioxide A solution of tert-butyl 4-oxo-2-thia-8-azaspiro[4.5]decane-8-carboxylate 2,2-dioxide (0.27 g, 0.890 mmol, 1.00 equiv), (R)-2-methylpropane-2-sulfinamide (215.73 mg, 1.78 mmol, 2.00 equiv), and titanium ethoxide (812 mg, 3.56 mmol, 4 equiv) in THF (65 mL) was stirred at 80° C. for 15 hours. After cooling to −4° C., MeOH (4.5 mL) was added, followed by the dropwise addition of $LiBH_4$ (2M, 445 µL, 1 equiv) and the resulting mixture was stirred for 1 hour at −4° C. The reaction mixture was poured into saturated $NaHCO_3$ (30 mL) and the aqueous phase was extracted with ethyl acetate (3×100 mL). The combined organic phase was washed with brine (3×10 mL), dried ($Na_2SO_4$), filtered and concentrated. The residue was purified by column chromatography ($SiO_2$, petroleum ether/ethyl acetate, 5/1 to 0:1) to give tert-butyl (S)-4-4(R)-tert-butylsulfinyl)amino)-2-thia-8-azaspiro[4.5]decane-8-carboxylate 2,2-dioxide (0.18 g, 0.440 mmol, 49%) as a white solid. $^1$H NMR (400 MHz, Chloroform-d) δ 4.06 (m, 1H), 3.95 (m, 1H), 3.75-3.58 (m, 1H), 3.52 (m, 1H), 3.33 (m, 1H), 3.27-3.02 (m, 2H), 2.94-2.78 (m, 2H), 1.83-1.69 (m, 4H), 1.47 (s, 9H), 1.28-1.24 (m, 9H).

Step 9. Synthesis of (R)—N—((S)-2,2-dioxido-2-thia-8-azaspiro[4.5]decan-4-yl)-2-methylpropane-2-sulfinamide To a solution of tert-butyl (S)-4-4(R)-tert-butylsulfinyl)amino)-2-thia-8-azaspiro[4.5]decane-8-carboxylate 2,2-dioxide (0.18 g, 0.440 mmol, 1 equiv) in DCM (3 mL) was added trifluoroacetic acid (2.51 g, 22.03 mmol, 1.63 mL, 50 equiv) in one portion and the resulting solution was stirred for 1 hour at 20° C. The reaction solution was concentrated to give (R)—N—((S)-2,2-dioxido-2-thia-8-azaspiro[4.5]decan-4-yl)-2-methylpropane-2-sulfinamide (0.2 g, 0.372 mmol, 84%, 2 TFA) as a light yellow oil. $^1$H NMR (400 MHz, MeOH-$d_4$) δ 4.15-4.07 (m, 1H), 3.73-3.66 (m, 1H), 3.64-3.52 (m, 1H), 3.49-3.36 (m, 3H), 3.28-3.12 (m, 3H), 3.10-2.96 (m, 1H), 2.30 (m, 1H), 2.18-1.74 (m, 4H), 1.32-1.24 (m, 9H).

Step 10. Synthesis of ethyl 3-((S)-4-4(R)-tert-butylsulfinyl)amino)-2,2-dioxido-2-thia-8-azaspiro[4.5]decan-8-yl)-6-(2,3-dichlorophenyl)-5-methylpyrazine-2-carboxylate To a solution of (R)—N—((S)-2,2-dioxido-2-thia-8-azaspiro[4.5]decan-4-yl)-2-methylpropane-2-sulfinamide (0.2 g, 0.648 mmol, 1 equiv) and ethyl 3-chloro-6-(2,3-dichlorophenyl)-5-methylpyrazine-2-carboxylate (224 mg, 0.648 mmol, 1 equiv) in isopropyl alcohol (3 mL) was added DIPEA (419 mg, 3.24 mmol, 564 mL, 5 equiv) in one portion at 85° C. under $N_2$. The mixture was concentrated in vacuum. The residue was purified by column chromatography ($SiO_2$, petroleum ether/ethyl acetate, 5/1 to 0:1) to give ethyl 3-((S)-4-(((R)-tert-butylsulfinyl)amino)-2,2-dioxido-2-thia-8-azaspiro[4.5]decan-8-yl)-6-(2,3-dichlorophenyl)-5-methylpyrazine-2-carboxylate (0.14 g, 0.226 mmol, 35%) as a white solid. $^1$H NMR (400 MHz, Chloroform-d) δ 7.55-7.49 (m, 1H), 7.32-7.28 (m, 2H), 4.43 (q, J=7.06 Hz, 2H), 4.09-3.90 (m, 3H), 3.71-3.63 (m, 1H), 3.56 (m, 1H), 3.38 (m, 1H), 3.34-3.23 (m, 2H), 3.23-3.08 (m, 2H), 2.30 (s, 3H), 2.03-1.85 (m, 4H), 1.40 (t, J=7.06 Hz, 3H), 1.27 (s, 9H).

Step 11. Synthesis of ethyl (S)-3-(4-amino-2,2-dioxido-2-thia-8-azaspiro[4.5]decan-8-yl)-6-(2,3-dichlorophenyl)-5-methylpyrazine-2-carboxylate The mixture of ethyl 3-((S)-4-4(R)-tert-butylsulfinyl)amino)-2,2-dioxido-2-thia-8-azaspiro[4.5]decan-8-yl)-6-(2,3-dichlorophenyl)-5-methylpyrazine-2-carboxylate (0.14 g, 0.226 mmol, 1 equiv) in HCl/MeOH (10 mL) was stirred at 20° C. for one hour. The reaction mixture was concentrated to give crude ethyl (S)-3-(4-amino-2,2-dioxido-2-thia-8-azaspiro[4.5]decan-8-yl)-6-(2,3-dichlorophenyl)-5-methylpyrazine-2-carboxylate (0.12 g) as a white solid used directly in the next reaction. $^1$H NMR (400 MHz, MeOH-d$_4$) δ 7.65 (m, 1H), 7.46-7.40 (m, 1H), 7.38-7.33 (m, 1H), 4.40 (q, J=7.06 Hz, 2H), 4.13-3.98 (m, 3H), 3.85-3.77 (m, 2H), 3.67-3.60 (m, 1H), 3.56-3.50 (m, 1H), 3.42 (m 1H), 3.24 (m, 2H), 2.28 (s, 3H), 2.06-1.85 (m, 4H), 1.41-1.34 (m, 3H). LC-MS (ESI): m/z: [M+H] calculated for $C_{22}H_{26}Cl_2N_4O_4S$: 513.1; found 513.0.

Step 12. Synthesis of (S)-4-amino-8-(5-(2,3-dichlorophenyl)-3-(hydroxymethyl)-6-methylpyrazin-2-yl)-2-thia-8-azaspiro[4.5]decane 2,2-dioxide To a solution of ethyl (S)-3-(4-amino-2,2-dioxido-2-thia-8-azaspiro[4.5]decan-8-yl)-6-(2,3-dichlorophenyl)-5-methylpyrazine-2-carboxylate (0.08 g, 0.155 mmol, 1 equiv) in THF (2 mL) was added LiAlH$_4$ (2M, 779.06 μL, 10 equiv) in one portion at 0° C. under N$_2$. The mixture was stirred at 0° C. for 0.1 hour. MeOH (0.5 mL) was added drop wise to the reaction mixture and the resulting solution was filtered and concentrated. The residue was purified by preparative HPLC to give (S)-4-amino-8-(5-(2,3-dichlorophenyl)-3-(hydroxymethyl)-6-methylpyrazin-2-yl)-2-thia-8-azaspiro[4.5]decane 2,2-dioxide (4.7 mg, 0.01 mmol, 6.4%) as the parent. $^1$H NMR (400 MHz, MeOH-d$_4$) δ 7.63 (m, 1H), 7.44-7.38 (m, 1H), 7.36-7.31 (m, 1H), 4.67 (s, 2H), 3.83-3.71 (m, 2H), 3.58-3.45 (m, 3H), 3.22-3.03 (m, 4H), 2.25 (s, 3H), 2.15-2.05 (m, 1H), 2.02-1.93 (m, 1H), 1.91-1.83 (m, 1H), 1.75 (m, 1H). LC-MS (ESI): m/z: [M+H] calculated for $C_{20}H_{24}Cl_2N_4O_3S$: 471.1; found 471.1.

Example 307—6-(4-amino-4-methylpiperidin-1-yl)-3-(2,3-dichlorophenyl)-5-(hydroxymethyl)-1,2-dihydropyrazin-2-one

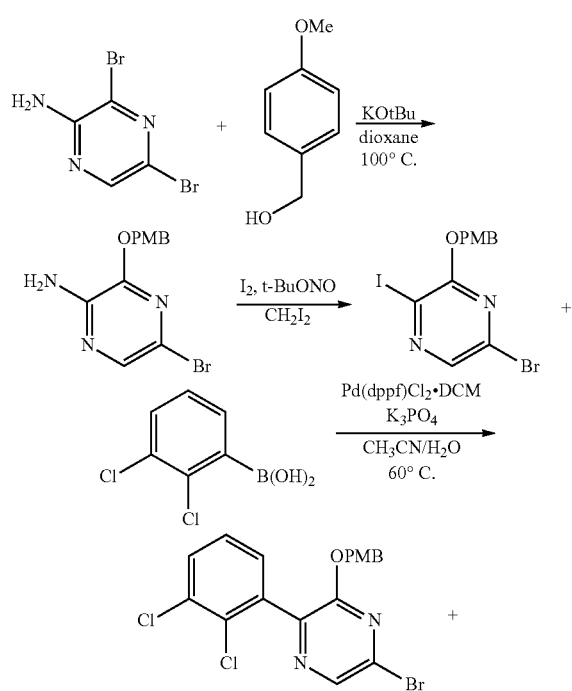

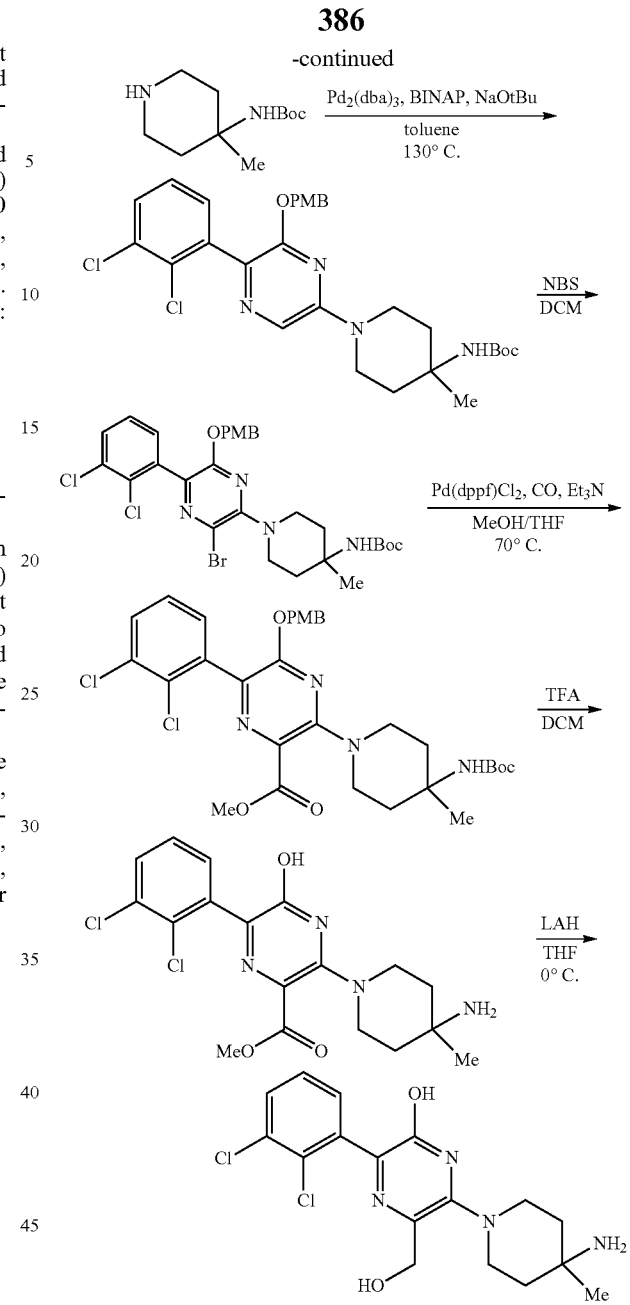

Step 1. Synthesis of 5-bromo-3-((4-methoxybenzyl)oxy)pyrazin-2-amine

To a solution of 3,5-dibromopyrazin-2-amine (10 g, 39.54 mmol, 1 equiv) and (4-methoxyphenyl)methanol (8.19 g, 59.31 mmol, 7.38 mL, 1.50 equiv) in dioxane (100 mL) was added KOt-Bu (6.66 g, 59.31 mmol, 1.50 equiv) at 25° C. The mixture was stirred at 100° C. for 2 hours at which time the cooled and quenched by addition water (30 mL). The product was extracted with EtOAc (3×30 mL). The combined organic layers were washed with brine (50 mL), dried (Na$_2$SO$_4$), filtered and concentrated under reduced pressure to give a residue. The residue was purified by column chromatography to give 5-bromo-3-((4-methoxybenzyl)oxy)pyrazin-2-amine (10 g, 32.24 mmol, 81%) as a yellow solid.

Step 2. Synthesis of 5-bromo-2-iodo-3-((4-methoxybenzyl)oxy)pyrazine

To a solution of 5-bromo-3-((4-methoxybenzyl)oxy) pyrazin-2-amine (10 g, 32.24 mmol, 1.00 equiv) in $CH_2I_2$ (20.00 mL) was added t-BuONO (13.30 g, 128.97 mmol, 15.29 mL, 4.00 equiv) and $I_2$ (9.82 g, 38.69 mmol, 7.79 mL, 1.20 equiv), the mixture was stirred at 25° C. for 3 hours. The reaction mixture was diluted with aqueous $Na_2S_2O_3$ (50 mL) and extracted with DCM (3×50 mL). The combined organic layers were washed with brine (30 mL), dried over $Na_2SO_4$, filtered and concentrated under reduced pressure to give a residue. The residue was purified by column chromatography to give 5-bromo-2-iodo-3-((4-methoxybenzyl)oxy)pyrazine (8 g, 19.00 mmol, 58% yield) as a white solid. LC-MS (ESI): m/z [M+H] calculated for $C_{12}H_{11}BrIN_2O_2$: 420.9; found 420.7.

Step 3. Synthesis of 5-bromo-2-(2,3-dichlorophenyl)-3-((4-methoxybenzyl)oxy)pyrazine To a solution of 5-bromo-2-iodo-3-((4-methoxybenzyl)oxy)pyrazine (8 g, 19.00 mmol, 1.00 equiv) and (2,3-dichlorophenyl)boronic acid (3.63 g, 19.00 mmol, 1 equiv) in $CH_3CN$ (30.00 mL) and $H_2O$ (3.00 mL) was added $K_3PO_4$ (8.07 g, 38.00 mmol, 2.00 equiv) and Pd(dppf) $Cl_2$.DCM (155.17 mg, 0.190 mmol, 0.01 equiv) at 20° C. The mixture was stirred at 60° C. for 2 hours under $N_2$. The cooled reaction mixture was diluted with $H_2O$ (10 mL) and extracted with EtOAc (3×10 mL). The combined organic layers were washed with brine (30 mL), dried ($Na_2SO_4$), filtered and concentrated under reduced pressure to give a residue. The residue was purified by column chromatography to give 5-bromo-2-(2,3-dichlorophenyl)-3-((4-methoxybenzyl)oxy)pyrazine (3 g, 6.82 mmol, 35% yield) as a colorless oil.

Step 4. Synthesis of tert-butyl (1-(5-(2,3-dichlorophenyl)-6-((4-methoxybenzyl)oxy)pyrazin-2-yl)-4-methylpiperidin-4-yl)carbamate Two equivalent batches were set up in parallel: To a solution of 5-bromo-2-(2,3-dichlorophenyl)-3-((4-methoxybenzyl)oxy)pyrazine (1 g, 2.27 mmol, 1.00 equiv) and tert-butyl N-(4-methyl-4-piperidyl)carbamate (633.00 mg, 2.95 mmol, 1.30 equiv) in toluene (15.00 mL) was added NaOt-Bu (436.70 mg, 4.54 mmol, 2.00 equiv), BINAP (141.48 mg, 0.227 mmol, 0.10 equiv) and $Pd_2(dba)_3$ (104.03 mg, 0.113 mmol, 0.05 equiv) at 20° C. The mixture was stirred at 130° C. for 3 hours by microwave heating under $N_2$. The two reactions were cooled, combined and concentrated. The residue was purified by column chromatography to give tert-butyl (1-(5-(2,3-dichlorophenyl)-6-((4-methoxybenzyl)oxy)pyrazin-2-yl)-4-methylpiperidin-4-yl)carbamate (1.2 g, 2.09 mmol, 46%) as a yellow oil.

Step 5. Synthesis of tert-butyl (1-(3-bromo-5-(2,3-dichlorophenyl)-6-((4-methoxybenzyl)oxy)pyrazin-2-yl)-4-methylpiperidin-4-yl)carbamate To a solution of tert-butyl (1-(5-(2,3-dichlorophenyl)-6-((4-methoxybenzyl)oxy)pyrazin-2-yl)-4-methylpiperidin-4-yl)carbamate (1 g, 1.74 mmol, 1 equiv) in DCM (10.00 mL) was added NBS (465.50 mg, 2.62 mmol, 1.50 equiv) at 0° C. The mixture was stirred at 0° C. for 1 hour at which time reaction mixture was quenched by addition saturated $NaHSO_3$ (3 mL), diluted with $H_2O$ (5 mL) and extracted with DCM (3×10 mL). The combined organic layers were washed with brine (30 mL), dried ($Na_2SO_4$), filtered and concentrated under reduced pressure to give a residue. The residue was purified by column chromatography to give tert-butyl (1-(3-bromo-5-(2,3-dichlorophenyl)-6-((4-methoxybenzyl)oxy)pyrazin-2-yl)-4-methylpiperidin-4-yl) carbamate (0.5 g, 0.766 mmol, 44%) as a yellow oil.

Step 6. Synthesis of methyl 3-[4-(tert-butoxycarbonylamino)-4-methyl-1-piperidyl]-6-(2,3-dichlorophenyl)-5-[(4-methoxyphenyl)methoxy]pyrazine-2-carboxylate To a solution of tert-butyl N-[1-[3-bromo-5-(2,3-dichlorophenyl)-6-[(4-methoxyphenyl)methoxy]pyrazin-2-yl]-4-methyl-4-piperidyl]carbamate (0.5 g, 0.766 mmol, 1.00 equiv) in THF (5.00 mL) and MeOH (10.00 mL) was added Pd(dppf)$Cl_2$ (56.08 mg, 0.076 mmol, 0.10 equiv) and triethylamine (232.65 mg, 2.30 mmol, 319 μL, 3.00 equiv) at 20° C. The mixture was stirred at 80° C. for 2 hours under CO (50 psi) at which time the reaction mixture was concentrated. The residue was purified by column chromatography to give methyl 3-[4-(tert-butoxycarbonylamino)-4-methyl-1-piperidyl]-6-(2,3-dichlorophenyl)-5-[(4-methoxyphenyl)methoxy]pyrazine-2-carboxylate (0.32 g, 0.506 mmol, 66%) as a yellow oil.

Step 7. Synthesis of methyl 3-(4-amino-4-methyl-1-piperidyl)-6-(2,3-dichlorophenyl)-5-hydroxy-pyrazine-2-carboxylate To a solution of methyl 3-[4-(tert-butoxycarbonylamino)-4-methyl-1-piperidyl]-6-(2,3-dichlorophenyl)-5-[(4-methoxyphenyl)methoxy]pyrazine-2-carboxylate (0.32 g, 0.506 mmol, 1.00 equiv) in DCM (5.00 mL) was added TFA (123.19 g, 1.08 mol, 80.00 mL, 2132.37 equiv). The mixture was stirred at 25° C. for 30 minutes at which time the reaction was quenched by the addition of saturated $Na_2CO_3$ (1 mL) at 0° C. The residue was concentrated under reduced pressure, treated with DCM/MeOH (10 mL, 10:1), and filtered. The filtrate was concentrated to give methyl 3-(4-amino-4-methyl-1-piperidyl)-6-(2,3-dichlorophenyl)-5-hydroxy-pyrazine-2-carboxylate (0.3 g, crude) as a yellow oil. The residue was used into the next step without further purification. LC-MS (ESI): m/z [M+H] calculated for $C_{18}H_{21}Cl_2N_4O_3$: 411.1; found 411.0.

Step 8. Synthesis of 6-(4-amino-4-methylpiperidin-1-yl)-3-(2,3-dichlorophenyl)-5-(hydroxymethyl)-1,2-dihydropyrazin-2-one To a solution of methyl 3-(4-amino-4-methyl-1-piperidyl)-6-(2,3-dichlorophenyl)-5-hydroxy-pyrazine-2-carboxylate (0.1 g, 0.243 mmol, 1 equiv) in THF (5 mL) was added LAH (18.46 mg, 0.486 mmol, 2 equiv) at 0° C. The mixture was stirred at 0° C. for 10 minutes at which time the reaction mixture was quenched by the addition of $H_2O$ (1 mL) at 0° C. The resulting solution was filtered and concentrated under reduced pressure to give a residue. The residue was purified by preparative HPLC to give 6-(4-amino-4-methylpiperidin-1-yl)-3-(2,3-dichlorophenyl)-5-(hydroxymethyl)-1,2-dihydropyrazin-2-one (5 mg, 0.0131 mmol, 5.4%) as a white solid. $^1$H NMR (400 MHz, Methanol-$d_4$) δ 7.40-7.42 (d, J=7.45 Hz, 1H) 7.21-7.24 (m, 2H) 4.47 (s, 2H) 3.43-3.46 (m, 2H) 3.13-3.21 (m, 2H) 1.75-1.87 (m, 4H) 1.33 (s, 3H) LC-MS (ESI): m/z [M+H] calculated for $C_{17}H_{21}Cl_2N_4O_2$: 383.1; found 383.1.

Example 308-6-(4-amino-4-methylpiperidin-1-yl)-3-
[(2,3-dichlorophenyl)sulfanyl]-5-(hydroxymethyl)-1,
2-dihydropyrazin-2-one

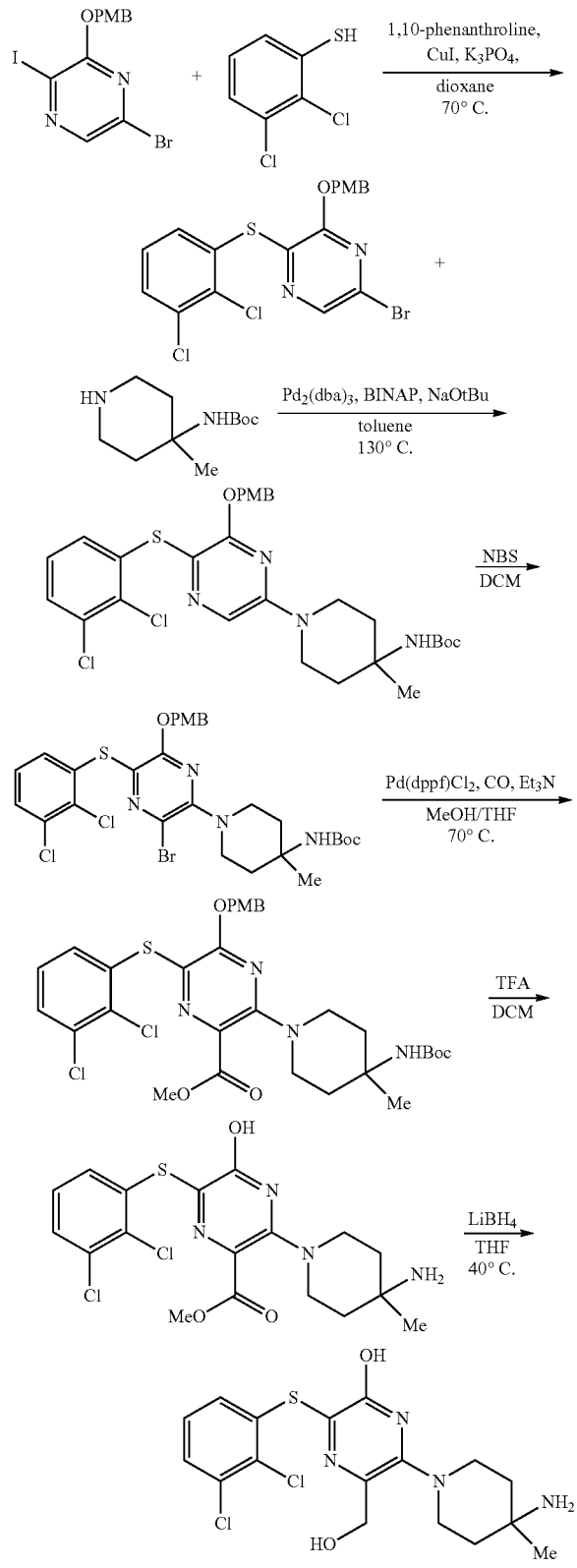

Step 1. Synthesis of 5-bromo-2-(2,3-dichlorophe-
nyl)sulfanyl-3-[(4-methoxyphenyl)methoxy]pyrazine To a solution of 5-bromo-2-iodo-3-[(4-methoxyphenyl) methoxy]pyrazine (2.68 g, 6.37 mmol, 1.00 equiv, Example 307) and 2,3-dichlorobenzenethiol (1.14 g, 6.37 mmol, 1.00 equiv) in dioxane (20.00 mL) was added CuI (121.23 mg, 0.636 mmol, 0.10 equiv), $K_3PO_4$ (1.62 g, 7.64 mmol, 1.20 equiv) and 1,10-phenanthroline (114.7 mg, 0.636 mmol, 0.10 equiv). The resulting mixture was stirred at 70° C. for 3 hours. The cooled reaction mixture was then diluted with $H_2O$ (10 mL) and extracted with EtOAc (3×10 mL). The combined organic layers were washed with brine (30 mL), dried ($Na_2SO_4$), filtered and concentrated under reduced pressure to give a residue. The residue was purified by column chromatography to give 5-bromo-2-(2,3-dichlorophenyl)sulfanyl-3-[(4-methoxyphenyl)methoxy]pyrazine (2.20 g, 4.66 mmol, 73%) as a white solid.

Step 2. Synthesis of tert-butyl N-[1-[5-(2,3-dichlorophenyl)sulfanyl-6-[(4-methoxyphenyl)methoxy] pyrazin-2-yl]-4-methyl-4-piperidyl]carbamate To a solution of 5-bromo-2-(2,3-dichlorophenyl)sulfanyl-3-[(4-methoxyphenyl)methoxy]pyrazine (1.40 g, 2.96 mmol, 1.00 equiv) and tert-butyl N-(4-methyl-4-piperidyl) carbamate (824.66 mg, 3.85 mmol, 1.30 equiv) in toluene (10.00 mL) was added NaOt-Bu (568.91 mg, 5.92 mmol, 2.00 equiv), BINAP (184.3 mg, 0.296.00 mmol, 0.10 equiv) and $Pd_2(dba)_3$ (135.53 mg, 0.148 mmol, 0.05 equiv) at 20° C. The mixture was stirred at 130° C. by microwave heating for 3 hours under $N_2$. The residue was purified by column chromatography to give tert-butyl N-[1-[5-(2,3-dichlorophenyl) sulfanyl-6-[(4-methoxyphenyl) methoxy] pyrazin-2-yl]-4-methyl-4-piperidyl] carbamate (500 mg, 0.825 mmol, 27%) as a yellow oil.

Step 3. Synthesis of tert-butyl-N-[1-[3-bromo-5-(2,
3-dichlorophenyl)sulfanyl-6-[(4-methoxyphenyl)
methoxy]pyrazin-2-yl]-4-methyl-4-piperidyl]car-
bamate To a solution of tert-butyl $N_{41}$-[5-(2,3-dichlorophenyl) sulfanyl-6-[(4-methoxyphenyl)methoxy]pyrazin-2-yl]-4-methyl-4-piperidyl]carbamate (500.00 mg, 0.825 mmol, 1.00 equiv) in DCM (10.00 mL) was added NBS (220.4 mg, 1.24 mmol, 1.50 equiv) at 0° C. The reaction mixture was stirred at 0° C. for 10 minutes and then quenched by the addition of aqueous $NaHSO_3$ (5 mL) at 0° C. The solution was diluted with $H_2O$ (10 mL) and the product extracted with DCM (3×10 mL). The combined organic layers were washed with brine (20 mL), dried ($Na_2SO_4$), filtered, and concentrated under reduced pressure to give a residue. The residue was purified by column chromatography to give tert-butyl N-[1-[3-bromo-5-(2,3-dichlorophenyl)sulfanyl-6-[(4-methoxyphenyl)methoxy]pyrazin-2-yl]-4-methyl-4-piperidyl]carbamate (500 mg, 0.730 mmol, 88%) as a yellow oil.

Step 4. Synthesis of methyl 3-[4-(tert-butoxycarbo-
nylamino)-4-methyl-1-piperidyl]-6-(2,3-dichloro-
phenyl)sulfanyl-5-[(4-methoxyphenyl)methoxy]
pyrazine-2-carboxylate To a solution of tert-butyl N-[1-[3-bromo-5-(2,3-dichlorophenyl)sulfanyl-6-[(4-methoxyphenyl)methoxy]pyrazin-2-yl]-4-methyl-4-piperidyl]carbamate (500 mg, 0.730 mmol, 1.00 equiv) in MeOH (10.00 mL) and THF (10.00 mL) was added Pd(dppf)Cl$_2$ (53.45 mg, 0.073 mmol, 0.10 equiv) and triethylamine (221.76 mg, 2.19 mmol, 304 µL, 3.00 equiv) at 20° C., The mixture was stirred at 70° C. for 2 hours under CO (50 psi) and the cooled reaction mixture was then concentrated. The residue was purified by column chromatography to give methyl 3-[4-(tert-butoxycarbonylamino)-4-methyl-1-piperidyl]-6-(2,3-dichlorophenyl)sulfanyl-5-[(4-methoxyphenyl)methoxy]pyrazine-2-carboxylate (350 mg, 0.527 mmol, 72%) as a yellow oil.

Step 5. Synthesis of methyl 3-(4-amino-4-methylpiperidin-1-yl)-6-((2,3-dichlorophenyl)thio)-5-hydroxypyrazine-2-carboxylate To a solution of methyl 3-[4-(tert-butoxycarbonylamino)-4-methyl-1-piperidyl]-6-(2,3-dichlorophenyl)sulfanyl-5-[(4-methoxyphenyl)methoxy]pyrazine-2-carboxylate (0.1 g, 0.151 mmol, 1.00 equiv) in DCM (3.00 mL) was added TFA (23.10 g, 202.58 mmol, 15.00 mL). The mixture was stirred at 25° C. for 0.5 hours. The reaction mixture was concentrated under reduced pressure and was adjusted to pH=7 with saturated Na$_2$CO$_3$ solution, then concentrated the mixture to give methyl 3-(4-amino-4-methylpiperidin-1-yl)-6-((2,3-dichlorophenyl)thio)-5-hydroxypyrazine-2-carboxylate (0.1 g, crude) as a yellow solid. LC-MS (ESI): m/z [M+H] calculated for C$_{17}$H$_{21}$Cl$_2$N$_4$O$_3$S: 443.1; found 442.9.

Step 6. Synthesis of 6-(4-amino-4-methylpiperidin-1-yl)-3-[(2,3-dichlorophenyl)sulfanyl]-5-(hydroxymethyl)-1,2-dihydropyrazin-2-one To a solution of methyl 3-(4-amino-4-methyl-1-piperidyl)-6-(2,3-dichlorophenyl)sulfanyl-5-hydroxy-pyrazine-2-carboxylate (0.1 g, 0.225 mmol, 1.00 equiv) in THF (5.00 mL) was added LiBH$_4$ (9.83 mg, 0.451 mmol, 2.00 equiv) at 0° C. The mixture was stirred at 40 C for 1 hour then quenched by the addition of H$_2$O (1 mL) at 0° C. The solution was filtered and concentrated to give a residue. The residue was purified by preparative HPLC to give 6-(4-amino-4-methylpiperidin-1-yl)-3-[(2,3-dichlorophenyl)sulfanyl]-5-(hydroxymethyl)-1,2-dihydropyrazin-2-one (2.5 mg, 0.006 mmol, 2.7% yield) as the parent. $^1$H NMR (400 MHz, Methanol-d$_4$) δ 7.27 (d, J=7.09 Hz, 1H) 7.05 (t, J=7.95 Hz, 1H) 6.94 (d, J=8.19 Hz, 1H) 4.41 (s, 2H) 3.52-3.55 (m, 2H), 1.75-1.95 (m, 4H), 1.39 (s, 3H). LC-MS (ESI): m/z [M+H] calculated for C$_{17}$H$_{21}$Cl$_2$N$_4$O$_2$S: 415.1; found 415.0.

Example 309—Synthesis of 3-({5-[(3S,4S)-4-amino-3-methyl-2-oxa-8-azaspiro[4.5]decan-8-yl]-6-(hydroxymethyl)-3-methylpyrazin-2-yl}sulfanyl)-2-chloro-N,N-dimethylbenzamide

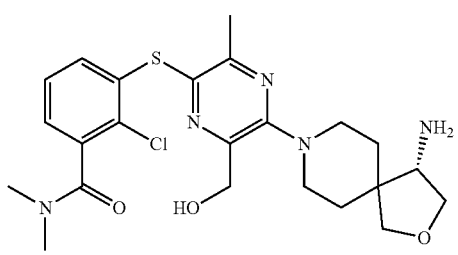 [SMILES: Cc1nc(N2CCC3(CC2)COC[C@H]3N)c(CO)nc1Sc1cccc(C(=O)N(C)C)c1Cl]

3-{5-[(3S,4S)-4-amino-3-methyl-2-oxa-8-azaspiro[4.5]decan-8-yl]-6-(hydroxymethyl)-3-methylpyrazin-2-yl}sulfanyl)-2-chloro-N,N-dimethylbenzamide was synthesized in the manner similar to Example 277, except 4-bromo-3-chloro-2-((tetrahydro-2H-pyran-4-yl)oxy)pyridines was substituted with 3-bromo-2-chloro-N,N-dimethylbenzamide. $^1$H NMR (500 MHz, Methanol-d$_4$) δ 8.47 (s, 2H), 7.33 (t, J=7.7 Hz, 1H), 7.25 (dd, J=7.6, 1.6 Hz, 1H), 7.21 (dd, J=7.8, 1.6 Hz, 1H), 4.57 (d, J=1.7 Hz, 2H), 4.30 (d, J=6.7 Hz, 1H), 3.96 (d, J=9.1 Hz, 1H), 3.85 (d, J=9.1 Hz, 1H), 3.74 (dd, J=32.2, 13.1 Hz, 3H), 3.41 (d, J=4.1 Hz, 1H), 3.13 (s, 3H), 2.91 (s, 3H), 2.50 (s, 3H), 2.01-1.84 (m, 4H), 1.72 (d, J=12.9 Hz, 1H), 1.32 (d, J=6.5 Hz, 3H). LC-MS (ESI) m/z: [M+H] calculated for C$_{24}$H$_{32}$ClN$_5$O$_3$S: 506.19; found 506.4.

Synthesis of 3-bromo-2-chloro-N,N-dimethylbenzamide

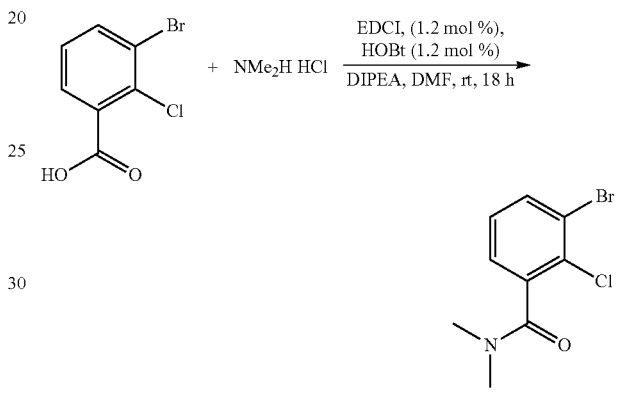

To a solution of 3-bromo-2-chlorobenzoic acid (200 mg, 849 µmol) in DMF (8.48 mL) was added dimethylamine hydrochloride (76.0 mg, 933 µmol), EDCI (193 mg, 1.01 mmol), HOBt (136 mg, 1.01 mmol), and DIPEA (367 µL, 2.12 mmol). The mixture was allowed to stir in a sealed vial at room temperature overnight. The resulting mixture was diluted with EtOAc and H$_2$O. The organic layer was separated and then washed three times with H$_2$O. The organic layer was dried over MgSO$_4$, filtered, and concentrated under reduced pressure. The residue was purified by flash chromatography to yield the 3-bromo-2-chloro-N,N-dimethylbenzamide (280 mg, 1.06 mmol, 63.2%). LCMS (ESI): m/z: [M+H] calcd for C$_9$H$_9$BrClNO: 261.96; found 261.8.

Biological Examples—SHP2 Allosteric Inhibition Assay

Without wishing to be bound by theory, SHP is allosterically activated through binding of bis-tyrosyl-phosphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

The phosphatase reactions were performed at room temperature in 96-well black polystyrene plate, flat bottom, non-binding surface (Corning, Cat #3650) using a final reaction volume of 100 µL and the following assay buffer conditions: 50 mM HEPES, pH 7.2, 100 mM NaCl, 0.5 mM EDTA, 0.05% P-20, 1 mM DTT.

The inhibition of SHP2 by compounds of the present disclosure (concentrations varying from 0.00005-10 μM) was monitored using an assay in which 0.2 nM of SHP2 was incubated with 0.5 μM of Activating Peptide 1 (sequence: H$_2$N-LN(pY)IDLDLV(dPEG8)LST(pY)ASINFQK-amide) or Activating Peptide 2 (sequence: H$_2$N-LN(pY)AQLWHA(dPEG8)LTI(pY)ATIRRF-amide). After 30-60-minutes incubation at 25° C., the surrogate substrate DiFMUP (Invitrogen, Cat # D6567) was added to the reaction and activity was determined by a kinetic read using a microplate reader (Envision, Perkin-Elmer or Spectramax M5, Molecular Devices). The excitation and emission wavelengths were 340 nm and 450 nm, respectively. Initial rates were determined from a linear fit of the data, and the inhibitor dose response curves were analyzed using normalized IC$_{50}$ regression curve fitting with control based normalization.

Using the above-protocol, SHP2 inhibition by certain compounds is shown in Table 13.

TABLE 13

SHP2 Inhibition of Tested Compounds

| Compound | SHP2 IC$_{50}$, nM |
|---|---|
| Compound 10 (Example 1) | 83 |
| Compound 31 (Example 23) | 43 |
| Compound 32 (Example 24) | 104 |
| Compound A-228 (Example 228) | 1.6 |

In some embodiments, compounds of the disclosure tested in the assay described above demonstrated an activity of less than 1000 nM. In some embodiments, compounds of the disclosure tested in the assay described above demonstrated an activity of about 10 nM to about 100 nM. In some embodiments, compounds of the disclosure tested in the assay described above demonstrated an activity of 10 nM to 100 nM. In some embodiments, compounds of the disclosure tested in the assay described above demonstrated an activity of less than 10 nM.

EQUIVALENTS

While the present disclosure has been described in conjunction with the specific embodiments set forth above, many alternatives, modifications and other variations thereof will be apparent to those of ordinary skill in the art. All such alternatives, modifications and variations are intended to fall within the spirit and scope of the present disclosure.

ENUMERATED EMBODIMENTS

Embodiment III-1

A compound of Formula I-W:

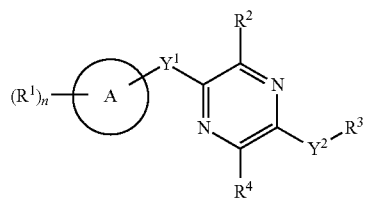

I-W or a pharmaceutically acceptable salt, prodrug, solvate, hydrate, tautomer, and isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

Y$^1$ is —S—, a direct bond, —NH—, —S(O)$_2$—, —S(O)$_2$—NH—, —C(═CH$_2$)—, —CH—, or —S(O)—;

Y$^2$ is —NR$^a$—, —(CR$^a_2$)$_m$—, —C(O)—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the pyrazine ring and the bond on the right side of the Y$^2$ moiety, as drawn, is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, ═O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is independently —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, —C$_1$-C$_6$alkyl, 3- to 12-membered heterocyclyl, or —(CH$_2$)$_n$-aryl, wherein each alkyl or cycloalkyl is optionally substituted with one or more —NH$_2$, or wherein 2 R$^a$, together with the carbon atom to which they are both attached, can combine to form a 3- to 8-membered cycloalkyl;

R$^b$ is independently, at each occurrence, —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is independently —H, —C$_1$-C$_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, spiroheterocycle, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_n NH_2$, —$(CH_2)_n OH$, —$COOR^b$, —$CONHR^b$, —$CONH(CH_2)_n COOR^b$, —$NHCOOR^b$, —$CF_3$, —$CHF_2$, —$CH_2F$, or =O;

$R^4$ is independently —H, -D, —$C_1$-$C_6$alkyl, —$C_1$-$C_6$haloalkyl, —$C_1$-$C_6$hydroxyalkyl, —$CF_2OH$, —CHFOH, —NH—$NHR^5$, —NH—$OR^5$, —O—$NR^5R^6$, —$OR^5$, —$NHC(O)R^5$, —$NHC(O)NHR^5$, —$NHS(O)_2R^5$, —$NHS(O)_2NHR^5$, —$S(O)_2OH$, —$C(O)OR^5$, —$NH(CH_2)_n OH$, —$C(O)NH(CH_2)_n OH$, —$C(O)NH(CH_2)_n R^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen; or $R^a$ and $R^4$, together with the atom or atoms to which they are attached, can combine to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —$S(O)_2$— in the heterocycle;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment III-2

The compound of Embodiment III-1, wherein the compound is Formula I:

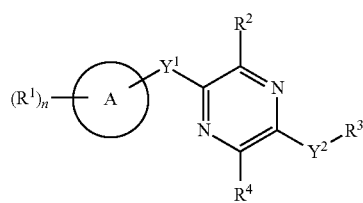

I or a pharmaceutically acceptable salt, prodrug, solvate, hydrate, tautomer, or isomer thereof, wherein:

A is 5- to 12-membered monocyclic or polycyclic cycloalkyl, heterocycloalkyl, aryl, or heteroaryl;

$Y^1$ is —S— or a direct bond;

$Y^2$ is —$NR^a$—, —$(CR^a_2)_m$—, —C(O)—, —$C(R^a)_2NH$—, —$(CR^a_2)_m O$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N(R^a)—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, or —$CO_2R^5$, wherein each alkyl, alkenyl, cycloalkenyl, alkynyl, or cycloalkyl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^2$ is independently —$OR^b$, —CN, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^a$ is independently, at each occurrence, —H, -D, —OH, —$C_3$-$C_8$cycloalkyl, or —$C_1$-$C_6$alkyl, wherein each alkyl or cycloalkyl is optionally substituted with one or more —$NH_2$, wherein 2 $R^a$, together with the carbon atom to which they are both attached, can combine to form a 3- to 8-membered cycloalkyl;

$R^b$ is independently, at each occurrence, —H, -D, —$C_1$-$C_6$alkyl, —$C_3$-$C_8$cycloalkyl, —$C_2$-$C_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —$C_1$-$C_6$alkyl or a 3- to 12-membered monocyclic or polycyclic heterocycle, wherein each alkyl or heterocycle is optionally substituted with one or more —$C_1$-$C_6$alkyl, —OH, or —$NH_2$; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with —$C_1$-$C_6$alkyl, —OH, or —$NH_2$;

$R^4$ is independently —H, -D, or —$C_1$-$C_6$alkyl, wherein each alkyl is optionally substituted with one or more —OH, —$NH_2$, halogen, or oxo; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo;

R$^5$ and R$^6$ are each independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

Embodiment III-3

The compound of Embodiment III-1, wherein the compound is Formula I-W6:

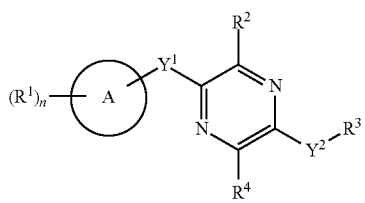

I-W6 or a pharmaceutically acceptable salt, prodrug, solvate, hydrate, tautomer, or isomer thereof, wherein:

A is a 5- to 12-membered monocyclic or polycyclic heteroaryl;

Y$^1$ is —S—;

Y$^2$ is —NR$^a$—; wherein the bond on the left side of Y$^2$, as drawn, is bound to the pyrazine ring and the bond on the right side of the Y$^2$ moiety, as drawn, is bound to R$^3$;

R$^3$ is combined with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^1$ is independently, at each occurrence, —H, —C$_1$-C$_6$alkyl, —OH, halogen, —NO$_2$, —CN, —NR$^5$R$^6$, —SR$^5$, —C(O)R$^5$, or —CO$_2$R$^5$;

R$^2$ is —C$_1$-C$_6$alkyl;

R$^b$ is independently, at each occurrence, —H or —C$_1$-C$_6$alkyl;

R$^4$ is —H, —C$_1$-C$_6$alkyl, —C$_1$-C$_6$haloalkyl, —C$_1$-C$_6$hydroxyalkyl, —CF$_2$OH, —CHFOH, —C(O)NH(CH$_2$)$_n$OH, —C(O)NH(CH$_2$)$_n$R$^b$, —C(O)R$^b$, —C(O)NR$^5$R$^6$, —OH, or —CN, wherein alkyl is optionally substituted with one or more —OH, —NH$_2$, halogen, or oxo; or R$^5$ and R$^6$ are each independently, at each occurrence, —H or —C$_1$-C$_6$alkyl; and n is independently, at each occurrence, 1, 2, 3, 4, 5, 6, 7, 8, 9, or 10.

Embodiment III-4

The compound of Embodiment III-1, wherein the compound is Formula I-W7:

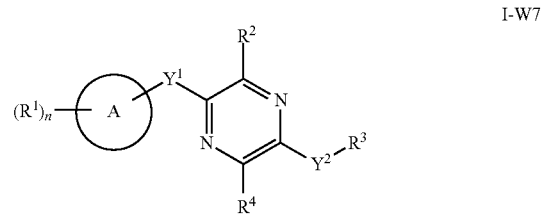

I-W7 or a pharmaceutically acceptable salt, prodrug, solvate, hydrate, tautomer, or isomer thereof, wherein:

A is a 5- to 12-membered monocyclic or polycyclic heteroaryl;

Y$^1$ is a direct bond;

Y$^2$ is —NR$^a$—; wherein the bond on the left side of Y$^2$, as drawn, is bound to the pyrazine ring and the bond on the right side of the Y$^2$ moiety, as drawn, is bound to R$^3$;

R$^3$ is combined with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

R$^1$ is independently, at each occurrence, —H, —C$_1$-C$_6$alkyl, —OH, halogen, —NO$_2$, —CN, —NR$^5$R$^6$, —SR$^5$, —C(O)R$^5$, or —CO$_2$R$^5$;

R$^2$ is —C$_1$-C$_6$alkyl;

R$^b$ is independently, at each occurrence, —H or —C$_1$-C$_6$alkyl;

R$^4$ is —H, —C$_1$-C$_6$alkyl, —C$_1$-C$_6$haloalkyl, —C$_1$-C$_6$hydroxyalkyl, —CF$_2$OH, —CHFOH, —C(O)NH(CH$_2$)$_n$OH, —C(O)NH(CH$_2$)$_n$R$^b$, —C(O)R$^b$, —C(O)NR$^5$R$^6$, —OH, or —CN, wherein alkyl is optionally substituted with one or more —OH, —NH$_2$, halogen, or oxo; or R$^5$ and R$^6$ are each independently, at each occurrence, —H or —C$_1$-C$_6$alkyl; and n is independently, at each occurrence, 1, 2, 3, 4, 5, 6, 7, 8, 9, or 10.

Embodiment III-5

A compound of Formula I-V1:

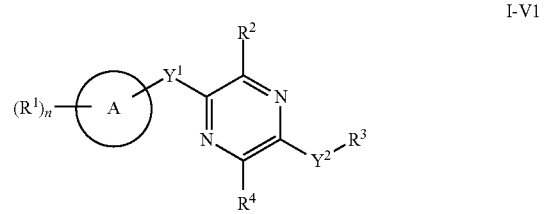

I-V1 or a pharmaceutically acceptable salt, prodrug, solvate, hydrate, tautomer, or isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —S(O)$_2$—, —S(O)$_2$—NH—, —C(=CH$_2$)—, —CH—, or —S(O)—;

$Y^2$ is —NR$^a$—, wherein the bond on the left side of $Y^2$, as drawn, is bound to the pyrazine ring and the bond on the right side of the $Y^2$ moiety, as drawn, is bound to $R^3$;

$R^a$ and $R^4$, together with the atom or atoms to which they are attached, are combined to form a monocyclic or polycyclic $C_3$-$C_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ is independently —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

$R^b$ is independently, at each occurrence, —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

$R^3$ is independently —H, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$—R$^b$, wherein each alkyl, spiroheterocycle, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl;

$R^5$ and $R^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

$R^7$ and $R^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN; and n is independently, at each occurrence, 0, 1, 2, 3, 4, 5, 6, 7, 8, 9, or 10.

Embodiment III-6

A compound of Formula I-V2:

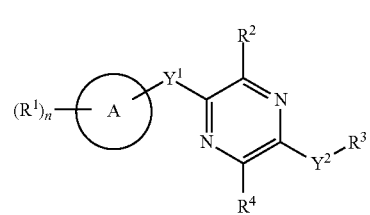

I-V2 or a pharmaceutically acceptable salt, prodrug, solvate, hydrate, tautomer, and isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S—, a direct bond, —NH—, —S(O)$_2$—, —S(O)$_2$—NH—, —C(=CH$_2$)—, —CH—, or —S(O)—;

$Y^2$ is —NR$^a$—, wherein the bond on the left side of $Y^2$, as drawn, is bound to the pyrazine ring and the bond on the right side of the $Y^2$ moiety, as drawn, is bound to $R^3$;

$R^3$ is combined with $R^a$ to form a 3- to 12-membered polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ is independently —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl; and wherein the heterocyclyl or heteroaryl is not attached via a nitrogen atom;

$R^b$ is independently, at each occurrence, —H, -D, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$, —$NR^5C(O)R^6$, heterocycle, aryl, heteroaryl, —$(CH_2)_nOH$, —$C_1$-$C_6$alkyl, —$CF_3$, —$CHF_2$, or —$CH_2F$;

$R^4$ is independently —H, -D, —$C_1$-$C_6$alkyl, —$C_1$-$C_6$haloalkyl, —$C_1$-$C_6$hydroxyalkyl, —$CF_2OH$, —CHFOH, —NH—$NHR^5$, —NH—$OR^5$, —O—$NR^5R^6$, —$NHR^5$, —$OR^5$, —$NHC(O)R^5$, —$NHC(O)NHR^5$, —$NHS(O)_2R^5$, —$NHS(O)_2NHR^5$, —$S(O)_2OH$, —$C(O)OR^5$, —$NH(CH_2)_nOH$, —$C(O)NH(CH_2)_nOH$, —$C(O)NH(CH_2)_nR^b$, —$C(O)R^b$, —$NH_2$, —OH, —CN, —$C(O)NR^5R^6$, —$S(O)_2NR^5R^6$, $C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —$NH_2$, —$OR^b$, halogen, or oxo; wherein each aryl or heteroaryl is optionally substituted with one or more —OH, —$NH_2$, or halogen;

$R^5$ and $R^6$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, -D, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN; and n is independently, at each occurrence, 0, 1, 2, 3, 4, 5, 6, 7, 8, 9, or 10.

Embodiment III-7

The compound of Embodiment III-5 or Embodiment III-6, wherein $R^2$ is —$NH_2$.

Embodiment III-8

The compound of any one of Embodiments III-1 to III-2 and Embodiments III-5 to III-7, wherein A is cycloalkyl.

Embodiment III-9

The compound of any one of Embodiments III-1 to III-2 and Embodiments III-5 to III-7, wherein A is heterocycloalkyl.

Embodiment III-10

The compound of any one of Embodiments III-1 to III-2 and Embodiments III-5 to III-7, wherein A is aryl.

Embodiment III-11

The compound of any one of Embodiments III-1 to III-2 and Embodiments III-5 to III-7, wherein A is heteroaryl.

Embodiment III-12

The compound of any one of Embodiments III-1 to III-7, wherein A is pyridinyl.

Embodiment III-13

The compound of any one of Embodiments III-1 to III-12, wherein n is 1 or 2.

Embodiment III-14

The compound of any one of Embodiments III-1 to III-13, wherein $R^1$ is independently, at each occurrence, —$C_1$-$C_6$alkyl, halogen, or —$NR^5R^6$.

Embodiment III-15

The compound of any one of Embodiments III-1 to III-13, wherein $R^1$ is independently selected from methyl, fluoro, chloro, and —$NH_2$.

Embodiment III-16

The compound of any one of Embodiments III-1 to III-2 and Embodiments III-5 to III-15, wherein $Y^1$ is —S—.

Embodiment III-17

The compound of any one of Embodiments III-1 to III-2 and Embodiments III-5 to III-15, wherein $Y^1$ is a direct bond.

Embodiment III-18

The compound of any of one of Embodiments III-1 to III-6 and Embodiments III-8 to III-17, wherein $R^2$ is —$OR^b$.

Embodiment III-19

The compound of Embodiment III-18, wherein $R^b$ is —H.

Embodiment III-20

The compound of Embodiment III-18, wherein $R^b$ is —$C_1$-$C_6$alkyl.

Embodiment III-21

The compound of any of one of Embodiments III-1 to III-6 and Embodiments III-8 to III-17, wherein $R^2$ is —CN.

Embodiment III-22

The compound of any of one of Embodiments III-1 to III-6 and Embodiments III-8 to III-17, wherein $R^2$ is —$C_1$-$C_6$alkyl.

Embodiment III-23

The compound of any of Embodiment III-22, wherein $R^2$ is methyl.

Embodiment III-24

The compound of any of one of Embodiments III-1 to III-6 and Embodiments III-8 to III-17, wherein $R^2$ is —$C_2$-$C_6$alkenyl.

Embodiment III-25

The compound of any of one of Embodiments III-1 to III-6 and Embodiments III-8 to III-17, wherein $R^2$ is —$C_2$-$C_6$alkynyl.

Embodiment III-26

The compound of any one of Embodiments III-1 to III-4 and Embodiments III-6 to III-25, wherein $R^4$ is —$C_1$-$C_6$alkyl, which is optionally substituted with one or more —OH, —$NH_2$, halogen, or oxo.

Embodiment III-27

The compound of Embodiment III-26, wherein $R^4$ is —$C_1$-$C_6$alkyl, which is substituted with —OH.

Embodiment III-28

The compound of Embodiment III-26, wherein $R^4$ is —$CH_2$—OH.

Embodiment III-29

The compound of any one of Embodiments III-1 to III-4 and Embodiments III-6 to III-25, wherein $R^4$ is —H.

Embodiment III-30

The compound of any one of Embodiments III-1 to III-4 and Embodiments III-6 to III-25, wherein $R^4$ is —CN.

Embodiment III-31

The compound of any one of Embodiments III-1 to III-4 and Embodiments III-6 to III-25, wherein $R^4$ is —$CF_2$OH or —CHFOH.

Embodiment III-32

The compound of any one of Embodiments III-1 to III-2 and Embodiments III-7 to III-31, wherein $Y^2$ is —$NR^a$—.

Embodiment III-33

The compound of any one of Embodiments III-1 to III-2 and Embodiments III-7 to III-31, wherein $Y^2$ is —$(CR^a_2)_m$—.

Embodiment III-34

The compound of any one of Embodiments III-1 to III-2, III-5, and III-7 to III-33, wherein $R^3$ is —$C_1$-$C_6$alkyl, which is optionally substituted with one or more —$C_1$-$C_6$alkyl, —OH, —$NH_2$, —$OR^b$, —$(CH_2)_n$OH, heterocyclyl, or spiroheterocyclyl.

Embodiment III-35

The compound of any one of Embodiments III-1 to III-34, wherein $R^a$ is —H.

Embodiment III-36

The compound of any one of Embodiments III-1 to III-2, III-5, III-7 to III-33, and III-35, wherein $R^3$ is 3- to 12-membered monocyclic or polycyclic heterocycle.

Embodiment III-37

The compound of any one of Embodiments III-1 to III-2, III-5, III-7 to III-33, and III-35, wherein $R^3$ is a 3- to 12-membered monocyclic heterocycle.

Embodiment III-38

The compound of any one of Embodiments III-1 to III-2, III-5 to III-33, and III-35, wherein $R^3$ is a 3- to 12-membered polycyclic heterocycle.

Embodiment III-39

The compound of any one of Embodiments III-1 to III-4 and III-7 to III-33, wherein $R^3$ and $R^a$ together with the atom to which they are attached combine to form a 3- to 12-membered monocyclic heterocycle, which is optionally substituted with —$C_1$-$C_6$alkyl, —OH, —$NH_2$, heteroaryl, heterocyclyl, —$(CH_2)_n NH_2$, —$COOR^b$, —$CONHR^b$, —$CONH(CH_2)_n COOR^b$, —$NHCOOR^b$, —$CF_3$, —$CHF_2$, or —$CH_2F$.

Embodiment III-40

The compound of any one of Embodiments III-1 to III-4 and III-6 to III-33, wherein $R^3$ and $R^a$ together with the atoms to which they are attached combine to form a 3- to 12-membered polycyclic heterocycle, which is optionally substituted with —$C_1$-$C_6$alkyl, —OH, —$NH_2$, heteroaryl, heterocyclyl, —$(CH_2)_n NH_2$, —$COOR^b$, —$CONHR^b$, —$CONH(CH_2)_n COOR^b$, —$NHCOOR^b$, —$CF_3$, —$CHF_2$, or —$CH_2F$.

Embodiment III-41

The compound of any one of Embodiments III-1 to III-4 and III-6 to III-33, wherein $R^3$ and $R^a$ together with the atoms to which they are attached combine to form a 5- to 12-membered spiroheterocycle, which is optionally substituted with —$C_1$-$C_6$alkyl, —OH, —$NH_2$, heteroaryl, heterocyclyl, —$(CH_2)_n NH_2$, —$COOR^b$, —$CONHR^b$, —$CONH(CH_2)_n COOR^b$, —$NHCOOR^b$, —$CF_3$, —$CHF_2$, or —$CH_2F$.

Embodiment III-42

The compound of Embodiment III-41, wherein $R^3$ and $R^a$ together with the atoms to which they are attached combine to form a 10- to 12-membered spiroheterocycle, which is optionally substituted with —$C_1$-$C_6$alkyl, —OH, —$NH_2$, heteroaryl, heterocyclyl, —$(CH_2)_n NH_2$, —$COOR^b$, —$CONHR^b$, —$CONH(CH_2)_n COOR^b$, —$NHCOOR^b$, —$CF_3$, —$CHF_2$, or —$CH_2F$.

Embodiment III-43

The compound of any of Embodiments III-1 to III-2, III-7 to III-25, III-32 to III-34, and III-36 to III-38, wherein $R^a$ and $R^4$ together with the atom to which they are attached combine to form a monocyclic or polycyclic 3- to 12-membered cycloalkyl.

Embodiment III-44

The compound of any of Embodiments III-1 to III-2, III-7 to III-25, III-32 to III-34, and III-36 to III-38, wherein $R^a$ and $R^4$ together with the atom to which they are attached combine to form a monocyclic or polycyclic 3- to 12-membered heterocycle.

Embodiment III-45

A compound, or a pharmaceutically acceptable salt, prodrug, solvate, hydrate, tautomer, or isomer thereof, selected from the group consisting of:

1
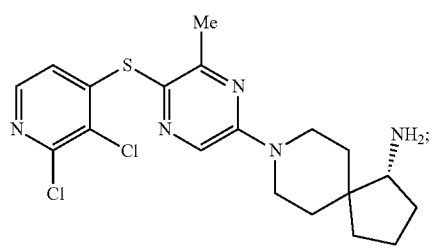

2
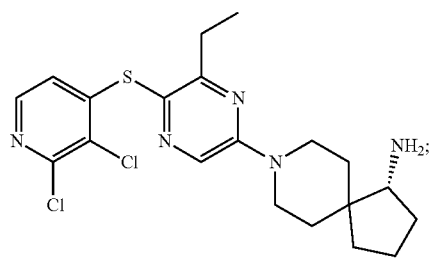

3
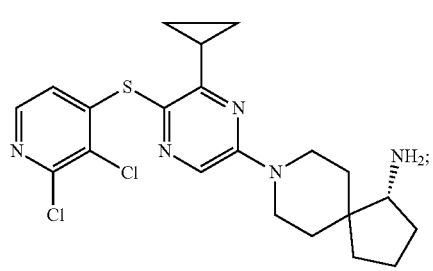

4
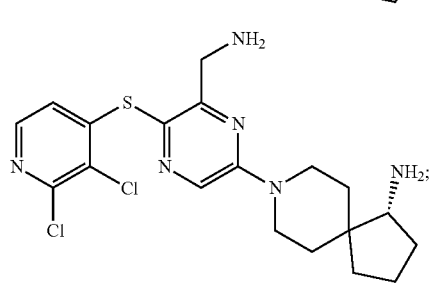

5
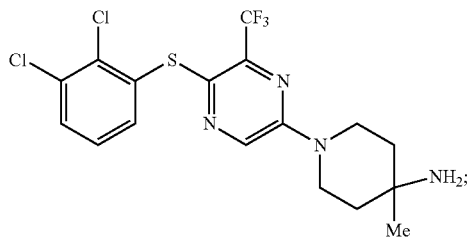

6
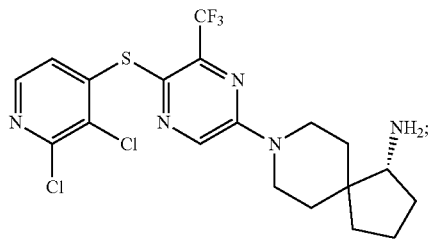

7
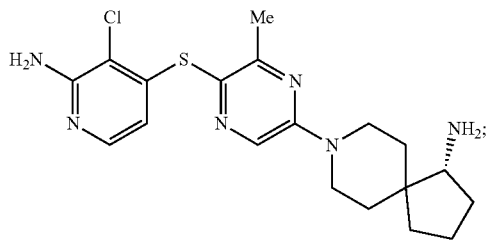

8
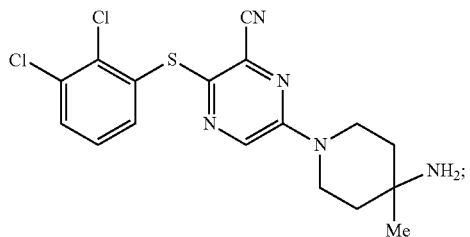

9
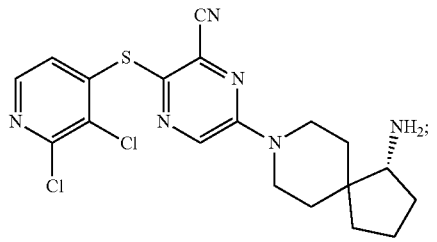

10
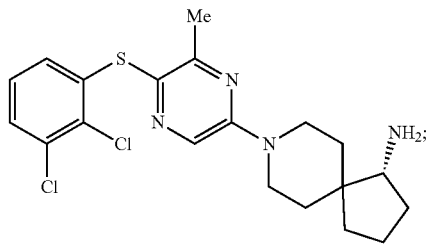

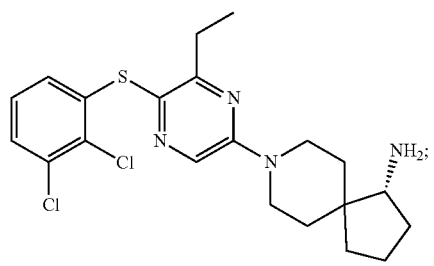 11
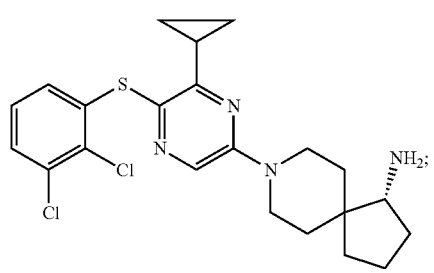 12
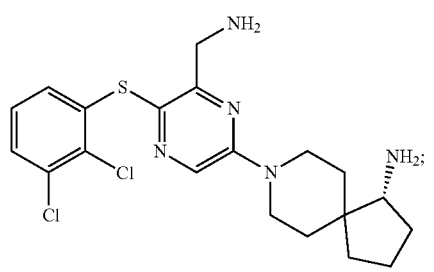 13
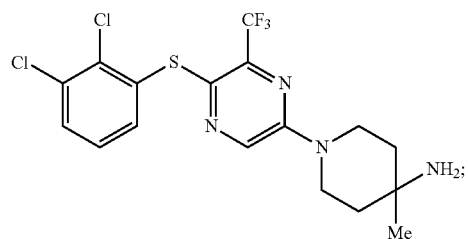 14
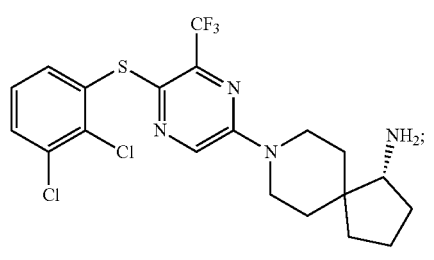 15
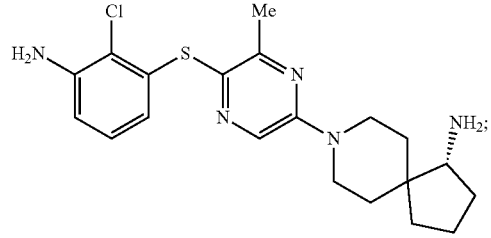 16
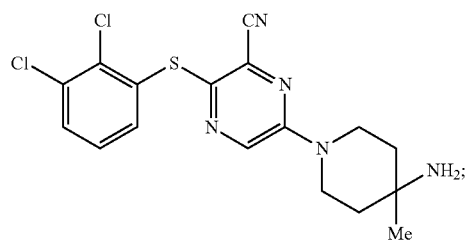 17
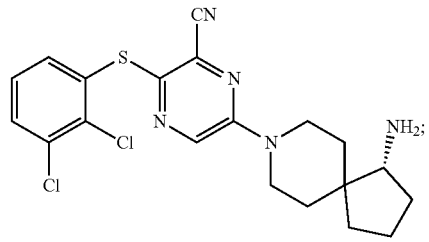 18
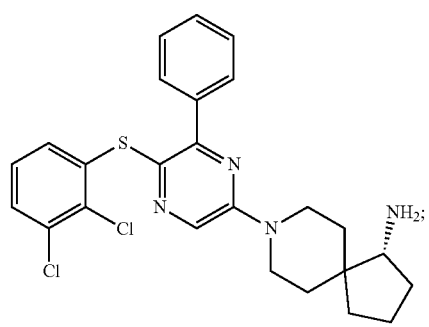 19
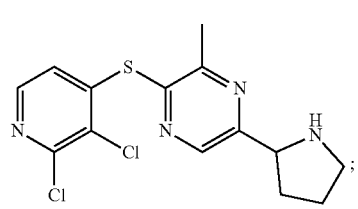 20
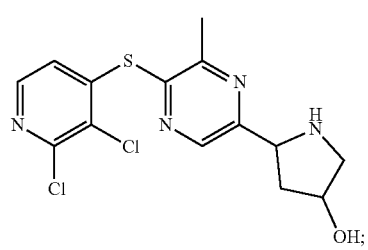 21
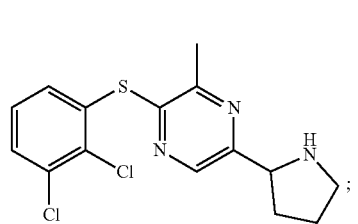 22

23
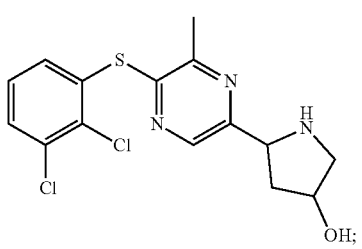
24
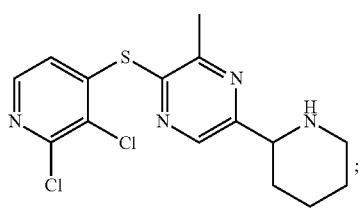
25
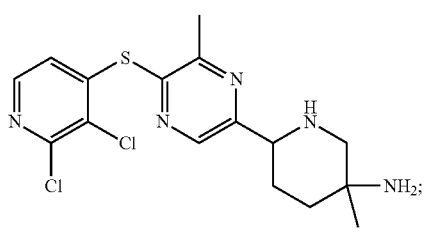
26
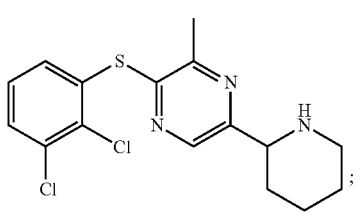
27
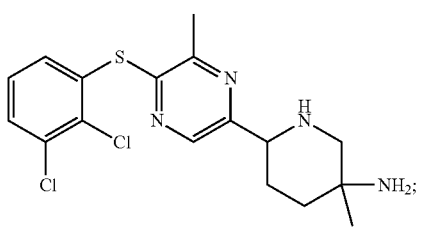
28
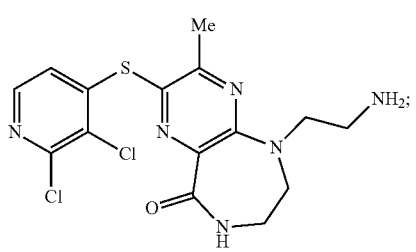
29
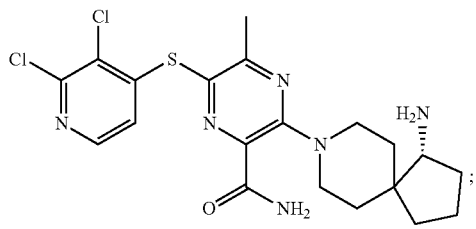
30
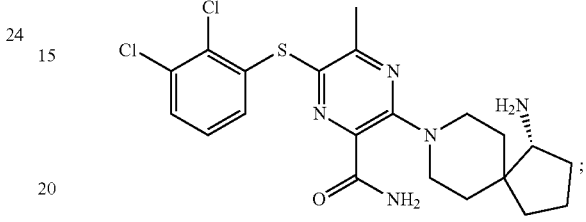
31
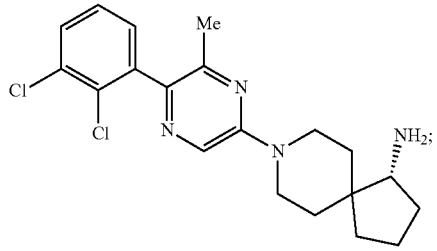
32
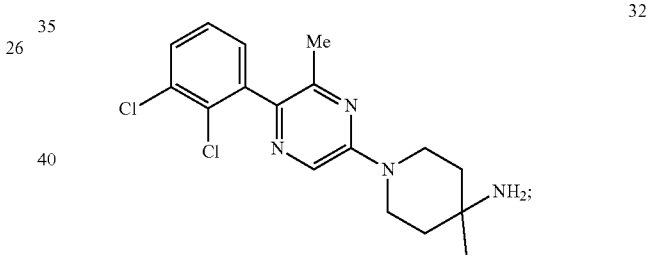
33
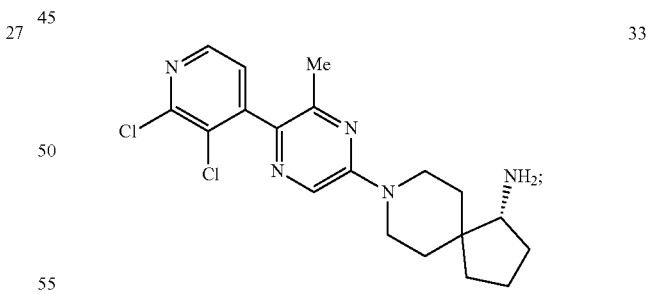
34
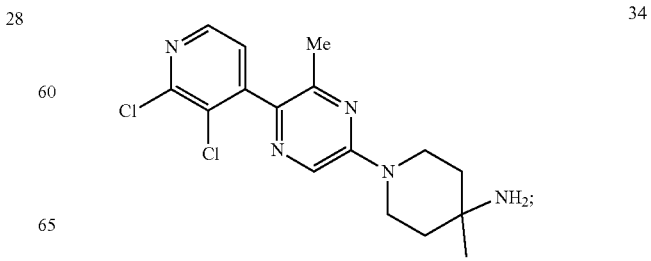

411
-continued
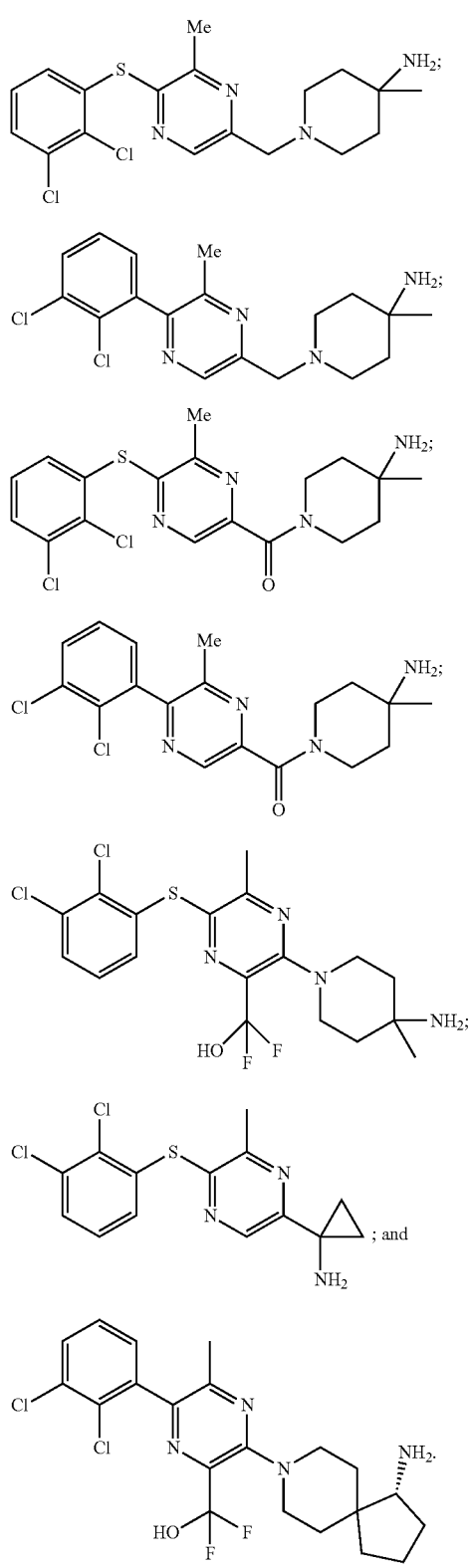
Embodiment III-46
A compound, or a pharmaceutically acceptable salt, prodrug, solvate, hydrate, tautomer, or isomer thereof, selected from the group consisting of:
412
| Compound # | Structure |
|---|---|
| A-1 | 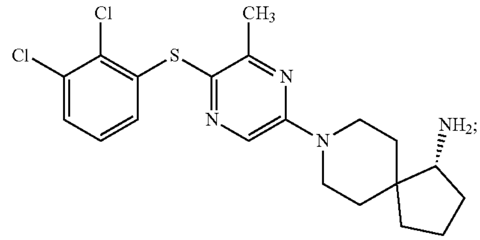 [SMILES: Cc1nc(N2CCC3(CCC[C@H]3N)CC2)cnc1Sc1cccc(Cl)c1Cl] |
| A-2 | 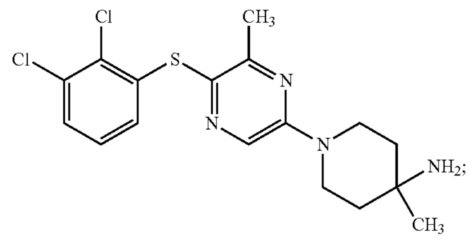 [SMILES: Cc1nc(N2CCC(C)(N)CC2)cnc1Sc1cccc(Cl)c1Cl] |
| A-3 | 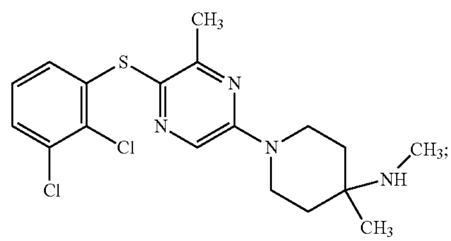 [SMILES: CNC1(C)CCN(c2cnc(Sc3cccc(Cl)c3Cl)c(C)n2)CC1] |
| A-4 | 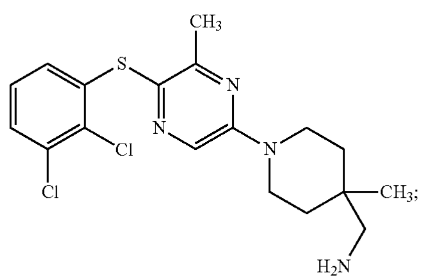 [SMILES: Cc1nc(N2CCC(C)(CN)CC2)cnc1Sc1cccc(Cl)c1Cl] |
| A-5 | 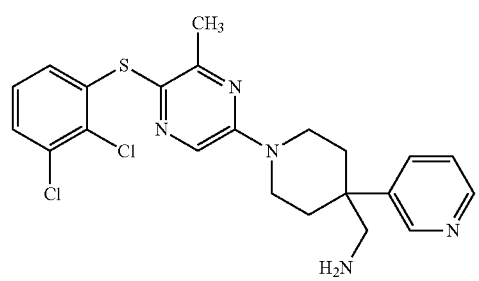 |
| A-6 | 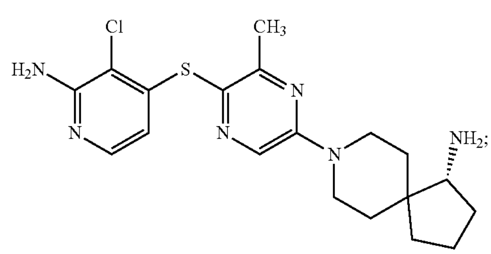 |

| Compound # | Structure |
|---|---|
| A-7 | 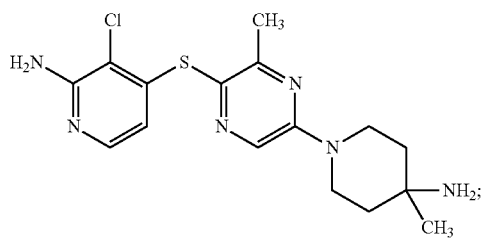 [SMILES: Cc1nc(N2CCC(C)(N)CC2)cnc1Sc1ccnc(N)c1Cl] |
| A-8 | 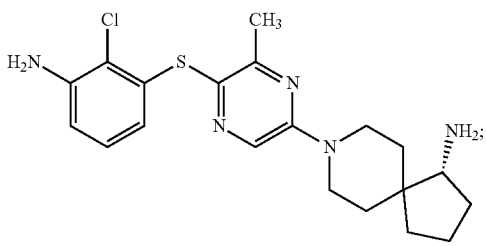 |
| A-9 | 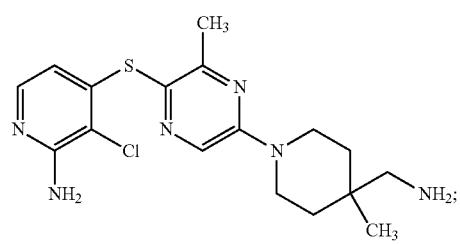 [SMILES: Cc1nc(N2CCC(C)(CN)CC2)cnc1Sc1ccnc(N)c1Cl] |
| A-10 | 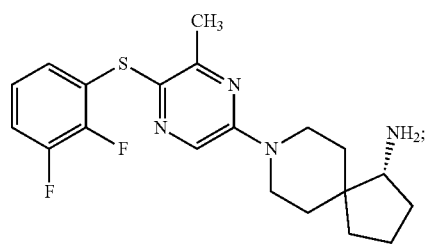 [SMILES: Cc1nc(N2CCC3(CCC[C@H]3N)CC2)cnc1Sc1cccc(F)c1F] |
| A-11 | 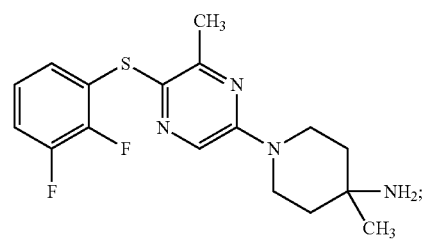 |
| A-12 | 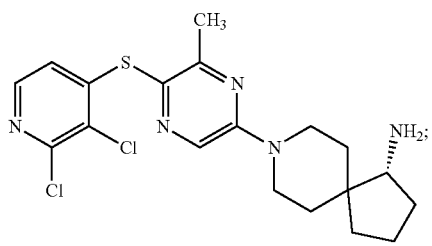 [SMILES: Cc1nc(N2CCC3(CCC[C@H]3N)CC2)cnc1Sc1ccnc(Cl)c1Cl] |
| A-13 | 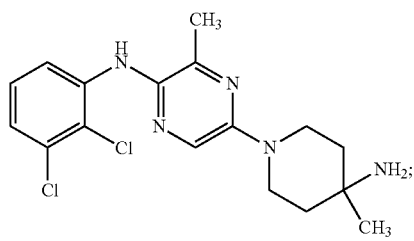 |
| A-14 | 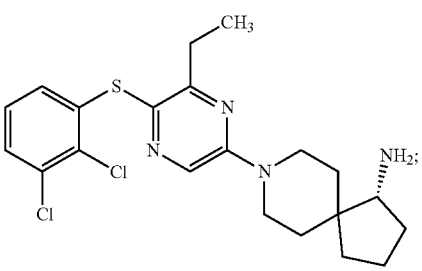 [SMILES: CCc1nc(N2CCC3(CCC[C@H]3N)CC2)cnc1Sc1cccc(Cl)c1Cl] |
| A-15 | 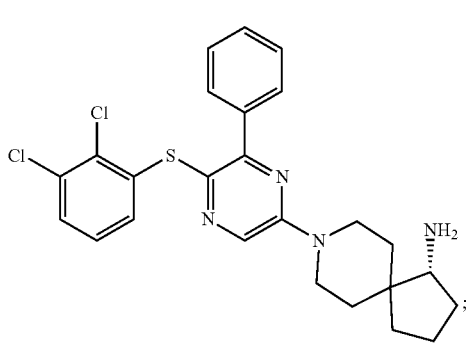 [SMILES: N[C@@H]1CCCC12CCN(c1cnc(Sc3cccc(Cl)c3Cl)c(-c3ccccc3)n1)CC2] |
| A-16 | 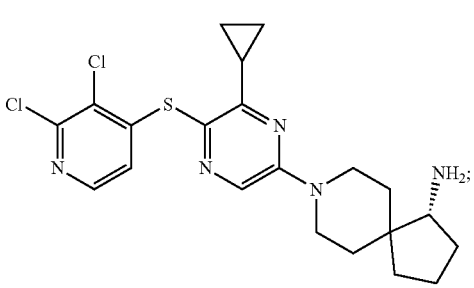 [SMILES: N[C@@H]1CCCC12CCN(c1cnc(Sc3ccnc(Cl)c3Cl)c(C3CC3)n1)CC2] |
| A-17 | 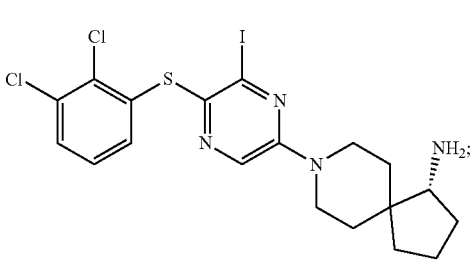 [SMILES: N[C@@H]1CCCC12CCN(c1cnc(Sc3cccc(Cl)c3Cl)c(I)n1)CC2] |

| Compound # | Structure |
|---|---|
| A-18 | 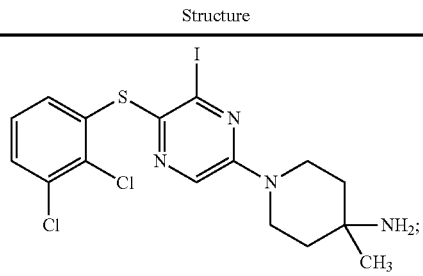 |
| A-19 | 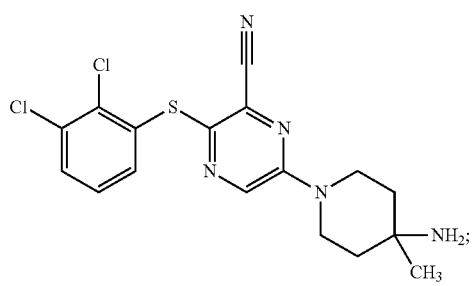 [SMILES: CC1(N)CCN(c2cnc(Sc3cccc(Cl)c3Cl)c(C#N)n2)CC1] |
| A-20 | 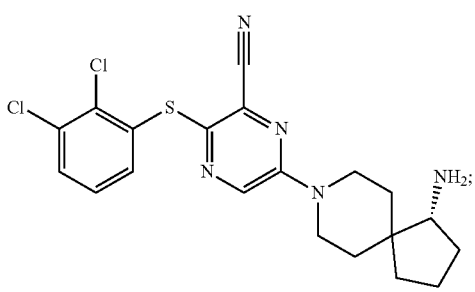 [SMILES: N#Cc1nc(N2CCC3(CCC[C@H]3N)CC2)cnc1Sc1cccc(Cl)c1Cl] |
| A-21 | 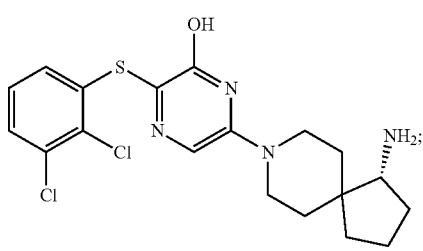 [SMILES: N[C@@H]1CCCC12CCN(c1cnc(Sc3cccc(Cl)c3Cl)c(O)n1)CC2] |
| A-22 | 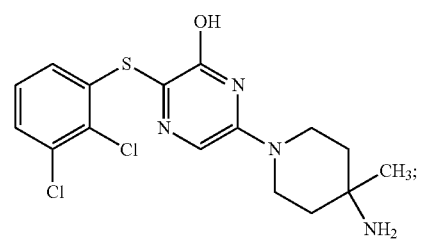 [SMILES: CC1(N)CCN(c2cnc(Sc3cccc(Cl)c3Cl)c(O)n2)CC1] |
| A-23 | 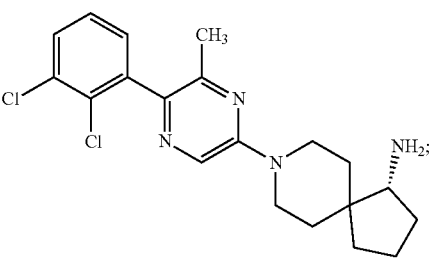 [SMILES: Cc1nc(N2CCC3(CCC[C@H]3N)CC2)cnc1-c1cccc(Cl)c1Cl] |
| Compound # | Structure |
|---|---|
| A-24 | 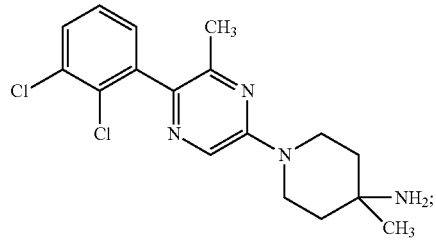 [SMILES: Cc1nc(N2CCC(C)(N)CC2)cnc1-c1cccc(Cl)c1Cl] |
| A-25 | 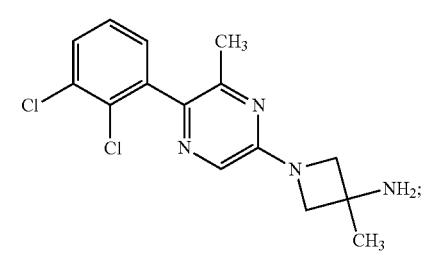 [SMILES: Cc1nc(N2CC(C)(N)C2)cnc1-c1cccc(Cl)c1Cl] |
| A-26 | 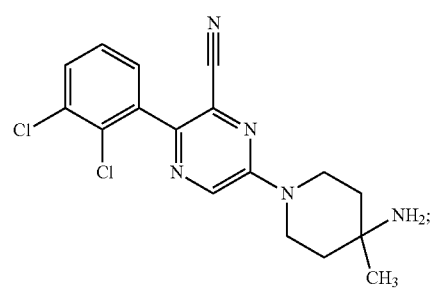 [SMILES: CC1(N)CCN(c2cnc(-c3cccc(Cl)c3Cl)c(C#N)n2)CC1] |
| A-27 | 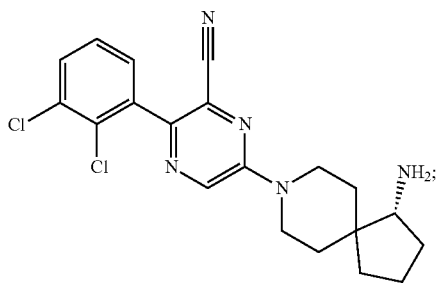 [SMILES: N#Cc1nc(N2CCC3(CCC[C@H]3N)CC2)cnc1-c1cccc(Cl)c1Cl] |
| A-28 | 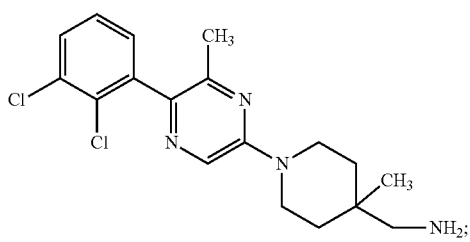 [SMILES: Cc1nc(N2CCC(C)(CN)CC2)cnc1-c1cccc(Cl)c1Cl] |

| Compound # | Structure |
|---|---|
| A-29 | 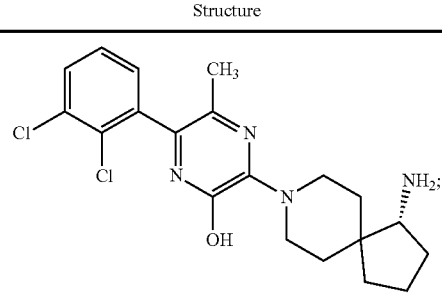 |
| A-30 | 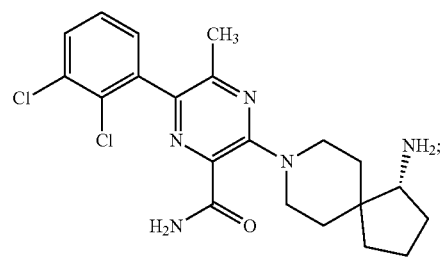 |
| A-31 | 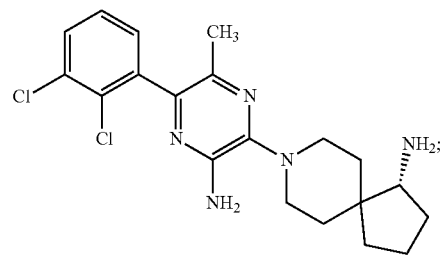 [SMILES: Cc1nc(N2CCC3(CCC[C@H]3N)CC2)c(O)nc1-c1cccc(Cl)c1Cl] |
| A-32 | 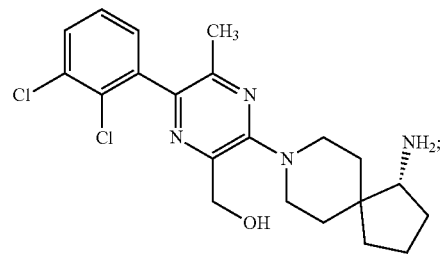 [SMILES: Cc1nc(N2CCC3(CCC[C@H]3N)CC2)c(CO)nc1-c1cccc(Cl)c1Cl] |
| A-33 | 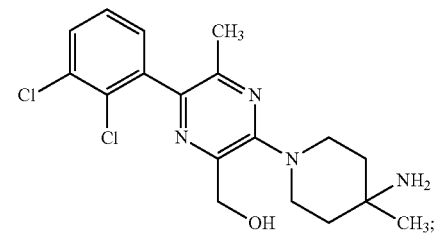 [SMILES: Cc1nc(N2CCC(C)(N)CC2)c(CO)nc1-c1cccc(Cl)c1Cl] |
| A-34 | 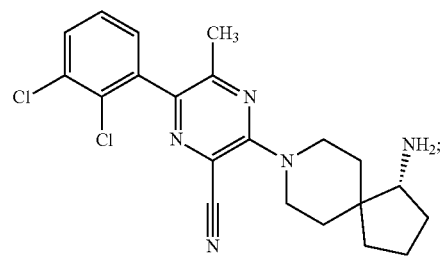 [SMILES: Cc1nc(N2CCC3(CCC[C@H]3N)CC2)c(C#N)nc1-c1cccc(Cl)c1Cl] |
| Compound # | Structure |
|---|---|
| A-35 | 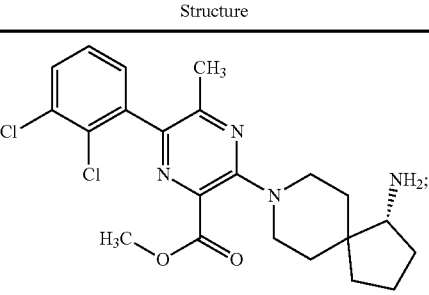 |
| A-36 | 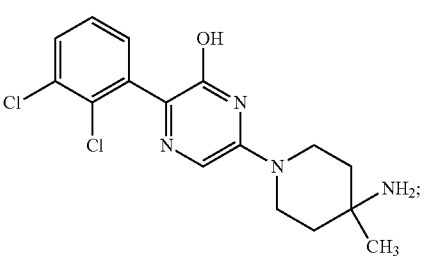 [SMILES: CC1(N)CCN(c2cnc(-c3cccc(Cl)c3Cl)c(O)n2)CC1] |
| A-37 | 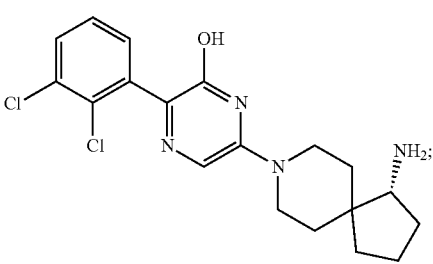 |
| A-38 | 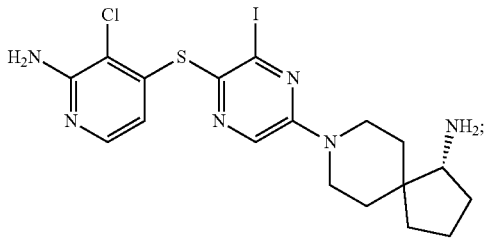 [SMILES: Nc1nccc(Sc2ncc(N3CCC4(CCC[C@H]4N)CC3)nc2I)c1Cl] |
| A-39 | 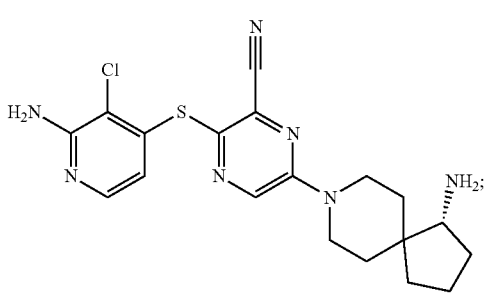 [SMILES: N#Cc1nc(N2CCC3(CCC[C@H]3N)CC2)cnc1Sc1ccnc(N)c1Cl] |

| Compound # | Structure |
|---|---|
| A-40 | 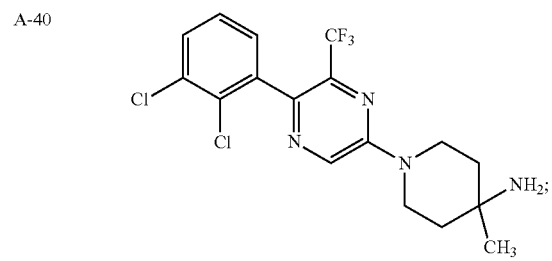 |
| A-41 | 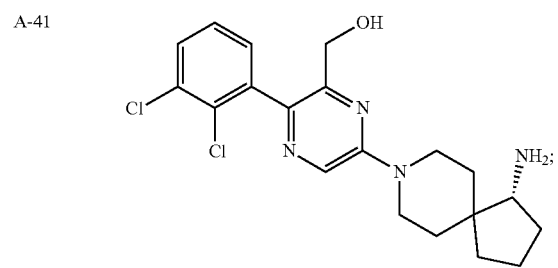 |
| A-42 | 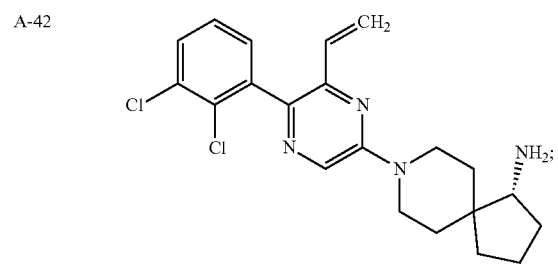 |
| A-43 | 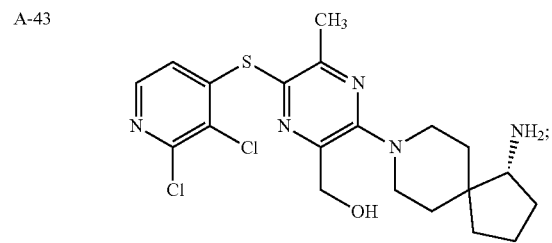 |
| A-44 | 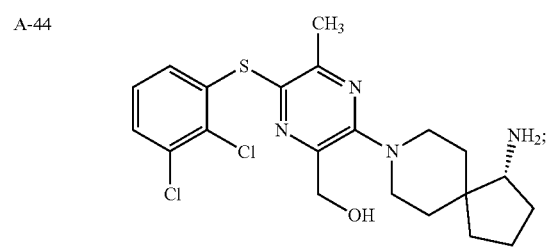 |
| A-45 | 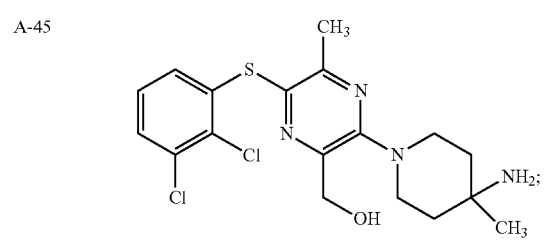 |
| Compound # | Structure |
|---|---|
| A-46 | 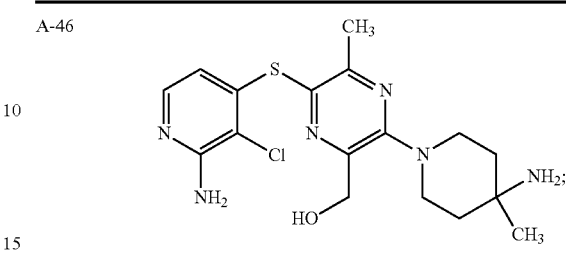 |
| A-47 | 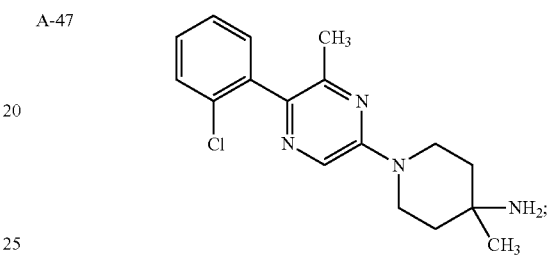 |
| A-48 | 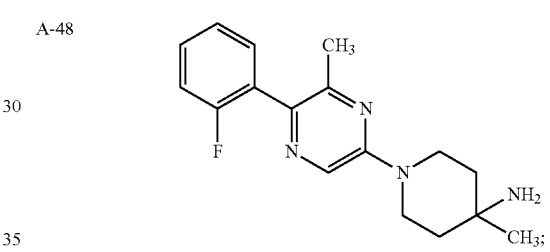 |
| A-49 | 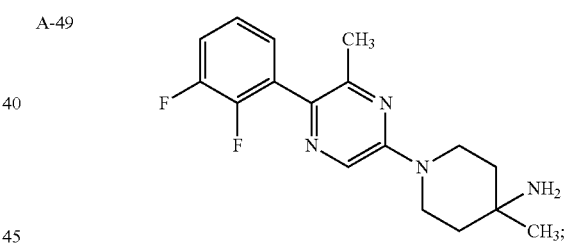 |
| A-50 | 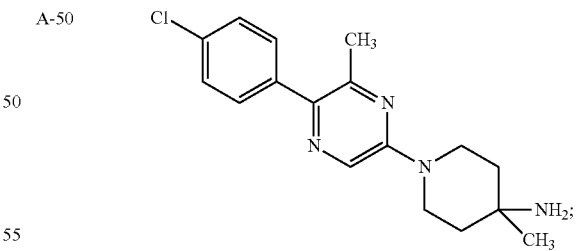 |
| A-51 | 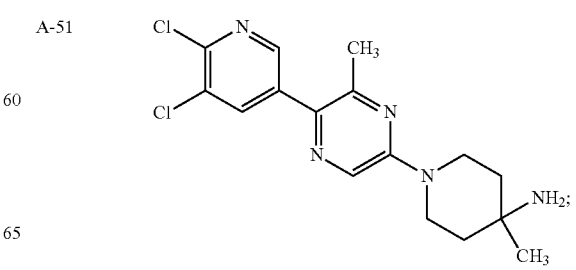 |

-continued

| Compound # | Structure |
|---|---|
| A-52 | (structure) |
| A-53 | (structure) |
| A-54 | (structure) |
| A-55 | (structure) |
| A-56 | (structure) |
| A-57 | (structure) |

-continued

| Compound # | Structure |
|---|---|
| A-58 | (structure) |
| A-59 | (structure) |
| A-60 | (structure) |
| A-61 | (structure) |
| A-62 | (structure) |
| A-63 | (structure) |
| A-64 | (structure) |

| Compound # | Structure |
|---|---|
| A-65 | (chemical structure) |
| A-66 | (chemical structure) |
| A-67 | (chemical structure) |
| A-68 | (chemical structure) |
| A-69 | (chemical structure) |
| A-70 | (chemical structure) |
| A-71 | (chemical structure) |

| Compound # | Structure |
|---|---|
| A-72 | (chemical structure) |
| A-73 | (chemical structure) |
| A-74 | (chemical structure) |
| A-75 | (chemical structure) |
| A-76 | (chemical structure) |
| A-77 | (chemical structure) |

| Compound # | Structure |
|---|---|
| A-78 | 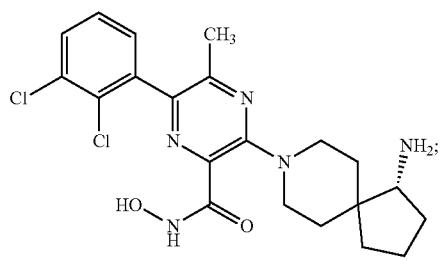 [SMILES: Cc1nc(N2CCC3(CCC[C@H]3N)CC2)c(C(=O)NO)nc1-c1cccc(Cl)c1Cl] |
| A-79 | 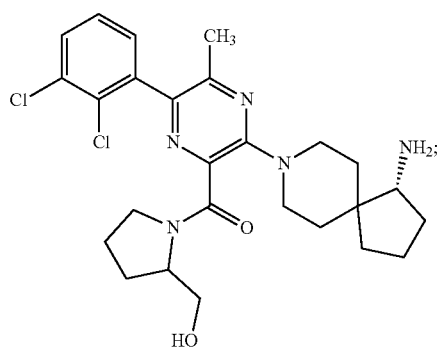 [SMILES: Cc1nc(N2CCC3(CCC[C@H]3N)CC2)c(C(=O)N2CCCC2CO)nc1-c1cccc(Cl)c1Cl] |
| A-80 | 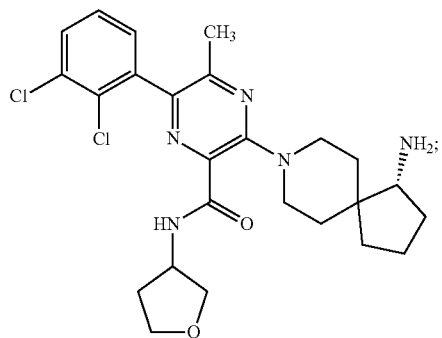 [SMILES: Cc1nc(N2CCC3(CCC[C@H]3N)CC2)c(C(=O)NC2CCOC2)nc1-c1cccc(Cl)c1Cl] |
| A-81 | 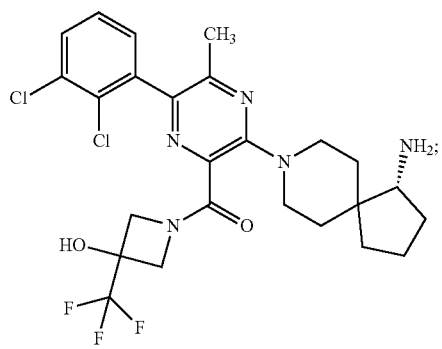 [SMILES: Cc1nc(N2CCC3(CCC[C@H]3N)CC2)c(C(=O)N2CC(O)(C(F)(F)F)C2)nc1-c1cccc(Cl)c1Cl] |
| A-82 | 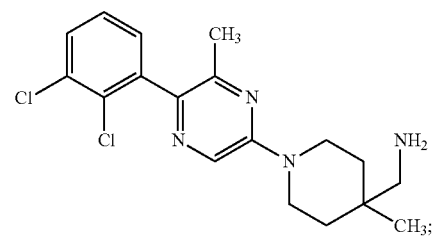 [SMILES: Cc1nc(N2CCC(C)(CN)CC2)cnc1-c1cccc(Cl)c1Cl] |
| Compound # | Structure |
|---|---|
| A-83 | 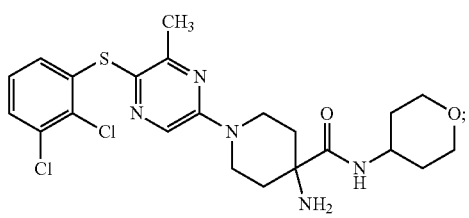 [SMILES: Cc1nc(N2CCC(N)(C(=O)NC3CCOCC3)CC2)cnc1Sc1cccc(Cl)c1Cl] |
| A-84 | 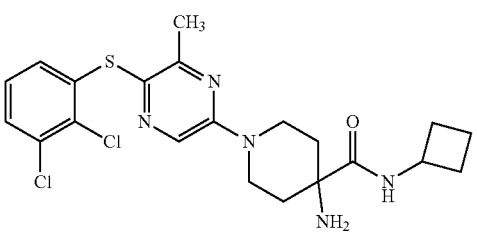 |
| A-85 | 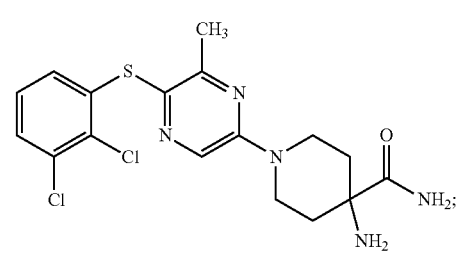 [SMILES: Cc1nc(N2CCC(N)(C(N)=O)CC2)cnc1Sc1cccc(Cl)c1Cl] |
| A-86 | 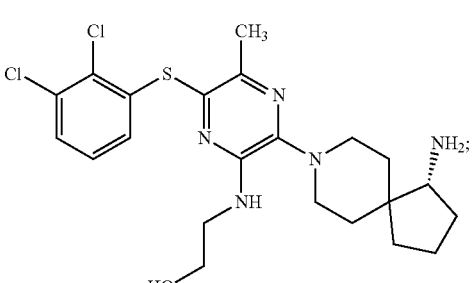 |
| A-87 | 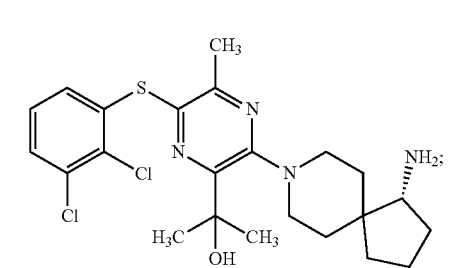 [SMILES: Cc1nc(N2CCC3(CCC[C@H]3N)CC2)c(C(C)(C)O)nc1Sc1cccc(Cl)c1Cl] |
| A-88 | 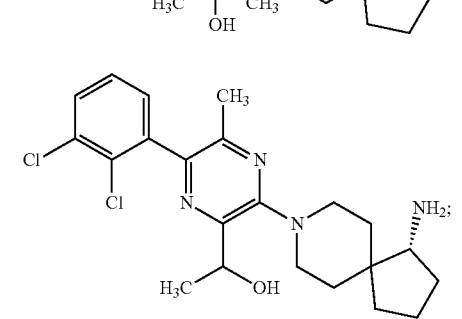 |

-continued
| Compound # | Structure |
|---|---|
| A-89 | 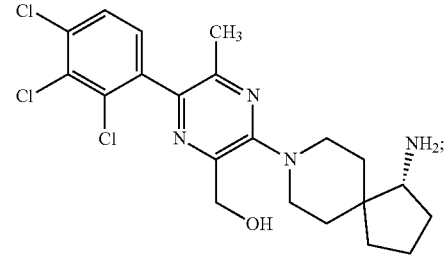 |
| A-90 | 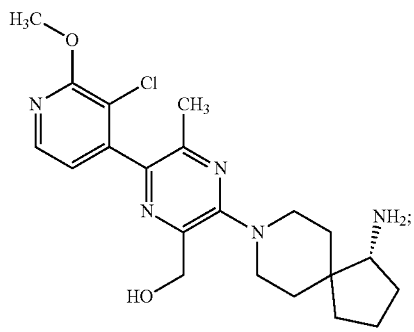 [SMILES: COc1nccc(-c2nc(CO)c(N3CCC4(CCC[C@H]4N)CC3)nc2C)c1Cl] |
| A-91 | 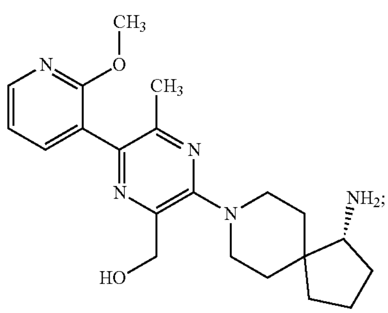 [SMILES: COc1ncccc1-c1nc(CO)c(N2CCC3(CCC[C@H]3N)CC2)nc1C] |
| A-92 | 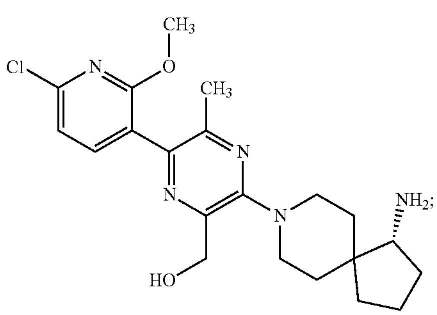 [SMILES: COc1nc(Cl)ccc1-c1nc(CO)c(N2CCC3(CCC[C@H]3N)CC2)nc1C] |
| A-93 | 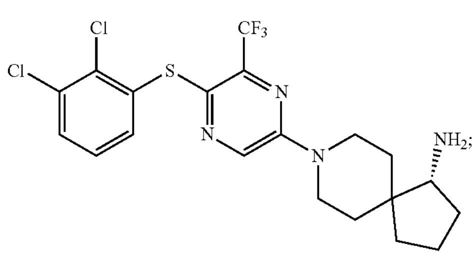 |
-continued
| Compound # | Structure |
|---|---|
| A-94 | 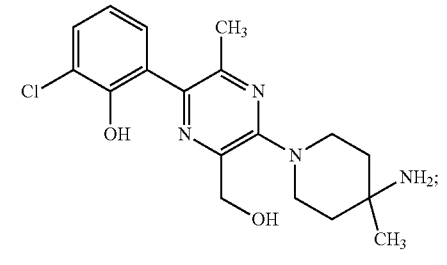 |
| A-95 | 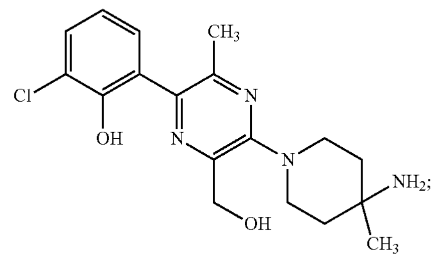 [SMILES: Cc1nc(N2CCC(C)(N)CC2)c(CO)nc1-c1cccc(Cl)c1O] |
| A-96 | 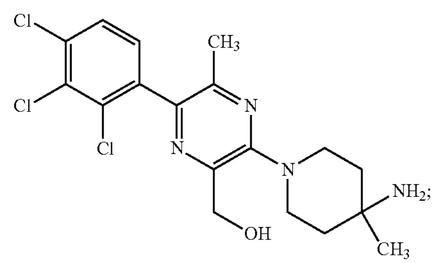 [SMILES: Cc1nc(N2CCC(C)(N)CC2)c(CO)nc1-c1ccc(Cl)c(Cl)c1Cl] |
| A-97 | 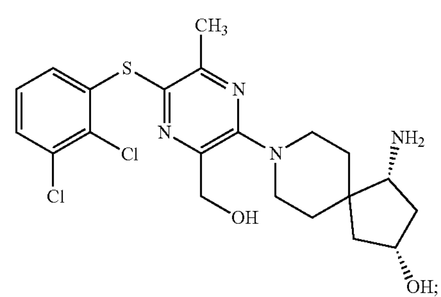 [SMILES: Cc1nc(N2CCC3(CC2)C[C@@H](O)C[C@H]3N)c(CO)nc1Sc1cccc(Cl)c1Cl] |
| A-98 | 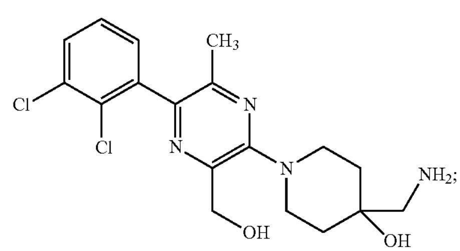 [SMILES: Cc1nc(N2CCC(O)(CN)CC2)c(CO)nc1-c1cccc(Cl)c1Cl] |

| Compound # | Structure |
|---|---|
| A-99 | 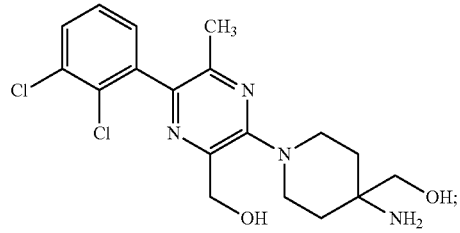 [SMILES: Cc1nc(N2CCC(N)(CO)CC2)c(CO)nc1-c1cccc(Cl)c1Cl] |
| A-100 | 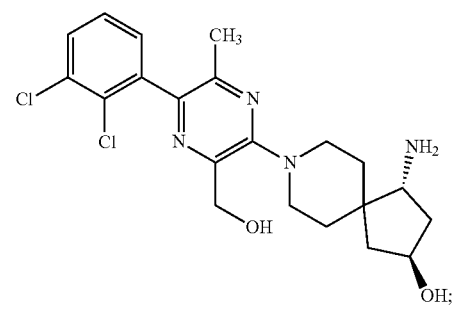 [SMILES: Cc1nc(N2CCC3(CC2)C[C@H](O)C[C@H]3N)c(CO)nc1-c1cccc(Cl)c1Cl] |
| A-101 | 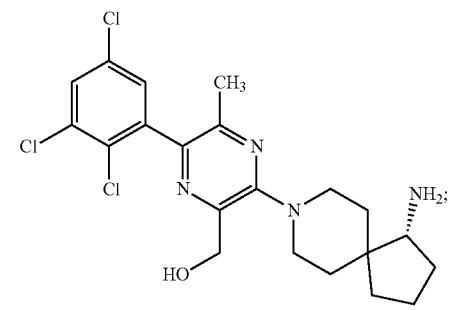 [SMILES: Cc1nc(N2CCC3(CCC[C@H]3N)CC2)c(CO)nc1-c1cc(Cl)cc(Cl)c1Cl] |
| A-102 | 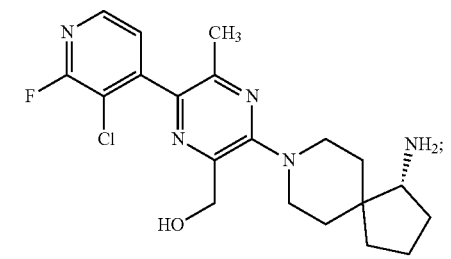 [SMILES: Cc1nc(N2CCC3(CCC[C@H]3N)CC2)c(CO)nc1-c1ccnc(F)c1Cl] |
| A-103 | 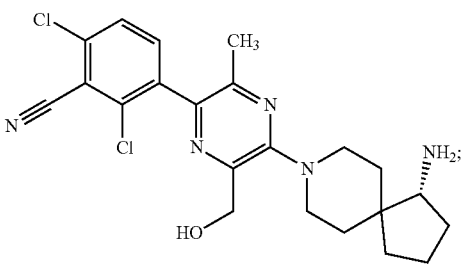 [SMILES: Cc1nc(N2CCC3(CCC[C@H]3N)CC2)c(CO)nc1-c1ccc(Cl)c(C#N)c1Cl] |
| Compound # | Structure |
|---|---|
| A-104 | 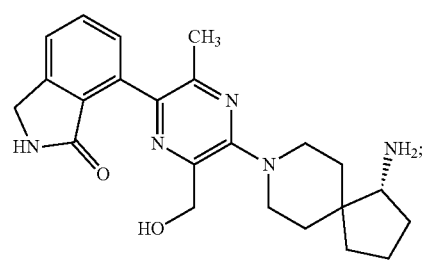 [SMILES: Cc1nc(N2CCC3(CCC[C@H]3N)CC2)c(CO)nc1-c1cccc2c1C(=O)NC2] |
| A-105 | 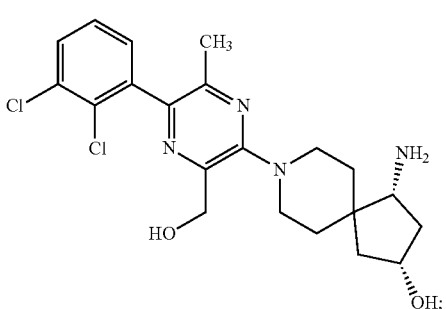 |
| A-106 | 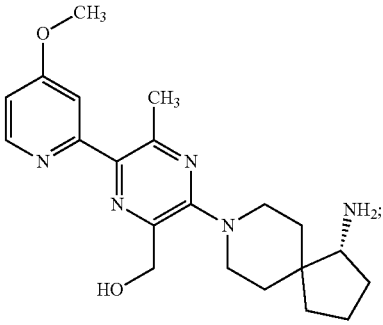 [SMILES: COc1ccnc(-c2nc(CO)c(N3CCC4(CCC[C@H]4N)CC3)nc2C)c1] |
| A-107 | 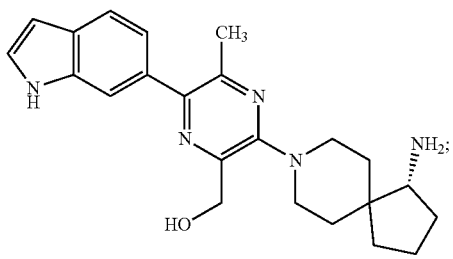 [SMILES: Cc1nc(N2CCC3(CCC[C@H]3N)CC2)c(CO)nc1-c1ccc2cc[nH]c2c1] |
| A-108 | 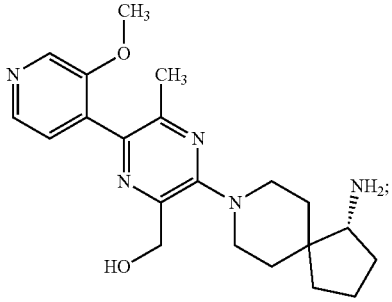 [SMILES: COc1cnccc1-c1nc(CO)c(N2CCC3(CCC[C@H]3N)CC2)nc1C] |

| Compound # | Structure |
|---|---|
| A-109 | 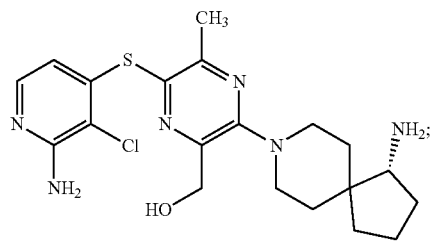 [SMILES: Cc1nc(N2CCC3(CCC[C@H]3N)CC2)c(CO)nc1Sc1ccnc(N)c1Cl] |
| A-110 | 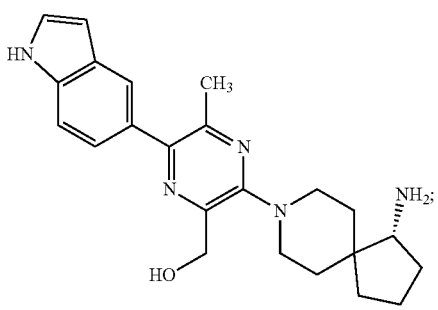 [SMILES: Cc1nc(N2CCC3(CCC[C@H]3N)CC2)c(CO)nc1-c1ccc2[nH]ccc2c1] |
| A-111 | 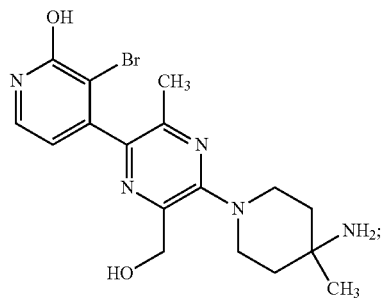 [SMILES: Cc1nc(N2CCC(C)(N)CC2)c(CO)nc1-c1ccnc(O)c1Br] |
| A-112 | 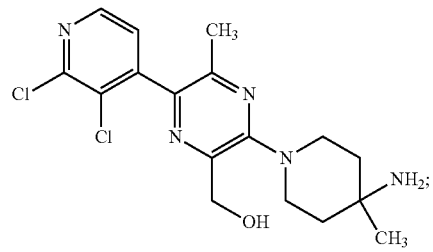 [SMILES: Cc1nc(N2CCC(C)(N)CC2)c(CO)nc1-c1ccnc(Cl)c1Cl] |
| A-113 | 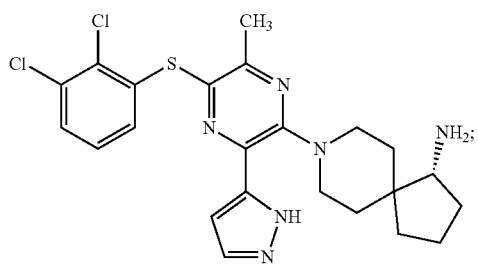 [SMILES: Cc1nc(N2CCC3(CCC[C@H]3N)CC2)c(-c2ccn[nH]2)nc1Sc1cccc(Cl)c1Cl] |
| Compound # | Structure |
|---|---|
| A-114 | 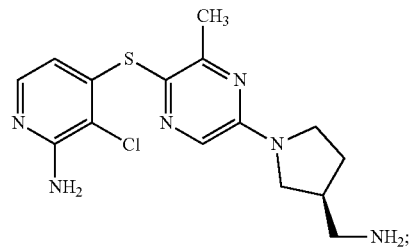 [SMILES: Cc1nc(N2CC[C@@H](CN)C2)cnc1Sc1ccnc(N)c1Cl] |
| A-115 | 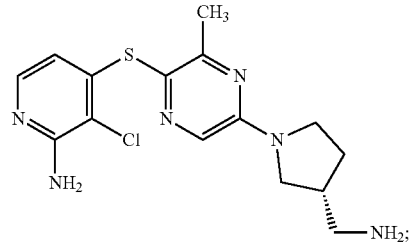 [SMILES: Cc1nc(N2CC[C@H](CN)C2)cnc1Sc1ccnc(N)c1Cl] |
| A-116 | 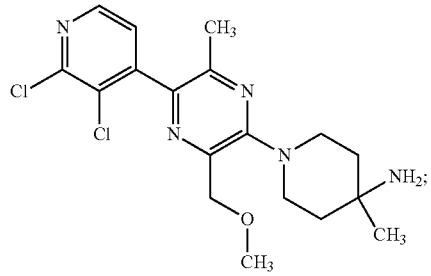 [SMILES: COCc1nc(-c2ccnc(Cl)c2Cl)c(C)nc1N1CCC(C)(N)CC1] |
| A-117 | 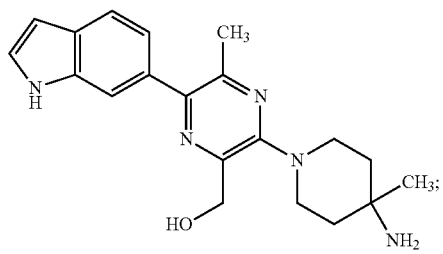 [SMILES: Cc1nc(N2CCC(C)(N)CC2)c(CO)nc1-c1ccc2cc[nH]c2c1] |
| A-118 | 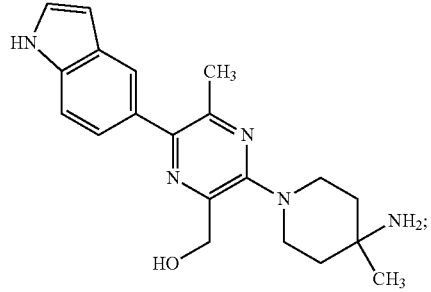 [SMILES: Cc1nc(N2CCC(C)(N)CC2)c(CO)nc1-c1ccc2[nH]ccc2c1] |

| Compound # | Structure |
|---|---|
| A-119 | |
| A-120 | |
| A-121 | |
| A-122 | |
| A-123 | |
| A-124 | 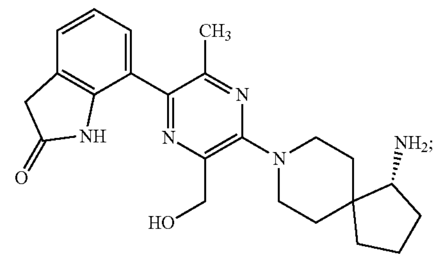 [SMILES: Cc1nc(N2CCC3(CCC[C@H]3N)CC2)c(CO)nc1-c1cccc2c1NC(=O)C2] |
| A-125 | 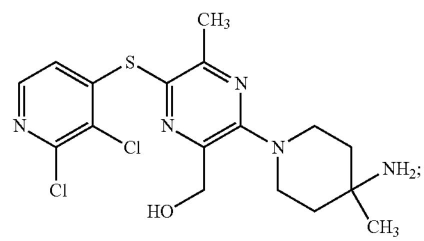 [SMILES: Cc1nc(N2CCC(C)(N)CC2)c(CO)nc1Sc1ccnc(Cl)c1Cl] |
| A-126 | 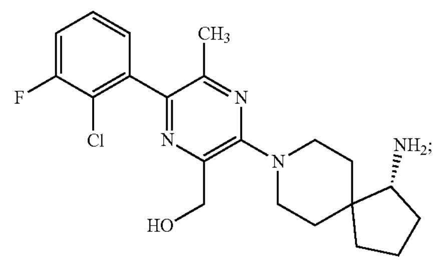 [SMILES: Cc1nc(N2CCC3(CCC[C@H]3N)CC2)c(CO)nc1-c1cccc(F)c1Cl] |
| A-127 | 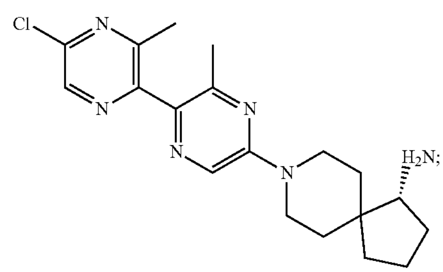 [SMILES: Cc1nc(Cl)cnc1-c1ncc(N2CCC3(CCC[C@H]3N)CC2)nc1C] |
| A-128 | 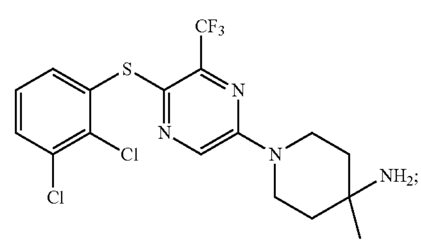 [SMILES: CC1(N)CCN(c2cnc(Sc3cccc(Cl)c3Cl)c(C(F)(F)F)n2)CC1] |
| A-129 | 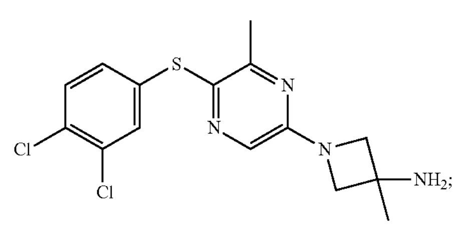 [SMILES: Cc1nc(N2CC(C)(N)C2)cnc1Sc1ccc(Cl)c(Cl)c1] |

| Compound # | Structure |
|---|---|
| A-130 | 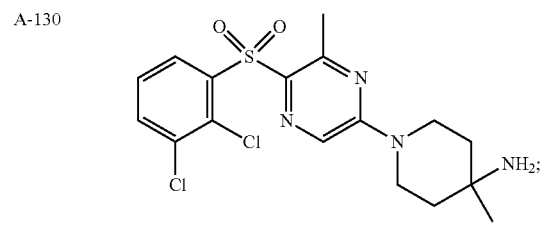 |
| A-131 | 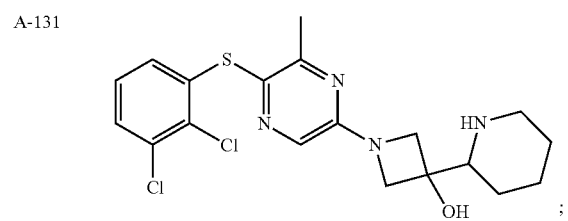 |
| A-132 | 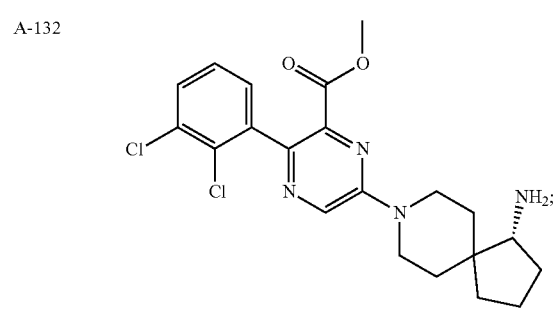 |
| A-133 | 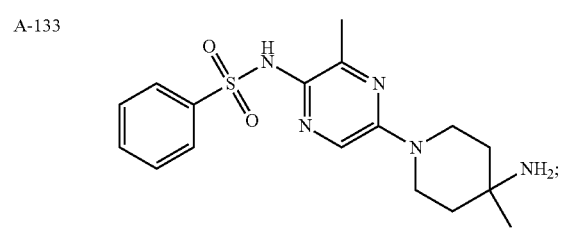 |
| A-134 | 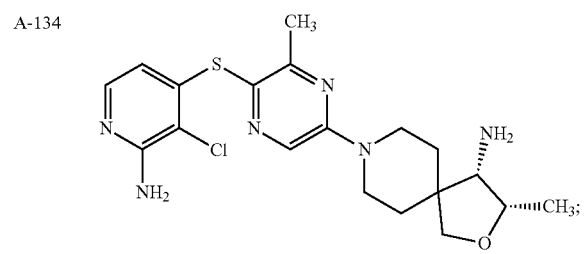 |
| A-135 | 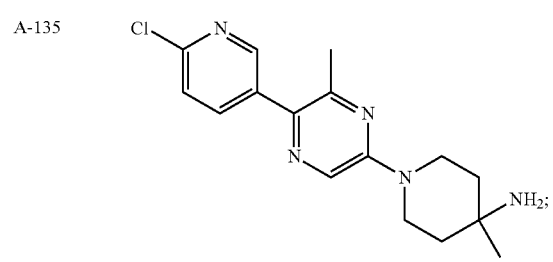 |
| A-136 | 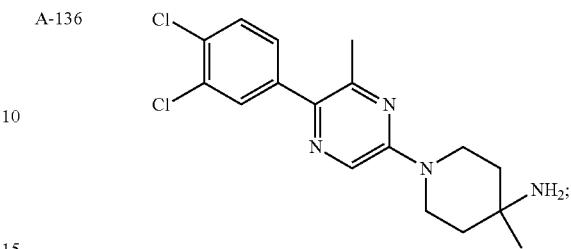 |
| A-137 | 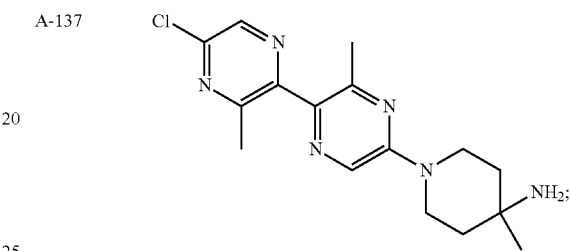 |
| A-138 | 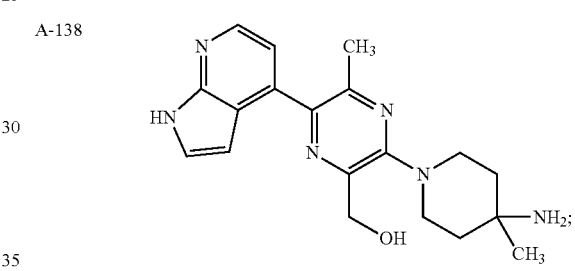 |
| A-139 | 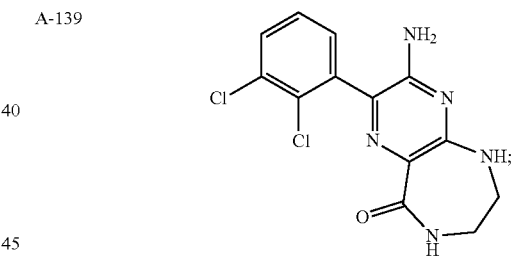 |
| A-140 | 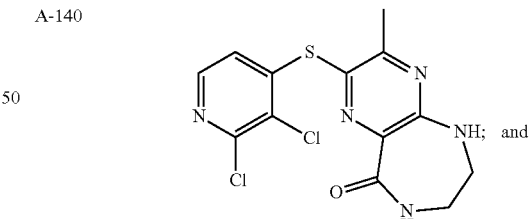 and |
| A-141 | 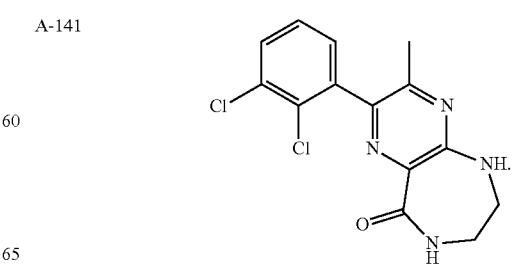 |

Embodiment III-47
A compound, or a pharmaceutically acceptable salt, prodrug, solvate, hydrate, tautomer, or isomer thereof, selected from the group consisting of:
| Compound # | Structure |
|---|---|
| A-142 | 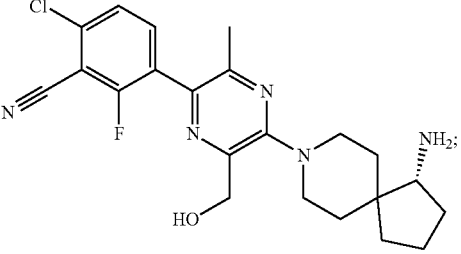 |
| A-143 | 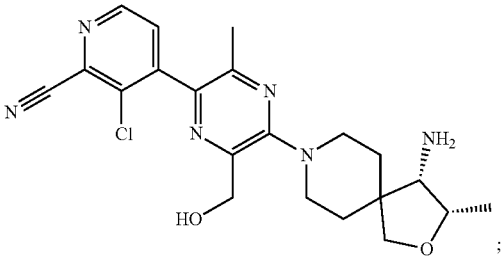 [SMILES: Cc1nc(N2CCC3(CC2)CO[C@@H](C)[C@H]3N)c(CO)nc1-c1ccnc(C#N)c1Cl] |
| A-144 | 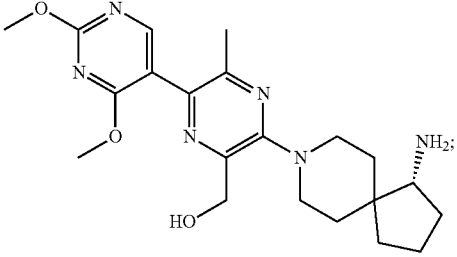 [SMILES: COc1ncc(-c2nc(CO)c(N3CCC4(CCC[C@H]4N)CC3)nc2C)c(OC)n1] |
| A-145 | 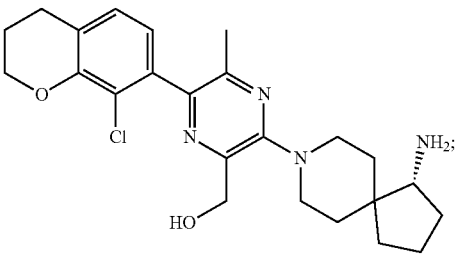 [SMILES: Cc1nc(N2CCC3(CCC[C@H]3N)CC2)c(CO)nc1-c1ccc2c(c1Cl)OCCC2] |
| A-146 | 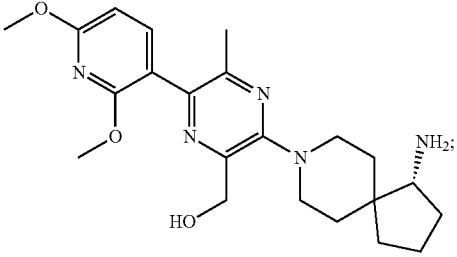 |

-continued
| Compound # | Structure |
|---|---|
| A-147 | 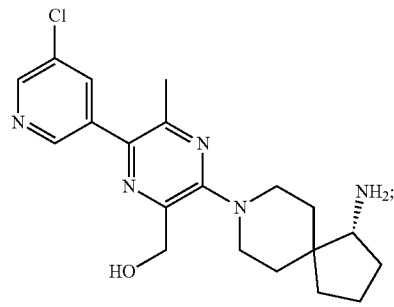 [SMILES: Cc1nc(N2CCC3(CCC[C@H]3N)CC2)c(CO)nc1-c1cncc(Cl)c1] |
| A-148 | 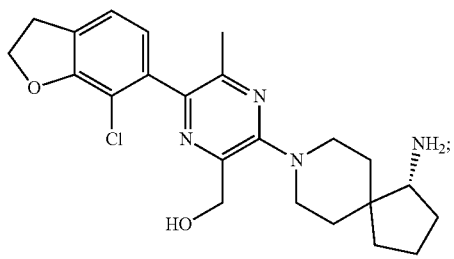 [SMILES: Cc1nc(N2CCC3(CCC[C@H]3N)CC2)c(CO)nc1-c1ccc2c(c1Cl)OCC2] |
| A-149 | 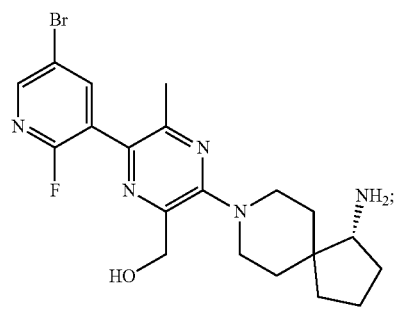 [SMILES: Cc1nc(N2CCC3(CCC[C@H]3N)CC2)c(CO)nc1-c1cc(Br)cnc1F] |
| A-150 | 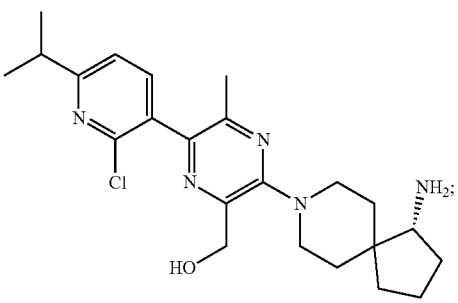 [SMILES: Cc1nc(N2CCC3(CCC[C@H]3N)CC2)c(CO)nc1-c1ccc(C(C)C)nc1Cl] |
| A-151 | 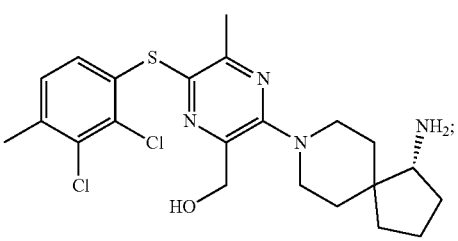 [SMILES: Cc1ccc(Sc2nc(CO)c(N3CCC4(CCC[C@H]4N)CC3)nc2C)c(Cl)c1Cl] |

-continued
| Compound # | Structure |
|---|---|
| A-152 | 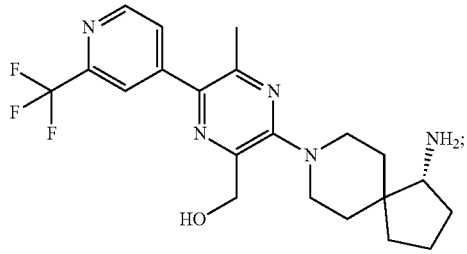 [SMILES: Cc1nc(N2CCC3(CCC[C@H]3N)CC2)c(CO)nc1-c1ccnc(C(F)(F)F)c1] |
| A-153 | 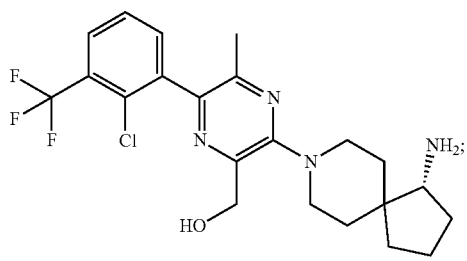 [SMILES: Cc1nc(N2CCC3(CCC[C@H]3N)CC2)c(CO)nc1-c1cccc(C(F)(F)F)c1Cl] |
| A-154 | 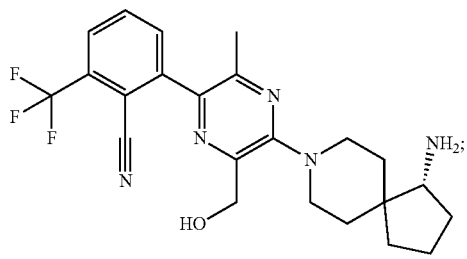 [SMILES: Cc1nc(N2CCC3(CCC[C@H]3N)CC2)c(CO)nc1-c1cccc(C(F)(F)F)c1C#N] |
| A-155 | 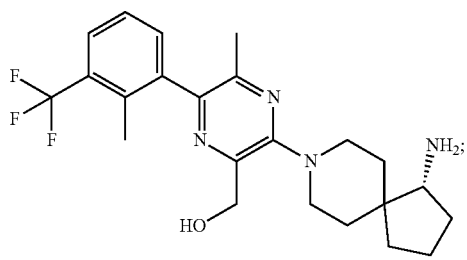 [SMILES: Cc1nc(N2CCC3(CCC[C@H]3N)CC2)c(CO)nc1-c1cccc(C(F)(F)F)c1C] |
| A-156 | 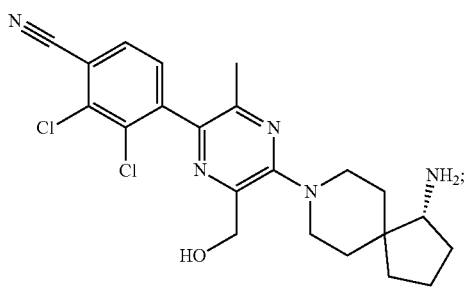 [SMILES: Cc1nc(N2CCC3(CCC[C@H]3N)CC2)c(CO)nc1-c1ccc(C#N)c(Cl)c1Cl] |

-continued

| Compound # | Structure |
|---|---|
| A-157 | 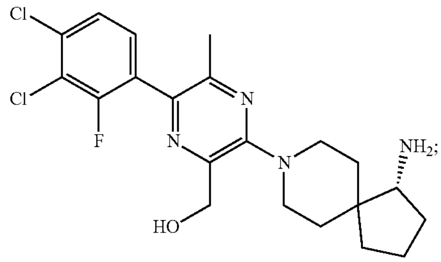 [SMILES: Cc1nc(N2CCC3(CCC[C@H]3N)CC2)c(CO)nc1-c1ccc(Cl)c(Cl)c1F] |
| A-158 | 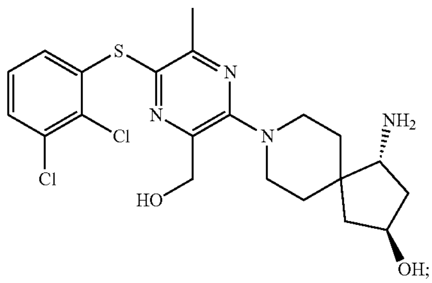 [SMILES: Cc1nc(N2CCC3(CC2)C[C@H](O)C[C@H]3N)c(CO)nc1Sc1cccc(Cl)c1Cl] |
| A-159 | 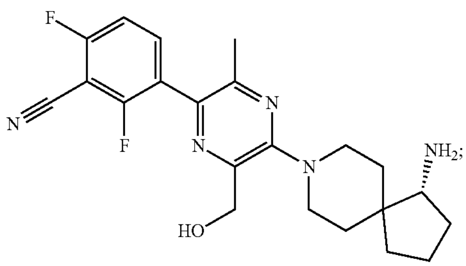 |
| A-160 | 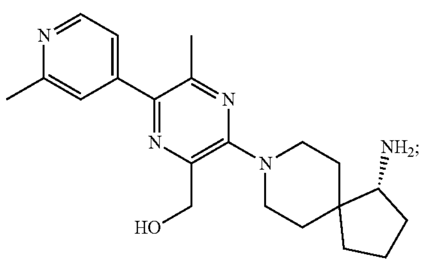 [SMILES: Cc1cc(-c2nc(CO)c(N3CCC4(CCC[C@H]4N)CC3)nc2C)ccn1] |
| A-161 | 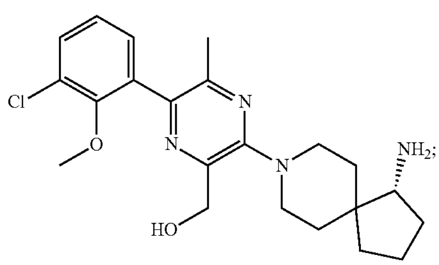 [SMILES: COc1c(Cl)cccc1-c1nc(CO)c(N2CCC3(CCC[C@H]3N)CC2)nc1C] |
| A-162 | 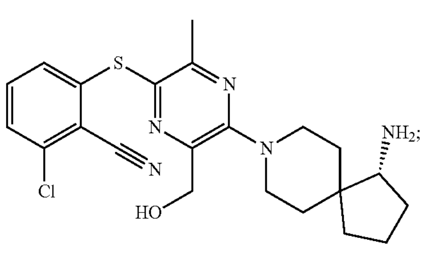 [SMILES: Cc1nc(N2CCC3(CCC[C@H]3N)CC2)c(CO)nc1Sc1cccc(Cl)c1C#N] |

-continued
| Compound # | Structure |
|---|---|
| A-163 | 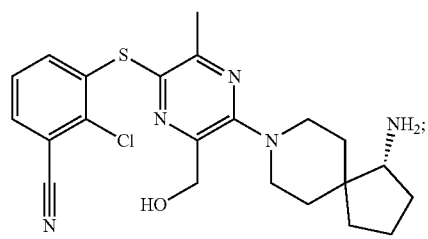 [SMILES: Cc1nc(N2CCC3(CCC[C@H]3N)CC2)c(CO)nc1Sc1cccc(C#N)c1Cl] |
| A-164 | 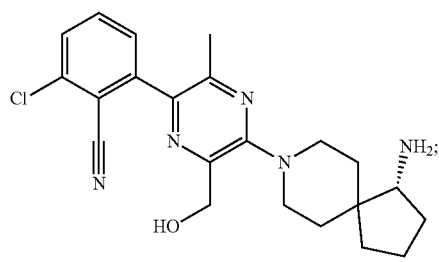 [SMILES: Cc1nc(N2CCC3(CCC[C@H]3N)CC2)c(CO)nc1-c1cccc(Cl)c1C#N] |
| A-165 | 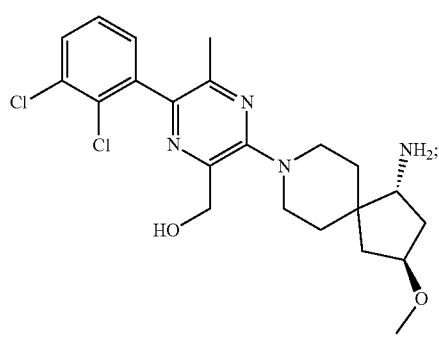 [SMILES: CO[C@@H]1C[C@@H](N)C2(CCN(c3nc(C)c(-c4cccc(Cl)c4Cl)nc3CO)CC2)C1] |
| A-166 | 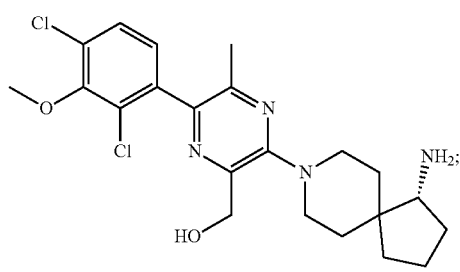 [SMILES: COc1c(Cl)ccc(-c2nc(CO)c(N3CCC4(CCC[C@H]4N)CC3)nc2C)c1Cl] |
| A-167 | 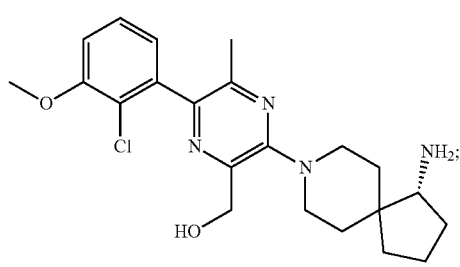 [SMILES: COc1cccc(-c2nc(CO)c(N3CCC4(CCC[C@H]4N)CC3)nc2C)c1Cl] |

-continued
| Compound # | Structure |
|---|---|
| A-168 | 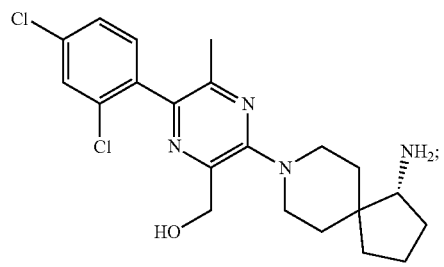 [SMILES: Cc1nc(N2CCC3(CCC[C@H]3N)CC2)c(CO)nc1-c1ccc(Cl)cc1Cl] |
| A-169 | 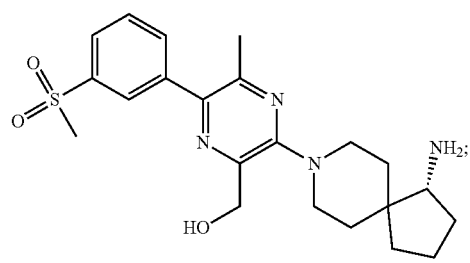 [SMILES: Cc1nc(N2CCC3(CCC[C@H]3N)CC2)c(CO)nc1-c1cccc(S(C)(=O)=O)c1] |
| A-170 | 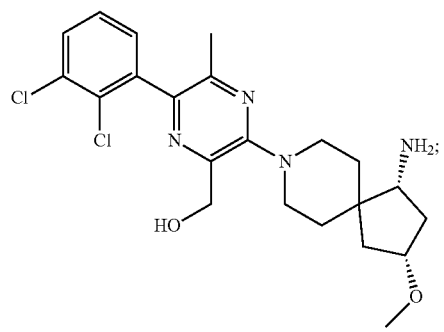 [SMILES: CO[C@H]1C[C@@H](N)C2(CCN(c3nc(C)c(-c4cccc(Cl)c4Cl)nc3CO)CC2)C1] |
| A-171 | 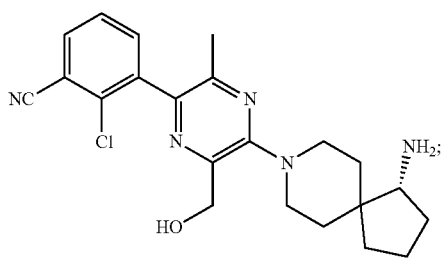 [SMILES: Cc1nc(N2CCC3(CCC[C@H]3N)CC2)c(CO)nc1-c1cccc(C#N)c1Cl] |
| A-172 | 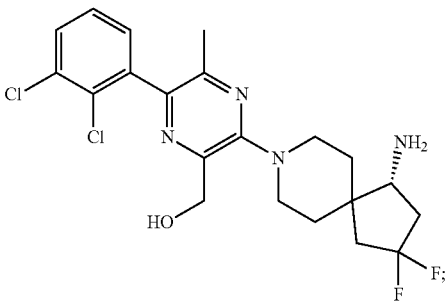 [SMILES: Cc1nc(N2CCC3(CC2)CC(F)(F)C[C@H]3N)c(CO)nc1-c1cccc(Cl)c1Cl] |

-continued
| Compound # | Structure |
|---|---|
| A-173 | 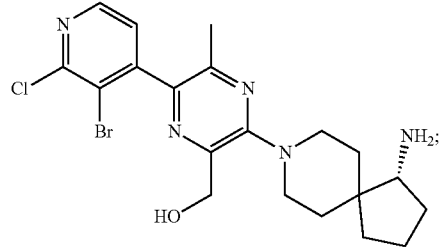 [SMILES: Cc1nc(N2CCC3(CCC[C@H]3N)CC2)c(CO)nc1-c1ccnc(Cl)c1Br] |
| A-174 | 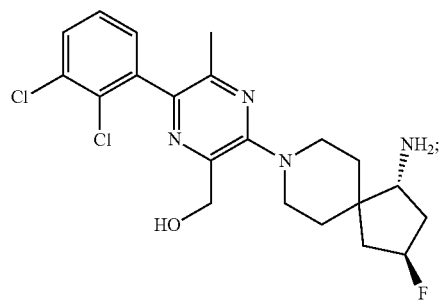 [SMILES: Cc1nc(N2CCC3(CC2)C[C@H](F)C[C@H]3N)c(CO)nc1-c1cccc(Cl)c1Cl] |
| A-175 | 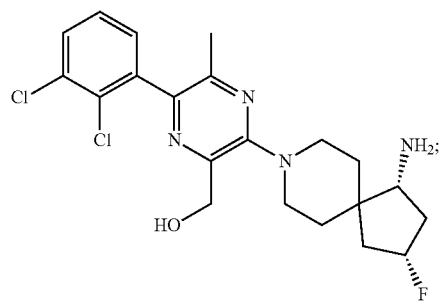 [SMILES: Cc1nc(N2CCC3(CC2)C[C@@H](F)C[C@H]3N)c(CO)nc1-c1cccc(Cl)c1Cl] |
| A-176 | 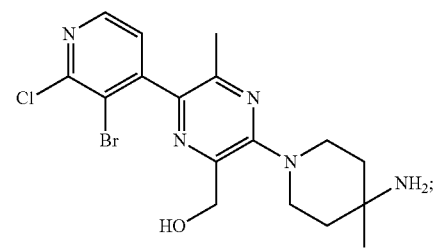 [SMILES: Cc1nc(N2CCC(C)(N)CC2)c(CO)nc1-c1ccnc(Cl)c1Br] |
| A-177 | 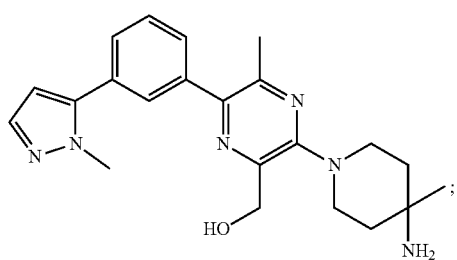 [SMILES: Cc1nc(N2CCC(C)(N)CC2)c(CO)nc1-c1cccc(-c2ccnn2C)c1] |

-continued

| Compound # | Structure |
|---|---|
| A-178 | 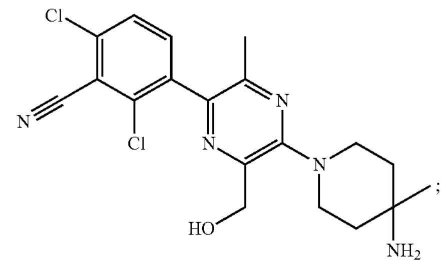 [SMILES: Cc1nc(N2CCC(C)(N)CC2)c(CO)nc1-c1ccc(Cl)c(C#N)c1Cl] |
| A-179 | 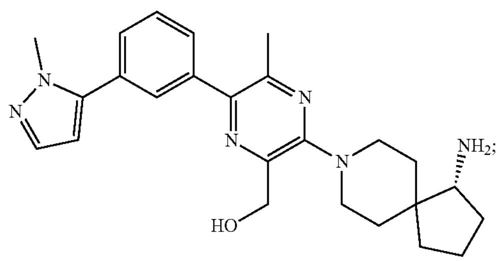 [SMILES: Cc1nc(N2CCC3(CCC[C@H]3N)CC2)c(CO)nc1-c1cccc(-c2ccnn2C)c1] |
| A-180 | 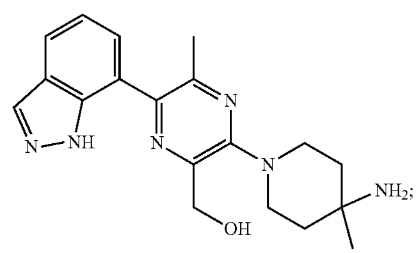 [SMILES: Cc1nc(N2CCC(C)(N)CC2)c(CO)nc1-c1cccc2cn[nH]c12] |
| A-181 | 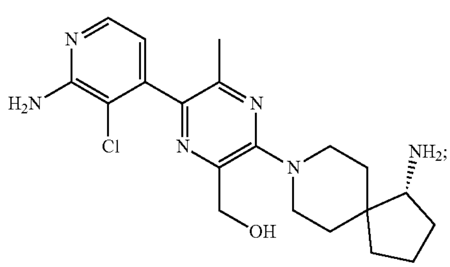 [SMILES: Cc1nc(N2CCC3(CCC[C@H]3N)CC2)c(CO)nc1-c1ccnc(N)c1Cl] |
| A-182 | 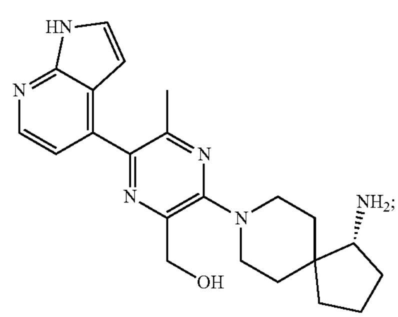 [SMILES: Cc1nc(N2CCC3(CCC[C@H]3N)CC2)c(CO)nc1-c1ccnc2[nH]ccc12] |

| Compound # | Structure |
|---|---|
| A-183 | 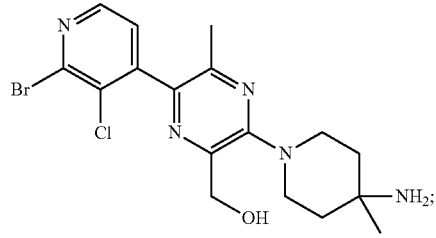 [SMILES: Cc1nc(N2CCC(C)(N)CC2)c(CO)nc1-c1ccnc(Br)c1Cl] |
| A-184 | 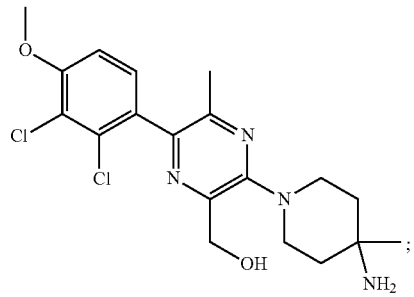 [SMILES: COc1ccc(-c2nc(CO)c(N3CCC(C)(N)CC3)nc2C)c(Cl)c1Cl] |
| A-185 | 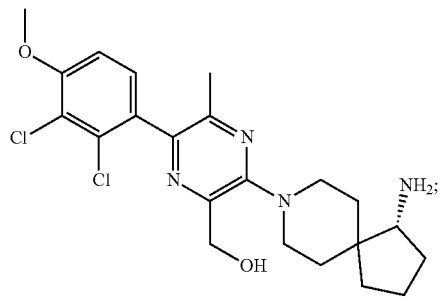 [SMILES: COc1ccc(-c2nc(CO)c(N3CCC4(CCC[C@H]4N)CC3)nc2C)c(Cl)c1Cl] |
| A-186 | 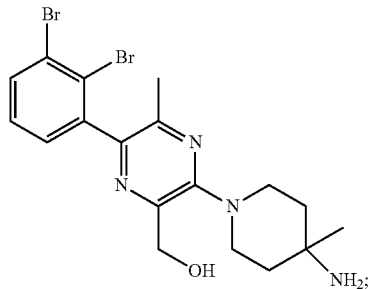 [SMILES: Cc1nc(N2CCC(C)(N)CC2)c(CO)nc1-c1cccc(Br)c1Br] |
| A-187 | 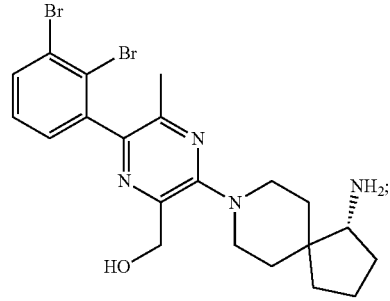 [SMILES: Cc1nc(N2CCC3(CCC[C@H]3N)CC2)c(CO)nc1-c1cccc(Br)c1Br] |

-continued
| Compound # | Structure |
|---|---|
| A-188 | 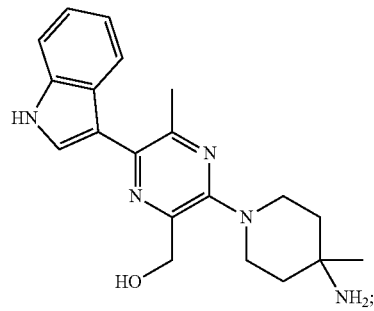 [SMILES: Cc1nc(N2CCC(C)(N)CC2)c(CO)nc1-c1c[nH]c2ccccc12] |
| A-189 | 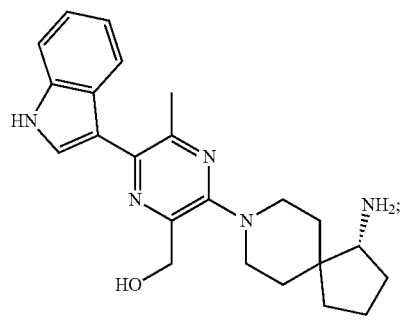 [SMILES: Cc1nc(N2CCC3(CCC[C@H]3N)CC2)c(CO)nc1-c1c[nH]c2ccccc12] |
| A-190 | 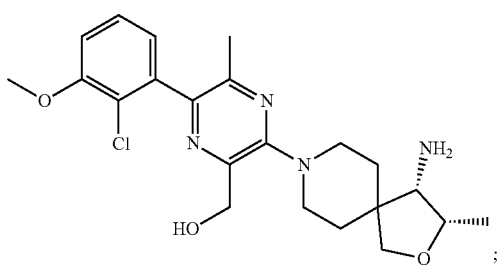 |
| A-191 | 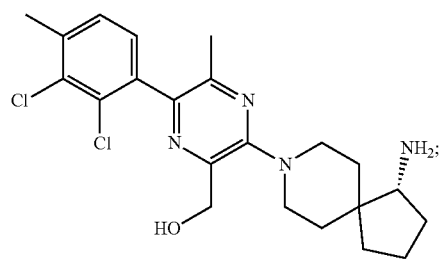 [SMILES: Cc1ccc(-c2nc(CO)c(N3CCC4(CCC[C@H]4N)CC3)nc2C)c(Cl)c1Cl] |
| A-192 | 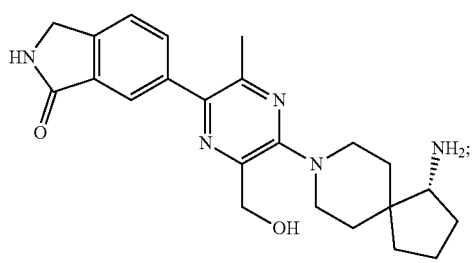 [SMILES: Cc1nc(N2CCC3(CCC[C@H]3N)CC2)c(CO)nc1-c1ccc2c(c1)C(=O)NC2] |

-continued
| Compound # | Structure |
|---|---|
| A-193 | 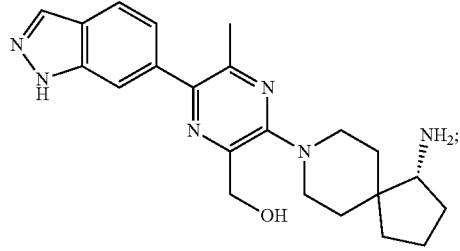 [SMILES: Cc1nc(N2CCC3(CCC[C@H]3N)CC2)c(CO)nc1-c1ccc2cn[nH]c2c1] |
| A-194 | 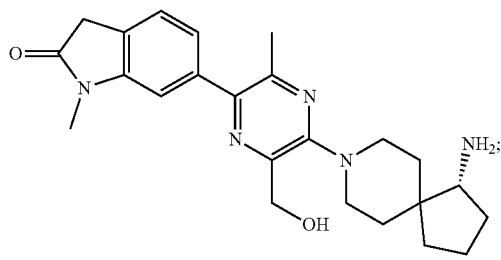 [SMILES: Cc1nc(N2CCC3(CCC[C@H]3N)CC2)c(CO)nc1-c1ccc2c(c1)N(C)C(=O)C2] |
| A-195 | 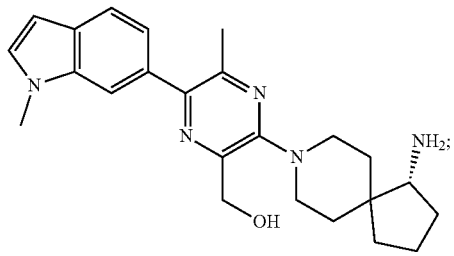 [SMILES: Cc1nc(N2CCC3(CCC[C@H]3N)CC2)c(CO)nc1-c1ccc2ccn(C)c2c1] |
| A-196 | 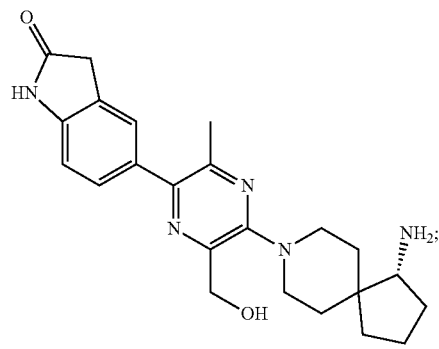 [SMILES: Cc1nc(N2CCC3(CCC[C@H]3N)CC2)c(CO)nc1-c1ccc2c(c1)CC(=O)N2] |
| A-197 | 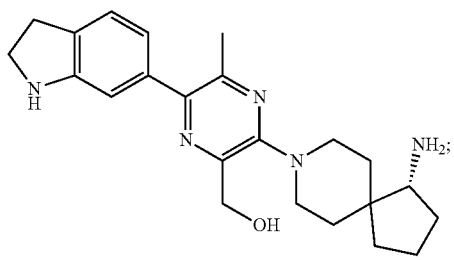 [SMILES: Cc1nc(N2CCC3(CCC[C@H]3N)CC2)c(CO)nc1-c1ccc2c(c1)NCC2] |

-continued
| Compound # | Structure |
|---|---|
| A-198 | 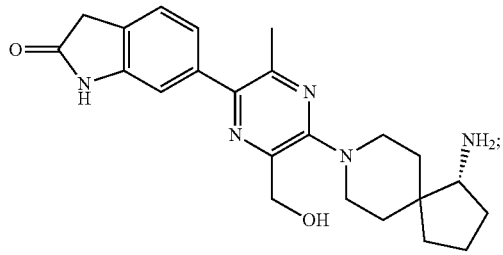 [SMILES: Cc1nc(N2CCC3(CCC[C@H]3N)CC2)c(CO)nc1-c1ccc2c(c1)NC(=O)C2] |
| A-199 | 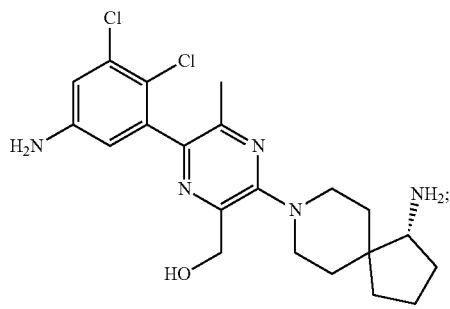 [SMILES: Cc1nc(N2CCC3(CCC[C@H]3N)CC2)c(CO)nc1-c1cc(N)cc(Cl)c1Cl] |
| A-200 | 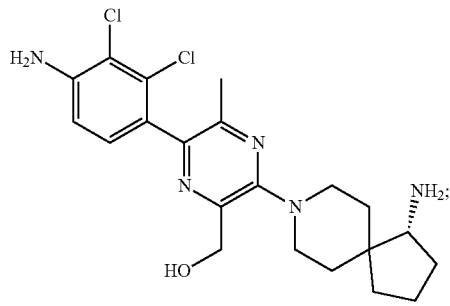 |
| A-201 | 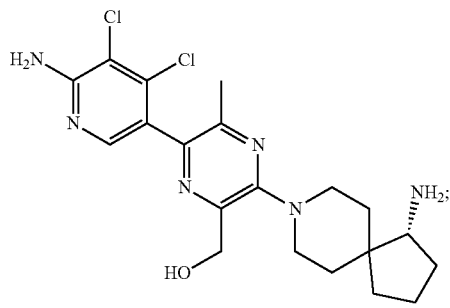 [SMILES: Cc1nc(N2CCC3(CCC[C@H]3N)CC2)c(CO)nc1-c1cnc(N)c(Cl)c1Cl] |
| A-202 | 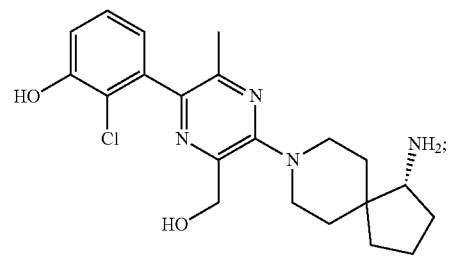 |

| Compound # | Structure |
|---|---|
| A-203 | 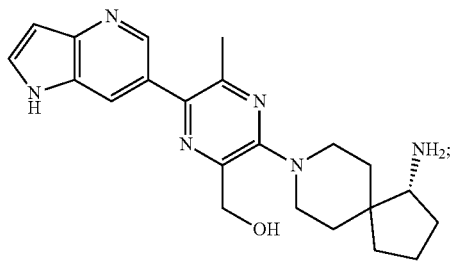 [SMILES: Cc1nc(N2CCC3(CCC[C@H]3N)CC2)c(CO)nc1-c1cnc2cc[nH]c2c1] |
| A-204 | 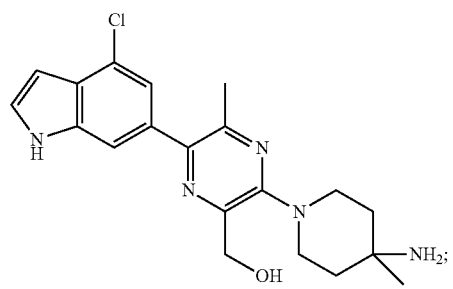 [SMILES: Cc1nc(N2CCC(C)(N)CC2)c(CO)nc1-c1cc(Cl)c2cc[nH]c2c1] |
| A-205 | 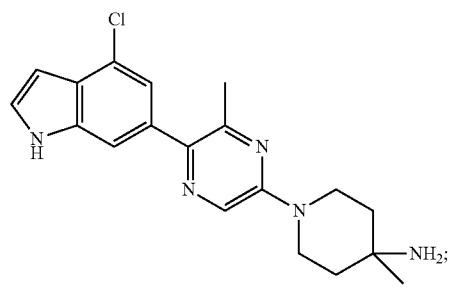 [SMILES: Cc1nc(N2CCC(C)(N)CC2)cnc1-c1cc(Cl)c2cc[nH]c2c1] |
| A-206 | 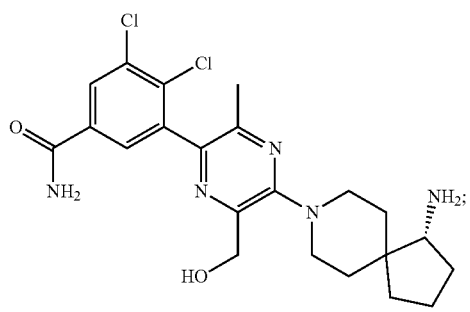 [SMILES: Cc1nc(N2CCC3(CCC[C@H]3N)CC2)c(CO)nc1-c1cc(C(N)=O)cc(Cl)c1Cl] |
| A-207 | 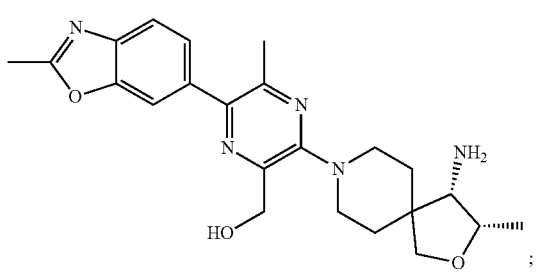 |

-continued
| Compound # | Structure |
|---|---|
| A-208 | 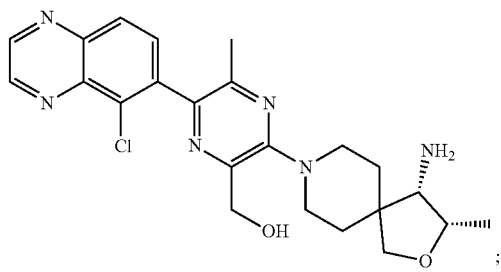 [SMILES: Cc1nc(N2CCC3(CC2)CO[C@@H](C)[C@H]3N)c(CO)nc1-c1ccc2nccnc2c1Cl] |
| A-209 | 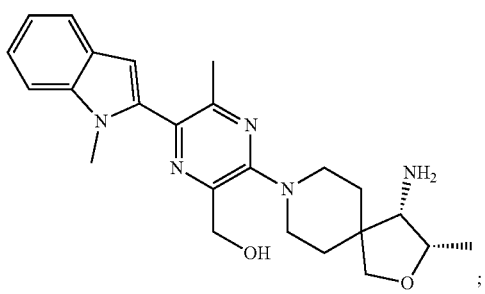 [SMILES: Cc1nc(N2CCC3(CC2)CO[C@@H](C)[C@H]3N)c(CO)nc1-c1cc2ccccc2n1C] |
| A-210 | 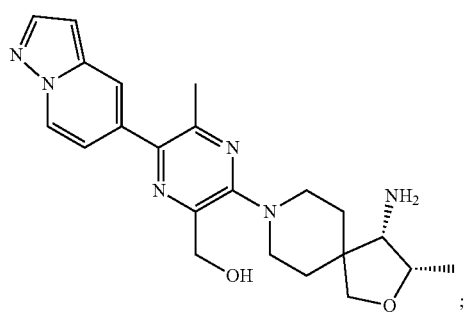 [SMILES: Cc1nc(N2CCC3(CC2)CO[C@@H](C)[C@H]3N)c(CO)nc1-c1ccn2nccc2c1] |
| A-211 | 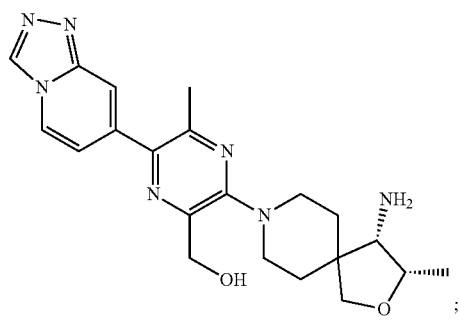 [SMILES: Cc1nc(N2CCC3(CC2)CO[C@@H](C)[C@H]3N)c(CO)nc1-c1ccn2cnnc2c1] |
| A-212 | 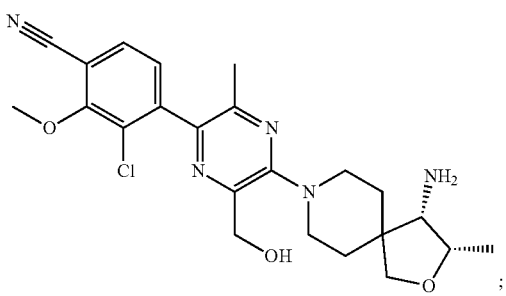 |

-continued

| Compound # | Structure |
|---|---|
| A-213 | 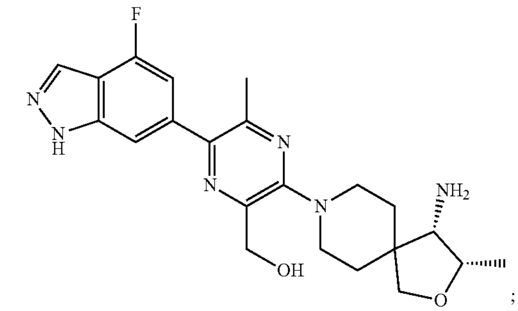 [SMILES: Cc1nc(N2CCC3(CC2)CO[C@@H](C)[C@H]3N)c(CO)nc1-c1cc(F)c2cn[nH]c2c1] |
| A-214 | 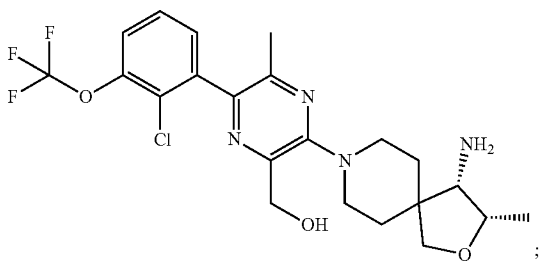 [SMILES: Cc1nc(N2CCC3(CC2)CO[C@@H](C)[C@H]3N)c(CO)nc1-c1cccc(OC(F)(F)F)c1Cl] |
| A-215 | 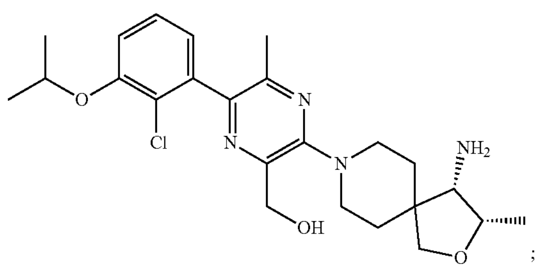 [SMILES: Cc1nc(N2CCC3(CC2)CO[C@@H](C)[C@H]3N)c(CO)nc1-c1cccc(OC(C)C)c1Cl] |
| A-216 | 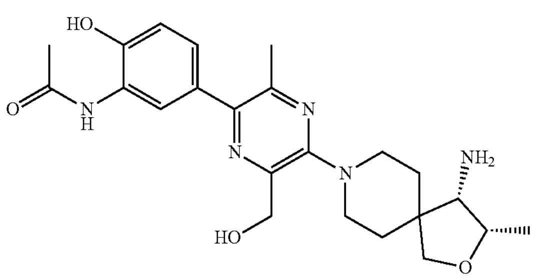 |
| A-217 | 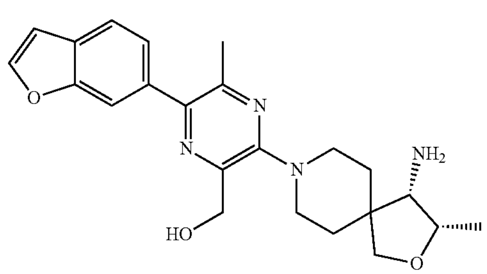 |

-continued
| Compound # | Structure |
|---|---|
| A-218 | 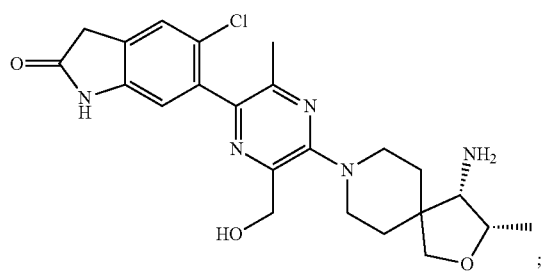 [SMILES: Cc1nc(N2CCC3(CC2)CO[C@@H](C)[C@H]3N)c(CO)nc1-c1cc2c(cc1Cl)CC(=O)N2] |
| A-219 | 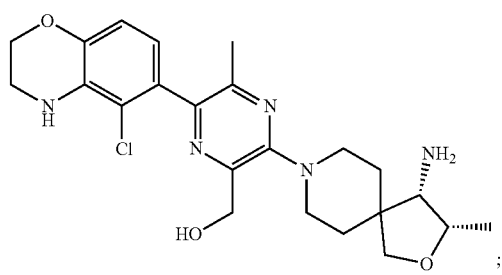 [SMILES: Cc1nc(N2CCC3(CC2)CO[C@@H](C)[C@H]3N)c(CO)nc1-c1ccc2c(c1Cl)NCCO2] |
| A-220 | 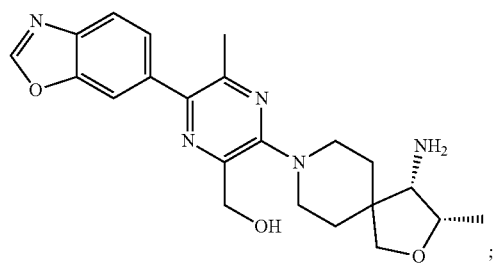 [SMILES: Cc1nc(N2CCC3(CC2)CO[C@@H](C)[C@H]3N)c(CO)nc1-c1ccc2ncoc2c1] |
| A-221 | 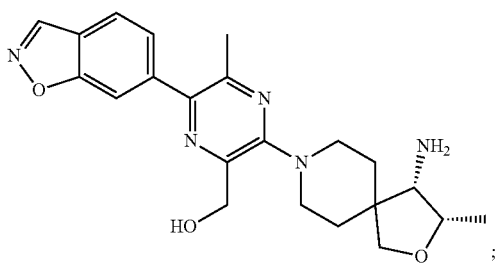 [SMILES: Cc1nc(N2CCC3(CC2)CO[C@@H](C)[C@H]3N)c(CO)nc1-c1ccc2cnoc2c1] |
| A-222 | 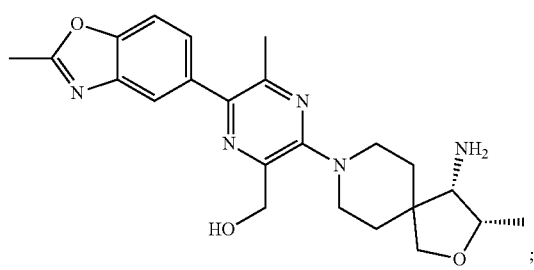 |

| Compound # | Structure |
|---|---|
| A-223 | 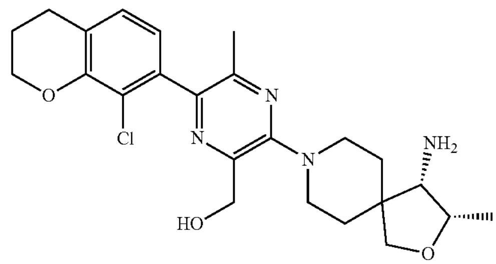 |
| A-224 | 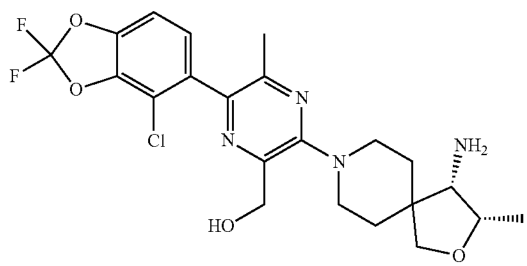 |
| A-225 | 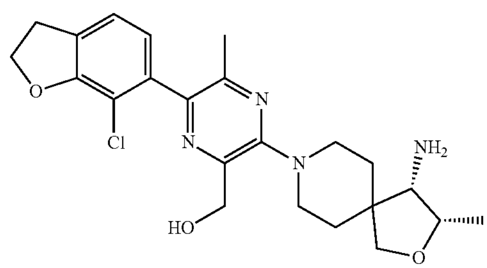 |
| A-226 | 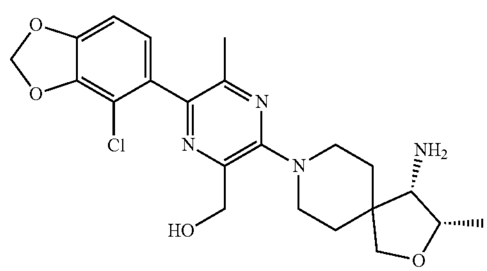 |
| A-227 | 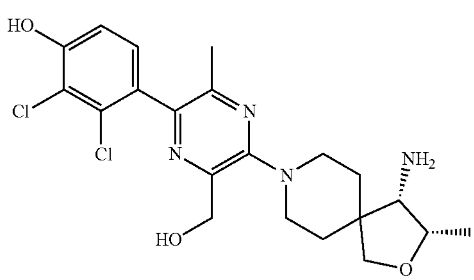 |

-continued
| Compound # | Structure |
|---|---|
| A-228 | 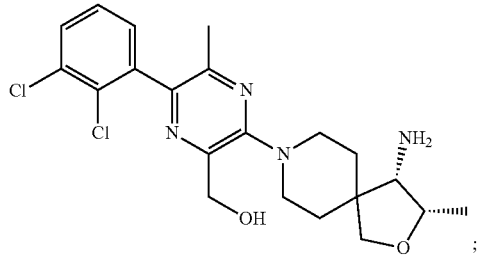 [SMILES: Cc1nc(N2CCC3(CC2)CO[C@@H](C)[C@H]3N)c(CO)nc1-c1cccc(Cl)c1Cl] |
| A-229 | 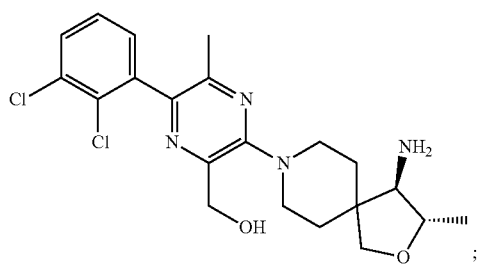 [SMILES: Cc1nc(N2CCC3(CC2)CO[C@@H](C)[C@@H]3N)c(CO)nc1-c1cccc(Cl)c1Cl] |
| A-230 | 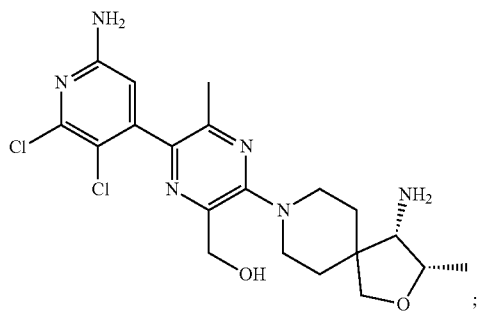 [SMILES: Cc1nc(N2CCC3(CC2)CO[C@@H](C)[C@H]3N)c(CO)nc1-c1cc(N)nc(Cl)c1Cl] |
| A-231 | 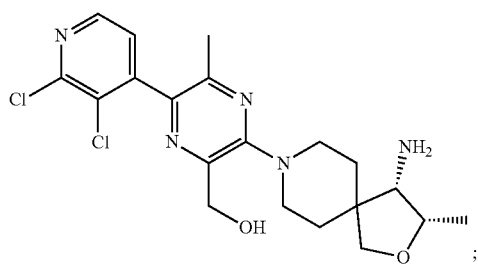 [SMILES: Cc1nc(N2CCC3(CC2)CO[C@@H](C)[C@H]3N)c(CO)nc1-c1ccnc(Cl)c1Cl] |
| A-232 | 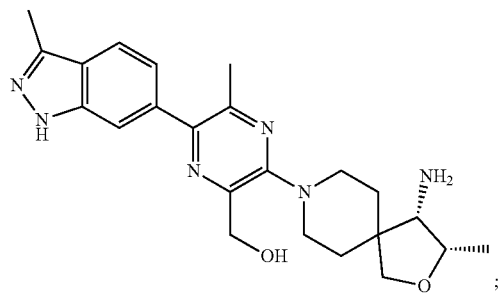 [SMILES: Cc1nc(N2CCC3(CC2)CO[C@@H](C)[C@H]3N)c(CO)nc1-c1ccc2c(C)n[nH]c2c1] |

| Compound # | Structure |
|---|---|
| A-233 | 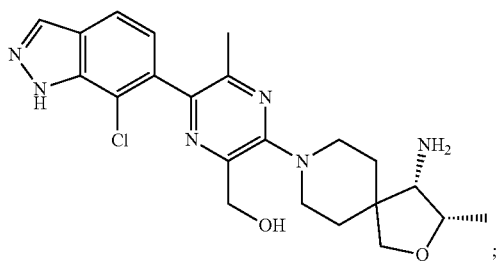 [SMILES: Cc1nc(N2CCC3(CC2)CO[C@@H](C)[C@H]3N)c(CO)nc1-c1ccc2cn[nH]c2c1Cl] |
| A-234 | 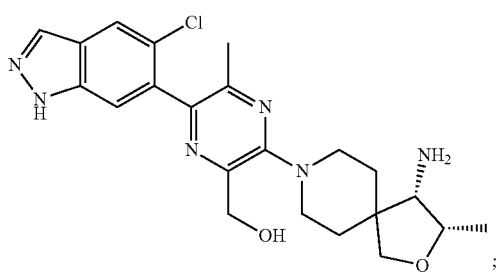 [SMILES: Cc1nc(N2CCC3(CC2)CO[C@@H](C)[C@H]3N)c(CO)nc1-c1cc2[nH]ncc2cc1Cl] |
| A-235 | 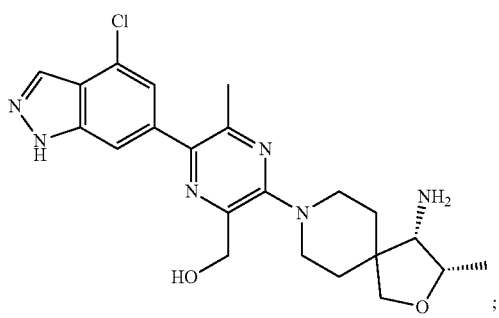 [SMILES: Cc1nc(N2CCC3(CC2)CO[C@@H](C)[C@H]3N)c(CO)nc1-c1cc(Cl)c2cn[nH]c2c1] |
| A-236 | 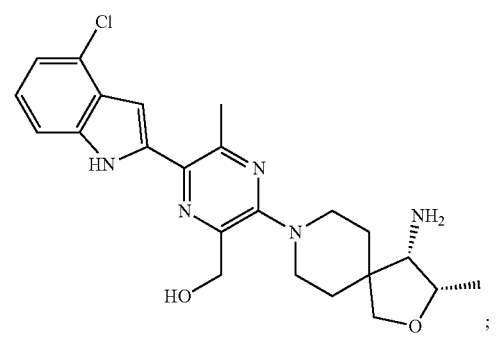 [SMILES: Cc1nc(N2CCC3(CC2)CO[C@@H](C)[C@H]3N)c(CO)nc1-c1cc2c(Cl)cccc2[nH]1] |
| A-237 | 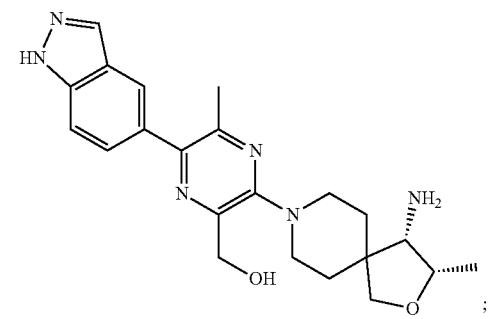 [SMILES: Cc1nc(N2CCC3(CC2)CO[C@@H](C)[C@H]3N)c(CO)nc1-c1ccc2[nH]ncc2c1] |

-continued
| Compound # | Structure |
|---|---|
| A-238 | 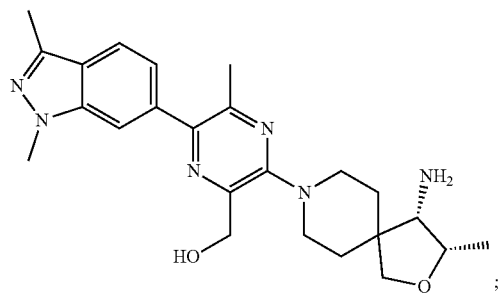 [SMILES: Cc1nc(N2CCC3(CC2)CO[C@@H](C)[C@H]3N)c(CO)nc1-c1ccc2c(C)nn(C)c2c1] |
| A-239 | 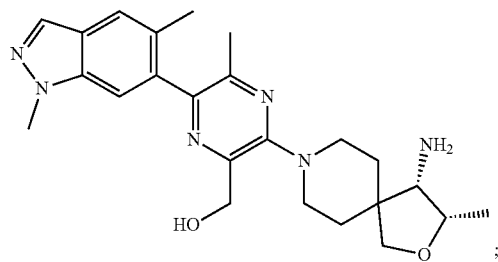 [SMILES: Cc1cc2cnn(C)c2cc1-c1nc(CO)c(N2CCC3(CC2)CO[C@@H](C)[C@H]3N)nc1C] |
| A-240 | 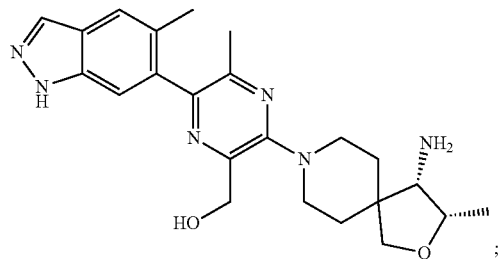 |
| A-241 | 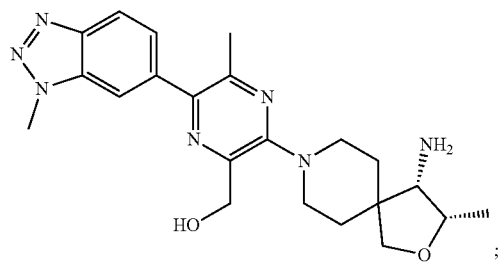 [SMILES: Cc1nc(N2CCC3(CC2)CO[C@@H](C)[C@H]3N)c(CO)nc1-c1ccc2nnn(C)c2c1] |
| A-242 | 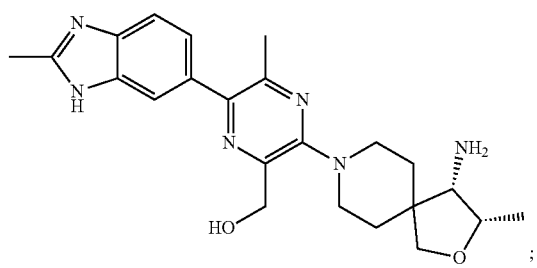 |

| Compound # | Structure |
|---|---|
| A-243 | 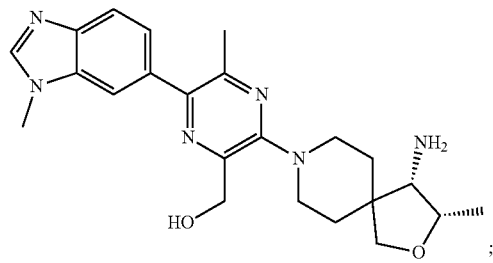 |
| A-244 | 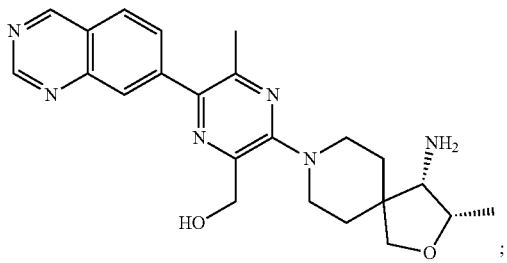 [SMILES: Cc1nc(N2CCC3(CC2)CO[C@@H](C)[C@H]3N)c(CO)nc1-c1ccc2cncnc2c1] |
| A-245 | 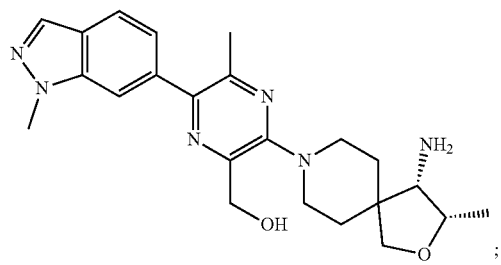 [SMILES: Cc1nc(N2CCC3(CC2)CO[C@@H](C)[C@H]3N)c(CO)nc1-c1ccc2cnn(C)c2c1] |
| A-246 | 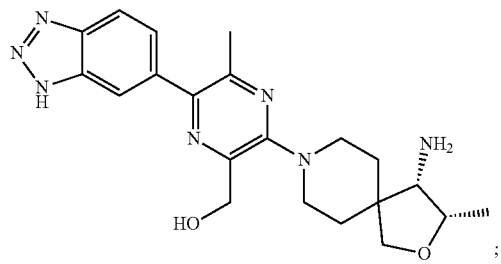 [SMILES: Cc1nc(N2CCC3(CC2)CO[C@@H](C)[C@H]3N)c(CO)nc1-c1ccc2nn[nH]c2c1] |
| A-247 | 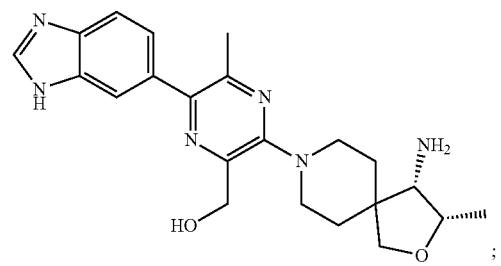 [SMILES: Cc1nc(N2CCC3(CC2)CO[C@@H](C)[C@H]3N)c(CO)nc1-c1ccc2nc[nH]c2c1] |

-continued
| Compound # | Structure |
|---|---|
| A-248 | 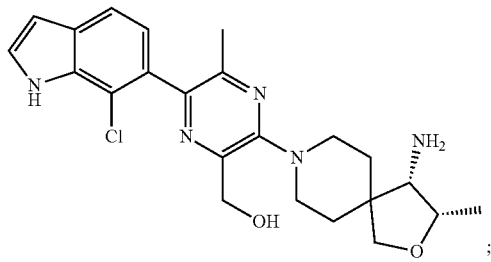 [SMILES: Cc1nc(N2CCC3(CC2)CO[C@@H](C)[C@H]3N)c(CO)nc1-c1ccc2cc[nH]c2c1Cl] |
| A-249 | 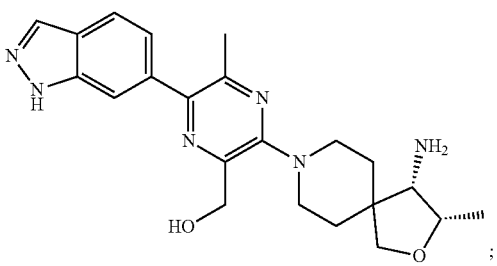 [SMILES: Cc1nc(N2CCC3(CC2)CO[C@@H](C)[C@H]3N)c(CO)nc1-c1ccc2cn[nH]c2c1] |
| A-250 | 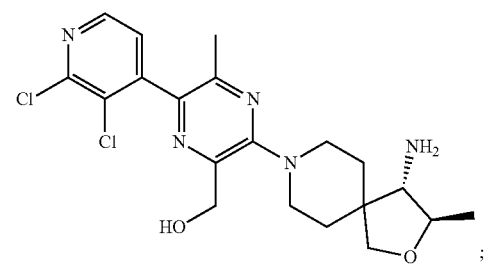 [SMILES: Cc1nc(N2CCC3(CC2)CO[C@H](C)[C@H]3N)c(CO)nc1-c1ccnc(Cl)c1Cl] |
| A-251 | 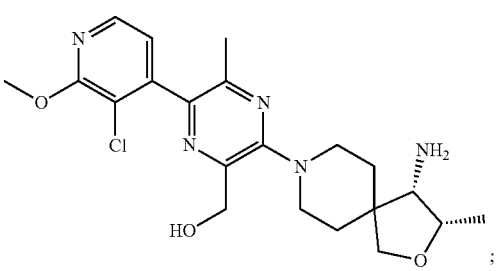 |
| A-252 | 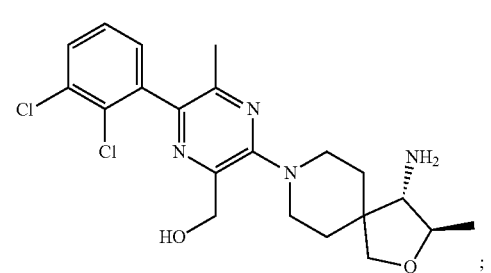 [SMILES: Cc1nc(N2CCC3(CC2)CO[C@H](C)[C@H]3N)c(CO)nc1-c1cccc(Cl)c1Cl] |

-continued
| Compound # | Structure |
|---|---|
| A-253 | 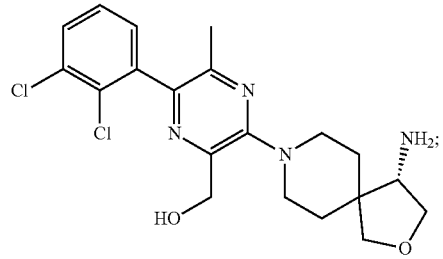 [SMILES: Cc1nc(N2CCC3(CC2)COC[C@H]3N)c(CO)nc1-c1cccc(Cl)c1Cl] |
| A-254 | 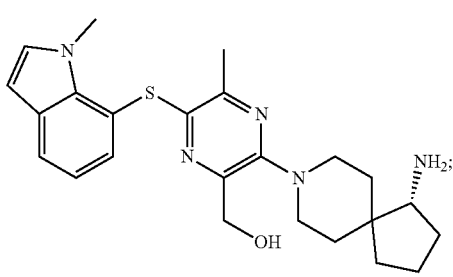 [SMILES: Cc1nc(N2CCC3(CCC[C@H]3N)CC2)c(CO)nc1Sc1cccc2ccn(C)c12] |
| A-255 | 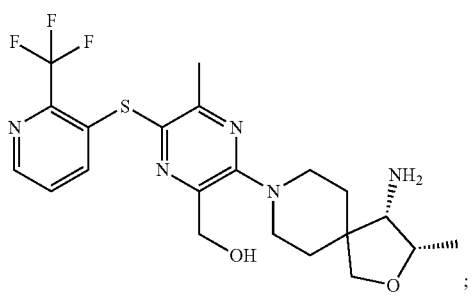 [SMILES: Cc1nc(N2CCC3(CC2)CO[C@@H](C)[C@H]3N)c(CO)nc1Sc1cccnc1C(F)(F)F] |
| A-256 | 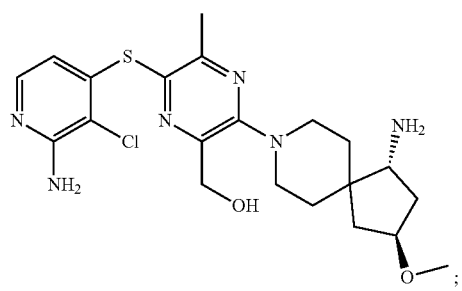 [SMILES: CO[C@@H]1C[C@@H](N)C2(CCN(c3nc(C)c(Sc4ccnc(N)c4Cl)nc3CO)CC2)C1] |
| A-257 | 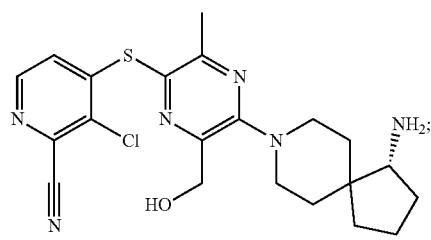 [SMILES: Cc1nc(N2CCC3(CCC[C@H]3N)CC2)c(CO)nc1Sc1ccnc(C#N)c1Cl] |

-continued
| Compound # | Structure |
|---|---|
| A-258 | 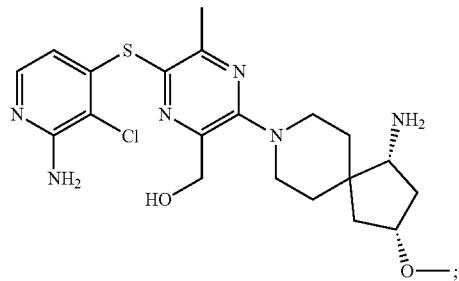 [SMILES: CO[C@H]1C[C@@H](N)C2(CCN(c3nc(C)c(Sc4ccnc(N)c4Cl)nc3CO)CC2)C1] |
| A-259 | 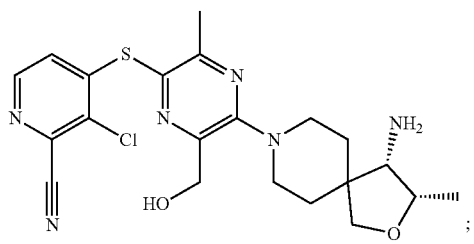 [SMILES: Cc1nc(N2CCC3(CC2)CO[C@@H](C)[C@H]3N)c(CO)nc1Sc1ccnc(C#N)c1Cl] |
| A-260 | 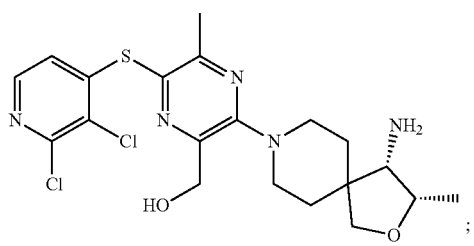 [SMILES: Cc1nc(N2CCC3(CC2)CO[C@@H](C)[C@H]3N)c(CO)nc1Sc1ccnc(Cl)c1Cl] |
| A-261 | 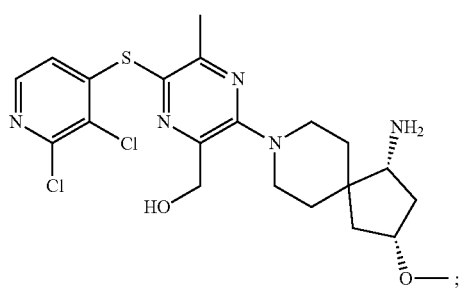 [SMILES: CO[C@H]1C[C@@H](N)C2(CCN(c3nc(C)c(Sc4ccnc(Cl)c4Cl)nc3CO)CC2)C1] |
| A-262 | 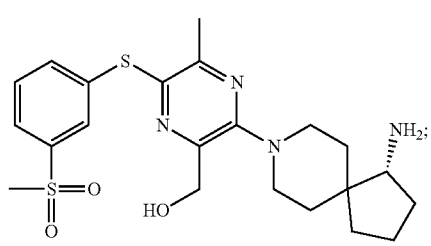 [SMILES: Cc1nc(N2CCC3(CCC[C@H]3N)CC2)c(CO)nc1Sc1cccc(S(C)(=O)=O)c1] |

-continued
| Compound # | Structure |
|---|---|
| A-263 | 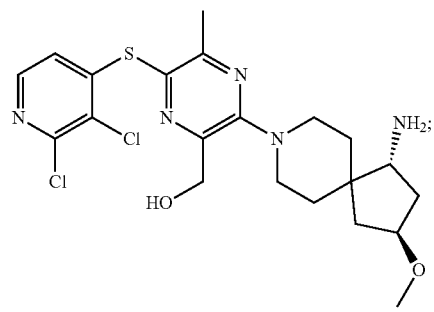 [SMILES: CO[C@@H]1C[C@@H](N)C2(CCN(c3nc(C)c(Sc4ccnc(Cl)c4Cl)nc3CO)CC2)C1] |
| A-264 | 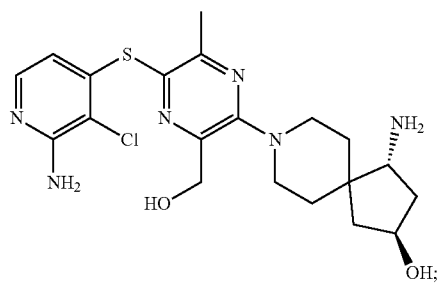 [SMILES: Cc1nc(N2CCC3(CC2)C[C@H](O)C[C@H]3N)c(CO)nc1Sc1ccnc(N)c1Cl] |
| A-265 | 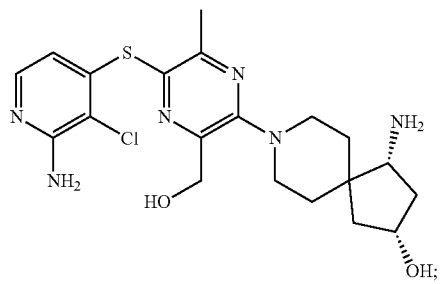 [SMILES: Cc1nc(N2CCC3(CC2)C[C@@H](O)C[C@H]3N)c(CO)nc1Sc1ccnc(N)c1Cl] |
| A-266 | 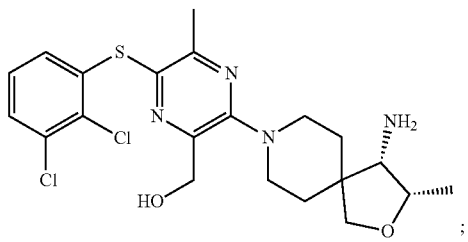 [SMILES: Cc1nc(N2CCC3(CC2)CO[C@@H](C)[C@H]3N)c(CO)nc1Sc1cccc(Cl)c1Cl] |
| A-267 | 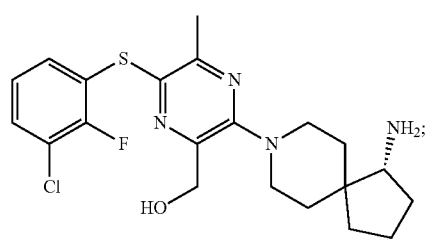 [SMILES: Cc1nc(N2CCC3(CCC[C@H]3N)CC2)c(CO)nc1Sc1cccc(Cl)c1F] |

-continued
| Compound # | Structure |
|---|---|
| A-268 | 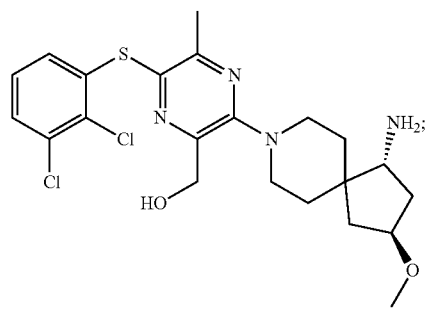 [SMILES: CO[C@@H]1C[C@@H](N)C2(CCN(c3nc(C)c(Sc4cccc(Cl)c4Cl)nc3CO)CC2)C1] |
| A-269 | 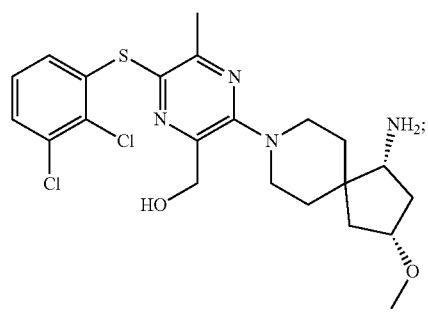 [SMILES: CO[C@H]1C[C@@H](N)C2(CCN(c3nc(C)c(Sc4cccc(Cl)c4Cl)nc3CO)CC2)C1] |
| A-270 | 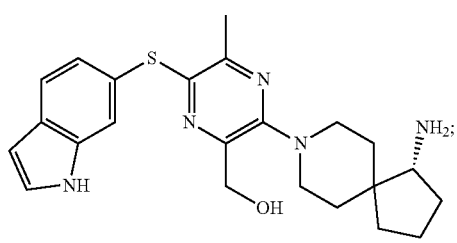 [SMILES: Cc1nc(N2CCC3(CCC[C@H]3N)CC2)c(CO)nc1Sc1ccc2cc[nH]c2c1] |
| A-271 | 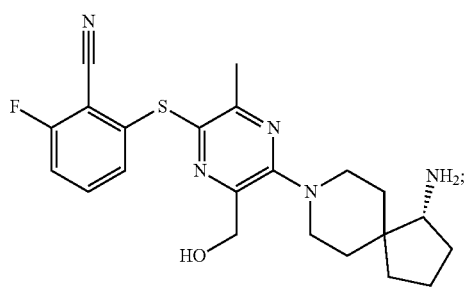 [SMILES: Cc1nc(N2CCC3(CCC[C@H]3N)CC2)c(CO)nc1Sc1cccc(F)c1C#N] |
| A-272 | 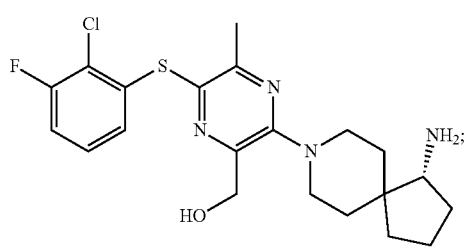 [SMILES: Cc1nc(N2CCC3(CCC[C@H]3N)CC2)c(CO)nc1Sc1cccc(F)c1Cl] |

| Compound # | Structure |
|---|---|
| A-273 | 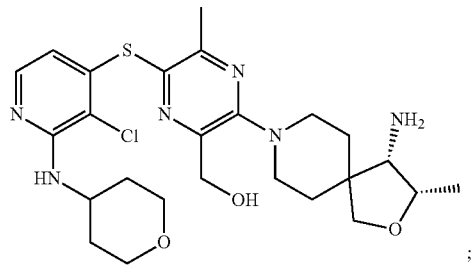 |
| A-274 | 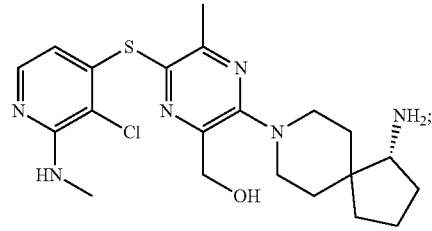 [SMILES: CNc1nccc(Sc2nc(CO)c(N3CCC4(CCC[C@H]4N)CC3)nc2C)c1Cl] |
| A-275 | 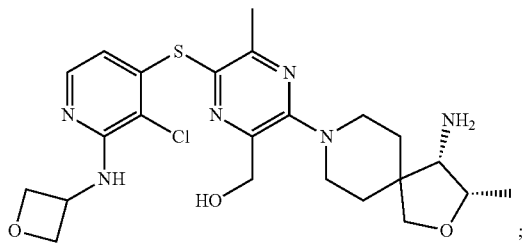 [SMILES: Cc1nc(N2CCC3(CC2)CO[C@@H](C)[C@H]3N)c(CO)nc1Sc1ccnc(NC2COC2)c1Cl] |
| A-276 | 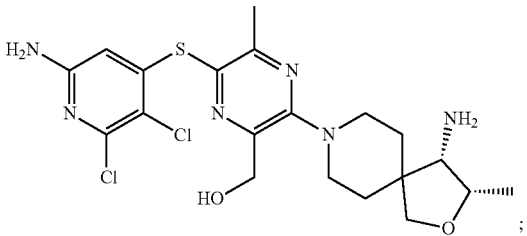 [SMILES: Cc1nc(N2CCC3(CC2)CO[C@@H](C)[C@H]3N)c(CO)nc1Sc1cc(N)nc(Cl)c1Cl] |
| A-277 | 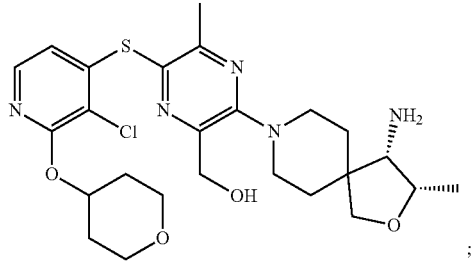 [SMILES: Cc1nc(N2CCC3(CC2)CO[C@@H](C)[C@H]3N)c(CO)nc1Sc1ccnc(OC2CCOCC2)c1Cl] |
| A-278 | 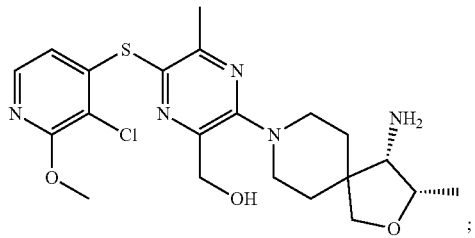 [SMILES: COc1nccc(Sc2nc(CO)c(N3CCC4(CC3)CO[C@@H](C)[C@H]4N)nc2C)c1Cl] |

-continued
| Compound # | Structure |
|---|---|
| A-279 | 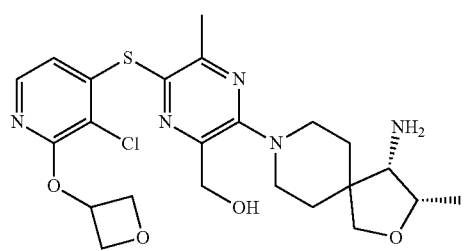 ; |
| A-280 | 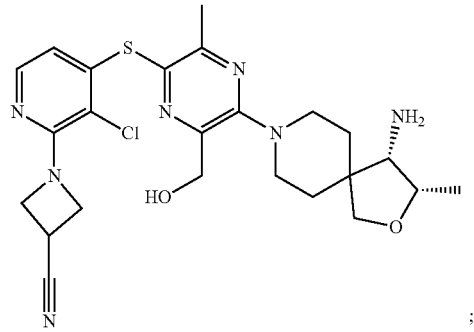 [SMILES: Cc1nc(N2CCC3(CC2)CO[C@@H](C)[C@H]3N)c(CO)nc1Sc1ccnc(N2CC(C#N)C2)c1Cl] ; |
| A-281 | 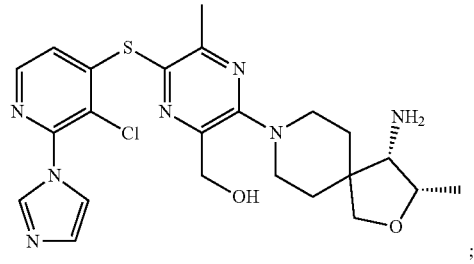 [SMILES: Cc1nc(N2CCC3(CC2)CO[C@@H](C)[C@H]3N)c(CO)nc1Sc1ccnc(-n2ccnc2)c1Cl] ; |
| A-282 | 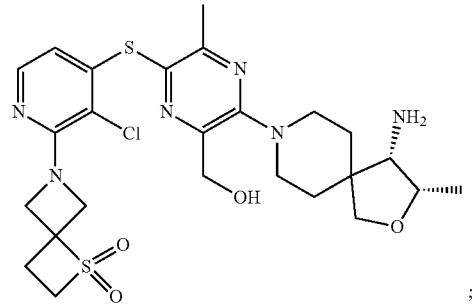 [SMILES: Cc1nc(N2CCC3(CC2)CO[C@@H](C)[C@H]3N)c(CO)nc1Sc1ccnc(N2CC3(CCS3(=O)=O)C2)c1Cl] ; |
| A-283 | 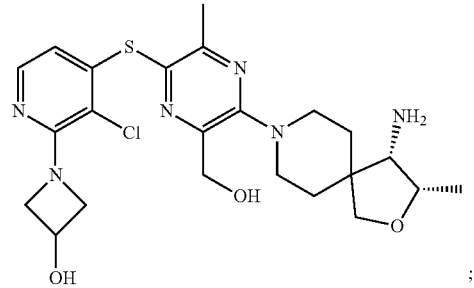 [SMILES: Cc1nc(N2CCC3(CC2)CO[C@@H](C)[C@H]3N)c(CO)nc1Sc1ccnc(N2CC(O)C2)c1Cl] ; |

-continued
| Compound # | Structure |
|---|---|
| A-284 | 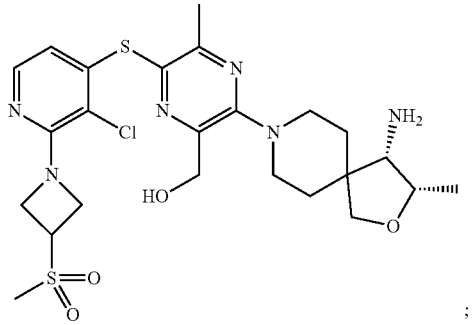 [SMILES: Cc1nc(N2CCC3(CC2)CO[C@@H](C)[C@H]3N)c(CO)nc1Sc1ccnc(N2CC(S(C)(=O)=O)C2)c1Cl] ; |
| A-285 | 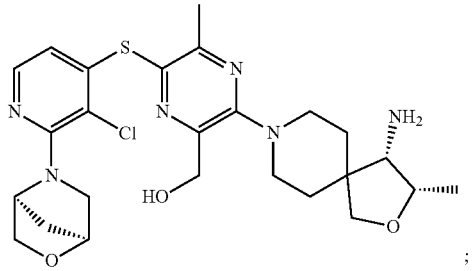 [SMILES: Cc1nc(N2CCC3(CC2)CO[C@@H](C)[C@H]3N)c(CO)nc1Sc1ccnc(N2C[C@@H]3C[C@H]2CO3)c1Cl] ; |
| A-286 | 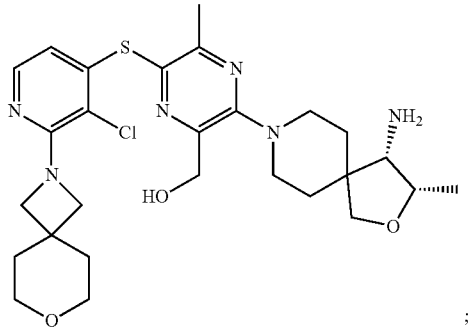 [SMILES: Cc1nc(N2CCC3(CC2)CO[C@@H](C)[C@H]3N)c(CO)nc1Sc1ccnc(N2CC3(CCOCC3)C2)c1Cl] ; |
| A-287 | 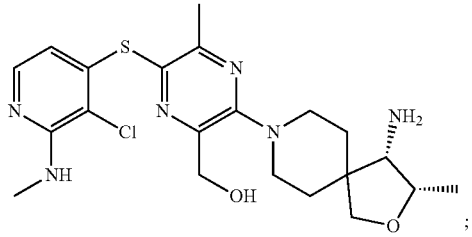 [SMILES: CNc1nccc(Sc2nc(CO)c(N3CCC4(CC3)CO[C@@H](C)[C@H]4N)nc2C)c1Cl] ; |
| A-288 | 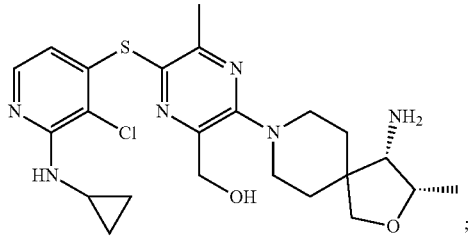 [SMILES: Cc1nc(N2CCC3(CC2)CO[C@@H](C)[C@H]3N)c(CO)nc1Sc1ccnc(NC2CC2)c1Cl] ; |

-continued
| Compound # | Structure |
|---|---|
| A-289 | 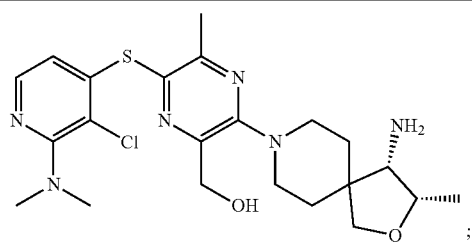 |
| A-290 | 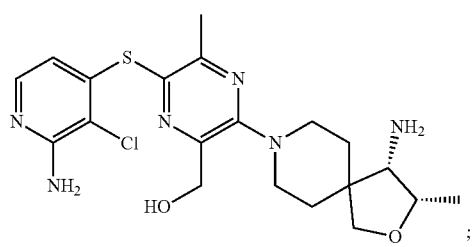 [SMILES: Cc1nc(N2CCC3(CC2)CO[C@@H](C)[C@H]3N)c(CO)nc1Sc1ccnc(N)c1Cl] |
| A-291 | 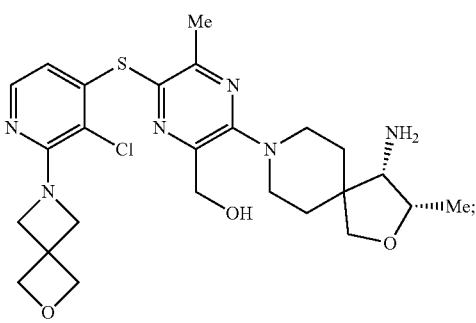 [SMILES: Cc1nc(N2CCC3(CC2)CO[C@@H](C)[C@H]3N)c(CO)nc1Sc1ccnc(N2CC3(COC3)C2)c1Cl] |
| A-292 | 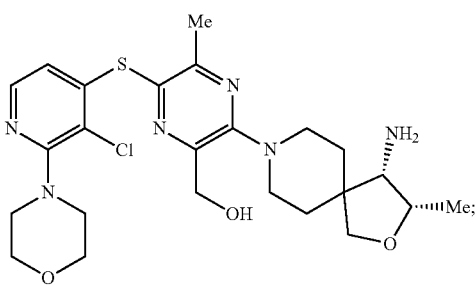 [SMILES: Cc1nc(N2CCC3(CC2)CO[C@@H](C)[C@H]3N)c(CO)nc1Sc1ccnc(N2CCOCC2)c1Cl] |
| A-293 | 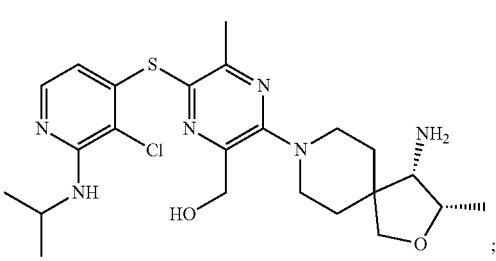 [SMILES: Cc1nc(N2CCC3(CC2)CO[C@@H](C)[C@H]3N)c(CO)nc1Sc1ccnc(NC(C)C)c1Cl] |

-continued
| Compound # | Structure |
|---|---|
| A-294 | 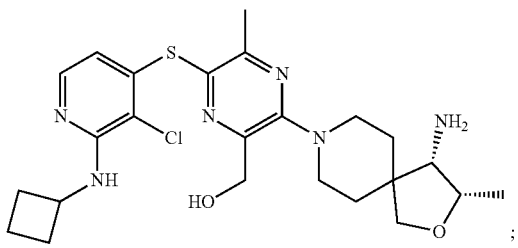 [SMILES: Cc1nc(N2CCC3(CC2)CO[C@@H](C)[C@H]3N)c(CO)nc1Sc1ccnc(NC2CCC2)c1Cl] |
| A-295 | 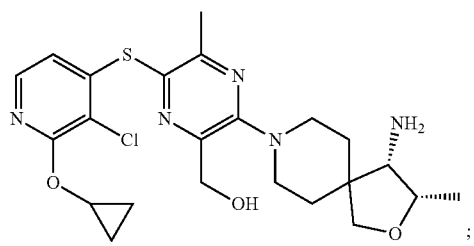 [SMILES: Cc1nc(N2CCC3(CC2)CO[C@@H](C)[C@H]3N)c(CO)nc1Sc1ccnc(OC2CC2)c1Cl] |
| A-296 | 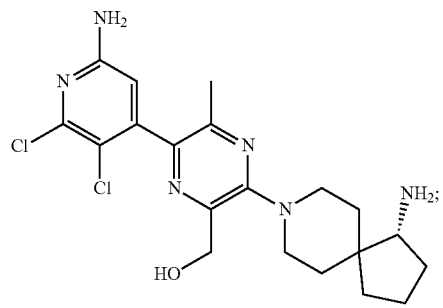 [SMILES: Cc1nc(N2CCC3(CCC[C@H]3N)CC2)c(CO)nc1-c1cc(N)nc(Cl)c1Cl] |
| A-297 | 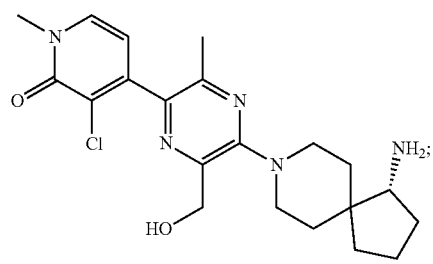 [SMILES: Cc1nc(N2CCC3(CCC[C@H]3N)CC2)c(CO)nc1-c1ccn(C)c(=O)c1Cl] |
| A-298 | 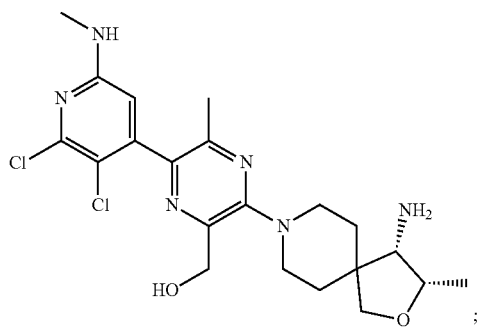 [SMILES: CNc1cc(-c2nc(CO)c(N3CCC4(CC3)CO[C@@H](C)[C@H]4N)nc2C)c(Cl)c(Cl)n1] |

-continued
| Compound # | Structure |
|---|---|
| A-299 | 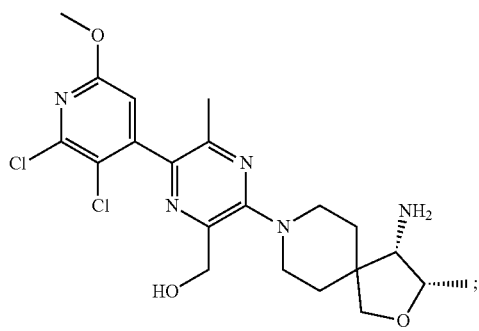 [SMILES: COc1cc(-c2nc(CO)c(N3CCC4(CC3)CO[C@@H](C)[C@H]4N)nc2C)c(Cl)c(Cl)n1] |
| A-300 | 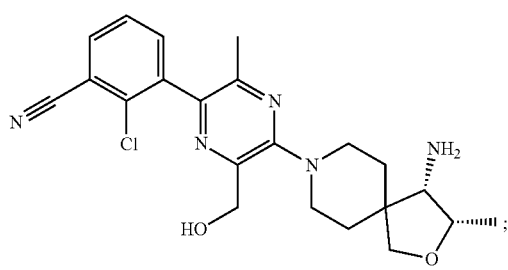 [SMILES: Cc1nc(N2CCC3(CC2)CO[C@@H](C)[C@H]3N)c(CO)nc1-c1cccc(C#N)c1Cl] |
| A-301 | 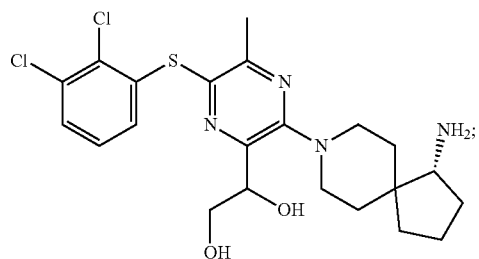 [SMILES: Cc1nc(N2CCC3(CCC[C@H]3N)CC2)c(C(O)CO)nc1Sc1cccc(Cl)c1Cl] |
| A-302 | 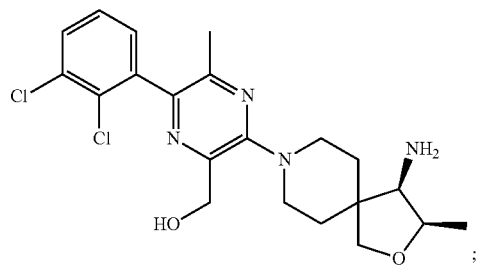 [SMILES: Cc1nc(N2CCC3(CC2)CO[C@H](C)[C@@H]3N)c(CO)nc1-c1cccc(Cl)c1Cl] |
| A-303 | 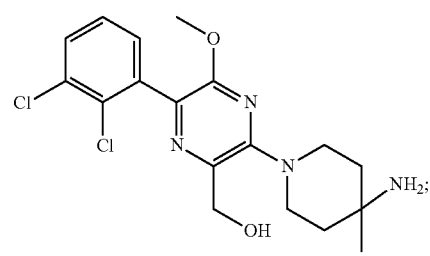 [SMILES: COc1nc(N2CCC(C)(N)CC2)c(CO)nc1-c1cccc(Cl)c1Cl] |

-continued
| Compound # | Structure |
|---|---|
| A-304 | 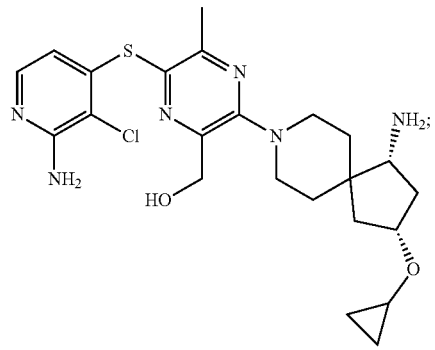 [SMILES: Cc1nc(N2CCC3(CC2)C[C@@H](OC2CC2)C[C@H]3N)c(CO)nc1Sc1ccnc(N)c1Cl] |
| A-305 | 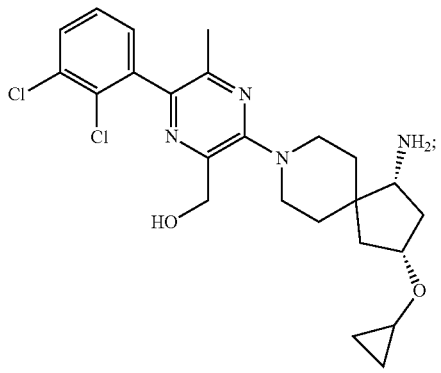 [SMILES: Cc1nc(N2CCC3(CC2)C[C@@H](OC2CC2)C[C@H]3N)c(CO)nc1-c1cccc(Cl)c1Cl] |
| A-306 | 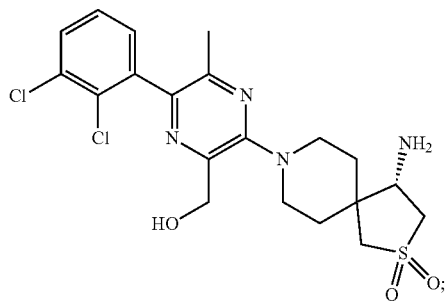 [SMILES: Cc1nc(N2CCC3(CC2)CS(=O)(=O)C[C@H]3N)c(CO)nc1-c1cccc(Cl)c1Cl] |
| A-307 | 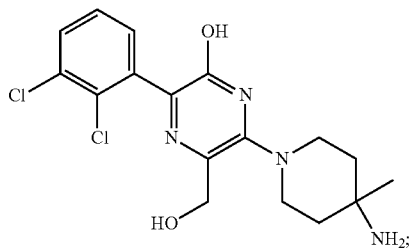 [SMILES: CC1(N)CCN(c2nc(O)c(-c3cccc(Cl)c3Cl)nc2CO)CC1] |
| A-308 | 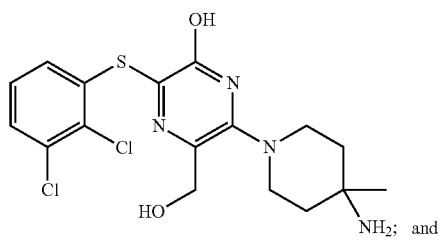 [SMILES: CC1(N)CCN(c2nc(O)c(Sc3cccc(Cl)c3Cl)nc2CO)CC1] |

| Compound # | Structure |
|---|---|
| A-309 | 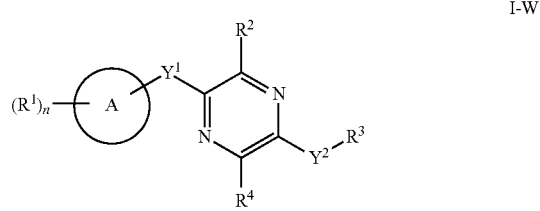 |

Embodiment III-48

A pharmaceutical composition comprising a compound of any one of Embodiments III-1 to III-47, or a pharmaceutically acceptable salt, prodrug, solvate, hydrate, tautomer, or isomer thereof, and a pharmaceutically acceptable carrier.

Embodiment III-49

A method of treating a disease associated with SHP2 modulation in a subject in need thereof, comprising administering to the subject an effective amount of a compound of any one of Embodiments III-1 to III-47, or a pharmaceutically acceptable salt, prodrug, solvate, hydrate, tautomer, or isomer thereof.

Embodiment III-50

The method of Embodiment III-49, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment III-51

A compound of any one of Embodiments III-1 to III-47, or a pharmaceutically acceptable salt, prodrug, solvate, hydrate, tautomer, or isomer thereof, for use as a medicament.

Embodiment III-52

A compound of any one of Embodiments III-1 to III-47, or a pharmaceutically acceptable salt, prodrug, solvate, hydrate, tautomer, or isomer thereof, for use in treating or preventing a disease associated with SHP2 modulation.

Embodiment III-53

Use of a compound of any one of Embodiments III-1 to III-47, or a pharmaceutically acceptable salt, prodrug, solvate, hydrate, tautomer, or isomer thereof, in the manufacture of a medicament for treating or preventing a disease associated with SHP2 modulation.

Embodiment III-54

A method of treating a disease associated with SHP2 modulation in a subject in need thereof, comprising administering to the subject an effective amount of a pharmaceutical composition of Embodiment III-48.

Embodiment III-55

The method of Embodiment III-54, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment III-56

A pharmaceutical composition of Embodiment III-48 for use as a medicament.

Embodiment III-57

A pharmaceutical composition of Embodiment III-48 for use in treating or preventing a disease associated with SHP2 modulation.

Embodiment III-58

Use of a pharmaceutical composition of Embodiment III-48 in the manufacture of a medicament for treating or preventing a disease associated with SHP2 modulation.

The invention claimed is:
1. A compound of Formula I-W:

I-W or a pharmaceutically acceptable salt, solvate, hydrate, or tautomer thereof, wherein:
A is cycloalkyl, heterocycloalkyl, aryl, or heteroaryl, wherein the cycloalkyl, heterocycloalkyl, aryl, and heteroaryl are 5- to 12-membered monocyclic or 5- to 12-membered polycyclic;
$Y^1$ is —S— or a direct bond;
$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C$ (O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the pyrazine ring and the bond on the right side of the Y$^2$ moiety, as drawn, is bound to R$^3$;

R$^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^2$ is independently —OH, —CN, —C$_1$-C$_6$alkyl, —C$_2$-C$_6$alkenyl, —C$_4$-C$_8$cycloalkenyl, —C$_2$-C$_6$alkynyl, F, Br, I, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO$_2$, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

R$^a$ is independently, at each occurrence, —H, -D, —OH, —C$_3$-C$_8$cycloalkyl, —C$_1$-C$_6$alkyl, 3- to 12-membered heterocyclyl, or —(CH$_2$)$_n$-aryl, wherein each alkyl or cycloalkyl is optionally substituted with one or more —NH$_2$, or wherein 2 R$^a$, together with the carbon atom to which they are both attached, can combine to form a 3- to 8-membered cycloalkyl;

R$^b$ is independently, at each occurrence, —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^3$ is independently —H, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$—R$^b$, wherein each alkyl, spiroheterocycle, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

R$^4$ is independently —H, -D, —C$_1$-C$_6$alkyl, —C$_1$-C$_6$haloalkyl, —C$_1$-C$_6$hydroxyalkyl, —CF$_2$OH, —CHFOH, —NH—NHR$^5$, —NH—OR$^5$, —O—NR$^5$R$^6$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —C(O)NR$^5$R$^6$, —S(O)$_2$NR$^5$R$^6$, C$_3$-C$_8$cycloalkyl, aryl, or heterocyclyl containing 1-5 heteroatoms selected from the group consisting of N, S, P, and O, wherein each alkyl, cycloalkyl, or heterocyclyl is optionally substituted with one or more —OH, —NH$_2$, —OR$^b$, halogen, or oxo; wherein each aryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, —NR$^7$R$^8$, —NO$_2$, —CF$_3$, or —CN;

R$^6$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

2. The compound of claim 1, wherein the compound is Formula I:

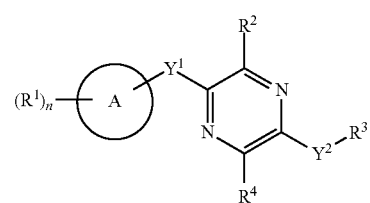

or a pharmaceutically acceptable salt, solvate, hydrate, or tautomer thereof, wherein:

A is 5- to 12-membered monocyclic or polycyclic heterocycloalkyl, aryl, or heteroaryl;

$Y^1$ is —S— or a direct bond;

$Y^2$ is —NR$^a$—, —(CR$^a{}_2$)$_m$—, —C(O)—, —C(R$^a$)$_2$NH—, —(CR$^a{}_2)_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of $Y^2$, as drawn, is bound to the pyrazine ring and the bond on the right side of the $Y^2$ moiety is bound to $R^3$;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, or —CO$_2$R$^5$, wherein each alkyl, alkenyl, cycloalkenyl, alkynyl, or cycloalkyl is optionally substituted with one or more —OH, —NO$_2$, oxo, —CN, —R$^5$, —OR$^5$, —NR$^5$R$^6$, NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ is independently —OH, —CN, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

$R^a$ is independently, at each occurrence, —H, -D, —OH, —C$_3$-C$_8$cycloalkyl, or —C$_1$-C$_6$alkyl, wherein each alkyl or cycloalkyl is optionally substituted with one or more —NH$_2$, wherein 2 R$^a$, together with the carbon atom to which they are both attached, can combine to form a 3- to 8-membered cycloalkyl;

$R^b$ is independently, at each occurrence, —H, -D, —C$_1$-C$_6$alkyl, —C$_3$-C$_8$cycloalkyl, —C$_2$-C$_6$alkenyl, or heterocyclyl containing 1-5 heteroatoms selected from the group consisting of N, S, P, and O; wherein each alkyl, cycloalkyl, alkenyl, or heterocycle is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^3$ is independently —C$_1$-C$_6$alkyl or a 3- to 12-membered monocyclic or polycyclic heterocycle, wherein each alkyl or heterocycle is optionally substituted with one or more —C$_1$-C$_6$alkyl, —OH, or —NH$_2$; or $R^3$ can combine with R$^a$ to form a 3- to 12-membered monocyclic or polycyclic heterocycle or a 5- to 12-membered spiroheterocycle, wherein each heterocycle or spiroheterocycle is optionally substituted with —C$_1$-C$_6$alkyl, —OH, or —NH$_2$;

$R^4$ is independently —H, -D, or —C$_1$-C$_6$alkyl, wherein each alkyl is optionally substituted with one or more —OH, —NH$_2$, halogen, or oxo; or $R^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo;

$R^5$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —NR$^7$R$^8$, —NO$_2$, or —CN;

$R^6$ is independently —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, or —CN;

$R^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

3. The compound of claim 1, wherein the compound is Formula I-W6:

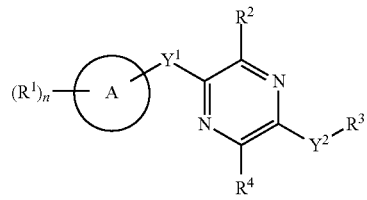

I-W6 or a pharmaceutically acceptable salt, solvate, hydrate, or tautomer thereof, wherein:

A is a 5- to 12-membered monocyclic or polycyclic heteroaryl;

$Y^1$ is —S—;

$Y^2$ is —NR$^a$—; wherein the bond on the left side of $Y^2$, as drawn, is bound to the pyrazine ring and the bond on the right side of the $Y^2$ moiety, as drawn, is bound to $R^3$;

$R^3$ is combined with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, —OH, —NH$_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F;

$R^1$ is independently, at each occurrence, —H, —C$_1$-C$_6$alkyl, —OH, halogen, —NO$_2$, —CN, —NR$^5$R$^6$, —SR$^5$, —C(O)R$^5$, or —CO$_2$R$^5$;

$R^2$ is —C$_1$-C$_6$alkyl;

$R^b$ is independently, at each occurrence, —H or —$C_1$-$C_6$alkyl;

$R^4$ is —H, —$C_1$-$C_6$alkyl, —$C_1$-$C_6$haloalkyl, —$C_1$-$C_6$hydroxyalkyl, —$CF_2OH$, —CHFOH, —C(O)NH$(CH_2)_n$OH, —C(O)NH$(CH_2)_n R^b$, —C(O)$R^b$, —C(O)NR$^5$R$^6$, or —OH, or CN, wherein alkyl is optionally substituted with one or more —OH, —$NH_2$, halogen, or oxo; or $R^5$ and $R^6$ are each independently, at each occurrence, —H or —$C_1$-$C_6$alkyl; and n is independently, at each occurrence, 1, 2, 3, 4, 5, 6, 7, 8, 9, or 10.

4. The compound of claim 1, or a pharmaceutically acceptable salt, solvate, hydrate, or tautomer thereof, wherein $Y^1$ is —S—.

5. The compound of claim 1, or a pharmaceutically acceptable salt, solvate, hydrate, or tautomer thereof, wherein $Y^1$ is a direct bond.

6. The compound of claim 1, or a pharmaceutically acceptable salt, solvate, hydrate, or tautomer thereof, wherein $Y^2$ is —(NR$^a$)—.

7. The compound of claim 6, or a pharmaceutically acceptable salt, solvate, hydrate, or tautomer thereof, wherein $R^3$ is —$C_1$-$C_6$alkyl, which is optionally substituted with one or more —$C_1$-$C_6$alkyl, —OH, —$NH_2$, —OR$^b$, —NHR$^b$, —(CH$_2$)$_n$OH, heterocyclyl, or spiroheterocyclyl.

8. The compound of claim 6, or a pharmaceutically acceptable salt, solvate, hydrate, or tautomer thereof, wherein $R^3$ and $R^a$ together with the atoms to which they are attached combine to form a 5- to 12-membered spiroheterocycle, which is optionally substituted with —$C_1$-$C_6$alkyl, —OH, —$NH_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

9. The compound of claim 8, or a pharmaceutically acceptable salt, solvate, hydrate, or tautomer thereof, wherein 5- to 12-membered spiroheterocycle comprises piperidinyl.

10. The compound of claim 9, or a pharmaceutically acceptable salt, solvate, hydrate, or tautomer thereof, wherein 5- to 12-membered spiroheterocycle comprises an oxygen.

11. The compound of claim 6, or a pharmaceutically acceptable salt, solvate, hydrate, or tautomer thereof, wherein $R^3$ and $R^a$ together with the atom to which they are attached combine to form a 3- to 12-membered monocyclic heterocycle, which is optionally substituted with —$C_1$-$C_6$alkyl, —OH, —$NH_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

12. The compound of claim 6, or a pharmaceutically acceptable salt, solvate, hydrate, or tautomer thereof, wherein $R^a$ and $R^4$ together with the atom to which they are attached combine to form a monocyclic or polycyclic 3- to 12-membered heterocycle.

13. The compound of claim 1, or a pharmaceutically acceptable salt, solvate, hydrate, or tautomer thereof, wherein $Y^2$ is —(CR$^a_2$)$_m$—.

14. The compound of claim 13, or a pharmaceutically acceptable salt, solvate, hydrate, or tautomer thereof, wherein $R^3$ and $R^a$ together with the atoms to which they are attached combine to form a 3- to 12-membered monocyclic heterocycle, which is optionally substituted with —$C_1$-$C_6$alkyl, —OH, —$NH_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

15. The compound of claim 1, or a pharmaceutically acceptable salt, solvate, hydrate, or tautomer thereof, wherein $Y^2$ is —C(O)—, —C(R$^a$)$_2$NH—, or —C(O)N(R$^a$)—.

16. The compound of claim 1, or a pharmaceutically acceptable salt, solvate, hydrate, or tautomer thereof, wherein $R^3$ and $R^a$ together with the atoms to which they are attached combine to form a 3- to 12-membered polycyclic heterocycle, which is optionally substituted with —$C_1$-$C_6$alkyl, —OH, —$NH_2$, heteroaryl, heterocyclyl, —(CH$_2$)$_n$NH$_2$, —COOR$^b$, —CONHR$^b$, —CONH(CH$_2$)$_n$COOR$^b$, —NHCOOR$^b$, —CF$_3$, —CHF$_2$, or —CH$_2$F.

17. The compound of claim 1, or a pharmaceutically acceptable salt, solvate, hydrate, or tautomer thereof, wherein A is heterocycloalkyl.

18. The compound of claim 1, or a pharmaceutically acceptable salt, solvate, hydrate, or tautomer thereof, wherein A is aryl.

19. The compound of claim 1, or a pharmaceutically acceptable salt, solvate, hydrate, or tautomer thereof, wherein A is heteroaryl.

20. The compound of claim 2, or a pharmaceutically acceptable salt, solvate, hydrate, or tautomer thereof, selected from the group consisting of:

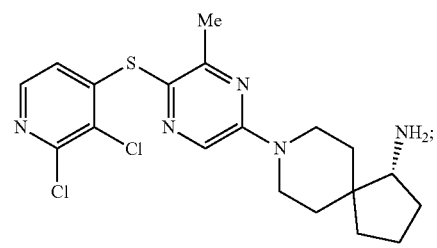

1

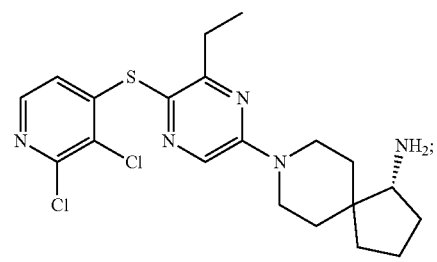

2

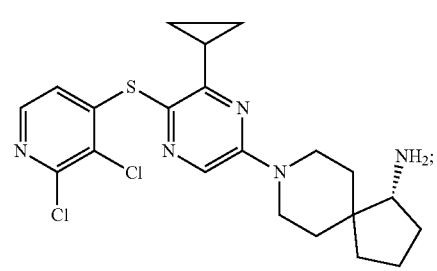

3

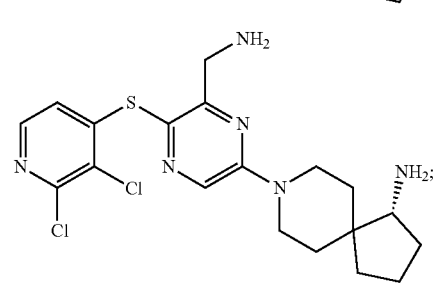

4

5
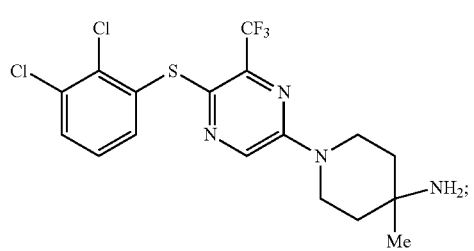
6
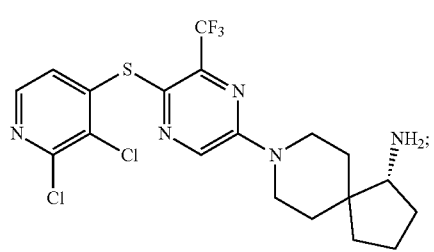
7
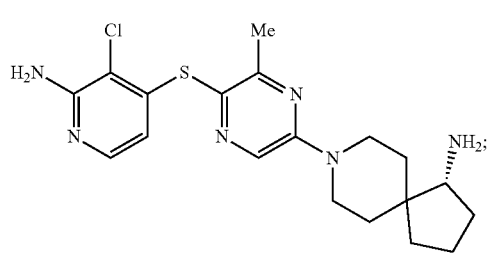
8
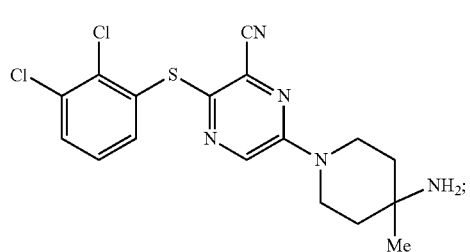
9
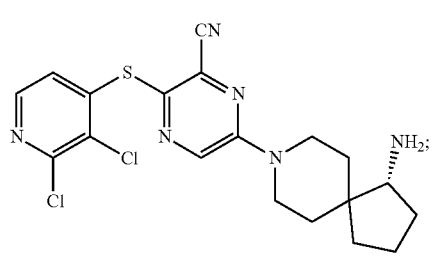 [SMILES: Cc1nc(N2CCC3(CCC[C@H]3N)CC2)cnc1Sc1ccnc(Cl)c1Cl]
10
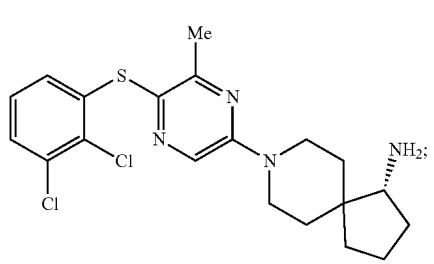
11
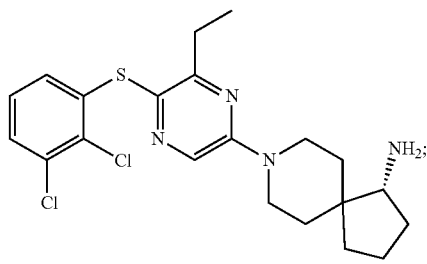
12
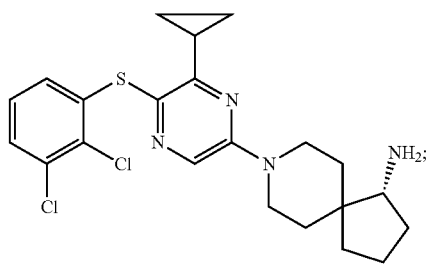
13
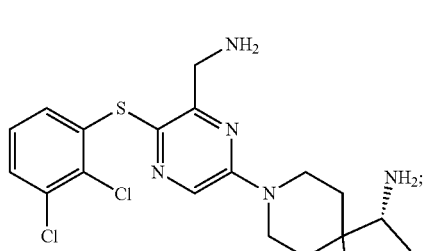
14
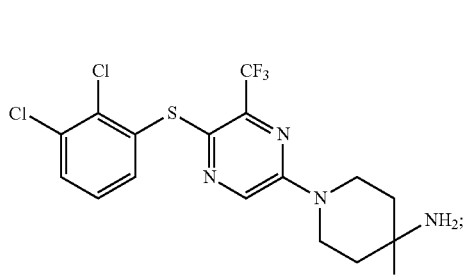
15
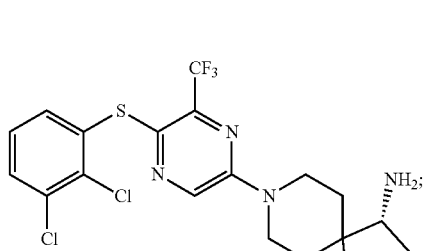
16
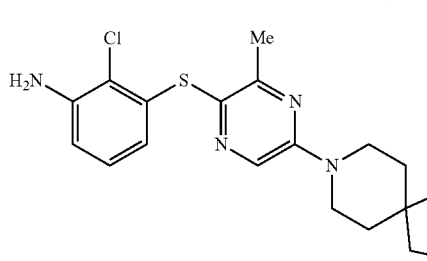

513
-continued
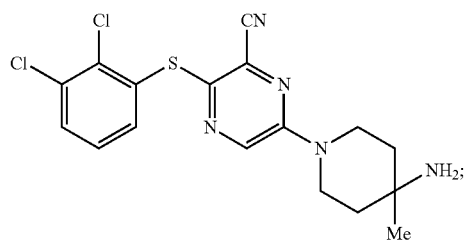
17
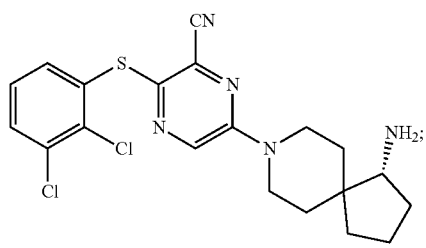
18
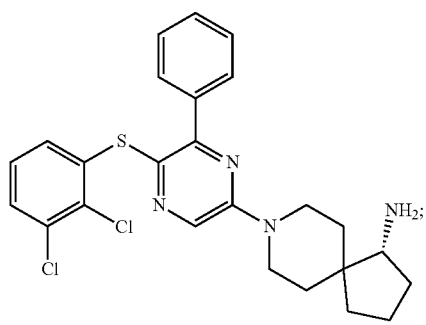
19
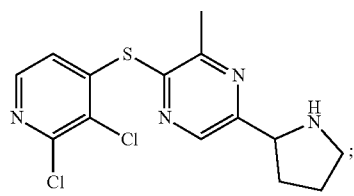
20
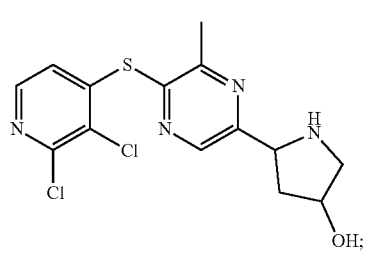
21
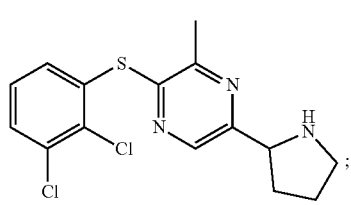
22
514
-continued
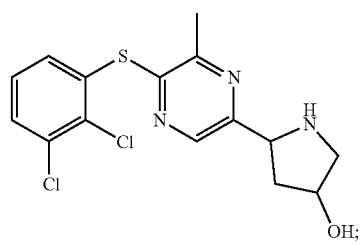
23
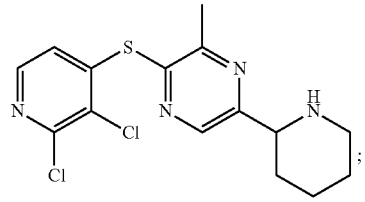
24
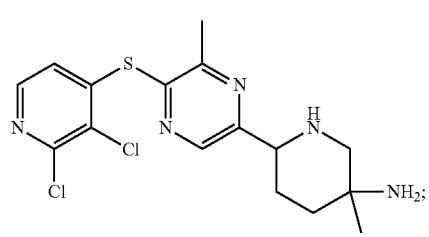
25
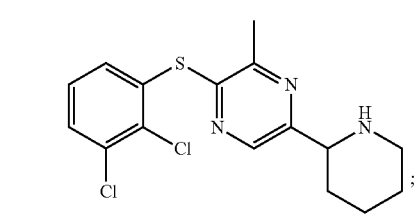
26
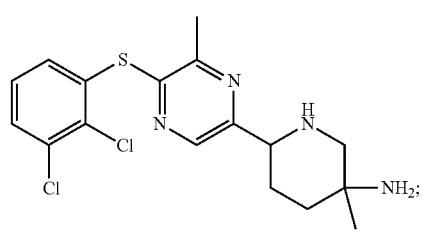
27
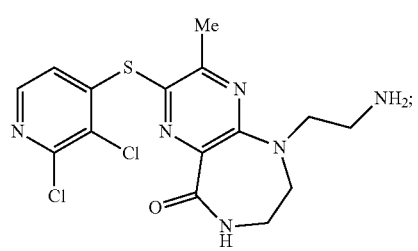
28
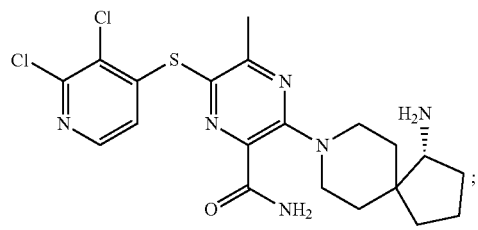
29

515
-continued
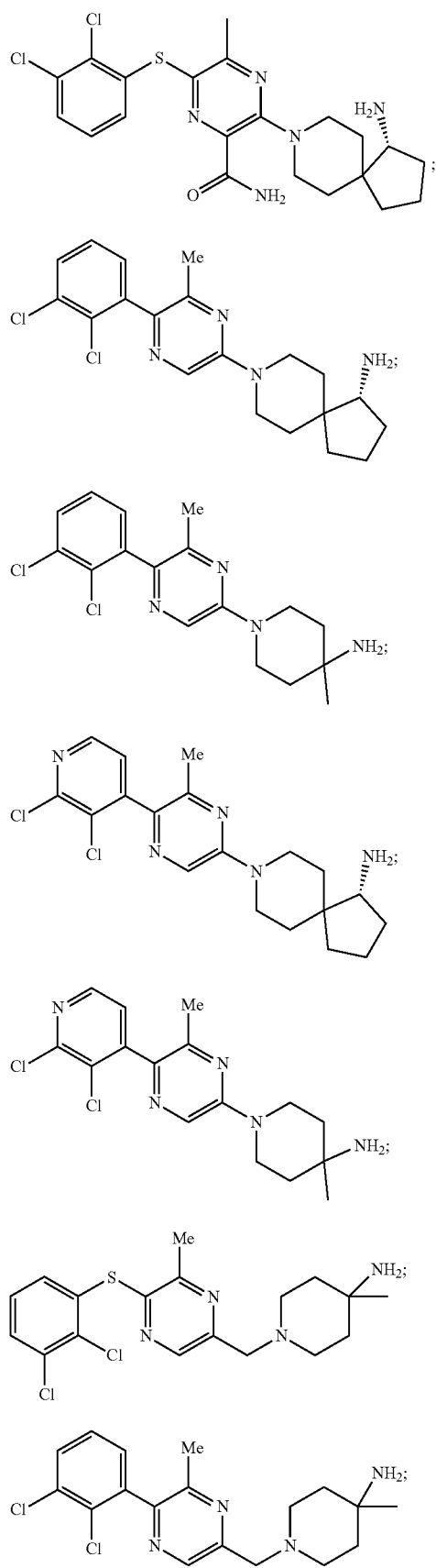
516
-continued
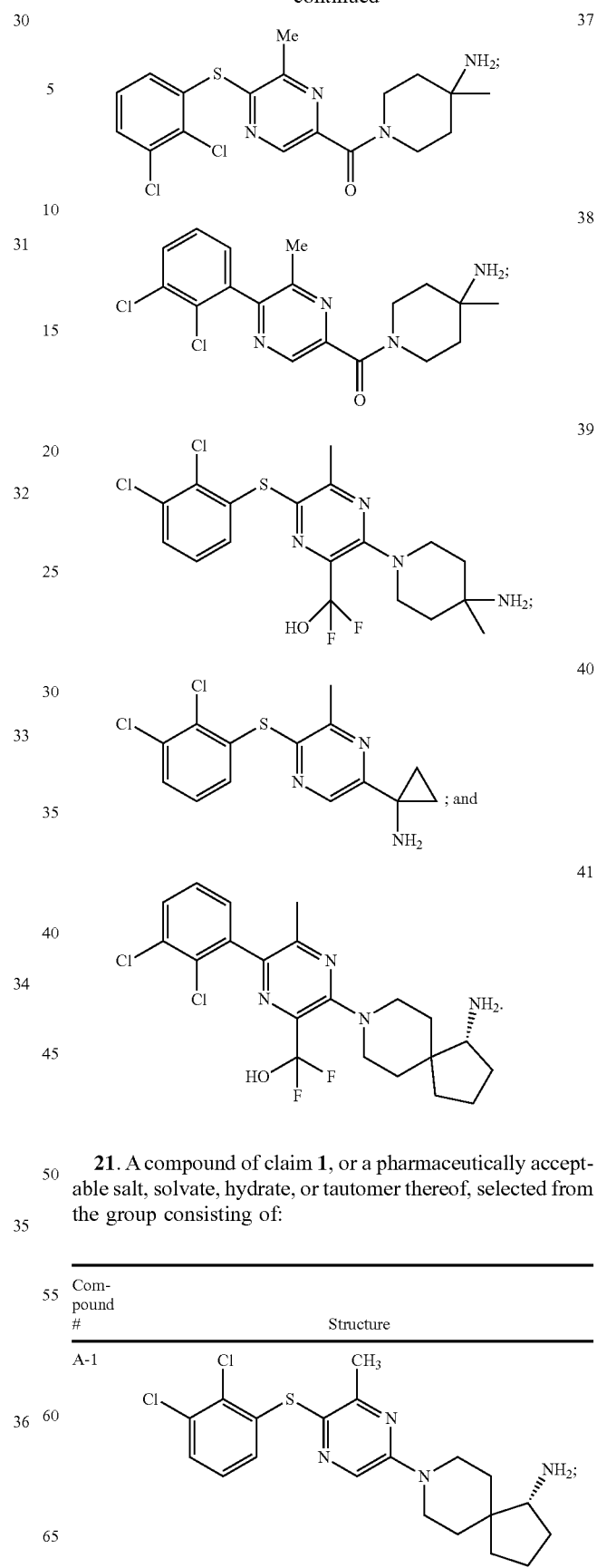
21. A compound of claim 1, or a pharmaceutically acceptable salt, solvate, hydrate, or tautomer thereof, selected from the group consisting of:

-continued

| Compound # | Structure |
|---|---|
| A-2 | (2,3-dichlorophenylthio)-3-methylpyrazine with 4-methyl-4-aminopiperidine |
| A-3 | (2,3-dichlorophenylthio)-3-methylpyrazine with 4-methyl-4-(methylamino)piperidine |
| A-4 | (2,3-dichlorophenylthio)-3-methylpyrazine with 4-methyl-4-(aminomethyl)piperidine |
| A-5 | (2,3-dichlorophenylthio)-3-methylpyrazine with 4-(pyridin-3-yl)-4-(aminomethyl)piperidine |
| A-6 | (2-amino-3-chloropyridin-4-ylthio)-3-methylpyrazine with 2-amino-8-azaspiro[4.5]decane |
| A-7 | (2-amino-3-chloropyridin-4-ylthio)-3-methylpyrazine with 4-methyl-4-aminopiperidine |

-continued

| Compound # | Structure |
|---|---|
| A-8 | (3-amino-2-chlorophenylthio)-3-methylpyrazine with 2-amino-8-azaspiro[4.5]decane |
| A-9 | (2-amino-3-chloropyridin-4-ylthio)-3-methylpyrazine with 4-methyl-4-(aminomethyl)piperidine |
| A-10 | (2,3-difluorophenylthio)-3-methylpyrazine with 2-amino-8-azaspiro[4.5]decane |
| A-11 | (2,3-difluorophenylthio)-3-methylpyrazine with 4-methyl-4-aminopiperidine |
| A-12 | (2,3-dichloropyridin-4-ylthio)-3-methylpyrazine with 2-amino-8-azaspiro[4.5]decane |
| A-14 | (2,3-dichlorophenylthio)-3-ethylpyrazine with 2-amino-8-azaspiro[4.5]decane |

-continued
| Compound # | Structure |
|---|---|
| A-15 | 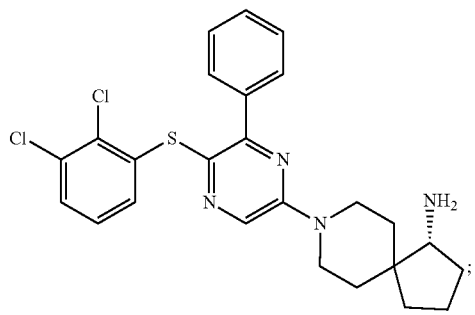 [SMILES: N[C@@H]1CCCC12CCN(c1cnc(Sc3cccc(Cl)c3Cl)c(-c3ccccc3)n1)CC2] |
| A-16 | 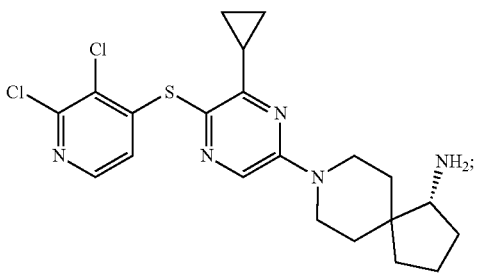 [SMILES: N[C@@H]1CCCC12CCN(c1cnc(Sc3ccnc(Cl)c3Cl)c(C3CC3)n1)CC2] |
| A-17 | 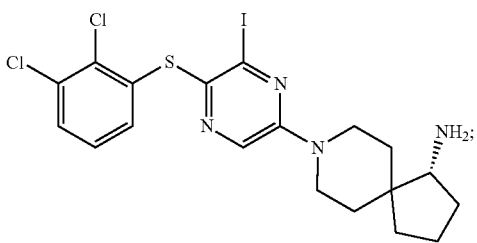 [SMILES: N[C@@H]1CCCC12CCN(c1cnc(Sc3cccc(Cl)c3Cl)c(I)n1)CC2] |
| A-18 | 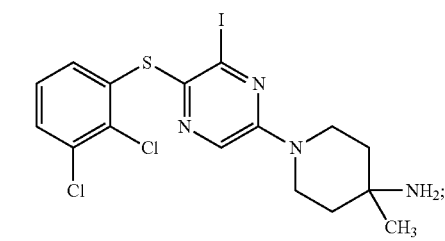 [SMILES: CC1(N)CCN(c2cnc(Sc3cccc(Cl)c3Cl)c(I)n2)CC1] |
| A-19 | 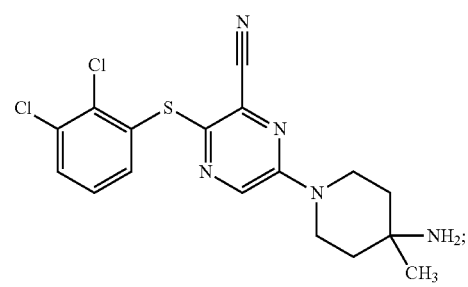 |
-continued
| Compound # | Structure |
|---|---|
| A-20 | 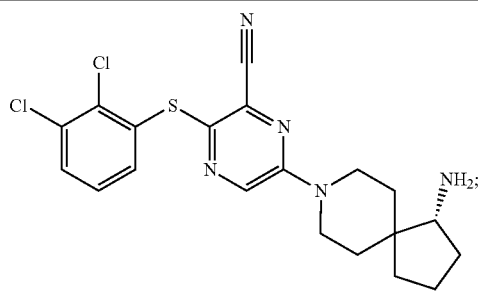 |
| A-21 | 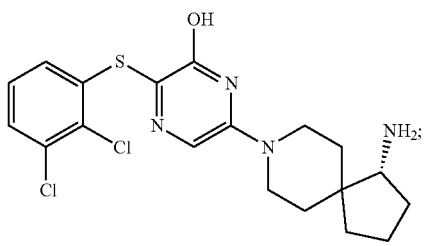 [SMILES: N[C@@H]1CCCC12CCN(c1cnc(Sc3cccc(Cl)c3Cl)c(O)n1)CC2] |
| A-22 | 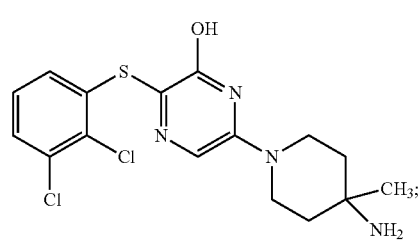 [SMILES: CC1(N)CCN(c2cnc(Sc3cccc(Cl)c3Cl)c(O)n2)CC1] |
| A-23 | 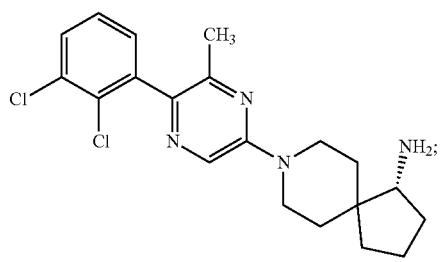 |
| A-24 | 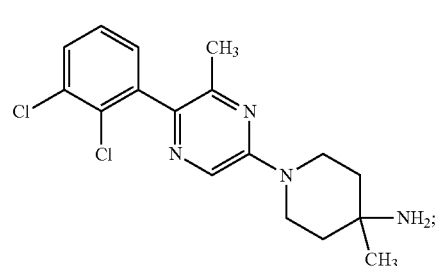 |
| A-25 | 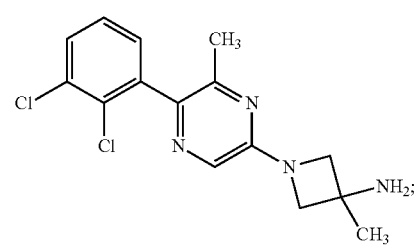 [SMILES: Cc1nc(N2CC(C)(N)C2)cnc1-c1cccc(Cl)c1Cl] |

| Compound # | Structure |
|---|---|
| A-26 | 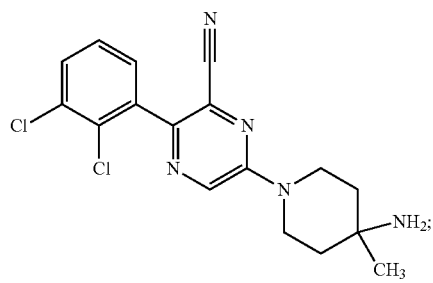 [SMILES: CC1(N)CCN(c2cnc(-c3cccc(Cl)c3Cl)c(C#N)n2)CC1] |
| A-27 | 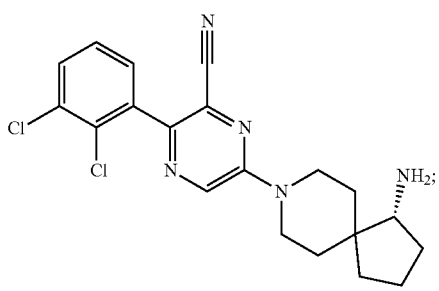 [SMILES: N#Cc1nc(N2CCC3(CCC[C@H]3N)CC2)cnc1-c1cccc(Cl)c1Cl] |
| A-28 | 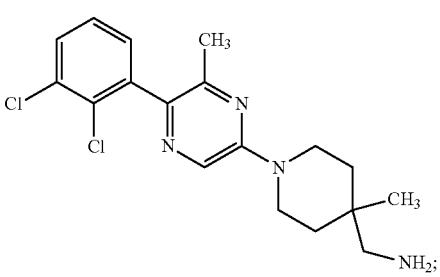 [SMILES: Cc1nc(N2CCC(C)(CN)CC2)cnc1-c1cccc(Cl)c1Cl] |
| A-29 | 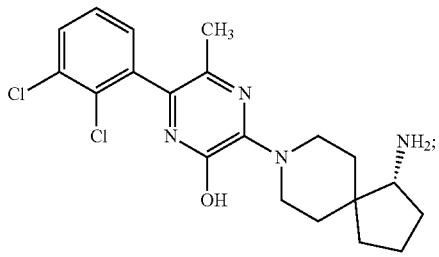 |
| A-30 | 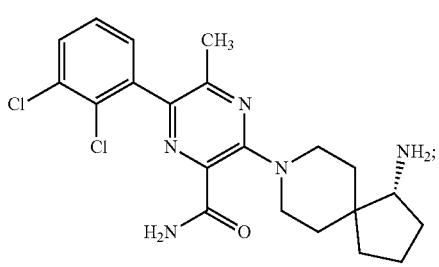 [SMILES: Cc1nc(N2CCC3(CCC[C@H]3N)CC2)c(C(N)=O)nc1-c1cccc(Cl)c1Cl] |
| Compound # | Structure |
|---|---|
| A-31 | 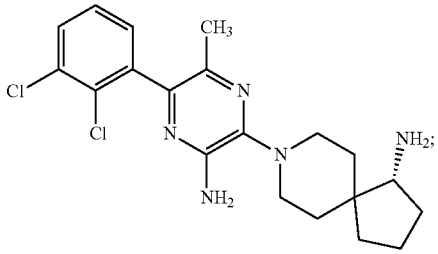 |
| A-32 | 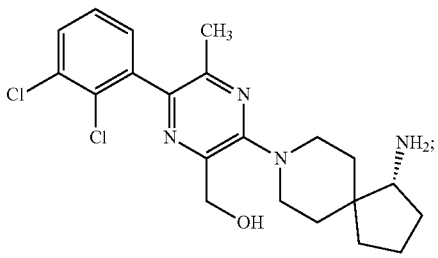 |
| A-33 | 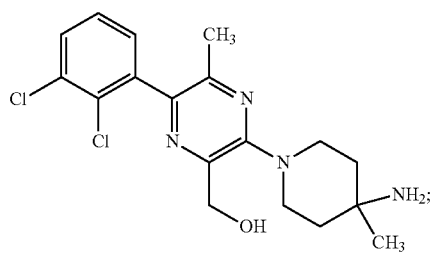 |
| A-35 | 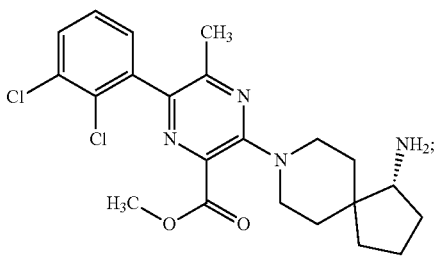 [SMILES: COC(=O)c1nc(-c2cccc(Cl)c2Cl)c(C)nc1N1CCC2(CCC[C@H]2N)CC1] |
| A-36 | 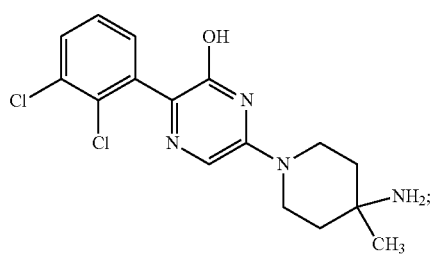 |
| A-37 | 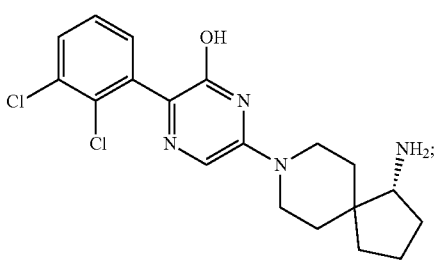 [SMILES: N[C@@H]1CCCC12CCN(c1cnc(-c3cccc(Cl)c3Cl)c(O)n1)CC2] |

| Compound # | Structure |
|---|---|
| A-38 | 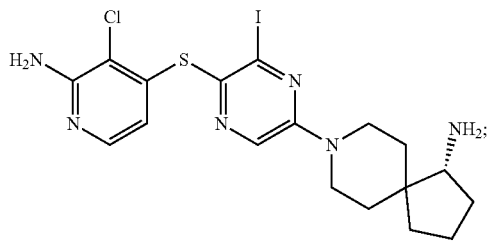 [SMILES: Nc1nccc(Sc2ncc(N3CCC4(CCC[C@H]4N)CC3)nc2I)c1Cl] |
| A-39 | 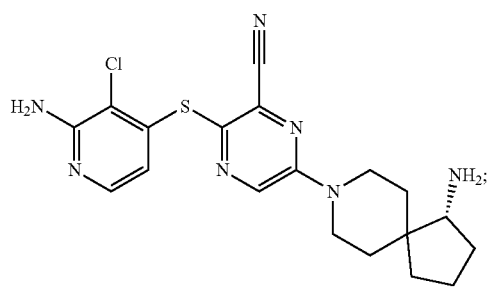 [SMILES: N#Cc1nc(N2CCC3(CCC[C@H]3N)CC2)cnc1Sc1ccnc(N)c1Cl] |
| A-40 | 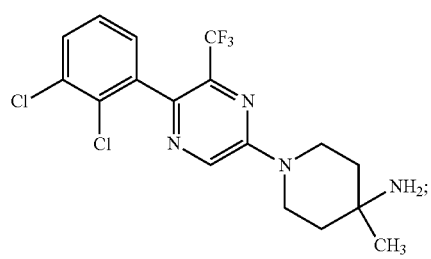 [SMILES: CC1(N)CCN(c2cnc(-c3cccc(Cl)c3Cl)c(C(F)(F)F)n2)CC1] |
| A-41 | 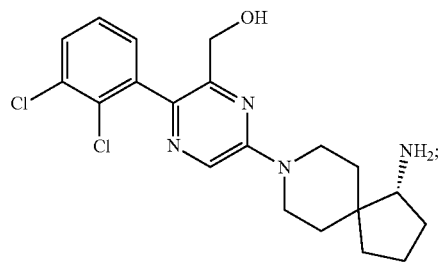 [SMILES: N[C@@H]1CCCC12CCN(c1cnc(-c3cccc(Cl)c3Cl)c(CO)n1)CC2] |
| A-42 | 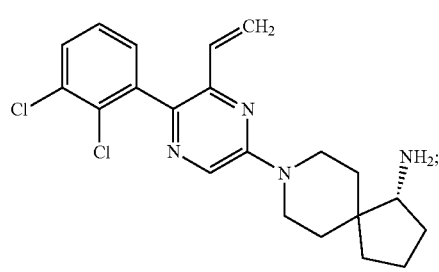 [SMILES: C=Cc1nc(N2CCC3(CCC[C@H]3N)CC2)cnc1-c1cccc(Cl)c1Cl] |
| A-43 | 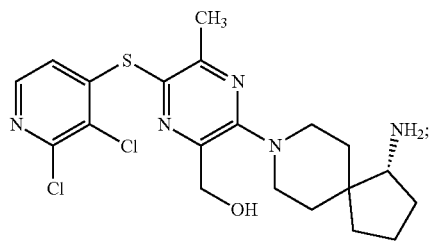 [SMILES: Cc1nc(N2CCC3(CCC[C@H]3N)CC2)c(CO)nc1Sc1ccnc(Cl)c1Cl] |
| A-44 | 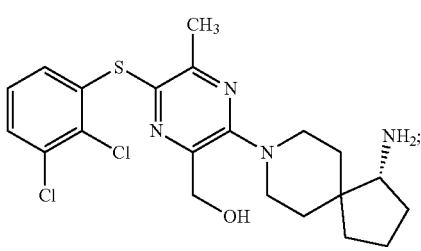 [SMILES: Cc1nc(N2CCC3(CCC[C@H]3N)CC2)c(CO)nc1Sc1cccc(Cl)c1Cl] |
| A-45 | 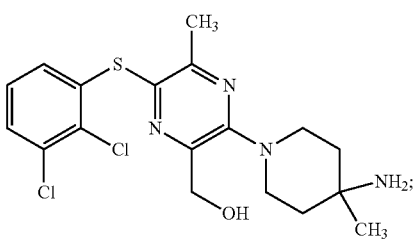 [SMILES: Cc1nc(N2CCC(C)(N)CC2)c(CO)nc1Sc1cccc(Cl)c1Cl] |
| A-46 | 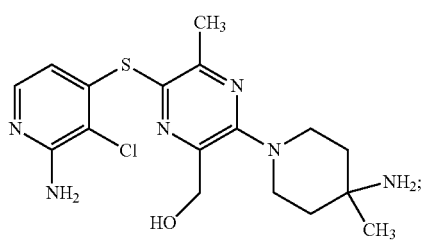 [SMILES: Cc1nc(N2CCC(C)(N)CC2)c(CO)nc1Sc1ccnc(N)c1Cl] |
| A-47 | 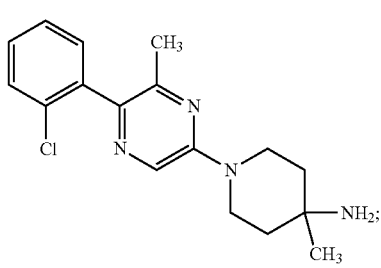 [SMILES: Cc1nc(N2CCC(C)(N)CC2)cnc1-c1ccccc1Cl] |
| A-48 | 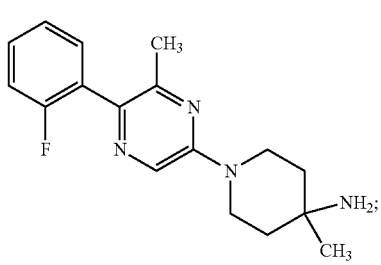 [SMILES: Cc1nc(N2CCC(C)(N)CC2)cnc1-c1ccccc1F] |

-continued

| Compound # | Structure |
|---|---|
| A-49 | (2,3-difluorophenyl)-3-methylpyrazine with 4-amino-4-methylpiperidine |
| A-50 | (4-chlorophenyl)-3-methylpyrazine with 4-amino-4-methylpiperidine |
| A-51 | (5,6-dichloropyridin-3-yl)-3-methylpyrazine with 4-amino-4-methylpiperidine |
| A-52 | 1-(4-chlorophenyl)vinyl-3-methylpyrazine with 4-amino-4-methylpiperidine |
| A-53 | (2,3-dichlorophenylthio)-3-methylpyrazine with 3-aminotropane |
| A-54 | (2,3-dichlorophenylthio)-3-methylpyrazine with 2-amino-2-azaspiro[3.3]heptane |

-continued

| Compound # | Structure |
|---|---|
| A-55 | (2,3-dichlorophenylthio)-3-methylpyrazine with 4-aminoazepane |
| A-56 | (2,3-dichlorophenylthio)-3-methylpyrazine with azaspiro cyclopentyl amine |
| A-57 | (2,3-dichlorophenylthio)-3-methylpyrazine with 1,4-diazepane |
| A-58 | (2,3-dichlorophenylthio)-3-methylpyrazine with 2-amino-7-azaspiro[3.5]nonane |
| A-59 | (2,3-dichlorophenylthio)-3-methylpyrazine with 2-(azetidin-3-yl)ethylamine |
| A-60 | (2,3-dichlorophenylthio)-3-methylpyrazine with 2-azaspiro[3.3]heptan-6-ylmethylamine |
| A-61 | (2,3-dichlorophenylthio)-3-methylpyrazine with (pyrrolidin-3-yl)methylamine |

| Compound # | Structure |
|---|---|
| A-62 | 3-methyl-6-[(4-aminobutyl)amino]-2-[(2,3-dichlorophenyl)thio]pyrazine |
| A-63 | 3-methyl-6-[(piperidin-4-ylmethyl)amino]-2-[(2,3-dichlorophenyl)thio]pyrazine |
| A-64 | 3-methyl-6-[(3-aminopropyl)amino]-2-[(2,3-dichlorophenyl)thio]pyrazine |
| A-65 | 3-methyl-6-[(N-methyl-tropan-3-yl)amino]-2-[(2,3-dichlorophenyl)thio]pyrazine |
| A-66 | 3-methyl-6-(3-azabicyclo[3.2.1]octan-8-ylamino)-2-[(2,3-dichlorophenyl)thio]pyrazine |
| A-67 | 3-methyl-6-(1-amino-3-azabicyclo[3.1.0]hexan-3-yl)-2-[(2,3-dichlorophenyl)thio]pyrazine |
| A-68 | 3-methyl-6-[((3-hydroxypiperidin-4-yl)methyl)amino]-2-[(2,3-dichlorophenyl)thio]pyrazine |
| A-69 | 3-methyl-6-[(cis-3-aminocyclopentyl)amino]-2-[(2,3-dichlorophenyl)thio]pyrazine |
| A-70 | 3-methyl-6-(tropan-3-ylamino)-2-[(2,3-dichlorophenyl)thio]pyrazine |
| A-71 | 3-methyl-6-[(2-aminoethyl)amino]-2-[(2,3-dichlorophenyl)thio]pyrazine |
| A-72 | 3-methyl-6-[(piperazin-2-ylmethyl)amino]-2-[(2,3-dichlorophenyl)thio]pyrazine |
| A-73 | 3-methyl-2-(2,3-dichloropyridin-4-yl)-6-[1-amino-2-azaspiro[4.5]decan-8-yl]pyrazine |
| A-74 | 3-methyl-2-(2,3-dichloropyridin-4-yl)-6-[4-amino-4-methylpiperidin-1-yl]pyrazine |

[Note: Structural drawings of compounds A-62 through A-74 are shown. Descriptions above are interpretive of the visible chemical structures.]

| Compound # | Structure |
|---|---|
| A-75 | 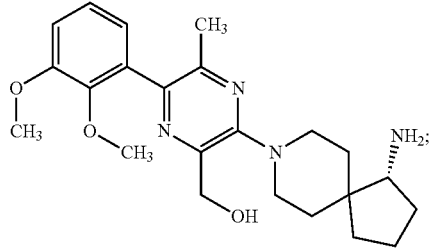 [SMILES: COc1cccc(-c2nc(CO)c(N3CCC4(CCC[C@H]4N)CC3)nc2C)c1OC] |
| A-76 | 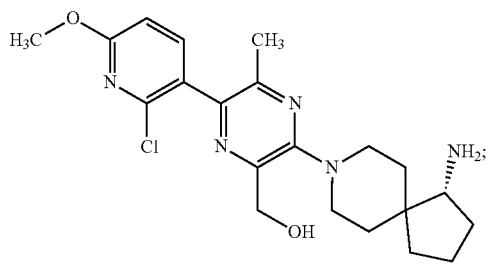 [SMILES: COc1ccc(-c2nc(CO)c(N3CCC4(CCC[C@H]4N)CC3)nc2C)c(Cl)n1] |
| A-77 | 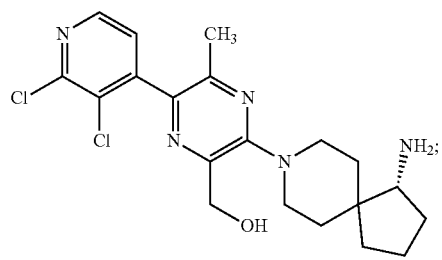 [SMILES: Cc1nc(N2CCC3(CCC[C@H]3N)CC2)c(CO)nc1-c1ccnc(Cl)c1Cl] |
| A-78 | 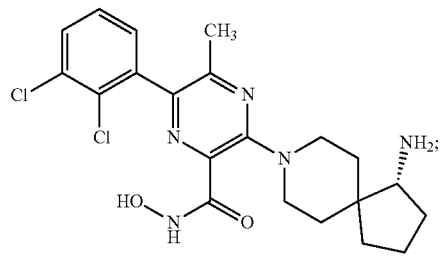 [SMILES: Cc1nc(N2CCC3(CCC[C@H]3N)CC2)c(C(=O)NO)nc1-c1cccc(Cl)c1Cl] |
| A-79 | 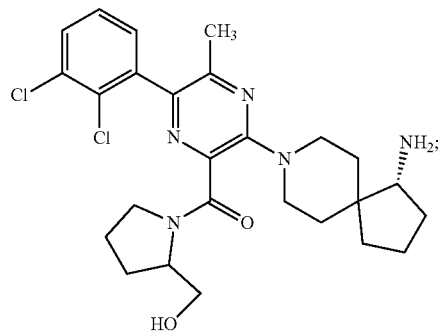 [SMILES: Cc1nc(N2CCC3(CCC[C@H]3N)CC2)c(C(=O)N2CCCC2CO)nc1-c1cccc(Cl)c1Cl] |
| Compound # | Structure |
|---|---|
| A-80 | 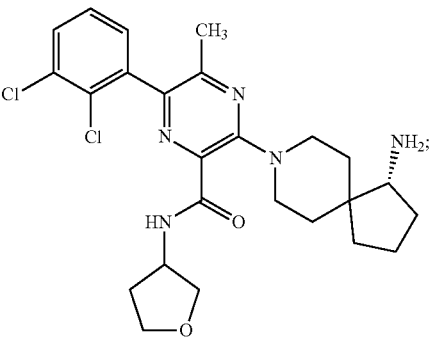 [SMILES: Cc1nc(N2CCC3(CCC[C@H]3N)CC2)c(C(=O)NC2CCOC2)nc1-c1cccc(Cl)c1Cl] |
| A-81 | 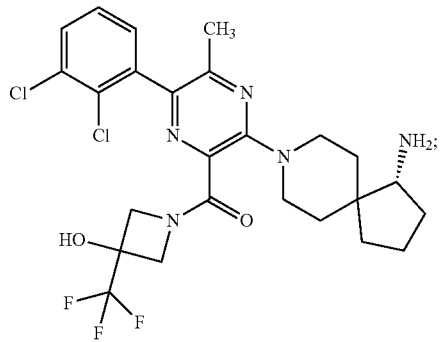 [SMILES: Cc1nc(N2CCC3(CCC[C@H]3N)CC2)c(C(=O)N2CC(O)(C(F)(F)F)C2)nc1-c1cccc(Cl)c1Cl] |
| A-82 | 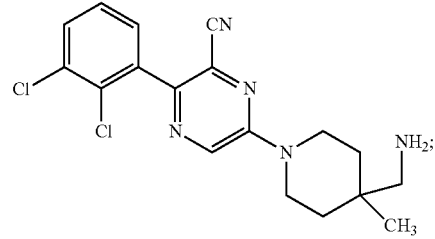 [SMILES: CC1(CN)CCN(c2cnc(-c3cccc(Cl)c3Cl)c(C#N)n2)CC1] |
| A-83 | 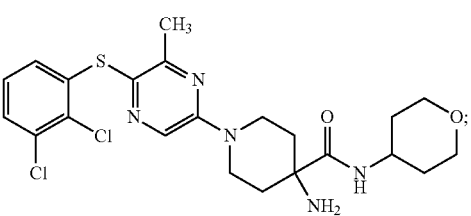 [SMILES: Cc1nc(N2CCC(N)(C(=O)NC3CCOCC3)CC2)cnc1Sc1cccc(Cl)c1Cl] |
| A-84 | 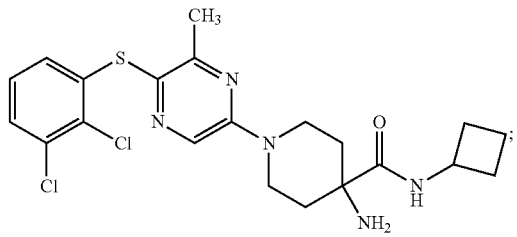 [SMILES: Cc1nc(N2CCC(N)(C(=O)NC3CCC3)CC2)cnc1Sc1cccc(Cl)c1Cl] |

| Compound # | Structure |
|---|---|
| A-85 | 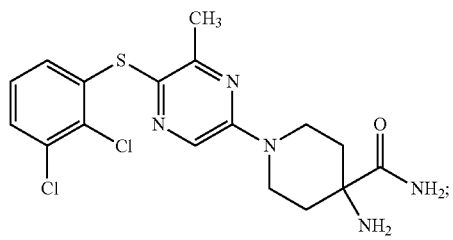 [SMILES: Cc1nc(N2CCC(N)(C(N)=O)CC2)cnc1Sc1cccc(Cl)c1Cl] |
| A-86 | 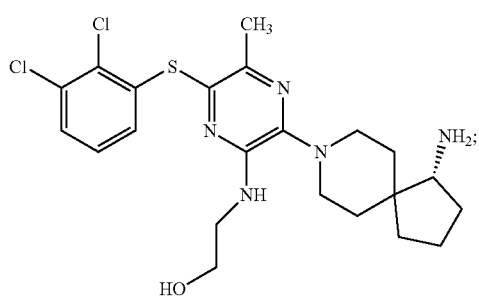 [SMILES: Cc1nc(N2CCC3(CCC[C@H]3N)CC2)c(NCCO)nc1Sc1cccc(Cl)c1Cl] |
| A-87 | 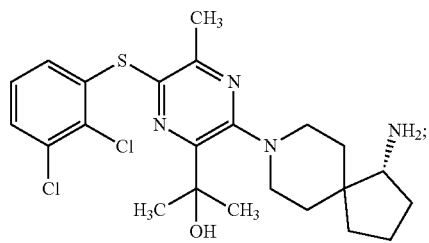 [SMILES: Cc1nc(N2CCC3(CCC[C@H]3N)CC2)c(C(C)(C)O)nc1Sc1cccc(Cl)c1Cl] |
| A-88 | 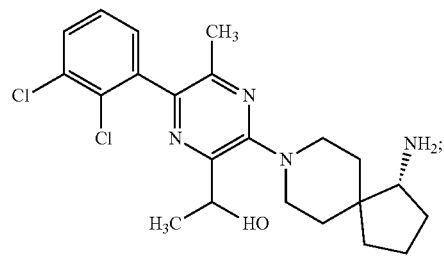 [SMILES: Cc1nc(N2CCC3(CCC[C@H]3N)CC2)c(C(C)O)nc1-c1cccc(Cl)c1Cl] |
| A-89 | 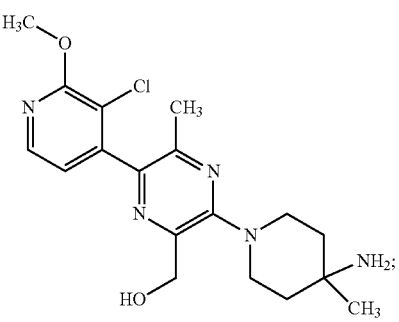 [SMILES: COc1nccc(-c2nc(CO)c(N3CCC(C)(N)CC3)nc2C)c1Cl] |
| A-90 | 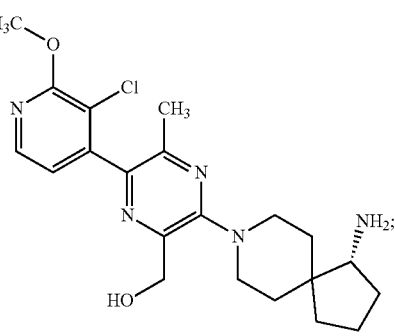 |
| A-91 | 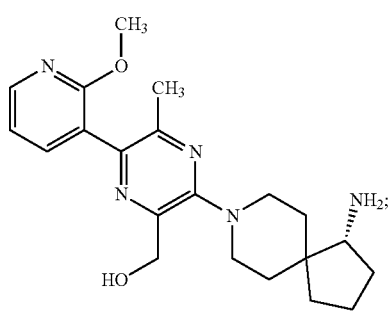 [SMILES: COc1ncccc1-c1nc(CO)c(N2CCC3(CCC[C@H]3N)CC2)nc1C] |
| A-92 | 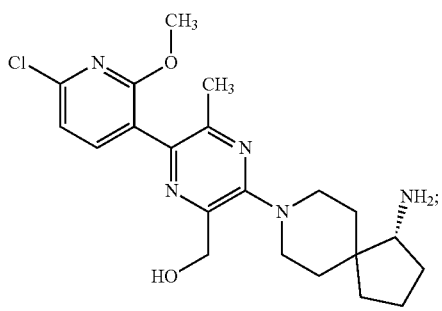 [SMILES: COc1nc(Cl)ccc1-c1nc(CO)c(N2CCC3(CCC[C@H]3N)CC2)nc1C] |
| A-93 | 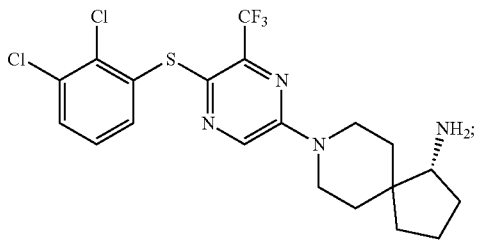 |
| A-94 | 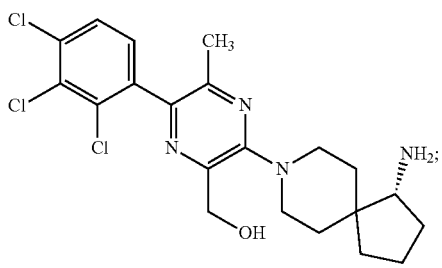 [SMILES: Cc1nc(N2CCC3(CCC[C@H]3N)CC2)c(CO)nc1-c1ccc(Cl)c(Cl)c1Cl] |

| Compound # | Structure |
|---|---|
| A-95 | 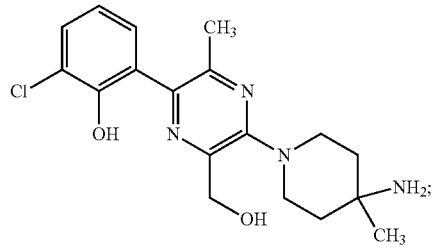 [SMILES: Cc1nc(N2CCC(C)(N)CC2)c(CO)nc1-c1cccc(Cl)c1O] |
| A-96 | 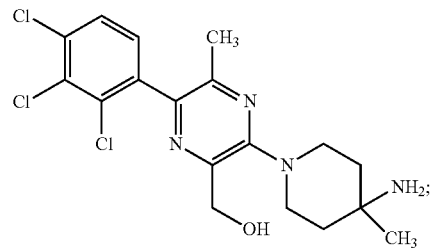 [SMILES: Cc1nc(N2CCC(C)(N)CC2)c(CO)nc1-c1ccc(Cl)c(Cl)c1Cl] |
| A-97 | 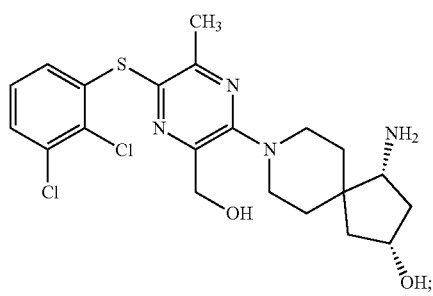 [SMILES: Cc1nc(N2CCC3(CC2)C[C@@H](O)C[C@H]3N)c(CO)nc1Sc1cccc(Cl)c1Cl] |
| A-98 | 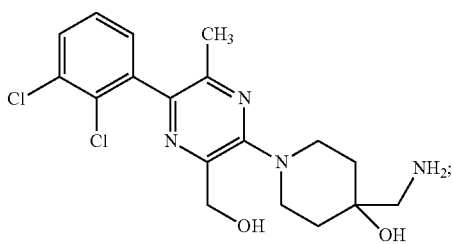 [SMILES: Cc1nc(N2CCC(O)(CN)CC2)c(CO)nc1-c1cccc(Cl)c1Cl] |
| A-99 | 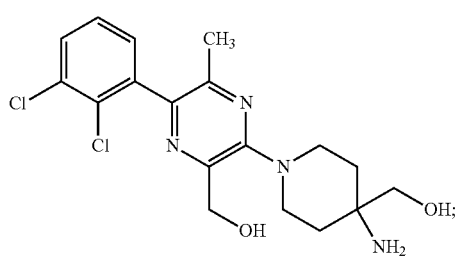 [SMILES: Cc1nc(N2CCC(N)(CO)CC2)c(CO)nc1-c1cccc(Cl)c1Cl] |
| A-100 | 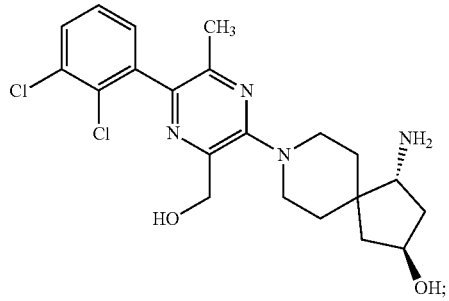 [SMILES: Cc1nc(N2CCC3(CC2)C[C@H](O)C[C@H]3N)c(CO)nc1-c1cccc(Cl)c1Cl] |
| A-101 | 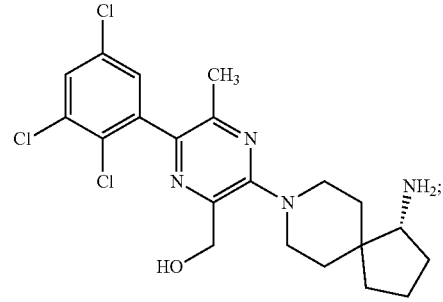 [SMILES: Cc1nc(N2CCC3(CCC[C@H]3N)CC2)c(CO)nc1-c1cc(Cl)cc(Cl)c1Cl] |
| A-102 | 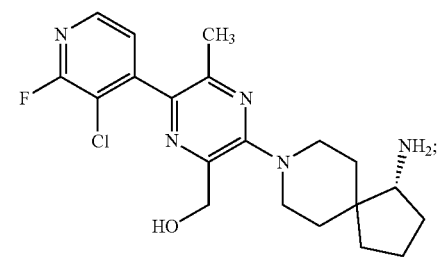 [SMILES: Cc1nc(N2CCC3(CCC[C@H]3N)CC2)c(CO)nc1-c1ccnc(F)c1Cl] |
| A-103 | 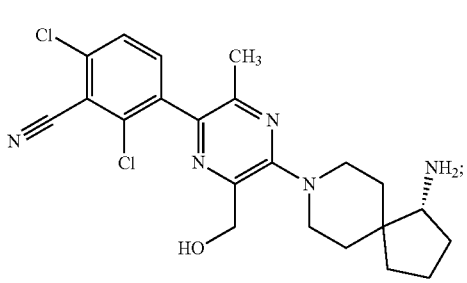 [SMILES: Cc1nc(N2CCC3(CCC[C@H]3N)CC2)c(CO)nc1-c1ccc(Cl)c(C#N)c1Cl] |
| A-104 | 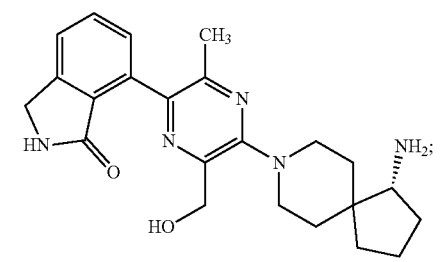 [SMILES: Cc1nc(N2CCC3(CCC[C@H]3N)CC2)c(CO)nc1-c1cccc2c1C(=O)NC2] |

| Compound # | Structure |
|---|---|
| A-105 | 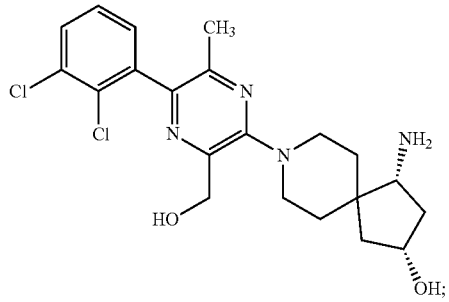 [SMILES: Cc1nc(N2CCC3(CC2)C[C@@H](O)C[C@H]3N)c(CO)nc1-c1cccc(Cl)c1Cl] |
| A-106 | 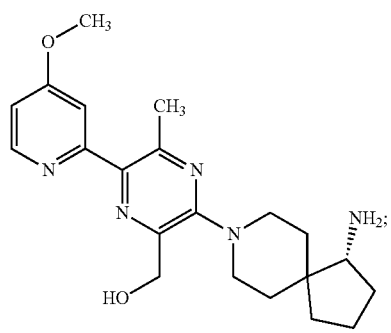 [SMILES: COc1ccnc(-c2nc(CO)c(N3CCC4(CCC[C@H]4N)CC3)nc2C)c1] |
| A-107 | 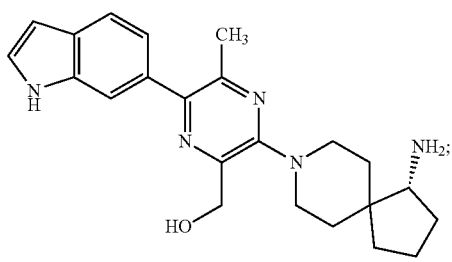 [SMILES: Cc1nc(N2CCC3(CCC[C@H]3N)CC2)c(CO)nc1-c1ccc2cc[nH]c2c1] |
| A-108 | 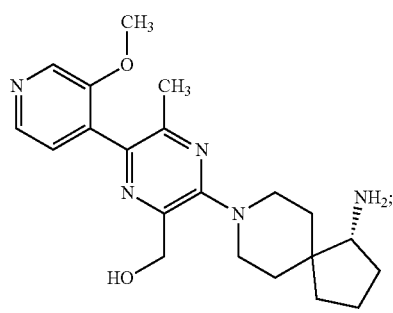 [SMILES: COc1cnccc1-c1nc(CO)c(N2CCC3(CCC[C@H]3N)CC2)nc1C] |
| A-109 | 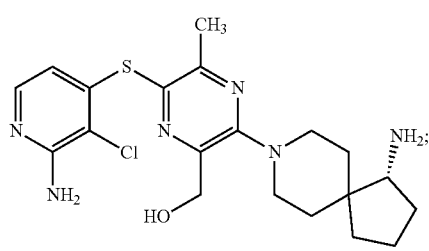 [SMILES: Cc1nc(N2CCC3(CCC[C@H]3N)CC2)c(CO)nc1Sc1ccnc(N)c1Cl] |
| A-110 | 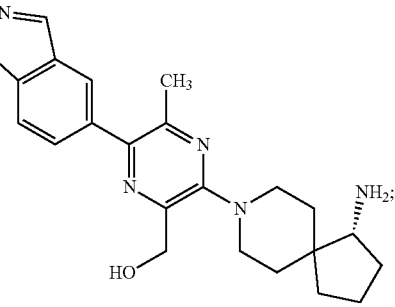 |
| A-111 | 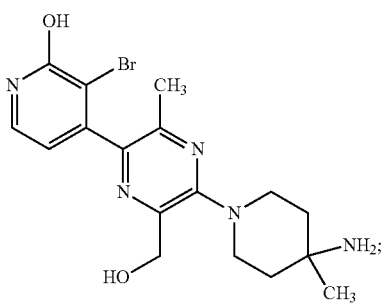 [SMILES: Cc1nc(N2CCC(C)(N)CC2)c(CO)nc1-c1ccnc(O)c1Br] |
| A-112 | 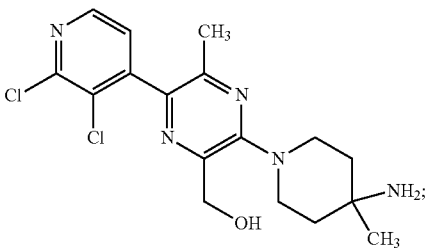 [SMILES: Cc1nc(N2CCC(C)(N)CC2)c(CO)nc1-c1ccnc(Cl)c1Cl] |
| A-113 | 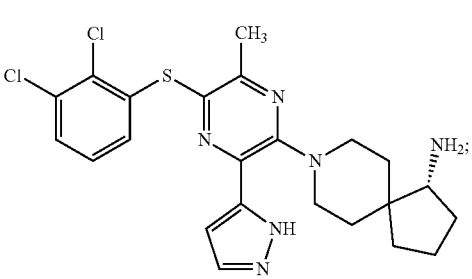 [SMILES: Cc1nc(N2CCC3(CCC[C@H]3N)CC2)c(-c2ccn[nH]2)nc1Sc1cccc(Cl)c1Cl] |
| A-114 | 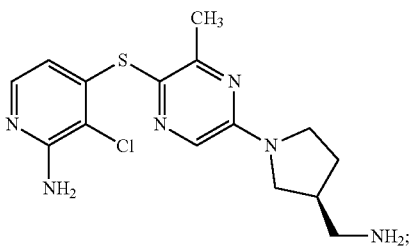 [SMILES: Cc1nc(N2CC[C@@H](CN)C2)cnc1Sc1ccnc(N)c1Cl] |

| Compound # | Structure |
|---|---|
| A-115 | 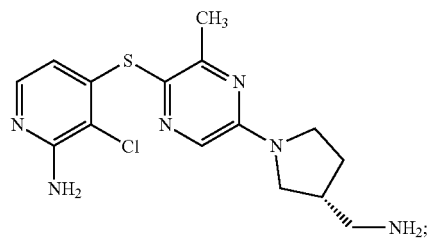 [SMILES: Cc1nc(N2CC[C@H](CN)C2)cnc1Sc1ccnc(N)c1Cl] |
| A-116 | 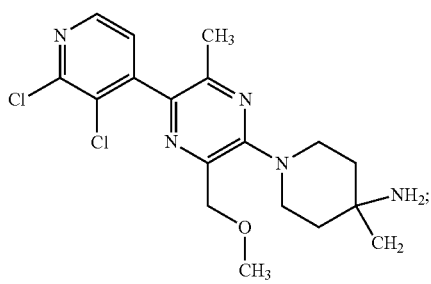 [SMILES: COCc1nc(-c2ccnc(Cl)c2Cl)c(C)nc1N1CCC(C)(N)CC1] |
| A-117 | 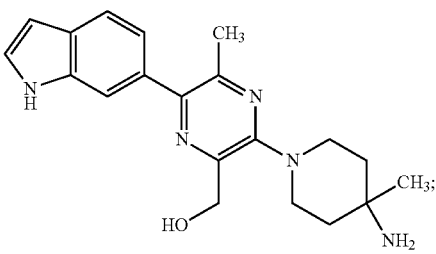 |
| A-118 | 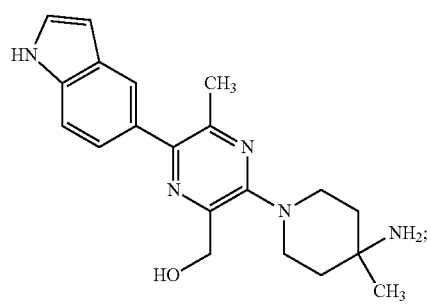 [SMILES: Cc1nc(N2CCC(C)(N)CC2)c(CO)nc1-c1ccc2[nH]ccc2c1] |
| A-119 | 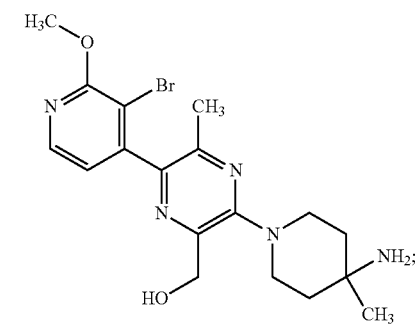 [SMILES: COc1nccc(-c2nc(CO)c(N3CCC(C)(N)CC3)nc2C)c1Br] |
| A-120 | 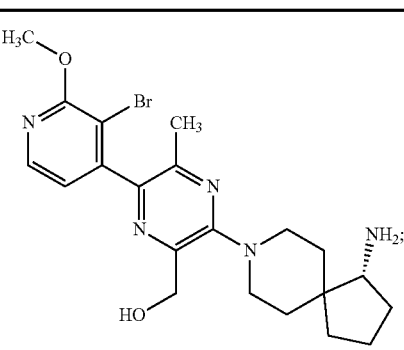 |
| A-121 | 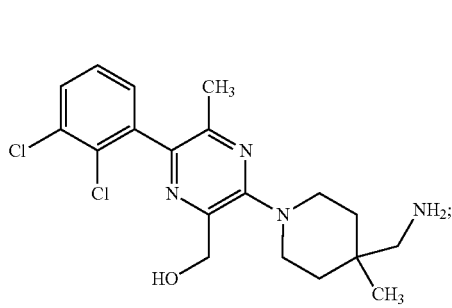 [SMILES: Cc1nc(N2CCC(C)(CN)CC2)c(CO)nc1-c1cccc(Cl)c1Cl] |
| A-122 | 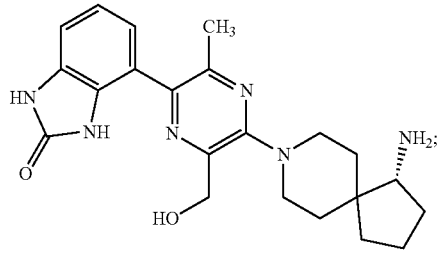 [SMILES: Cc1nc(N2CCC3(CCC[C@H]3N)CC2)c(CO)nc1-c1cccc2[nH]c(=O)[nH]c12] |
| A-123 | 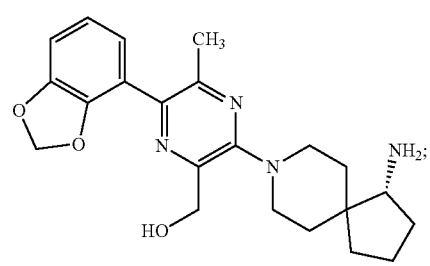 [SMILES: Cc1nc(N2CCC3(CCC[C@H]3N)CC2)c(CO)nc1-c1cccc2c1OCO2] |
| A-124 | 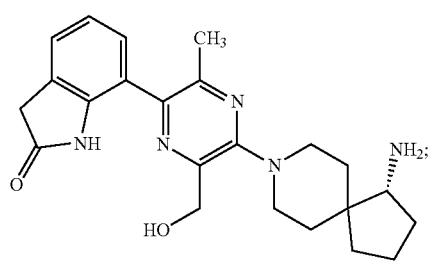 [SMILES: Cc1nc(N2CCC3(CCC[C@H]3N)CC2)c(CO)nc1-c1cccc2c1NC(=O)C2] |

| Compound # | Structure |
|---|---|
| A-125 | 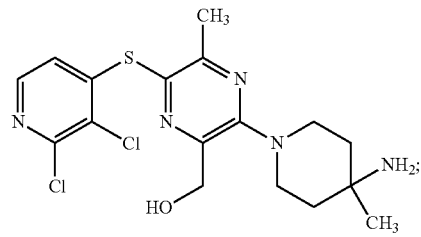 [SMILES: Cc1nc(N2CCC(C)(N)CC2)c(CO)nc1Sc1ccnc(Cl)c1Cl] |
| A-126 | 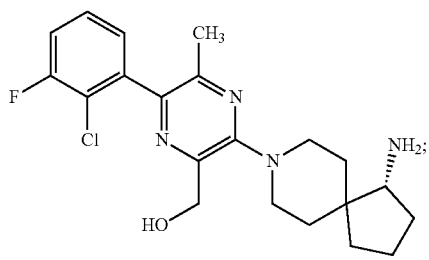 |
| A-127 | 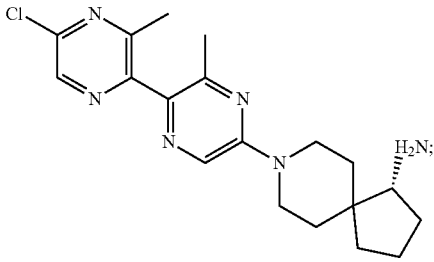 [SMILES: Cc1nc(Cl)cnc1-c1ncc(N2CCC3(CCC[C@H]3N)CC2)nc1C] |
| A-128 | 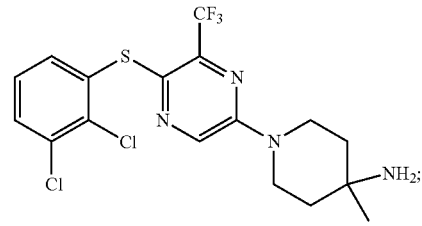 [SMILES: CC1(N)CCN(c2cnc(Sc3cccc(Cl)c3Cl)c(C(F)(F)F)n2)CC1] |
| A-129 | 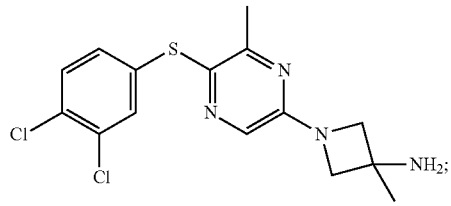 [SMILES: Cc1nc(N2CC(C)(N)C2)cnc1Sc1ccc(Cl)c(Cl)c1] |
| A-130 | 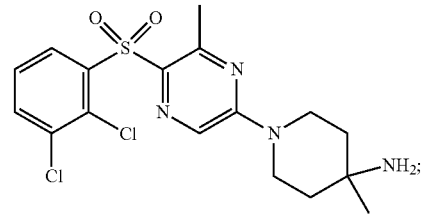 [SMILES: Cc1nc(N2CCC(C)(N)CC2)cnc1S(=O)(=O)c1cccc(Cl)c1Cl] |
| A-131 | 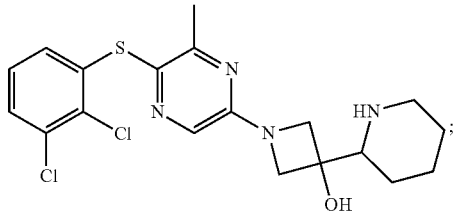 [SMILES: Cc1nc(N2CC(O)(C3CCCCN3)C2)cnc1Sc1cccc(Cl)c1Cl] |
| A-132 | 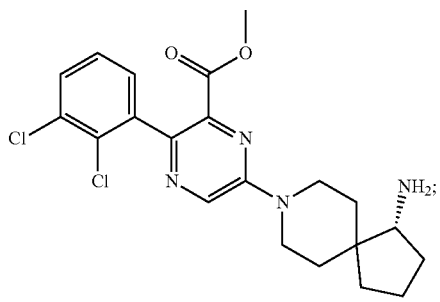 [SMILES: COC(=O)c1nc(N2CCC3(CCC[C@H]3N)CC2)cnc1-c1cccc(Cl)c1Cl] |
| A-133 | 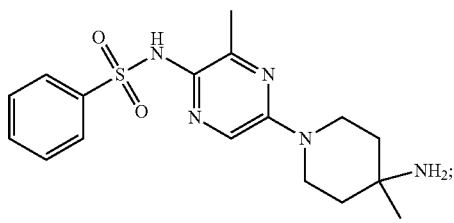 [SMILES: Cc1nc(N2CCC(C)(N)CC2)cnc1NS(=O)(=O)c1ccccc1] |
| A-134 | 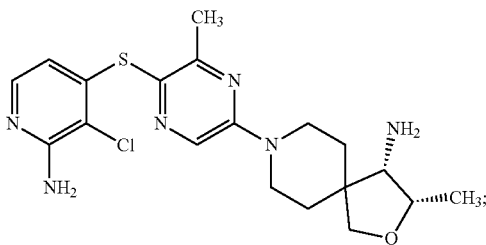 [SMILES: Cc1nc(N2CCC3(CC2)CO[C@@H](C)[C@H]3N)cnc1Sc1ccnc(N)c1Cl] |
| A-135 | 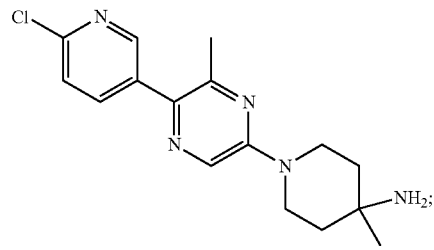 [SMILES: Cc1nc(N2CCC(C)(N)CC2)cnc1-c1ccc(Cl)nc1] |
| A-136 | 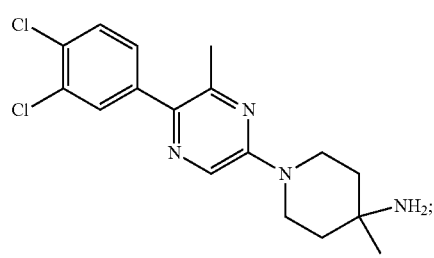 [SMILES: Cc1nc(N2CCC(C)(N)CC2)cnc1-c1ccc(Cl)c(Cl)c1] |

| Compound # | Structure |
|---|---|
| A-137 | 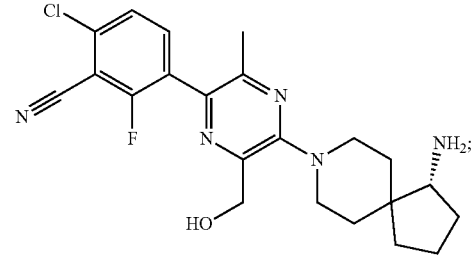 [SMILES: Cc1nc(N2CCC3(CCC[C@H]3N)CC2)c(CO)nc1-c1ccc(Cl)c(C#N)c1F] |
| A-138 | |
| A-139 | |
| A-140 | |
| A-141 | |
| Compound # | Structure |
|---|---|
| A-142 | 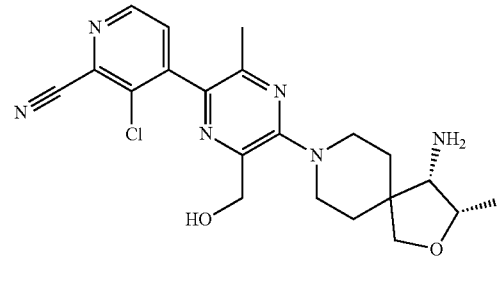 |
| A-143 | |
| A-144 | |
| A-145 | |
| A-146 | |
22. A compound of claim 1, or a pharmaceutically acceptable salt, solvate, hydrate, or tautomer thereof, selected from the group consisting of:

| Compound # | Structure |
|---|---|
| A-147 | 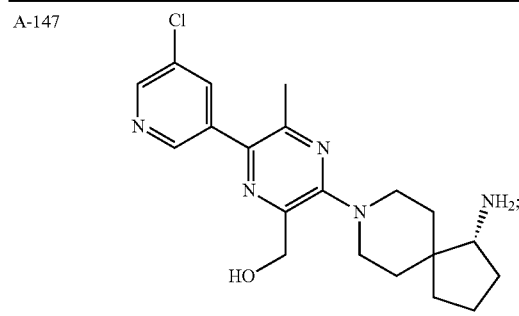 |
| A-148 | 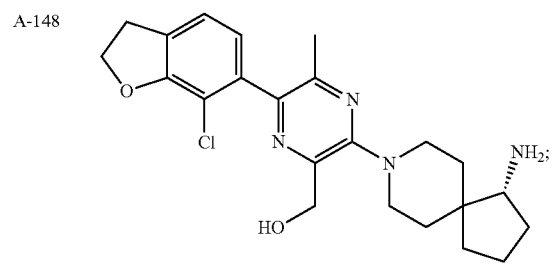 |
| A-149 | 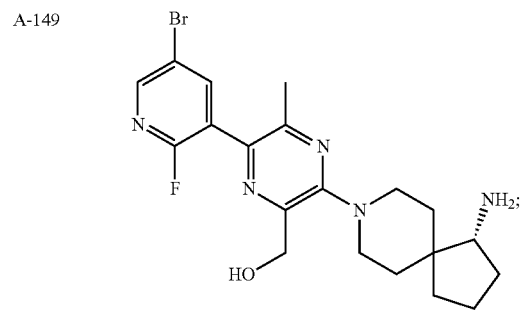 |
| A-150 | 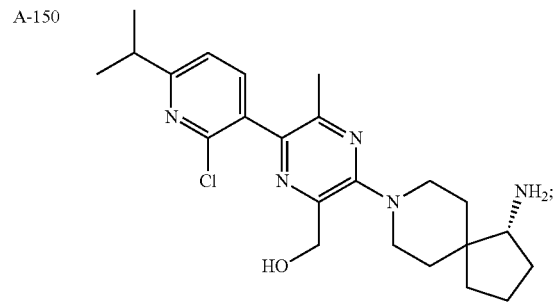 |
| A-151 | 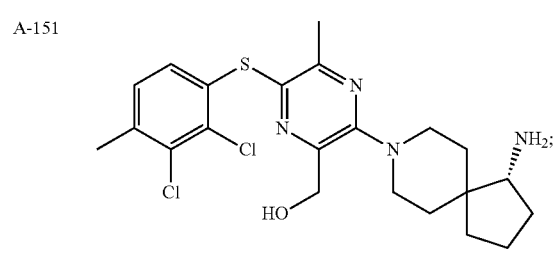 |
| Compound # | Structure |
|---|---|
| A-152 | 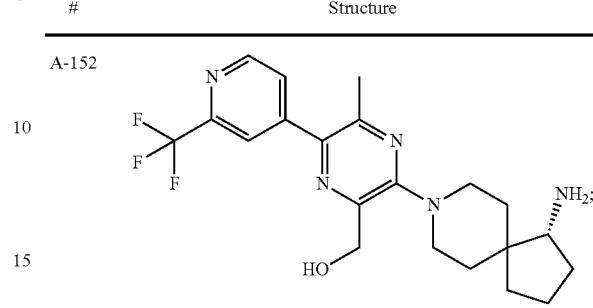 |
| A-153 | 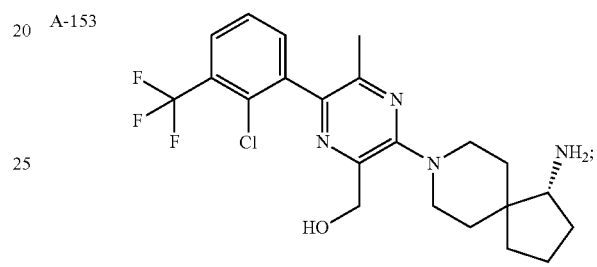 |
| A-154 | 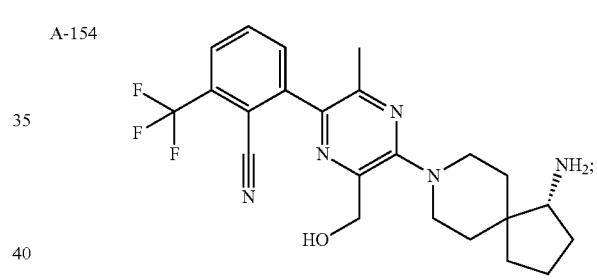 |
| A-155 | 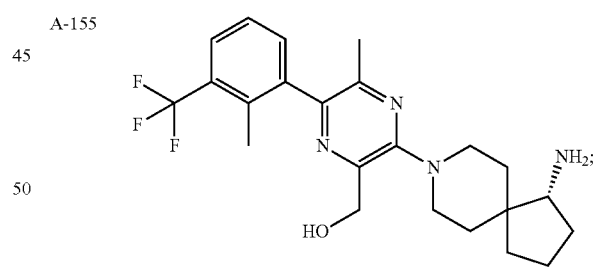 |
| A-156 | 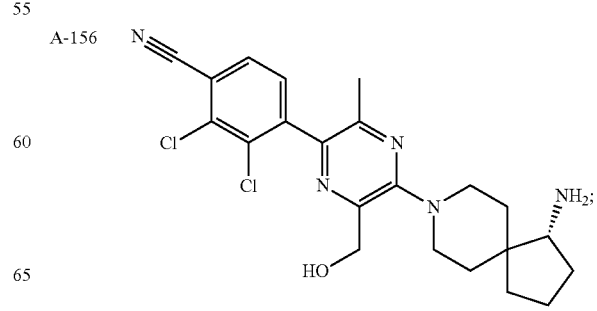 |

| Compound # | Structure |
|---|---|
| A-157 | 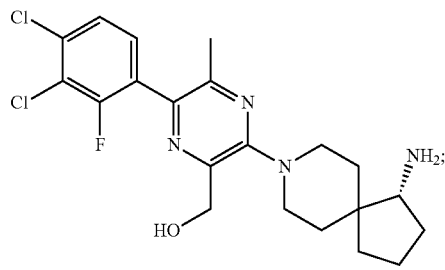 [SMILES: Cc1nc(N2CCC3(CCC[C@H]3N)CC2)c(CO)nc1-c1ccc(Cl)c(Cl)c1F] |
| A-158 | 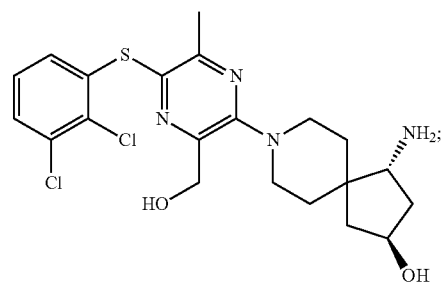 [SMILES: Cc1nc(N2CCC3(CC2)C[C@H](O)C[C@H]3N)c(CO)nc1Sc1cccc(Cl)c1Cl] |
| A-159 | 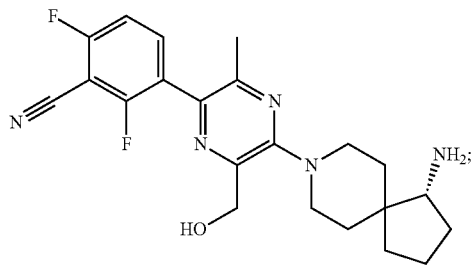 [SMILES: Cc1nc(N2CCC3(CCC[C@H]3N)CC2)c(CO)nc1-c1ccc(F)c(C#N)c1F] |
| A-160 | 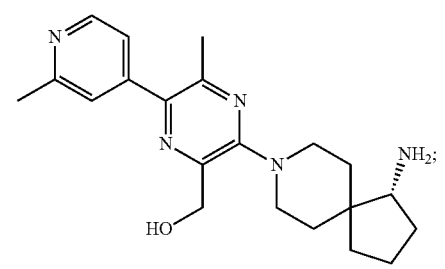 [SMILES: Cc1cc(-c2nc(CO)c(N3CCC4(CCC[C@H]4N)CC3)nc2C)ccn1] |
| A-161 | 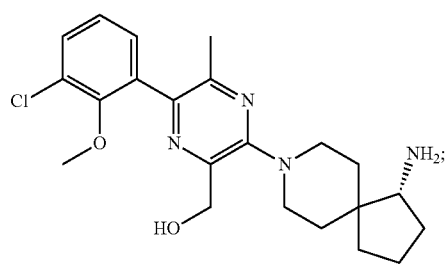 [SMILES: COc1c(Cl)cccc1-c1nc(CO)c(N2CCC3(CCC[C@H]3N)CC2)nc1C] |
| Compound # | Structure |
|---|---|
| A-162 | 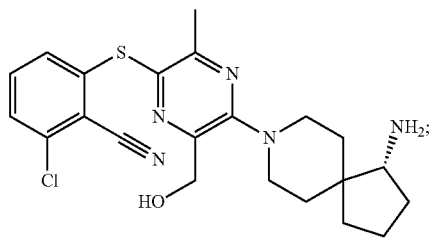 [SMILES: Cc1nc(N2CCC3(CCC[C@H]3N)CC2)c(CO)nc1Sc1cccc(Cl)c1C#N] |
| A-163 | 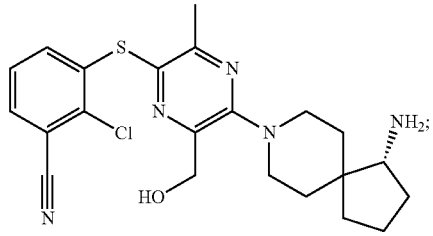 [SMILES: Cc1nc(N2CCC3(CCC[C@H]3N)CC2)c(CO)nc1Sc1cccc(C#N)c1Cl] |
| A-164 | 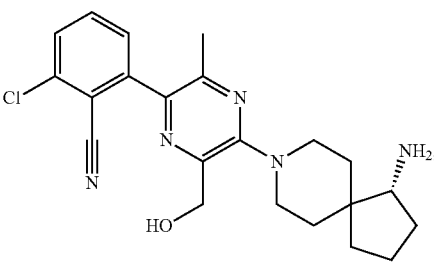 |
| A-165 | 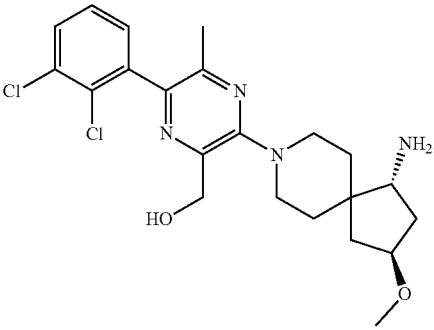 |
| A-166 | 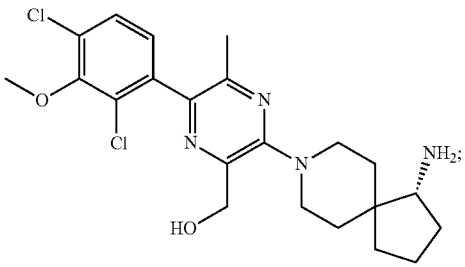 [SMILES: COc1c(Cl)ccc(-c2nc(CO)c(N3CCC4(CCC[C@H]4N)CC3)nc2C)c1Cl] |

| Compound # | Structure |
|---|---|
| A-167 | 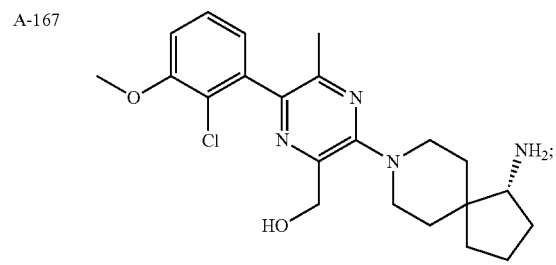 |
| A-168 | 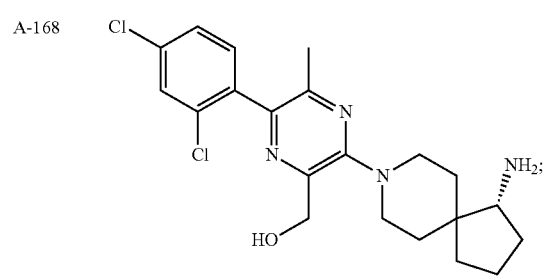 |
| A-169 | 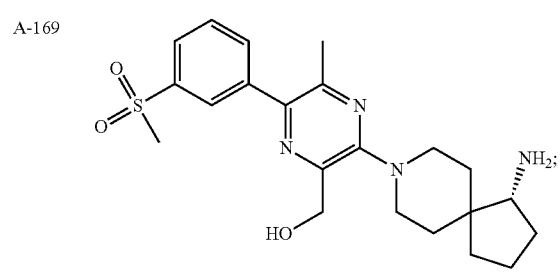 |
| A-170 | 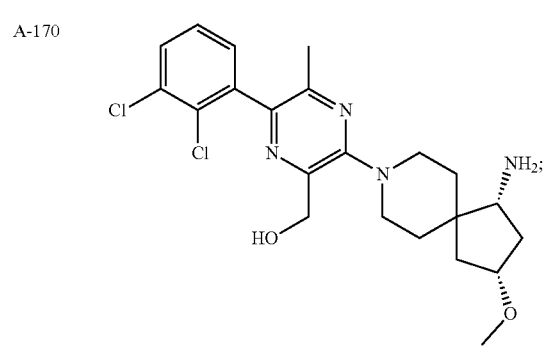 |
| A-171 | 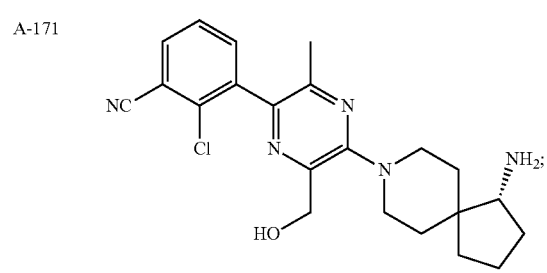 |
| A-172 | 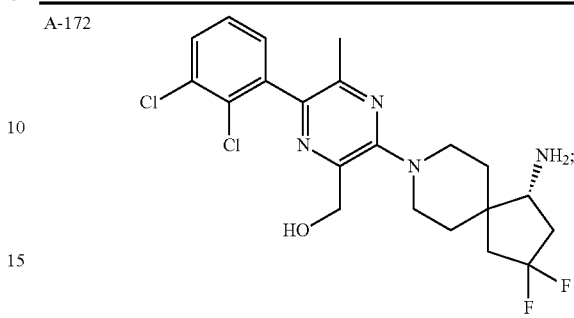 |
| A-173 | 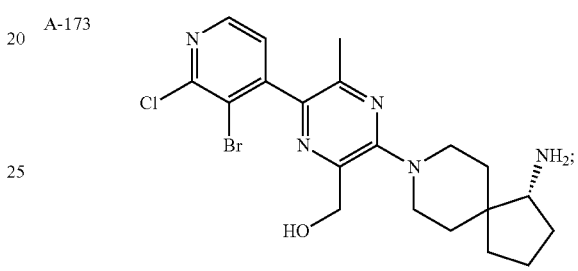 |
| A-174 | 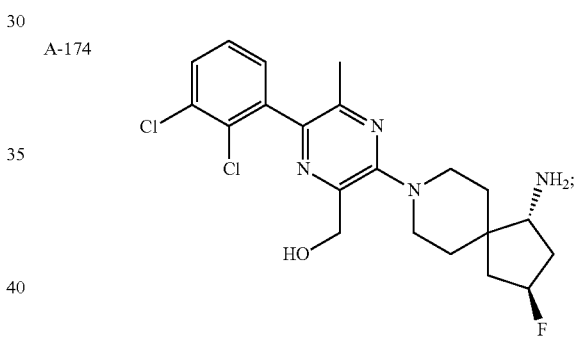 |
| A-175 | 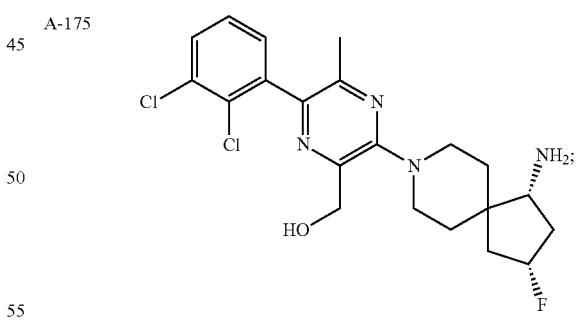 |
| A-176 | 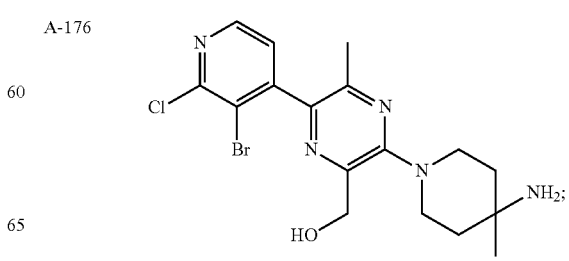 |

| Compound # | Structure |
|---|---|
| A-177 | 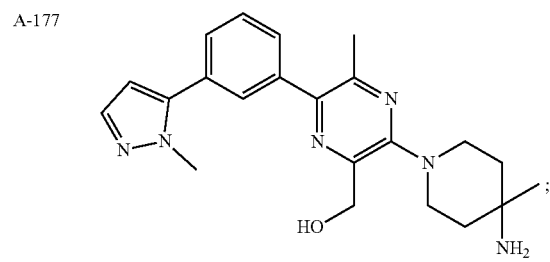 |
| A-178 | 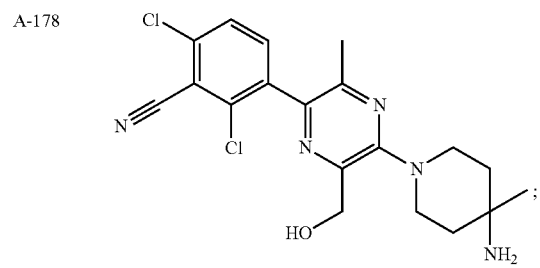 |
| A-179 | 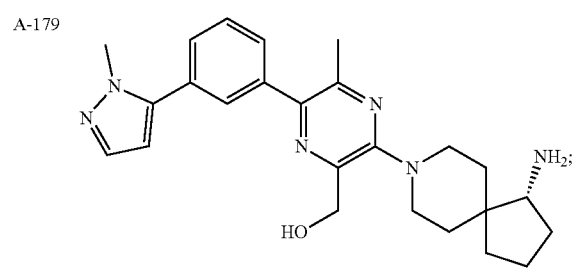 |
| A-180 | 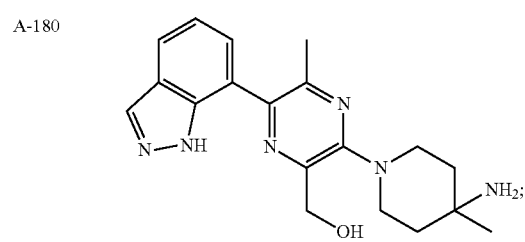 |
| A-181 | 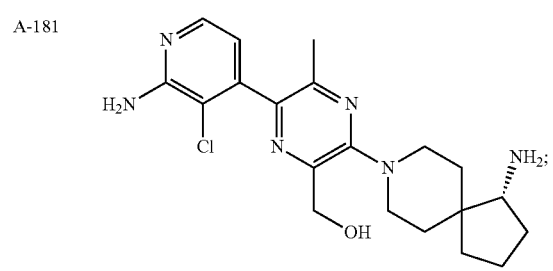 |
| Compound # | Structure |
|---|---|
| A-182 | 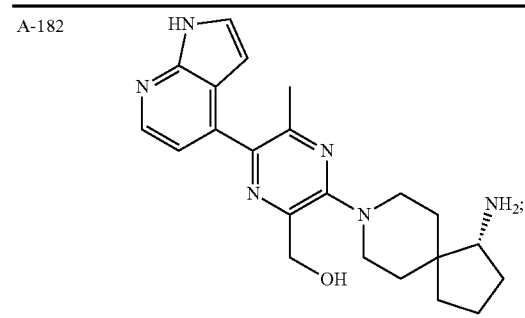 |
| A-183 | 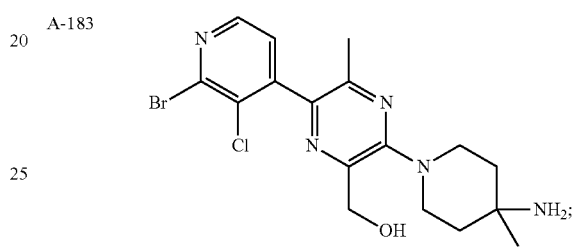 |
| A-184 | 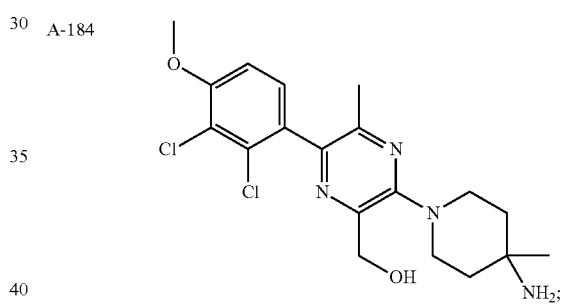 |
| A-185 | 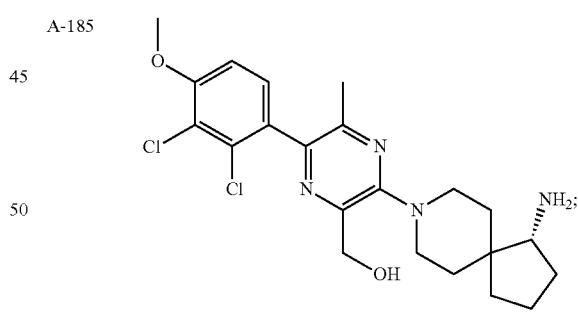 |
| A-186 | 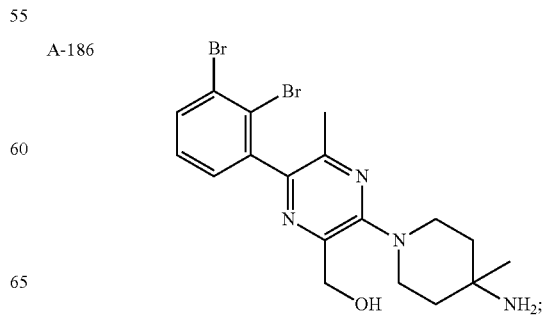 |

| Compound # | Structure |
|---|---|
| A-187 | 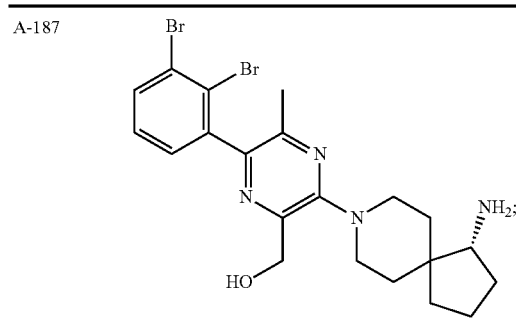 |
| A-188 | 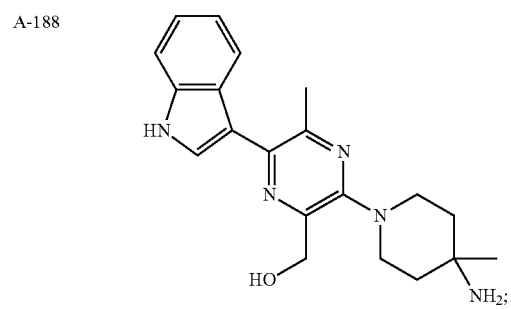 |
| A-189 | 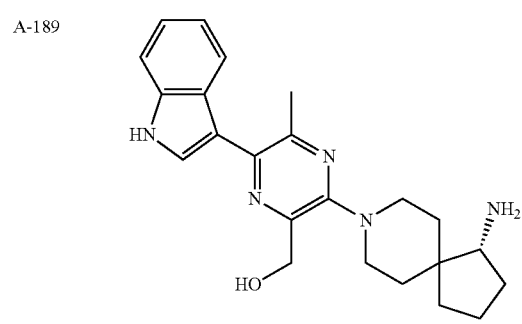 |
| A-190 | 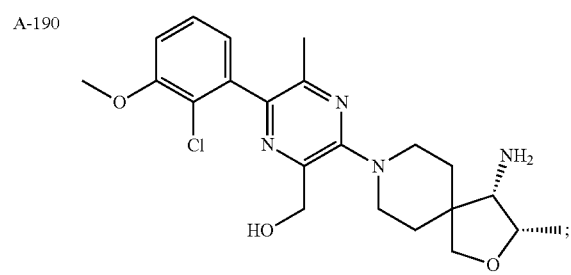 |
| A-191 | 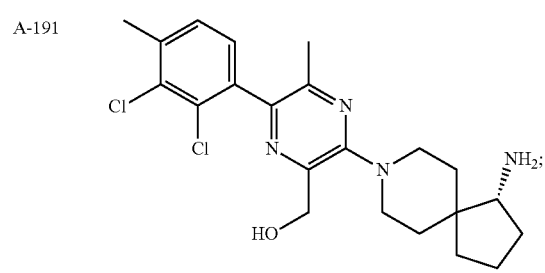 |
| A-192 | 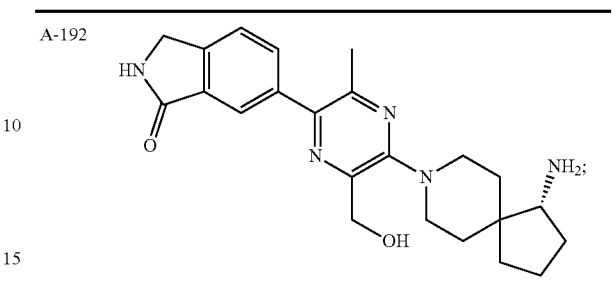 |
| A-193 | 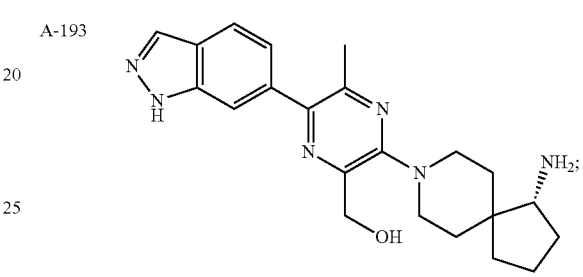 |
| A-194 | 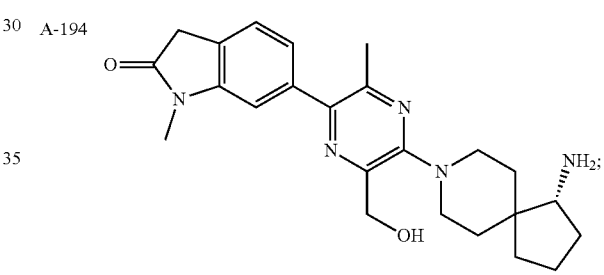 |
| A-195 | 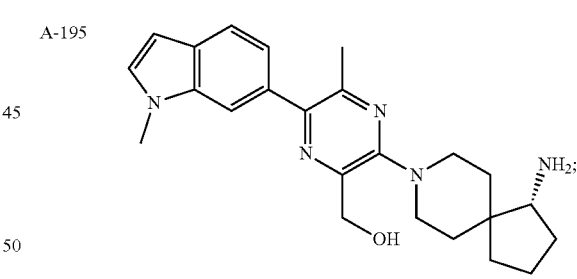 |
| A-196 | 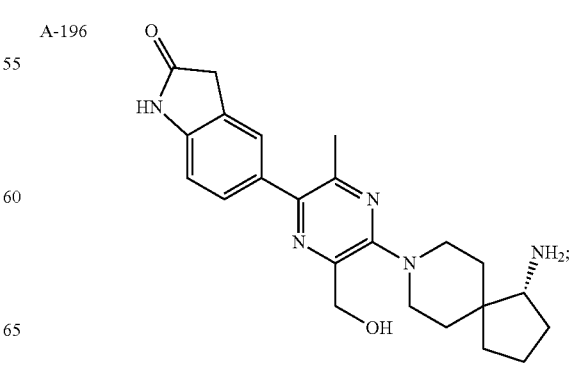 |

| Compound # | Structure |
|---|---|
| A-197 | 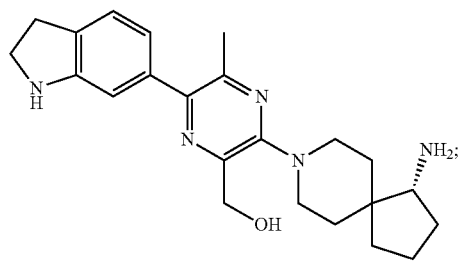 [SMILES: Cc1nc(N2CCC3(CCC[C@H]3N)CC2)c(CO)nc1-c1ccc2c(c1)NCC2] |
| A-198 | 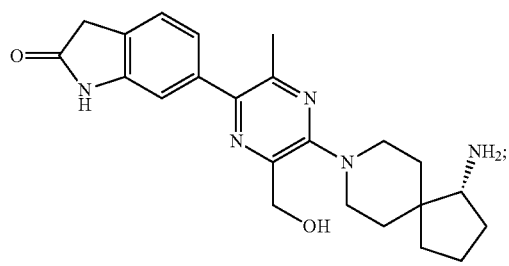 [SMILES: Cc1nc(N2CCC3(CCC[C@H]3N)CC2)c(CO)nc1-c1ccc2c(c1)NC(=O)C2] |
| A-199 | 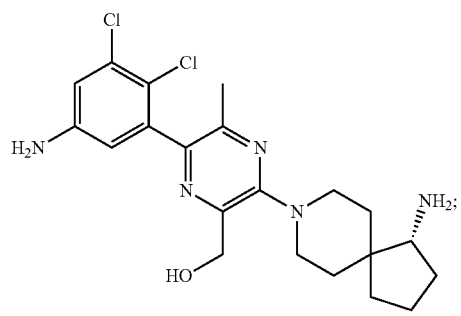 [SMILES: Cc1nc(N2CCC3(CCC[C@H]3N)CC2)c(CO)nc1-c1cc(N)cc(Cl)c1Cl] |
| A-200 | 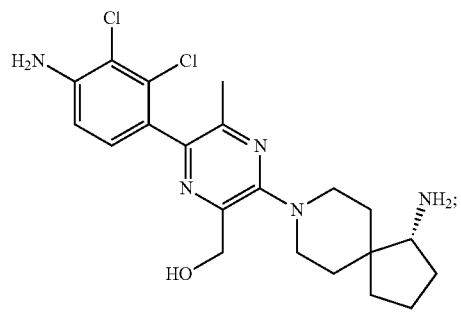 |
| A-201 | 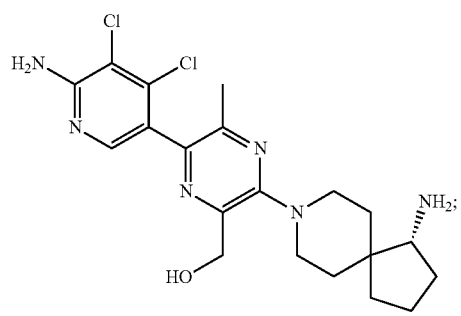 [SMILES: Cc1nc(N2CCC3(CCC[C@H]3N)CC2)c(CO)nc1-c1cnc(N)c(Cl)c1Cl] |
| Compound # | Structure |
|---|---|
| A-202 | 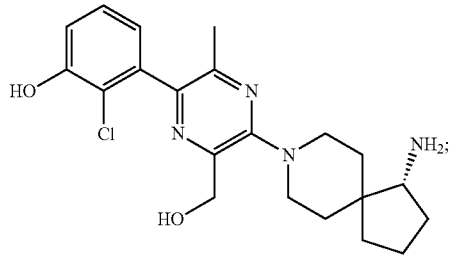 |
| A-203 | 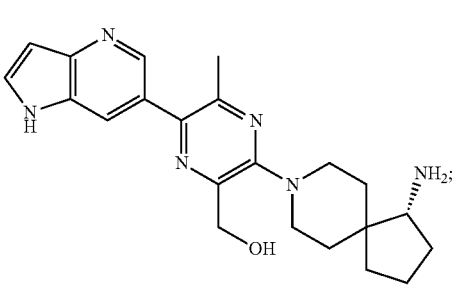 [SMILES: Cc1nc(N2CCC3(CCC[C@H]3N)CC2)c(CO)nc1-c1cnc2cc[nH]c2c1] |
| A-204 | 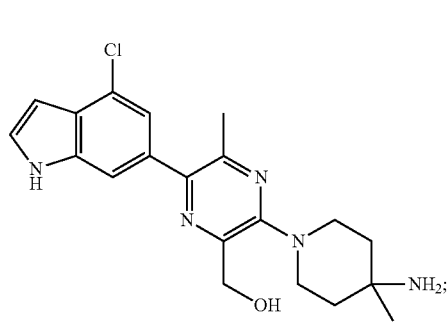 [SMILES: Cc1nc(N2CCC(C)(N)CC2)c(CO)nc1-c1cc(Cl)c2cc[nH]c2c1] |
| A-205 | 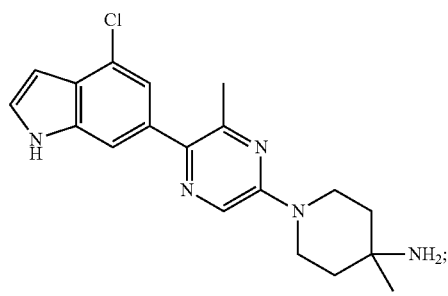 [SMILES: Cc1nc(N2CCC(C)(N)CC2)cnc1-c1cc(Cl)c2cc[nH]c2c1] |
| A-206 | 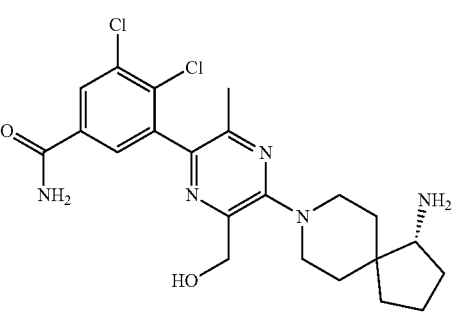 |

| Compound # | Structure |
|---|---|
| A-207 | 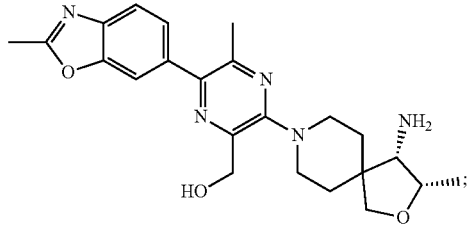 |
| A-208 | 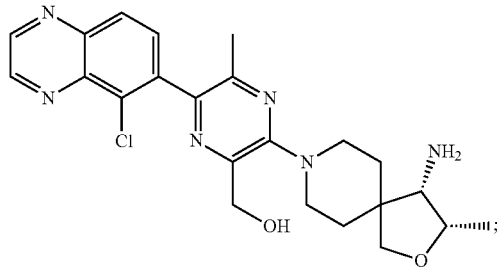 [SMILES: Cc1nc(N2CCC3(CC2)CO[C@@H](C)[C@H]3N)c(CO)nc1-c1ccc2nccnc2c1Cl] |
| A-209 | 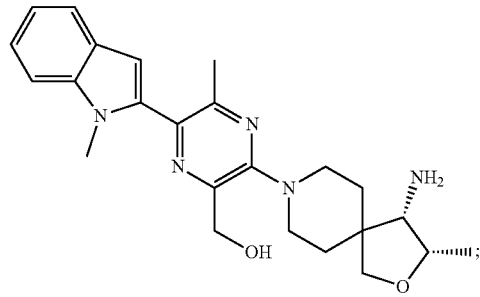 [SMILES: Cc1nc(N2CCC3(CC2)CO[C@@H](C)[C@H]3N)c(CO)nc1-c1cc2ccccc2n1C] |
| A-210 | 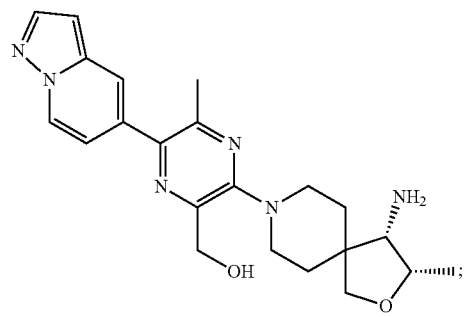 [SMILES: Cc1nc(N2CCC3(CC2)CO[C@@H](C)[C@H]3N)c(CO)nc1-c1ccn2nccc2c1] |
| A-211 | 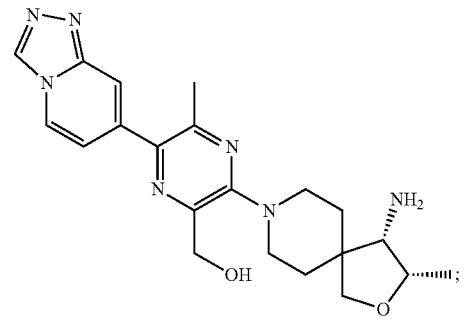 [SMILES: Cc1nc(N2CCC3(CC2)CO[C@@H](C)[C@H]3N)c(CO)nc1-c1ccn2cnnc2c1] |
| A-212 | 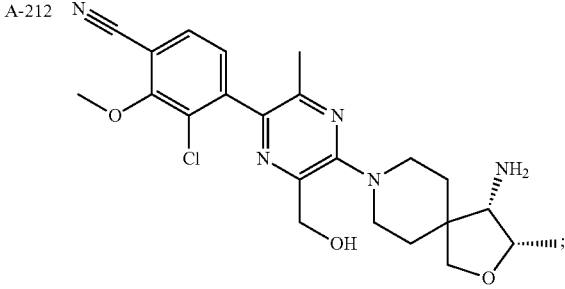 |
| A-213 | 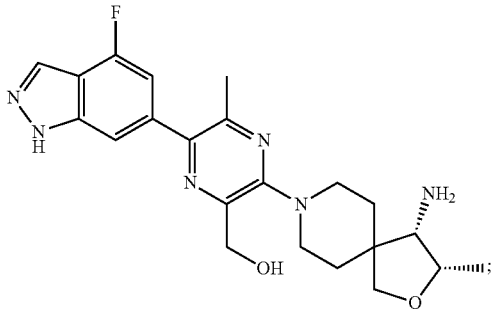 |
| A-214 | 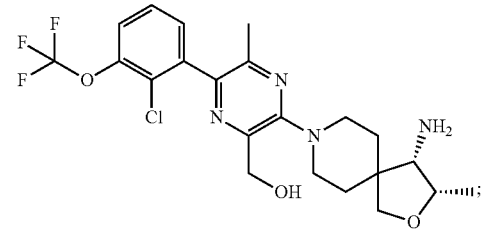 |
| A-215 | 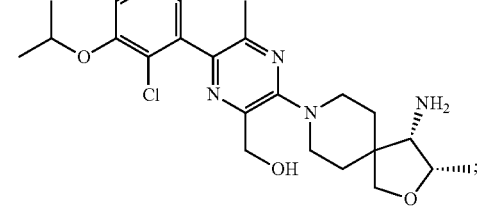 |
| A-216 | 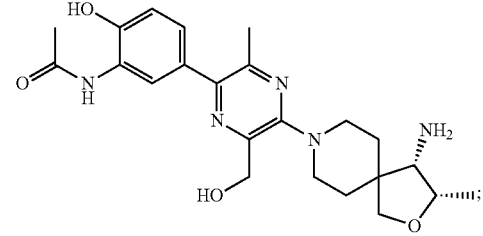 [SMILES: CC(=O)Nc1cc(-c2nc(CO)c(N3CCC4(CC3)CO[C@@H](C)[C@H]4N)nc2C)ccc1O] |

| Compound # | Structure |
|---|---|
| A-217 | 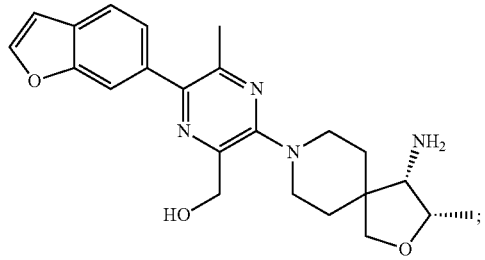 [SMILES: Cc1nc(N2CCC3(CC2)CO[C@@H](C)[C@H]3N)c(CO)nc1-c1ccc2ccoc2c1] |
| A-218 | 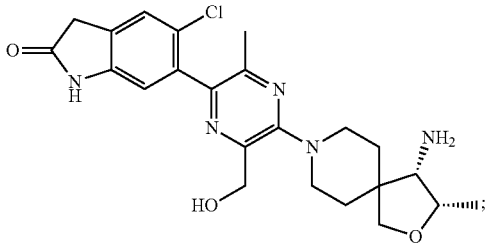 [SMILES: Cc1nc(N2CCC3(CC2)CO[C@@H](C)[C@H]3N)c(CO)nc1-c1cc2c(cc1Cl)CC(=O)N2] |
| A-219 | 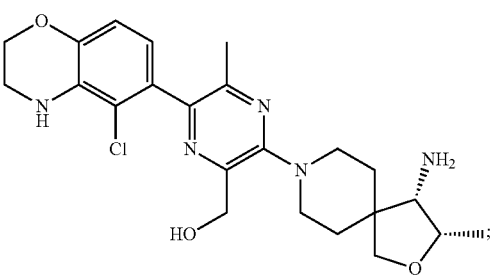 [SMILES: Cc1nc(N2CCC3(CC2)CO[C@@H](C)[C@H]3N)c(CO)nc1-c1ccc2c(c1Cl)NCCO2] |
| A-220 | 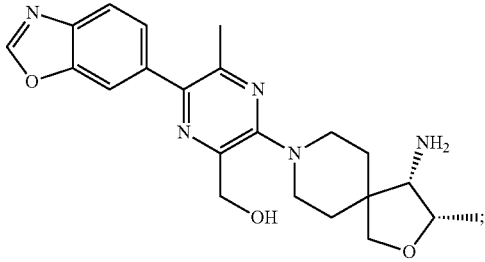 [SMILES: Cc1nc(N2CCC3(CC2)CO[C@@H](C)[C@H]3N)c(CO)nc1-c1ccc2ncoc2c1] |
| A-221 | 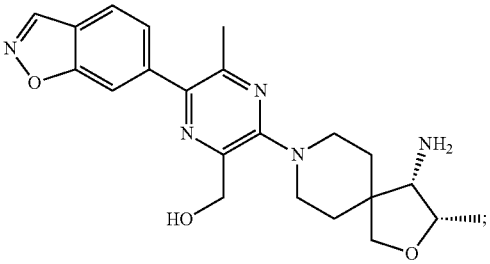 [SMILES: Cc1nc(N2CCC3(CC2)CO[C@@H](C)[C@H]3N)c(CO)nc1-c1ccc2cnoc2c1] |
| A-222 | 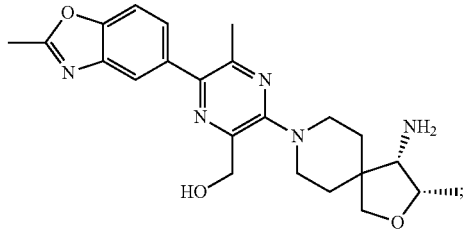 |
| A-223 | 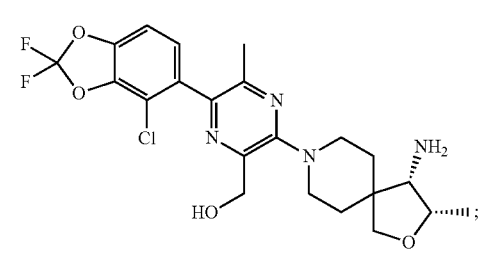 [SMILES: Cc1nc(N2CCC3(CC2)CO[C@@H](C)[C@H]3N)c(CO)nc1-c1ccc2c(c1Cl)OC(F)(F)O2] |
| A-224 | 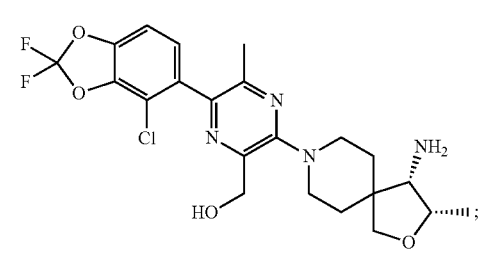 [SMILES: Cc1nc(N2CCC3(CC2)CO[C@@H](C)[C@H]3N)c(CO)nc1-c1ccc2c(c1Cl)OC(F)(F)O2] |
| A-225 | 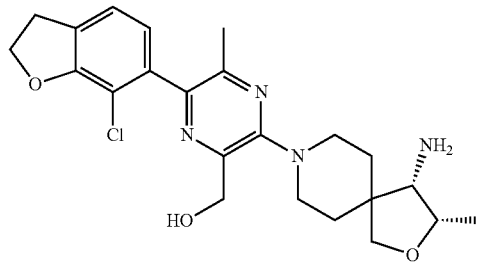 |
| A-226 | 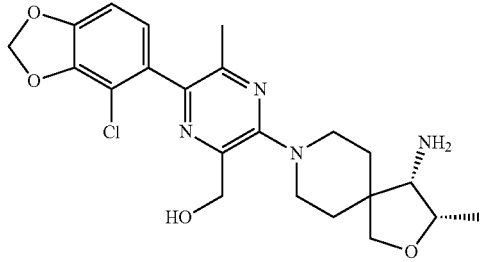 |

| Compound # | Structure |
|---|---|
| A-227 | 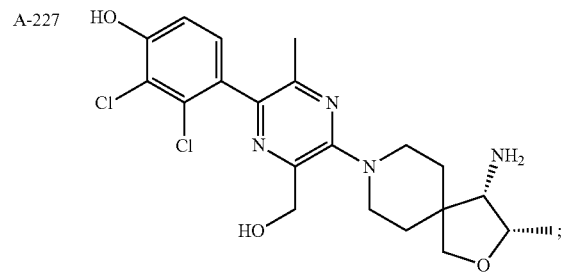 |
| A-228 | 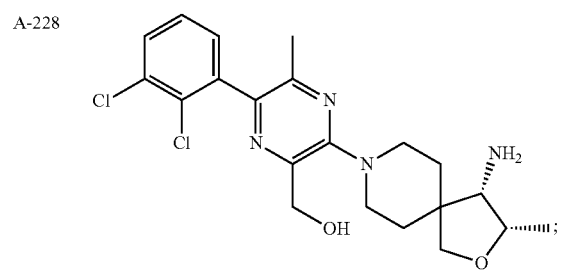 |
| A-229 | 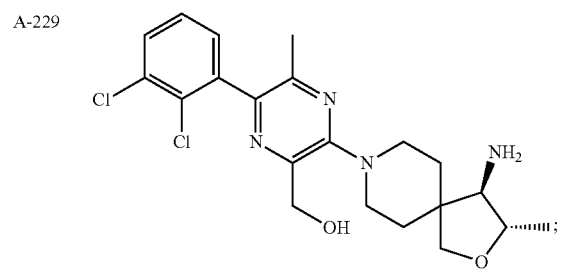 |
| A-230 | 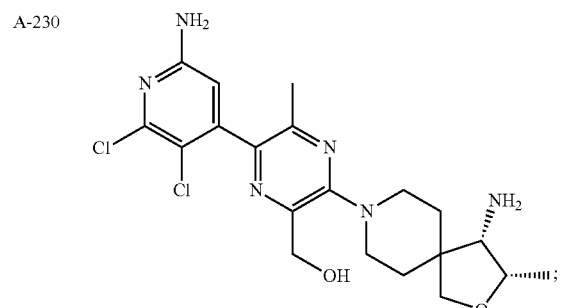 |
| A-231 | 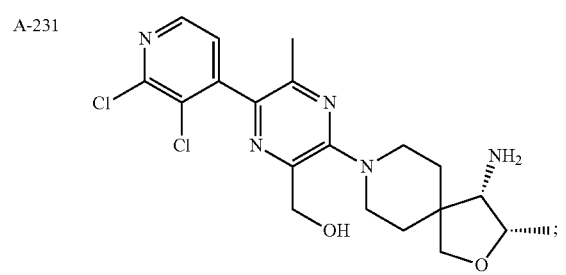 |
| A-232 | 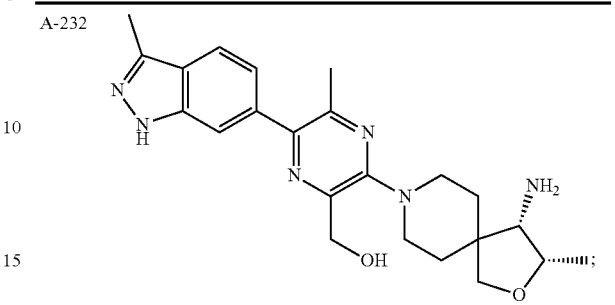 |
| A-233 | 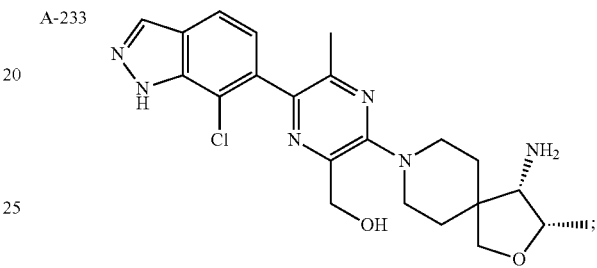 |
| A-234 | 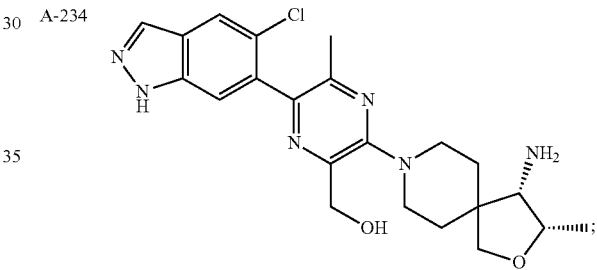 |
| A-235 | 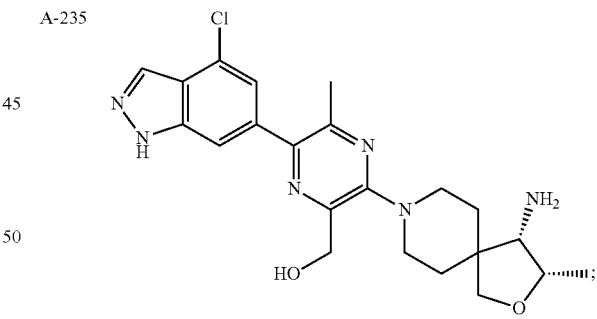 |
| A-236 | 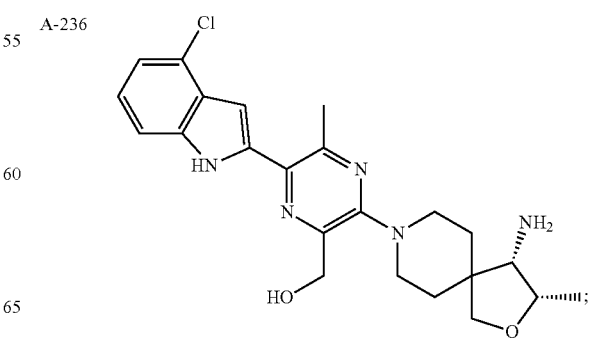 |

| Compound # | Structure |
|---|---|
| A-237 | 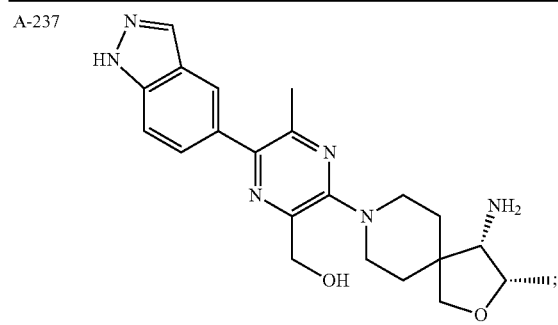 |
| A-238 | 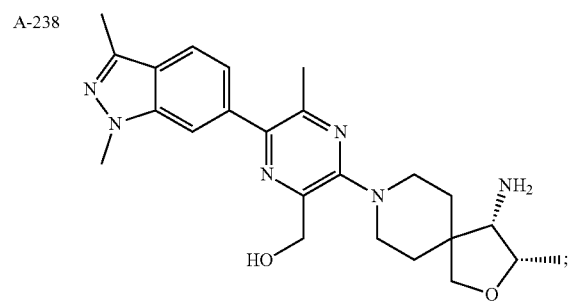 |
| A-239 | 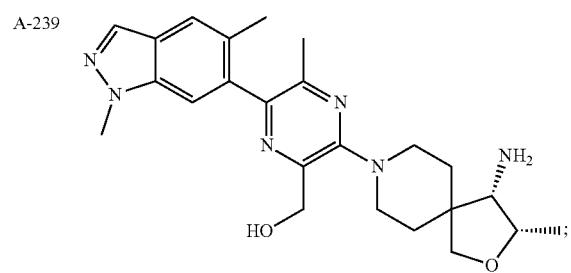 |
| A-240 | 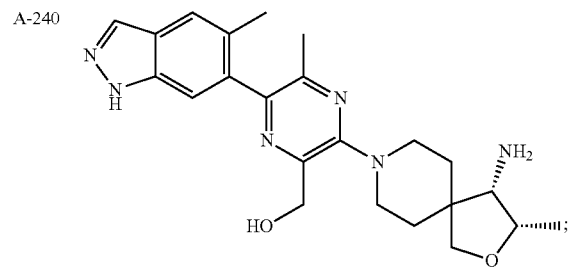 |
| A-241 | 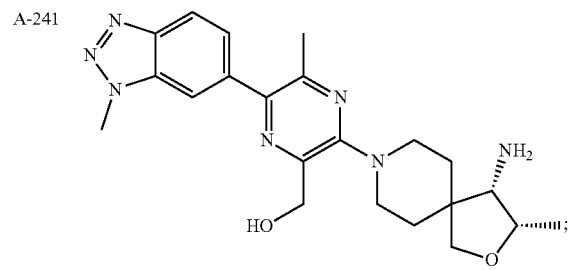 |
| A-242 | 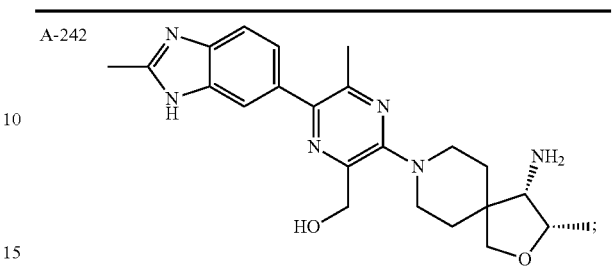 |
| A-243 | 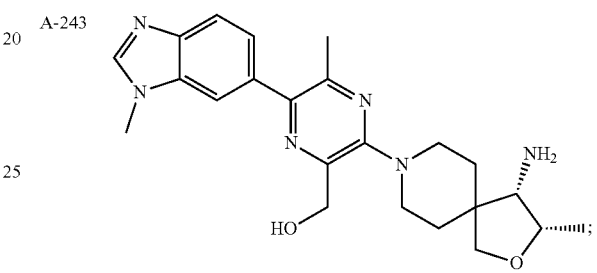 |
| A-244 | 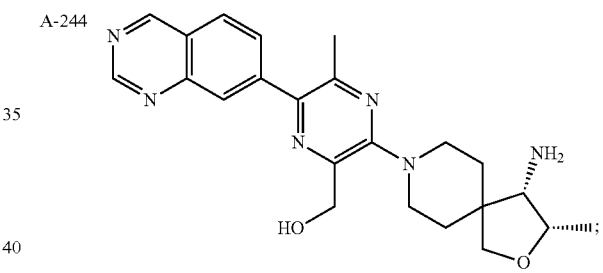 |
| A-245 | 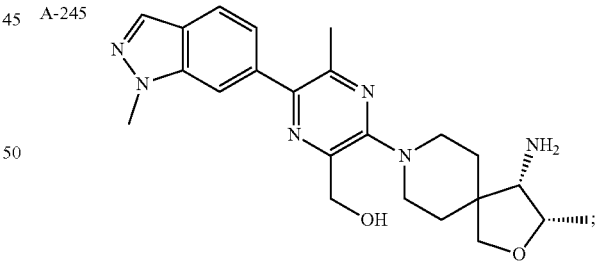 |
| A-246 | 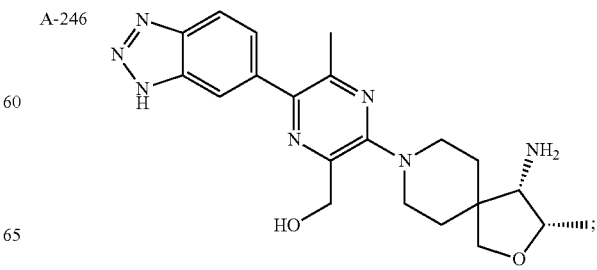 |

| Compound # | Structure |
|---|---|
| A-247 | 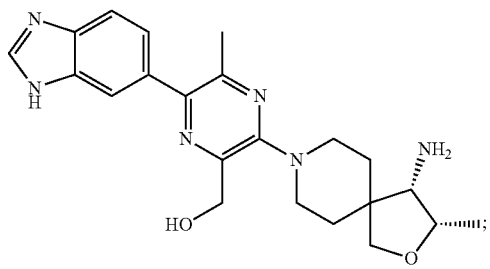 [SMILES: Cc1nc(N2CCC3(CC2)CO[C@@H](C)[C@H]3N)c(CO)nc1-c1ccc2nc[nH]c2c1] |
| A-248 | 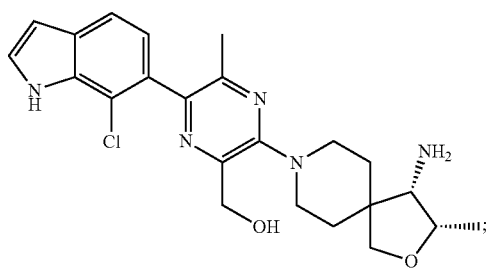 [SMILES: Cc1nc(N2CCC3(CC2)CO[C@@H](C)[C@H]3N)c(CO)nc1-c1ccc2cc[nH]c2c1Cl] |
| A-249 | 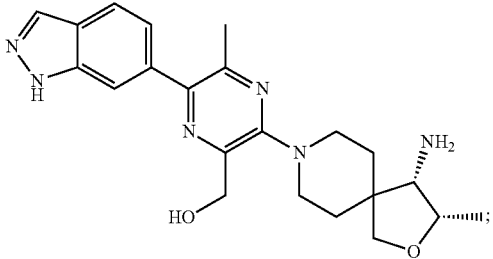 |
| A-250 | 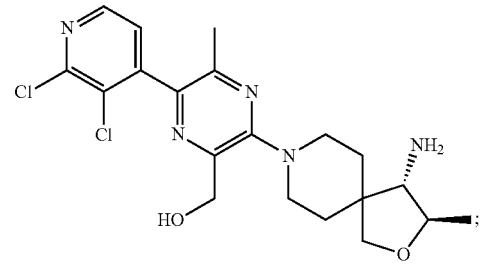 [SMILES: Cc1nc(N2CCC3(CC2)CO[C@H](C)[C@H]3N)c(CO)nc1-c1ccnc(Cl)c1Cl] |
| A-251 | 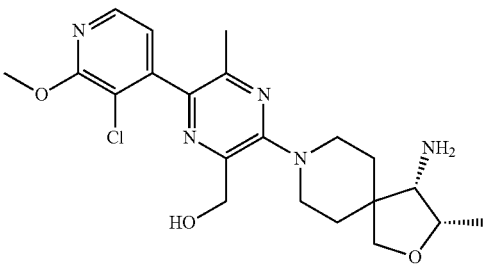 |
| Compound # | Structure |
|---|---|
| A-252 | 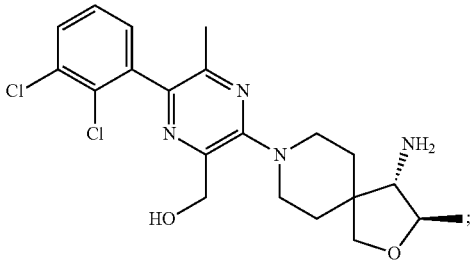 [SMILES: Cc1nc(N2CCC3(CC2)CO[C@H](C)[C@H]3N)c(CO)nc1-c1cccc(Cl)c1Cl] |
| A-253 | 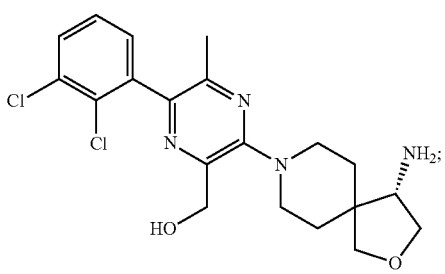 [SMILES: Cc1nc(N2CCC3(CC2)COC[C@H]3N)c(CO)nc1-c1cccc(Cl)c1Cl] |
| A-254 | 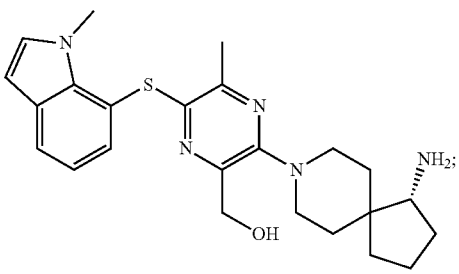 [SMILES: Cc1nc(N2CCC3(CCC[C@H]3N)CC2)c(CO)nc1Sc1cccc2ccn(C)c12] |
| A-255 | 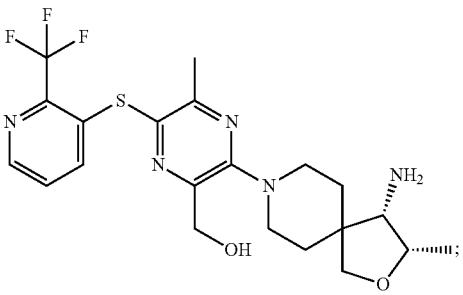 [SMILES: Cc1nc(N2CCC3(CC2)CO[C@@H](C)[C@H]3N)c(CO)nc1Sc1cccnc1C(F)(F)F] |
| A-256 | 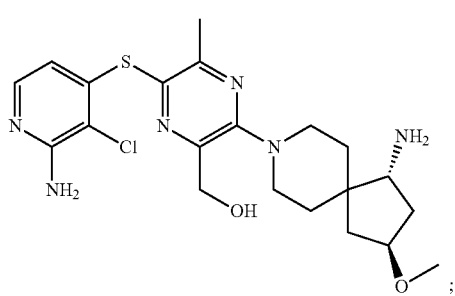 [SMILES: CO[C@@H]1C[C@@H](N)C2(CCN(c3nc(C)c(Sc4ccnc(N)c4Cl)nc3CO)CC2)C1] |

| Compound # | Structure |
|---|---|
| A-257 | 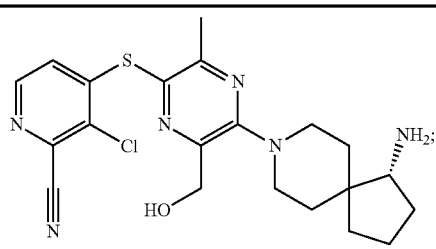 |
| A-258 | 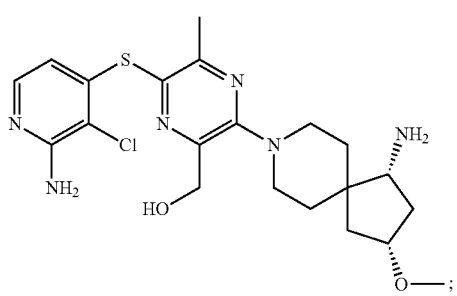 [SMILES: CO[C@H]1C[C@@H](N)C2(CCN(c3nc(C)c(Sc4ccnc(N)c4Cl)nc3CO)CC2)C1] |
| A-259 | 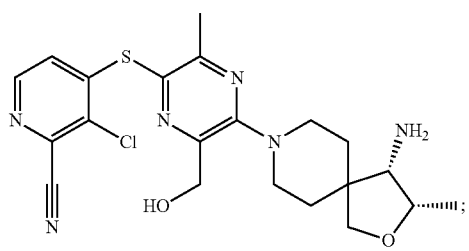 [SMILES: Cc1nc(N2CCC3(CC2)CO[C@@H](C)[C@H]3N)c(CO)nc1Sc1ccnc(C#N)c1Cl] |
| A-260 | 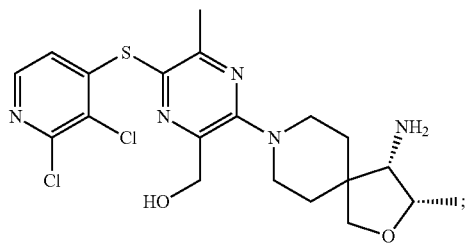 [SMILES: Cc1nc(N2CCC3(CC2)CO[C@@H](C)[C@H]3N)c(CO)nc1Sc1ccnc(Cl)c1Cl] |
| A-261 | 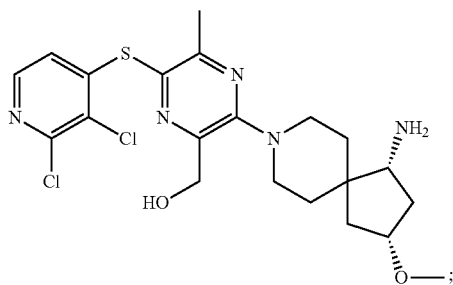 [SMILES: CO[C@H]1C[C@@H](N)C2(CCN(c3nc(C)c(Sc4ccnc(Cl)c4Cl)nc3CO)CC2)C1] |
| Compound # | Structure |
|---|---|
| A-262 | 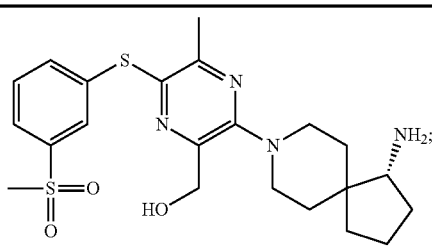 |
| A-263 | 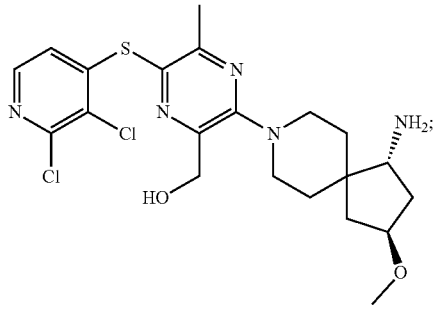 [SMILES: CO[C@@H]1C[C@@H](N)C2(CCN(c3nc(C)c(Sc4ccnc(Cl)c4Cl)nc3CO)CC2)C1] |
| A-264 | 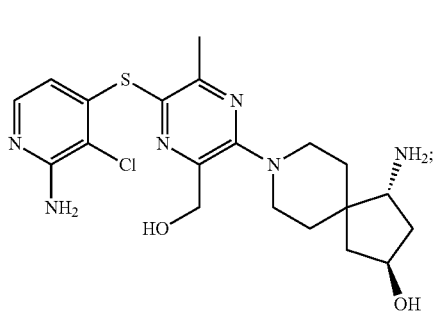 [SMILES: Cc1nc(N2CCC3(CC2)C[C@H](O)C[C@H]3N)c(CO)nc1Sc1ccnc(N)c1Cl] |
| A-265 | 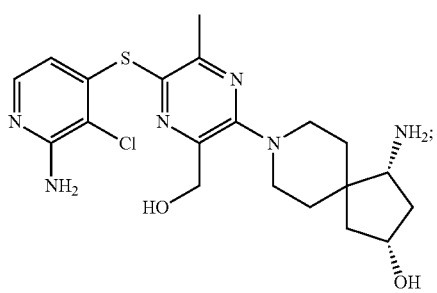 [SMILES: Cc1nc(N2CCC3(CC2)C[C@@H](O)C[C@H]3N)c(CO)nc1Sc1ccnc(N)c1Cl] |
| A-266 | 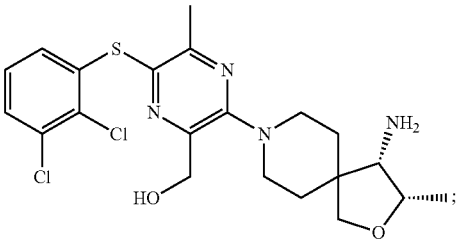 [SMILES: Cc1nc(N2CCC3(CC2)CO[C@@H](C)[C@H]3N)c(CO)nc1Sc1cccc(Cl)c1Cl] |

| Compound # | Structure |
|---|---|
| A-267 | |
| A-268 | |
| A-269 | |
| A-270 | |
| A-271 | |
| A-272 | 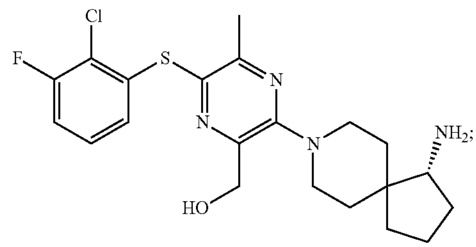 [SMILES: Cc1nc(N2CCC3(CCC[C@H]3N)CC2)c(CO)nc1Sc1cccc(F)c1Cl] |
| A-273 | 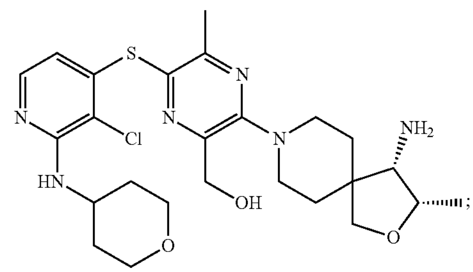 [SMILES: Cc1nc(N2CCC3(CC2)CO[C@@H](C)[C@H]3N)c(CO)nc1Sc1ccnc(NC2CCOCC2)c1Cl] |
| A-274 | 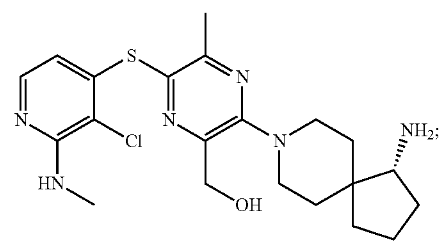 [SMILES: CNc1nccc(Sc2nc(CO)c(N3CCC4(CCC[C@H]4N)CC3)nc2C)c1Cl] |
| A-275 | 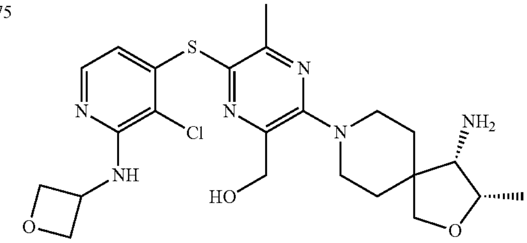 |
| A-276 | 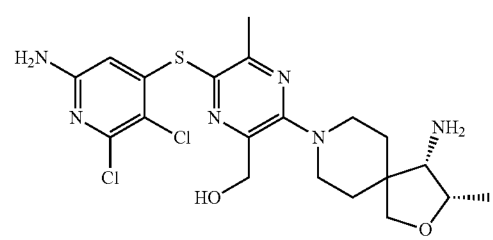 |
| A-277 | 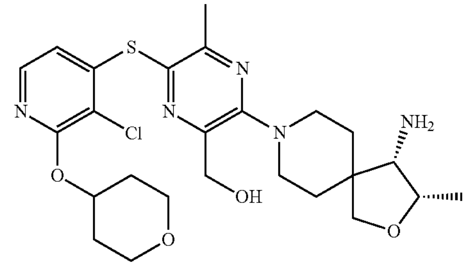 |

| Compound # | Structure |
|---|---|
| A-278 | 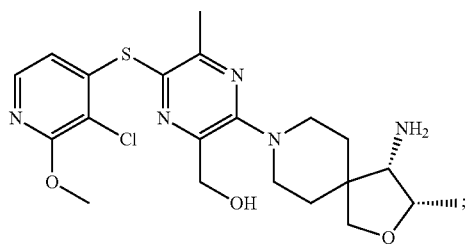 [SMILES: COc1nccc(Sc2nc(CO)c(N3CCC4(CC3)CO[C@@H](C)[C@H]4N)nc2C)c1Cl] |
| A-279 | 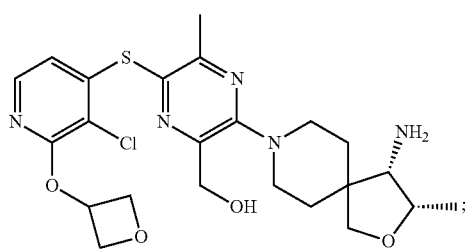 [SMILES: Cc1nc(N2CCC3(CC2)CO[C@@H](C)[C@H]3N)c(CO)nc1Sc1ccnc(OC2COC2)c1Cl] |
| A-280 | 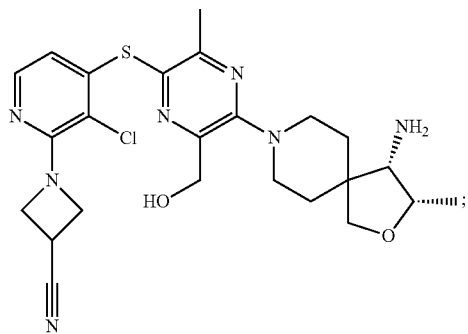 [SMILES: Cc1nc(N2CCC3(CC2)CO[C@@H](C)[C@H]3N)c(CO)nc1Sc1ccnc(N2CC(C#N)C2)c1Cl] |
| A-281 | 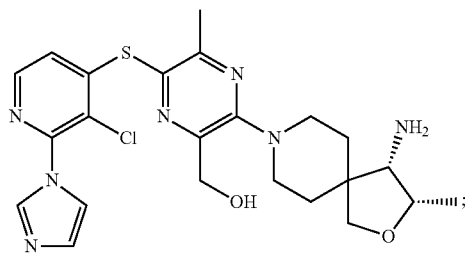 [SMILES: Cc1nc(N2CCC3(CC2)CO[C@@H](C)[C@H]3N)c(CO)nc1Sc1ccnc(-n2ccnc2)c1Cl] |
| A-282 | 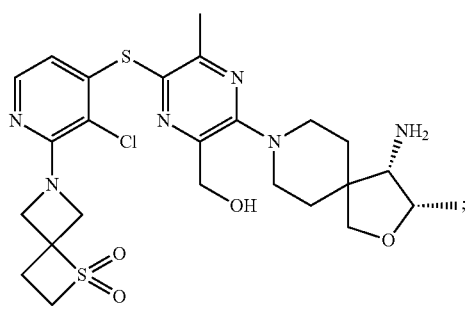 [SMILES: Cc1nc(N2CCC3(CC2)CO[C@@H](C)[C@H]3N)c(CO)nc1Sc1ccnc(N2CC3(CCS3(=O)=O)C2)c1Cl] |
| Compound # | Structure |
|---|---|
| A-283 | 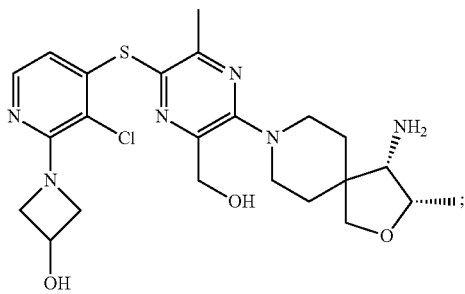 [SMILES: Cc1nc(N2CCC3(CC2)CO[C@@H](C)[C@H]3N)c(CO)nc1Sc1ccnc(N2CC(O)C2)c1Cl] |
| A-284 | 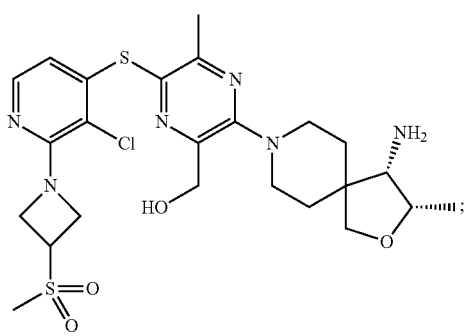 [SMILES: Cc1nc(N2CCC3(CC2)CO[C@@H](C)[C@H]3N)c(CO)nc1Sc1ccnc(N2CC(S(C)(=O)=O)C2)c1Cl] |
| A-285 | 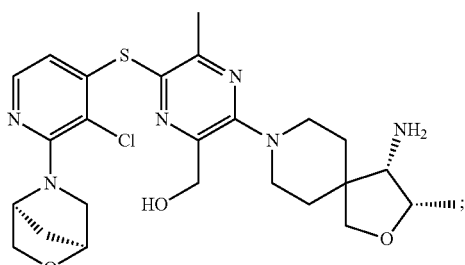 |
| A-286 | 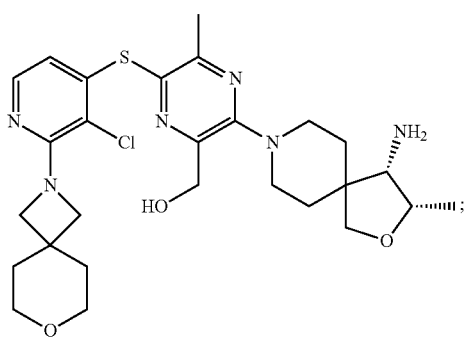 [SMILES: Cc1nc(N2CCC3(CC2)CO[C@@H](C)[C@H]3N)c(CO)nc1Sc1ccnc(N2CC3(CCOCC3)C2)c1Cl] |
| A-287 | 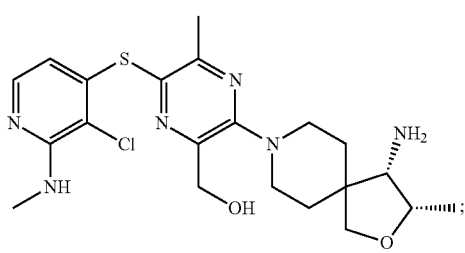 [SMILES: CNc1nccc(Sc2nc(CO)c(N3CCC4(CC3)CO[C@@H](C)[C@H]4N)nc2C)c1Cl] |

| Compound # | Structure |
|---|---|
| A-288 | 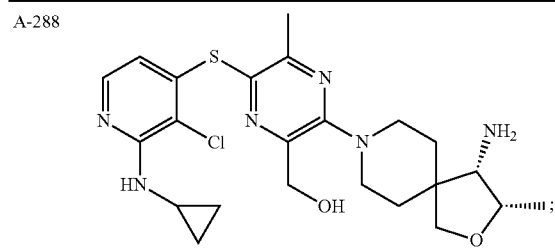 |
| A-289 | 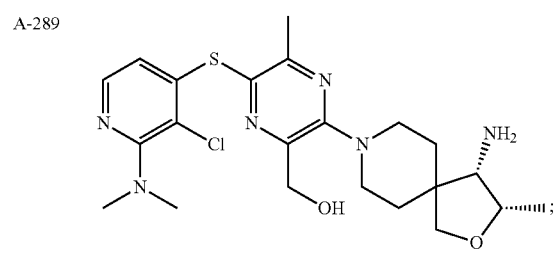 |
| A-290 | 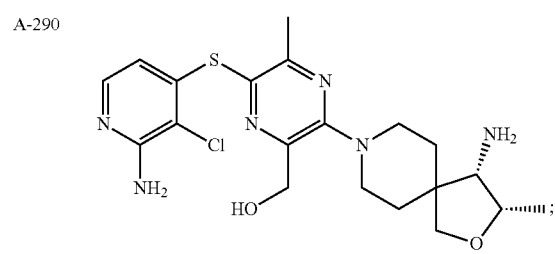 |
| A-291 | 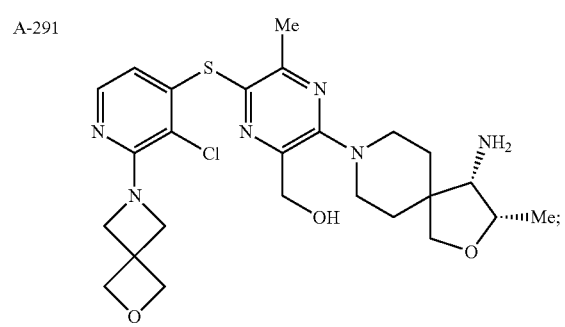 |
| A-292 | 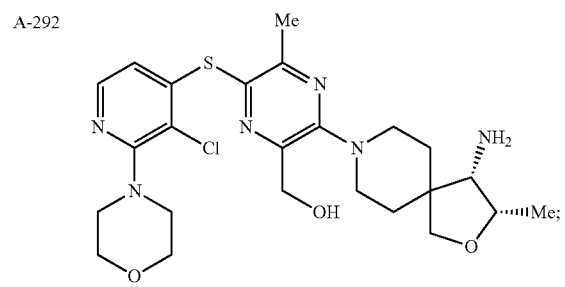 |
| A-293 | 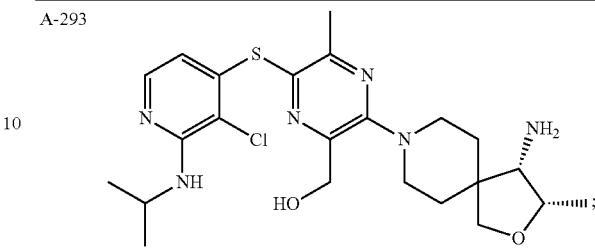 |
| A-294 | 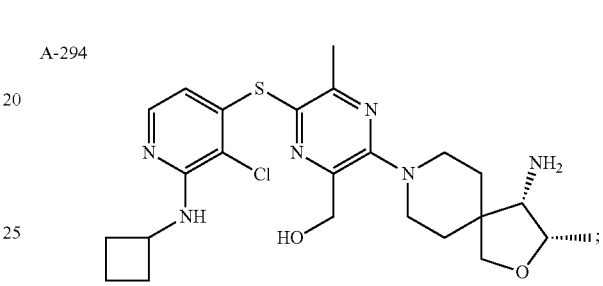 |
| A-295 | 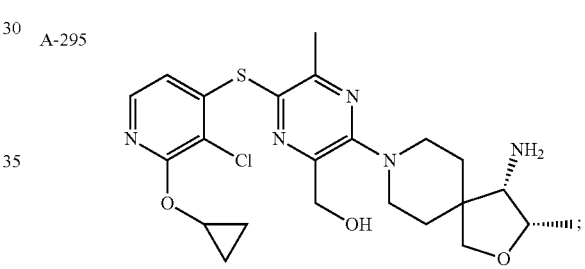 |
| A-296 | 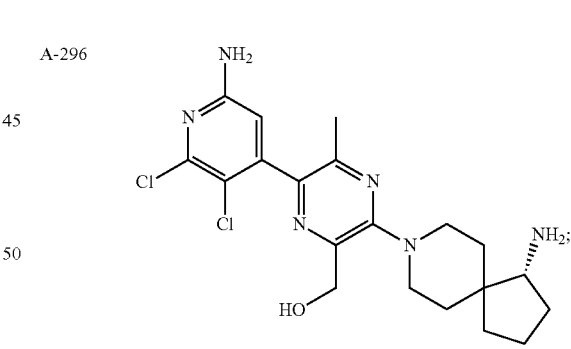 |
| A-297 | 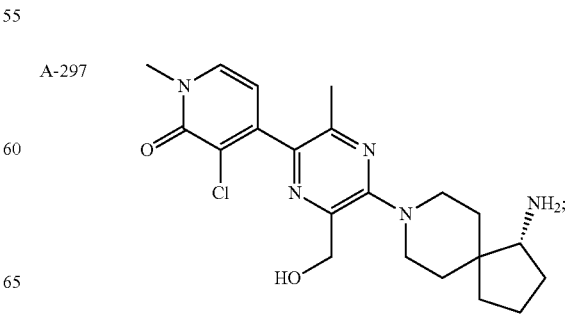 |

| Compound # | Structure |
|---|---|
| A-298 | 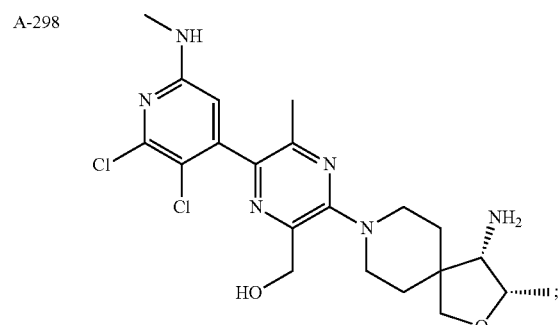 |
| A-299 | 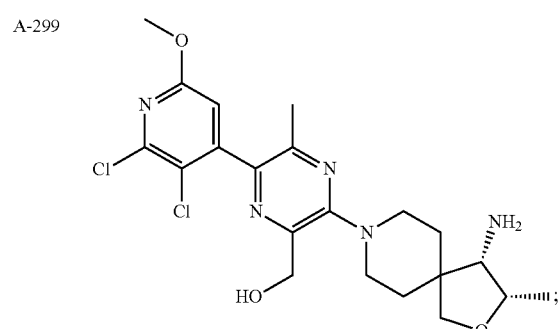 |
| A-300 | 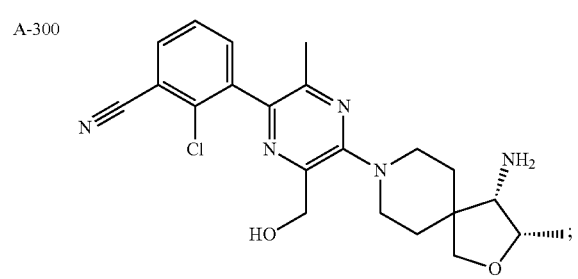 |
| A-301 | 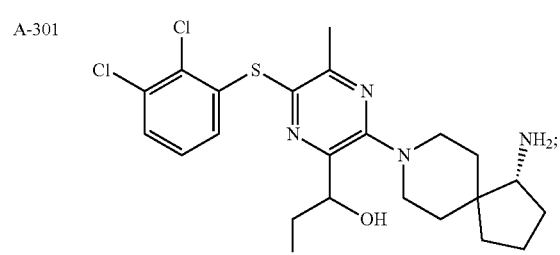 |
| A-302 | 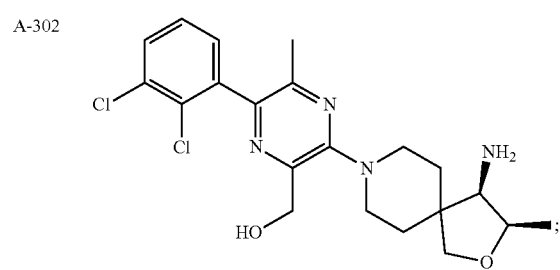 |
| Compound # | Structure |
|---|---|
| A-303 | 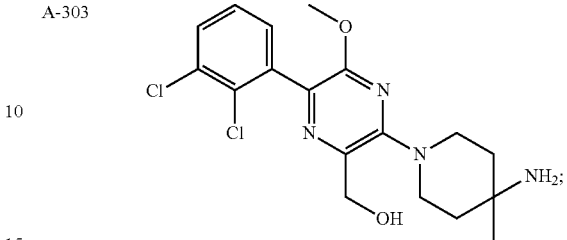 |
| A-304 | 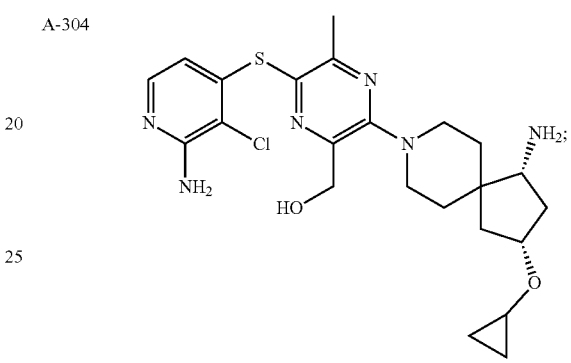 |
| A-305 | 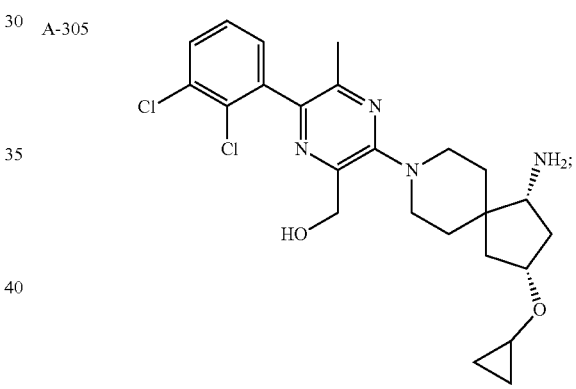 |
| A-306 | 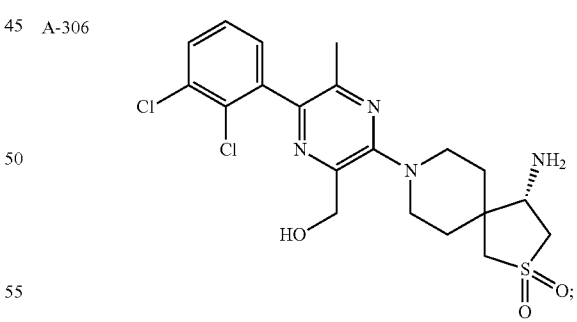 |
| A-307 | 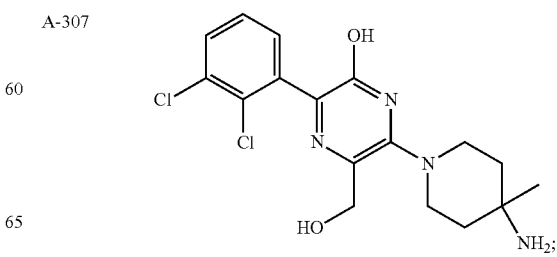 |

-continued

| Compound # | Structure |
|---|---|
| A-308 | 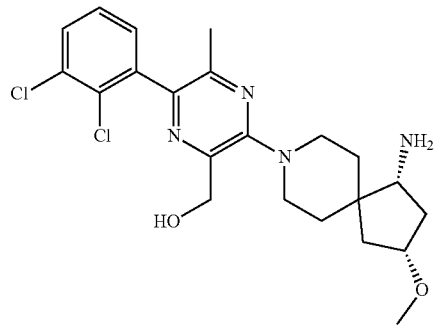 [SMILES: CO[C@H]1C[C@@H](N)C2(CCN(c3nc(C)c(-c4cccc(Cl)c4Cl)nc3CO)CC2)C1] |
| A-309 | 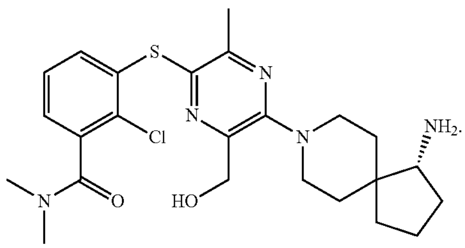 [SMILES: Cc1nc(N2CCC3(CCC[C@H]3N)CC2)c(CO)nc1Sc1cccc(C(=O)N(C)C)c1Cl] |

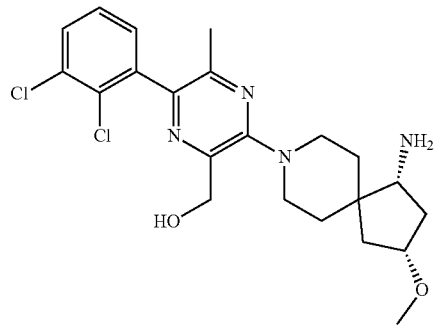 [SMILES: CO[C@H]1C[C@@H](N)C2(CCN(c3nc(C)c(-c4cccc(Cl)c4Cl)nc3CO)CC2)C1]

23. The compound of claim 1, or a pharmaceutically acceptable salt, solvate, hydrate, or tautomer thereof, wherein the compound is

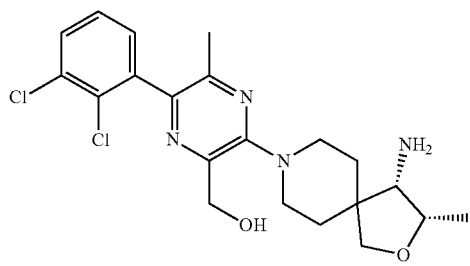 [SMILES: Cc1nc(N2CCC3(CC2)CO[C@@H](C)[C@H]3N)c(CO)nc1-c1cccc(Cl)c1Cl]

(A170).

24. The compound of claim 1, or a pharmaceutically acceptable salt, solvate, hydrate, or tautomer thereof, wherein the compound is (A228).

25. The compound of claim 1, or a pharmaceutically acceptable salt, solvate, hydrate, or tautomer thereof, wherein the compound is

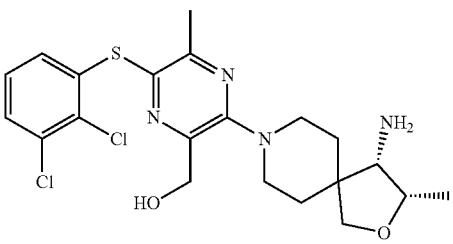 [SMILES: Cc1nc(N2CCC3(CC2)CO[C@@H](C)[C@H]3N)c(CO)nc1Sc1cccc(Cl)c1Cl]

(A266).

26. The compound of claim 1, or a pharmaceutically acceptable salt, solvate, hydrate, or tautomer thereof, wherein the compound is

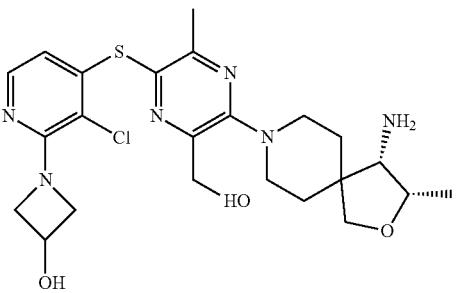 [SMILES: Cc1nc(N2CCC3(CC2)CO[C@@H](C)[C@H]3N)c(CO)nc1Sc1ccnc(N2CC(O)C2)c1Cl]

(A283).

27. The compound of claim 1, or a pharmaceutically acceptable salt, solvate, hydrate, or tautomer thereof, wherein the compound is

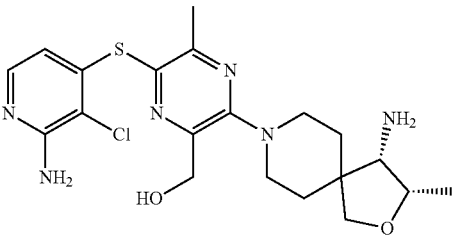

(A290).

28. A compound that is

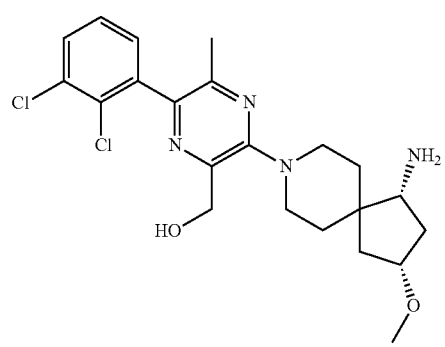 [SMILES: CO[C@H]1C[C@@H](N)C2(CCN(c3nc(C)c(-c4cccc(Cl)c4Cl)nc3CO)CC2)C1]

(A170).

29. A compound that is

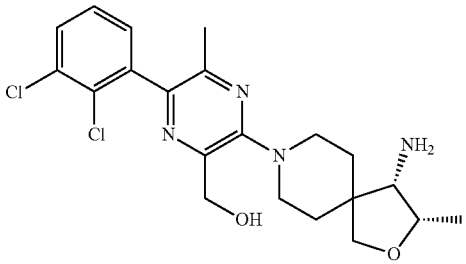 [SMILES: Cc1nc(N2CCC3(CC2)CO[C@@H](C)[C@H]3N)c(CO)nc1-c1cccc(Cl)c1Cl]

(A228).

30. A compound that is

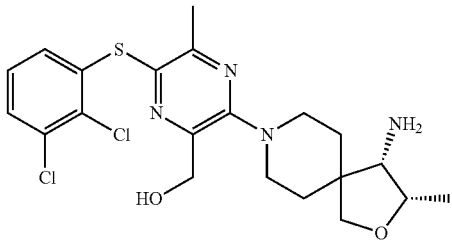 [SMILES: Cc1nc(N2CCC3(CC2)CO[C@@H](C)[C@H]3N)c(CO)nc1Sc1cccc(Cl)c1Cl]

(A266).

31. A compound that is

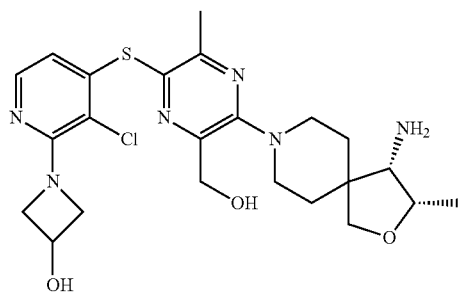 [SMILES: Cc1nc(N2CCC3(CC2)CO[C@@H](C)[C@H]3N)c(CO)nc1Sc1ccnc(N2CC(O)C2)c1Cl]

(A283).

32. A compound that is

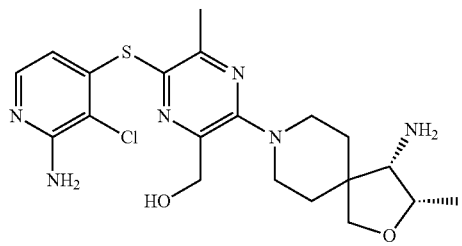 [SMILES: Cc1nc(N2CCC3(CC2)CO[C@@H](C)[C@H]3N)c(CO)nc1Sc1ccnc(N)c1Cl]

(A290).

33. A compound of Formula I-W:

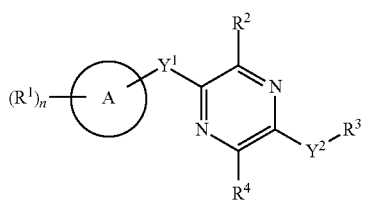

I-W or a pharmaceutically acceptable salt, solvate, hydrate, or tautomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$Y^1$ is —S— or a direct bond;

$Y^2$ is —NR$^a$—, —(CR$^a_2$)$_m$—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —OC(O)N(R$^a$)—, —N(R$^a$)C(O)O—, —C(O)N(R$^a$)O—, —N(R$^a$)C(S)—, or —C(S)N(R$^a$)—; where in the bond on the left side of $Y^2$, as drawn, is bound to the pyrazine ring and the bond on the right side of the $Y^2$ moiety, as drawn, is bound to $R^3$;

$R^1$ is independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$R^2$ is independently —OH, —CN, —C$_1$-C$_6$alkyl, —C$_2$-C$_6$alkenyl, —C$_4$-C$_8$cycloalkenyl, —C$_2$-C$_6$alkynyl, F, Br, I, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl; and wherein the heterocyclyl or heteroaryl is not attached via a nitrogen atom;

$R^a$ is independently, at each occurrence, —H, -D, —OH, —C$_3$-C$_8$cycloalkyl, —C$_1$-C$_6$alkyl, 3- to 12-membered heterocyclyl, or —(CH$_2$)$_n$-aryl, wherein each alkyl or cycloalkyl is optionally substituted with one or more —NH$_2$, or wherein 2 R$^a$, together with the carbon atom to which they are both attached, can combine to form a 3- to 8-membered cycloalkyl;

$R^b$ is independently, at each occurrence, —H, -D, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

$R^3$ is combined with $R^a$ to form a 3- to 12-membered polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, heteroaryl, heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O;

R$^4$ is independently —H, -D, —C$_1$-C$_6$alkyl, —C$_1$-C$_6$haloalkyl, —C$_1$-C$_6$hydroxyalkyl, —CF$_2$OH, —CHFOH, —NH—NHR$^5$, —NH—OR$^5$, —O—NR$^5$R$^6$, —NHC(O)R$^5$, —NHC(O)NHR$^5$, —NHS(O)$_2$R$^5$, —NHS(O)$_2$NHR$^5$, —S(O)$_2$OH, —C(O)OR$^5$, —NH(CH$_2$)$_n$OH, —C(O)NH(CH$_2$)$_n$OH, —C(O)NH(CH$_2$)$_n$R$^b$, —C(O)R$^b$, —NH$_2$, —OH, —C(O)NR$^5$R$^6$, —S(O)$_2$NR$^5$R$^6$, C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O, wherein each alkyl, cycloalkyl, or heterocyclyl is optionally substituted with one or more —OH, —NH$_2$, —OR$^b$, halogen, or oxo; wherein each aryl or heteroaryl is optionally substituted with one or more —OH, —NH$_2$, or halogen; or R$^a$ and R$^4$, together with the atom or atoms to which they are attached, can combine to form a monocyclic or polycyclic C$_3$-C$_{12}$cycloalkyl or a monocyclic or polycyclic 3- to 12-membered heterocycle, wherein the cycloalkyl or heterocycle is optionally substituted with oxo; wherein the heterocycle optionally comprises —S(O)$_2$— in the heterocycle;

R$^5$ and R$^6$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, -D, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently, at each occurrence, 1, 2, 3, 4, 5 or 6; and n is independently, at each occurrence, 0, 1, 2, 3, 4, 5, 6, 7, 8, 9, or 10.

34. A pharmaceutical composition comprising a compound of claim 1, or a pharmaceutically acceptable salt, solvate, hydrate, or tautomer thereof, and a pharmaceutically acceptable carrier.

35. The pharmaceutical composition of claim 34, wherein the compound is

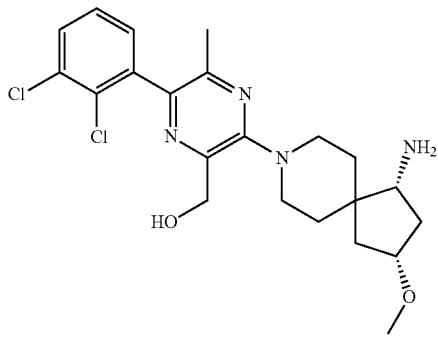 [SMILES: CO[C@H]1C[C@@H](N)C2(CCN(c3nc(C)c(-c4cccc(Cl)c4Cl)nc3CO)CC2)C1]

(A170), or a pharmaceutically acceptable salt, solvate, hydrate, or tautomer thereof.

36. The pharmaceutical composition of claim 34, wherein the compound is

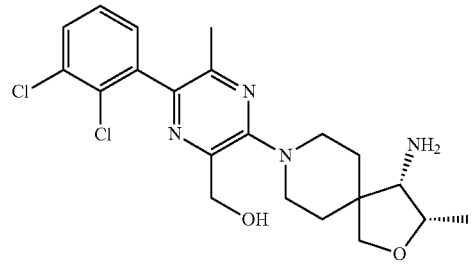 [SMILES: Cc1nc(N2CCC3(CC2)CO[C@@H](C)[C@H]3N)c(CO)nc1-c1cccc(Cl)c1Cl]

(A228), or a pharmaceutically acceptable salt, solvate, hydrate, or tautomer thereof.

37. The pharmaceutical composition of claim 34, wherein the compound is

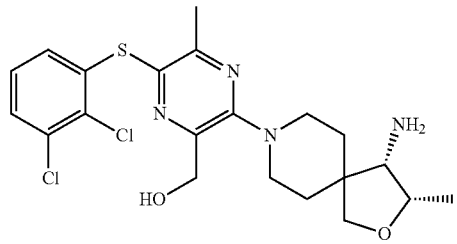 [SMILES: Cc1nc(N2CCC3(CC2)CO[C@@H](C)[C@H]3N)c(CO)nc1Sc1cccc(Cl)c1Cl]

(A266), or a pharmaceutically acceptable salt, solvate, hydrate, or tautomer thereof.

38. The pharmaceutical composition of claim 34, wherein the compound is

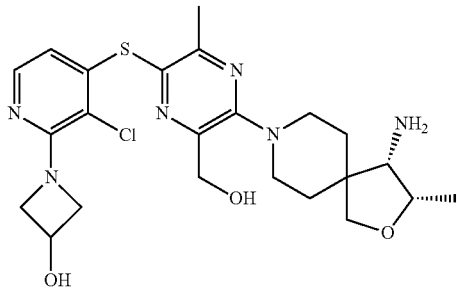 [SMILES: Cc1nc(N2CCC3(CC2)CO[C@@H](C)[C@H]3N)c(CO)nc1Sc1ccnc(N2CC(O)C2)c1Cl]

(A283), or a pharmaceutically acceptable salt, solvate, hydrate, or tautomer thereof.

39. The pharmaceutical composition of claim 34, wherein the compound is

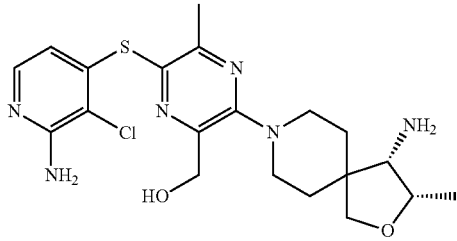 [SMILES: Cc1nc(N2CCC3(CC2)CO[C@@H](C)[C@H]3N)c(CO)nc1Sc1ccnc(N)c1Cl]

(A290), or a pharmaceutically acceptable salt, solvate, hydrate, or tautomer thereof.

40. A method of treating a disease selected from the group consisting of Noonan Syndrome, Leopard Syndrome, juvenile myelomonocytic leukemias, neuroblastoma, melanoma, acute myeloid leukemia and cancers of the breast, lung and colon in a subject in need thereof, comprising administering to the subject an effective amount of a compound of claim 1, or a pharmaceutically acceptable salt, solvate, hydrate, or tautomer thereof.

41. The method of claim 40, wherein the compound is

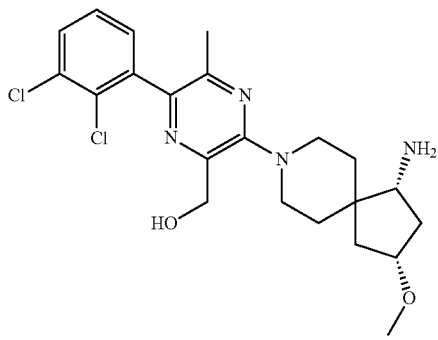 [SMILES: CO[C@H]1C[C@@H](N)C2(CCN(c3nc(C)c(-c4cccc(Cl)c4Cl)nc3CO)CC2)C1]

(A170), or a pharmaceutically acceptable salt, solvate, hydrate, or tautomer thereof.

42. The method of claim 41, wherein the disease is a cancer of the breast, lung or colon.

43. The method of claim 40, wherein the compound is

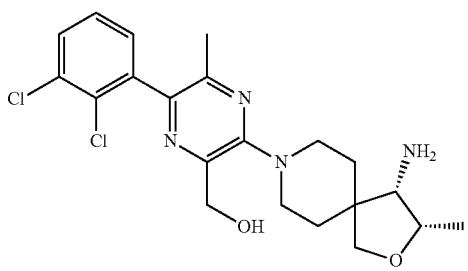 [SMILES: Cc1nc(N2CCC3(CC2)CO[C@@H](C)[C@H]3N)c(CO)nc1-c1cccc(Cl)c1Cl]

(A228), or a pharmaceutically acceptable salt, solvate, hydrate, or tautomer thereof.

44. The method of claim 43, wherein the disease is a cancer of the breast, lung or colon.

45. The method of claim 40, wherein the compound is

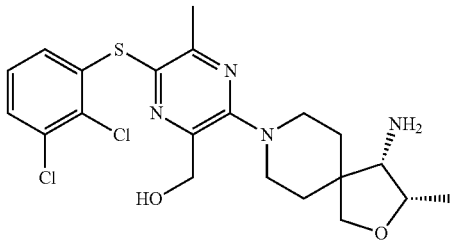 [SMILES: Cc1nc(N2CCC3(CC2)CO[C@@H](C)[C@H]3N)c(CO)nc1Sc1cccc(Cl)c1Cl]

(A266), or a pharmaceutically acceptable salt, solvate, hydrate, or tautomer thereof.

46. The method of claim 45, wherein the disease is a cancer of the breast, lung or colon.

47. The method of claim 40, wherein the compound is

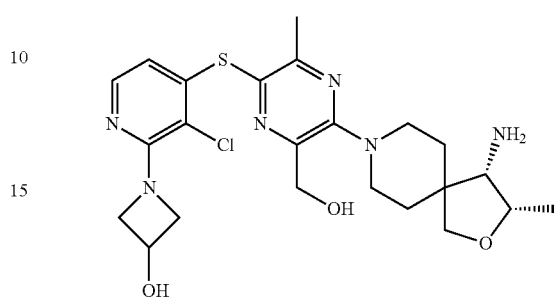

(A283), or a pharmaceutically acceptable salt, solvate, hydrate, or tautomer thereof.

48. The method of claim 47, wherein the disease is a cancer of the breast, lung or colon.

49. The method of claim 40, wherein the compound is

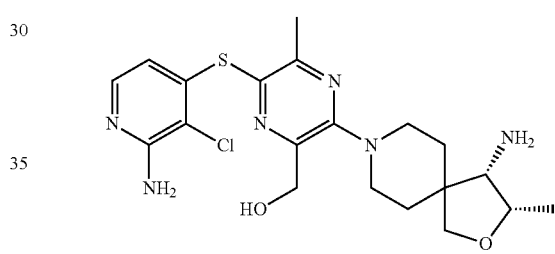

(A290), or a pharmaceutically acceptable salt, solvate, hydrate, or tautomer thereof.

50. The method of claim 49, wherein the disease is a cancer of the breast, lung or colon.

* * * * *

UNITED STATES PATENT AND TRADEMARK OFFICE
CERTIFICATE OF CORRECTION

PATENT NO. : 10,590,090 B2
APPLICATION NO. : 16/228324
DATED : March 17, 2020
INVENTOR(S) : Elena S. Koltun et al.

Page 1 of 1

It is certified that error appears in the above-identified patent and that said Letters Patent is hereby corrected as shown below:

In the Claims

In Column 509, Claim 3, Lines 3-8, please replace:
"$R^4$ is –H, –$C_1$-$C_6$alkyl, –$C_1$-$C_6$haloalkyl, –$C_1$-$C_6$hydroxyalkyl, –$CF_2OH$, –CHFOH, –C(O)NH(CH$_2$)$_n$OH, –C(O)NH(CH$_2$)$_n$R$^b$, -C(O)R$^b$, –C(O)NR$^5$R$^6$, or -OH, or -CN, wherein alkyl is optionally substituted with one or more –OH, –NH$_2$, halogen, or oxo; or"

With:
-- $R^4$ is –H, –$C_1$-$C_6$alkyl, –$C_1$-$C_6$haloalkyl, –$C_1$-$C_6$hydroxyalkyl, –$CF_2OH$, –CHFOH, –C(O)NH(CH$_2$)$_n$OH, –C(O)NH(CH$_2$)$_n$R$^b$, -C(O)R$^b$, –C(O)NR$^5$R$^6$, or -OH, wherein alkyl is optionally substituted with one or more –OH, –NH$_2$, halogen, or oxo; or --

Signed and Sealed this
Sixteenth Day of June, 2020

Andrei Iancu
*Director of the United States Patent and Trademark Office*